United States Patent
Ogawa et al.

[11] Patent Number: 6,096,735
[45] Date of Patent: *Aug. 1, 2000

[54] BENZOHETEROCYCLIC DERIVATIVES

[75] Inventors: Hidenori Ogawa; Kazumi Kondo, both of Tokushima; Hiroshi Yamashita, Tokyo; Keizo Kan; Takayuki Matsuzaki, both of Tokushima; Tomoichi Shinohara, Naruto; Yoshihisa Tanada, Naruto; Muneaki Kurimura, Naruto; Michiaki Tominaga, Tokushima; Yoichi Yabuuchi, Tokushima, all of Japan

[73] Assignee: Otsuka Pharmaceutical Company, Limited, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/737,432

[22] PCT Filed: Jun. 7, 1995

[86] PCT No.: PCT/JP95/01124

§ 371 Date: Nov. 13, 1996

§ 102(e) Date: Nov. 13, 1996

[87] PCT Pub. No.: WO95/34540

PCT Pub. Date: Dec. 21, 1995

[30] Foreign Application Priority Data

Jun. 15, 1994 [JP] Japan ................................ 7-132355
Mar. 3, 1995 [JP] Japan ................................ 8-70727

[51] Int. Cl.[7] ............ C07D 223/16; C07D 243/12; A61K 31/47; A61K 31/55
[52] U.S. Cl. .............. 514/213; 540/571; 540/593
[58] Field of Search ................. 540/571, 593; 514/213

[56] References Cited

U.S. PATENT DOCUMENTS

| | | | |
|---|---|---|---|
| 5,244,898 | 9/1993 | Ogawa et al. | 540/593 |
| 5,258,510 | 11/1993 | Ogawa et al. | 540/476 |
| 5,498,609 | 3/1996 | Ogawa et al. | 540/593 |
| 5,559,230 | 9/1996 | Ogawa et al. | 540/473 |
| 5,622,947 | 4/1997 | Ogawa et al. | 540/593 |
| 5,753,644 | 5/1998 | Ogawa et al. | 540/593 |
| 5,753,677 | 5/1998 | Ogawa | 514/311 |

FOREIGN PATENT DOCUMENTS

| | | |
|---|---|---|
| 0 620003 | 10/1994 | European Pat. Off. . |
| 91-05549 | 5/1991 | WIPO . |
| 94-04525 | 3/1994 | WIPO . |
| 94-08582 | 4/1994 | WIPO . |

*Primary Examiner*—Mukund J. Shah
*Assistant Examiner*—Bruck Kifle
*Attorney, Agent, or Firm*—Sughrue, Mion, Zinn, Macpeak & Seas, PLLC

[57] ABSTRACT

A benzoheterocyclic derivative of the following formula [1]:

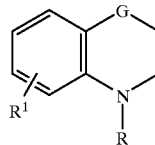

[1]

and pharmaceutically acceptable salts thereof, which show excellent anti-vasopressin activity, vasopressin agonistic activity and oxytocin antagonistic activity, and are useful as a vasopressin antagonist, vasopressin agonist or oxytocin antagonist.

17 Claims, No Drawings

BENZOHETEROCYCLIC DERIVATIVES

TECHNICAL FIELD

The present invention relates to novel benzoheterocyclic derivatives having excellent vasopressin antagonistic activities, vasopressin agonistic activities and oxytocin antagonistic activities.

BACKGROUND ART

Various benzoheterocyclic compounds analogous to the compounds of the present invention have been known to have anti-vasopressin activities in European Patent Publication No. 0382128 (published on Aug. 15, 1990), WO 91/05549 (published on May 2, 1991), WO 91/16916 (published on Nov. 14, 1991), WO 94/08582 (published on Apr. 28, 1994), WO 94/12476 (published on Jun. 9, 1994), JP-A-5-320135 (published on Dec. 3, 1993), JP-A-6-16643 (published on Jan. 25, 1994), and JP-A-6-157480 (published on Jun. 3, 1994), among which, for example, JP-A-6-16643 discloses the following compounds.

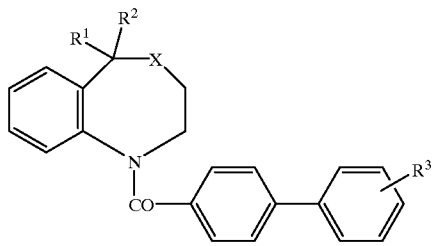

Some other literatures disclose various benzoheterocyclic compounds which are analogous to the compounds of the present invention in the chemical structure but are different in the pharmacological properties. For example, EP-A-294647 discloses some analogous compounds having positive inotropic action, vasodilating activity and platelet agglutination inhibiting activity, wherein the intermediate compounds of the following formula are also disclosed.

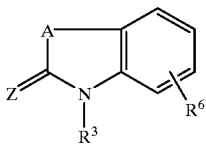

U.S. Pat. Nos. 3,542,760 (issued Nov. 24, 1970), 3,516,987 (issued Jun. 23, 1970) and 3,458,498 (issued Jul. 29, 1969) disclose also the following compounds which are useful as diuretics, hypoglycemics, antibacterials or anticonvulsants.

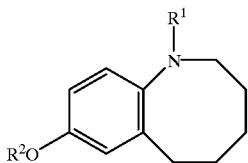

J. Chem. Soc. Perkin Trans., 1, 1985, pp. 1381–1385 discloses the following compounds but does not mention any pharmacological activity thereof.

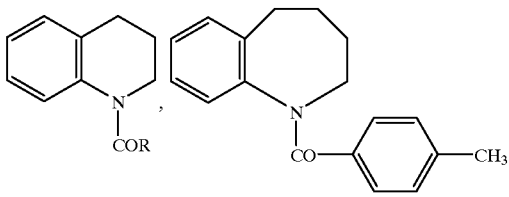

DISCLOSURE OF INVENTION

An object of the present invention is to provide a benzoheterocyclic derivative of the following formula [1]:

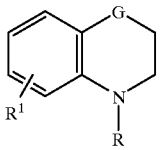

[1]

wherein G is a group of the formula:

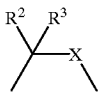

or a group of the formula:

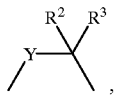

$R^1$ is a hydrogen atom, a halogen atom, a lower alkyl group, a lower alkoxy group, a hydroxy group, a lower alkanoyloxy group, an amino-lower alkoxy group having optionally a substituent selected from a lower alkyl group and a lower alkanoyl group, an amino group having optionally a lower alkyl substituent, a carboxy-substituted lower alkoxy group, a lower alkoxycarbonyl-substituted lower alkoxy group, or an aminocarbonyl-lower alkoxy group having optionally a lower alkyl substituent, $R^2$ is a group of the formula: —$NR^4R^5$ (in which $R^4$ and $R^5$ are the same or different, and each a hydrogen atom, a lower alkyl group having optionally a hydroxy substituent or a benzoyl group having optionally a halogen substituent on the phenyl ring); a hydrogen atom; a hydroxy group; a lower alkoxy group; a carboxy-substituted lower alkyl group; a cyano-substituted lower alkyl group; a tetrazolyl-substituted lower alkyl group; a lower alkanoyloxy-substituted lower alkyl group; a lower alkoxycarbonyl-substituted lower alkyl group; an amino-substituted lower alkanoyloxy group having optionally a lower alkyl substituent; a lower alkoxycarbonyl-substituted lower alkoxy group; a carboxy-substituted lower alkoxy group; a lower alkanoyl group; or a group of the formula: —$(O)_m$—A—$(CO)_u NR^6R^7$ (in which m and u are each 0 or 1, but both m and n should not be simultaneously 0, A is a lower alkylene group, $R^6$ and $R^7$ are the same or different and each a hydrogen atom, a lower alkoxy group, a lower alkyl group, an amino-substituted lower alkyl group having optionally a lower alkyl substituent, a carbamoyl-substituted lower alkyl group, an adamantyl-substituted lower alkyl group, a lower alkylsulfonyl group, or a phenyl group having optionally a halogen substituent, or $R^6$ and $R^7$ may bind together with the nitrogen atom to which they bond to form a 5- to 7-membered saturated heterocyclic group with or without being intervened with another nitrogen atom or an oxygen atom, said heterocyclic group being optionally substituted by a lower alkyl group or a phenyl-lower alkyl group), $R^3$ is a hydrogen atom or a hydroxy-substituted lower alkyl group, or $R^2$ and $R^3$ may bind together to form an oxo group, a lower alkylidene group, a lower alkoxy-substituted lower alkylidene group, a lower alkoxycarbonyl-substituted lower alkylidene group, or a phenyl-substituted lower alkylidene group, R is a pyridylcarbonyl group which may optionally have a substituent selected from a phenyl group having optionally a lower alkyl substituent and a pyridyl group on the pyridine ring; a 9-oxofluorenyl group; a quinolylcarbonyl group having optionally a phenyl substituent on the quinoline ring; an adamantylcarbonyl group; a thienylcarbonyl group having optionally a phenyl substituent on the thiophene ring; a thiazolylcarbonyl group having optionally a phenyl substituent on the thiazole ring; a cycloalkylcarbonyl group; or a group of the formula:

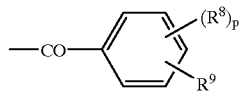

(in which p is 1 or 2, $R^8$ is a hydrogen atom, a lower alkyl group, a hydroxy group, an amino group having optionally a lower alkanoyl substituent, a nitro group, a halogen atom or a lower alkoxy group, $R^9$ is a group of the formula: $-NR^{10}R^{11}$ (in which $R^{10}$ is a hydrogen atom, a lower alkyl group, or a lower alkanoyl group having optionally a halogen substituent, $R^{11}$ is a lower alkyl group, a lower alkanoyl group having optionally a substituent selected from a halogen atom and a hydroxy group, a cycloalkyl group, a phenyl-lower alkyl group having optionally a substituent selected from a lower alkyl group and a halogen atom on the phenyl ring, and having optionally a hydroxy substituent on the alkyl moiety, a phenoxy-lower alkyl group having optionally a lower alkyl substituent on the phenyl ring, a phenoxy-lower alkanoyl group having optionally a substituent selected from a lower alkyl group, a phenyl group, a lower alkoxy group, a halogen-substituted lower alkyl group, an amino group having optionally a lower alkyl substituent, a nitro group, a lower alkanoyl-substituted amino group and a halogen atom on the phenyl ring, and having optionally a halogen substituent on the lower alkanoyl moiety, an aminocarbonyl group having optionally a substituent selected from a lower alkyl group, a pyridyl-lower alkyl group and a phenyl-lower alkyl group, a lower alkoxycarbonyl group having optionally a halogen substituent, a lower alkoxy-substituted lower alkanoyl group, a lower alkanoyloxy-substituted lower alkanoyl group, a phenoxy-lower alkoxycarbonyl group, a benzofurylcarbonyl group, a benzimidazolylcarbonyl group, a quinolylcarbonyl group, a quinolyloxy-substituted lower alkanoyl group, a phenyl-lower alkoxycarbonyl group, a group of the formula:

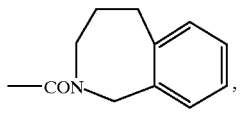

a tetrahydroisoquinolylcarbonyl group, a benzoyl-lower alkyl group, a tetrahydroquinolyloxy-substituted lower alkanoyl group having optionally a substituent selected from a lower alkyl group and an oxo group on the quinoline ring, a lower alkylsulfonyl group, a pyridyl-lower alkoxycarbonyl group, a fluorenyl-lower alkoxycarbonyl group, a lower alkenyloxycarbonyl group, a tetrahydronaphthyloxy-substituted lower alkanoyl group, a phenyl-lower alkenyl-carbonyl group, a piperidinyl-lower alkoxycarbonyl group having optionally a substituent selected from a lower alkanoyl group, a lower alkoxycarbonyl group and a lower alkyl group on the piperidine ring, or $R^{10}$ and $R^{11}$ may bind together with the nitrogen atom to which they bond to form an isoindoline ring); a hydrogen atom; a lower alkanoyloxy group; a lower alkanoyl group; a lower alkoxy group; a benzoyl group having optionally a lower alkyl substituent on the phenyl ring; a cycloalkyl group; a lower alkyl group; a lower alkylthio group; a phenyl-lower alkanoyl group having optionally a lower alkyl substituent on the phenyl ring; a phenyl group having optionally a substituent selected from a lower alkyl group, a lower alkoxy group, a phenyl-lower alkoxy group, a hydroxy group, a lower alkanoyloxy group, a halogen-substituted lower alkoxy group, a nitro group, an amino group having optionally a lower alkanoyl substituent, a phenyl group, and an amino-substituted lower alkoxy group having optionally a lower alkyl substituent; a phenoxy group; a phenoxy-lower alkyl group having optionally a lower alkyl substituent on the phenyl ring; a phenyl-lower alkyl group having optionally a lower alkyl substituent on the phenyl ring; an anilino-lower alkyl group having optionally a lower alkyl substituent on the phenyl ring; a phenyl-lower alkoxy group having optionally a substituent selected from a halogen atom, a lower alkoxycarbonyl group and an aminocarbonyl group having optionally a substituent selected from a lower alkyl group and an amino-substituted lower alkyl group having optionally a lower alkyl substituent on the phenyl ring; a benzoyl-lower alkoxy group having optionally a halogen substituent on the phenyl ring; a phenyl-lower alkenyl group having optionally a halogen substituent on the phenyl ring; a benzoyl-lower alkyl group having optionally a lower alkyl substituent on the phenyl ring; a pyrrolidinyl-substituted lower alkoxy group; a saturated or unsaturated 5- to 11-membered heteromonocyclic or heterobicyclic group having 1 to 4 heteroatoms selected from a nitrogen atom, an oxygen atom and a sulfur atom, and said heterocyclic group being optionally substituted by 1 to 3 groups selected from a lower alkyl group, a phenyl group, a lower alkanoyl group, a halogen atom, a phenyl-lower alkyl group and an oxo group; a cycloalkenyl group; a phenyl-lower alkylamino-carbonyl group; an aminosulfonyloxy group having optionally a lower alkyl substituent; a cyano group; or a group of the formula: $-(A)_m-CHR^{12}R^{13}$ (in which A is the same as defined above, $R^{12}$ is a hydrogen atom, a hydroxy group or a lower alkanoyloxy group, $R^{13}$ is a phenyl group having optionally a lower alkyl substituent or a phenyl-lower alkyl group having optionally a lower alkyl substituent on the phenyl ring, and m is 0 or 1)), X is a methylene group, a single bond, a group of the formula: =CH— or a group of the formula: $-NR^{14}-$ (in which R¹⁴ is a hydrogen atom, a lower alkyl group or a lower alkanoyl group), Y is a group of the formula: —NR^A (in which R^A is a hydrogen atom, a lower alkoxycarbonyl-substituted lower alkyl group, a carboxy-substituted lower alkyl group or a group of the formula: —ACONR^B R^C (in which R^B and R^C are the same or different and each a hydrogen atom or a lower alkyl group, or R^B and R^C may bind together with the nitrogen atom to which they bond to form a 5- to 7-membered saturated heterocyclic group with or without being intervened with another nitrogen atom or an oxygen atom, and said heterocyclic group optionally being substituted by a lower alkyl group)), provided that when R² is a group of the formula: —NR⁴R⁵ (in which R⁴ and R⁵ are the same or different and each a hydrogen atom, a lower alkyl group or a benzoyl group), a hydrogen atom, a hydroxy group, a lower alkoxycarbonyl-substituted lower alkoxy group, a carboxy-substituted lower alkoxy group, a lower alkoxy group, a lower alkanoyloxy-substituted lower alkyl group, a group of the formula: —(O)$_m$—A—(CO)$_u$NR⁶R⁷ (m and u are the same as defined above, R⁶ and R⁷ are the same or different and each a hydrogen atom or a lower alkyl group, or R⁶ and R⁷ may bind together with the nitrogen atom to which they bond to form a 5- to 6-membered saturated heterocyclic group with or without being intervened with another nitrogen atom or an oxygen atom, and said heterocyclic group optionally being substituted by a lower alkyl group), or an amino-substituted lower alkanoyloxy group having optionally a lower alkyl substituent; or R² and R³ may bind together to form an oxo group or a lower alkylidene group; and when R is a group of the formula:

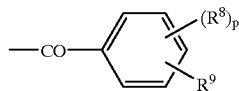

and R⁸ in said group is a hydrogen atom, a lower alkyl group, a hydroxy group, a halogen atom, a lower alkoxy group or an amino group, then R⁹ should not be a hydrogen atom, a phenyl-lower alkoxycarbonyl group, nor a group of the formula: —NR¹⁰R¹¹ (R¹¹ is a lower alkanoyl group or a phenoxy-lower alkanoyl group having optionally 1 to 3 substituents selected from a lower alkyl group and a lower alkoxy group on the phenyl ring), or when R¹ is a hydrogen atom, R² is a hydrogen atom, an amino group, a mono-lower alkylamino group or a di-lower alkylamino group, or R² and R³ may bind together to form an oxo group, then R⁹ should not be a phenyl group having optionally a substituent selected from a hydroxy group, a lower alkyl group, a lower alkoxy group and a lower alkanoyloxy group on the phenyl ring, or when R⁹ is a group of the formula:

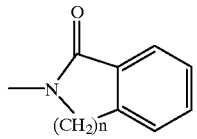

(n is 1 or 2), and G is a group of the formula:

(R² and R³ are the same as defined above), then X should not be a methylene group nor a group of the formula: =CH—, or when one of R¹⁰ and R¹¹ is a hydrogen atom, the other should not be a lower alkyl group, or a pharmaceutically acceptable salt thereof.

The present inventors have intensively studied and have found that the compounds of the formula [1] and a pharmaceutically acceptable salt thereof have excellent vasopressin antagonistic activities, vasopressin agonistic activities and excellent oxytocin antagonistic activities.

The compounds of the formula [1] of the present invention and a pharmaceutically acceptable salt thereof show excellent vasopressin antagonistic activity, for example, vasodilating activity, hypotensive activity, activity for inhibiting saccharide release in liver, activity for inhibiting growth of mesangium cells, water diuretic activity, platelet agglutination inhibitory activity, inhibitory activity for vomiting, activity for promoting urea excretion, inhibitory activity on secretion of factor VIII, activity for promoting heart function, activity for inhibiting constriction of mesangium cells, inhibitory activity on production of saccharide in liver, inhibitory activity on aldosterone secretion, inhibitory activity on production of endotheline, regulation activity on renin secretion, memory regulation activity, thermoregulation activity, activity for regulating production of prostaglandin, and hence, they are useful as vasodilators, hypotensive agents, water diuretics, platelet agglutination inhibitors, promoters for urea excretion, agent for heart failure, agent for renal failure, etc., and are used in the prophylaxis or treatment of hypertension, edema, ascites, heart failure, renal function disorder, vasopressin parasecretion syndrome (SIADH), hepatocirrhosis, hyponatremia, hypokalemia, diabetes, circulation disorder, motion sickness, water metabolism disorder, renal failure, various diseases associated with ischemic, and the like. Besides, the compounds of the present invention and a pharmaceutically acceptable salt thereof are characteristic in very few side effects and a prolonged action for a long time in a living body.

The compounds [1] of the present invention and a pharmaceutically acceptable salt thereof also show vasopressin agonistic activities, for example, effects on various urinary disorders, polyuria or hemostatic disorders, and hence, they are useful in the prophylaxis or treatment of pollakisuria, diabetes insipidus, urine incontinence, enuresis, especially nocturnal enuresis, spontaneous hemorrhage, hemophilia, von Willebrand's disease, uremia, congenital and acquired platelet dysfunction, hemostatic derangement caused by surgical procedures or accidental trauma, or hepatic cirrhosis.

In addition, the compounds [1] of the present invention and a pharmaceutically acceptable salt thereof also show oxytocin antagonistic activities, for example, inhibitory effect on uterine smooth muscle constriction, inhibitory effect on milk secretion, inhibitory effect on synthesis and secretion of prostaglandin, and vasodilating activity, and hence, they are useful in the protection or treatment of oxytocin-associated diseases, especially premature delivery, dysmenorrhea, endometritis, or in stopping labor preparatory to Caesarian delivery.

The benzoheterocyclic derivatives of the formula [1] of the present invention especially include the following compounds.

(1) A benzoheterocyclic derivative of the formula [1] or a salt thereof, wherein G is a group of the formula: —C($R^2$)($R^3$)—X—, X is a methylene group, $R^1$ is the same as defined above in the definition for the formula [1], $R^2$ is a group of the formula: —$NR^4R^5$ (in which $R^4$ and $R^5$ are the same as defined above in the definition for the formula [1]), $R^3$ is a hydrogen atom or a hydroxy-substituted lower alkyl group, R is a pyridylcarbonyl group having optionally a substituent selected from a phenyl group having optionally a lower alkyl substituent on the phenyl ring and a pyridyl group on the pyridine ring.

(2) A benzoheterocyclic derivative of the formula [1] or a salt thereof, wherein G, X, $R^1$, $R^3$ and R are the same as defined in above (1), and $R^2$ is a hydrogen atom.

(3) A benzoheterocyclic derivative of the formula [1] or a salt thereof, wherein G, X, $R^1$, $R^3$ and R are the same as defined in above (1), and $R^2$ is a hydroxy group.

(4) A benzoheterocyclic derivative of the formula [1] or a salt thereof, wherein G, X, $R^1$, $R^3$ and R are the same as defined in above (1), and $R^2$ is a carboxy-substituted lower alkyl group.

(5) A benzoheterocyclic derivative of the formula [1] or a salt thereof, wherein G, X, $R^1$, $R^3$ and R are the same as defined in above (1), and $R^2$ is a lower alkoxycarbonyl-substituted lower alkyl group.

(6) A benzoheterocyclic derivative of the formula [1] or a salt thereof, wherein G, X, $R^1$, $R^3$ and R are the same as defined in above (1), and $R^2$ is an amino-substituted lower alkanoyloxy group having optionally a lower alkyl substituent.

(7) A benzoheterocyclic derivative of the formula [1] or a salt thereof, wherein G, X, $R^1$, $R^3$ and R are the same as defined in above (1), and $R^2$ is a lower alkanoyl group.

(8) A benzoheterocyclic derivative of the formula [1] or a salt thereof, wherein G, X, $R^1$ and R are the same as defined in above (1), and $R^2$ and $R^3$ bind together to form an oxo group.

(9) A benzoheterocyclic derivative of the formula [1] or a salt thereof, wherein G, X, $R^1$ and R are the same as defined in above (1), and $R^2$ and $R^3$ bind together to form a lower alkylidene group.

(10) A benzoheterocyclic derivative of the formula [1] or a salt thereof, wherein G, X, $R^1$ and R are the same as defined in above (1), and $R^2$ and $R^3$ bind together to form a lower alkoxy-substituted lower alkylidene group.

(11) A benzoheterocyclic derivative of the formula [1] or a salt thereof, wherein G, X, $R^1$ and R are the same as defined in above (1), and $R^2$ and $R^3$ bind together to form a lower alkoxycarbonyl-substituted lower alkylidene group.

(12) A benzoheterocyclic derivative of the formula [1] or a salt thereof, wherein G, X, $R^1$ and R are the same as defined in above (1), and $R^2$ and $R^3$ bind together to form a phenyl-substituted lower alkylidene group.

(13) A benzoheterocyclic derivative of the formula [1] or a salt thereof, wherein G is a group of the formula: —C($R^2$)($R^3$)—X—, X is a methylene group, $R^1$ is the same as defined above in the definition for the formula [1], $R^2$ is a group of the formula: —$NR^4R^5$ ($R^4$ and $R^5$ are the same as defined above in the definition for the formula [1]), $R^3$ is a hydrogen atom or a hydroxy-substituted lower alkyl group, and R is a group of the formula:

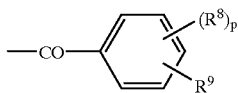

($R^9$ and p are the same as defined above, and $R^8$ is a hydrogen atom).

(14) A benzoheterocyclic derivative of the formula [1] or a salt thereof, wherein G, X, $R^1$, $R^3$ and R are the same as defined in above (13), and $R^2$ is a hydrogen atom.

(15) A benzoheterocyclic derivative of the formula [1] or a salt thereof, wherein G, X, $R^1$, $R^3$ and R are the same as defined in above (13), and $R^2$ is a hydroxy group.

(16) A benzoheterocyclic derivative of the formula [1] or a salt thereof, wherein G, X, $R^1$, $R^3$ and R are the same as defined in above (13), and $R^2$ is a carboxy-substituted lower alkyl group.

(17) A benzoheterocyclic derivative of the formula [1] or a salt thereof, wherein G, X, $R^1$, $R^3$ and R are the same as defined in above (13), and $R^2$ is a lower alkoxycarbonyl-substituted lower alkyl group.

(18) A benzoheterocyclic derivative of the formula [1] or a salt thereof, wherein G, X, $R^1$, $R^3$ and R are the same as defined in above (13), and $R^2$ is an amino-substituted lower alkanoyloxy group having optionally a lower alkyl substituent.

(19) A benzoheterocyclic derivative of the formula [1] or a salt thereof, wherein G, X, $R^1$, $R^3$ and R are the same as defined in above (13), and $R^2$ is a lower alkanoyl group.

(20) A benzoheterocyclic derivative of the formula [1] or a salt thereof, wherein G, X, $R^1$ and R are the same as defined in above (13), and $R^2$ and $R^3$ bind together to form an oxo group.

(21) A benzoheterocyclic derivative of the formula [1] or a salt thereof, wherein G, X, $R^1$ and R are the same as defined in above (13), and $R^2$ and $R^3$ bind together to form a lower alkylidene group.

(22) A benzoheterocyclic derivative of the formula [1] or a salt thereof, wherein G, X, $R^1$ and R are the same as defined in above (13), and $R^2$ and $R^3$ bind together to form a lower alkoxy-substituted lower alkylidene group.

(23) A benzoheterocyclic derivative of the formula [1] or a salt thereof, wherein G, X, $R^1$ and R are the same as defined in above (13), and $R^2$ and $R^3$ bind together to form a lower alkoxycarbonyl-substituted lower alkylidene group.

(24) A benzoheterocyclic derivative of the formula [1] or a salt thereof, wherein G, X, $R^1$ and R are the same as defined in above (13), and $R^2$ and $R^3$ bind together to form a phenyl-substituted lower alkylidene group.

(25) A benzoheterocyclic derivative of the formula [1] or a salt thereof, wherein G is a group of the formula: —C($R^2$)($R^3$)—X—, X is a methylene group, $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

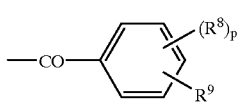

($R^9$ and p are the same as defined above in the formula [1], and $R^8$ is a lower alkyl group).

(26) A benzoheterocyclic derivative of the formula [1] or a salt thereof, wherein G, X, $R^1$, $R^3$ and R are the same as defined in above (25), and $R^2$ is a hydrogen atom.

(27) A benzoheterocyclic derivative of the formula [1] or a salt thereof, wherein G, X, $R^1$, $R^3$ and R are the same as defined in above (25), and $R^2$ is a hydroxy group.
(28) A benzoheterocyclic derivative of the formula [1] or a salt thereof, wherein G, X, $R^1$, $R^3$ and R are the same as defined in above (25), and $R^2$ is a carboxy-substituted lower alkyl group.
(29) A benzoheterocyclic derivative of the formula [1] or a salt thereof, wherein G, X, $R^1$, $R^3$ and R are the same as defined in above (25), and $R^2$ is a lower alkoxycarbonyl-substituted lower alkyl group.
(30) A benzoheterocyclic derivative of the formula [1] or a salt thereof, wherein G, X, $R^1$, $R^3$ and R are the same as defined in above (25), and $R^2$ is an amino-substituted lower alkanoyloxy group having optionally a lower alkyl substituent.
(31) A benzoheterocyclic derivative of the formula [1] or a salt thereof, wherein G, X, $R^1$, $R^3$ and R are the same as defined in above (25), and $R^2$ is a lower alkanoyl group.
(32) A benzoheterocyclic derivative of the formula [1] or a salt thereof, wherein G, X, $R^1$ and R are the same as defined in above (25), and $R^2$ and $R^3$ bind together to form an oxo group.
(33) A benzoheterocyclic derivative of the formula [1] or a salt thereof, wherein G, X, $R^1$ and R are the same as defined in above (25), and $R^2$ and $R^3$ bind together to form a lower alkylidene group.
(34) A benzoheterocyclic derivative of the formula [1] or a salt thereof, wherein G, X, $R^1$ and R are the same as defined in above (25), and $R^2$ and $R^3$ bind together to form a lower alkoxy-substituted lower alkylidene group.
(35) A benzoheterocyclic derivative of the formula [1] or a salt thereof, wherein G, X, $R^1$ and R are the same as defined in above (25), and $R^2$ and $R^3$ bind together to form a lower alkoxycarbonyl-substituted lower alkylidene group.
(36) A benzoheterocyclic derivative of the formula [1] or a salt thereof, wherein G, X, $R^1$ and R are the same as defined in above (25), and $R^2$ and $R^3$ bind together to form a phenyl-substituted lower alkylidene group.
(37) A benzoheterocyclic derivative of the formula [1] or a salt thereof, wherein G is a group of the formula: —C($R^2$)($R^3$)—X—, X is a methylene group, $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

—CO—⟨ring with ($R^8$)$_p$ and $R^9$⟩

($R^9$ and p are the same as defined above in the formula [1], and $R^8$ is a hydroxy group).
(38) A benzoheterocyclic derivative of the formula [1] or a salt thereof, wherein G, X, $R^1$, $R^3$ and R are the same as defined in above (37), and $R^2$ is a hydrogen atom.
(39) A benzoheterocyclic derivative of the formula [1] or a salt thereof, wherein G, X, $R^1$, $R^3$ and R are the same as defined in above (37), and $R^2$ is a hydroxy group.
(40) A benzoheterocyclic derivative of the formula [1] or a salt thereof, wherein G, X, $R^1$, $R^3$ and R are the same as defined in above (37), and $R^2$ is a carboxy-substituted lower alkyl group.
(41) A benzoheterocyclic derivative of the formula [1] or a salt thereof, wherein G, X, $R^1$, $R^3$ and R are the same as defined in above (37), and $R^2$ is a lower alkoxycarbonyl-substituted lower alkyl group.
(42) A benzoheterocyclic derivative of the formula [1] or a salt thereof, wherein G, X, $R^1$, $R^3$ and R are the same as defined in above (37), and $R^2$ is an amino-substituted lower alkanoyloxy group having optionally a lower alkyl substituent.
(43) A benzoheterocyclic derivative of the formula [1] or a salt thereof, wherein G, X, $R^1$, $R^3$ and R are the same as defined in above (37), and $R^2$ is a lower alkanoyl group.
(44) A benzoheterocyclic derivative of the formula [1] or a salt thereof, wherein G, X, $R^1$ and R are the same as defined in above (37), and $R^2$ and $R^3$ bind together to form an oxo group.
(45) A benzoheterocyclic derivative of the formula [1] or a salt thereof, wherein G, X, $R^1$ and R are the same as defined in above (37), and $R^2$ and $R^3$ bind together to form a lower alkylidene group.
(46) A benzoheterocyclic derivative of the formula [1] or a salt thereof, wherein G, X, $R^1$ and R are the same as defined in above (37), and $R^2$ and $R^3$ bind together to form a lower alkoxy-substituted lower alkylidene group.
(47) A benzoheterocyclic derivative of the formula [1] or a salt thereof, wherein G, X, $R^1$ and R are the same as defined in above (37), and $R^2$ and $R^3$ bind together to form a lower alkoxycarbonyl-substituted lower alkylidene group.
(48) A benzoheterocyclic derivative of the formula [1] or a salt thereof, wherein G, X, $R^1$ and R are the same as defined in above (37), and $R^2$ and $R^3$ bind together to form a phenyl-substituted lower alkylidene group.
(49) A benzoheterocyclic derivative of the formula [1] or a salt thereof, wherein G is a group of the formula: —C($R^2$)($R^3$)—X—, X is methylene group, $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

—CO—⟨ring with ($R^8$)$_p$ and $R^9$⟩

($R^9$ and p are the same as defined above in the formula [1], and $R^8$ is a nitro group).
(50) A benzoheterocyclic derivative of the formula [1] or a salt thereof, wherein G, X, $R^1$, $R^3$ and R are the same as defined in above (49), and $R^2$ is a hydrogen atom.
(51) A benzoheterocyclic derivative of the formula [1] or a salt thereof, wherein G, X, $R^1$, $R^3$ and R are the same as defined in above (49), and $R^2$ is a hydroxy group.
(52) A benzoheterocyclic derivative of the formula [1] or a salt thereof, wherein G, X, $R^1$, $R^3$ and R are the same as defined in above (49), and $R^2$ is a carboxy-substituted lower alkyl group.
(53) A benzoheterocyclic derivative of the formula [1] or a salt thereof, wherein G, X, $R^1$, $R^3$ and R are the same as defined in above (49), and $R^2$ is a lower alkoxycarbonyl-substituted lower alkyl group.
(54) A benzoheterocyclic derivative of the formula [1] or a salt thereof, wherein G, X, $R^1$, $R^3$ and R are the same as defined in above (49), and $R^2$ is an amino-substituted lower alkanoyloxy group having optionally a lower alkyl substituent.
(55) A benzoheterocyclic derivative of the formula [1] or a salt thereof, wherein G, X, $R^1$, $R^3$ and R are the same as defined in above (49), and $R^2$ is a lower alkanoyl group.

(56) A benzoheterocyclic derivative of the formula [1] or a salt thereof, wherein G, X, $R^1$ and R are the same as defined in above (49), and $R^2$ and $R^3$ bind together to form an oxo group.
(57) A benzoheterocyclic derivative of the formula [1] or a salt thereof, wherein G, X, $R^1$ and R are the same as defined in above (49), and $R^2$ and $R^3$ bind together to form a lower alkylidene group.
(58) A benzoheterocyclic derivative of the formula [1] or a salt thereof, wherein G, X, $R^1$ and R are the same as defined in above (49), and $R^2$ and $R^3$ bind together to form a lower alkoxy-substituted lower alkylidene group.
(59) A benzoheterocyclic derivative of the formula [1] or a salt thereof, wherein G, X, $R^1$ and R are the same as defined in above (49), and $R^2$ and $R^3$ bind together to form a lower alkoxycarbonyl-substituted lower alkylidene group.
(60) A benzoheterocyclic derivative of the formula [1] or a salt thereof, wherein G, X, $R^1$ and R are the same as defined in above (49), and $R^2$ and $R^3$ bind together to form a phenyl-substituted lower alkylidene group.
(61) A benzoheterocyclic derivative of the formula [1] or a salt thereof, wherein G is a group of the formula: —C($R^2$)($R^3$)—X—, X is a methylene group, $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

—CO—⟨phenyl with $(R^8)_p$ and $R^9$⟩

($R^9$ and p are the same as defined above in the formula [1], and $R^8$ is a halogen atom).
(62) A benzoheterocyclic derivative of the formula [1] or a salt thereof, wherein G, X, $R^1$, $R^3$ and R are the same as defined in above (61), and $R^2$ is a hydrogen atom.
(63) A benzoheterocyclic derivative of the formula [1] or a salt thereof, wherein G, X, $R^1$, $R^3$ and R are the same as defined in above (61), and $R^2$ is a hydroxy group.
(64) A benzoheterocyclic derivative of the formula [1] or a salt thereof, wherein G, X, $R^1$, $R^3$ and R are the same as defined in above (61), and $R^2$ is a carboxy-substituted lower alkyl group.
(65) A benzoheterocyclic derivative of the formula [1] or a salt thereof, wherein G, X, $R^1$, $R^3$ and R are the same as defined in above (61), and $R^2$ is a lower alkoxycarbonyl-substituted lower alkyl group.
(66) A benzoheterocyclic derivative of the formula [1] or a salt thereof, wherein G, X, $R^1$, $R^3$ and R are the same as defined in above (61), and $R^2$ is an amino-substituted lower alkanoyloxy group having optionally a lower alkyl substituent.
(67) A benzoheterocyclic derivative of the formula [1] or a salt thereof, wherein G, X, $R^1$, $R^3$ and R are the same as defined in above (61), and $R^2$ is a lower alkanoyl group.
(68) A benzoheterocyclic derivative of the formula [1] or a salt thereof, wherein G, X, $R^1$ and R are the same as defined in above (61), and $R^2$ and $R^3$ bind together to form an oxo group.
(69) A benzoheterocyclic derivative of the formula [1] or a salt thereof, wherein G, X, $R^1$ and R are the same as defined in above (61), and $R^2$ and $R^3$ bind together to form a lower alkylidene group.
(70) A benzoheterocyclic derivative of the formula [1] or a salt thereof, wherein G, X, $R^1$ and R are the same as defined in above (61), and $R^2$ and $R^3$ bind together to form a lower alkoxy-substituted lower alkylidene group.
(71) A benzoheterocyclic derivative of the formula [1] or a salt thereof, wherein G, X, $R^1$ and R are the same as defined in above (61), and $R^2$ and $R^3$ bind together to form a lower alkoxycarbonyl-substituted lower alkylidene group.
(72) A benzoheterocyclic derivative of the formula [1] or a salt thereof, wherein G, X, $R^1$ and R are the same as defined in above (61), and $R^2$ and $R^3$ bind together to form a phenyl-substituted lower alkylidene group.
(73) A benzoheterocyclic derivative of the formula [1] or a salt thereof, wherein G is a group of the formula: —C($R^2$)($R^3$)—X—, X is a methylene group, $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

—CO—⟨phenyl with $(R^8)_p$ and $R^9$⟩

($R^9$ and p are the same as defined above in the formula [1], and $R^8$ is a lower alkoxy group).
(74) A benzoheterocyclic derivative of the formula [1] or a salt thereof, wherein G, X, $R^1$, $R^3$ and R are the same as defined in above (73), and $R^2$ is a hydrogen atom.
(75) A benzoheterocyclic derivative of the formula [1] or a salt thereof, wherein G, X, $R^1$, $R^3$ and R are the same as defined in above (73), and $R^2$ is a hydroxy group.
(76) A benzoheterocyclic derivative of the formula [1] or a salt thereof, wherein G, X, $R^1$, $R^3$ and R are the same as defined in above (73), and $R^2$ is a carboxy-substituted lower alkyl group.
(77) A benzoheterocyclic derivative of the formula [1] or a salt thereof, wherein G, X, $R^1$, $R^3$ and R are the same as defined in above (73), and $R^2$ is a lower alkoxycarbonyl-substituted lower alkyl group.
(78) A benzoheterocyclic derivative of the formula [1] or a salt thereof, wherein G, X, $R^1$, $R^3$ and R are the same as defined in above (73), and $R^2$ is an amino-substituted lower alkanoyloxy group having optionally a lower alkyl substituent.
(79) A benzoheterocyclic derivative of the formula [1] or a salt thereof, wherein G, X, $R^1$, $R^3$ and R are the same as defined in above (73), and $R^2$ is a lower alkanoyl group.
(80) A benzoheterocyclic derivative of the formula [1] or a salt thereof, wherein G, X, $R^1$ and R are the same as defined in above (73), and $R^2$ and $R^3$ bind together to form an oxo group.
(81) A benzoheterocyclic derivative of the formula [1] or a salt thereof, wherein G, X, $R^1$ and R are the same as defined in above (73), and $R^2$ and $R^3$ bind together to form a lower alkylidene group.
(82) A benzoheterocyclic derivative of the formula [1] or a salt thereof, wherein G, X, $R^1$ and R are the same as defined in above (73), and $R^2$ and $R^3$ bind together to form a lower alkoxy-substituted lower alkylidene group.
(83) A benzoheterocyclic derivative of the formula [1] or a salt thereof, wherein G, X, $R^1$ and R are the same as defined in above (73), and $R^2$ and $R^3$ bind together to form a lower alkoxycarbonyl-substituted lower alkylidene group.
(84) A benzoheterocyclic derivative of the formula [1] or a salt thereof, wherein G, X, $R^1$ and R are the same as defined in above (73), and $R^2$ and $R^3$ bind together to form a phenyl-substituted lower alkylidene group

(85) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a pyridylcarbonyl group having optionally a substituent selected from a phenyl group having optionally a lower alkyl substituent on the phenyl ring and a pyridyl group on the pyridine ring.

(86) A benzoheterocyclic derivative of the formula [1] or a salt thereof, wherein G, X, $R^1$, $R^3$ and R are the same as defined in above (85), and $R^2$ is a hydrogen atom.

(87) A benzoheterocyclic derivative of the formula [1] or a salt thereof, wherein G, X, $R^1$, $R^3$ and R are the same as defined in above (85), and $R^2$ is a hydroxy group.

(88) A benzoheterocyclic derivative of the formula [1] or a salt thereof, wherein G, X, $R^1$, $R^3$ and R are the same as defined in above (85), and $R^2$ is a carboxy-substituted lower alkyl group.

(89) A benzoheterocyclic derivative of the formula [1] or a salt thereof, wherein G, X, $R^1$, $R^3$ and R are the same as defined in above (85), and $R^2$ is a lower alkoxycarbonyl-substituted lower alkyl group.

(90) A benzoheterocyclic derivative of the formula [1] or a salt thereof, wherein G, X, $R^1$, $R^3$ and R are the same as defined in above (85), and $R^2$ is an amino-substituted lower alkanoyloxy group having optionally a lower alkyl substituent.

(91) A benzoheterocyclic derivative of the formula [1] or a salt thereof, wherein G, X, $R^1$, $R^3$ and R are the same as defined in above (85), and $R^2$ is a lower alkanoyl group.

(92) A benzoheterocyclic derivative of the formula [1] or a salt thereof, wherein G, X, $R^1$ and R are the same as defined in above (85), and $R^2$ and $R^3$ bind together to form an oxo group.

(93) A benzoheterocyclic derivative of the formula [1] or a salt thereof, wherein G, X, $R^1$ and R are the same as defined in above (85), and $R^2$ and $R^3$ bind together to form a lower alkylidene group.

(94) A benzoheterocyclic derivative of the formula [1] or a salt thereof, wherein G, X, $R^1$ and R are the same as defined in above (85), and $R^2$ and $R^3$ bind together to form a lower alkoxy-substituted lower alkylidene group.

(95) A benzoheterocyclic derivative of the formula [1] or a salt thereof, wherein G, X, $R^1$ and R are the same as defined in above (85), and $R^2$ and $R^3$ bind together to form a lower alkoxycarbonyl-substituted lower alkylidene group.

(96) A benzoheterocyclic derivative of the formula [1] or a salt thereof, wherein G, X, $R^1$ and R are the same as defined in above (85), and $R^2$ and $R^3$ bind together to form a phenyl-substituted lower alkylidene group.

(97) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

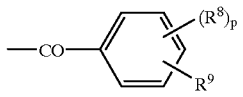

($R^9$ and p are the same as defined above in the formula [1], and $R^8$ is a hydrogen atom).

(98) A benzoheterocyclic derivative of the formula [1] or a salt thereof, wherein G, X, $R^1$, $R^3$ and R are the same as defined in above (97), and $R^2$ is a hydrogen atom.

(99) A benzoheterocyclic derivative of the formula [1] or a salt thereof, wherein G, X, $R^1$, $R^3$ and R are the same as defined in above (97), and $R^2$ is a hydroxy group.

(100) A benzoheterocyclic derivative of the formula [1] or a salt thereof, wherein G, X, $R^1$, $R^3$ and R are the same as defined in above (97), and $R^2$ is a carboxy-substituted lower alkyl group.

(101) A benzoheterocyclic derivative of the formula [1] or a salt thereof, wherein G, X, $R^1$, $R^3$ and R are the same as defined in above (97), and $R^2$ is a lower alkoxycarbonyl-substituted lower alkyl group.

(102) A benzoheterocyclic derivative of the formula [1] or a salt thereof, wherein G, X, $R^1$, $R^3$ and R are the same as defined in above (97), and $R^2$ is an amino-substituted lower alkanoyloxy group having optionally a lower alkyl substituent.

(103) A benzoheterocyclic derivative of the formula [1] or a salt thereof, wherein G, X, $R^1$, $R^3$ and R are the same as defined in above (97), and $R^2$ is a lower alkanoyl group.

(104) A benzoheterocyclic derivative of the formula [1] or a salt thereof, wherein G, X, $R^1$ and R are the same as defined in above (97), and $R^2$ and $R^3$ bind together to form an oxo group.

(105) A benzoheterocyclic derivative of the formula [1] or a salt thereof, wherein G, X, $R^1$ and R are the same as defined in above (97), and $R^2$ and $R^3$ bind together to form a lower alkylidene group.

(106) A benzoheterocyclic derivative of the formula [1] or a salt thereof, wherein G, X, $R^1$ and R are the same as defined in above (97), and $R^2$ and $R^3$ bind together to form a lower alkoxy-substituted lower alkylidene group.

(107) A benzoheterocyclic derivative of the formula [1] or a salt thereof, wherein G, X, $R^1$ and R are the same as defined in above (97), and $R^2$ and $R^3$ bind together to form a lower alkoxycarbonyl-substituted lower alkylidene group.

(108) A benzoheterocyclic derivative of the formula [1] or a salt thereof, wherein G, X, $R^1$ and R are the same as defined in above (97), and $R^2$ and $R^3$ bind together to form a phenyl-substituted lower alkylidene group.

(109) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

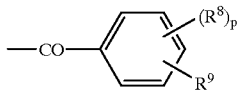

($R^9$ and p are the same as defined above in the formula [1], and $R^8$ is a lower alkyl group).

(110) A benzoheterocyclic derivative of the formula [1] or a salt thereof, wherein G, X, $R^1$, $R^3$ and R are the same as defined in above (109), and $R^2$ is a hydrogen atom.
(111) A benzoheterocyclic derivative of the formula [1] or a salt thereof, wherein G, X, $R^1$, $R^3$ and R are the same as defined in above (109), and $R^2$ is a hydroxy group.
(112) A benzoheterocyclic derivative of the formula [1] or a salt thereof, wherein G, X, $R^1$, $R^3$ and R are the same as defined in above (109), and $R^2$ is a carboxy-substituted lower alkyl group.
(113) A benzoheterocyclic derivative of the formula [1] or a salt thereof, wherein G, X, $R^1$, $R^3$ and R are the same as defined in above (109), and $R^2$ is a lower alkoxycarbonyl-substituted lower alkyl group.
(114) A benzoheterocyclic derivative of the formula [1] or a salt thereof, wherein G, X, $R^1$, $R^3$ and R are the same as defined in above (109), and $R^2$ is an amino-substituted lower alkanoyloxy group having optionally a lower alkyl substituent.
(115) A benzoheterocyclic derivative of the formula [1] or a salt thereof, wherein G, X, $R^1$, $R^3$ and R are the same as defined in above (109), and $R^2$ is a lower alkanoyl group.
(116) A benzoheterocyclic derivative of the formula [1] or a salt thereof, wherein G, X, $R^1$ and R are the same as defined in above (109), and $R^2$ and $R^3$ bind together to form an oxo group.
(117) A benzoheterocyclic derivative of the formula [1] or a salt thereof, wherein G, X, $R^1$ and R are the same as defined in above (109), and $R^2$ and $R^3$ bind together to form a lower alkylidene group.
(118) A benzoheterocyclic derivative of the formula [1] or a salt thereof, wherein G, X, $R^1$ and R are the same as defined in above (109), and $R^2$ and $R^3$ bind together to form a lower alkoxy-substituted lower alkylidene group.
(119) A benzoheterocyclic derivative of the formula [1] or a salt thereof, wherein G, X, $R^1$ and R are the same as defined in above (109), and $R^2$ and $R^3$ bind together to form a lower alkoxycarbonyl-substituted lower alkylidene group.
(120) A benzoheterocyclic derivative of the formula [1] or a salt thereof, wherein G, X, $R^1$ and R are the same as defined in above (109), and $R^2$ and $R^3$ bind together to form a phenyl-substituted lower alkylidene group.
(121) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

—CO—⟨ring with $(R^8)_p$ and $R^9$⟩

($R^9$ and p are the same as defined above in the formula [1], and $R^8$ is a hydroxy group).
(122) A benzoheterocyclic derivative of the formula [1] or a salt thereof, wherein G, X, $R^1$, $R^3$ and R are the same as defined in above (121), and $R^2$ is a hydrogen atom.
(123) A benzoheterocyclic derivative of the formula [1] or a salt thereof, wherein G, X, $R^1$, $R^3$ and R are the same as defined in above (121), and $R^2$ is a hydroxy group.
(124) A benzoheterocyclic derivative of the formula [1] or a salt thereof, wherein G, X, $R^1$, $R^3$ and R are the same as defined in above (121), and $R^2$ is a carboxy-substituted lower alkyl group.
(125) A benzoheterocyclic derivative of the formula [1] or a salt thereof, wherein G, X, $R^1$, $R^3$ and R are the same as defined in above (121), and $R^2$ is a lower alkoxycarbonyl-substituted lower alkyl group.
(126) A benzoheterocyclic derivative of the formula [1] or a salt thereof, wherein G, X, $R^1$, $R^3$ and R are the same as defined in above (121), and $R^2$ is an amino-substituted lower alkanoyloxy group having optionally a lower alkyl substituent.
(127) A benzoheterocyclic derivative of the formula [1] or a salt thereof, wherein G, X, $R^1$, $R^3$ and R are the same as defined in above (121), and $R^2$ is a lower alkanoyl group.
(128) A benzoheterocyclic derivative of the formula [1] or a salt thereof, wherein G, X, $R^1$ and R are the same as defined in above (121), and $R^2$ and $R^3$ bind together to form an oxo group.
(129) A benzoheterocyclic derivative of the formula [1] or a salt thereof, wherein G, X, $R^1$ and R are the same as defined in above (121), and $R^2$ and $R^3$ bind together to form a lower alkylidene group.
(130) A benzoheterocyclic derivative of the formula [1] or a salt thereof, wherein G, X, $R^1$ and R are the same as defined in above (121), and $R^2$ and $R^3$ bind together to form a lower alkoxy-substituted lower alkylidene group.
(131) A benzoheterocyclic derivative of the formula [1] or a salt thereof, wherein G, X, $R^1$ and R are the same as defined in above (121), and $R^2$ and $R^3$ bind together to form a lower alkoxycarbonyl-substituted lower alkylidene group.
(132) A benzoheterocyclic derivative of the formula [1] or a salt thereof, wherein G, X, $R^1$ and R are the same as defined in above (121), and $R^2$ and $R^3$ bind together to form a phenyl-substituted lower alkylidene group.
(133) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

—CO—⟨ring with $(R^8)_p$ and $R^9$⟩

($R^9$ and p are the same as defined above in the formula [1], and $R^8$ is a nitro group).
(134) A benzoheterocyclic derivative of the formula [1] or a salt thereof, wherein G, X, $R^1$, $R^3$ and R are the same as defined in above (133), and $R^2$ is a hydrogen atom.
(135) A benzoheterocyclic derivative of the formula [1] or a salt thereof, wherein G, X, $R^1$, $R^3$ and R are the same as defined in above (133), and $R^2$ is a hydroxy group.
(136) A benzoheterocyclic derivative of the formula [1] or a salt thereof, wherein G, X, $R^1$, $R^3$ and R are the same as defined in above (133), and $R^2$ is a carboxy-substituted lower alkyl group.
(137) A benzoheterocyclic derivative of the formula [1] or a salt thereof, wherein G, X, $R^1$, $R^3$ and R are the same as defined in above (133), and $R^2$ is a lower alkoxycarbonyl-substituted lower alkyl group.
(138) A benzoheterocyclic derivative of the formula [1] or a salt thereof, wherein G, X, $R^1$, $R^3$ and R are the same as defined in above (133), and $R^2$ is an amino-substituted lower alkanoyloxy group having optionally a lower alkyl substituent.

(139) A benzoheterocyclic derivative of the formula [1] or a salt thereof, wherein G, X, $R^1$, $R^3$ and R are the same as defined in above (133), and $R^2$ is a lower alkanoyl group.

(140) A benzoheterocyclic derivative of the formula [1] or a salt thereof, wherein G, X, $R^1$ and R are the same as defined in above (133), and $R^2$ and $R^3$ bind together to form an oxo group.

(141) A benzoheterocyclic derivative of the formula [1] or a salt thereof, wherein G, X, $R^1$ and R are the same as defined in above (133), and $R^2$ and $R^3$ bind together to form a lower alkylidene group.

(142) A benzoheterocyclic derivative of the formula [1] or a salt thereof, wherein G, X, $R^1$ and R are the same as defined in above (133), and $R^2$ and $R^3$ bind together to form a lower alkoxy-substituted lower alkylidene group.

(143) A benzoheterocyclic derivative of the formula [1] or a salt thereof, wherein G, X, $R^1$ and R are the same as defined in above (133), and $R^2$ and $R^3$ bind together to form a lower alkoxycarbonyl-substituted lower alkylidene group.

(144) A benzoheterocyclic derivative of the formula [1] or a salt thereof, wherein G, X, $R^1$ and R are the same as defined in above (133), and $R^2$ and $R^3$ bind together to form a phenyl-substituted lower alkylidene group.

(145) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

$$-CO-\underset{R^9}{\underset{\|}{\bigcirc}}-(R^8)_p$$

($R^9$ and p are the same as defined above in the formula [1], and $R^8$ is a halogen atom).

(146) A benzoheterocyclic derivative of the formula [1] or a salt thereof, wherein G, X, $R^1$, $R^3$ and R are the same as defined in above (145), and $R^2$ is a hydrogen atom.

(147) A benzoheterocyclic derivative of the formula [1] or a salt thereof, wherein G, X, $R^1$, $R^3$ and R are the same as defined in above (145), and $R^2$ is a hydroxy group.

(148) A benzoheterocyclic derivative of the formula [1] or a salt thereof, wherein G, X, $R^1$, $R^3$ and R are the same as defined in above (145), and $R^2$ is a carboxy-substituted lower alkyl group.

(149) A benzoheterocyclic derivative of the formula [1] or a salt thereof, wherein G, X, $R^1$, $R^3$ and R are the same as defined in above (145), and $R^2$ is a lower alkoxycarbonyl-substituted lower alkyl group.

(150) A benzoheterocyclic derivative of the formula [11 or a salt thereof, wherein G, X, $R^1$, $R^3$ and R are the same as defined in above (145), and $R^2$ is an amino-substituted lower alkanoyloxy group having optionally a lower alkyl substituent.

(151) A benzoheterocyclic derivative of the formula [1] or a salt thereof, wherein G, X, $R^1$, $R^3$ and R are the same as defined in above (145), and $R^2$ is a lower alkanoyl group.

(152) A benzoheterocyclic derivative of the formula [1] or a salt thereof, wherein G, X, $R^1$ and R are the same as defined in above (145), and $R^2$ and $R^3$ bind together to form an oxo group.

(153) A benzoheterocyclic derivative of the formula [1] or a salt thereof, wherein G, X, $R^1$ and R are the same as defined in above (145), and $R^2$ and $R^3$ bind together to form a lower alkylidene group.

(154) A benzoheterocyclic derivative of the formula [1] or a salt thereof, wherein G, X, $R^1$ and R are the same as defined in above (145), and $R^2$ and $R^3$ bind together to form a lower alkoxy-substituted lower alkylidene group.

(155) A benzoheterocyclic derivative of the formula [1] or a salt thereof, wherein G, X, $R^1$ and R are the same as defined in above (145), and $R^2$ and $R^3$ bind together to form a lower alkoxycarbonyl-substituted lower alkylidene group.

(156) A benzoheterocyclic derivative of the formula [1] or a salt thereof, wherein G, X, $R^1$ and R are the same as defined in above (145), and $R^2$ and $R^3$ bind together to form a phenyl-substituted lower alkylidene group.

(157) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a group of the formula:

$$-CO-\underset{R^9}{\underset{\|}{\bigcirc}}-(R^8)_p$$

($R^9$ and p are the same as defined above in the formula [1], and $R^8$ is a lower alkoxy group).

(158) A benzoheterocyclic derivative of the formula [1] or a salt thereof, wherein G, X, $R^1$, $R^3$ and R are the same as defined in above (157), and $R^2$ is a hydrogen atom.

(159) A benzoheterocyclic derivative of the formula [1] or a salt thereof, wherein G, X, $R^1$, $R^3$ and R are the same as defined in above (157), and $R^2$ is a hydroxy group.

(160) A benzoheterocyclic derivative of the formula [1] or a salt thereof, wherein G, X, $R^1$, $R^3$ and R are the same as defined in above (157), and $R^2$ is a carboxy-substituted lower alkyl group.

(161) A benzoheterocyclic derivative of the formula [1] or a salt thereof, wherein G, X, $R^1$, $R^3$ and R are the same as defined in above (157), and $R^2$ is a lower alkoxycarbonyl-substituted lower alkyl group.

(162) A benzoheterocyclic derivative of the formula [1] or a salt thereof, wherein G, X, $R^1$, $R^3$ and R are the same as defined in above (157), and $R^2$ is an amino-substituted lower alkanoyloxy group having optionally a lower alkyl substituent.

(163) A benzoheterocyclic derivative of the formula [1] or a salt thereof, wherein G, X, $R^1$, $R^3$ and R are the same as defined in above (157), and $R^2$ is a lower alkanoyl group.

(164) A benzoheterocyclic derivative of the formula [1] or a salt thereof, wherein G, X, $R^1$ and R are the same as defined in above (157), and $R^2$ and $R^3$ bind together to form an oxo group.

(165) A benzoheterocyclic derivative of the formula [1] or a salt thereof, wherein G, X, $R^1$ and R are the same as defined in above (157), and $R^2$ and $R^3$ bind together to form a lower alkylidene group.

(166) A benzoheterocyclic derivative of the formula [1] or a salt thereof, wherein G, X, $R^1$ and R are the same as defined in above (157), and $R^2$ and $R^3$ bind together to form a lower alkoxy-substituted lower alkylidene group.

(167) A benzoheterocyclic derivative of the formula [1] or a salt thereof, wherein G, X, $R^1$ and R are the same as defined in above (157), and $R^2$ and $R^3$ bind together to form a lower alkoxycarbonyl-substituted lower alkylidene group.

(168) A benzoheterocyclic derivative of the formula [1] or a salt thereof, wherein G, X, $R^1$ and R are the same as defined in above (157), and $R^2$ and $R^3$ bind together to form a phenyl-substituted lower alkylidene group.

(169) A benzoheterocyclic derivative of the formula [1] or a salt thereof, wherein G is a group of the formula: —C($R^2$)($R^3$)—X—, X is a methylene group, $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a 9-oxofluorenyl group.

(170) A benzoheterocyclic derivative of the formula [1] or a salt thereof, wherein G, X, $R^1$, $R^3$ and R are the same as defined in above (169), and $R^2$ is a hydrogen atom.

(171) A benzoheterocyclic derivative of the formula [1] or a salt thereof, wherein G, X, $R^1$, $R^3$ and R are the same as defined in above (169), and $R^2$ is a hydroxy group.

(172) A benzoheterocyclic derivative of the formula [1] or a salt thereof, wherein G, X, $R^1$, $R^3$ and R are the same as defined in above (169), and $R^2$ is a carboxy-substituted lower alkyl group.

(173) A benzoheterocyclic derivative of the formula [1] or a salt thereof, wherein G, X, $R^1$, $R^3$ and R are the same as defined in above (169), and $R^2$ is a lower alkoxycarbonyl-substituted lower alkyl group.

(174) A benzoheterocyclic derivative of the formula [1] or a salt thereof, wherein G, X, $R^1$, $R^3$ and R are the same as defined in above (169), and $R^2$ is an amino-substituted lower alkanoyloxy group having optionally a lower alkyl substituent.

(175) A benzoheterocyclic derivative of the formula [1] or a salt thereof, wherein G, X, $R^1$, $R^3$ and R are the same as defined in above (169), and $R^2$ is a lower alkanoyl group.

(176) A benzoheterocyclic derivative of the formula [1] or a salt thereof, wherein G, X, $R^1$ and R are the same as defined in above (169), and $R^2$ and $R^3$ bind together to form an oxo group.

(177) A benzoheterocyclic derivative of the formula [1] or a salt thereof, wherein G, X, $R^1$ and R are the same as defined in above (169), and $R^2$ and $R^3$ bind together to form a lower alkylidene group.

(178) A benzoheterocyclic derivative of the formula [1] or a salt thereof, wherein G, X, $R^1$ and R are the same as defined in above (169), and $R^2$ and $R^3$ bind together to form a lower alkoxy-substituted lower alkylidene group.

(179) A benzoheterocyclic derivative of the formula [1] or a salt thereof, wherein G, X, $R^1$ and R are the same as defined in above (169), and $R^2$ and $R^3$ bind together to form a lower alkoxycarbonyl-substituted lower alkylidene group.

(180) A benzoheterocyclic derivative of the formula [1] or a salt thereof, wherein G, X, $R^1$ and R are the same as defined in above (169), and $R^2$ and $R^3$ bind together to form a phenyl-substituted lower alkylidene group.

(181) A benzoheterocyclic derivative of the formula [1] or a salt thereof, wherein G is a group of the formula: —C($R^2$)($R^3$)—X—, X is a group of the formula: —$NR^{14}$— ($R^{14}$ is the same as defined above in the formula [1]), $R^1$ is the same as defined above in the formula [1], $R^2$ is a group of the formula: —$NR^4R^5$ ($R^4$ and $R^5$ are the same as defined above in the formula [1]), $R^3$ is a hydrogen atom or a hydroxy-substituted lower alkyl group, and R is a 9-oxofluorenyl group.

(182) A benzoheterocyclic derivative of the formula [1] or a salt thereof, wherein G, X, $R^1$, $R^3$ and R are the same as defined in above (181), and $R^2$ is a hydrogen atom.

(183) A benzoheterocyclic derivative of the formula [1] or a salt thereof, wherein G, X, $R^1$, $R^3$ and R are the same as defined in above (181), and $R^2$ is a hydroxy group.

(184) A benzoheterocyclic derivative of the formula [1] or a salt thereof, wherein G, X, $R^1$, $R^3$ and R are the same as defined in above (181), and $R^2$ is a carboxy-substituted lower alkyl group.

(185) A benzoheterocyclic derivative of the formula [1] or a salt thereof, wherein G, X, $R^1$, $R^3$ and R are the same as defined in above (181), and $R^2$ is a lower alkoxycarbonyl-substituted lower alkyl group.

(186) A benzoheterocyclic derivative of the formula [1] or a salt thereof, wherein G, X, $R^1$, $R^3$ and R are the same as defined in above (181), and $R^2$ is an amino-substituted lower alkanoyloxy group having optionally a lower alkyl substituent.

(187) A benzoheterocyclic derivative of the formula [1] or a salt thereof, wherein G, X, $R^1$, $R^3$ and R are the same as defined in above (181), and $R^2$ is a lower alkanoyl group.

(188) A benzoheterocyclic derivative of the formula [1] or a salt thereof, wherein G, X, $R^1$ and R are the same as defined in above (181), and $R^2$ and $R^3$ bind together to form an oxo group.

(189) A benzoheterocyclic derivative of the formula [1] or a salt thereof, wherein G, X, $R^1$ and R are the same as defined in above (181), and $R^2$ and $R^3$ bind together to form a lower alkylidene group.

(190) A benzoheterocyclic derivative of the formula [1] or a salt thereof, wherein G, X, $R^1$ and R are the same as defined in above (181), and $R^2$ and $R^3$ bind together to form a lower alkoxy-substituted lower alkylidene group.

(191) A benzoheterocyclic derivative of the formula [1] or a salt thereof, wherein G, X, $R^1$ and R are the same as defined in above (181), and $R^2$ and $R^3$ bind together to form a lower alkoxycarbonyl-substituted lower alkylidene group.

(192) A benzoheterocyclic derivative of the formula [1] or a salt thereof, wherein G, X, $R^1$ and R are the same as defined in above (181), and $R^2$ and $R^3$ bind together to form a phenyl-substituted lower alkylidene group Each group in the above formula [1] specifically means the following groups.

The lower alkoxy group includes a straight chain or branched chain alkoxy group having 1 to 6 carbon atoms, for example, methoxy, ethoxy, propoxy, isopropoxy, butoxy, tert-butoxy, pentyloxy, hexyloxy, etc.

The lower alkyl group includes a straight chain or branched chain alkyl group having 1 to 6 carbon atoms, for example, methyl, ethyl, propyl, isopropyl, butyl, iso-butyl, tert-butyl, pentyl, hexyl, etc.

The halogen atom is fluorine atom, chlorine atom, bromine atom or iodine atom.

The lower alkanoyloxy group includes a straight chain or branched chain alkanoyloxy group having 1 to 6 carbon atoms, for example, formyloxy, acetyloxy, propionyloxy, butyryloxy, isobutyryloxy, pentanoyloxy, tert-butylcarbonyloxy, hexanoyloxy, and the like.

The lower alkanoyl group having optionally a halogen substituent includes a straight chain or branched chain alkanoyl group having 1 to 6 carbon atoms which may optionally be substituted by 1 to 3 halogen atoms, for example, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionoyl, 4,4,4-trichlorobutyryl, 4-fluorobutyryl, 5-chloropentanoyl, 3-chloro-2-methylpropionyl, 6-bromohexanoyl, 5,6-dibromohexanoyl, and the like.

The amino-lower alkoxy group having optionally a substituent selected from a lower alkyl group and a lower alkanoyl group includes a straight chain or branched chain alkoxy group having 1 to 6 carbon atoms which is substituted by an amino group being optionally substituted by 1 to 2 groups selected from a straight chain or branched chain alkyl group having 1 to 6 carbon atoms and a straight chain or branched chain alkanoyl group having 1 to 6 carbon atoms, for example, aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, acetylaminomethoxy, 1-acetylaminoethoxy, 2-propionylaminoethoxy, 3-isopropionylaminopropoxy, 4-butyrylaminobutoxy, 5-pentanoylaminopentyloxy, 6-hexanoylaminohexyloxy, formylaminomethoxy, methylaminomethoxy, 1-ethylaminoethoxy, 2-propylaminoethoxy, 3-isopropylaminoproxy, 4-butylaminobutoxy, 5-pentylaminopentyloxy, 6-hexylaminohexyloxy, dimethylaminomethoxy, (N-ethyl-N-propylamino)methoxy, 2-(N-methyl-N-hexylamino) ethoxy, and the like.

The amino group having optionally a lower alkyl substituent includes an amino group which may optionally be substituted by 1 to 2 straight chain or branched chain alkyl groups having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and the like.

The lower alkoxycarbonyl-substituted lower alkoxy group includes a straight chain or branched chain alkoxy group having 1 to 6 carbon atoms which is substituted by a straight chain or branched chain alkoxycarbonyl group having 1 to 6 carbon atoms in the alkoxy moiety, for example, methoxycarbonylmethoxy, 3-methoxycarbonylpropoxy, ethoxycarbonylmethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, hexyloxycarbonylmethoxy, and the like.

The carboxy-substituted lower alkoxy group includes a carboxyalkoxy group wherein the alkoxy moiety is a straight chain or branched chain alkoxy group having 1 to 6 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, and the like.

The aminocarbonyl-lower alkoxy group having a lower alkyl substituent includes a straight chain or branched chain alkoxy group having 1 to 6 carbon atoms which is substituted by an aminocarbonyl group having 1 to 2 straight chain or branched chain alkyl groups having 1 to 6 carbon atoms, for example, methylaminocarbonylmethoxy, 1-ethylaminocarbonylethoxy, 2-propylaminocarbonylethoxy, 3-isopropylaminocarbonylpropoxy, 4-butylaminocarbonylbutoxy, 5-pentylaminocarbonylpentyloxy, 6-hexylaminocarbonylhexyloxy, dimethylaminocarbonylmethoxy, 3-diethylaminocarbonylpropoxy, diethylaminocarbonylmethoxy, (N-ethyl-N-propylamino)carbonylmethoxy, 2-(N-methyl-N-hexylamino)carbonylethoxy, and the like.

The benzoyl group having optionally a halogen substituent on the phenyl ring includes a benzoyl group having optionally 1 to 3 halogen substituents on the phenyl ring, for example, benzoyl, 2-chlorobenzoyl, 3-chlorobenzoyl, 4-chlorobenzoyl, 2-fluorobenzoyl, 3-fluorobenzoyl, 4-fluorobenzoyl, 2-bromobenzoyl, 3-bromobenzoyl, 4-bromobenzoyl, 2-iodobenzoyl, 3-iodobenzoyl, 4-iodobenzoyl, 3,4-dichlorobenzoyl, 2,6-dichlorobenzoyl, 2,3-dichlorobenzoyl, 2,4-dichlorobenzoyl, 3,4-difluorobenzoyl, 3,5-dibromobenzoyl, 3,4,5-trichlorobenzoyl, and the like.

The carboxy-substituted lower alkyl group includes a carboxylalkyl group wherein the alkyl moiety is a straight chain or branched chain alkyl group having 1 to 6 carbon atoms, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxylpropyl, and the like.

The lower alkoxycarbonyl-substituted lower alkyl group includes a straight chain or branched chain alkyl group having 1 to 6 carbon atoms which is substituted by a straight chain or branched chain alkoxycarbonyl group having 1 to 6 carbon atoms in the alkoxy moiety, for example, methoxycarbonylmethyl, 3-methoxycarbonypropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

The amino-substituted lower alkanoyloxy group having optionally a lower alkyl substituent includes a straight chain or branched chain alkanoyloxy group having 2 to 6 carbon atoms which is substituted by an amino group having optionally 1 to 2 straight chain or branched chain alkyl groups having 1 to 6 carbon atoms, for example, 2-aminoacetyloxy, 3-aminopropionyloxy, 2-aminopropionyloxy, 4-aminobutyryloxy, 2,2-dimethyl-3-aminopropionyloxy, 5-aminopentanoyloxy, 6-aminohexanoyloxy, 2-methyl-3-aminopropionyloxy, 2-methylaminoacetyloxy, 3-ethylaminopropionyloxy, 2-propylaminopropionyloxy, 4-isopropylaminobutyryloxy, 4-butylaminobutyryloxy, 4-tert-butyaminobutyryloxy, 5-pentylaminopentanoyloxy, 6-hexylaminohexanoyloxyl, 2-dimethylaminoacetyloxy, 3-diethylaminopropionyloxy, 2-dimethylaminopropionyloxy, 2-(N-ethyl-N-propylamino)acetyloxy, 3-(N-methyl-N-hexylamino)propionyloxy, and the like.

The lower alkanoyl group includes a straight chain or branched chain alkanoyl group having 1 to 6 carbon atoms, for example, formyl, acetyl, propionyl, butyryl, isobutyryl, pentanoyl, t-butylcarbonyl, hexanoyl, and the like.

The lower alkylidene group includes a straight chain or branched chain alkylidene group having 1 to 6 carbon atoms, for example, methylidene, ethylidene, propylidene, isopropylidene, butylidene, pentylidene, hexylidene, and the like.

The lower alkoxycarbonyl-substituted lower alkylidene group includes a straight chain or branched chain alkylidene group having 1 to 6 carbon atoms which is substituted by a straight chain or branched chain alkoxycarbonyl group having 1 to 6 carbon atoms in the alkoxy moiety, for example, ethoxycarbonylmethylidene, 2-methoxycarbonylethylidene, 3-isopropoxycarbonylpropylidene, 2-propoxycarbonylisopropylidene, 4-butoxycarbonylbutylidene, 5-pentyloxycarbonylpentylidene, 6-hexyloxycarbonylhexylidene, and the like.

The lower alkoxy-substituted lower alkylidene group includes a straight chain or branched chain alkylidene group having 1 to 6 carbon atoms which is substituted by a straight chain or branched chain alkoxy group having 1 to 6 carbon atoms, for example, methoxymethylidene, 2-ethoxyethylidene, 3-propoxypropylidene, 2-isopropoxyisopropylidene, 4-butoxybutylidene, 5-pentyloxypentylidene, 6-hexyloxyhexylidene, and the like.

The phenyl-substituted lower alkylidene group includes a straight chain or branched chain alkylidene having 1 to 6 carbon atoms which is substituted by a phenyl group, for example, phenylmethylidene, 2-phenylethylidene, 3-phenylpropylidene, 2-phenylpropylidene, 4-phenylbutylidene, 5-phenylpentylidene, 6-phenylhexylidene, and the like.

The lower alkylene group includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, etc.

The amino-substituted lower alkyl group having optionally a lower alkyl substituent includes a straight chain or branched chain alkyl group having 1 to 6 carbon atoms which is substituted by an amino group having optionally 1 to 2 straight chain or branched chain alkyl substituents having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-dimethylaminoethyl, (N-ethyl-N-propylamino)methyl, 2-(N-methyl-N-hexylamino)ethyl, and the like.

The 5- to 7-membered saturated heterocyclic group which is formed by binding $R^6$ and $R^7$ or $R^B$ and $R^C$ together with the adjacent nitrogen atom to which they bond with or without being intervening with another nitrogen atom or an oxygen atom, for example, pyrrolidinyl, piperidinyl, piperazinyl, morpholino, homopiperazinyl, and the like.

The above heterocyclic group having a substituent selected from a lower alkyl group and a phenyl-lower alkyl group includes the above mentioned heterocyclic groups having 1 to 3 sustituents selected from a straight chain or branched chain alkyl group having 1 to 6 carbon atoms, and a straight chain or branched chain alkyl group having 1 to 6 carbon atoms which is substituted by 1 to 2 phenyl groups, for example, 4-methylpiperazinyl, 3,4-dimethylpiperazinyl, 3-ethylpyrrolidinyl, 2-propylpyrrolidinyl, 1-methylpyrrolidinyl, 3,4,5-trimethylpiperidinyl, 4-butylpiperidinyl, 3-pentylmorpholino, 4-ethylhomopiperazinyl, 4-methylhomopiperazinyl, 4-hexylpiperazinyl, 4-diphenylmethylpiperazinyl, 4-benzylpiperazinyl, 3-methyl-4-benzylpiperazinyl, 3-(2-phenylethyl)pyrrolidinyl, 2-(1-phenylethyl)pyrrolidinyl, 4-(3-phenylpropyl)piperidinyl, 3-(4-phenylbutyl)morpholino, 3-(5-phenylpentyl)piperidinyl, 4-(6-phenylhexyl)piperazinyl, and the like.

The above heterocyclic group substituted by a lower alkyl group includes the above mentioned heterocyclic groups being substituted by 1 to 3 straight chain or branched chain alkyl groups having 1 to 6 carbon atoms, for example, 4-methylpiperazinyl, 3,4-dimethylpiperazinyl, 3-ethylpyrrolidinyl, 2-propylpyrrolidinyl, 1-methylpyrrolidinyl, 3,4,5-trimethylpiperidinyl, 4-butylpiperidinyl, 3-pentylmorpholino, 4-methylhomopiperazinyl, 4-hexylpiperazinyl, and the like.

The phenyl group having optionally a lower alkyl substituent includes a phenyl group which may optionally have 1 to 3 straight chain or branched chain alkyl substituents having 1 to 6 carbon atoms, for example, phenyl, 2-methylphenyl, 3-methylphenyl, 4-methylphenyl, 2-ethylphenyl, 3-propylphenyl, 4-butylphenyl, 2-pentylphenyl, 3-hexylphenyl, 3,4-dimethylphenyl, 3,4,5-trimethylphenyl, and the like.

The phenyl group having optionally a lower alkoxy substituent includes a phenyl group which may optionally have 1 to 3 straight chain or branched chain alkoxy substituents having 1 to 6 carbon atoms, for example, phenyl, 2-methoxyphenyl, 3-methoxyphenyl, 4-methoxyphenyl, 2-ethoxyphenyl, 3-propoxyphenyl, 4-butoxyphenyl, 2-pentyloxyphenyl, 3-hexyloxyphenyl, 2,4-dimethoxyphenyl, 3,4-diethoxyphenyl, 3,4,5-trimethoxyphenyl, and the like.

The pyridylcarbonyl group having optionally a substituent selected from a phenyl group having optionally a lower alkyl substituent and a pyridyl group on the pyridine ring includes a pyridylcarbonyl group having optionally a substituent selected from a phenyl group having optionally 1 to 3 straight chain or branched chain alkyl substituents having 1 to 6 carbon atoms and a pyridyl group on the pyridine ring, for example, pyridylcarbonyl, 2-phenylpyridylcarbonyl, 3-phenylpyridylcarbonyl, 4-phenylpyridylcarbonyl, 2-(2-methylphenyl)pyridylcarbonyl, 3-(2-ethylphenyl)pyridylcarbonyl, 4-(3-propylphenyl)pyridylcarbonyl, 2-(4-butylphenyl)pyridylcarbonyl, 3-(2-pentylphenyl)pyridylcarbonyl, 4-(3-hexylphenyl)pyridylcarbonyl, 2-(3,4-dimethylphenyl)pyridylcarbonyl, 3-(3,4,5-trimethylphenyl)pyridylcarbonyl, 3-(2-pyridyl)pyridylcarbonyl, 2-(3-pyridyl)pyridylcarbonyl, 4-(4-pyridyl)pyridylcarbonyl, and the like.

The phenyl-lower alkyl group having optionally a substituent selected from a lower alkyl group and a halogen atom on the phenyl ring, and having optionally a hydroxy substituent on the alkyl moiety includes a phenylalkyl group wherein the alkyl moiety is a straight chain or branched chain alkyl group having 1 to 6 carbon atoms, and said alkyl moiety having optionally a hydroxy substituent, and the phenyl ring may optionally have 1 to 3 substituents selected from a straight chain or branched chain alkyl group having 1 to 6 carbon atoms and a halogen atom, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 2-fluorobenzyl, 1-(4-chlorophenyl) ethyl, 3-(2-fluorophenyl)propyl, 4-(3-fluorophenyl)butyl, 5-(4-fluorophenyl)pentyl, 1,1-dimethyl-2-(2-bromophenyl) ethyl, 6-(3-bromophenyl)hexyl, 4-bromobenzyl, 2-(2-iodophenyl)ethyl, 1-(3-iodophenyl)ethyl, 3-(4-iodophenyl) propyl, 3,4-dichlorobenzyl, 3,5-dichlorobenzyl, 2,6-dichlorobenzyl, 2,3-dichlorobenzyl, 2,4-dichlorobenzyl, 3,4-difluorobenzyl, 3,5-dibromobenzyl, 3,4,5-trichlorobenzyl, 3,5-dichloro-4-hydroxybenzyl, 3,5-dimethyl-4-hydroxybenzyl, 2-methoxy-3-chlorobenzyl, 2-methylbenzyl, 2-(2-methylphenyl)ethyl, 1-(3- methylphenyl)ethyl, 3-(4-methylphenyl)propyl, 4-(2-ethylphenyl)butyl, 5-(3-propylphenyl)pentyl, 6-(4-butylphenyl)hexyl, 2-(2-pentylphenyl)ethyl, 1-(3-hexylphenyl)ethyl, 3-(3,4-dimethylphenyl)propyl, 2-(3,4,5-trimethylphenyl)ethyl, (2-methyl-6-chlorophenyl)methyl, 3-phenyl-2-hydroxypropyl, 2-phenyl-2-hydroxyethyl, 1-phenyl-1-hydroxymethyl, 3-(4-methylphenyl)-3-hydroxypropyl, 4-(3-chlorophenyl)-4-hydroxybutyl, 5-(2-bromophenyl)-5-hydroxypentyl, 6-(4-fluorophenyl)-6-hydroxyhexyl, and the like.

The phenoxy-lower alkyl group having optionally a lower alkyl substituent on the phenyl ring includes a straight chain or branched chain alkyl group having 1 to 6 carbon atoms which is substituted by a phenoxy group having optionally 1 to 3 straight chain or branched chain alkyl substituents having 1 to 6 carbon atoms on the phenyl ring, for example, phenoxymethyl, 2-phenoxyethyl, 1-phenoxyethyl, 4-phenoxybutyl, 5-phenoxypentyl, 6-phenoxyhexyl, 1,1-dimethyl-2-phenoxyethyl, 2-methyl-3-phenoxypropyl, (2-methylphenoxy)methyl, 2-(2-methylphenoxy)ethyl, 3-phenoxypropyl, 4-(3-methylphenoxy)butyl, 5-(2-ethylphenoxy)pentyl, 6-(3-propylphenoxy)hexyl, 4-(butylphenoxy)methyl, 2-(2-pentylphenoxy)ethyl, 1-(3-hexylphenoxy)ethyl, 3-(3,4 -dimethylphenoxy)propyl, 2-(3,4,5-trimethylphenoxy)ethyl, and the like.

The phenoxy-lower alkanoyl group having optionally a substituent selected from a lower alkyl group, a phenyl group, a lower alkoxy group, a halogen-substituted lower alkyl group, an amino group having optionally a lower alkyl substituent, a nitro group, a lower alkanoyl-substituted amino group and a halogen atom on the phenyl ring, and having optionally a halogen substituent on the alkanoyl moiety includes a phenoxyalkanoyl group which may optionally have 1 to 3 substituents selected from a straight chain or branched chain alkyl group having 1 to 6 carbon atoms, a phenyl group, a straight chain or branched chain alkoxy group having 1 to 6 carbon atoms, a straight chain or branched chain alkyl group having 1 to 6 carbon atoms being substituted by 1 to 3 halogen atoms, an amino group having optionally 1 to 2 straight chain or branched chain alkyl substituents having 1 to 6 carbon atoms, a nitro group, an amino group substituted by a straight chain or branched chain alkanoyl group having 1 to 6 carbon atoms and a halogen atom on the phenyl ring, and the alkanoyl moiety is a straight chain or branched chain alkanoyl group having 2 to 6 carbon atoms which may optionally have 1 to 3 halogen substituents, for example, 2-phenoxyacetyl, 2-phenoxypropionyl, 3-phenoxypropionyl, 2-phenoxybutyryl, 4-phenoxybutyryl, 2,2-dimethyl-3-phenoxypropionyl, 5-phenoxypentanoyl, 6-phenoxyhexanoyl, 2-(2-chlorophenoxy)acetyl, 2-(3-chlorophenoxy)acetyl, 2-(4-chlorophenoxy)acetyl, 2-(2-fluorophenoxy)acetyl, 2-(3-fluorophenoxy)acetyl, 3-(4-fluorophenoxy)propionyl, 2-(2-bromophenoxy)propionyl, 4-(3-bromophenoxy)butyryl, 5-(4-bromophenoxy)pentanoyl, 6-(2-iodophenoxy)hexanoyl, 2-(3-iodophenoxy)acetyl, 3-(4-iodophenoxy)propionyl, 4-(3,4-dichlorophenoxy)butyryl, 2-(3,4-dichlorophenoxy)acetyl, 2-(2,6-dichlorophenoxy)acetyl, 2-(2,3-dichlorophenoxy)acetyl, 2-(2,4-dichlorophenoxy)acetyl, 2-(3,4-difluorophenoxy)acetyl, 3-(3,5-dibromophenoxy)propionoyl, 2-(3,4,5-trichlorophenoxy)acetyl, 2-(2-methylphenoxy)acetyl, 2-(3-methylphenoxy)acetyl, 2-(4-methylphenoxy)acetyl, 3-(2-ethylphenoxy)propionyl, 2-(3-ethylphenoxy)propionyl, 4-(4-ethylphenoxy)butyryl, 5-(4-isopropylphenoxy)pentanoyl, 6-(3-butylphenoxy)hexanoyl, 3-(4-pentylphenoxy)propionyl, 2-(4-hexylphenoxy)acetyl, 2-(3,4-dimethylphenoxy)acetyl, 2-(3,4-diethylphenoxy)acetyl, 2-(2,4-dimethylphenoxy)acetyl, 2-(2,5-dimethylphenoxy)acetyl, 2-(2,6-dimethylphenoxy)acetyl, 2-(3,4,5-trimethylphenoxy)acetyl, 2-(3-chloro-4-methylphenoxy)acetyl, 2-(3-dimethylaminophenoxy)acetyl, 2-(3-nitrophenoxy)acetyl, 2-(2-methoxyphenoxy)acetyl, 2-(3-methoxyphenoxy)acetyl, 2-(4-methoxyphenoxy)acetyl, 2-(2-phenylphenoxy)acetyl, 2-(2-trifluoromethylphenoxy)acetyl, 3-(2-aminophenoxy)propionyl, 4-(4-ethylaminophenoxy)butyryl, 5-(2,3-dimethoxyphenoxy)pentanoyl, 6-(2,4,6-trimethoxyphenoxy)hexanoyl, 3-(2-ethoxyphenoxy)propionyl, 4-(3-propoxyphenoxy)propionyl, 2-(4-butoxyphenoxy)acetyl, 3-(4-pentyloxyphenoxy)propionyl, 4-(4-hexyloxyphenoxy)butyryl, 3-(2-nitrophenoxy)propionyl, 4-(4-nitrophenoxy)butyryl, 3-(3-phenylphenoxy)propionyl, 4-(4-phenylphenoxy)butyryl, 5-[3-(2,2,2-trichloroethyl)phenoxy]pentanoyl, 6-[4-(5-bromohexyl)phenoxy]hexanoyl, 2-(4-phenyl-2-methoxyphenoxy)acetyl, 2-(2-phenyl-4-methylphenoxy)acetyl, 2-(2,4,6-trinitrophenoxy)acetyl, 2-(2,4-dinitrophenoxy)acetyl, 2-(3-phenyl-2-dimethylaminophenoxy)acetyl, 2-phenoxy-2,2-difluoroacetyl, 3-(3-dimethylaminophenoxy)-3-bromopropionyl, 4-(3-nitrophenoxy)-3,4,4-trichlorobutyryl, 5-(2-methoxyphenoxy)-5-iodopentanoyl, 2-(2,6-dichlorophenoxy)-2-chloroacetyl, 2-(4-methylphenoxy)-2,2,-difluoroacetyl, 2-(2-phenylphenoxy)-2,2-difluoroacetyl, 6-(2-phenylphenoxy)-6-bromohexanoyl, 2-(2-acetylaminophenoxy)acetyl, and the like.

The aminocarbonyl group having optionally a substituent selected from a lower alkyl group, a pyridyl-lower alkyl group and a phenyl-lower alkyl group includes an aminocarbonyl group which may optionally have 1 to 2 substituents selected from a straight chain or branched chain alkyl group having 1 to 6 carbon atoms, a pyridyl-alkyl group wherein the alkyl moiety is a straight chain or branched chain alkyl group having 1 to 6 carbon atoms and a phenylalkyl group wherein the alkyl moiety is a straight chain or branched chain alkyl group having 1 to 6 carbon atoms, for example, aminocarbonyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl, N-ethyl-N-(pyridylmethyl)aminocarbonyl, N-ethyl-N-benzylaminocarbonyl, benzylaminocarbonyl, (2-phenylethyl)aminocarbonyl, (1-phenylethyl)aminocarbonyl, (3-phenylpropyl)aminocarbonyl, (4-phenybutyl)aminocarbonyl, (5-phenylpentyl)aminocarbonyl, (6-phenylhexyl)aminocarbonyl, N-methyl-N-benzylaminocarbonyl, pyridylmethylaminocarbonyl, (2-pyridylethyl)aminocarbonyl, (3-pyridylpropyl)aminocarbonyl, (4-pyridylbutyl)aminocarbonyl, (5-pyridylpentyl)aminocarbonyl, (6-pyridylhexyl)aminocarbonyl, N-(pyridylmethyl)-N-benzylaminocarbonyl, N-methyl-N-(pyridylmethyl)aminocarbonyl, and the like.

The benzoyl group having optionally a lower alkyl substituent on the phenyl ring includes a benzoyl group having optionally 1 to 3 straight chain or branched chain alkyl substituents having 1 to 6 carbon atoms on the phenyl ring, for example, benzoyl, 2-methylbenzoyl, 3-methylbenzoyl, 4-methylbenzoyl, 2-ethylbenzoyl, 3-propylbenzoyl, 4-butylbenzoyl, 2-pentylbenzoyl, 3-hexylbenzoyl, 3,4-dimethylbenzoyl, 3,4,5-trimethylbenzoyl, and the like.

The cycloalkyl group includes a cycloalkyl group having 3 to 8 carbon atoms, for example, cyclopropyl, cyclobutyl, cyclopentyl, cyclohexyl, cycloheptyl, cyclooctyl, and the like.

The lower alkylthio group includes a straight chain or branched chain alkylthio group having 1 to 6 carbon atoms, for example, methylthio, ethylthio, propylthio, isopropylthio, butylthio, tert-butylthio, pentylthio, hexylthio, and the like.

The phenyl-lower alkanoyl group having optionally a lower alkyl substituent on the phenyl ring includes a phenylalkanoyl group wherein the alkanoyl moiety is a straight chain or branched chain alkanoyl group having 2 to 6 carbon atoms, which may optionally have 1 to 3 straight chain or branched chain alkyl substituents having 1 to 6 carbon atoms on the phenyl ring, for example, 2-phenylacetyl, 3-phenylpropionyl, 4-phenylbutyryl, 2,2-dimethyl-3-phenylpropionyl, 5-phenylpentanoyl, 6-phenylhexanoyl, 2-(2-methylphenyl)acetyl, 2-(3-methylphenyl)acetyl, 2-(4-methylphenyl)acetyl, 3-(2-ethylphenyl)propionyl, 2-(3-ethylphenyl)propionyl, 4-(4-ethylphenyl)butyryl, 5-(4-isopropylphenyl)pentanoyl, 6-(3-butylphenyl)hexanoyl, 3-(4-pentylphenyl)propionyl, 2-(4-hexylphenyl)acetyl, 2-(3,4-dimethylphenyl)acetyl, 2-(3,4-diethylphenyl)acetyl, 2-(2,4-dimethylphenyl)acetyl, 2-(2,5-dimethylphenyl)acetyl, 2-(2,6-dimethylphenyl)acetyl, 2-(3,4,5-trimethylphenyl)acetyl, and the like.

The halogen-substituted lower alkoxy group includes a straight chain or branched chain alkoxy group having 1 to 6 carbon atoms which is substituted by 1 to 3 halogen atoms, for example, trifluoromethoxy, trichloromethoxy, chloromethoxy, bromomethoxy, fluoromethoxy, iodomethoxy, difluoromethoxy, dibromomethoxyl, 2-chloroethoxy, 2,2,2-trifluoroethoxy, 2,2,2-trichloroethoxy, 3-bromopropoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, and the like.

The amino-substituted lower alkoxy group having optionally a lower alkyl substituent includes a straight chain or branched chain alkoxy group having 1 to 6 carbon atoms which is substituted by an amino group having optionally 1 to 2 straight chain or branched chain alkyl substituents having 1 to 6 carbon atoms, for example, aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-isopropylaminobutoxy, 4-butylaminobutoxy, 4-tert-butylaminobutoxy, 5-pentylaminopentyloxy, 6-hexylaminohexyloxy, dimethylaminomethoxy, 2-diethylaminoethoxy, 2-dimethylaminoethoxy, (N-ethyl-N-propylamino)methoxy, 2-(N-methyl-N-hexylamino)ethoxy, and the like.

The phenyl group having optionally a substituent selected from a lower alkyl group, a lower alkoxy group, a phenyl-lower alkoxy group, a hydroxy group, a lower alkanoyloxy group, a halogen-susbstituted lower alkoxy group, a nitro group, an amino group having optionally a lower alkanoyl substituent, a phenyl group and an amino-substituted lower alkoxy group having optionally a lower alkyl substituent includes a phenyl group which may optionally have 1 to 3 substituents selected from a straight chain or branched chain alkyl group having 1 to 6 carbon atoms, a straight chain or branched chain alkoxy group having 1 to 6 carbon atoms, a hydroxy group, a straight chain or branched chain alkanoyloxy group having 1 to 6 carbon atoms, a straight chain or branched chain alkoxy group having 1 to 6 carbon atoms which is substituted by 1 to 3 halogen atoms, a nitro group, an amino group having optionally a straight chain or branched chain alkanoyl group having 1 to 6 carbon atoms, a phenyl group, and a straight chain or branched chain alkoxy group having 1 to 6 carbon atoms which is substituted by an amino group having optionally 1 to 2 straight chain or branched chain alkyl substituents having 1 to 6 carbon atoms, for example, phenyl, 2-methylphenyl, 3-methylphenyl, 4-methylphenyl, 2-ethylphenyl, 3-propylphenyl, 4-butylphenyl, 2-pentylphenyl, 3-hexylphenyl, 3,4-dimethylphenyl, 3,4,5-trimethylphenyl, 2-methoxyphenyl, 3-methoxyphenyl, 4-methoxyphenyl, 2-ethoxyphenyl, 4-ethoxyphenyl, 3-propoxyphenyl, 4-propoxyphenyl, 4-butoxyphenyl, 2-pentyloxyphenyl, 3-hexyloxyphenyl, 2,4-dimethoxyphenyl, 3,4-diethoxyphenyl, 3,4,5-trimethoxyphenyl, 2-hydroxyphenyl, 3-hydroxyphenyl, 4-hydroxyphenyl, 2,4-dihydroxyphenyl, 3,4-dihydroxyphenyl, 2,4,6-trihydroxyphenyl, 2-acetyloxyphenyl, 3-propionyloxyphenyl, 2-benzyloxyphenyl, 3-benzyloxyphenyl, 4-benzyloxyphenyl, 2-(2-phenylethoxy)phenyl, 3-(3-phenylpropoxy)phenyl, 4-(4-phenylbutoxy)phenyl, 3-(1-phenylethoxy)phenyl, 2-(5-phenylpentyloxy)phenyl, 3-(6-phenylhexyloxy)phenyl, 2,4-dibenzyloxyphenyl, 3,4-dibenzyloxyphenyl, 3,4,5-tribenzyloxyphenyl, 4-butyryloxyphenyl, 2-pentanoyloxyphenyl, 4-hexanoyloxyphenyl, 2,4-diacetyloxyphenyl, 2,6-diacetyloxyphenyl, 3,4,5-triacetyloxyphenyl, 2-trifluoromethoxyphenyl, 3-(2-chloroethoxy)phenyl, 2-(3-bromopropoxy)phenyl, 4-iodomethoxyphenyl, 2-(2,3-dichloropropoxy)phenyl, 3-(4-fluorobutoxy)phenyl, 4-(3-chloro-2-methylpropoxy)phenyl, 2-(5-bromohexyloxy)phenyl, 3-(5,6-dichlorohexyloxy)phenyl, 4-(2,2,2-trichloroethoxy)phenyl, 2,4-bistrifluoromethoxyphenyl, 2,4,6-tri(trifluoromethoxy)phenyl, 2-aminomethoxyphenyl, 3-(1-aminoethoxy)phenyl, 4-(3-aminopropoxy)phenyl, 2-(4-aminobutoxy)phenyl, 3-(5-aminopentyloxy)phenyl, 4-(6-aminohexyloxy)phenyl, 2-methylaminomethoxyphenyl, 3-(2-propylaminoethoxy) phenyl, 2-(3-isopropylaminopropoxy)phenyl, 4-(4-butylaminobutoxy)phenyl, 2-(5-pentylaminopentyloxy) phenyl, 3-(6-hexylaminohexyloxy)phenyl, 4-dimethylaminomethoxyphenyl, 2-(N-ethyl-N-propylaminomethoxy)phenyl, 2-methyl-4-methoxyphenyl, 2-methyl-6-hydroxyphenyl, 4-methyl-2-(3-bromopropoxy) phenyl, 4-methoxy-2-(3-isopropylaminopropoxy)phenyl, 2-phenylphenyl, 3-phenylphenyl, 4-phenylphenyl, 2-nitrophenyl, 3-nitrophenyl, 4-nitrophenyl, 2,3-dinitrophenyl, 2,4,6-trinitrophenyl, 2-aminophenyl, 3-aminophenyl, 4-aminophenyl, 2,4-diaminophenyl, 3,4,5-triaminophenyl, 4-acetylaminophenyl, 2-propionylaminophenyl, 3-butyrylaminophenyl, 4-pentanoylaminophenyl, 4-hexanoylaminophenyl, 2,3-diacetylaminophenyl, 2,4,6-triacetylaminophenyl, and the like.

The anilino-lower alkyl group having optionally a lower alkyl substituent on the phenyl ring includes an anilino-alkyl group wherein the alkyl moiety is a straight chain or branched chain alkyl group having 1 to 6 carbon atoms, which may optionally have 1 to 3 straight chain or branched chain alkyl substituents having 1 to 6 carbon atoms on the phenyl ring, for example, anilinomethyl, 2-anilinoethyl, 1-anilinoethyl, 3-anilinopropyl, 4-anilinobutyl, 1,1- dimethyl-2-anilinoethyl, 5-anilinopentyl, 6-anilinohexyl, 2-methyl-3-anilinopropyl, (2-methylanilino)methyl, 2-(2-methylanilino)ethyl, 1-(3-methylanilino)ethyl, 3-(4-methylanilino)propyl, 4-(2-ethylanilino)butyl, 5-(3-propylanilino)pentyl, 6-(4-butylanilino)hexyl, 2-(2-pentylanilino)ethyl, 1-(3-hexylanilino)ethyl, 3-(3,4-dimethylanilino)propyl, 2-(3,4,5-trimethylanilino)ethyl, and the like.

The phenyl-lower alkoxy group having optionally a substituent selected from a halogen atom, a lower alkoxycarbonyl group and an aminocarbonyl group having optionally a substituent selected from a lower alkyl group and an amino-lower alkyl group having optionally a lower alkyl substituent on the phenyl ring includes a phenylalkoxy group wherein the alkoxy moiety is a straight chain or branched chain alkoxy group having 1 to 6 carbon atoms, which may optionally have 1 to 3 substituents selected from a halogen atom, a straight chain or branched chain alkoxycarbonyl group having 1 to 6 carbon atoms in the alkoxy moiety, and an aminocarbonyl group having optionally 1 to 2 substituents selected from a straight chain or branched chain alkyl group having 1 to 6 carbon atoms and a straight chain or branched chain alkyl group having 1 to 6 carbon atoms which is substituted by an amino group having optionally 1 to 2 straight chain or branched chain alkyl substituents having 1 to 6 carbon atoms on the phenyl ring, for example, phenylmethoxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, (2-chlorophenyl)methoxy, (2-bromophenyl)methoxy, 2-(4-fluorophenyl)ethoxy, 1-(4-bromophenyl)ethoxy, 3-(3-bromophenyl)propoxy, 4-(4 -chlorophenyl)butoxy, 5-(2-iodophenyl)pentyloxy, 6-(3-iodophenyl)hexyloxy, (2,6-dichlorophenyl)methoxy, (2,3-dichlorophenyl)methoxy, (2,4-dichlorophenyl)methoxy, (3,4-difluorophenyl)methoxy, (3,4,5-trichlorophenyl)methoxy, (2-methoxycarbonylphenyl)methoxy, (3-ethoxycarbonylphenyl)methoxy, 2-(4-isopropoxycarbonylphenyl)ethoxy, 3-(2-butoxycarbonylphenyl)propoxy, 4-(3-pentyloxycarbonylphenyl)butoxy, 5-(4-hexyloxycarbonylphenyl)pentyloxy, 6-(2-methoxycarbonylphenyl)hexyloxy, (2,4-dimethoxycarbonylphenyl)methoxy, (2,4,6-triethoxycarbonylphenyl)methoxy, (2-carbamoylphenyl)methoxy, 2-(3-methylaminocarbonylphenyl)ethoxy, 1-(4-ethylaminocarbonylphenyl)ethoxy, 3-(2-isopropylaminocarbonylphenyl)propoxy, 4-(3-butylaminocarbonylphenyl)butoxy, 5-(4-pentylaminocarbonylphenyl)pentyloxy, 6-(2-hexylaminocarbonylphenyl)hexyloxy, (2-dimethylaminocarbonylphenyl)methoxy, 2-(3-dibutylaminocarbonylphenyl)ethoxy, 1-(4-dihexylaminocarbonylphenyl)ethoxy, 3-[2-(N-ethyl-N-propylaminocarbonyl)phenyl]propoxy, (2-aminomethylaminocarbonylphenyl)methoxy, 2-[3-(2-aminoethylaminocarbonyl)phenyl]ethoxy, 3-[4-(3-aminopropylaminocarbonyl)phenyl]propoxy, 4-[2-(4-aminobutylaminocarbonyl)phenyl]butoxy, 5-[3-(5-aminopentylaminocarbonyl)phenyl]pentyloxy, 6-[4-(6-aminohexylaminocarbonyl)phenyl]hexyloxy, [2-(N-methyl-N-methylaminomethyl)aminocarbonylphenyl]methoxy, 2-[3-(3-isopropylaminopropylaminocarbonyl)phenyl]ethoxy, 3-{4-[N-propyl-N-(5-pentylaminopentyl)aminocarbonyl]-phenyl}propoxy, {2-[N-methyl-N-(2-diethylaminoethyl)aminocarbonyl]phenyl}-methoxy, (2-[N,N-bis(diethylaminoethyl)aminocarbonyl]phenyl]methoxy, 4-[3-(N-ethyl-N-propylamino)methylaminocarbonylphenyl]butoxy, 5-[4-{N-[2-(N-methyl-N-hexylamino)ethyl]-N-ethylaminocarbonyl}phenyl]pentyloxy, 6-{4-chloro-2-[N-butyl-N-(6-hexylaminohexyl)aminocarbonyl]phenyl}hexyloxy, [2-bromo-4-(N-hexyl-N-dimethylaminomethyl)aminocarbonylphenyl]methoxy, (2-methoxycarbonyl-3-chlorophenyl)methoxy, and the like.

The benzoyl-lower alkoxy group having optionally a halogen substituent on the phenyl ring includes a benzoylalkoxy group wherein the alkoxy moiety is a straight chain or branched chain alkoxy group having 1 to 6 carbon atoms, which may optionally have 1 to 3 halogen substituents on the phenyl ring, for example, benzoylmethoxy, 2-benzoylethoxy, 1-benzoylethoxy, 3-benzoylpropoxy, 4-benzoylbutoxy, 5-benzoylhexyloxy, 6-benzoylhexyloxy, 1,1-dimethyl-2-benzoylethoxy, 2-methyl-3-benzoylpropoxy, 2-(2-chlorobenzoyl)ethoxy, 1-(3-chlorobenzoyl)ethoxy, (4-chlorobenzoyl)methoxy, 3-(2-fluorobenzoyl)propoxy, 4-(3-fluorobenzoyl)butoxy, 5-(4-fluorobenzoyl)pentyloxy, 6-(2-bromobenzoyl)hexyloxy, 1,1-dimethyl-2-(3-bromobenzoyl)ethoxy, 2-methyl-3-(4-bromobenzoyl)propoxy, (2-iodobenzoyl)methoxy, 2-(3-iodobenzoyl)ethoxy, 3-(4-iodobenzoyl)propoxy, 4-(3,4-dichlorobenzoyl)butoxy, 5-(2,6-dichlorobenzoyl)pentyloxy, 6-(2,3-dichlorobenzoyl)hexyloxy, (2,4-dichlorobenzoyl)methoxy, (3,4-difluorobenzoyl)methoxy, (3,5-dibromobenzoyl)methoxy, (3,4,5-trichlorobenzoyl)methoxy, and the like.

The phenyl-lower alkenyl group having optionally a halogen substituent on the phenyl ring includes a straight chain or branched chain alkenyl group having 2 to 6 carbon atoms, which is substituted by a phenyl group having optionally 1 to 3 halogen substituents on the phenyl ring, for example, styryl, 3-phenyl-2-propenyl, 3-phenyl-1-propenyl, 4-phenyl-3-butenyl, 4-phenyl-2-butenyl, 4-phenyl-1-butenyl, 5-phenyl-4-pentenyl, 5-phenyl-3-pentenyl, 5-phenyl-2-pentenyl, 5-phenyl-1-pentenyl, 1-methyl-3-phenyl-2-butenyl, 6-phenyl-5-hexenyl, 1-methylstyryl, 2-, 3- or 4-chlorostyryl, 3-(4-bromophenyl)-2-propenyl, 3-(3-fluorophenyl)-1-propenyl, 4-(4-iodophenyl)-3-butenyl, 5-(2-chlorophenyl)-4-pentenyl, 2-methyl-3-bromostyryl, 3,4-dichlorostyryl, 3,4,5-trichlorostyryl, and the like.

The benzoyl-lower alkyl group having optionally a lower alkyl substituent on the phenyl ring includes a benzoylalkyl group wherein the alkyl moiety is a straight chain or branched chain alkyl group having 1 to 6 carbon atoms, which may optionally have 1 to 3 alkyl substituents having 1 to 6 carbon atoms on the phenyl ring, for example, benzoylmethyl, 2-benzoylethyl, 1-benzoylethyl, 3-benzoylpropyl, 4-benzoylbutyl, 1,1-dimethyl-2-benzoylethyl, 5-benzoylpentyl, 6-benzoylhexyl, 2-methyl-3-benzoylpropyl, 2-(methylbenzoyl)methyl, 2-(2-methylbenzoyl)ethyl, 1-(3-methylbenzoyl)ethyl, 3-(4-methylbenzoyl)propyl, 4-(2-ethylbenzoyl)butyl, 5-(3-propylbenzoyl)pentyl, 6-(4-butylbenzoyl)hexyl, 2-(2-pentylbenzoyl)ethyl, 1-(3-hexylbenzoyl)ethyl, 3-(3,4-dimethylbenzoyl)propyl, 2-(3,4,5-trimethylbenzoyl)ethyl, and the like.

The pyrrolidinyl-substituted lower alkoxy group includes a pyrrolidinylalkoxy group wherein the alkoxy moiety is a straight chain or branched chain alkoxy group having 1 to 6 carbon atoms, for example, (2-pyrrolidinyl)methoxy, 2-(2-pyrrolidinyl)ethoxy, 1-(3-pyrrolidinyl)ethoxy, 3-(2-pyrrolidinyl)propoxy, 4-(3-pyrrolidinyl)butoxy, 5-(2-pyrrolidinyl)pentyloxy, 6-(3-pyrrolidinyl)hexyloxy, 1,1- dimethyl-2-(2-pyrrolidinyl)ethoxy, 2-methyl-3-(3-pyrrolidinyl)propoxy, 5-(1-pyrrolidinyl)pentyloxy, 2-(1-pyrrolidinyl)ethoxy, and the like.

The phenyl-lower alkyl group having optionally a lower alkyl substituent on the phenyl ring includes a phenylalkyl group wherein the alkyl moiety is a straight chain or branched chain alkyl group having 1 to 6 carbon atoms, which may optionally have 1 to 3 straight chain or branched chain alkyl substituents having 1 to 6 carbon atoms on the phenyl ring, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-methylbenzyl, 2-(2-methylphenyl)ethyl, 1-(3-methylphenyl)ethyl, 3-(4-methylphenyl)propyl, 4-(2-ethylphenyl)butyl, 5-(3-propylphenyl)pentyl, 6-(4-butylphenyl)hexyl, 2-(2-pentylphenyl)ethyl, 1-(3-hexylphenyl)ethyl, 3-(3,4-dimethylphenyl)propyl, 2-(3,4,5-trimethylphenyl)ethyl, (2-methyl-6-chlorophenyl)methyl, and the like.

The lower alkoxycarbonyl group includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, tert-butoxycarbonyl, pentyloxycarbonyl, hexyoxycarbonyl, and the lilke.

The aminocarbonyl group having optionally a substituent selected from a lower alkyl group and an amino-substituted lower alkyl group having optionally a lower alkyl substituent includes an aminocarbonyl group which may optionally have 1 to 2 substituents selected from a straight chain or branched chain alkyl group having 1 to 6 carbon atoms and a straight chain or branched chain alkyl group having 1 to 6 carbon atoms which is substituted by an amino group having optionally 1 to 2 straight chain or branched chain alkyl substituents having 1 to 6 carbon atoms, for example, aminocarbonyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl, aminomethylaminocarbonyl, 2-aminoethylaminocarbonyl, 1-aminoethylaminocarbonyl, 3-aminopropylaminocarbonyl, 4-aminobutylaminocarbonyl, 5-aminopentylaminocarbonyl, 6-aminohexylaminocarbonyl, 1,1-dimethyl-2-aminoethylaminocarbonyl, 2-methyl-3-aminopropylaminocarbonyl, methylaminomethylaminocarbonyl, 1-ethylaminoethylaminocarbonyl, 2-propylaminoethylaminocarbonyl, 3-isopropylaminopropylaminocarbonyl, 4-butylaminobutylaminocarbonyl, 5-pentylaminopentylaminocarbonyl, 6-hexylaminohexylaminocarbonyl, dimethylaminomethylaminocarbonyl, 2-diethylaminoethylaminocarbonyl, 2-dimethylaminoethylaminocarbonyl, (N-ethyl-N-propylamino)methylaminocarbonyl, 2-(N-methyl-N-hexylamino)ethylaminocarbonyl, N-methyl-N-(2-diethylaminoethyl)aminocarbonyl, N-ethyl-N-(methylaminomethyl)aminocarbonyl, and the like.

The lower alkyl group having optionally a hydroxy substituent includes a straight chain or branched chain alkyl group having 1 to 6 carbon atoms which may optionally have 1 to 3 hydroxy substituents, for example, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, and the like.

The carbamoyl-lower alkyl group includes a carbamoylalkyl group wherein the alkyl moiety is a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, and the like.

The adamantyl-substituted lower alkyl group includes an adamantyl-alkyl group wherein the alkyl moiety is a straight chain or branched chain alkyl group having 1 to 6 carbon atoms, for example, adamantylmethyl, 2-adamantylethyl, 1-adamantylethyl, 3-adamantylpropyl, 4-adamantylbutyl, 5-adamantylpentyl, 6-adamantylhexyl, 1,1-dimethyl-2-adamantylethyl, 2-methyl-3-adamantylpropyl, and the like.

The lower alkylsulfonyl group includes an alkylsulfonyl group wherein the alkyl moiety is a straight chain or branched chain alkyl group having 1 to 6 carbon atoms, for example, methylsulfonyl, ethylsulfonyl, propylsulfonyl, isopropylsulfonyl, butylsulfonyl, tert-butylsulfonyl, pentylsulfonyl, hexylsulfonyl, and the like.

The hydroxy-substituted lower alkyl group includes a straight chain or branched chain alkyl group having 1 to 6 carbon atoms which have 1 to 3 hydroxy substituents, for example, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, and the like.

The phenyl-lower alkyl group includes a straight chain or branched chain alkyl group having 1 to 6 carbon atoms, which is substituted by 1 to 2 phenyl groups, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, diphenylmethyl, 2,2-diphenylethyl, and the like.

The quinolylcarbonyl group having optionally a phenyl substituent on the quinoline ring includes, for example, quinolylcarbonyl, 2-phenylquinolylcarbonyl, 3-phenylquinolylcarbonyl, 4-phenylquinolylcarbonyl, 5-phenylquinolylcarbonyl, 6-phenylquinolylcarbonyl, 7-phenylquinolylcarbonyl, 8-phenylquinolylcarbonyl, and the like.

The thienylcarbonyl group having optionally a phenyl substituent on the thiophene ring includes, for example, thienylcarbonyl, 2-phenylthienylcarbonyl, 3-phenylthienylcarbonyl, 4-phenylthienylcarbonyl, and the like.

The thiazolylcarbonyl group having optionally a phenyl substituent on the thiazole ring includes, for example, thiazolylcarbonyl, 2-phenylthiazolylcarbonyl, 4-phenylthiazolylcarbonyl, 5-phenylthiazolylcarbonyl, and the like.

The cycloalkylcarbonyl group includes a cycloalkylcarbonyl group having 3 to 8 carbon atoms in the cycloalkyl moiety, for example, cyclopropylcarbonyl, cyclobutylcarbonyl, cyclopentylcarbonyl, cyclohexylcarbonyl, cycloheptylcarbonyl, cyclooctylcarbonyl, and the like.

The lower alkanoyl group having optionally a substituent selected from a halogen atom and a hydroxy group includes a straight chain or branched chain alkanoyl group having 1 to 6 carbon atoms which may optionally have 1 to 3 substituents selected from a halogen atom and a hydroxy group, for example, in addition to the above-mentioned lower alkanoyl groups having optionally a halogen substituent, 2-hydroxyacetyl, 3-hydroxypropionyl, 2-hydroxypropionyl, 4-hydroxybutyryl, 5-hydroxypentanoyl, 6-hydroxyhexanoyl, 2,2-dimethyl-3-hydroxypropionyl, and the like.

The halogen-substituted lower alkyl group includes a straight chain or branched chain alkyl group having 1 to 6 carbon atoms which is substituted by 1 to 3 halogen atoms, for example, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-bromopropyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, and the like.

The amino group having optionally a lower alkyl substituent includes an amino group having optionally 1 to 2 straight chain or branched chain alkyl substituents having 1 to 6 carbon atoms, for example, amino, methylamino, ethylamino, propylamino, isopropylamino, butylamino, tertbutylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and the like.

The lower alkoxycarbonyl group having optionally a halogen substituent includes a straight chain or branched chain alkoxycarbonyl group having 1 to 6 carbon atoms in the alkoxy moiety, which may optionally have 1 to 3 halogen substituents, for example, in addition to the above-mentioned lower alkoxycarbonyl groups, trifluoromethoxycarbonyl, trichloromethoxycarbonyl, chloromethoxycarbonyl, bromomethoxycarbonyl, fluoromethoxycarbonyl, iodomethoxycarbonyl, difluoromethoxycarbonyl, dibromomethoxycarbonyl, 2-chloroethoxycarbonyl, 2,2,2-trifluoroethoxycarbonyl, 2,2,2-trichloroethoxycarbonyl, 3-bromopropoxy, 3-chloropropoxy, 2,3-dichloropropoxy, 4,4,4-trichlorobutoxycarbonyl, 4-fluorobutoxycarbonyl, 5-chloropentyloxycarbonyl, 3-chloro-2-methylpropoxycarbonyl, 5-bromohexyloxycarbonyl, 5,6-dichlorohexyloxycarbonyl, and the like.

The lower alkoxy-substituted lower alkanoyl group includes an alkoxyalkanoyl group wherein the alkanoyl moiety is a straight chain or branched chain alkanoyl group having 2 to 6 carbon atoms and the alkoxy moiety is a straight chain or branched chain alkoxy group having 1 to 6 carbon atoms, for example, 2-methoxyacetyl, 3-methoxypropionyl, 2-ethoxyacetyl, 3-ethoxypropionyl, 4-ethoxybutyryl, 3-propoxypropionyl, 2-methoxypropionyl, 6-propoxyhexanoyl, 5-isopropoxypentanoyl, 2,2-dimethyl-3-butoxypropionyl, 2-methyl-3-tert-butoxypropionyl, 2-pentyloxyacetyl, 2-hexyloxyacetyl, and the like.

The lower alkanoyloxy-substituted lower alkanoyl group includes an alkanoyloxyalkanoyl group wherein the alkanoyl moieties are a straight chain or branched chain alkanoyl group having 2 to 6 carbon atoms which is substituted by a straight chain or branched chain alkanoyloxy group having 1 to 6 carbon atoms, for example, 2-acetyloxyacetyl, 3-acetyloxypropionyl, 2-propionyloxyacetyl, 3-propionyloxypropionyl, 4-propionyloxybutyryl, 3-butyryloxypropionyl, 2-acetyloxypropionyl, 6-propionyloxyhexanoyl, 5-butyryloxypentanoyl, 2,2-dimethyl-3-butyryloxypropionyl, 2-pentanoyloxyacetyl, 2-hexanoyloxyacetyl, and the like.

The quinolyloxy-substituted alkanoyl group includes a quinolyloxyalkanoyl group wherein the alkanoyl moiety is a straight chain or branched chain alkanoyl group having 2 to 6 carbon atoms, for example, 2-quinolyloxyacetyl, 3-quinolyloxypropionyl, 2-quinolyloxypropionyl, 4-quinolyloxybutyryl, 2,2-dimethyl-3-quinolyloxypropionyl, 5-quinolyloxypentanoyl, 6-quinolyloxyhexanoyl, and the like.

The phenyl-lower alkoxycarbonyl group includes a phenylalkoxycarbonyl group wherein the alkoxycarbonyl moiety is a straight chain or branched chain alkoxycarbonyl group having 1 to 6 carbon atoms in the alkoxy moiety, for example, benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, and the like.

The benzoyl-lower alkyl group includes a benzoylalkyl group wherein the alkyl moiety is a straight chain or branched chain alkyl group having 1 to 6 carbon atoms, for example, benzoylmethyl, 2-benzoylethyl, 1-benzoylethyl, 3-benzoylpropyl, 4-benzoylbutyl, 5-benzoylpentyl, 6-benzoylhexyl, 1,1-dimethyl-2-benzoylethyl, 2-methyl-3-benzoylpropyl, and the like.

The tetrahydroquinolyloxy-substituted lower alkanoyl group having optionally a substituent selected from a lower alkyl group and an oxo group on the quinoline ring includes a straight chain or branched chain alkanoyl group having 2 to 6 carbon atoms, which is substituted by a tetrahydroquinolyloxy group having optionally 1 to 3 substituents selected from a straight chain or branched chain alkyl group having 1 to 6 carbon atoms and an oxo group on the quinoline ring, for example, 2-tetrahydroquinolyloxyacetyl, 3-tetrahydroquinolyloxypropionyl, 2-tetrahydroquinolyloxypropionyl, 4-tetrahydroquinolyloxybutyryl, 2,2-dimethyl-3-tetrahydroquinolyloxypropionyl, 5-tetrahydroquinolyloxypentanoyl, 6-tetrahydroquinolyloxyhexanoyl, 2-(1-methyltetrahydroquinolyloxy)acetyl, 2-(2-oxotetrahydroquinolyloxy)acetyl, 3-(2-ethyltetrahydroquinolyloxy)propionyl, 2-(3-propyltetrahydroquinolyloxy)propionyl, 4-(4-butyltetrahydroquinolyloxy)butyryl, 2,2-dimethyl-3-(5-pentyltetrahydroquinolyloxy)propionyl, 5-(6-hexyltetrahydroquinolyloxy)pentanoyl, 6-(7-methyltetrahydroquinolyloxy)hexanoyl, 2-(8-methyltetrahydroquinolyloxy)acetyl, 2-(1,4-dimethyltetrahydroquinolyloxy)acetyl, 2-(2,4,6-trimethyltetrahydroquinolyloxy)acetyl, 2-(1-methyl-2-oxotetrahydroquinolyloxy)acetyl, 3-(2-oxotetrahydroquinolyloxy)propionyl, 4-(2-oxotetrahydroquinolyloxy)butyryl, 5-(2-oxotetrahydroquinolyloxy)pentanoyl, 6-(2-oxotetrahydroquinolyloxy)hexanoyl, 2-(1,6-dimethyl-2-oxotetrahydroquinolyloxy)acetyl, and the like.

The tetrahydronaphthyloxy-lower alkanoyl group includes a tetrahydronaphthyloxyalkanoyl group wherein the alkanoyl group is a straight chain or branched chain alkanoyl group having 2 to 6 carbon atom, for example, 2-tetrahydronaphthyloxyacetyl, 3-tetrahydronaphthyloxypropionyl, 2-tetrahydronaphthyloxypropionyl, 4-tetrahydronaphthyloxybutyryl, 2,2-dimethyl-3-tetrahydronaphthyloxypropionyl, 5-tetrahydronaphthyloxypentanoyl, 6-tetrahydronaphthyloxyhexanoyl, and the like.

The phenyl-lower alkenylcarbonyl group includes a phenylalkenylcarbonyl group wherein the alkenylcarbonyl moiety is a straight chain or branched chain alkenylcarbonyl group having 3 to 6 carbon atoms in the alkenyl moiety, for example cinnamoyl, 3-phenyl-2-propenylcarbonyl, 3-phenyl-1-propenylcarbonyl, 4-phenyl-3-butenylcarbonyl, 4-phenyl-2-butenylcarbonyl, 4-phenyl-1-butenylcarbonyl, 5-phenyl-4-pentenylcarbonyl, 5-phenyl-3-pentenylcarbonyl, 5-phenyl-2-pentenylcarbonyl, 5-phenyl-1-pentenylcarbonyl, 1-methyl-3-phenyl-2-butenylcarbonyl, 1-methylcinnamoyl, and the like.

The cycloalkenyl group includes a cycloalkenyl group having 3 to 8 carbon atoms, for example, cyclopropenyl, cyclobutenyl, cyclopentenyl, cyclohexenyl, cycloheptenyl, cyclooctenyl, and the like.

The phenyl-lower alkylaminocarbonyl group includes a phenylalkylaminocarbonyl group wherein the alkyl moiety is a straight chain or branched chain alkyl group having 1 to 6 carbon atoms, for example, benzylaminocarbonyl, (2-phenylethyl)aminocarbonyl, (1-phenylethyl)aminocarbonyl, (3-phenylpropyl)aminocarbonyl, (4-phenylbutyl)aminocarbonyl, (5-phenylpentyl)aminocarbonyl, (6-phenylhexyl)aminocarbonyl, (1,1-dimethyl-2-phenylethyl)aminocarbonyl, (2-methyl-3-phenylpropyl)aminocarbonyl, and the like.

The 5- to 11-membered, saturated or unsaturated heteromonocyclic or heterobicyclic group containing 1 to 4 heteroatoms selected from a nitrogen atom, an oxygen atom and a sulfur atom includes, for example, pyrrolidinyl, piperidinyl, piperazinyl, morpholino, thiomorpholino, pyridyl, homopiperazinyl, 1,2,5,6-tetrahydropyridyl, thienyl, quinolyl, 1,4-dihydroquinolyl, benzothiazolyl, pyrazyl, pyrimidyl, pyridazyl, pyrrolyl, carbostyril, 3,4-dihydrocarbostyril, 1,2,3,4-tetrahydroquinolyl, indolyl, isoindolyl, indolinyl, benzimidazolyl, benzoxazolyl, imidazolidinyl, isoquinolyl, quinazolidinyl, 1,2,3,4-tetrahydroquinolyl, 1,2-dihydroisoquinolyl, quinoxalinyl, cinnolinyl, phthalazinyl, 1,2,3,4-tetrazolyl, 1,2,4-triazolyl, chromanyl, isoindolinyl, isochromanyl, pyrazolyl, imidazolyl, pyrazolidinyl, imidazo[1,2-a]pyridyl, benzofuryl, 2,3-dihydrobenzo[b]furyl, benzothienyl, 1-azacycloheptyl, 4H-chromenyl, 1H-indazolyl, isoindolinyl, 2-imidazolinyl, 2-pyrrolinyl, furyl, oxazolyl, isooxazolyl, thiazolyl, isothiazolyl, pyranyl, pyrazolidinyl, 2-pyrazolinyl, quinuclidinyl, 1,4-benzoxazinyl, 3,4-dihydro-2H-1,4-benzoxazinyl, 3,4-dihydro-2H-1,4-benzothiazinyl, 1,4-benzothiadinyl, 1,2,3,4-tetrahydroquinoxalinyl, 1,3-dithia-2,4-dihydronaphthalenyl, tetrahydro-1,3-oxazinyl, tetrahydrooxazolyl, 1,4-dithianaphthalenyl, and the like.

The above-mentioned heterocyclic group having 1 to 3 substituents selected from a lower alkyl group, a phenyl group, a lower alkanoyl group, a halogen atom, a phenyl-lower alkyl group and an oxo group includes the above-mentioned heterocyclic groups having 1 to 3 substituents selected from a straight chain or branched chain alkyl group having 1 to 6 carbon atoms, a phenyl group, a straight chain or branched chain alkanoyl group having 1 to 6 carbon atoms, a halogen atom, a phenylalkyl group wherein the alkyl moiety is a straight chain or branched chain alkyl group having 1 to 6 carbon atoms and an oxo group, for example, 1-oxo-1,2,3,4-tetrahydroisoquinolyl, 2-oxopiperidinyl, 2-oxo-1-azabicycloheptyl, 2-oxopyrrolidinyl, 5-phenylthiazolyl, 1-methylimidazolyl, 1-propylimidazolyl, 4-methylimidazolyl, 4-phenylimidazolyl, 1,4-dimethylpyrrolyl, 4-methylpiperazinyl, 4-phenylpiperidinyl, 4-methylthiazolyl, 2-oxothiazolyl, 5-ethylthiazolyl, 4-phenylthiazolyl, 4-propylthiazolyl, 5-butylthiazolyl, 4-pentylthiazolyl, 2-hexylthiazolyl, 4,5-dimethylthiazolyl, 5-phenyl-4-methylthiazolyl, 1-ethylimidazolyl, 4-propylimidazolyl, 5-butylimidazolyl, 1-pentylimidazolyl, 1-hexylimidazolyl, 1,4-dimethylimidazolyl, 1,4,5-trimethylimidazolyl, 1-phenylimidazolyl, 2-phenylimidazolyl, 5-phenylimidazolyl, 1-methyl-4-phenylimidazolyl, 3-methyl-1,2,4-triazolyl, 5-ethyl-1,2,4-triazolyl, 3-phenyl-1,2,4-triazolyl, 2-oxo-1-methylimidazolyl, 2-oxoimidazolyl, 2-ethylpyrrolyl, 3-propylpyrrolyl, 5-butylpyrrolyl, 4-pentylpyrrolyl, 2-hexylpyrrolyl, 2,4,5-trimethylpyrrolyl, 2-phenylpyrrolyl, 2,5-diphenylpyrrolyl, 2-methyl-5-phenylpyrrolyl, 2-oxopyrrolyl, 1-methyl-1,2,3,4-tetrazolyl, 1-phenyl-1,2,3,4-tetrazolyl, 1-ethyl-1,2,3,4-tetrazolyl, 1-propyl-1,2,3,4-tetrazolyl, 1-butyl-1,2,3,4-tetrazolyl, 1-pentyl-1,2,3,4-tetrazolyl, 1-hexyl-1,2,3,4-tetrazolyl, 1-phenyl-1,2,3,4-tetrazolyl, 2-methylpyridyl, 3-ethylpyridyl, 4-propylpyridyl, 2-butylpyridyl, 3-pentylpyridyl, 4-hexylpyridyl, 2-phenylpyridyl, 3-phenylpyridyl, 4-phenylpyridyl, 2,4-dimethylpyridyl, 2,4,6-trimethylpyridyl, 2-methyl-4-phenylpyridyl, 2,4-diphenylpyridyl, 2,4,6-triphenylpyridyl, 2-oxopyridyl, 4-oxopyridyl, 4-methyl-2-oxopyridyl, 2-phenyl-4-oxopyridyl, 3-methylimidazo[1,2-a]pyridyl, 4-ethylimidazo[1,2-a]pyridyl, 3-phenylimidazo[1,2-a]pyridyl, 5-phenylimidazo[1,2-a]pyridyl, 3-methyl-1H-indazolyl, 3-phenyl-1H-indazolyl, 1-methyl-1,2,3,4-tetrahydroisoquinolyl, 5-ethyl-1,2,3,4-tetrahydroisoquinoly, 6-phenyl-1,2,3,4-tetrahydroisoquinolyl, 1-oxo-6-methyl-1,2,3,4-tetrahydroisoquinolyl, 1-oxo-7-phenyl-1,2,3,4-tetrahydroisoquinolyl, 3,4-dimethylpiperazinyl, 3-ethylpyrrolidinyl, 2-propylpyrrolidinyl, 1-methylpyrrolidinyl, 3,4,5-trimethylpiperidinyl, 4-butylpiperidinyl, 4-pentylmorpholino, 4-hexylpiperazinyl, 4-butylpiperidinyl, 3-pentylmorpholino, 4-hexylpiperazinyl, 3-methylthiomorpholino, 4-phenylpiperazinyl, 3-phenylpyrrolidinyl, 2-oxo-4-methylpiperidinyl, 2-oxo-3-methylpyrrolidinyl, 2-oxo-4-phenylpiperidinyl, 4-methyl-1-azabicycloheptyl, 5-phenyl-1-azacycloheptyl, 6-methyl-2-oxo-1-azacycloheptyl, 1-methyl-2-oxoimidazolidinyl, 1-isobutyl-2-oxoimidazolidinyl, 1-benzyl-2-oxoimidazolidinyl, 2-oxotetrahydro-1,3-oxazinyl, 3-phenyl-2-oxo-1-azacycloheptyl, 2-oxotetrahydrooxazolyl, 3-chloropyridyl, 4-methylpiperazinyl, 4-isobutylpiperazinyl, 4-methylhomopiperazinyl, 4-acetylpiperazinyl, 4-benzylpiperazinyl, 4-ethylhomopiperazinyl, and the like.

The cyano-substituted lower alkyl group includes a cyanoalkyl group wherein the alkyl moiety is a straight chain or branched chain alkyl group having 1 to 6 carbon atoms, for example, cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, 2-methyl-3-cyanopropyl, and the like.

The tetrazolyl-substituted lower alkyl group includes a tetrazolylalkyl group wherein the alkyl moiety is a straight chain or branched chain alkyl group having 1 to 6 carbon atoms, for example, tetrazolylmethyl, 2-tetrazolylethyl, 1-tetrazolylethyl, 3-tetrazolylpropyl, 4-tetrazolylbutyl, 5-tetrazolylpentyl, 6-tetrazolylhexyl, 1,1-dimethyl-2-tetrazolylethyl, 2-methyl-3-tetrazolylpropyl, and the like.

The lower alkanoyloxy-substituted lower alkyl group includes a straight chain or branched chain alkyl group having 1 to 6 carbon atoms, which is substituted by a straight chain or branched chain alkanoyloxy group having 2 to 6 carbon atoms, for example, acetyoxymethyl, 2-propionyloxyethyl, 1-butyryloxyethyl, 3-acetyloxypropyl, 4-acetyloxybutyl, 4-isobutyryloxybutyl, 5-pentanoyloxypentyl, 6-acetyloxyhexyl, 6-tert-butylcarbonyloxyhexyl, 1,1-dimethyl-2-hexanoyloxyethyl, 2-methyl-3-acetyloxypropyl, and the like.

The amino group having optionally a lower alkanoyl substituent includes an amino group having optionally a straight chain or branched chain alkanoyl group having 1 to 6 carbon atoms, for example, amino, formylamino, acetylamino, propionylamino, butyrylamino, isobutyrylamino, pentanoylamino, tert-butylcarbonylamino, hexanoylamino, and the like.

The pyridyl-lower alkyl group includes a pyridylalkyl group wherein the alkyl moiety is a straight chain or branched chain alkyl group having 1 to 6 carbon atoms, for example, (4-pyridyl)methyl, 1-(3-pyridyl)ethyl, 2-(2-pyridyl)ethyl, 3-(2-pyridyl)propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl, and the like.

The phenoxy-lower alkoxycarbonyl group includes a phenoxyalkoxycarbonyl group wherein the alkoxycarbonyl moiety is a straight chain or branched chain alkoxycarbonyl group having 1 to 6 carbon atoms in the alkoxy moiety, for example, phenoxymethoxycarbonyl, 2-phenoxyethoxycarbonyl, 1-phenoxyethoxycarbonyl, 3-phenoxypropoxycarbonyl, 4-phenoxybutoxycarbonyl, 5-phenoxypentyloxycarbonyl, 6-phenoxyhexyloxycarbonyl, 1,1-dimethyl-2-phenoxyethoxycarbonyl, 2-methyl-3-phenoxypropoxycarbonyl, and the like.

The pyridyl-lower alkoxycarbonyl group includes a pyridylalkoxycarbonyl group wherein the alkoxycarbonyl group is a straight chain or branched chain alkoxycarbonyl group having 1 to 6 carbon atoms in the alkoxy moiety, for example, (4-pyridyl)methoxycarbonyl, (2-pyridyl)methoxycarbonyl, (3-pyridyl)methoxycarbonyl, 2-(2-pyridyl)ethoxycarbonyl, 1-(1-pyridyl)ethoxycarbonyl, 3-(3-pyridyl)propoxycarbonyl, 4-(4-pyridyl)butoxycarbonyl, 5-(3-pyridyl)pentyloxycarbonyl, 6-(2-pyridyl)hexyloxycarbonyl, 1,1-dimethyl-2-(4-pyridyl)ethoxycarbonyl, 2-mehyl-3-(3-pyridyl)propoxycarbonyl, and the like.

The fluorenyl-lower alkoxycarbonyl group includes a fluorenylalkoxycarbonyl group wherein the alkoxycarbonyl moiety is a straight chain or branched chain alkoxycarbonyl group having 1 to 6 carbon atoms in the alkoxy moiety, for example, (5-fluorenyl)methoxycarbonyl, 2-(2-fluorenyl)ethoxycarbonyl, 1-(1-fluorenyl)ethoxycarbonyl, 3-(3-fluorenyl)propoxycarbonyl, 4-(4-fluorenyl)butoxycarbonyl, 5-(5-fluorenyl)pentyloxycarbonyl, 6-(1-fluorenyl)hexyloxycarbonyl, 1,1-dimethyl-2-(2-fluorenyl)ethoxycarbonyl, 2-methyl-3-(3 -fluorenyl)propoxycarbonyl, and the like.

The lower alkenyloxycarbonyl group includes an alkenyloxycarbonyl group wherein the alkenyloxycarbonyl moiety is a straight chain or branched chain alkenyloxycarbonyl group having 2 to 6 carbon atoms in the alkenyloxy moiety, for example, vinyloxycarbonyl, allyloxycarbonyl, 2-butenyloxycarbonyl, 3-butenyloxycarbonyl, 1-methylallyloxycarbonyl, 2-pentenyloxycarbonyl, 2-hexenyloxycarbonyl.

The piperidinyl-lower alkoxycarbonyl group having optionally a substituent selected from a lower alkanoyl group, a lower alkoxycarbonyl group and a lower alkyl group on the piperidine ring includes a piperidinylalkoxycarbonyl group wherein the alkoxycarbonyl group is a straight chain or branched chain alkoxycarbonyl group having 1 to 6 carbon atoms in the alkoxy moiety, which may have optionally 1 to 3 substituents selected from a straight chain or branched chain alkanoyl group having 1 to 6 carbon atoms, a straight chain or branched chain alkoxycarbonyl group having 1 to 6 carbon atoms in the alkoxy moiety and a straight chain or branched chain alkyl group having 1 to 6 carbon atoms, for example, (4-piperidinyl) methoxycarbonyl, 2-(3-piperidinyl)ethoxycarbonyl, 1-(2-piperidinyl)ethoxycarbonyl, 3-(1-piperidinyl) propoxycarbonyl, 4-(4-piperidinyl)butoxycarbonyl, 5-(3-piperidinyl)pentyloxycarbonyl, 6-(2-piperidinyl) hexyloxycarbonyl, 1,1-dimethyl-2-(4-piperidinyl) ethoxycarbonyl, 2-methyl-3-(1-piperidinyl) propoxycarbonyl, (1-ethyl-4-piperidinyl)methoxycarbonyl, (1-t-butoxycarbonyl-4-piperidinyl)methoxycarbonyl, (1-acetyl-4-piperidinyl)methoxycarbonyl, 2-(1-methyl-4-piperidinyl)ethoxycarbonyl, 1-(4-propyl-2-piperidinyl) ethoxycarbonyl, 3-(4-butyl-3-piperidinyl)propoxycarbonyl, 4-(3-pentyl-2-piperidinyl)butoxycarbonyl, 5-(1-hexyl-4-piperidinyl)pentyloxycarbonyl, (1,2-dimethyl-4-piperidinyl)methoxycarbonyl, (3,4,5-trimethyl-1-piperidinyl)methoxycarbonyl, 2-(1-methoxycarbonyl-4-piperidinyl)ethoxycarbonyl, 1-(1-ethoxycarbonyl-4-piperidinyl)ethoxycarbonyl, 3-(4-propoxycarbonyl-1-piperidinyl)propoxycarbonyl, 4-(3-pentyloxycarbonyl-2-piperidinyl)butoxycarbonyl, 5-(1-hexyloxycarbonyl-4-piperidinyl)pentyloxycarbonyl, 6-(4-methoxycarbonyl-1-piperidinyl)hexyoxycarbonyl, 2-(2-acetyl-1-piperidinyl) ethoxycarbonyl, 1-(3-propionyl-2-piperidinyl) ethoxycarbonyl, 3-(4-butyryl-3-piperidinyl) propoxycarbonyl, 4-(4-pentanoyl-1 -piperidinyl) butoxycarbonyl, 5-(1-hexanoyl-4-piperidinyl) pentyloxycarbonyl, 6-(1-acetyl-2-methyl-4-piperidinyl) hexyoxycarbonyl, (1-ethoxycarbonyl-2,6-dimethyl-4-piperidinyl)methoxycarbonyl, and the like.

The aminosulfonyloxy group having optionally a lower alkyl substituent includes an aminosulfonyloxy group having optionally 1 to 2 straight chain or branched chain alkyl substituents having 1 to 6 carbon atoms, for example, aminosulfonyloxy, methylaminosulfonyloxy, ethylaminosulfonyloxy, propylaminosulfonyloxy, isopropylaminosulfonyloxy, butylaminosulfonyloxy, tert-butylaminosulfonyloxy, pentylaminosulfonyloxy, hexylaminosulfonyloxy, dimethylaminosulfonyloxy, diethylaminosulfonyloxy, dipropylaminosulfonyloxy, dibutylaminosulfonyloxy, dipentylaminosulfonyloxy, dihexylaminosulfonyloxy, N-methyl-N-ethylaminosulfonyloxy, N-ethyl-N-propylaminosulfonyloxy, N-methyl-N-butylaminosulfonyloxy, N-methyl-N-hexylaminosulfonyloxy, and the like.

The phenyl-lower alkyl group includes a phenylalkyl group wherein the alkyl moiety is a straight chain or branched chain alkyl group having 1 to 6 carbon atoms, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, and the like.

The lower alkanoyl-substituted amino group includes an amino group substituted by a straight chain or branched chain alkanoyl group having 1 to 6 carbon atoms, for example, formylamino, acetylamino, propionylamino, butyrylamino, isobutyrylamino, pentanoylamino, tert-butycarbonylamino, hexanoylamino, and the like.

The benzoheterocyclic derivatives of the present invention can be prepared by the following processes.

Reaction Scheme-1

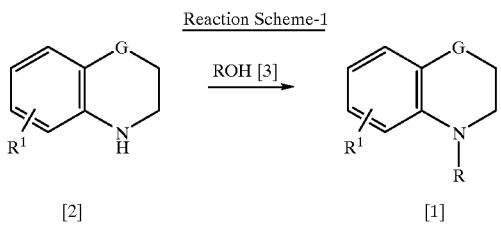

wherein G, $R^1$, $R^2$, $R^3$, R and X are the same as defined above.

The process of Reaction Scheme-1 is carried out by reacting a benzoheterocyclic compound [2] and a carboxylic acid compound [3] by the conventional amido bond producing reaction. The amido bond producing reaction can be carried out under the conditions for the conventional amido bond producing reaction, for example, (a) a mixed acid anhydride process, i.e. a process of reacting the carboxylic acid compound [3] with an alkyl carbonate to form a mixed acid anhydride and reacting the resultant with the amine compound [2], (b) an activated ester process, i.e. a process of converting the carboxylic acid compound [3] into an activated ester such as p-nitrophenyl ester, N-hydroxysuccinimide ester, 1-hydroxybenzotriazole ester, etc., and reacting the resultant with the amine compound [2], (c) a carbodiimide process, i.e. a process of condensing the carboxylic acid compound [3] and the amine compound [2] in the presence of an activating agent such as dicyclohexylcarbodiimide, carbonyldiimidazole, etc., (d) other processes, i.e. a process of converting the carboxylic acid compound [3] into a carboxylic anhydride by treating it with a dehydrating agent such as acetic anhydride, and reacting the resultant with the amine compound [2]; a process of reacting an ester of the carboxylic acid compound [3] with a lower alcohol and the amine compound [2] at a high temperature under high pressure; a process of reacting an acid halide compound of the carboxylic acid compound [3], i.e. a carboxylic acid halide, with the amine compound [2], and the like.

The mixed acid anhydride used in the above mixed acid anhydride process (a) is obtained by the known Schötten-Baumann reaction, and the reaction product is used without isolating from the reaction mixture for the reaction with the amine compound [2] to give the desired compound [1] of the present invention. The above Schötten-Baumann reaction is usually carried out in the presence of a basic compound. The basic compound is any conventional compounds used in the Schötten-Baumann reaction and includes, for example, organic basic compounds such as triethylamine, trimethylamine, pyridine, dimethylaniline, 1-methyl-2-pyrrolidine (NMP), N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), and inorganic basic compounds such as potassium carbonate, sodium carbonate, potassium hydrogen carbonate, sodium hydrogen carbonate, etc. The reaction is usually carried out at a temperature from about −20° C. to about 100° C., preferably at a temperature from 0° C. to about 50° C., for about 5 minutes to about 10 hours, preferably for 5 minutes to about 2 hours.

The reaction between the mixed acid anhydride thus obtained and the amine compound [2] is usually carried out at a temperature from −20° C. to about 150° C., preferably at a temperature from 10° C. to about 50° C., for 5 minutes to about 10 hours, preferably for 5 minutes to about 5 hours. The mixed acid anhydride process is usually carried out in a solvent. The solvent may be any conventional solvents which are usually used in the mixed acid anhydride process and includes, for example, halogenated hydrocarbons (e.g. chloroform, dichloromethane, dichloroethane, etc.), aromatic hydrocarbons (e.g. benzene, p-chlorobenzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, acetonitrile, hexamethylphosphoric triamide, etc.), or a mixture of these solvents. The alkyl halocarbonate used in the mixed acid anhydride process includes, for example, methyl chloroformate, methyl bromoformate, ethyl chloroformate, ethyl bromoformate, isobutyl chloroformate, and the like. In said process, the carboxylic acid compound [3], the alkyl halocarbonate and the amine compound [2] are usually used in each equimolar amount, but preferably, the alkyl halocarbonate and the carboxylic acid compound [3] are used each in an amount of about 1 to 1.5 mole to 1 mole of the amine compound [2].

Among the above other processes (d), in case of the process of reacting the carboxylic acid halide with the amine compound [2], the reaction is usually carried out in the presence of a basic compound in an appropriate solvent. The basic compound is any conventional compounds and includes, for example, in addition to the basic compounds used in the above Schötten-Baumann reaction, sodium hydroxide, potassium hydroxide, sodium hydride, potassium hydride, and the like. The solvent includes, for example, in addition to the solvents used in the mixed acid anhydride process, alcohols (e.g. methanol, ethanol, propanol, butanol, 3-methoxy-1-butanol, ethylcellosolve, methylcellosolve, etc.), pyridine, acetone, water, and the like. The amount of the amine compound [2] and the carboxylic acid halide is not critical, but the carboxylic acid halide is usually used at least in equimolar amount, preferably about in an amount of 1 mole to 5 moles to 1 mole of the amine compound [2]. The reaction is usually carried out at a temperature from about −20° C. to about 180° C., preferably at a temperature from 0° C. to about 150° C., for about 5 minutes to about 30 hours.

The amido bond producing reaction in above Reaction Scheme-1 may also be carried out by reacting the carboxylic acid compound [3] and the amine compound [2] in the presence of a condensing agent such as phosphorus compounds (e.g. phenylphosphine-2,2'-dithiodipyridine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, etc.).

The reaction is usually carried out in the presence of the solvent and the basic compound as used in the above reaction of the carboxylic acid halide and the amine compound [2] at a temperature from −20° C. to 150° C., preferably at a temperature from 0° C. to about 100° C., for about 5 minutes to about 30 hours. The condensing agent and the carboxylic acid compound [3] are used at least in an equimolar amount, preferably in an amount of about 1 to 2 moles, to 1 mole of the amine compound [2].

Reaction Scheme-2

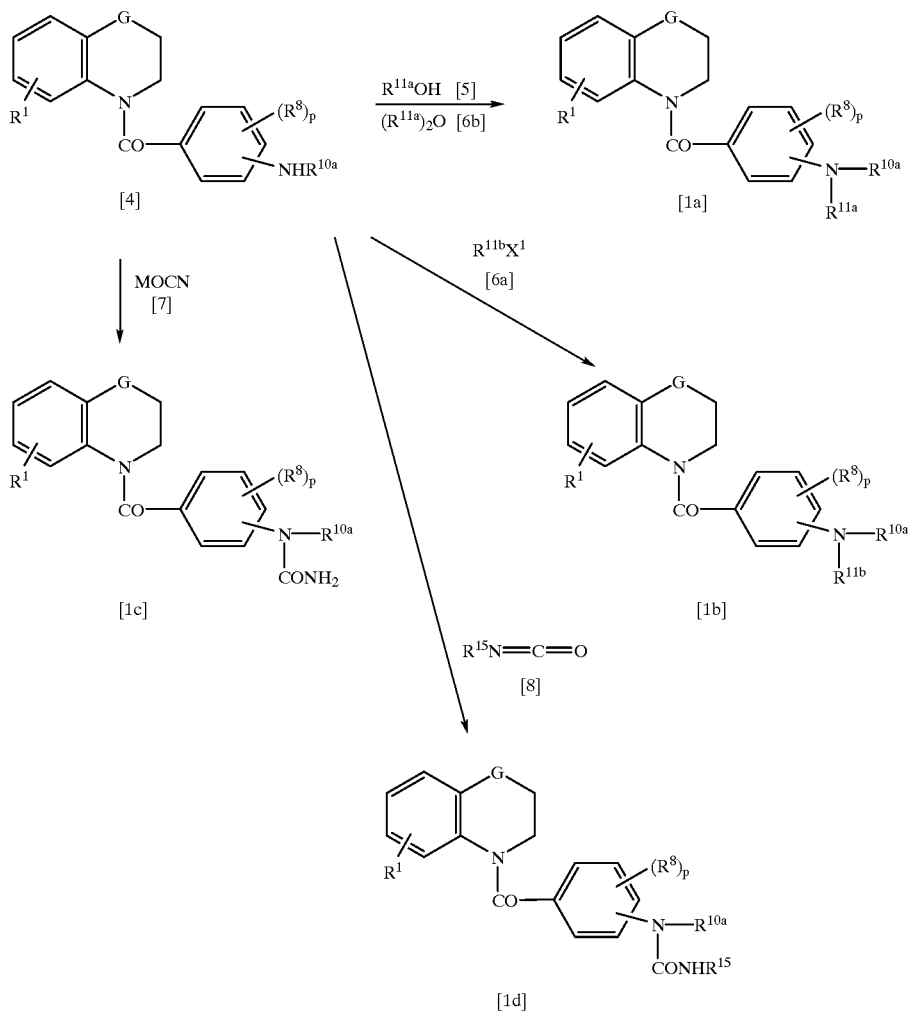

wherein G, p, $R^1$, $R^2$, $R^3$, $R^8$ and X are the same as defined above, $R^{10a}$ is a hydrogen atom, a lower alkyl group or a lower alkanoyl group having optionally a halogen substituent, $R^{11a}$ is a lower alkanoyl group having optionally a substituent selected from a halogen atom and a hydroxy group, a phenoxy-lower alkanoyl group having optionally a substituent selected from a lower alkyl group, a phenyl group, a lower alkoxy group, a halogen-substituted lower alkyl group, an amino group having optionally a lower alkyl substituent, a nitro group, a lower alkanoyl-substituted amino group and a halogen atom, wherein the alkanoyl moiety may optionally be substituted by a halogen atom, a lower alkoxy-substituted lower alkanoyl group, a lower alkanoyloxy-substituted lower alkanoyl group, a group of the formula:

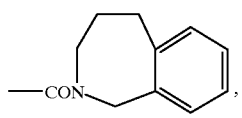

a phenoxy-lower alkoxycarbonyl group, a quinolylcarbonyl group, a quinolyloxy-substituted lower alkanoyl group, a tetrahydroquinolyloxy-substituted lower alkanoyl group having optionally a substituent selected from a lower alkyl group and an oxo group on the quinoline ring, a pyridyl-lower alkoxycarbonyl group, a fluorenyl-lower alkoxycarbonyl group, a lower alkenyloxycarbonyl group, a tetrahydronaphthyloxy-substituted lower alkanoyl group, a piperidinyl-lower alkoxycarbonyl group having optionally a substituent selected from a lower alkanoyl group, a lower alkoxycarbonyl group and a lower alkyl group on the piperidine ring, a lower alkoxycarbonyl group having optionally a halogen substituent, a benzofurylcarbonyl group, a benzimidazolylcarbonyl group, a tetrahydroisoquinolylcarbonyl group, a phenyl-lower alkoxycarbonyl group or a phenyl-lower alkenylcarbonyl group, $R^{11b}$ is a lower alkyl group, a cycloalkyl group, a phenyl-lower alkyl group having optionally a substituent selected from a lower alkyl group and a halogen atom on the phenyl ring, wherein the alkyl moiety may optionally be substituted by a hydroxy group, a phenoxy-lower alkyl group having optionally a lower alkyl substituent on the phenyl ring, an aminocarbonyl group having optionally a substituent selected from a lower alkyl group, a pyridyl-lower alkyl group and a phenyl-lower alkyl group, a benzoyl-lower alkyl group or a lower alkylsulfonyl group, $X^1$ is a halogen atom, M is an alkali metal such as sodium, potassium, etc., and $R^{15}$ is a lower alkyl group, a pyridyl-lower alkyl group or a phenyl-lower alkyl group.

The reaction of the compound [4] and the compound [5] is carried out in the same conditions as in the reaction of the compound [2] and the compound [3] in above Reaction Scheme-1.

The reaction of the compound [4] and the compound [6a] is usually carried out in the presence or absence of a basic compound in an appropriate inert solvent. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, t-butanol, etc.), acetic acid, ethyl acetate, acetone, acetonitrile, pyridine, dimethylsulfoxide, dimethylformamide, hexamethylphosphoric triamide, or a mixture of these solvents. The basic compound includes, for example, carbonates or hydrogen carbonates of alkali metal (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methylate, sodium ethylate, etc.), or organic basic compounds such as pyridine, N-ethyldiisopropylamine, dimethylaminopyridine, triethylamine, 1,5-diazabicyclo[4.3.0]nonene-5 (DBN), 1,8-diazabicyclo[5.4.0]undecene-7 (DBU), 1,4-diazabicyclo[2.2.2]octane (DABCO). The amount of the compound [4] and the compound [6a] is not critical, but the compound [6a] is usually used at least in an equimolar amount, preferably in an amount of 1 to 10 moles, to 1 mole of the compound [4]. The reaction is usually carried out at a temperature from 0° C. to about 200° C., preferably at a temperature from 0° C. to about 170° C., for 30 minutes to about 75 hours. There may be added an alkali metal halide such as sodium iodide, potassium iodide, copper powder, etc. into the reaction system.

The reaction of the compound [4] and the compound [6b] is carried out under the same condition as in the reaction of the compound [1t] and the compound [18] in the following Reaction Scheme-9.

The reaction of the compound [4] and the compound [7] is carried out in the presence of an acid in an appropriate solvent. The acid includes, for example, organic acids (e.g. acetic acid, trifluoroacetic acid, etc.), or inorganic acids (e.g. hydrochloric acid, sulfuric acid, etc.). The solvent may be the same solvents as those used in the reaction of the carboxylic acid halide and the amine compound [2] in above Reaction Scheme-1. The compound [7] is used at least in an equimolar amount, preferably in an amount of 1 to 3 moles, to 1 mole of the compound [4]. The reaction is carried out at a temperature from 0° C. to about 150° C., preferably at a temperature from room temperature to about 100° C., for 10 minutes to about 5 hours.

The reaction of the compound [4] and the compound [8] is carried out in the presence or absence of a basic compound, preferably in the absence of a basic compound, in an appropriate solvent or without a solvent. The solvent and the basic compound used therein are the same ones as those used in the reaction of the carboxylic acid halide and the amine compound [2] in above Reaction Scheme-1.

The compound [8] is usually used at least in an amount of 1 to 5 moles, preferably in an amount of 1 to 3 moles, to 1 mole of the compound [4]. The reaction is usually carried out at a temperature from 0° C. to about 200° C., preferably at a temperature from room temperature to 150° C., for 5 minutes to about 30 hours. There may be added a boron compound such as boron trifluoride ethyl ether, etc. into the reaction system.

Reaction Scheme-3

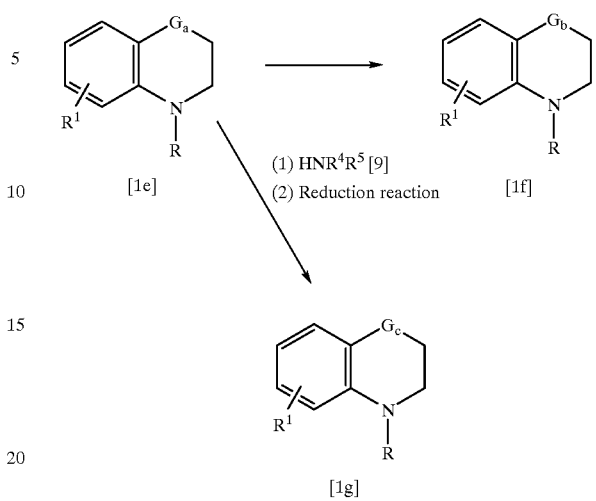

wherein $R^1$ and R are the same as defined above, $G^a$ is a group of the formula:

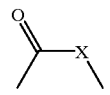

or a group of the formula:

$G_b$ is a group of the formula:

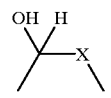

or a group of the formula:

$G_c$ is a group of the formula

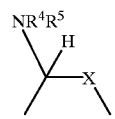

or a group of the formula:

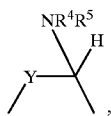

and X, Y, R⁴ and R⁵ are the same as defined above.

The reaction of converting the compound [1e] into the compound [1f] is carried out by reduction. The reduction reaction is carried out by using a hydrogenating agent. The hydrogenating agent includes, for example, lithium aluminum hydride, lithium borohydride, sodium borohydride, diboran, etc., and is used at least in an equimolar amount, preferably in an amount of 1 to 15 moles, to 1 mole of the starting compound. The reduction reaction is usually carried out in an appropriate solvent such as water, lower alcohols (e.g. methanol, ethanol, isopropanol, etc.), ethers (e.g. tetrahydrofuran, diethyl ether, diisopropyl ether, diglyme, etc.), or a mixture of these solvents. The reduction is usually carried out at a temperature from about −60° C. to 150° C., preferably at a temperature from −30° C. to 100° C., for about 10 minutes to 15 hours. When lithium aluminum hydride or diboran is used as a reducing agent, the reaction is preferably carried out in an anhydrous solvent such as tetrahydrofuran, diethyl ether, diisopropyl ether, diglyme, etc.

The reaction of converting the compound [1e] into the compound [1g] is carried out in an appropriate solvent or without a solvent in the presence or absence of a dehydrating agent. The solvent includes, for example, alcohols (e.g. methanol, ethanol, isopropanol, etc.), aromatic hydrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylacetamide, N-methylpyrrolidone, etc.), or a mixture of these solvents. The dehydrating agent includes, for example, drying agents which are conventionally used for drying solvents (e.g. molecular sieves, etc.), mineral acids (e.g. hydrochloric acid, sulfuric acid, boron trifluoride, etc.), organic acids (e.g. p-toluenesulfonic acid, acetic acid, etc.). The reaction is usually carried out at a temperature from room temperature to 250° C., preferably at a temperature from about 50° C. to about 200° C., for one to about 48 hours. The amount of the compound [9] is not critical, but it is used at least in an equimolar amount, preferably in an amount of 1 mole to excess amount, to 1 mole of the compound [1e]. The dehydrating agent is used in an excess amount when a drying agent is used, and when an acid is used as a dehydrating agent, it is used in a catalytic amount.

The subsequent reduction is carried out by various reduction reactions, for example, by catalytic hydrogenation in the presence of a catalyst in an appropriate solvent. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst is, for example, palladium, palladium-black, palladium-carbon, platinum, platinum oxide, copper chromite, Raney nickel, and the like. The catalyst is usually used in an amount of 0.02 to 1 mole to 1 mole of the starting compound. The reaction is usually carried out at a temperature from −20° C. to about 100° C., preferably at a temperature from 0° C. to about 70° C., under a pressure of 1 atm to 10 atms of hydrogen, for 0.5 hour to about 20 hours.

The above mentioned conditions for the reduction can be employed in the present reduction, but the reduction using a hydrogenating agent is more preferable. The hydrogenating agent includes, for example, lithium aluminum hydride, sodium borohydride, sodium cyanoborohydride, diboran, etc., and is used at least in an amount of 0.1 mole, preferably in an amount of 0.1 mole to 10 moles, to 1 mole of the compound [1e]. The reduction is carried out in an appropriate solvent such as water, lower alcohols (e.g. methanol, ethanol, isopropanol, etc.), ethers (e.g. tetrahydrofuran, diethyl ether, diglyme, etc.), dimethylformamide, or a mixture of these solvents, at a temperature from about −60° C. to about 50° C., preferably at a temperature from −30° C. to room temperature, for about 10 minutes to about 5 hours. When lithium aluminum hydride or diboran is used as a reducing agent, an anhydrous solvent such as diethyl ether, tetrahydrofuran, diglyme, etc., is preferably used.

Reaction Scheme-4

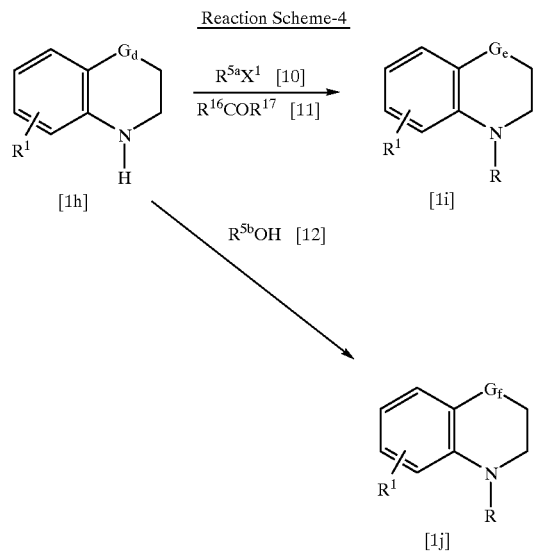

wherein R¹, R and X¹ are the same as defined above, R⁵ᵃ is a lower alkyl group having optionally a hydroxy substituent, R¹⁶ and R¹⁷ are each a hydrogen atom or a lower alkyl group, R⁵ᵇ is a benzoyl group having optionally a halogen substituent on the phenyl ring, G_d is a group of the formula:

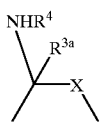

or a group of the formula:

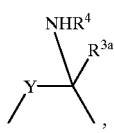

$G_e$ is a group of the formula:

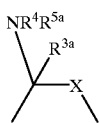

or a group of the formula:

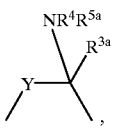

$G_f$ is a group of the formula:

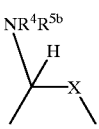

or a group of the formula:

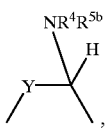

$R^{3a}$ is a hydrogen atom or a hydroxy-substituted lower alkyl group, and X, Y, $R^4$, $R^{5a}$ and $R^{5b}$ are the same as defined above.

The reaction of the compound [1h] and the compound [10] is carried out under the same conditions as those in the reaction of the compound [4] and the compound [6] in above Reaction Scheme-2.

The reaction of the compound [1h] and the compound [11] is carried out in the presence of a reducing agent in an appropriate solvent or without a solvent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture thereof. The reducing agent includes, for example, formic acid, ammonium formate, alkali metal salts of fatty acids (e.g. sodium formate, etc.), hydrogenating agents (e.g. sodium borohydride, sodium cyanoborohydride, lithium aluminum hydride, etc.), catalysts (e.g. palladium-black, palladium-carbon, platinum oxide, platinum-black, Raney nickel, etc.), and the like.

When formic acid is used as a reducing agent, the reaction is usually carried out at a temperature from room temperature to about 200° C., preferably at a temperature from about 50° C. to about 150° C., for about one to about 10 hours. Formic acid is used in an excess amount to the compound [1h].

When a hydrogenating agent is used, the reaction is usually carried out at a temperature from about −30° C. to about 100° C., preferably at a temperature from about 0° C. to about 70° C., for about 30 minutes to about 12 hours. The hydrogenating agent is used in an amount of 1 mole to 20 moles, preferably in an amount of 1 mole to 6 moles, to 1 mole of the compound [1h]. Especially, when lithium aluminum hydride is used as a reducing agent, the solvent is preferably ethers (e.g. diethyl ether, dioxane, tetrahydrofuran, diglyme, etc.) or aromatic hydrocarbons (e.g. benzene, toluene, xylene, etc.).

Moreover, when a catalyst is used, the reaction is usually carried out under atmospheric pressure to 20 atms of hydrogen, preferably, under atmospheric pressure to 10 atms of hydrogen, or in the presence of a hydrogen donor such as formic acid, ammonium formate, cyclohexene, hydrazine hydrate, etc., at a temperature from −30° C. to 100° C., preferably at a temperature from 0° C. to 60° C., for about one to 12 hours. The catalyst is usually used in an amount of 0.1 to 40% by weight, preferably in an amount of 1 to 20% by weight to the amount of the compound [1h]. The hydrogen donor is usually used in an excess amount to the compound [1h].

The compound [11] is usually used at least in an equimolar amount, preferably in an amount of 1 mole to excess amount, to 1 mole of the compound [1h].

The reaction of the compound [11] and the compound [12] is carried out under the same conditions as those of the reaction of the compound [2] and the compound [3] in above Reaction Scheme-1.

Reaction Scheme-5

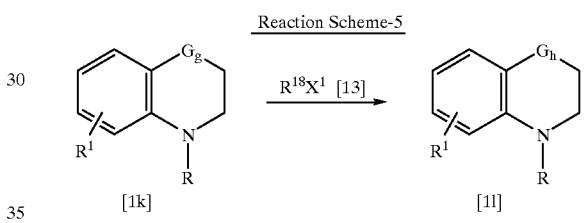

wherein $R^1$, R and $X^1$ are the same as defined above, $R^{18}$ is an amino-substituted lower alkanoyl group having optionally a lower alkyl substituent, a lower alkyl group, a lower alkoxycarbonyl-substituted lower alkyl group, a carboxy-substituted lower alkyl group or a group of the formula: —ACONR$^6$R$^7$ (A, $R^6$ and $R^7$ are the same as defined above), $G_g$ is a group of the formula:

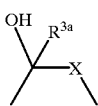

or a group of the formula:

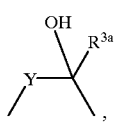

$G_h$ is a group of the formula:

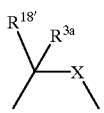

or a group of the formula:

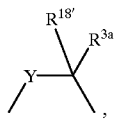

X, Y and $R^{3a}$ are the same as defined above, $R^{18'}$ is an amino-substituted lower alkanoyloxy group having optionally a lower alkyl substituent, a lower alkoxy group, a lower alkoxycarbonyl-substituted lower alkoxy group, a carboxy-substituted lower alkoxy group or a group of the formula: —O—ACONR$^6$R$^7$ (A, R$^6$ and R$^7$ are the same as defined above).

The reaction of the compound [1k] and the compound [13] is carried out under the same conditions as those in the reaction of the compound [4] and the compound [6a] in above Reaction Scheme-2.

Reaction Scheme-6

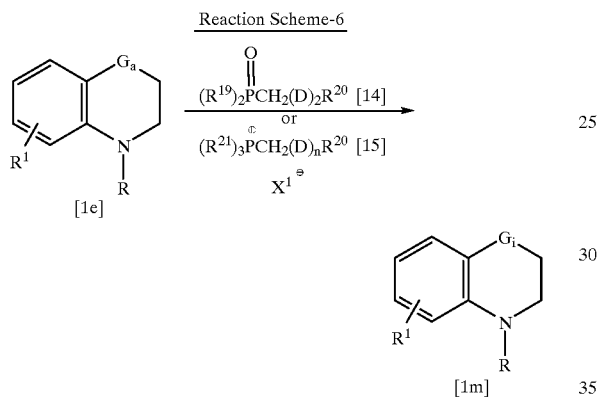

wherein $R^1$, R, $X^1$ and $G^a$ are the same as defined above, $G_i$ is a group of the formula:

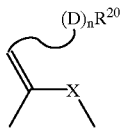

or a group of the formula:

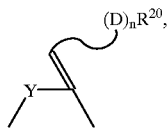

X and Y are the same as defined above, $R^{19}$ is a lower alkoxy group, $R^{20}$ is a hydrogen atom, a lower alkoxycarbonyl group, a lower alkoxy group or a phenyl group, D is a lower alkylene group, n is 0 or 1, and $R^{21}$ is a phenyl group.

The reaction of the compound [1e] and the compound [14] or the compound [15] is carried out in the presence of a basic compound in an appropriate solvent. The basic compound includes, for example, inorganic bases (e.g. sodium, potassium, sodium hydride, sodium amide, sodium hydroxide, potassium hydroxide, sodium carbonate, potassium carbonate, sodium hydrogen carbonate, etc.), organic bases such as alkali metal alcoholates (e.g. sodium methylate, sodium ethylate, potassium t-butoxide, etc.), an alkyl lithium, aryl lithium or lithium amide (e.g. methyl lithium, n-butyl lithium, phenyl lithium, lithium diisopropyl amide, etc.), pyridine, piperidine, quinoline, triethylamine, N,N-dimethylaniline, and the like. The solvent may be any solvent which does not affect the reaction, for example, ethers (e.g. diethyl ether, dioxane, tetrahydrofuran, monoglyme, diglyme, etc.), aromatic hydrocarbons (e.g. benzene, toluene, xylene, etc.), hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature from −80° C. to 150° C., preferably at a temperature from −80° C. to about 120° C., for 0.5 to about 15 hours.

Reaction Scheme-7

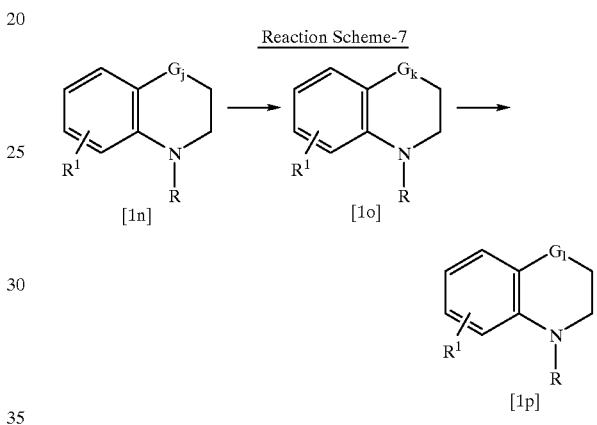

wherein $R^1$ and R are the same as defined above, $G_j$ is a group of the formula:

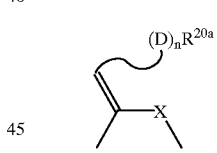

or a group of the formula:

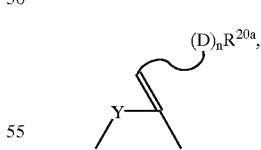

$G_k$ is a group of the formula:

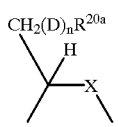

or a group of the formula:

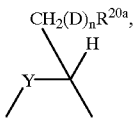

$G_l$ is a group of the formula:

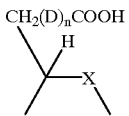

or a group of the formula:

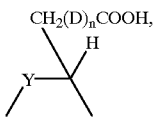

X, Y and D are the same as defined above, and $R^{20a}$ is a lower alkoxycarbonyl group.

The reaction of converting the compound [1n] into the compound [1o] is carried out under the same conditions as those in the reduction reaction of converting the compound [1e] into the compound [1g] in above Reaction Scheme-3. When a hydrogenating agent is used in said reduction reaction, there may preferably be added a metal halide such as a nickel chloride into the reaction system.

The compound [1n] may be also converted into the compound [1o] by reducing the compound [1n] with metal magnesium-methanol. The reaction is usually carried out at a temperature from 0° C. to 50° C., preferably at a temperature from 0° C. to room temperature, for one to about 10 hours. Metal magnesium is usually used in an amount of 1 to 10 moles, preferably in an amount of 1 to 7 moles, to 1 mole of the compound [1n]. When the compound [1n] wherein X is a methylene group is used in this reaction, there may be obtained the compound [1o] wherein X is a methylene group and the compound [1o] wherein X is a group of the formula: =CH—, but these compounds [1o] are easily separated.

The reaction of converting the compound [1o] into the compound [1p] is carried out in the presence or absence of an acid or a basic compound in an appropriate solvent or without a solvent. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acid, etc.). The basic compounds includes, for example, metal carbonates (e.g. sodium carbonate, potassium carbonate, etc.), metal hydroxides (e.g. sodium hydroxide, potassium hydroxide, calcium hydroxide, lithium hydroxide, etc.), and the like. The reaction is usually carried out at a temperature from room temperature to 200° C., preferably at a temperature from room temperature to 150° C., for 10 minutes to about 25 hours.

The compound [1p] is also prepared by treating the compound [1o] in an appropriate solvent in the presence of a dialkyl sulfide-Lewis acid such as dimethyl sulfide-aluminum chloride. The solvent may be the same solvents for the reaction of the compound [4] and the compound [6a] in above Reaction Scheme-2. The reaction is usually carried out at a temperature from 0° C. to 70° C., preferably at a temperature from 0° C. to 50° C., for one to 10 hours.

Reaction Scheme-8

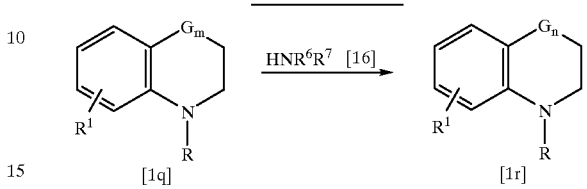

wherein $R^1$ and R are the same as defined above, $G_m$ is a group of the formula:

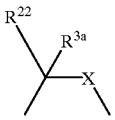

or a group of the formula:

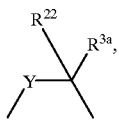

$G_n$ is a group of the formula:

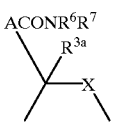

or a group of the formula:

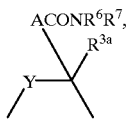

$R^{22}$ is a carboxy-substituted lower alkyl group, and $R^{3a}$, $R^6$, $R^7$, A, X and Y are the same as defined above.

The reaction of the compound [1q] and the compound [16] is carried out under the same conditions as those in the reaction of the compound [2] and the compound [3] in above Reaction Scheme-1.

Reaction Scheme-9

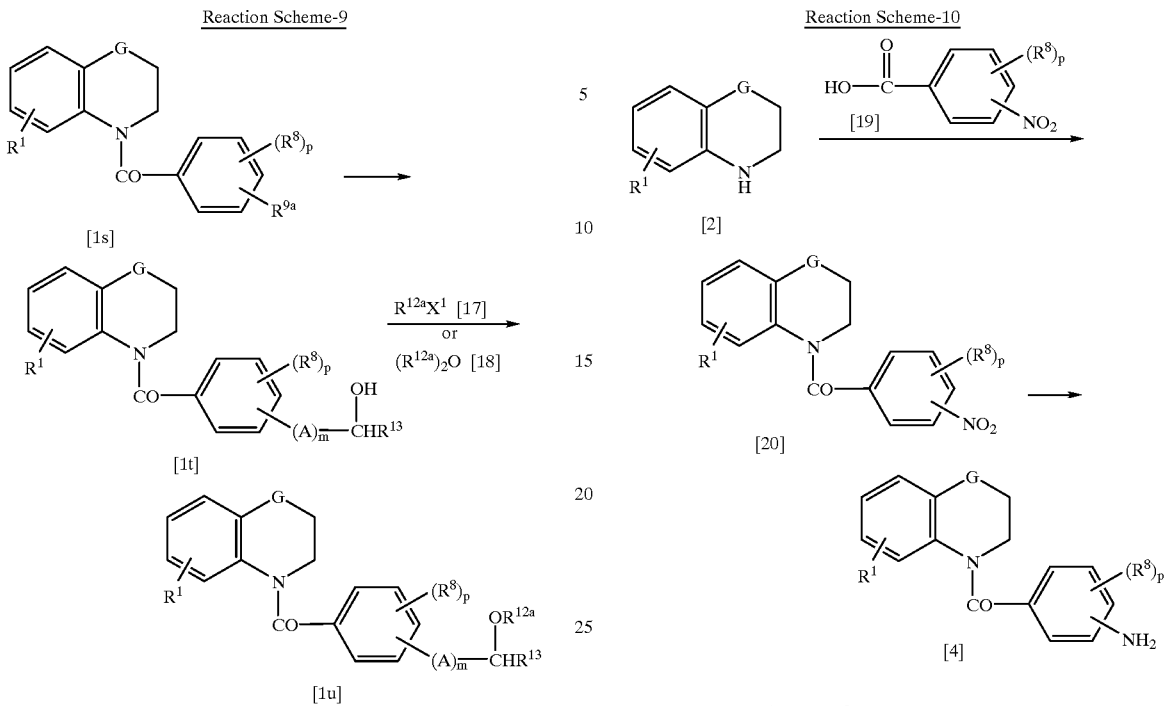

Reaction Scheme-10 wherein G, p, $R^1$, $R^8$, $X^1$, A, m and $R^{13}$ are the same as defined above, $R^{9a}$ is a benzoyl group having optionally a lower alkyl substituent on the phenyl ring, a phenyl-lower alkanoyl group having optionally a lower alkyl substituent on the phenyl ring or a benzoyl-lower alkyl group having optionally a lower alkyl substituent on the phenyl ring, and $R^{12a}$ is a lower alkanoyl group.

The reaction of converting the compound [1s] into the compound [1t] is carried out under the same conditions as those in the reaction of converting the compound [1e] into the compound [1f] in above Reaction Scheme-3.

The reaction of the compound [1t] and the compound [17] is carried out under the same conditions as those in the reaction of the compound [4] and the compound [6a] in above Reaction Scheme-2.

The reaction of the compound [1t] and the compound [18] is carried out in the presence or absence of a basic compound in an appropriate solvent or without a solvent. The solvent includes, for example, the above-mentioned aromatic hydrocarbons, lower alcohols (e.g. methanol, ethanol, propanol, etc.), dimethyl formamide, dimethyl sulfoxide, halogenated hydrocarbons (e.g. chloroform, methylene chloride, etc.), acetone, pyridine, and the like. The basic compound includes, for example, organic bases (e.g. triethylamine, pyridine, etc.), sodium hydroxide, potassium hydroxide, sodium hydride, and the like. The reaction is also carried out in the presence of a mineral acid (e.g. sulfuric acid, etc.) in a solvent such as acetic acid.

The compound [18] is used in an amount of 1 mole to excess amount, to 1 mole of the starting compound. The reaction is usually carried out at a temperature from 0° C. to about 200° C., preferably at a temperature from 0° C. to about 150° C., for 0.5 hour to about 20 hours.

The starting compound [2a] can be prepared by the processes as illustrated by the following Reaction Scheme.

wherein G, p, $R^1$ and $R^8$ are the same as defined above.

The reaction of the compound [2] and the compound [19] is carried out under the same conditions as those in the reaction of the compound [2] and the compound [3] in above Reaction Scheme-1.

The reaction of converting the compound [20] into the compound [4] is carried out by (i) subjecting the compound [20] to reduction reaction by using a catalyst in an appropriate solvent, or (ii) subjecting the compound [20] to reduction reaction by using a mixture of a metal or a metal salt with an acid, a metal or a metal salt with an alkali metal hydroxide, a sulfide, an ammonium salt in an appropriate inert solvent.

When (i) a catalyst is used, the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethylformamide, etc.), or a mixture of these solvents. The catalyst includes, for example, palladium, palladium-black, palladium-carbon, platinum, platinum oxide, copper chromite, Raney nickel, and the like. The catalyst is used in an amount of 0.02 to 1 mole, to 1 mole of the starting compound. The reaction is usually carried out at a temperature from −20° C. to 150° C., preferably at a temperature from 0° C. to about 100° C., under a pressure of 1 to 10 atms of hydrogen, for 0.5 hour to 10 hours. There may be added an acid such as hydrochloric acid into the reaction system.

When the method (ii) is employed, there is used as a reducing agent a mixture of iron, zinc, tin or stannous chloride and a mineral acid (e.g. hydrochloric acid, sulfuric acid, etc.), or a mixture of iron, iron sulfide, zinc or tin and an alkali metal hydroxide (e.g. sodium hydroxide, etc.), a sulfide (e.g. ammonium sulfide, etc.), aqueous ammonia, an ammonium salt (e.g. ammonium chloride, etc.). The inert solvent includes, for example, water, acetic acid, methanol, ethanol, dioxane, and the like. The conditions for the above reduction can be selected according to the kinds of the reducing agent to be used. For example, when a mixture of stannous chloride and hydrochloric acid is used as a reducing agent, the reaction is preferably carried out at a temperature from 0° C. to about 80° C., for 0.5 hour to about 10 hours. The reducing agent may be used at least in an equimolar amount, usually in an amount of 1 to 5 moles, to 1 mole of the starting compound.

The starting compound [3] is prepared by the processes as illustrated by the following Reaction Schemes.

example, ethers (e.g. 1,2-dimethoxyethane, diethyl ether, tetrahydrofuran, dioxane, etc.), acetonitrile, dimethylformamide, and the like. The catalyst includes, for example, palladium compounds or nickel compounds such as tetrakistriphenylphosphine palladium [Pd(PPh$_3$)$_4$], palladium acetate [Pd(OCOCH$_3$)$_2$], palladium chloride [PdCl$_2$], bistriphenylphosphinenickel dichloride [Ni(PPh$_3$)$_2$Cl$_2$], and the like. The reaction is usually carried out at a temperature

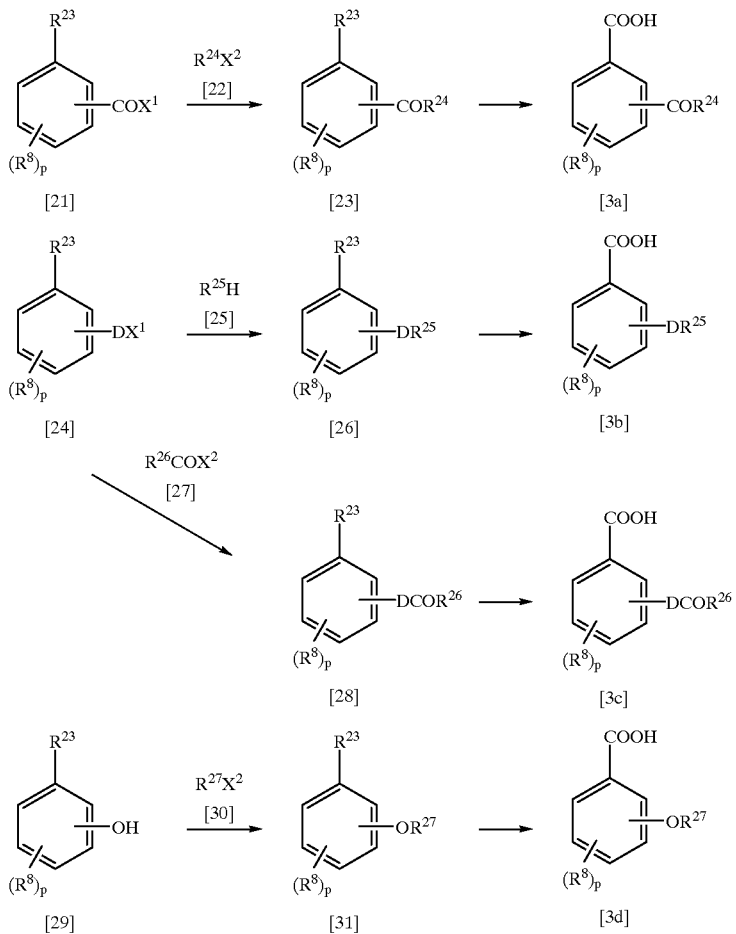

Reaction Scheme-11 wherein p, R$^8$, D and X$^1$ are the same as defined above, R$^{24}$ is a phenyl-lower alkyl group having optionally a lower alkyl substituent on the phenyl ring, X$^2$ is a halogen atom, R$^{23}$ is a lower alkoxycarbonyl group, R$^{25}$ is a phenoxy group having optionally a lower alkyl substituent on the phenyl ring, R$^{26}$ is a phenyl group having optionally a lower alkyl substituent on the phenyl ring, R$^{27}$ is a phenyl-lower alkyl group having optionally a substituent selected from a halogen atom, a lower alkoxycarbonyl group and an aminocarbonyl group having optionally a substituent selected from a lower alkyl group and an amino-substituted lower alkyl group having optionally a lower alkyl substituent, or a benzoyl-lower alkyl group having optionally a halogen substituent on the phenyl ring.

The reaction of the compound [21] and the compound [22] and the reaction of the compound [24] and the compound [27] are carried out in the presence of zinc and a catalyst in an appropriate solvent. The solvent includes, for from 0° C. to 70° C., preferably at a temperature from 0° C. to about 50° C., for 1 hour to about 80 hours.

The compound [24] or the compound [27] is used at least in an equimolar amount, preferably in an amount of 1 to 2 moles, to 1 mole of the compound [21] or the compound [22], respectively. The catalyst is usually used in an amount of 0.01 to about 1 mole, preferably in an amount of 0.03 to about 0.3 mole, to 1 mole of the starting compound.

The reaction of the compound [24] and the compound [25] and the reaction of the compound [29] and the compound [30] are carried out under the same conditions as those in the reaction of the compound [4] and the compound [6a] in above Reaction Scheme-2.

The reaction of converting the compound [23], [26], [28] or [31] into the compound [3a], [3b], [3c] or [3d], respectively, is carried out under the same conditions as those in the reaction of converting the compound [1o] into the compound [1p] in above Reaction Scheme-7.

Reaction Scheme-12

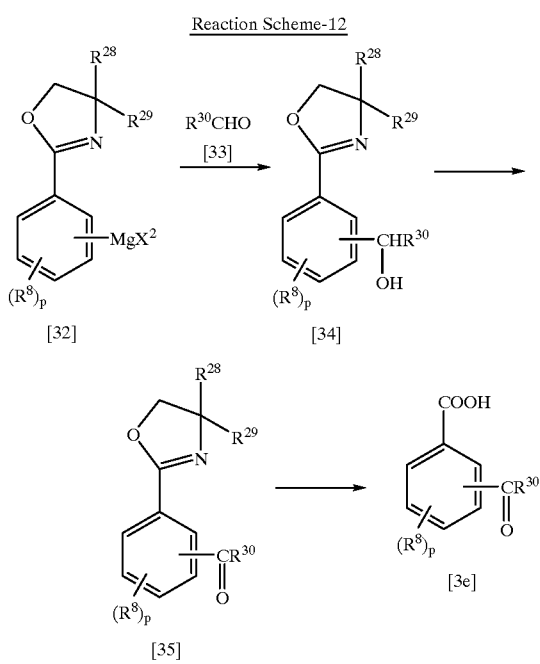

wherein $R^{28}$ and $R^{29}$ are each a lower alkyl group, $R^{30}$ is a phenyl group having optionally a lower alkyl substituent on the phenyl ring, and p, $R^8$ and $X^2$ are the same as defined above.

The reaction of the compound [32] and the compound [33] is carried out in an appropriate solvent. The solvent may be any solvents used in Grignard reaction, but preferably ethers (e.g. diethyl ether, dioxane, tetrahydrofuran, etc.), aromatic hydrocarbons (e.g. benzene, toluene, etc.), saturated hydrocarbons (e.g. pentane, hexane, heptane, cyclohexane, etc.), and the like. The compound [33] is usually used at least in an equimolar amount, preferably in an amount of 1 to 2 moles, to 1 mole of the compound [32]. The reaction is usually carried out at a temperature from −70° C. to 50° C., preferably at a temperature from −30° C. to room temperature, for 1 to about 50 hours.

The reaction of converting the compound [34] into the compound [35] is carried out in the presence of an oxidizing agent in an appropriate solvent. The oxidizing agent includes, for example, chromic acid pyridinium salts (e.g. pyridinium chlorochromate, pyridinium dichlorochromate, etc.), dimethyl sulfoxide-oxazolyl chloride, dichromic acid, dichromates (e.g. sodium dichromate, potassium dichromate, etc.), permanganic acid, permanganates (e.g. potassium permanganate, sodium permanganate, etc.), manganese dioxide, 2,3-dichloro-5,6-dicyano-1,4-benzoquinone (DDQ), and the like. The solvent used in the reaction with an oxidizing agent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), ethers (e.g. tetrahydrofuran, diethyl ether, dioxane, etc.), dimethylsulfoxide, dimethylformamide, or a mixture of these solvents. The oxidizing agent is usually used at least in an equimolar amount, preferably in an amount of 1 mole to 25 moles, to 1 mole of the starting compound. The reaction is usually carried out at a temperature from about 0° C. to about 100° C., preferably at a temperature from 0° C. to about 70° C., for 1 hour to about 7 hours.

The reaction of converting the compound [35] into the compound [3e] is carried out by subjecting the compound [35] to alkylation in the presence of an alkylating agent in an appropriate solvent, followed by subjecting the product to hydrolysis, or by subjecting directly the compound [35] to hydrolysis.

In the alkylation of the compound [35], the alkylating agent used therein includes, for example, an alkyl halide such as methyl iodide, etc. The alkylation reaction is usually carried out at a temperature from room temperature to about 200° C., preferably at a temperature from room temperature to about 150° C., for 1hour to about 30 hours. The solvent includes, for example, ethers (e.g. dioxane, tetrahydrofuran, ethylene glycol dimethyl ether, diethyl ether, etc.), aromatic hydrocarbons (e.g. benzene, toluene, xylene, etc.), halogenated hydrocarbons (e.g. dichloromethane, chloroform, carbon tetrachloride, etc.), lower alcohols (e.g. methanol, ethanol, isopropanol, etc.), polar solvents (e.g. dimethylsulfoxide, dimethylformamide, hexamethylphosphoric triamide, acetone, acetonitrile, nitromethane, etc.), and the like. The alkylating agent is usually used in an equimolar amount, preferably in an amount of 1 to 8 moles, to 1 mole of the compound [35].

The subsequent hydrolysis may be carried out by a conventional method, for example, by in the presence of a basic compound (e.g. sodium carbonate, potassium carbonate, lithium hydroxide, sodium hydroxide, potassium hydroxide, barium hydroxide, etc.), or a mineral acid (e.g. hydrochloric acid, sulfuric acid, etc.), or an organic acid (e.g. acetic acid, etc.), in a solvent such as water, alcohols (e.g. methanol, ethanol, isopropanol, etc.), ketones (e.g. acetone, methyl ethyl ketone, etc.), ethers (e.g. dioxane, ethylene glycol dimethyl ether, etc.), acetic acid, or a mixture of these solvents. The reaction is usually carried out at a temperature from room temperature to 200° C., preferably at a temperature from room temperature to 150° C., for 0.5 hour to 20 hours.

In the reaction of subjecting directly the compound [35] to hydrolysis, the reaction is carried out under the same conditions as those in the above hydrolysis. The reaction is carried out for 1 hour to 30 hours.

The compound [3e] is also prepared by subjecting the compound [35] to hydrolysis in the presence of a mineral acid (e.g. sulfuric acid, hydrochloric acid, nitric acid, etc.), or in the presence of an organic acid (e.g. acetic acid, aromatic sulfonic acid, etc.) under the same conditions such as solvents, reaction temperature, reaction period, as those in the above hydrolysis reaction.

The starting compound [32] is prepared by the processes as illustrated in the following Reaction Scheme.

Reaction Scheme-13

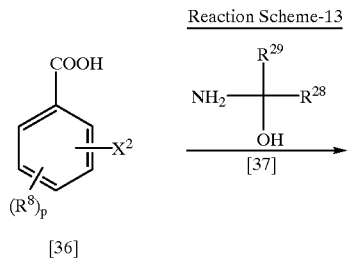

-continued

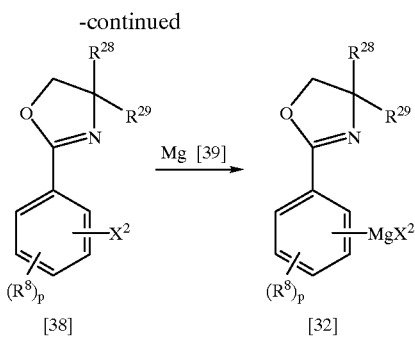

wherein p, $R^8$, $X^2$, $R^{28}$, $R^{29}$ and $X^2$ are the same as defined above.

The reaction of the compound [36] and the compound [37] is carried out under the same conditions as those in the reaction of the compound [2] and the compound [3] in above Reaction Scheme-1 wherein a carboxylic acid halide is used. The compound [37] is used at least in an equimolar amount, preferably in an amount of 1 to 2 moles, to 1 mole of the compound [36].

The reaction of the compound [38] and the compound [39] is carried out in a solvent such as ethers (e.g. diethyl ether, tetrahydrofuran, dioxane, monoglyme, diglyme, etc.), aromatic hydrocarbons (e.g. benzene, toluene, xylene, etc.), aliphatic hydrocarbons (e.g. n-hexane, heptane, cyclohexane, etc.), at a temperature from 0° C. to 150° C., preferably at a temperature from 0° C. to about 100° C., for 0.5 hour to about 5 hours. The compound [39] is used at least in an equimolar amount, preferably in an amount of 1 to 1.5 mole, to 1 mole of the compound [38].

Reaction Scheme-14

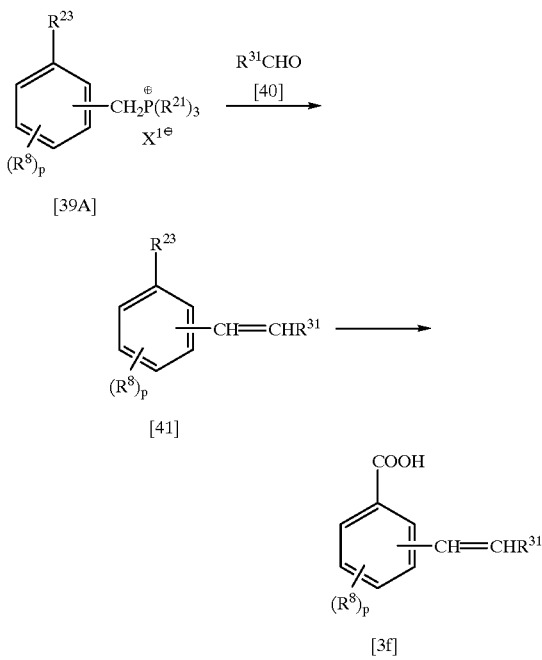

wherein p, $R^8$, $R^{23}$, $R^{21}$ and $X^1$ are the same as defined above, and $R^{31}$ is a phenyl group having optionally a halogen substituent.

The reaction of the compound [39A] and the compound [40] is carried out under the same conditions as those in the reaction of the compound [1e] and the compound [14] or the compound [15] in above Reaction Scheme-6.

The reaction of converting the compound [41] into the compound [3f] is carried out under the same conditions as those in the reaction of converting the compound [1o] into the compound [1p] in above Reaction Scheme-6.

Reaction Scheme-15

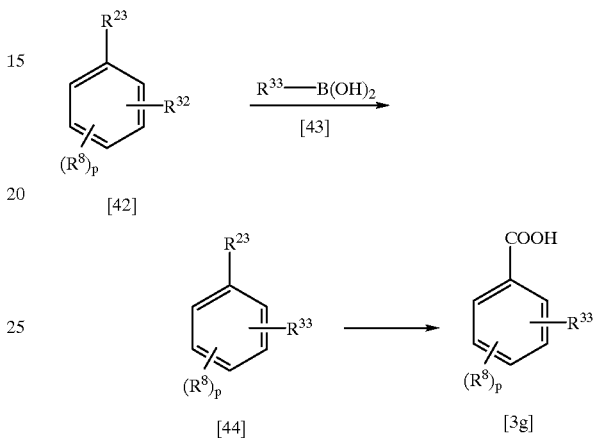

wherein p, $R^8$ and $R^{23}$ are the same as defined above, $R^{32}$ is a lower alkylsulfonyloxy group having optionally a halogen substituent, or a halogen atom, and $R^{33}$ is a phenyl group having optionally a substituent selected from a lower alkyl group, a lower alkoxy group, a phenyl-lower alkoxy group, a nitro group, an amino group having optionally a lower alkanoyl substituent, a hydroxy group, a lower alkanoyloxy group, a halogen-substituted lower alkoxy group, a phenyl group and an amino-substituted lower alkoxy group having optionally a lower alkyl substituent.

The reaction of the compound [42] and the compound [43] is carried out in an appropriate solvent in the presence or absence of a lithium compound such as lithium chloride, etc., in the presence of a basic compound and a catalyst. The solvent may be the same solvents as those used in the reaction of the compound [38] and the compound [39] in above Reaction Scheme-13. The basic compound may be the same basic compounds as those used in the reaction of the compound [2] and the compound [3] in above Reaction Scheme-1 wherein a carboxylic acid halide is used. The catalyst includes, for example, tetrakis(triphenylphosphine) palladium, palladium chloride, and the like. The reaction is usually carried out at a temperature from room temperature to 200° C., preferably at a temperature from room temperature to about 150° C., for one to about 10 hours. The basic compound and the lithium compound are each used at least in an equimolar amount, preferably in an amount of 1 to 2 moles, to 1 mole of the compound [42]. The catalyst is used in a catalytic amount.

The reaction of converting the compound [44] into the compound [3g] is carried out under the same conditions as those in the reaction of converting the compound [1o] into the compound [1p] in above Reaction Scheme-7.

Reaction Scheme-16

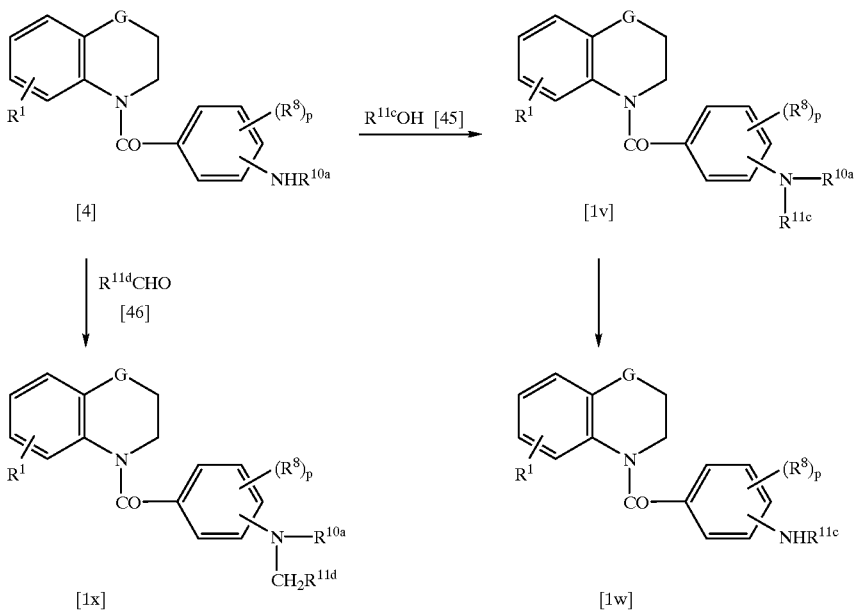

wherein G, p, $R^1$, $R^8$ and $R^{10a}$ are the same as defined above, $R^{11c}$ is a phenyl-lower alkyl group having optionally a substituent selected from a lower alkyl group and a halogen atom on the phenyl ring, and having optionally a hydroxy substituent on the alkyl moiety, a benzoyl-lower alkyl group, or a phenoxy-lower alkyl group having optionally a lower alkyl substituent on the phenyl ring, $R^{11d}$ is in addition to the groups for $R^{11c}$, a phenyl group having optionally a substituent selected from a lower alkyl group and a halogen atom.

The reaction of the compound [4] and the compound [45] is carried out in the presence of a dialkyl azodicarboxylate (e.g. diethyl azodicarboxylate, dibutyl diazodicarboxylate, etc.), a dialkyl azodicarboxyamide (e.g. 1,1'-azodicarbonyldi(piperidine), etc.), and a phosphorus compound (e.g. a trialkylphosphine, a triarylphosphine, etc.). The solvent includes, for example, ethers (e.g. tetrahydrofuran, 1,2-dimethoxyethane, diethyl ether, diisopropyl ether, diglyme, etc.), aromatic hydrocarbons (e.g. benzene, toluene, etc.), or a mixture of these solvents. The dialkyl azodicarboxylate, the phosphorus compound and the compound [45] are each used at least in an equimolar amount, preferably in an amount of 1 to 3 moles, to 1 mole of the compound [4]. The reaction is usually carried out at a temperature from –20° C. to 100° C., preferably at a temperature from –20° C. to 50° C., for 1 hour to 30 hours.

The compound [1v] wherein $R^{10a}$ is a lower alkanoyl group having optionally a halogen substituent may be converted into the corresponding compound [1w] by subjecting the compound [1v] to hydrolysis. The hydrolysis is carried out under the same conditions as those in the hydrolysis of the compound [1] wherein $R^9$ is a phenyl group having at least one lower alkanoyloxy substituent on the phenyl ring.

The reaction of the compound [4] and the compound [46] is carried out under the same conditions as those in the reaction of converting the compound [1e] into the compound [1g] in above Reaction Scheme-3. The compound [46] is used at least in an equimolar amount, preferably in an amount of 1 to 3 moles, to 1 mole of the compound [4].

Reaction Scheme-17

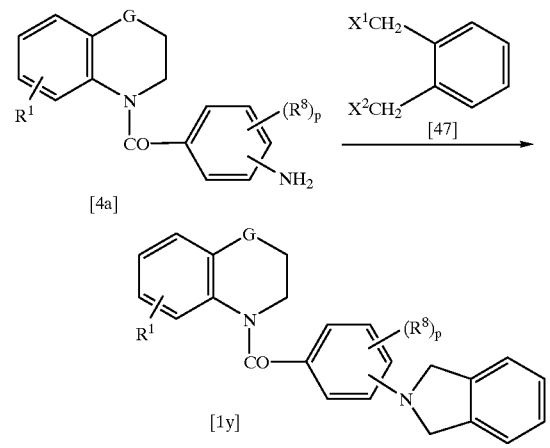

wherein G, p, $R^1$, $R^8$, $X^1$ and $X^2$ are the same as defined above.

The reaction of the compound [4a] and the compound [47] is carried out under the same conditions as those in the reaction of the compound [4] and the compound [6a] in above Reaction Scheme-2.

Reaction Scheme-18

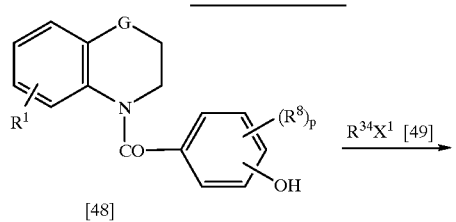

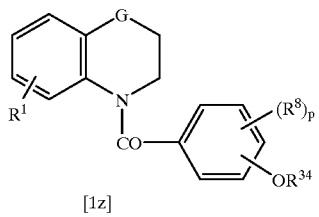

[1z]

wherein G, p, $R^1$, $R^8$ and $X^1$ are the same as defined above, and $R^{34}$ is a lower alkyl group, a lower alkanoyl group, a phenyl-lower alkyl group having optionally a substituent selected from a halogen atom, a lower alkoxycarbonyl group, an aminocarbonyl group having optionally a substituent selected from a lower alkyl group and an amino-substituted lower alkyl group having optionally a lower alkyl substituent on the phenyl ring, or a pyrrolidinyl-substituted lower alkyl group.

The reaction of the compound [48] and the compound [49] is carried out under the same conditions as those in the reaction of the compound [4] and the compound [6a] in above Reaction Scheme-2.

Reaction Scheme-19

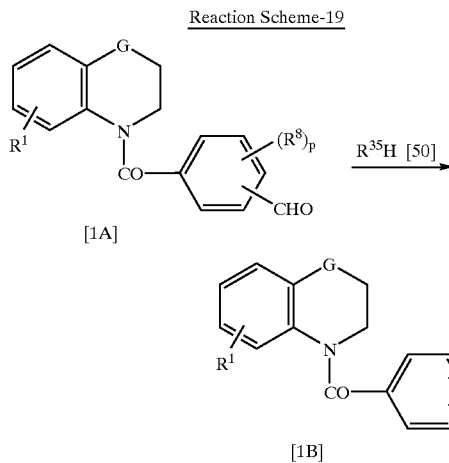

wherein G, p, $R^1$ and $R^8$ are the same as defined above, and $R^{35}$ is an anilino group having optionally a lower alkyl substituent on the phenyl ring.

The reaction of the compound [1A] and the compound [50] is carried out under the same conditions as those in the reaction of converting the compound [1e] into the compound [1g] in above Reaction Scheme-3. The compound [50] is used at least in an equimolar amount, preferably in an amount of 1 to 5 moles, to 1 mole of the compound [1A].

Reaction Scheme-20

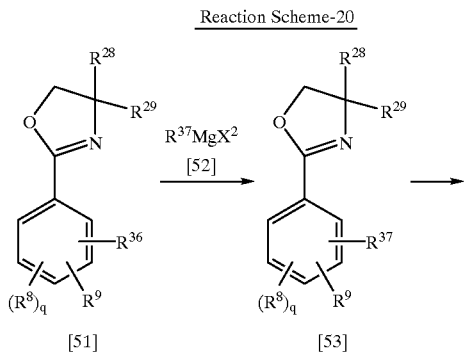

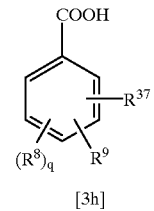

[3h]

wherein $R^{36}$ is a lower alkoxy group or a halogen atom, $R^{37}$ is a lower alkyl group, $R^8$, $R^{28}$, $R^{29}$, $R^9$ and $X^2$ are the same as defined above, and q is 0 or 1.

The reaction of the compound [51] and the compound [52] is carried out under the same conditions as those in the reaction of the compound [32] and the compound [33] in above Reaction Scheme-12. The compound [52] is used at least in an equimolar amount, preferably in an amount of 1 to 2 moles, to 1 mole of the compound [51].

Reaction Scheme-21

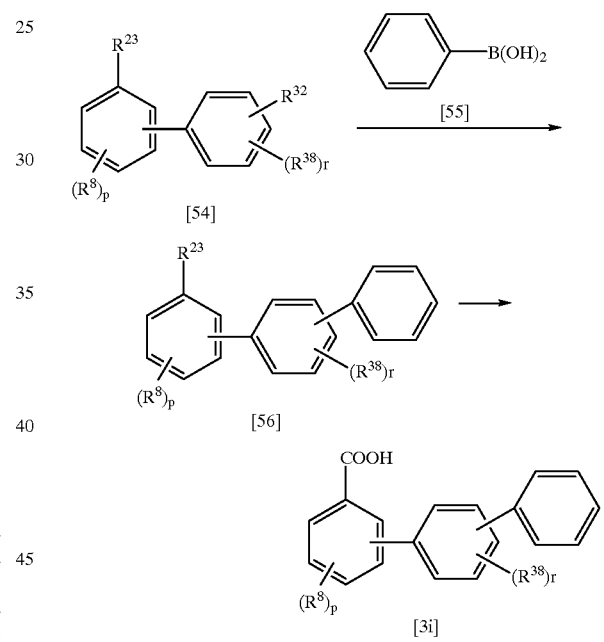

wherein $R^8$, p, $R^{32}$ and $R^{23}$ are the same as defined above, $R^{38}$ is a lower alkyl group, a lower alkoxy group, a phenyl-lower alkoxy group, a hydroxy group, a lower alkanoyloxy group, a halogen-substituted lower alkoxy group, a nitro group, an amino group having optionally a lower alkanoyl substituent, a phenyl group, or an amino-substituted lower alkoxy group having optionally a lower alkyl substituent, and r is 0, 1 or 2.

The reaction of the compound [54] and the compound [55] is carried out under the same conditions as those in the reaction of the compound [42] and the compound [43] in above Reaction Scheme-15.

The reaction of converting the compound [56] into the compound [3i] is carried out under the same conditions as those in the reaction of converting the compound [44] into the compound [3g] in above Reaction Scheme-15.

Reaction Scheme-22

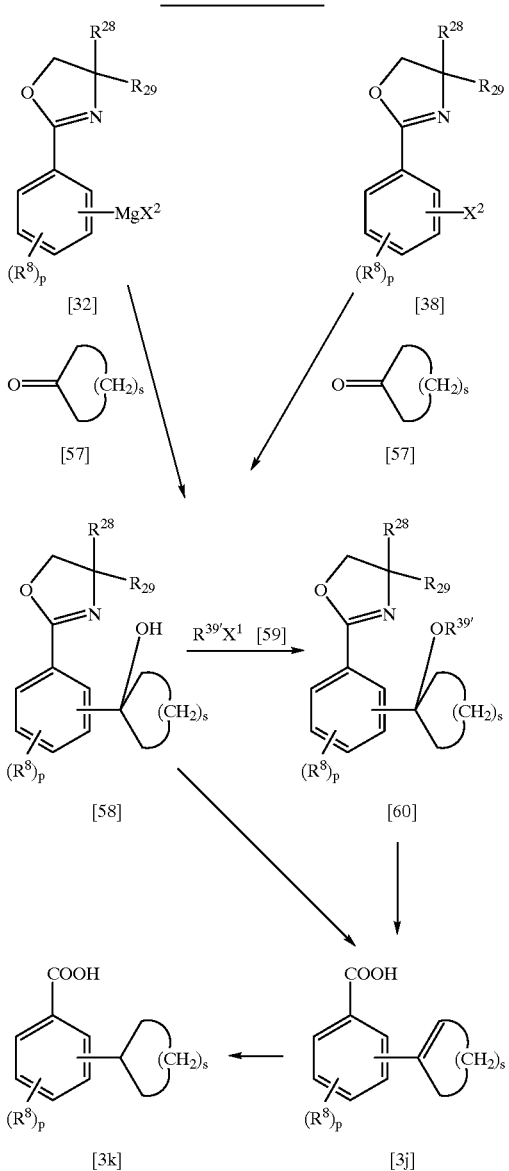

wherein $R^{28}$, $R^{29}$, $R^8$, p, $X^1$ and $X^2$ are the same as defined above, s is an integer of 0 to 5, and $R^{39'}$ is a lower alkyl group.

The reaction of the compound [32] and the compound [57] is carried out under the same conditions as those in the reaction of the compound [32] and the compound [33] in above Reaction Scheme-12.

The reaction of the compound [58] and the compound [59] is carried out under the same conditions as those in the reaction of the compound [4] and the compound [6a] in above Reaction Scheme-2.

The reaction of the compound [38] and the compound [57] is carried out under the same conditions as those in the reaction of the compound [1e] and the compound [14] or the compound [15] in above Reaction Scheme-6. The compound [57] is used at least in an equimolar amount, preferably in an amount of 1 to 1.5 mole, to 1 mole of the compound [38].

The reaction of converting the compound [58] or the compound [60] into the compound [3j] is carried out under the same conditions as those in the reaction of converting the compound [1o] into the compound [1p] in above Reaction Scheme-7, except the reaction is carried out for 1 hour to about 50 hours.

The reaction of converting the compound [3j] into the compound [3k] is carried out under the same conditions as those in the reaction of converting the compound [1e] into the compound [1g] in above Reaction Scheme-3.

Reaction Scheme-23

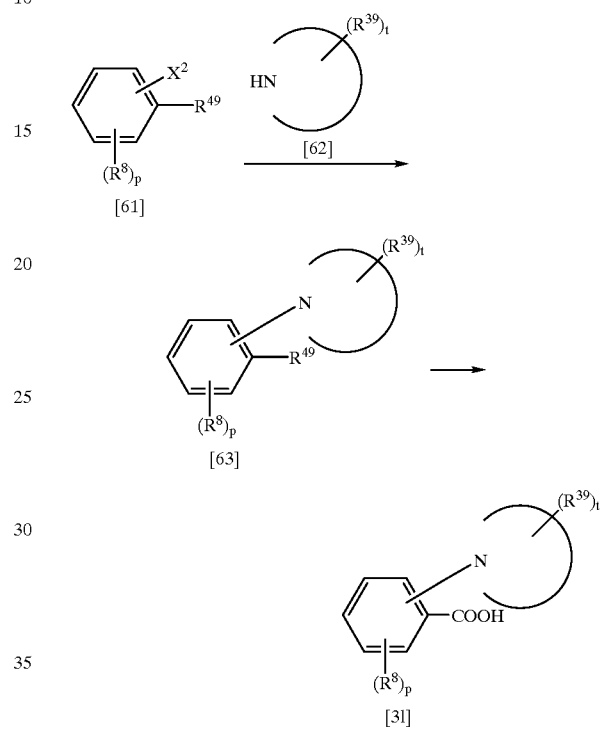

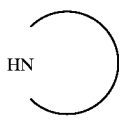

wherein $R^8$, p and $X^2$ are the same as defined above, $R^{49}$ is a cyano group, a lower alkoxycarbonyl group or a carboxy group, $R^{39}$ is a lower alkyl group, a phenyl group, a lower alkanoyl group, a halogen atom, a phenyl lower alkyl group, or an oxo group, and t is an integer of 0 to 3, and the group of the formula:

is a 5- to 11-membered, saturated or unsaturated heteromonocyclic or heterobicyclic group containing 1 to 4 heteroatoms selected from a nitrogen atom, an oxygen atom and a sulfur atom.

The reaction of the compound [61] and the compound [62] is carried out under the same conditions as those in the reaction of the compound [4] and the compound [6a] in above Reaction Scheme-2.

When the compound [63] is a compound of the formula [63] wherein $R^{49}$ is a cyano group or a lower alkoxycarbonyl group, the reaction of converting the compound [63] into the compound [3k] is carried out under the same conditions as those in the reaction of converting the compound [1o] into the compound [1p] in above Reaction Scheme-7.

Reaction Scheme-24

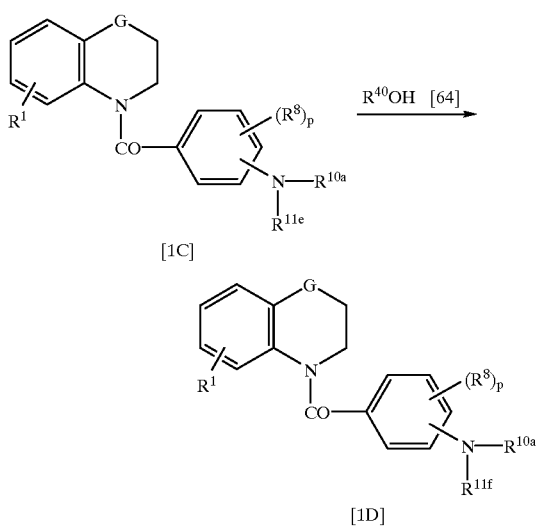

wherein G, $R^1$, $R^8$, p and $R^{10a}$ are the same as defined above, $R^{11e}$ is a lower alkanoyl group having a halogen substituent, $R^{40}$ is a phenyl group having optionally a substituent selected from a lower alkyl group, a phenyl group, a lower alkoxy group, a halogen-substituted lower alkyl group, an amino group having optionally a lower alkyl substituent, a lower alkanoyl-substituted amino group, a nitro group and a halogen atom, a lower alkyl group, a lower alkanoyl group, a quinolyl group, a tetrahydroquinolyl group having optionally a substituent selected from a lower alkyl group and an oxo group on the quinoline ring, or a tetrahydronaphthyl group, $R^{11f}$ is a phenoxy-lower alkanoyl group having optionally a substituent selected from a lower alkyl group, a phenyl group, a lower alkoxy group, a halogen-substituted lower alkyl group, an amino group having optionally a lower alkyl substituent, a lower alkanoyl-substituted amino group, a nitro group and a halogen atom on the phenyl ring, a lower alkoxy-substituted lower alkanoyl group, a lower alkanoyloxy-substituted lower alkanoyl group, a quinolyloxy-substituted lower alkanoyl group, a tetrahydroquinolyloxy-substituted lower alkanoyl group having optionally a substituent selected from a lower alkyl group and an oxo group on the quinoline ring, or a tetrahydronaphthyloxy-substituted lower alkanoyl group.

The reaction of the compound [1C] and the compound [63] is carried out under the same conditions as those in the reaction of the compound [4] and the compound [6a] in above Reaction Scheme-2.

The compound [1D] wherein $R^{11f}$ is a lower alkanoyloxy-substituted lower alkanoyl group is reacted under the same conditions as those in the reaction of converting the compound [1o] into the compound [1p] in above Reaction Scheme-7 to give the compound [1D] wherein the corresponding $R^{11f}$ is a lower alkanoyl group having a hydroxy substituent.

Reaction Scheme-25

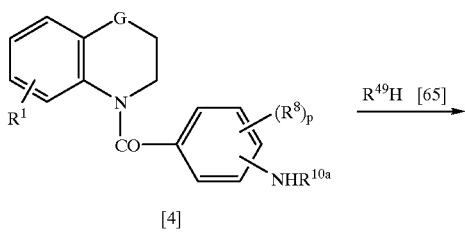

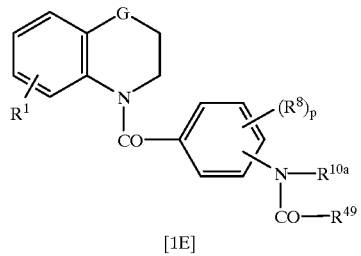

wherein $R^1$, G, $R^8$, p and $R^{10a}$ are the same as defined above, and $R^{49}$ is a tetrahydroisoquinolyl group or a group of the formula:

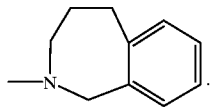

The reaction of converting the compound [4] into the compound [1E] is carried out by (i) reacting the compound [4] with a carbonylating agent in the presence of a basic compound in an appropriate solvent, followed by (ii) reacting the resulting product with the compound [65] in the presence of a basic compound in an appropriate solvent.

The solvent and the basic compound used in the above process (i) may be each the same ones as those used in the reaction of reacting a carboxylic acid halide with the amine compound [2] in above Reaction Scheme-1. The carbonylating agent includes, for example, carbonyldiimidazole, phosgene, diphosgene, urea, triphosgene, etc. The carbonylating agent is usually used in an amount of 0.05 to 1 mole, preferably in an amount of 0.1 to 1 mole, to 1 mole of the compound [4]. The reaction is usually carried out at a temperature from 0° C. to 200° C., preferably at a temperature from 0° C. to about 180° C., for 1 hour to about 10 hours.

The solvent and the basic compound used in the above process (ii) may be each the same ones as those used in the process (i). The processes (i) and (ii) are carried out in one-pot system. The compound [65] is used in an amount of 1 to 5 moles, preferably in an amount of 1 to 3 moles, to 1 mole of the compound [4]. The reaction is usually carried out at a temperature from room temperature to 150° C., preferably at a temperature from room temperature to about 120° C., for 0.5 hour to about 5 hours.

Reaction Scheme-26

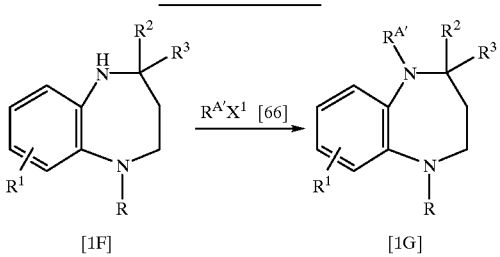

wherein $R^1$, $R^2$, $R^3$, R and $X^1$ are the same as defined above, and $R^{A'}$ is the same groups as those for $R^A$ other than a hydrogen atom.

The reaction of the compound [1F] and the compound [66] is carried out under the same conditions as those in the reaction of the compound [4] and the compound [6a] in above Reaction Scheme-2.

Reaction Scheme-27

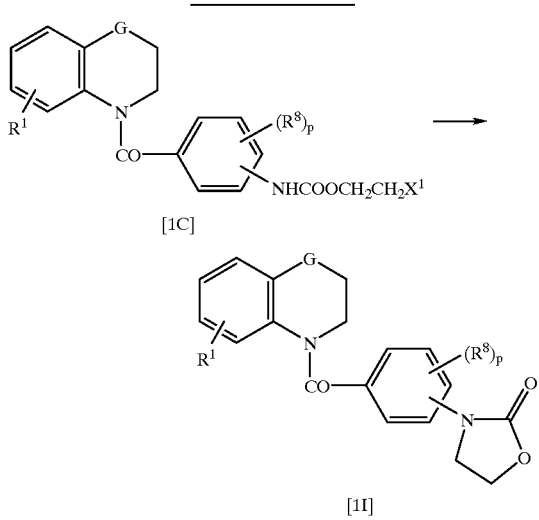

wherein $R^1$, G, $R^8$, p and $X^1$ are the same as defined above.

The reaction of converting the compound [1H] into the compound [1I] is carried out under the same conditions as those in the reaction of the compound [4] and the compound [6a] in above Reaction Scheme-2.

Reaction Scheme-28

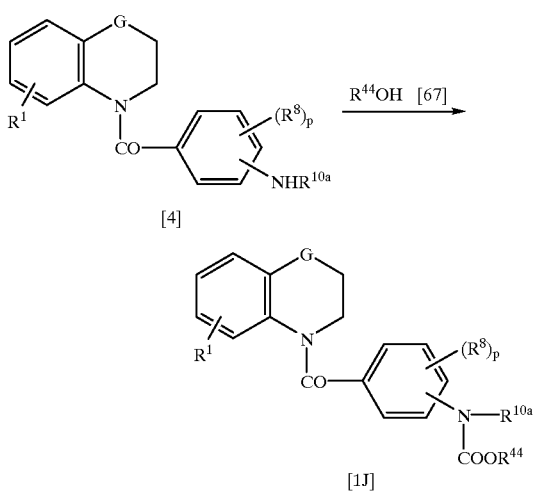

wherein $R^1$, G, $R^8$, p and $R^{10a}$ are the same as defined above, $R^{44}$ is a lower alkyl group having optionally a halogen substituent, a phenoxy-lower alkyl group, a phenyl-lower alkyl group, a pyridyl-lower alkyl group, a fluorenyl-lower alkyl group, a lower alkenyl group or a piperidinyl-lower alkyl group having optionally a substituent selected from a lower alkanoyl group, a lower alkoxycarbonyl group and a lower alkyl group on the piperidine ring.

The reaction of converting the compound [4] into the compound [67] is carried out under the same conditions as those in the reaction of converting the compound [4] into the compound [1E] in above Reaction Scheme-25.

Reaction Scheme-29

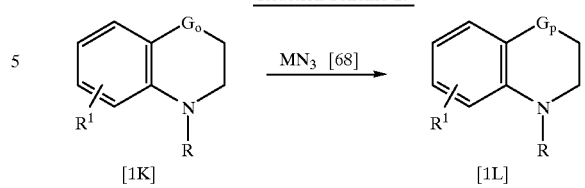

wherein $R^1$ and R are the same as defined above, $G_o$ is a group of the formula:

or a group of the formula:

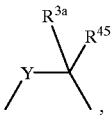

$G_p$ is a group of the formula:

or a group of the formula:

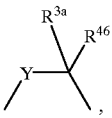

$R^{3a}$, X and Y are the same as defined above, $R^{45}$ is a cyano-substituted lower alkyl group, $R^{46}$ is a tetrazolyl-substituted lower alkyl group, and M is an alkali metal such as sodium, potassium, etc.

The reaction of converting the compound [1K] into the compound [1L] is carried out by reacting the compound [1K] with the compound [68] in the presence of a basic compound in an appropriate solvent. The solvent includes, for example, halogenated hydrocarbons (e.g. chloroform, dichloromethane, dichloroethane, carbon tetrachloride, etc.), alcohols (e.g. methanol, ethanol, isopropanol, etc.), aromatic hydrocarbons (e.g. benzene, toluene, xylene, etc.), ethers (e.g. dioxane, diethylene glycol dimethyl ether, diethyl ether, tetrahydrofuran, etc.), polar solvents (e.g. dimethylformamide, dimethylacetamide, N-methylpyrrolidone, acetic anhydride, acetonitrile, dimethyl sulfoxide, hexamethylphosphoric triamide, etc.). The basic compound includes, for example, inorganic bases (e.g. sodium hydroxide, potassium hydroxide, sodium carbonate, sodium hydrogen carbonate, potassium hydrogen carbonate, potassium carbonate, sodium methoxide, sodium ethoxide, sodium hydride, sodium, potassium, sodium amide, etc.), or organic bases (e.g. N,N-dimethylaniline, piperidine, pyridine, triethylamine, sodium acetate, potassium acetate, etc.). The compound [68] is used at least in an equimolar amount, preferably in an amount of 1 to 5 moles, to 1 mole of the compound [1K]. The reaction is usually carried out at a temperature from room temperature to 200° C., preferably at a temperature from 50° C. to about 150° C., for 1 hour to about 40 hours.

Reaction Scheme-30

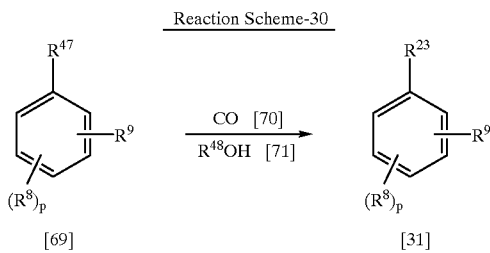

wherein $R^8$, p, $R^9$ and $R^{23}$ are the same as defined above, $R^{47}$ is a lower alkylsulfonyloxy group having optionally a halogen substituent, and $R^{48}$ is a lower alkyl group.

The reaction of the compound [69], carbon monooxide [70] and the compound [71] is carried out in the presence of a catalyst and a basic compound in an appropriate solvent. The solvent and the basic compound used therein are the same ones as those used in the reaction of the compound [2] and the compound [3] in above Reaction Scheme-1 wherein a carboxylic acid halide is used. The catalyst includes, for example, palladium acetate, 1,3-bis(diphenylphosphino) propane (dppp), and the like. The reaction is usually carried out at a temperature from room temperature to 200° C., preferably at a temperature from room temperature to about 150° C., for 1 hour to about 10 hours. The compound [70], the compound [71] and the catalyst are each used in an excess amount to the compound [69].

Reaction Scheme-31

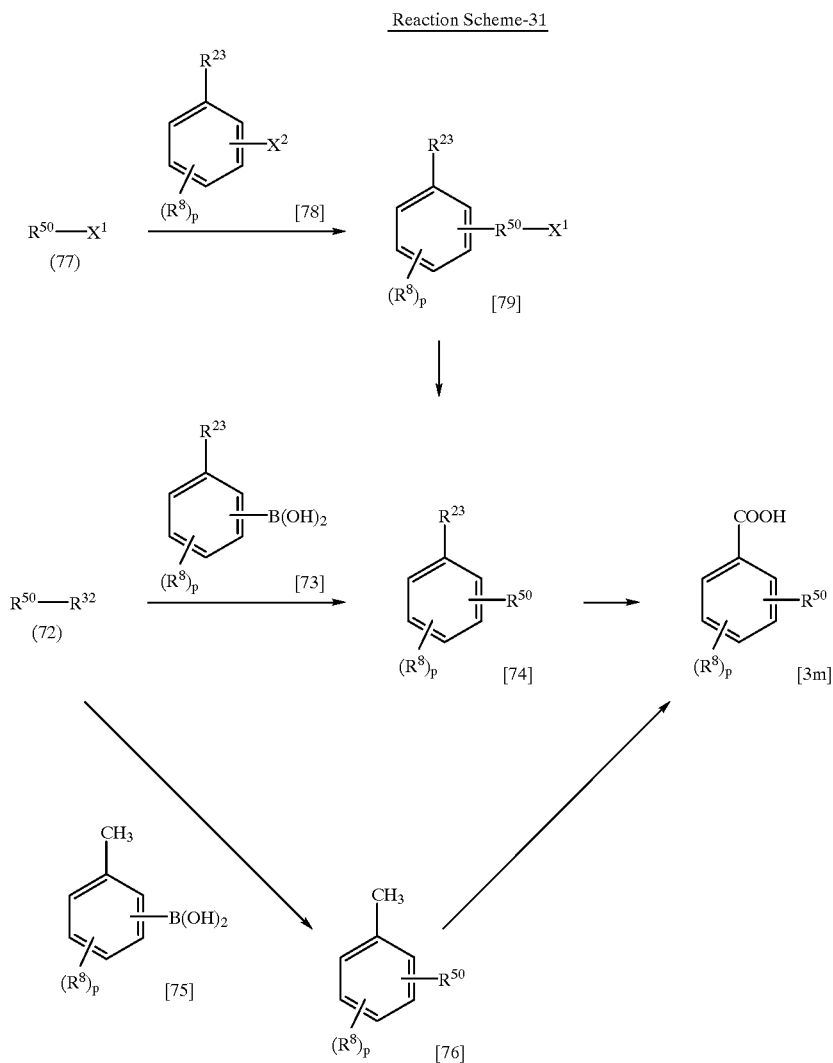

wherein $R^{50}$ is a 5- to 11-membered, saturated or unsaturated heteromonocyclic or heterobicyclic group containing 1 to 4 heteroatoms selected from a nitrogen atom, an oxygen atom and a sulfur atom, and said heterocyclic group being optionally substituted by 1 to 3 groups selected from a lower alkyl group, a phenyl group, a lower alkanoyl group, a halogen atom, a phenyl-lower alkyl group and an oxo group, and $R^{32}$, $R^{23}$, $R^8$, p, $X^1$ and $X^2$ are the same as defined above.

The reaction of the compound [72] and the compound [73] is carried out under the same conditions as in the reaction of the compound [54] and the compound [55] in above Reaction Scheme-21.

The reaction of converting the compound [74] into the compound [3 m] is carried out under the same conditions as in the reaction of converting the compound [1o] into the compound [1p] in above Reaction Scheme-7.

The reaction of the compound [72] and the compound [75] is carried out under the same conditions as in the reaction of the compound [54] and the compound [55] in above Reaction Scheme-21.

The reaction of converting the compound [76] into the compound [3 m] is carried out in the presence of a basic compound and an oxidizing agent in an appropriate solvent. The solvent and the oxidizing agent used therein are the same ones as those used in the reaction of converting the compound [34] into the compound [35] in above Reaction Scheme-12.

The basic compound includes, for example, sodium hydroxide, potassium hydroxide, sodium hydride, etc.

The oxidizing agent is used at least in an equimolar amount, preferably in an amount of 1 to 4 moles, to 1 mole of the compound [76].

The reaction is usually carried out at a temperature from 0° C. to about 150° C., preferably at a temperature from 0° C. to about 120° C., for about 1 hour to about 7 hours.

The reaction of the compound [77] and the compound [78] is carried out by treating the compound [77] with a basic compound in an appropriate solvent, at a temperature from −80° C. to 500°, preferably at a temperature from −80° C. to room temperature, for 0.5 hour to 5 hours, and followed by reacting the product with the compound [78] in the presence of a zinc compound (e.g. zinc, zinc chloride, etc.), a catalyst and a basic compound in the same solvent.

The basic compound used for the treatment of the compound [77] includes an alkyl lithium, an aryl lithium, or a lithium amide, for example, methyl lithium, n-butyl lithium, phenyl lithium, lithium diisopropylamide, and the like. The basic compound is used at least in an quimolar amount, preferably in an amount of 1 to 2 moles, to 1 mole of the compound [77]. The solvent and the catalyst are the same as those in the reaction of the compound [21] and the compound [22] in above Reaction Scheme-1 1, and are used in the same amount as those in said reaction in above Reaction Scheme-11.

The reaction of the product derived from the compound [77] and the compound [78] is usually carried out at a temperature from 0° C. to 150° C., preferably at a temperature from 0° C. to 100° C., for 1 hour to about 10 hours.

The basic compound used in the reaction of the product derived from the compound [77] and the compound [78] includes, for example, in addition to diisopropylethylamine, the same basic compounds used in the reaction of a carboxylic acid halide of the compound [3] and the amine compound [2] in above Reaction Scheme-1.

The zinc compound and the basic compound used in the reaction of the product derived from the compound [77] and the compound [78] are used at least in an equimolar amount, preferably in an amount of 1 to 2 moles, to 1 mole of the compound [77].

The reaction of converting the compound [79] into the compound [74] is carried out by subjecting the compound [79] to catalytic hydrogenation in an appropriate solvent. The solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethyl formamide, etc.), or a mixture of these solvents. The catalyst includes, for example, palladium, palladium-black, palladium-carbon, platinum, platinum oxide, copper chromite, Raney nickel, and the like. The catalyst is usually used in an amount of 0.02 to 1 mole, to 1 mole of the starting compound. The reaction is usually carried out at a temperature from −20° C. to about 150° C., preferably at a temperature from 0° C. to about 100° C., under 1 to 10 atms of hydrogen, for 0.5 hour to about 10 hours. There may be added sodium acetate, etc. into the reaction system.

Reaction Scheme-32

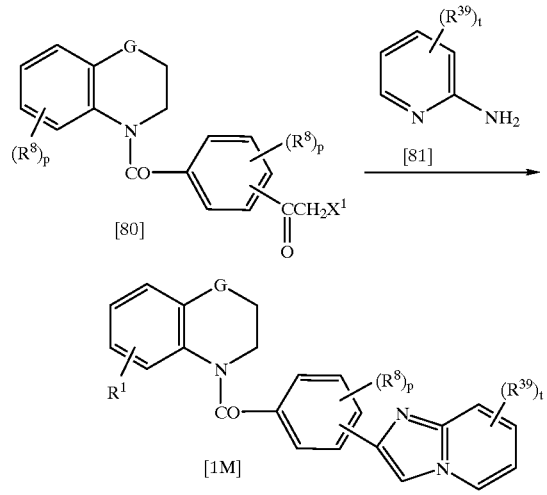

wherein $R^1$, G, $R^8$, p, $X^1$, $R^{39}$ and t are the same as defined above.

The reaction of the compound [80] and the compound [81] is carried our under the same conditions as in the reaction of the compound [4] and the compound [6a] in above Reaction Scheme-2.

Reaction Scheme-33

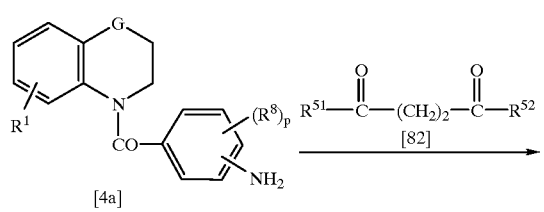

-continued

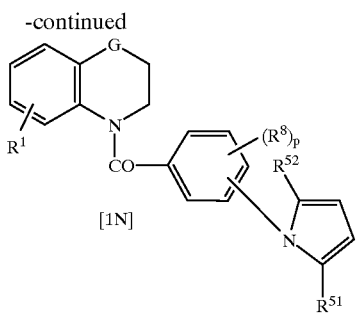

[1N]

wherein $R^1$, G, $R^8$ and p are the same as defined above, and $R^{51}$ and $R^{52}$ are each a lower alkyl group.

The reaction of the compound [4a] and the compound [82] is carried out in the presence of an acid in an appropriate solvent. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.).

The reaction is usually carried out at a temperature from room temperature to about 200° C., preferably at a temperature from room temperature to about 150° C., for 0.5 hour to about 5 hours. The compound [82] is used at least in an equimolar amount, preferably in an mount of 1 to 2 moles, to 1 mole of the compound [4a].

The compound of the formula [1] wherein $R^1$ is a hydroxy group can be prepared by subjecting the compound of the formula [1] wherein $R^1$ is a lower alkoxy group to de-alkylation. The de-alkylation reaction is carried out in the presence of an acid in an appropriate solvent. The solvent includes, for example, water, lower alcohols (e.g. methanol, ethanol, isopropanol, etc.), ethers (e.g. dioxane, tetrahydrofuran, etc.), halogenated hydrocarbons (e.g. dichloromethane, chloroform, carbon tetrachloride, etc.), polar solvents (e.g. acetonitrile, etc.), organic acids (e.g. acetic acid, etc.), or a mixture of these solvents. The acid includes, for example, mineral acids (e.g. hydrochloric acid, sulfuric acid, hydrobromic acid, etc.), Lewis acids (e.g. boron trifluoride, aluminum chloride, boron tribromide, etc.), iodides (e.g. sodium iodide, potassium iodide, etc.), and a mixture of a Lewis acid and a iodide. The reaction is usually carried out at a temperature from room temperature to 150° C., preferably at a temperature from room temperature to 120° C., for 0.5 hour to 15 hours.

The compound of the formula [1] wherein $R^9$ is a phenyl group having at least one phenyl-lower alkoxy substituent on the phenyl ring is converted into the compound of the formula [1] wherein $R^9$ is a phenyl group having at least one hydroxy substituent on the phenyl ring by subjecting it to catalytic reduction. The catalytic reduction is carried out in the presence of a reducing agent in an appropriate solvent. The solvent includes, for example, water, alcohols (e.g. methanol, ethanol, isopropanol, etc.), acetic acid, ethyl acetate, ethers (e.g. dioxane, tetrahydrofuran, diethyl ether, diglyme, etc.), aromatic hydrocarbons (e.g. benzene, toluene, xylene, etc.), or a mixture of these solvents. The reducing agent includes, for example, catalysts such as palladium-black, palladium-carbon, platinum oxide, platinum-black, platinum-carbon, Raney nickel, etc. The reaction is usually carried out at a temperature from −30° to 100° C., preferably at a temperature from 0° C. to 60° C., under a pressure from atmospheric pressure to 20 atms of hydrogen, preferably under a pressure from atmospheric pressure to 10 atms of hydrogen. The catalyst is usually used in an amount of 0.1 to 40% by weight, preferably in an amount of 0.1 to 20% by weight, to the amount of the starting compound.

The compound of the formula [1] wherein $R^9$ is a phenyl group having at least one lower alkanoyloxy substituent on the phenyl ring, or a lower alkanoyloxy group can be converted into the compound of the formula [1] wherein $R^9$ is a phenyl group having at least one hydroxy substituent on the phenyl ring or a hydroxy group, respectively, by subjecting them to hydrolysis. The hydrolysis is carried out in the presence of an acid or a basic compound in an appropriate solvent or without a solvent. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether etc.), fatty acids (e.g. formic acid, acetic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acids, etc.), and the like. The basic compound includes, for example, metal carbonates (e.g. sodium carbonate, potassium carbonate, etc.), metal hydroxides (e.g. lithium hydroxide, sodium hydroxide, potassium hydroxide, calcium hydroxide, etc.), and the like. The reaction is usually carried out at a temperature from room temperature to about 200° C., preferably at a temperature from room temperature to about 150° C., for 0.5 to about 25 hours.

The compound of the formula [1] wherein $R^8$ is a lower alkoxy group can be converted into the compound of the formula [1] wherein $R^8$ is a hydroxy group by subjecting it to de-alkylation reaction. The compound [1] wherein $R^9$ is a phenyl group having at least one lower alkoxy substituent on the phenyl ring can be converted into the compound of the formula [1] wherein $R^9$ is a phenyl group having at least one hydroxy substituent on the phenyl ring by subjecting it to de-alkylation reaction. The de-alkylation reaction is carried out in the presence of an acid in an appropriate solvent. The solvent includes, for example, water, lower alcohols (e.g. methanol, ethanol, isopropanol, etc.), ethers (e.g. dioxane, tetrahydrofuran, etc.), halogenated hydrocarbons (e.g. dichloromethane, chloroform, carbon tetrachloride, etc.), polar solvents (e.g. acetonitrile, etc.), organic acids (e.g. acetic acid, etc.), or a mixture of these solvents. The acid includes, for example, mineral acids (e.g. hydrochloric acid, sulfuric acid, hydrobromic acid, etc.), Lewis acids (e.g. boron trifluoride, aluminum chloride, boron tribromide, etc.), iodides (e.g. sodium iodide, potassium iodide, etc.), and a mixture of a Lewis acid and a iodide. The reaction is usually carried out at a temperature from room temperature to 150° C., preferably at a temperature from room temperature to 120° C., for 0.5 hour to about 15 hours.

The compound of the formula [1] wherein $R^{11}$ is a phenoxy-lower alkanoyl group having at least one amino substituent on the phenyl ring can be converted into the compound of the formula [1] wherein $R^{11}$ is a phenoxy-lower alkanoyl group having at least one amino substituent having a lower alkyl substituent on the phenyl ring by reacting it with a compound of the formula: $R^{41}X^1$ [10a] (wherein $R^{41}$ is a lower alkyl group and $X^1$ is the same as defined above), or a compound of the formula: $R^{16}COR^{17}$ [11] (wherein $R^{16}$ and $R^{17}$ are the same as defined above) under the same conditions as those in the reaction of the compound [1 h] and the compound [10] or the compound [11] in above Reaction Scheme-4.

The compound of the formula [1] wherein $R^9$ is a 5- to 11-membered, saturated or unsaturate heteromonocyclic or heterobicyclic group containing 1 to 4 heteroatoms selected from a nitrogen atom, an oxygen atom and a sulfur atom wherein these heteroatoms may optionally be substituent, and said heterocyclic group has a secondary amino group on the heterocyclic nucleus, is reacted with a compound of the formula: $R^{42}X$ [10b] (wherein X is the same as defined above and $R^{42}$ is a lower alkyl group, a phenyl-lower alkyl group or a lower alkanoyl group) or a group of the formula: $R^{16}COR^{17}$ [11] (wherein $R^{16}$ and $R^{17}$ are the same as defined above) under the same conditions as those in the reaction of the compound [1 h] with the compound [10] or the compound [11] in above Reaction Scheme-4, to give the compound of the formula [1] wherein the corresponding $R^9$ is the above heterocyclic group wherein the secondary amino group on the heterocyclic nucleus is substituted by a lower alkyl group, a phenyl-lower alkyl group or a lower alkanoyl group, or reacted with a compound of the formula: $R^{43}OH$ [12a] (wherein $R^{43}$ is a lower alkanoyl group) under the same conditions as those in the reaction of the compound [2] with the compound [3] in above Reaction Scheme-1 to give the compound of the formula [1] wherein the corresponding $R^9$ is a heterocyclic group wherein the secondary amino group on the heterocyclic nucleus is substituted by a lower alkanoyl group.

Among the desired compounds [1] of the present invention, the compounds having an acidic group can easily be converted into salts by treating with a pharmaceutically acceptable basic compound. The basic compound includes, for example, metal hydroxides (e.g. sodium hydroxide, potassium hydroxide, lithium hydroxide, calcium hydroxide, etc.), alkali metal carbonates or hydrogen carbonates (e.g. sodium carbonate, sodium hydrogen carbonate, etc.) and alkali metal alcoholates (e.g. sodium methylate, potassium ethylate, etc.). Besides, among the desired compounds [1] of the present invention, the compounds having a basic group can easily be converted into acid addition salts thereof by treating with a pharmaceutically acceptable acid. The acid includes, for example, inorganic acids (e.g. sulfuric acid, nitric acid, hydrochloric acid, hydrobromic acid, etc.), and organic acids (e.g. acetic acid, p-toluenesulfonic acid, ethanesulfonic acid, oxalic acid, maleic acid, fumaric acid, citric acid, succinic acid, benzoic acid, etc.). These salts show as well excellent pharmacological activities as the desired compounds [1].

In addition, the compounds [1] of the present invention include stereoisomers and optical isomers, and these isomers are also useful as a vasopressin antagonist, vasopressin agonist or an oxytocin antagonist.

The compounds of the present invention thus obtained can easily be isolated and purified by conventional isolation methods. The isolation methods are, for example, distillation method, recrystallization method, column chromatography, ion exchange chromatography, gel chromatography, affinity chromatography, preparative thin layer chromatography, extraction with a solvent, and the like.

The desired compounds [1] of the present invention and salts thereof are useful as a vasopressin antagonist, vasopressin agonistic activities and an oxytocin antagonist, and are used in the form of a conventional pharmaceutical preparation. The preparation is prepared by using conventional diluents or carriers such as fillers, thickening agents, binders, wetting agent, disintegrators, surfactants, lubricants, and the like. The pharmaceutical preparations can be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starch, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of the present invention and the above carriers into hard gelatin capsules or soft capsules in usual manner. In the preparation of injections, the solutions, emulsions and suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the desired compound of the present invention to be incorporated into the vasopressin antagonist, vasopressin agonist or the oxytocin antagonist is not specified but may be selected from a broad range, but usually, it is preferably in the range of 1 to 70% by weight, more preferably 5 to 50% by weight.

The vasopressin antagonist, the vasopressin agonist or the oxytocin antagonist containing as an active ingredient the compounds [1] of the present invention or a salt thereof may be administered in any method, and a suitable method for administration may be determined in accordance with various forms of preparations, ages, sexes and other conditions of the patients, the degree of severity of diseases, and the like. For example, tablets, pills, solutions, suspensions, emulsions, granules and capsules are administered orally.

The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the vasopressin antagonist, the vasopressin agonist and the oxytocin antagonist of the present invention may be selected in accordance with the usage, ages, sexes and other conditions of the patients, the degree of severity of the diseases, and the like, but it is usually in the range of about 0.6 to 50 mg of the active compound of the present invention per 1 kg of body weight of the patient per day. The active compound is preferably contained in an amount of about 10 to about 1000 mg per the dosage unit.

BEST MODE FOR CARRYING OUT THE INVENTION

EXAMPLES

The present invention is illustrated in more detail by the following Preparations of vasopressin antagonist, vasopressin agonist or oxytocin antagonist, Reference Examples of processes for preparing the starting compounds to be used for preparing the desired compounds of the present invention, and Examples of processes for preparing the desired compounds, and Experiments of the activities of the desired compounds of the present invention.

PREPARATION 1

Film coated tables are prepared from the following components.

| Components | Amount |
| --- | --- |
| 7-Chloro-5-[(4-methyl-1-piperazinyl)carbonyl-methyl]-1-[2-methoxy-4-(2-methylphenyl)-benzoyl]-2,3,4,5-tetrahydro-1H-benzazepine | 150 g |
| Avicel (trademark of microcrystalline cellulose manufactured by Asahi Chemical Industry, Co., Ltd., Japan) | 40 g |
| Corn Starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded and the mixture is tabletted by using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

PREPARATION 2

Tablets are prepared from the following components.

| Components | Amount |
| --- | --- |
| 7-Chloro-5-{[N-(2-diethylaminoethyl)-N-methyl amino]carbonylmethyl}-1-(3,4-dimethoxybenzoyl)-2,3,4,5-tetrahydro-1H-benzazepine | 150 g |

-continued

| Components | Amount |
| --- | --- |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed. The mixture is screened with No. 60 screen and is granulated with an alcohol solution containing polyvinylpyrrolidone, Carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard them from wetting. Undercoating is applied to the core tablets. In order to administer the tablets orally, the core tablets are vanished several times. In order to give round shape and smooth surface to the tablets, further undercoating and coating with a lubricant are applied thereto. The tablets are further coated with a coloring coating materials until the desired colored tablets are obtained. After drying, the coated tablets are polished to obtain the desired tablets having uniform gross.

PREPARATION 3

An injection preparation is prepared from the following components.

| Components | Amount |
| --- | --- |
| 7-Chloro-5-[(4-methyl-1-piperazinyl)carbonyl-methyl]-1-[2-methoxy-4-(2,4-dichlorobenzylamino)-benzoyl]-2,3,4,5-tetrahydro-1H-benzazepine | 5 g |
| Polyethylene glycol (molecular weight; 4000) | 0.3 g |
| Sodium chloride | 0.9 g |
| Polyoxyethylene-sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of about half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

4-Chloromethylbenzoic acid methyl ester (26.36 g) is dissolved in 1,2-dimethoxyethane (700 ml), and thereto are added with stirring zinc powder (20.6 g) and bistriphenylphosphine palladium dichloride (5 g) over an ice-bath. To the mixture is added dropwise o-toluoyl chloride (26.5 g), and the mixture is stirred over an ice-bath for three hours, and then stirred at room temperature for three days. The insoluble materials are removed by filtration, and the residue is washed with ethyl acetate. To the mother liquor is added a saturated sodium hydrogen carbonate solution, and the mixture is extracted with ethyl acetate. The organic layer is washed successively with a saturated sodium hydrogen carbonate solution, a 0.5N hydrochloric acid and a saturated sodium chloride solution, dried over magnesium sulfate and concentrated. The residue is purified by silica gel column chromatography (solvent; ethyl acetate:n-hexane= 50:1~10:1), and recrystallized from toluene/n-hexane to give 4-[(2-methyl-benzoyl)methyl]benzoic acid methyl ester (15 g).

REFERENCE EXAMPLE 2

4-Methoxycarbonylbenzyltriphenylphosphonium chloride (19.1 g) and sodium methylate (2.77 g) are suspended in methanol (20 ml), and the mixture is stirred at room temperature for one hour. To the mixture is added o-chlorobenzaldehyde (5 g), and the mixture is stirred at room temperature for one hour. Sodium methylate (5.54 g) is added to the mixture, and the mixture is stirred at room temperature for one hour. The reaction mixture is concentrated, and to the residue is added water, and the mixture is extracted with ethyl acetate. The organic layer is washed successively with water, a 0.5N hydrochloric acid and a saturated sodium chloride solution, and dried over magnesium sulfate, and concentrated. To the residue is added diethyl ether/n-hexane, and the insoluble materials are removed by filtration. The mother liquor is concentrated, and the residue is purified by silica gel column chromatography (solvent; n-hexane:ethyl acetate =30:1). Methyl 4-(2-chlorostyryl)benzoate (cis form) (2.15 g) is firstly eluted, and then, methyl 4-(2-chlorostyryl)benzoate (trans form) (1.42 g) is eluted, and both are collected as white powder.

REFERENCE EXAMPLE 3

A mixture of methyl 4-(2-chlorostyryl)benzoate (trans form) (1.42 g), 5N sodium hydroxide (1.6 ml) and methanol (20 ml) is stirred at room temperature for three hours, and refluxed for two hours. The mixture is evaporated to remove the methanol, and to the residue is added water. The mixture is acidified with conc. hydrochloric acid, and stirred at room temperature for 16 hours. The precipitated crystals are collected by filtration to give 4-(2-chlorostyryl)benzoic acid (1.36 g) as white powder.

REFERENCE EXAMPLE 4

4-Bromobenzoic acid (7.2 g) and thionyl chloride (20 ml) are refluxed for one hour, and concentrated. To the residue is added toluene, and the mixture is concentrated. The obtained 4-bromobenzoic chloride is added dropwise to a mixture of 2-amino-2-methyl-1-propanol (5.1 ml), triethylamine (10 ml) and dichloromethane (70 ml) under ice-cooling. The reaction mixture is stirred at room temperature for five hours, and thereto is added ice, and the mixture is extracted with dichloromethane. The organic layer is washed successively with 0.5N hydrochloric acid, a saturated aqueous sodium hydrogen carbonate solution and a saturated sodium chloride solution, dried over magnesium sulfate, and concentrated. The residue is dissolved in dichloromethane (50 ml), and thereto is added dropwise thionyl chloride (7.8 ml) under ice-cooling. The mixture is stirred at room temperature for three hours, cooled with ice, and basified with a 5N aqueous sodium hydroxide solution. The mixture is extracted with dichloromethane, and the organic layer is washed with water, dried over magnesium sulfate to give 2-(4-bromophenyl)-4,4-dimethyl-2-oxazoline (8.35 g) as colorless oil.

B.p. 162–164° C./22 mmHg

REFERENCE EXAMPLE 5

To a solution of 2-(4-bromophenyl)-4,4-dimethyl-2-oxazoline (1 g) in dry tetrahydrofuran (10 ml) are added dropwise magnesium (526 mg) and dry tetrahydrofuran (50 ml) under refluxing. The heating of the mixture is stopped, and thereto is added 2-(4-bromphenyl)-4,4-dimethyl-2-oxazoline (4 g) at a slowly refluxing rate, during which the mixture is stirred for 30 minutes, and then thereto is added o-tolualdehyde (2.16 ml) under ice-cooling. The mixture is stirred under ice-cooling for one hour, and stirred at room temperature for two hours, and the reaction is quenched with adding thereto a saturated aqueous ammonium chloride solution. The mixture is extracted with ethyl acetate, and the organic layer is washed successively with 1N hydrochloric acid, a saturated aqueous sodium hydrogen carbonate solution and a saturated sodium chloride solution, dried over magnesium sulfate, and concentrated. The residue is purified by silica gel column chromatography (solvent; n-hexane:ethyl acetate=4~2:1) to give 2-{4-[1-(2-methylphenyl)-1-hydroxymethyl]phenyl}-4,4-dimethyl-2-oxazoline (3.07 g) as white powder.

$^1$H-NMR (200 MHz, CDCl$_3$) δ ppm: 1.35 (6H, s), 2.24 (3H, s), 3.04 (1H, d, J=4 Hz), 4.08 (1H, s), 5.99 (1H, d, J=4Hz), 7.03–7.05 (6H, m), 7.76–7.94 (2H, m)

REFERENCE EXAMPLE 6

2-{4-[1-(2-Methylphenyl)-1-hydroxymethyl]phenyl}-4,4-dimethyl-2-oxazoline (3.0 g), manganese dioxide (20 g) and dichloromethane (50 ml) are mixed at room temperature. The mixture is stirred at room temperature for two hours, and refluxed for three hours. The insoluble materials are removed by filtration through celite, and washed with chloroform, and the mother liquor is concentrated to give 2-[4-(2-methylbenzoyl)phenyl]-4,4-dimethyl-2-oxazoline (2.86 g) as pale yellow oil.

$^1$H-NMR (200 MHz, CDCl$_3$) δ ppm: 1.40 (6H, s), 2.33 (3H, s), 4.14 (2H, s), 7.12–7.54 (4H, m), 7.76–7.92 (2H, m), 7.95–8.14 (2H, m)

REFERENCE EXAMPLE 7

2-[4-(2-Methylbenzoyl)phenyl]-4,4-dimethyl-2-oxazoline (2.86 g) and 4.5M hydrochloric acid (150 ml) are refluxed for 8 hours. The mixture is cooled to room temperature, and thereto is added water. The precipitates are collected by filtration to give 4-(2-methylbenzoyl)benzoic acid (2.23 g) as white powder.

$^1$H-NMR (200 MHz, CDCl$_3$) δ ppm: 2.37 (3H, s), 7.19–7.58 (4H, m), 7.80–8.03 (2H, m), 8.10–8.35 (2H, m), 10.4 (1H, brs)

REFERENCE EXAMPLE 8

To a solution of 3-methoxy-4-trifluoromethylsulfonyloxybenzoic acid methyl ester (5 g) in toluene (200 ml) is added tetrakis(triphenylphosphine) palladium (0.9 g) under argon atmosphere, and the mixture is stirred at room temperature for five minutes. To the mixture are added (2-methylphenyl)boric acid (3.2 g), lithium chloride (1.01 g) and a 2M aqueous sodium carbonate solution (11.9 ml), and the mixture is stirred at 100° C. for two hours. To the mixture is added water, and the mixture is filtered through celite to remove the palladium. The filtrate is extracted with diethyl ether, and the ether layer is washed with water, dried, and evaporated. The residue is purified by silica gel column chromatography (solvent; n-hexane→ethyl acetate:n-hexane=1:10) to give 3-methoxy-4-(2-methylphenyl)benzoic acid methyl ester (4.07 g) as oil.

$^1$H-NMR (200 MHz, CDCl$_3$) δ ppm: 2.12 (3H, s), 3.82 (3H, s), 3.95 (3H, s), 7.02–7.48 (5H, m), 7.63 (1H, d, J=1.51 Hz), 7.71 (1H, dd, J=1.5 Hz, 7.74 Hz)

The suitable starting compounds are treated in the same manner as in Reference Example 8 to give the compounds of Examples 22, 23 and 35–64 as mentioned below.

REFERENCE EXAMPLE 9

2-(4-Phenyl-2-methoxyphenyl)-4,4-dimethyl-2-oxazoline (3.00 g) is dissolved in tetrahydrofuran (30 ml) under argon atmosphere, and the mixture is stirred with cooling over an ice-bath. To the mixture is added dropwise gradually an about 2M solution of 1-n-propylmagnesium bromide in tetrahydrofuran (8.0 ml) at the same temperature. After addition, the mixture is warmed to room temperature, and stirred for 16 hours. The reaction solution is stirred with cooling over an ice-bath, and thereto is added a saturated aqueous ammonium chloride solution (30 ml). The mixture is warmed to room temperature, and the organic layer is collected. The aqueous layer is extracted with ethyl acetate (30 ml×2), and the extract is combined with the organic layer, washed with a saturated aqueous sodium chloride solution (100 ml×2), dried over magnesium sulfate, and evaporated to remove the solvent. The residue is purified by silica gel column chromatography (solvent; dichloromethane:n-hexane=1:2→1:1), and evaporated to remove the solvent to give 2-(4-phenyl-2-n-propylphenyl)-4,4-dimethyl-2-oxazoline (2.81 g) as colorless transparent viscous oil.

$^1$H-NMR (200 MHz, CDCl$_3$) δ ppm: 0.98 (3H, t, J=11.3 Hz), 1.39 (6H, s), 1.52–1.77 (2H, m), 2.99 (2H, dd, J=7.5Hz, J=9.5 Hz), 4.08 (2H, s), 7.30–7.51 (5H, m), 7.52–7.63 (2H, m), 7.78 (1H, d, J=6.5 Hz)

REFERENCE EXAMPLE 10

To a mixture of conc. hydrochloric acid (30 ml) and glacial acetic acid (10 ml) is added 2-(4-phenyl-2-n-propylphenyl)-4,4-dimethyl-2-oxazoline (2.70 g), and the mixture is refluxed for three days (nine hours×3). The reaction solution is concentrated to about half volume thereof under reduced pressure, and cooled over an ice-bath. The precipitated crystals are collected by filtration, and purified by silica gel column chromatography (solvent; dichloromethane→dichloromethane:methanol=50:1). The desired fractions are combined, evaporated to remove the solvent, and the crystalline residue is recrystallized from n-hexane to give 4-phenyl-2-n-propylbenzoic acid (1.67 g) as colorless needles.

M.p. 107.5–108.5° C.

REFERENCE EXAMPLE 11

To a solution of 2-(4-bromo-2-methylphenyl)-4,4-dimethyl-2-oxazoline (5 g) in dry tetrahydrofuran (40 ml) is added dropwise a 1.6M solution of n-butyl lithium in n-hexane (14.0 ml) at −70° C. The mixture is stirred at the same temperature for 30 minutes, and thereto is added dropwise cyclohexanone (2.1 ml), and the mixture is stirred for one hour. To the mixture is added water, and the mixture is evaporated to remove the tetrahydrofuran, and then extracted with diethyl ether. The diethyl ether layer is dried over anhydrous magnesium sulfate, evaporated to remove the solvent, and the residue is purified by silica gel column chromatography (solvent; dichloromethane:methanol= 100:1→60:1), recrystallized from acetone/n-hexane to give 2-[4-(1-hydroxy-1-cyclohexyl)-2-methylphenyl]-4,4-dimethyl-2-oxazoline (4.29 g) as white powder.

$^1$H-NMR (200 MHz, CDCl$_3$) δ ppm: 1.14–1.98 (11H, m), 1.38 (6H, s), 2.57 (3H, s), 4.05 (2H, s), 7.19–7.45 (2H, m), 7.72 (1H, d, J=8.1 Hz)

REFERENCE EXAMPLE 12

To a solution of 2-[4-(1-hydroxy-1-cyclohexyl)-2-methylphenyl]-4,4-dimethyl-2-oxazoline (4.29 g) in acetic acid (40 ml) is added a 10% hydrochloric acid (20 ml), and the mixture is refluxed for two days. The precipitated crystals are collected by filtration, washed with water, and dried to give 4-cyclohexenyl-2-methylbenzoic acid (2.61 g) as white powder.

$^1$H-NMR (200 MHz, CDCl$_3$) δ ppm: 1.55–1.93 (4H, m), 2.13–2.31 and 2.32–2.56 (each 2H, each m), 2.66 (3H, s), 6.17–6.34 (1H, m), 7.15–7.42 (2H, m), 7.90–8.18 (1H, m)

REFERENCE EXAMPLE 13

To a solution of 4-cyclohexenyl-2-methylbenzoic acid (2.61 g) in ethanol (30 ml) and ethyl acetate (30 ml) is added 5% palladium-carbon (0.4 g), and the mixture is stirred at room temperature under atmospheric pressure of hydrogen gas for 30 minutes. The palladium-carbon is removed by filtration through celite, and the filtrate is evaporated to remove the solvent. The precipitated crystals are collected by filtration, crystallized from acetone/n-hexane, and washed to give 4-cyclohexyl-2-methylbenzoic acid (2.27 g) as white powder.

M.p. 129–130° C.

REFERENCE EXAMPLE 14

4-Phenylpiperidine (0.5 g), p-fluorobenzonitrile (0.37 g) and potassium carbonate (0.78 g) are dissolved in N-methylpiperidone (5 ml), and the mixture is stirred at 1 20° C. for five hours. To the reaction solution is added ethyl acetate (50 ml), and the mixture is washed with water, dried over magnesium sulfate, filtered, and concentrated under reduced pressure. To the resulting residue is added methanol, and the insoluble crystals are collected by filtration, dried under reduced pressure to give 4-phenyl-1-(4-cyanophenyl)-piperidine (0.39 g) as white needles.

M.p. 167–169° C.

REFERENCE EXAMPLE 15

To 4-phenyl-1-(4-cyanophenyl)piperidine (0.39 g) are added acetic acid (10 ml) and conc. hydrochloric acid (10 ml), and the mixture is refluxed for five hours. The reaction solution is concentrated, and to the residue is added diethyl ether/methanol. The insoluble crystals are collected by filtration, and dried under reduced pressure to give 4-phenyl-1-(4-carboxyphenyl)piperidine (0.39 g) as white powder.

M.p. 257–259° C. (decomposed)

REFERENCE EXAMPLE 16

Homopiperazine (100 g) is dissolved in ethanol (500 ml), and thereto is added dropwise gradually ethyl iodide (19.8 ml). The mixture is stirred at room temperature overnight, and the insoluble materials are removed by filtration. The filtrate is evaporated to remove the solvent. Purification is perfomed by distillation to give 1-ethylhomopiperazine (50 g) as colorless oil.

B.p. 86–88° C./37 mmHg $^1$H-NMR (200 MHz, CDCl$_3$) δ ppm: 1.06 (3H, t, J=7.2 Hz), 1.68–1.93 (2H, m), 2.54 (2H, q, J=7.2 Hz), 2.63–2.76 (7H, m), 2.87–3.01 (2H, m)

REFERENCE EXAMPLE 17

To a solution of 4-phenyl-2-chloro-1-trifluoromethylsulfonyloxybenzene (35 g) in dimethylformamide (300 ml) are added palladium acetate (1.17 g), 1,3-bis(diphenylphosphino)propane (4.29 g), ethanol (91.5 ml) and triethylamine (29.0 ml) under carbon monooxide atmosphere, and the mixture is heated with stirring at 80–90° C. for 6 hours. To the reaction solution is added water, and further added a small amount of n-hexane. The mixture is extracted with ethyl acetate, and the ethyl acetate layer is washed with water, dried, and the residue is purified by silica gel column chromatography (solvent; n-hexane →ethyl acetate:n-hexane=1:100) to give ethyl 4-phenyl-2-chlorobenzoate (20.9 g) as colorless oil.

$^1$H-NMR (200 MHz, CDCl$_3$) δ ppm: 1.42 (3H, t, J=7.0 Hz), 4.42 (2H, q, J=7.0 Hz), 7.28–7.78 and 7.85–8.18 (all 8H, m)

The suitable starting compounds are treated in the same manner as in Reference Example 17 to give the following compounds.

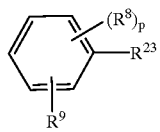

REFERENCE EXAMPLE 18

Structure

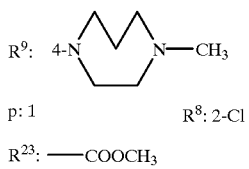

p: 1   R$^8$: 2-Cl

R$^{23}$: ——COOCH$_3$

Crystalline form: Brown Oil
Form: Free

REFERENCE EXAMPLE 19

Structure

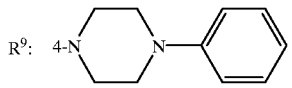

p: 1   R$^8$: 2-Cl

R$^{23}$: ——COOCH$_3$

Crystalline form: Brown Oil
Form: Free

REFERENCE EXAMPLE 20

Structure

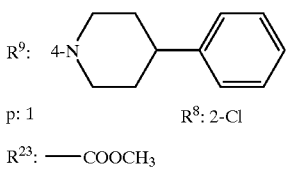

p: 1   R$^8$: 2-Cl

R$^{23}$: ——COOCH$_3$

Crystalline form: White powder
Form: Free

REFERENCE EXAMPLE 21

Structure

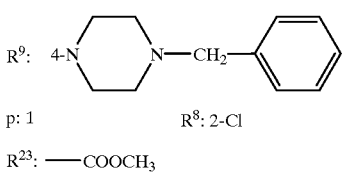

p: 1   R$^8$: 2-Cl

R$^{23}$: ——COOCH$_3$

Crystalline form: Yellow oil
Form: Free

REFERENCE EXAMPLE 22

Structure

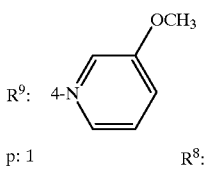

p: 1   R$^8$: 2-CH$_3$

R$^{23}$: ——COOCH$_3$

Crystalline form: White powder
Form: Free

REFERENCE EXAMPLE 23

Structure

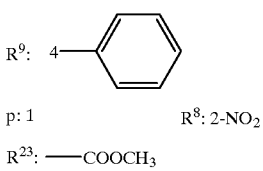

p: 1   R$^8$: 2-NO$_2$

R$^{23}$: ——COOCH$_3$

Crystalline form: Yellow viscous oi
Form: Free 1

REFERENCE EXAMPLE 24

Structure

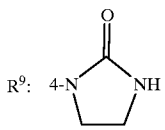

$R^9$: 4- p: 1     $R^8$: 2-Cl $R^{23}$: —COOCH$_3$

Crystalline form: White powder
Form: Free

REFERENCE EXAMPLE 25

Structure

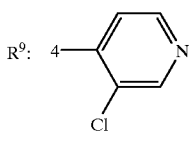

$R^9$: 4- p: 1     $R^8$: 2-CH$_3$ $R^{23}$: —COOCH$_3$

Crystalline form: Pale yellow solid
Form: Free

REFERENCE EXAMPLE 26

Structure

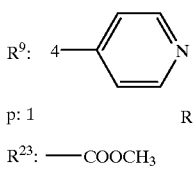

$R^9$: 4- p: 1     $R^8$: 2-CH$_3$ $R^{23}$: —COOCH$_3$

Crystalline form: Pale yellow oil
Form: Free

REFERENCE EXAMPLE 27

Structure

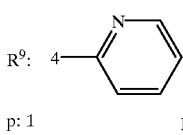

$R^9$: 4- p: 1     $R^8$: H $R^{23}$: —COOCH$_3$

Crystalline form: Pale yellow powder
Solvent for recrystallization: Chloroform/diethyl ether
M.p. 96–98° C.
Form: Free

REFERENCE EXAMPLE 28

Structure

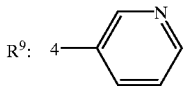

$R^9$: 4- p: 1     $R^8$: H $R^{23}$: —COOCH$_3$

Crystalline form: Pale yellow powder
Solvent for recrystallization: Chloroform/diethyl ether
M.p. 100–102° C.
Form: Free

REFERENCE EXAMPLE 29

Structure

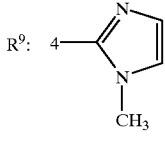

$R^9$: 4- p: 1     $R^8$: H $R^{23}$: —COOCH$_3$

Crystalline form: Pale brown powder
Solvent for recrystallization: Chloroform/diethyl ether
M.p. 126–128° C.
Form: Free

REFERENCE EXAMPLE 30

Structure

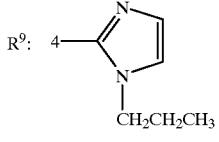

$R^9$: 4- p: 1     $R^8$: H $R^{23}$: —COOCH$_3$

Crystalline form: Brown oil
Form: Free

REFERENCE EXAMPLE 31

Structure

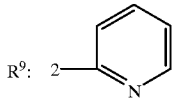

$R^9$: 2- p: 1     $R^8$: H $R^{23}$: —COOCH$_3$

Crystalline form: Pale brown oil
Form: Free

REFERENCE EXAMPLE 32

Structure

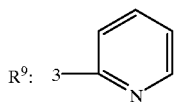

p: 1  R⁸: H
R²³: —COOCH₃

Crystalline form: Pale yellow oil
Form: Free

REFERENCE EXAMPLE 33

Structure

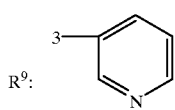

p: 1  R⁸: H
R²³: —COOCH₃

Crystalline form: Pale yellow oil
Form: Free

REFERENCE EXAMPLE 34

Structure

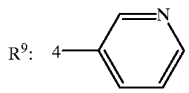

p: 1  R⁸: 2-CH₃
R²³: —COOCH₃

Crystalline form: Brown oil
Form: Free

REFERENCE EXAMPLE 35

Structure

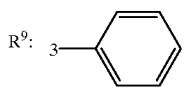

p:1  R⁸:H
R²³:—COOCH₃

Crystalline form: Colorless oil
Form: Free

REFERENCE EXAMPLE 36

Structure

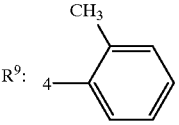

p:1  R⁸:2—OCH₃
R²³:—COOCH₃

Crystalline form: Slightly yellow oil
Form: Free

REFERENCE EXAMPLE 37

Structure

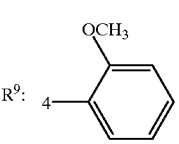

p:1  R⁸:2—OCH₃
R²³:—COOCH₃

Crystalline form: Colorless oil
Form: Free

REFERENCE EXAMPLE 38

Structure

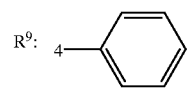

p:1  R⁸:2—OCH₃
R²³:—COOCH₃

Crystalline form: Colorless oil
Form: Free

REFERENCE EXAMPLE 39

Structure

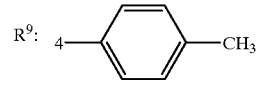

p:2  R⁸:3,5-di-OCH₃
R²³:—COOCH₃

Crystalline form: Colorless prisms
Form: Free

REFERENCE EXAMPLE 40

Structure

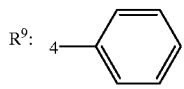

p:1  R$^8$:3—OCH$_3$
R$^{23}$:—COOCH$_3$

Crystalline form: Colorless oil
Form: Free

REFERENCE EXAMPLE 41

Structure

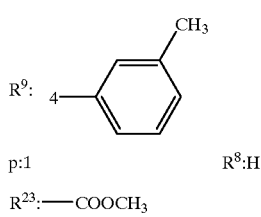

p:1  R$^8$:H
R$^{23}$:—COOCH$_3$

Crystalline form: White powder
Form: Free

REFERENCE EXAMPLE 42

Structure

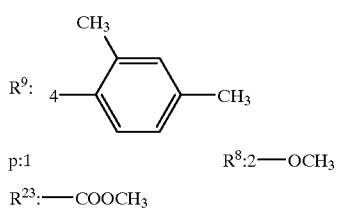

p:1  R$^8$:2—OCH$_3$
R$^{23}$:—COOCH$_3$

Crystalline form: Colorless oil
Form: Free

REFERENCE EXAMPLE 43

Structure

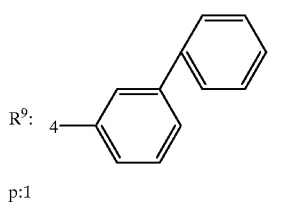

p:1  R$^8$:H
R$^{23}$:—CO$_2$C$_2$H$_5$

Crystalline form: White powder
Form: Free

REFERENCE EXAMPLE 44

Structure

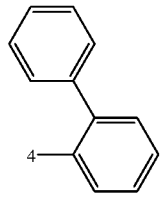

p:1  R$^8$:H
R$^{23}$:—CO$_2$C$_2$H$_5$

Crystalline form: Colorless oil
Form: Free

REFERENCE EXAMPLE 45

Structure

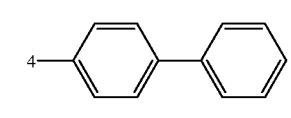

p:1  R$^8$:H
R$^{23}$:—CO$_2$C$_2$H$_5$

Crystalline form: White powder
Form: Free

REFERENCE EXAMPLE 46

Structure

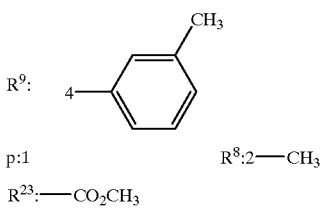

p:1  R$^8$:2—CH$_3$
R$^{23}$:—CO$_2$CH$_3$

Crystalline form: Slightly yellow oil
Form: Free

REFERENCE EXAMPLE 47

Structure

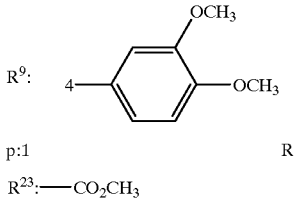

p:1  R$^8$:2—OCH$_3$
R$^{23}$:—CO$_2$CH$_3$

Crystalline form: White powder
Form: Free

REFERENCE EXAMPLE 48

Structure

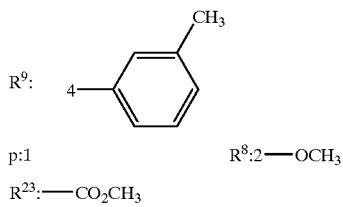

p:1     $R^8$:2—$OCH_3$ $R^{23}$:—$CO_2CH_3$

Crystalline form: Colorless oil
Form: Free

REFERENCE EXAMPLE 49

Structure

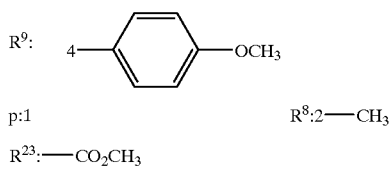

p:1     $R^8$:2—$CH_3$ $R^{23}$:—$CO_2CH_3$

Crystalline form: White powder
Form: Free

REFERENCE EXAMPLE 50

Structure

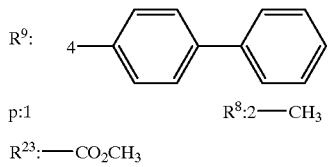

p:1     $R^8$:2—$CH_3$ $R^{23}$:—$CO_2CH_3$

Crystalline form: White powder
Form: Free

REFERENCE EXAMPLE 51

Structure

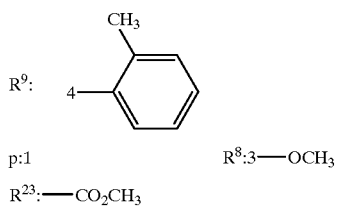

p:1     $R^8$:3—$OCH_3$ $R^{23}$:—$CO_2CH_3$

Crystalline form: Colorless oil
Form: Free

REFERENCE EXAMPLE 52

Structure

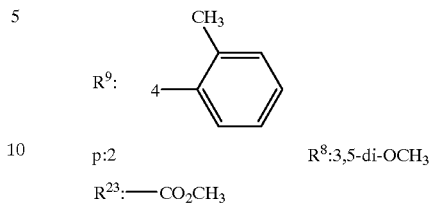

p:2     $R^8$:3,5-di-$OCH_3$ $R^{23}$:—$CO_2CH_3$

Crystalline form: White powder
Form: Free

REFERENCE EXAMPLE 53

Structure

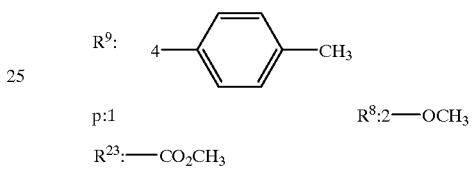

p:1     $R^8$:2—$OCH_3$ $R^{23}$:—$CO_2CH_3$

Crystalline form: Colorless prisms
Form: Free

REFERENCE EXAMPLE 54

Structure

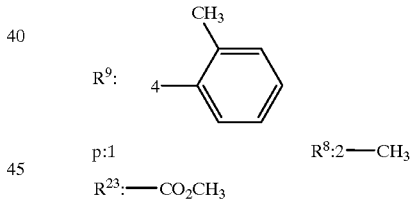

p:1     $R^8$:2—$CH_3$ $R^{23}$:—$CO_2CH_3$

Crystalline form: Colorless oil
Form: Free

REFERENCE EXAMPLE 55

Structure

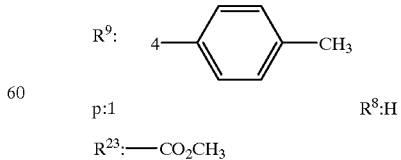

p:1     $R^8$:H $R^{23}$:—$CO_2CH_3$

Crystalline form: White powder
Form: Free

REFERENCE EXAMPLE 56

Structure

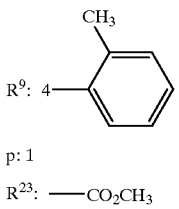

p: 1  R$^8$: H
R$^9$: 4—
R$^{23}$: —CO$_2$CH$_3$

Crystalline form: White powder
Form: Free

REFERENCE EXAMPLE 57

Structure

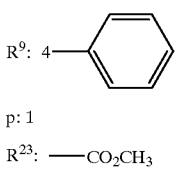

p: 1  R$^8$: 2-CH$_3$
R$^9$: 4—
R$^{23}$: —CO$_2$CH$_3$

Crystalline form: Colorless prisms
Form: Free

REFERENCE EXAMPLE 58

Structure

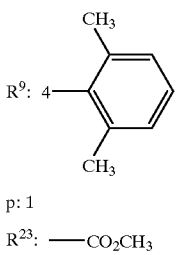

p: 1  R$^8$: 2-OCH$_3$
R$^9$: 4—
R$^{23}$: —CO$_2$CH$_3$

Crystalline form: Colorless oil
Form: Free

REFERENCE EXAMPLE 59

Structure

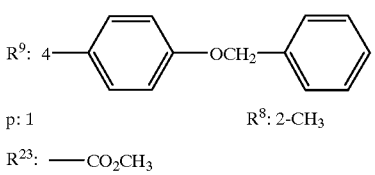

p: 1  R$^8$: 2-CH$_3$
R$^9$: 4—
R$^{23}$: —CO$_2$CH$_3$

Crystalline form: White powder
Form: Free

REFERENCE EXAMPLE 60

Structure

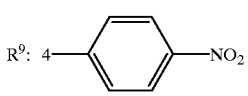

p: 1  R$^8$: 2-CH$_3$
R$^9$: 4—
R$^{23}$: —CO$_2$CH$_3$

Crystalline form: Slightly yellow powder
Form: Free

REFERENCE EXAMPLE 61

Structure

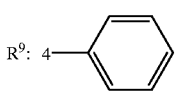

p: 1  R$^8$: 2-Cl
R$^9$: 4—
R$^{23}$: —CO$_2$C$_2$H$_5$

Crystalline form: Colorless oil
Form: Free

REFERENCE EXAMPLE 62

Structure

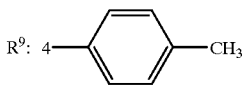

p: 1  R$^8$: 2-CH$_3$
R$^9$: 4—
R$^{23}$: —CO$_2$CH$_3$

Crystalline form: Slightly yellow powder
Form: Free

REFERENCE EXAMPLE 63

Structure

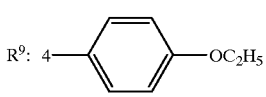

p: 1  R$^8$: 2-CH$_3$
R$^9$: 4—
R$^{23}$: —CO$_2$CH$_3$

Crystalline form: White powder
Form: Free

REFERENCE EXAMPLE 64

Structure

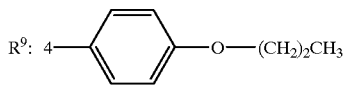

p: 1     R⁸: 2-CH₃

R²³: —CO₂CH₃

Crystalline form: White powder
Form: Free

The suitable starting compounds are treated in the same manner as in Reference Example 3, 7, 10 or 12 to give the following compounds.

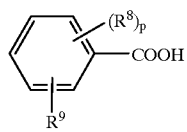

REFERENCE EXAMPLE 65

Structure

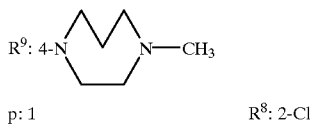

p: 1     R⁸: 2-Cl

Crystalline form: White powder
Form: Free

REFERENCE EXAMPLE 66

Structure

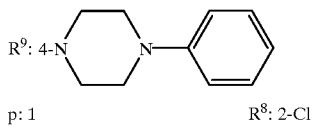

p: 1     R⁸: 2-Cl

Crystalline form: Yellow powder
Form: Free

REFERENCE EXAMPLE 67

Structure

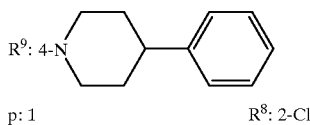

p: 1     R⁸: 2-Cl

Crystalline form: White powder
Form: Free

REFERENCE EXAMPLE 68

Structure

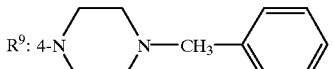

p: 1     R⁸: 2-Cl

Crystalline form: White powder
Form: Free

REFERENCE EXAMPLE 69

Structure

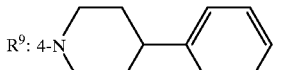

p: 1     R⁸: H

Crystalline form: White powder
M.p. 257–259° C. (decomposed)
Form: Free

REFERENCE EXAMPLE 70

Structure

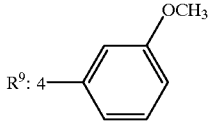

p: 1     R⁸: 2-CH₃

Crystalline form: White powder
Form: Free

REFERENCE EXAMPLE 71

Structure

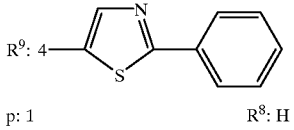

p: 1     R⁸: H

Crystalline form: Brown powder
M.p. 233–235° C.
Form: Free

REFERENCE EXAMPLE 72

Structure

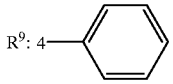

-continued p: 1    R⁸: 2-C₂H₅

Crystalline form: Colorless plates
Solvent for recrystallization: n-Hexane/chloroform
M.p. 164–165° C.
Form: Free

REFERENCE EXAMPLE 73

Structure

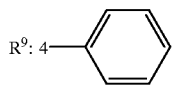

p: 1    R⁸: 2-n-C₃H₇

Crystalline form: Colorless needles
Solvent for recrystallization: n-Hexane
M.p. 107.5–108.5° C.
Form: Free

REFERENCE EXAMPLE 74

Structure

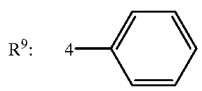

p: 1    R⁸: 2-NO₂

Crystalline form: Red brown powder
M.p. 199–201° C.
Form: Free

REFERENCE EXAMPLE 75

Structure

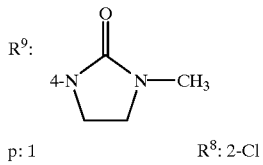

p: 1    R⁸: 2-Cl

Crystalline form: White powder
Form: Free

REFERENCE EXAMPLE 76

Structure

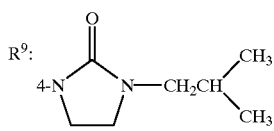

-continued p: 1    R⁸: 2-Cl

Crystalline form: White powder
Form: Free

REFERENCE EXAMPLE 77

Structure

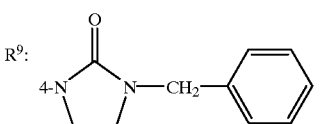

p: 1    R⁸: 2-Cl

Crystalline form: Slightly red powder
Form: Free

REFERENCE EXAMPLE 78

Structure

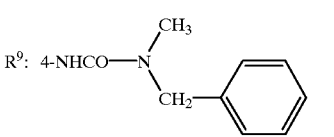

p: 1    R⁸: H

Crystalline form: White powder
Form: Free

REFERENCE EXAMPLE 79

Structure

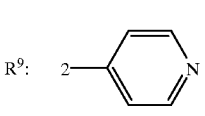

p: 1    R⁸: H

Crystalline form: White powder
Form: Free

REFERENCE EXAMPLE 80

Structure

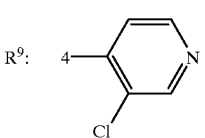

p: 1    R⁸: 2-CH₃

Crystalline form: White powder
Form: Hydrochloride

REFERENCE EXAMPLE 81

Structure

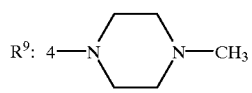

p: 1    R⁸: H

Crystalline form: Brown powder
Form: Free

REFERENCE EXAMPLE 82

Structure

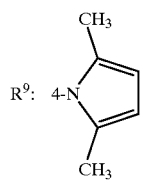

p: 1    R⁸: 2-OCH₃

Crystalline form: Pale brown powder
Solvent for recrystallization: Chloroform/diethyl ether
M.p. 133–135° C.
Form: Free

REFERENCE EXAMPLE 83

Structure

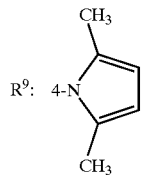

p: 1    R⁸: 3-OCH₃

Crystalline form: Brown powder
Solvent for recrystallization: Chloroform/diethyl ether
M.p. 126–128° C.
Form: Free

REFERENCE EXAMPLE 84

Structure

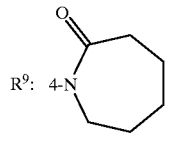

p: 1    R⁸: H

Crystalline form: White powder
Solvent for recrystallization: Chloroform/diethyl ether
M.p. 198–201° C.
Form: Free

REFERENCE EXAMPLE 85

Structure

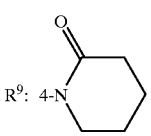

p: 1    R⁸: H

Crystalline form: White powder
Solvent for recrystallization: Chloroform/diethyl ether
M.p. 236–239° C.
Form: Free

REFERENCE EXAMPLE 86

Structure

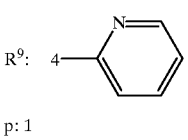

p: 1    R⁸: H

Crystalline form: White needles
Solvent for recrystallization: Methanol/diethyl ether
M.p. 257–260° C.
Form: Free

REFERENCE EXAMPLE 87

Structure

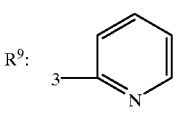

p: 1    R⁸: H

Crystalline form: Pale brown powder
Solvent for recrystallization: Methanol/diethyl ether
M.p. 201–203° C.
Form: Free

REFERENCE EXAMPLE 88

Structure

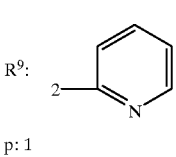

p: 1    R⁸: H

Crystalline form: White powder
Solvent for recrystallization: Methanol/diethyl ether
M.p. 230° C. (decomposed)
Form: Hydrochloride

REFERENCE EXAMPLE 89

Structure

R⁹: 2-(pyridin-3-yl)

p: 1   R⁸: H

Crystalline form: White powder
Solvent for recrystallization: Methanol/diethyl ether
M.p. 206–207° C.
Form: Hydrochloride

REFERENCE EXAMPLE 90

Structure

R⁹: 3-(pyridin-3-yl)

p: 1   R⁸: H

Crystalline form: Pale yellow powder
Solvent for recrystallization: Ethanol/diethyl ether
M.p. 266–269° C.
Form: Hydrochloride

REFERENCE EXAMPLE 91

Structure

R⁹: 4-(pyridin-3-yl)

p: 1   R⁸: 2-CH₃

Crystalline form: Pale yellow powder
Solvent for recrystallization: Methanol
M.p. 276–279° C.
Form: Hydrochloride

REFERENCE EXAMPLE 92

Structure

R⁹: 3-(phenyl)

p: 1   R⁸: H

Crystalline form: White powder
Solvent for recrystallization: Methanol/diethyl ether
M.p. 161–163° C.
Form: Free

REFERENCE EXAMPLE 93

Structure

R⁹: 4-(1-methylimidazol-2-yl), N–CH₃ p: 1   R⁸: H

Crystalline form: Pale yellow powder
Solvent for recrystallization: Methanol/diethyl ether
M.p. 250–251° C.
Form: Free

REFERENCE EXAMPLE 94

Structure

R⁹: 4-(1-propylimidazol-2-yl), N–CH₂CH₂CH₃ p: 1   R⁸: H

Crystalline form: Yellow amorphous
Form: Free

REFERENCE EXAMPLE 95

Structure

R⁹: 4-(benzothiazol-2-yl)

p: 1   R⁸: H

Crystalline form: White needles
Form: Free

REFERENCE EXAMPLE 96

Structure

R⁹: 4-(pyridin-3-yl)

p: 1   R⁸: H

Crystalline form: Pale yellow needles
Solvent for recrystallization: Methanol/diethyl ether
M.p. 309–311° C.
Form: Hydrochloride

REFERENCE EXAMPLE 97

Structure

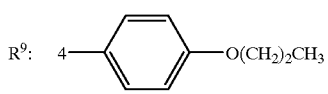

p: 1    R⁸: 2-CH₃

Crystalline form: White powder
Solvent for recrystallization: Acetone/n-hexane
M.p. 198–200° C.
Form: Free

REFERENCE EXAMPLE 98

Structure

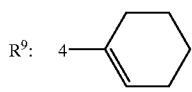

p: 1    R⁸: 2-CH₃

Crystalline form: White powder
Form: Free

REFERENCE EXAMPLE 99

Structure

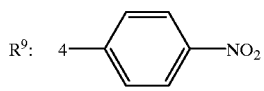

p: 1    R⁸: 2-CH₃

Crystalline form: White powder
Form: Free

REFERENCE EXAMPLE 100

Structure

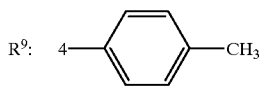

p: 1    R⁸: 2-CH₃

Crystalline form: White powder
Solvent for recrystallization: Acetone/n-hexane
M.p. 208° C.
Form: Free

REFERENCE EXAMPLE 101

Structure

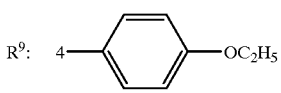

p: 1    R⁸: 2-CH₃

Crystalline form: White powder
Solvent for recrystallization: Acetone/n-hexane
M.p. 234–236° C.
Form: Free

REFERENCE EXAMPLE 102

Structure

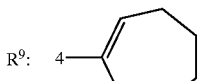

p: 1    R⁸: 2-CH₃

Crystalline form: White powder
Form: Free

REFERENCE EXAMPLE 103

Structure

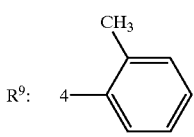

p: 1    R⁸: 2-OCH₃

Crystalline form: White powder
Solvent for recrystallization: Acetone/n-hexane
M.p. 132–133° C.
Form: Free

REFERENCE EXAMPLE 104

Structure

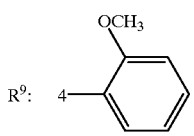

p: 1    R⁸: 2-OCH₃

Crystalline form: Colorless prisms
Solvent for recrystallization: Ethyl acetate
M.p. 153–154° C.
Form: Free

REFERENCE EXAMPLE 105

Structure

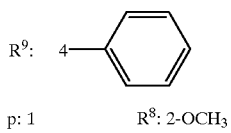

p: 1    R⁸: 2-OCH₃

Crystalline form: Colorless prisms
Solvent for recrystallization: Ethyl acetate
M.p. 118–119° C.
Form: Free

REFERENCE EXAMPLE 106

Structure

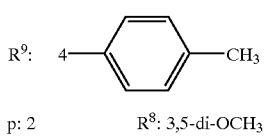

p: 2    R⁸: 3,5-di-OCH₃

Crystalline form: White powder
Solvent for recrystallization: Acetone/n-hexane
M.p. 239–240° C.
Form: Free

REFERENCE EXAMPLE 107

Structure

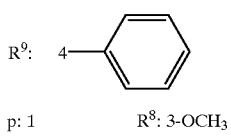

p: 1    R⁸: 3-OCH₃

Crystalline form: White powder
Solvent for recrystallization: Acetone/n-hexane
M.p. 179–182° C.
Form: Free

REFERENCE EXAMPLE 108

Structure

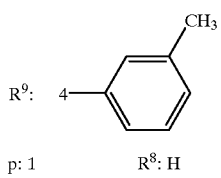

p: 1    R⁸: H

Crystalline form: White powder
Solvent for recrystallization: Acetone/n-hexane
M.p. 194–197° C.
Form: Free

REFERENCE EXAMPLE 109

Structure

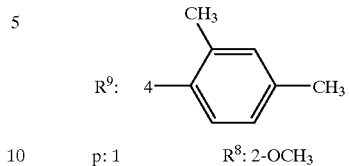

p: 1    R⁸: 2-OCH₃

Crystalline form: White powder
Solvent for recrystallization: Acetone/n-hexane
M.p. 149–150° C.
Form: Free

REFERENCE EXAMPLE 110

Structure

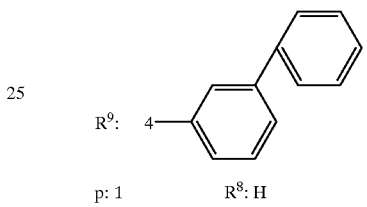

p: 1    R⁸: H

Crystalline form: White powder
Solvent for recrystallization: Ethanol/diethyl ether
M.p. 202–204° C.
Form: Free

REFERENCE EXAMPLE 111

Structure

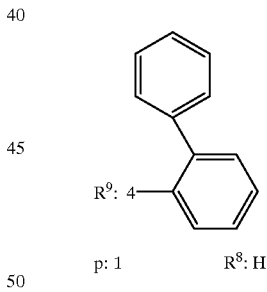

p: 1    R⁸: H

Crystalline form: White powder
Form: Free

REFERENCE EXAMPLE 112

Structure

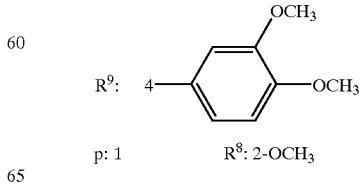

p: 1    R⁸: 2-OCH₃

Crystalline form: White powder

REFERENCE EXAMPLE 113

Structure

R⁹: 4—[phenyl with CH₃ at top]
p: 1    R⁸: 2-OCH₃

Crystalline form: White powder
Form: Free

REFERENCE EXAMPLE 114

Structure

R⁹: 4—[phenyl]—OCH₃
p: 1    R⁸: 2-CH₃

Crystalline form: White powder
Form: Free

REFERENCE EXAMPLE 115

Structure

R⁹: 4—[biphenyl]
p: 1    R⁸: 2-CH₃

Crystalline form: White powder
Solvent for recrystallization: Ethanol/diethyl ether
M.p. 262–265° C.
Form: Free

REFERENCE EXAMPLE 116

Structure

R⁹: 4—[phenyl with CH₃ at top]
p: 1    R⁸: 3-OCH₃

Crystalline form: White powder
Form: Free

Solvent for recrystallization: Acetone/n-hexane
M.p. 134–135° C.
Form: Free

REFERENCE EXAMPLE 117

Structure

R⁹: 4—[phenyl]—OCH₃
p: 1    R⁸: 3-OCH₃

Crystalline form: White powder
Solvent for recrystallization: Acetone/n-hexane
M.p. 146–147° C.
Form: Free

REFERENCE EXAMPLE 118

Structure

R⁹: 4—[phenyl with CH₃ at top]
p: 1    R⁸: 2-CH₃

Crystalline form: White powder
Solvent for recrystallization: Acetone/n-hexane
M.p. 132–133° C.
Form: Free

REFERENCE EXAMPLE 119

Structure

R⁹: 4—[cyclohexyl]
p: 1    R⁸: 2-CH₃

Crystalline form: White powder
Solvent for recrystallization: Acetone/n-hexane
M.p. 129–130° C.
Form: Free

REFERENCE EXAMPLE 120

Structure

R⁹: 4—[cycloheptyl]
p: 1    R⁸: 2-CH₃

Crystalline form: White powder
Form: Free

REFERENCE EXAMPLE 121

Structure

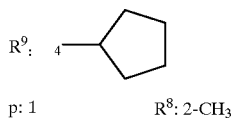

p: 1    R⁸: 2-CH₃

Crystalline form: Pale yellow powder
Form: Free

REFERENCE EXAMPLE 122

Structure

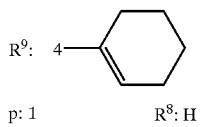

p: 1    R⁸: H

Crystalline form: White powder
Form: Free

REFERENCE EXAMPLE 123

Structure

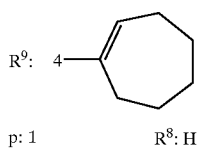

p: 1    R⁸: H

Crystalline form: White powder
Form: Free

REFERENCE EXAMPLE 124

Structure

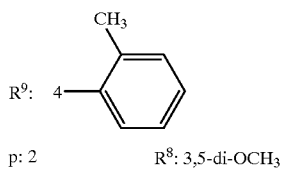

p: 2    R⁸: 3,5-di-OCH₃

Crystalline form: White powder
Solvent for recrystallization: Acetone/n-hexane
M.p. 231–232° C.
Form: Free

REFERENCE EXAMPLE 125

Structure

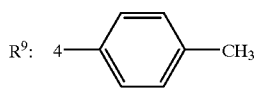

-continued p: 1    R⁸: 2-OCH₃

Crystalline form: White powder
Solvent for recrystallization: Acetone/n-hexane
M.p. 159–160° C.
Form: Free

REFERENCE EXAMPLE 126

Structure

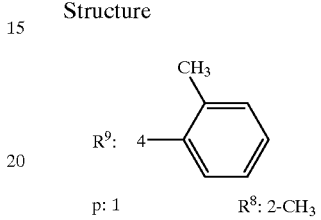

p: 1    R⁸: 2-CH₃

Crystalline form: White powder
Solvent for recrystallization: Acetone/n-hexane
M.p. 117–118° C.
Form: Free

REFERENCE EXAMPLE 127

Structure

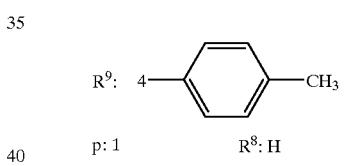

p: 1    R⁸: H

Crystalline form: White powder
Solvent for recrystallization: Ethanol/diethyl ether
M.p. 246–248° C.
Form: Free

REFERENCE EXAMPLE 128

Structure

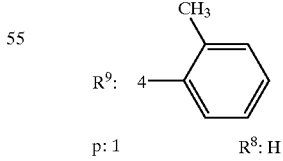

p: 1    R⁸: H

Crystalline form: Colorless prisms
Solvent for recrystallization: Acetone/n-hexane
M.p. 185–187° C.
Form: Free

REFERENCE EXAMPLE 129

Structure

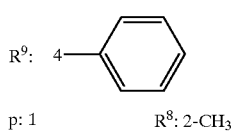

p: 1    R⁸: 2-CH₃

Crystalline form: White powder
Form: Free

REFERENCE EXAMPLE 130

Structure

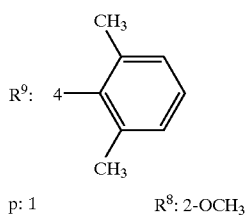

p: 1    R⁸: 2-OCH₃

Crystalline form: White powder
Solvent for recrystallization: Acetone/n-hexane
M.p. 145–148° C.
Form: Free

REFERENCE EXAMPLE 131

Structure

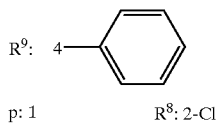

p: 1    R⁸: 2-Cl

Crystalline form: White powder
Solvent for recrystallization: Acetone/n-hexane
M.p. 164° C.
Form: Free The suitable starting compounds are treated in the same manner as in Reference Example 17 to give the following compounds.

REFERENCE EXAMPLE 132

Structure

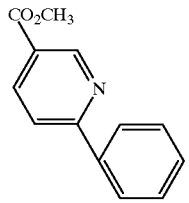

Crystalline form: White needles
$^1$H-NMR (200 MHz, CDCl$_3$) δ ppm: 3.97 (3H, s), 7.48–7.62 (3H, m), 7.81 (1H, dd, J=8.0 Hz, J=0.8 Hz), 7.98–8.17 (2H, m), 8.34 (1H, dd, J=8.0 Hz, J=2.2 Hz), 9.28 (1H, dd, J=2.2 Hz, J=0.8 Hz)

Form: Free

REFERENCE EXAMPLE 133

Structure

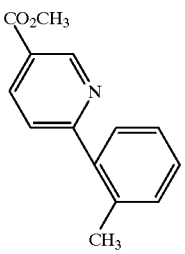

Crystalline form: White powder
$^1$H-NMR (200 MHz, CDCl$_3$) δ ppm: 2.38 (3H, s), 3.98 (3H, s), 7.19–7.50 (4H, m), 7.50 (1H, dd, J=8.0 Hz, J=0.8 Hz), 8.35 (1H, dd, J=8.0 Hz, J=2.0 Hz), 9.30 (1H, dd, J=2.0 Hz, J=0.8 Hz)

Form: Free

REFERENCE EXAMPLE 134

Structure

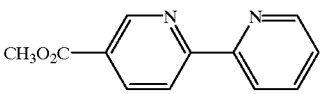

Crystalline form: Pale brown powder
Solvent for recrystallization: Chloroform/diethyl ether
M.p. 110–111° C.
Form: Free The suitable starting compounds are treated in the same manner as in Reference Example 3, 7, 10 or 12 to give the following compounds.

REFERENCE EXAMPLE 135

Structure

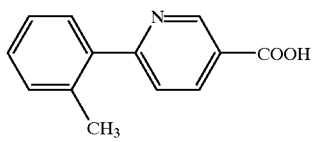

Crystalline form: Colorless needles
M.p. 191–192° C.
Form: Free

REFERENCE EXAMPLE 136

Structure

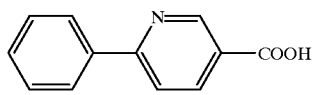

Crystalline form: Colorless needles
M.p. 228–230° C.
Form: Free

REFERENCE EXAMPLE 137

Structure

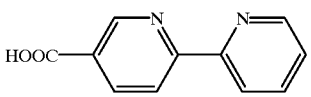

Crystalline form: Pale brown needles
Solvent for recrystallization: Methanolidiethyl ether
M.p. 253–255° C.
Form: Hydrochloride The suitable starting compounds are treated in the same manner as in Reference Example 17 to give the following compounds.

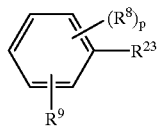

REFERENCE EXAMPLE 138

Structure

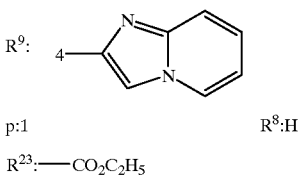

p:1    $R^8$:H
$R^{23}$:—$CO_2C_2H_5$

Crystalline form: White powder
$^1$H-NMR (200 MHz, DMSO-$d_6$) δ ppm: 6.80–6.95 (1H, m), 7.20–7.35 (1H, m), 7.55–7.65 (1H, m), 7.98–8.16 (4H, m), 8.45–8.60 (2H, m), 1.34 (3H, t, J=7.2 Hz), 4.33 (2H, q, J=7.2 Hz)

REFERENCE EXAMPLE 139

Structure

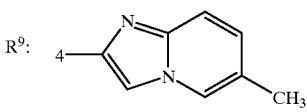

-continued
p:1    $R^8$:H
$R^{23}$:—$CO_2C_2H_5$

Crystalline form: White powder
$^1$H-NMR (200 MHz, DMSO-$d_6$) δ ppm: 1.34 (3H, t, J=7.2 Hz), 2.29 (3H, s), 4.33 (2H, q, J=7.2 Hz), 7.10–7.20 (1H, m), 7.50–7.58 (1H, m), 7.95–8.15 (4H, m), 8.33 (1H, s), 8.43 (1H, s)

REFERENCE EXAMPLE 140

Structure $R^9$:    4—NH—C(=O)—$CH_2Cl$
p:1    $R^8$:H
$R^{23}$:—$CO_2C_2H_5$

Crystalline form: White powder
$^1$H-NMR (200 MHz, CDCl$_3$) δ ppm: 1.40 (3H, t, J=7.2 Hz), 4.21 (2H, s), 4.37 (2H, q, J=7.2 Hz), 7.60–7.70 (2H, m), 8.00–8.11 (2H, m), 8.42 (1H, brs)

REFERENCE EXAMPLE 141

Structure $R^9$:    4—NH—C(=O)—$CH_2Cl$
p:1    $R^8$:2-$CH_3$
$R^{23}$:—$CO_2CH_3$ Crystalline form: White powder
$^1$H-NMR (200 MHz, CDCl$_3$) δ ppm: 2.61 (3H, s), 3.88 (3H, s), 4.20 (2H, s), 7.40–7.55 (2H, m), 7.90–8.01 (1H, m), 8.30 (1H, brs)

The suitable starting compounds are treated in the same manner as in Reference Example 3, 7, 10 or 12 to give the following compounds.

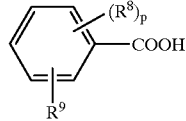

REFERENCE EXAMPLE 142

Structure $R^9$: 4-[imidazo[1,2-a]pyridin-2-yl]
p:1    $R^8$:H

Crystalline form: White powder
$^1$H-NMR (200 MHz, DMSO-$d_6$) δ ppm: 7.40–7.55 (1H, m), 7.85–8.03 (2H, m), 8.03–8.25 (4H, m), 8.85–9.00 (2H, m), 12.4–14.1 (1H, brs)

REFERENCE EXAMPLE 143

Structure

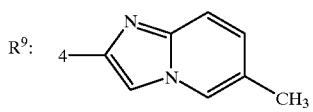

p:1    R⁸:H

Crystalline form: White powder

¹H-NMR (200 MHz, DMSO-d₆) δ ppm: 2.41 (3H, s), 7.75–7.95 (2H, m), 7.95–8.25 (4H, m), 8.70 (1H, s), 8.85 (1H, s), 12.6–13.6 (1H, brs)

REFERENCE EXAMPLE 144

Structure

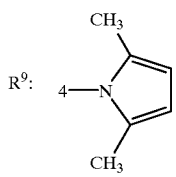

p:1    R⁸:H

Crystalline form: Light brown powder

¹H-NMR (200 MHz, CDCl₃) δ ppm: 2.07 (6H, s), 5.94 (2H, s), 7.30–7.40 (2H, m), 8.20–8.30 (2H, m), 10.7–12.1 (1H, brs)

The data of NMR analysis of the compounds of the above Reference Examples are as follows.

The suitable starting compounds are treated in the same manner as in Reference Example 17 to give the following compounds.

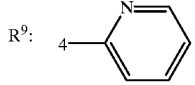

REFERENCE EXAMPLE 145

Structure

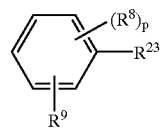

p:1    R⁸:2-CH₃

R²³:—COOCH₃

Crystalline form: Pale yellow oil

Form: Free

REFERENCE EXAMPLE 146

Structure

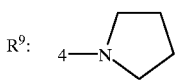

p:1    R⁸:2-Cl

R²³:—COOCH₃

Crystalline form: Yellow prisms

Form: Free

REFERENCE EXAMPLE 147

Structure

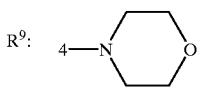

p:1    R⁸:2-Cl

R²³:—COOCH₃

Crystalline form: Yellow needles

Form: Free

REFERENCE EXAMPLE 148

Structure

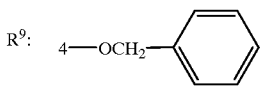

p:1    R⁸:2-CH₃

R²³:—COOCH₃

Crystalline form: Colorless viscous oil

Form: Free

REFERENCE EXAMPLE 149

Structure

R⁹: 4-OH p: 1    R⁸: 2-CH₃

R²³:    —COOCH₃

Crystalline form: White powder

Solvent for recrystallization: n-Hexane/ethyl acetate

M.p. 97–98.5° C.

Form: Free

REFERENCE EXAMPLE 150

Structure

R$^9$: 4-OCH(CH$_3$)$_2$
p: 1
R$^8$: 2-CH$_3$
R$^{23}$: —COOCH$_3$

Crystalline form: Colorless viscous oil
Form: Free

REFERENCE EXAMPLE 151

Structure

R$^9$: 4-O(CH$_2$)$_3$CH$_3$
p: 1
R$^8$: 2-CH$_3$
R$^{23}$: —COOCH$_3$

Crystalline form: Colorless viscous oil
Form: Free

REFERENCE EXAMPLE 152

Structure

R$^9$: 4-OCH$_2$CH(CH$_3$)$_2$
p: 1
R$^8$: 2-CH$_3$
R$^{23}$: —COOCH$_3$

Crystalline form: Colorless viscous oil
Form: Free

REFERENCE EXAMPLE 153

Structure

R$^9$: 4-NHCOCF$_3$
p: 1
R$^8$: 2-Cl
R$^{23}$: —COOCH$_3$

Crystalline form: White powder
Form: Free

REFERENCE EXAMPLE 154

Structure

R$^9$: 4-OCH$_2$COOH
p: 1
R$^8$: 2-CH$_3$
R$^{23}$: —COOCH$_3$

Crystalline form: White powder
Solvent for recrystallization: Dichloromethane/n-hexane
Form: Free

REFERENCE EXAMPLE 156

Structure

R$^9$:
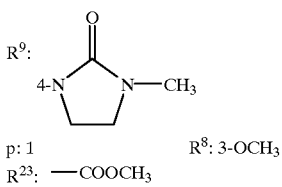
p: 1
R$^8$: 2-Cl
R$^{23}$: —COOCH$_3$

Crystalline form: Yellow powder
Solvent for recrystallization: Ethyl acetate/n-hexane
M.p. 118–123° C.
Form: Free

REFERENCE EXAMPLE 157

Structure

R$^9$:
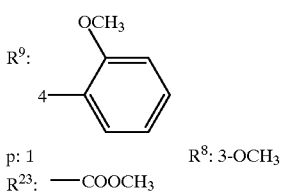
p: 1
R$^8$: 3-OCH$_3$
R$^{23}$: —COOCH$_3$

Crystalline form: White powder
Form: Free

REFERENCE EXAMPLE 158

Structure

R$^9$:
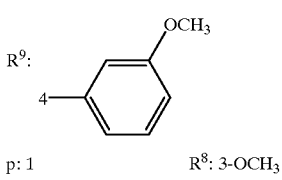
p: 1
R$^8$: 3-OCH$_3$
R$^{23}$: —COOCH$_3$

Crystalline form: White powder
Form: Free

REFERENCE EXAMPLE 159

Structure

R$^9$:
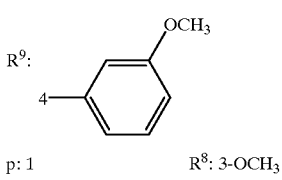
p: 1
R$^8$: 3-OCH$_3$
R$^{23}$: —COOCH$_3$

Crystalline form: Colorless oil
Form: Free

REFERENCE EXAMPLE 160

Structure

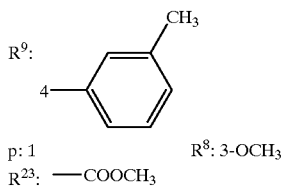

p: 1  R⁸: 3-OCH₃
R²³: —COOCH₃

REFERENCE EXAMPLE 161

Structure

R⁹: 4-NHCOO(CH₂)₂C(CH₃)₃
p: 1  R⁸: 2-OCH₃
R²³: —COOCH₃

Crystalline form: Colorless oil
Form: Free

The suitable starting compounds are treated in the same manner as in Reference Example 3, 7, 10 or 12 to give the following compounds.

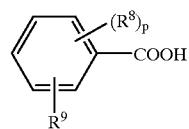

REFERENCE EXAMPLE 162

Structure

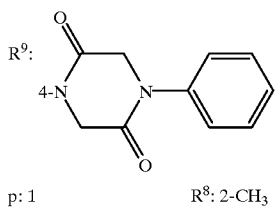

p: 1  R⁸: 2-CH₃

Crystalline form: Pale brown powder
Solvent for recrystallization: Chloroform/diethyl ether
Form: Free

REFERENCE EXAMPLE 163

Structure

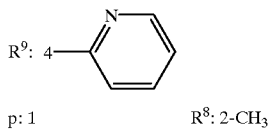

p: 1  R⁸: 2-CH₃

Crystalline form: White powder
Solvent for recrystallization: Ethanol/diethyl ether
Form: Hydrochloride

REFERENCE EXAMPLE 164

Structure

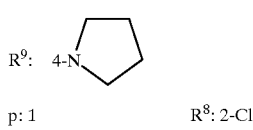

p: 1  R⁸: 2-Cl

Crystalline form: White powder
Form: Hydrochloride

REFERENCE EXAMPLE 165

Structure

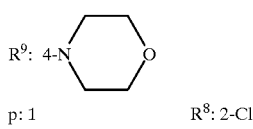

p: 1  R⁸: 2-Cl

Crystalline form: White powder
Form: Free

REFERENCE EXAMPLE 166

Structure

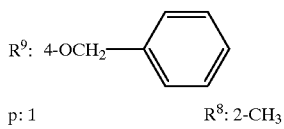

p: 1  R⁸: 2-CH₃

Crystalline form: White powder
Solvent for recrystallization: Ethyl acetate/n-hexane
M.p. 127.5–130° C.
Form: Free

REFERENCE EXAMPLE 167

Structure

R⁹: 4-OCH(CH₃)₂
p: 1  R⁸: 2-CH₃

Crystalline form: White powder
Form: Free

REFERENCE EXAMPLE 168

Structure

R⁹: 4-O(CH₂)₃CH₃
p: 1  R⁸: 2-CH₃

Crystalline form: White powder
Form: Free

REFERENCE EXAMPLE 169

Structure

R⁹: 4-OCH₂CH(CH₃)₂
p: 1          R⁸: 2-CH₃

Crystalline form: Pale yellow powder

Form: Free

REFERENCE EXAMPLE 170

Structure

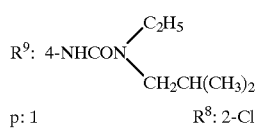

p: 1          R⁸: 2-Cl

Crystalline form: White powder

Form: Free

REFERENCE EXAMPLE 171

Structure

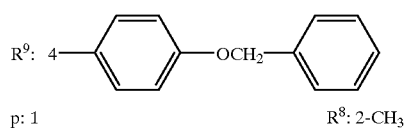

p: 1          R⁸: 2-CH₃

Crystalline form: White powder

Form: Free

REFERENCE EXAMPLE 173

Structure

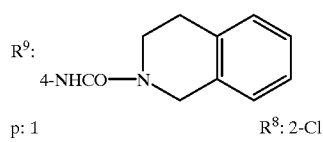

p: 1          R⁸: 2-Cl

Crystalline form: White powder

Form: Free

REFERENCE EXAMPLE 174

Structure

R⁹: 4-CH₂CH(CH₃)₂
p: 1          R⁸: 2-CH₃

Crystalline form: White powder

Form: Free

REFERENCE EXAMPLE 175

Structure

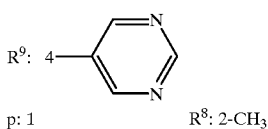

p: 1          R⁸: 2-CH₃

Crystalline form: Yellow powder

Form: Free

REFERENCE EXAMPLE 176

Structure

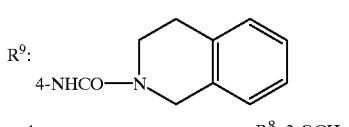

p: 1          R⁸: 3-OCH₃

Crystalline form: White powder

Form: Free

REFERENCE EXAMPLE 177

Structure

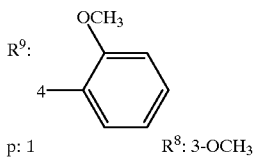

p: 1          R⁸: 3-OCH₃

Crystalline form: White powder

M.p. 170–171° C.

Form: Free

REFERENCE EXAMPLE 178

Structure

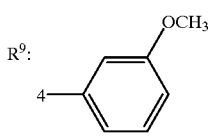

p: 1          R⁸: 3-OCH₃

Crystalline form: White powder

M.p. 128–129° C.

Form: Free

REFERENCE EXAMPLE 179

Structure

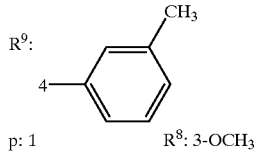

p: 1    $R^8$: 3-OCH$_3$

Crystalline form: White powder
M.p. 146–147° C.
Form: Free

REFERENCE EXAMPLE 180

Structure

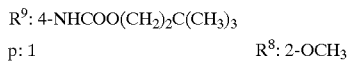

p: 1    $R^8$: 2-OCH$_3$

Crystalline form: White powder
Form: Free

The data of NMR analysis of the compounds of the above Reference Examples are as follows.

NMR analysis:

The compound of Reference Example 18

$^1$H-NMR (200 MHz, CDCl$_3$) δ ppm: 1.90–3.06 [all 9H, m, 2.38 (s)], 3.30–3.72 (4H, m), 3.85 (3H, s), 6.35–6.81 [all 2H, m, 6.53 (dd, J=8.93 Hz, J=8.99 Hz), 6.67 (d, J=2.32 Hz)], 7.83 (1H, d, J=8.95 Hz)

The compound of Reference Example 19

$^1$H-NMR (200 MHz, CDCl$_3$) δ ppm: 2.92–3.60 (all 8H, m), 3.88 (3H, s), 6.79–7.48 and 7.78–7.79 [all 8H, m, 6.79 (dd, J=8.92 Hz, J=8.92 Hz)]

The compound of Reference Example 20

$^1$H-NMR (200 MHz, CDCl$_3$) δ ppm: 1.68–2.09 [all 4H, m, 1.77 (d, J=3.30 H), 1.84 (d, J=4.20 Hz)], 2.61–3.12 (all 3H, m), 3.75–4.10 [all 5H, m, 3.87 (s)], 6.78 (1H, dd, J=8.96 Hz, J=8.97 Hz), 6.92 (1H, d, J=2.58 Hz), 7.15–7.41 (all 5H, m), 7.86 (1H, d, J=8.92 Hz)

The compound of Reference Example 21

$^1$H-NMR (200 MHz, CDCl$_3$) δ ppm: 2.57 (3H, t, J=5.21 Hz), 3.31 (3H, t, J=5.23 Hz), 3.55 (2H, s), 3.86 (3H, s), 6.72 (1H, dd, J=8.95 Hz, J=8.94 Hz), 6.85 (1H, d, J=2.56 Hz), 7.19–7.49 (5H, m), 7.82 (1H, d, J=8.91 Hz)

The compound of Reference Example 22

$^1$H-NMR (200 MHz, CDCl$_3$) δ ppm: 2.66 (3H, s), 3.85 (3H, s), 3.89 (3H, s), 6.81–7.60 (6H, m), 7.85–8.08 (1H, m)

The compound of Reference Example 23

$^1$H-NMR (200 MHz, CDCl$_3$) δ ppm: 3.94 (3H, s), 7.39–7.70 (5H, m), 7.79–7.92 (2H, m), 8.02–8.11 (1H, m)

The compound of Reference Example 24

$^1$H-NMR (200 MHz, DMSO-d$_6$) δ ppm: 3.4–3.55 (2H, m), 3.8 (3H, s), 3.8–3.95 (2H, m), 7.36 (1H, s), 7.50 (1H, dd, J=8.8 Hz, J=2 Hz), 7.82 (1H, d, J=8.8 Hz), 7.86 (1H, d, J=2 Hz)

The compound of Reference Example 25

$^1$H-NMR (200 MHz, CDCl$_3$) δ ppm: 2.67 (3H, s), 3.93 (3H, s), 7.22–7.43 (3H, m), 7.95–8.08 (1H, m), 8.48–8.63 (1H, m), 8.65–8.75 (1H, m)

The compound of Reference Example 26

$^1$H-NMR (200 MHz, CDCl$_3$) δ ppm: 2.69 (3H, s), 3.93 (3H, s), 7.41–7.63 (4H, m), 7.95–8.08 (1H, m), 8.62–8.76 (2H, m)

The compound of Reference Example 30

$^1$H-NMR (200 MHz, CDCl$_3$) δ ppm: 0.88 (3H, t, J=7.4 Hz), 1.05 (3H, t, J=7.4 Hz), 1.80 (3H, hept, J=7.4 Hz), 4.00 (2H, t, J=7.4 Hz), 4.31 (3H, t, J=7.4 Hz), 7.06 (1H, d, J=1.1 Hz), 7.17 (1H, d, J=1.1 Hz), 7.60–7.76 (2H, m), 8.06–8.22 (2H, m)

The compound of Reference Example 31

$^1$H-NMR (200 MHz, CDCl$_3$) δ ppm: 3.68 (3H, s), 7.20–7.36 (1H, m), 7.40–7.66 (4H, m), 7.66–7.90 (2H, m), 8.58–8.74 (1H, m)

The compound of Reference Example 32

$^1$H-NMR (200 MHz, CDCl$_3$) δ ppm: 3.96 (3H, s), 7.22–7.35 (1H, m), 7.56 (1H, t, J=7.8 Hz), 7.72–7.86 (2H, m), 8.09 (1H, dt, J=1.5 Hz, J=7.8 Hz), 8.24 (1H, ddd, J=1.2 Hz, J=1.8 Hz, J=7.8 Hz), 8.65 (1H, t, J=1.6 Hz), 8.69–8.77 (1H, m)

The compound of Reference Example 33

$^1$H-NMR (250 MHz, CDCl$_3$) δ ppm: 3.96 (3H, s), 7.39 (1H, ddd, J=0.8 Hz, J=4.8 Hz, J=7.8 Hz), 7.57 (1H, t, J=7.8 Hz), 7.75–7.83 (1H, m), 7.87–7.97 (1H, m), 8.08 (1H, dt, J=1.3 Hz, J=7.8 Hz), 8.27 (1H, t, J=1.6 Hz), 8.63 (1H, dd, J=1.6 Hz, J=4.8 Hz), 8.88 (1H, dd, J=0.7 Hz, J=2.4 Hz)

The compound of Reference Example 34

$^1$H-NMR (250 MHz, CDCl$_3$) δ ppm: 2.69 (3H, s), 3.92 (3H, s), 7.32–7.53 (3H, m), 7.89 (1H, ddd, J=1.7 Hz, J=2.3 Hz, J=7.1 Hz), 8.03 (1H, d, J=8.6 Hz), 8.63 (1H, dd, J=1.6 Hz, J=4.8 Hz), 8.86 (1H, dd, J=0.7 Hz, J=1.6 Hz)

The compound of Reference Example 35

$^1$H-NMR (250 MHz, CDCl$_3$) δ ppm: 3.95 (3H, s), 7.32–7.56 (4H, m), 7.59–7.66 (2H, m), 7.75–7.83 (1H, m), 7.99–8.07 (1H, m), 8.25–8.33 (1H, m)

The compound of Reference Example 36

$^1$H-NMR (200 MHz, CDCl$_3$) δ ppm: 2.27 (3H, s), 3.91 (3H, s), 3.92 (3H, s), 6.86–7.04 (2H, m), 7.16–7.41 (4H, m), 7.76–7.96 (1H, m)

The compound of Reference Example 37

$^1$H-NMR (200 MHz, CDCl$_3$) δ ppm: 3.81, 3.90 and 3.93 (each 3H, each s), 6.87–7.23 (4H, m), 7.29–7.52 (2H, m), 7.76–7.92 (1H, m)

The compound of Reference Example 38

$^1$H-NMR (200 MHz, CDCl$_3$) δ ppm: 3.91 and 3.97 (each 3H, each s), 7.11–7.28 (2H, m), 7.32–7.55 (3H, m), 7.56–7.70 (2H, m), 7.89 (1H, d, J=8.0 Hz)

The compound of Reference Example 39

$^1$H-NMR (200 MHz, CDCl$_3$) δ ppm: 2.39 (3H, s), 3.79 (6H, s), 3.95 (3H, s), 7.23 (4H, s), 7.33 (2H, s)

The compound of Reference Example 40

$^1$H-NMR (200 MHz, CDCl$_3$) δ ppm: 3.87 and 3.94 (each 3H, each s), 7.21– 7.50 (4H, m), 7.51–7.61 (2H, m), 7.62–7.83 (2H, m)

The compound of Reference Example 41

$^1$H-NMR (200 MHz, CDCl$_3$) δ ppm: 2.43 and 3.94 (each 3H, each s), 7.08–7.29 (1H, m), 7.30–7.50 (3H, m), 7.58–7.72 (2H, m), 8.02–8.18 (2H, m)

The compound of Reference Example 42

$^1$H-NMR (200 MHz, CDCl$_3$) δ ppm: 2.24, 2.37, 3.90 and 3.91 (each 3H, each s), 6.78–6.98 (2H, m), 7.00–7.19 (3H, m), 7.73–7.90 (1H, m)

The compound of Reference Example 43

¹H-NMR (250 MHz, CDCl₃) δ ppm: 1.42 (3H, t, J=7.1 Hz), 4.41 (2H, q, J=7.1 Hz), 7.27–7.90 and 8.02–8.22 (all 13H, m)

The compound of Reference Example 44

¹H-NMR (200 MHz, CDCl₃) δ ppm: 1.37 (3H, t, J=7.1 Hz), 4.34 (2H, q, J=7.1 Hz), 7.01–7.31 and 7.32–7.68 (all 11H, m), 7.79–8.00 (2H, m)

The compound of Reference Example 45

¹H-NMR (200 MHz, CDCl₃) δ ppm: 1.47 (3H, t, J=7 Hz), 4.41 (2H, q, J=7 Hz), 7.29–7.57, 7.58–7.84 and 8.03–8.21 (all 13H, m)

The compound of Reference Example 46

¹H-NMR (200 MHz, CDCl₃) δ ppm: 2.42 (3H, s), 2.67 (3H, s), 3.91 (3H, s), 7.07–7.59 (6H, m), 7.87–8.11 (1H, m)

The compound of Reference Example 47

¹H-NMR (200 MHz, CDCl₃) δ ppm: 3.91, 3.94, 3.97 and 3.98 (each 3H, each s), 6.96 (1H, d, J=8.3 Hz), 7.03–7.24 (4H, m), 7.88 (1H, d, J=7.9 Hz)

The compound of Reference Example 48

¹H-NMR (200 MHz, CDCl₃) δ ppm: 2.43, 3.91 and 3.98 (each 3H, each s), 7.04–7.29 (3H, m), 7.30–7.51 (3H, m), 7.88 (1H, d, J=7.9 Hz)

The compound of Reference Example 49

¹H-NMR (200 MHz, CDCl₃) δ ppm: 2.67 (3H, s), 3.86 (3H, s), 3.90 (3H, s), 6.90–7.08 (2H, m), 7.35–7.49 (2H, m) and 7.50–7.66 (2H, m), 7.89–8.07 (1H, m)

The compound of Reference Example 50

¹H-NMR (200 MHz, CDCl₃) δ ppm: 2.69 (3H, s), 3.92 (3H, s), 7.27–7.81 and 7.95–8.11 (all 12H, m)

The compound of Reference Example 51

¹H-NMR (200 MHz, CDCl₃) δ ppm: 2.12 (3H, s), 3.82 (3H, s), 3.95 (3H, s), 7.02–7.48 (5H, m), 7.63 (1H, d, J=1.4 Hz), 7.71 (1H, dd, J=7.7 Hz, J=1.4 Hz)

The compound of Reference Example 52

¹H-NMR (200 MHz, CDCl₃) δ ppm: 2.05 (3H, s), 3.77 (6H, s), 3.96 (3H, s), 7.03–7.18 (1H, m), 7.19–7.32 (3H, m), 7.34 (2H, s)

The compound of Reference Example 53

¹H-NMR (200 MHz, CDCl₃) δ ppm: 2.40, 3.90 and 3.97 (each 3H, each s), 7.09–7.34 (4H, m), 7.42–7.59 (2H, m), 7.87 (1H, d, J=7.9 Hz)

The compound of Reference Example 54

¹H-NMR (200 MHz, CDCl₃) δ ppm: 2.26, 2.65 and 3.91 (each 3H, each s), 7.08–7.38 (6H, m), 7.89–8.02 (1H, m)

The compound of Reference Example 55

¹H-NMR (200 MHz, CDCl₃) δ ppm: 2.41 and 3.93 (each 3H, each s), 7.17–7.34 (2H, m), 7.46–7.57 (2H, m), 7.58–7.72 (2H, m), 8.02–8.16 (2H, m)

The compound of Reference Example 56

¹H-NMR (200 MHz, CDCl₃) δ ppm: 2.26 and 3.94 (each 3H, each s), 7.14–7.35 (4H, m), 7.36–7.52 (2H, m), 7.99–8.18 (2H, m)

The compound of Reference Example 57

¹H-NMR (200 MHz, CDCl₃) δ ppm: 2.68 (3H, s), 3.91 (3H, s), 7.29–7.54 and 7.55–7.72 (all 7H, m), 7.91–8.08 (1H, m)

The compound of Reference Example 58

¹H-NMR (200 MHz, CDCl₃) δ ppm: 2.04 (6H, s), 3.88 and 3.92 (each 3H, each s), 6.71–6.85 (2H, m), 7.06–7.48 (3H, m), 7.78–7.93 (1H, m)

The compound of Reference Example 59

¹H-NMR (200 MHz, CDCl₃) δ ppm: 2.66 (3H, s), 3.90 (3H, s), 5.12 (2H, s), 6.98–7.12 (2H, m), 7.20–7.68 (10H, m)

The compound of Reference Example 60

¹H-NMR (200 MHz, CDCl₃) δ ppm: 2.70 (3H, s), 3.93 (3H, s), 7.38–7.58 (2H, m), 7.68–7.87 (2H, m), 7.98–8.12 (1H, m), 8.21–8.46 (2H, m)

The compound of Reference Example 61

¹H-NMR (200 MHz, CDCl₃) δ ppm: 1.42 (3H, t, J=7.0 Hz), 4.42 (2H, q, J=7.0 Hz), 7.28–7.78 and 7.85–8.18 (all 8H, m)

The compound of Reference Example 62

¹H-NMR (200 MHz, CDCl₃) δ ppm: 2.40 (3H, s), 2.67 (3H, s), 3.90 (3H, s), 7.18–7.31 (2H, m), 7.37–7.58 (4H, m), 7.91–8.05 (1H, m)

The compound of Reference Example 63

¹H-NMR (200 MHz, CDCl₃) δ ppm: 1.44 (3H, t, J=7.0 Hz), 2.66 (3H, s), 3.90 (3H, s), 4.10 (2H, q, J=7.0 Hz), 6.88–7.06 (2H, m), 7.34–7.49 (2H, m), 7.50–7.64 (2H, m), 7.89–8.06 (1H, m)

The compound of Reference Example 64

¹H-NMR (200 MHz, CDCl₃) δ ppm: 1.06 (3H, t, J=7.4 Hz), 1.70–1.97 (2H, m), 2.66 (3H, s), 3.90 (3H, s), 3.97 (2H, d, J=6.5 Hz), 6.89–7.08 (2H, m), 7.35–7.48 (2H, m), 7.49–7.64 (2H, m), 7.89–8.08 (1H, m)

The compound of Reference Example 65

¹H-NMR (200 MHz, DMSO-d₆) δ ppm: 1.40–2.90 and 3.21–3.90 [all 13H, m, 2.33 (s)], 6.50–8.40 [all 4H, m, 7.71 (d, J=8.41 Hz)]

The compound of Reference Example 66

¹H-NMR (200 MHz, CDCl₃) δ ppm: 2.85–4.90 (all 9H, m), 6.79–7.38 and 7.45–7.69 (all 7H, m)

The compound of Reference Example 68

¹H-NMR (200 MHz, DMSO-d₆) δ ppm: 2.60–4.75 (all 11H, m), 6.80–7.85 [all 8H, m, 7.77 (d, J=8.80 Hz)]

The compound of Reference Example 70

¹H-NMR (200 MHz, CDCl₃) δ ppm: 2.74 (3H, s), 3.88 (3H, s), 5.82–8.39 [all 8H, m, 6.95 (d, J=8.0 Hz), 8.15 (d, J=8.52 Hz)]

The compound of Reference Example 75

¹H-NMR (200 MHz, DMSO-d₆) δ ppm: 2.77 (3H, s), 3.42–3.50 (2H, m), 3.78–3.86 (2H, m), 7.49 (1H, dd, J=8.8 Hz, J=2.2 Hz), 7.83 (1H, d, J=8.8 Hz), 7.84 (1H, d, J=2.2 Hz), 12.6–13.3 (1H, m)

The compound of Reference Example 76

¹H-NMR (200 MHz, DMSO-d6) δ ppm: 0.86 (6H, d, J=6.6 Hz), 1.8–2.05 (1H, m), 3.0 (2H, d, J=7.2 Hz), 3.4–3.55 (2H, m), 3.8–3.95 (2H, m), 7.49 (1H, dd, J=8.8 Hz, J=2.2 Hz), 7.83 (1H, d, J=8.8 Hz), 7.85 (1H, d, J=2.2 Hz), 12.8–13.1 (1H, m)

The compound of Reference Example 77

¹H-NMR (200 MHz, DMSO-d₆) δ ppm: 3.3–3.41 (2H, m), 3.75–3.95 (2H, m), 4.39 (2H, s), 7.2–7.45 (5H, m), 7.5 (1H, dd, J=9 Hz, J=2.2 Hz), 7.84 (1H, d, J=9 Hz), 7.88 (1H, d, J=2.2 Hz)

The compound of Reference Example 78

¹H-NMR (200 MHz, DMSO-d₆) δ ppm: 2.93 (3H, s), 4.56 (2H, s), 7.20–7.50 (5H, m), 7.62 (2H, d, J=8.7 Hz), 7.81 (2H, d, J=8.7 Hz), 8.76 (1H, s)

The compound of Reference Example 79

¹H-NMR (200 MHz, DMSO-d₆) δ ppm: 7.38–7.51 (1H, m), 7.51–7.95 (4H, m), 7.95–8.10 (1H, m), 8.68–8.95 (2H, m), 10.3–13.5 (1H, br)

The compound of Reference Example 80

$^1$H-NMR (200 MHz, DMSO-$d_6$) δ ppm: 2.58 (3H, s), 7.38–7.48 (2H, m), 7.48–7.64 (1H, m), 7.46–8.01 (1H, m), 8.63 (1H, d, J=5.0 Hz), 8.80 (1H, s)

The compound of Reference Example 81

$^1$H-NMR (200 MHz, DMSO-d6) δ ppm: 2.22 (3H, s), 2.30–2.58 (4H, m), 3.15–3.40 (4H, m), 6.85–7.05 (2H, m), 7.15–7.84 (2H, m), 11.75–12.80 (1H, brs)

The compound of Reference Example 94

$^1$H-NMR (200 MHz, DMSO-$d_6$) δ ppm: 0.77 (3H, t, J=7.3 Hz), 1.75 (2H, q, J=7.3 Hz), 4.15 (2H, t, J=7.3 Hz), 7.31–7.97 (3H, m), 8.02 (1H, d, J=1.7 Hz), 8.11–8.27 (2H, m)

The compound of Reference Example 95

$^1$H-NMR (200 MHz, DMSO-$d_6$) δ ppm: 7.19 (1H, s), 7.35–7.64 (2H, m), 7.69 (1H, s), 8.00–8.30 (4H, m), 10.40–11.62 (1H, brs)

The compound of Reference Example 98

$^1$H-NMR (200 MHz, CDCl$_3$) δ ppm: 1.55–1.94 (4H, m), 2.13–2.30 (2H, m), 2.31–2.56 (2H, m), 2.66 (3H, s), 6.18–6.35 (1H, m), 7.15–7.42 (2H, m), 7.90–8.18 (1H, m)

The compound of Reference Example 99

$^1$H-NMR (200 MHz, DMSO-$d_6$) δ ppm: 2.62 (3H, s), 7.58–7.82 (2H, m), 7.88–8.19 (3H, m), 8.21–8.48 (2H, m), 12.97 (1H, s)

The compound of Reference Example 102

$^1$H-NMR (200 MHz, CDCl$_3$) δ ppm: 1.42–2.00 (6H, m), 2.18–2.46 (2H, m), 2.47–2.79 (2H, m), 2.66 (3H, s), 6.21 (1H, t, J=6.7 Hz), 7.05–7.40 (1H, m), 7.88–8.12 (1H, m)

The compound of Reference Example 111

$^1$H-NMR (200 MHz, CDCl$_3$) δ ppm: 7.03–7.31 (7H, m), 7.32–7.58 (4H, m), 7.95 (2H, d, J=8.35 Hz)

The compound of Reference Example 113

$^1$H-NMR (200 MHz, CDCl$_3$) δ ppm: 2.30 and 4.15 (each 3H, each s), 7.09–7.48 (6H, m), 8.23 (1H, d, J=8.1 Hz), 10.00–11.42 (1H, m)

The compound of Reference Example 114

$^1$H-NMR (200 MHz, CDCl$_3$) δ ppm: 2.73 and 3.87 (each 3H, each s), 7.00 and 7.59 (each 2H, each dd, J=8.8 Hz, J=2.1 Hz), 7.36–7.52 (2H, m), 8.03–8.21 (1H, m)

The compound of Reference Example 116

$^1$H-NMR (200 MHz, CDCl$_3$) δ ppm: 2.14 and 3.85 (each 3H, each s), 7.09–7.41 (5H, m), 7.71 (1H, d, J=1.4 Hz), 7.82 (1H, dd, J=8.0 Hz, J=1.5 Hz)

The compound of Reference Example 120

$^1$H-NMR (200 MHz, CDCl$_3$) δ ppm: 1.21–2.06 and 2.48–2.82 (all 13H, m), 2.63 (3H, s), 4.84–6.49 (1H, m), 6.98–7.19 (2H, m), 7.99 (1H, d, J=8.7 Hz)

The compound of Reference Example 121

$^1$H-NMR (200 MHz, CDCl$_3$) δ ppm: 1.40–2.23 and 2.87–3.14 (all 9H, m), 2.64 (3H, s), 6.98–7.24 (2H, m), 8.00 (1H, d, J=8.7 Hz)

The compound of Reference Example 122

$^1$H-NMR (200 MHz, DMSO-$_6$) δ ppm: 1.49–1.88 (4H, m), 2.08–2.19 and 2.20–2.52 (each 2H, each m), 6.20–6.40 (1H, m), 7.51 and 7.87 (each 2H, each d, each J=8.4 Hz), 12.42–13.18 (1H, m)

The compound of Reference Example 123

$^1$H-NMR (200 MHz, DMSO-$d_6$) δ ppm: 1.49–1.68 (4H, m), 1.69–1.91 (2H, m), 2.18–2.37 (2H, m), 2.45–2.67 (2H, m), 6.23 (1H, t, J=6.7 Hz), 7.42 and 7.86 (each 2H, each d, each J=8.4 Hz), 7.28–7.79 (1H, m)

The compound of Reference Example 129

$^1$H-NMR (200 MHz, CDCl$_3$) δ ppm: 2.75 (3H, m), 7.29–7.74 (7H, m), 8.10–8.22(1H,m)

The compound of Reference Example 153

$^1$H-NMR (200 MHz, CDCl$_3$) δ ppm: 3.94 (s, 3H), 7.58 (dd, J=8.6, 2.2 Hz, 1H), 7.78 (d, J=2.2 Hz,1H), 7.90 (d, J=8.6 Hz,1H), 8.32 (1H, brs)

The compound of Reference Example 145

$^1$H-NMR (200 MHz, CDCl$_3$) δ ppm: 2.70 (3H, s), 3.92 (3H, s), 7.22–7.35 (1H, m), 7.70–7.96 (4H, m), 8.03 (1H, d, J=8.2 Hz), 8.67–8.78 (1H, m)

The compound of Reference Example 157

$^1$H-NMR (200 MHz, CDCl$_3$) δ ppm: 2.88 (3H, s), 3.41–3.50 (2H, m), 3.79–3.89 (2H, m), 3.89 (3H, s), 3.90 (3H, s), 7.49 (1H, d, J=8.2 Hz), 7.87 (1H, d, J=1.7 Hz), 7.65 (1H, dd, J=8.2 Hz, 1.7 Hz)

The compound of Reference Example 158

$^1$H-NMR (200 MHz, CDCl$_3$) δ ppm: 3.77, 3.83, 3.93 (each 3H, eash s), 6.89–7.08 (2H, m), 7.15–7.44 (3H, m), 7.54–7.79 (2H, m)

The compound of Reference Example 159

$^1$H-NMR (200 MHz, CDCl$_3$) δ ppm: 3.84, 3.88, 3.94 (each 3H, each s), 6.83–6.98 (1H, m), 7.02–7.15 (2H, m), 7.27–7.43 (2H, m), 7.64 (1H, d, J=1.4 Hz), 7.71 (1H, dd, J=1.6 Hz, J=7.8 Hz)

The compound of Reference Example 162

$^1$H-NMR (200 MHz, DMSO-$d_6$) δ ppm: 2.55 (3H, s), 4.53 (2H, s), 4.55 (2H, s), 7.25–7.55 (7H, m), 7.88 (1H, d, J=9 Hz), 12.88 (1H, s)

The compound of Reference Example 163

$^1$H-NMR (200 MHz, DMSO-$d_6$) δ ppm: 2.62 (3H, s), 7.70–7.82 (1H, m), 7.90–8.13 (3H, m), 8.20–8.40 (2H, m), 8.72–8.86 (1H, m)

The compound of Reference Example 170

$^1$H-NMR (200 MHz, CDCl$_3$) δ ppm: 0.97 (6H, d, J=6.6 Hz), 1.23 (3H, t, J=7.0 Hz), 1.85–2.10 (1H, m), 3.13 (2H, d, J=7.5 Hz), 3.39 (2H, q, J=7 Hz), 6.54 (1H, s), 7.36 (1H, dd, J=8.7 Hz, J=2.2 Hz), 7.63 (1H, d, J=2.2 Hz), 7.98 (1H, d, J=8.7 Hz)

The compound of Reference Example 171

$^1$H-NMR (200 MHz, DMSO-$d_6$) δ ppm: 2.57 (3H, s), 5.17 (2H, s), 6.58–6.92, 6.93–8.03 (total 12H, m), 12.56–12.94 (1H, m)

The compound of Reference Example 173

$^1$H-NMR (250 MHz, DMSO-$d_6$) δ ppm: 2.84 (2H, t, J=4.6 Hz), 3.70 (2H, t, J=4.6 Hz), 4.64 (2H, s), 7.17 (4H, s), 7.54 (1H, dd, J=7 Hz, J=1.6 Hz), 7.76–7.83 (2H, m), 9.01 (1H, s)

The compound of Reference Example 175

$^1$H-NMR (200 MHz, DMSO-$d_6$) δ ppm: 2.61 (3H, s), 4.10–5.40 (2H, brs), 7.32–7.90 (4H, m), 7.95 (1H, d, J=8.2 Hz), 9.22 (1H, d, J=5.8 Hz)

The compound of Reference Example 176

$^1$H-NMR (200 MHz, DMSO-$_6$) δ ppm: 2.86 (2H, t, J=5.8 Hz), 3.67 (2H, t, J=5.8 Hz), 3.89 (3H, s), 4.63 (2H, s), 7.18 (4H, s), 7.4–7.6 (2H, m), 7.84 (1H, s), 7.95 (1H, d, J=8.2 Hz)

The compound of Reference Example 174

$^1$H-NMR (200 MHz, DMSO-$d_6$) δ ppm: 0.83 (6H, d, J=6.6 Hz), 1.68–1.97 (1H, m), 2.42 (2H, d, J=7.2 Hz), 2.48 (3H, s), 6.93–7.13 (2H, m), 7.74 (1H, d, J=8.5 Hz)

The compound of Reference Example 146

$^1$H-NMR (200 MHz, CDCl$_3$) δ ppm: 1.92–2.18, 3.21–3.45 (total 8H, m), 3.85 (3H, s), 6.38 (1H, dd, J=2.5 Hz, J=2.5 Hz), 6.52 (1H, d, J=2.45 Hz), 7.88 (1H, d, J=11.3 Hz)

The compound of Reference Example 147

$^1$H-NMR (200 MHz, CDCl$_3$) δ ppm: 3.29 (4H, t, J=4.8 Hz), 3.84 (4H, t, J=5.1 Hz), 3.87 (3H, s), 6.73 (1H, dd, J=2.8 Hz, J=2.6 Hz), 6.86 (1H, d, J=2.7 Hz), 7.85 (1H, d, J=9.0 Hz)

The compound of Reference Example 161

$^1$H-NMR (200 MHz, CDCl$_3$) δ ppm: 0.79–1.02 (9H, m with s at 0.96), 1.59 (2H, t, J=7.8 Hz), 3.86 (3H, s), 3.89 (3H, s), 4.23 (2H, t, J=7.5 Hz), 6.90 (1H, dd, J=8.5 Hz, J=8.5 Hz), 7.03 (1H, s), 7.43 (1H, d, J=1.7 Hz), 7.80 (1H, d, J=8.5 Hz)

The compound of Reference Example 164

$^1$H-NMR (200 MHz, DMSO-d$_6$) δ ppm: 1.85–2.12 (4H, m), 3.12–3.46 (4H, m), 6.35–6.62 (2H, m), 7.74 (1H, d, J=8.6 Hz), 12.35 (1H, brs)

The compound of Reference Example 165

$^1$H-NMR (200 MHz, DMSO-d$_6$) δ ppm: 3.25 (4H, t, J=5.0 Hz), 3.70 (4H, t, J=5.0 Hz), 6.80–7.09 (2H, m), 7.75 (1H, d, J=8.7 Hz)

The compound of Reference Example 180

$^1$H-NMR (200 MHz, DMSO-d$_6$) δ ppm: 0.93 (9H, s), 1.55 (2H, t, J=7.5 Hz), 3.76 (3H, s), 4.15 (2H, t, J=7.4 Hz), 7.05 (1H, dd, J=8.6 Hz, J=8.6 Hz), 7.34 (1H, d, J=1.6 Hz), 7.64 (1H, d, J=8.9 Hz), 9.88 (1H, s)

The compound of Reference Example 148

$^1$H-NMR (200 MHz, CDCl$_3$) δ ppm: 2.60 (3H, s), 3.85 (3H, s), 5.09 (2H, s), 6.72–6.99 [2H, m, (6.83, 1H, s)], 7.25–7.48 (5H, m), 7.93 (1H, d, J=9.1 Hz)

The compound of Reference Example 150

$^1$H-NMR (200 MHz, CDCl$_3$) δ ppm: 1.35 (6H, d, J=6.1 Hz), 2.59 (3H, s), 3.85 (3H, s), 4.49–4.71 (1H, m), 6.61–6.78 (2H, m), 7.82–7.98 (1H, m)

The compound of Reference Example 151

$^1$H-NMR (200 MHz, CDCl$_3$) δ ppm: 0.98 (3H, t, J=7.8 Hz), 1.30–1.89 (4H, m), 2.59 (3H, s), 3.85 (3H, s), 4.13 (2H, t, J=6.5 Hz), 6.68–6.80 (2H, m), 7.83–7.99 (1H, m)

The compound of Reference Example 152

$^1$H-NMR (200 MHz, CDCl$_3$) δ ppm: 1.03 (6H, d, J=6.7 Hz), 1.98–2.21 (1H, m), 2.59 (3H, s), 3.75 (2H, d, J=6.6 Hz), 3.85 (3H, s), 6.66–6.81 (2H, m), 7.82–7.99 (1H, m)

The compound of Reference Example 154

$^1$H-NMR (200 MHz, DMSO-d$_6$) δ ppm: 2.50 (3H, s), 3.78 (3H, s), 4.75 (2H, s), 6.73–6.93 (2H, m), 7.82 (1H, d, J=8.5 Hz), 13.09 (1H, brs)

The compound of Reference Example 167

$^1$H-NMR (200 MHz, DMSO-d$_6$) δ ppm: 1.26 (6H, d, J=6.0 Hz), 2.49 (3H, s), 4.56–4.80 (1H, m), 6.69–6.85 (2H, m), 7.75–7.85 (1H, m), 12.39 (1H, s)

The compound of Reference Example 168

$^1$H-NMR (200 MHz, DMSO-d$_6$) δ ppm: 0.93 (3H, t, J=7.3 Hz), 1.33–1.55 (2H, m), 1.57–1.81 (2H, m), 2.51 (3H, s), 4.01 (2H, t, J=6.4 Hz), 6.72–6.90 [2H, m, (6.83 (1H, s))], 7.82 (1H, d, J=7.6 Hz), 12.41 (1H, s)

The compound of Reference Example 169

$^1$H-NMR (200 MHz, DMSO-d$_6$) δ ppm: 0.96 (6H, d, J=6.7 Hz), 1.87–2.15 (1H, m), 2.50 (3H, s), 3.78 (2H, d, J=6.5 Hz), 6.72–6.88 [2H, m, 6.82 (1H, s)], 7.81 (1H, d, J=7.8 Hz), 12.40 (1H, brs)

EXAMPLE 1

4-Ethoxy-2-methoxybenzoic acid (0.33 g) is dissolved in thionyl chloride (10 ml), and the mixture is refluxed for 30 minutes. The mixture is concentrated under reduced pressure, and thereto is added toluene (20 ml), and the mixture is concentrated again under reduced pressure. The resulting 4-ethoxy-2-methoxybenzoyl chloride is dissolved in dichloromethane (10 ml), and the mixture is cooled at 0° C. over an ice-bath, and thereto is added 7-chloro-5-[N-methyl-N-(2-diethylaminoethyl)amino]carbonylmethyl-2,3,4,5-tetrahydro-1H-benzazepine (0.5 g). To the mixture is added triethylamine (0.6 ml), and the mixture is stirred at the same temperature for two hours. To the reaction solution is added water, and the mixture is extracted with dichloromethane. The extract is dried over sodium carbonate, and purified by silica gel column chromatography (solvent; dichloromethane:methanol =50:1~5:1). The resulting oily product is dissolved in ethanol, and thereto is added conc. hydrochloric acid (0.1 ml), and the mixture is concentrated under reduce pressure to give 7-chloro-5-[N-methyl-N-(2-diethylaminoethyl)amino]carbonyl-methyl-1-(2-methoxy-4-ethoxybenzoyl)-2,3,4,5-tetrahydro-1H-benzazepine hydrochloride (0.2 g) in a colorless amorphous.

$^1$H-NMR (200 MHz, DMSO-d$_6$) δ ppm: 0.98–2.06 (13H, m), 2.61–4.88 (21H, m), 6.18–7.45 (6H, m), 10.42–11.52 (1H, m)

EXAMPLE 2

To 4-cyclohexylbenzoic acid (2 g) is added thionyl chloride (20 ml), and the mixture is refluxed for two hours. The mixture is evaporated to remove the thionyl chloride to give 4-cyclohexylbenzoyl chloride. To a solution of 5-ethoxycarbonylmethyl-7-chloro-2,3,4,5-tetrahydro-1H-benzazepine (2.2 g) in dichloromethane (50 ml) is added pyridine (3.3 g), and to the mixture is added with stirring the above obtained 4-cyclohexylbenzoyl chloride under ice-cooling, and the mixture is stirred at room temperature overnight. To the reaction solution is added water, and the mixture is extracted with dichloro-methane. The extract is washed with diluted hydrochloric acid, and washed with water, and dried over magnesium sulfate. The mixture is evaporated to remove the solvent, and the residue is purified by silica gel column chromatography (solvent; dichloromethane) to give 5-ethoxycarbonylmethyl-7-chloro-1-(4-cyclohexylbenzoyl)-2,3,4,5-tetrahydro-1H-benzazepine (4 g) as colorless oil.

$^1$H-NMR (200 MHz, CDCl$_3$) δ ppm: 1.27 (3H, t, J=7.1 Hz), 1.20–2.20 (14H, m), 2.30–2.50 (1H, m), 2.60–3.05 (3H, m), 3.10–3.35 (1H, m), 4.10–4.40 (2H, m), 4.45–4.65 (1H, m), 6.57 (1H, d, J=8.4 Hz), 6.96 (1H, d, J=8.1 Hz), 7.00 (2H, d, J=8.0 Hz), 7.10–7.35 (3H, m)

EXAMPLE 3

To a solution of 5-ethoxycarbonylmethyl-7-chloro-1-(4-cyclohexyl-benzoyl)-2,3,4,5-tetrahydro-1H-benzazepine (2 g) in ethanol (20 ml) is added a 5N aqueous sodium hydroxide solution (5 ml), and the mixture is stirred at room temperature overnight. The reaction solution is acidified with hydrochloric acid, and the mixture is extracted with dichloromethane. The extract is washed with water, dried over magnesium sulfate, and evaporated to remove the solvent to give 5-carboxymethyl-7-chloro-1-(4-cyclohexylbenzoyl)-2,3,4,5-tetrahydro-1H-benzazepine (1.8 g) in colorless amorphous.

$^1$H-NMR (200 MHz, CDCl$_3$) δ ppm: 1.20–2.25 (14H, m), 2.30–2.55 (1H, m), 2.60–3.30 (3H, m), 3.50–3.90 (1H, m), 4.45–4.60 and 5.10–5.30 (1H, m), 6.15 (1H, brs), 6.59 (1H, d, J=8.3 Hz), 6.85–7.00 (3H, m), 7.10–7.35 (3H, m)

The starting compounds are treated in the same manner as Example 3 to give the compounds of Examples 52, 68, 77, 78, 81–83, 87, 90, 96, 101, 103, 104, 109, 117–118, 120 and 131–135.

EXAMPLE 4

To a solution of 5-carboxymethyl-7-chloro-1-(4-cyclohexylbenzoyl)-2,3,4,5-tetrahydro-1H-benzazepine (0.7 g) in dichloromethane (50 ml) is added with stirring N,N-bis(2-oxo-3-oxazolidinyl)phosphinic chloride (0.54 g) under ice-cooling, and the mixture is stirred at room temperature for 15 minutes. To the mixture are added with stirring N-methylpiperazine (0.24 ml) and triethylamine (0.46 ml) under ice-cooling, and the mixture is stirred at room temperature overnight. To the reaction solution is added water, and the mixture is extracted with dichloromethane. The extract is washed with water, dried over magnesium sulfate, and evaporated to remove the solvent. The residue is purified by silica gel column chromatography (solvent; dichloromethane:—methanol=40:1) to give 7-chloro-5-[(4-methyl-1-piperazinyl)carbonylmethyl]-1-(4-cyclohexylbenzoyl)-2,3,4,5-tetrahydro-1H-benzazepine (0.7 g) as colorless amorphous.

$^1$H-NMR (200 MHz, CDCl$_3$) δ ppm: 1.20–3.40 (22H, m), 2.21 and 2.34 (3H, s), 3.50–3.90 (5H, m), 4.40–4.60 and 5.05–5.20 (1H, m), 6.50–6.60 (1H, m), 6.85–6.95 (1H, m), 7.00–7.15 (3H, m), 7.25–7.50 (2H, m)

The suitable starting compounds are treated in the same manner as in Example 4 to give the compounds of Examples 7, 9, 11–18, 20–22, 24, 25, 28–36, 38–40, 46–48, 55–67, 70–72, 74–76, 79, 84, 85, 88, 91–94, 98, 121–126, 137 and 138.

EXAMPLE 5

7-Chloro-5-[(4-methyl-1-piperazinyl)carbonylmethyl]-1-{4-[2-(2-methylphenyl)acetyl]benzoyl}-2,3,4,5-tetrahydro-1H-benzazepine (2.06 g) is dissolved in a mixture of methylene chloride (20 ml) and methanol (20 ml), and thereto ia added with stirring sodium borohydride (0.28 g) under cooling over an ice-bath. The mixture is stirred for two hours over an ice-bath, and the mixture is evaporated to remove almost of the solvent. To the residue is added water, and the mixture is extracted with methylene chloride. The organic layer is washed with a saturated aqueous sodium chloride solution, dried over magnesium sulfate, and concentrated. The residue is purified by silica gel column chromatography (solvent; methylene chloride:methanol =20~10:1) to give 7-chloro-5-[(4-methyl-1-piperazinyl)carbonylmethyl]-1-{4-[2-(2-methyl-phenyl)-1-hydroxyethyl]benzoyl}-2,3,4,5-tetrahydro-1H-benzazepine (2.08 g) as colorless amorphous.

$^1$H-NMR (200 MHz, CDCl$_3$) δ ppm: 1.1–4.0, 4.35–4.65, 4.65–5.0 and 5.0–5.25 (all 27H, m), 6.4–6.65 (1H, m), 6.75–7.6 (10H, m)

The suitable starting compounds are treated in the same manner as in Example 5 to give the compounds of Examples 22, 46 and 94.

EXAMPLE 6

To a mixture of 7-chloro-5-[(4-methyl-1-piperazinyl)carbonyl-methyl]-1-{4-[2-(2-methylphenyl)-1-hydroxyethyl]benzoyl}-2,3,4,5-tetrahydro-1H-benzazepine (0.5 g), acetic acid (5 ml) and acetic anhydride (3 ml) is added a drop of conc. sulfuric acid, and the mixture is stirred at room temperature for 12 hours, and subsequently stirred at a temperature from 60–70° C. for 6 hours. The reaction mixture is poured into ice-water, and thereto is added ethyl acetate (30 ml). The mixture is basified with sodium hydrogen carbonate, and extracted with ethyl acetate. The organic layer is washed successively with a saturated aqueous sodium hydrogen carbonate solution and a saturated aqueous sodium chloride solution, dried over magnesium sulfate, and concentrated. The residue is purified by silica gel column chromatography (solvent; methylene chloride:methanol= 20:1) to give 7-chloro-5-[(4-methyl-1-piperazinyl) carbonylmethyl]-1-{4-[2-(2-methylphenyl)-1-acetyloxyethyl]-benzoyl}-2,3,4,5-tetrahydro-1H-benzazepine (0.36 g) as colorless amorphous.

$^1$H-NMR (200 MHz, CDCl$_3$) δ ppm: 1.1–4.0, 4.35–4.7 and 4.95–5.25 (all 28H, m), 5.7–6.0 (1H, m), 6.4–6.65 (1H, m), 6.75–7.6 (10H, m)

The suitable starting compounds are treated in the same manner as in Example 6 to give the compounds of Examples 12 and 48.

The suitable starting compounds are treated in the same manner as in Examples 1 and 2 to give the following compounds.

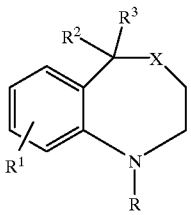

EXAMPLE 7

Structure

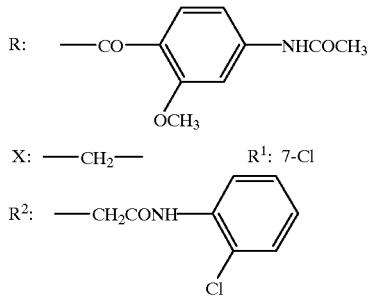

R$^3$: H

Crystalline form: White powder

Solvent for recrystallization: Acetone/n-hexane

M.p. 146–148° C.

Form: Free

EXAMPLE 8

Structure

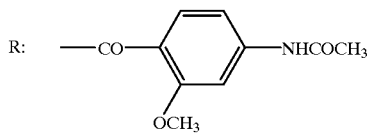

-continued

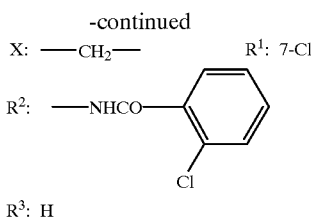

X: —CH₂—  R¹: 7-Cl
R²: —NHCO—
R³: H

Crystalline form: White powder
Solvent for recrystallization: Acetone/diethyl ether
M.p. 184–186° C.
Form: Free

EXAMPLE 9

Structure

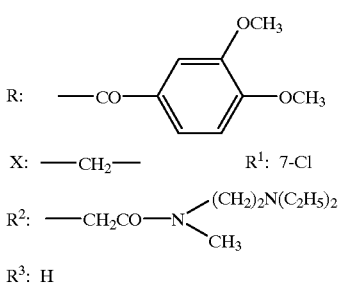

R: —CO—
X: —CH₂—  R¹: 7-Cl
R²: —CH₂CO—N(CH₂)₂N(C₂H₅)₂ / CH₃
R³: H

Crystalline form: Colorless amorphous
NMR analysis: 1)
Form: Free

EXAMPLE 10

Structure

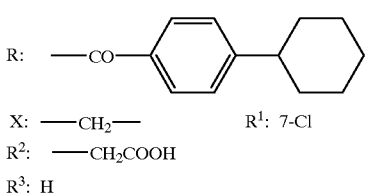

R: —CO—
X: —CH₂—  R¹: 7-Cl
R²: —CH₂COOH
R³: H

Crystalline form: Colorless amorphous
NMR analysis: 2)
Form: Free

EXAMPLE 11

Structure

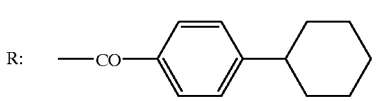

R: —CO—

-continued

X: —CH₂—  R¹: 7-Cl
R²: —CH₂CO—N   N—CH₃
R³: H

Crystalline form: Colorless amorphous
NMR analysis: 3)
Form: Free

EXAMPLE 12

Structure

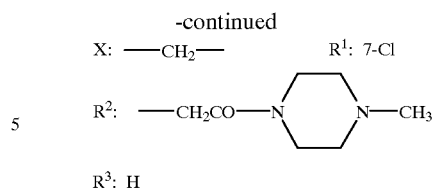

R: —CO—
X: —CH₂—  R¹: 7-Cl
R²: —CH₂CO—N(CH₂)₂N(C₂H₅)₂ / CH₃
R³: H

Crystalline form: Colorless amorphous
NMR analysis: 4)
Form: Hydrochloride

EXAMPLE 13

Structure

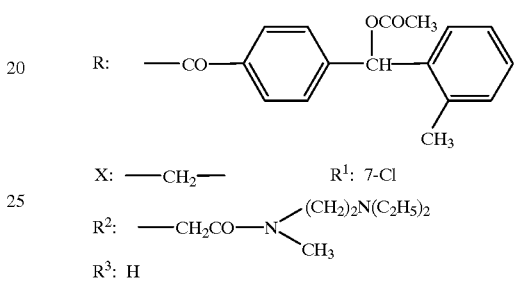

R: —CO—
X: —CH₂—  R¹: 7-Cl
R²: —CH₂CO—N   N—CH₃
R³: H

Crystalline form: White powder
Solvent for recrystallization: Acetone/n-hexane
M.p. 186–187° C.
Form: Free

EXAMPLE 14

Structure

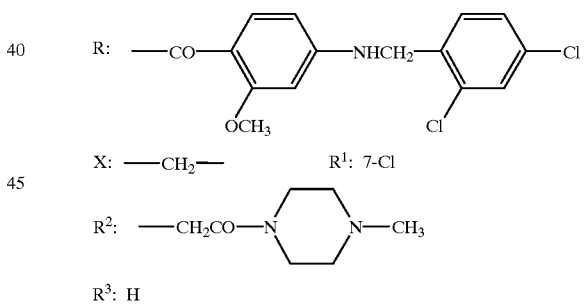

R: —CO—

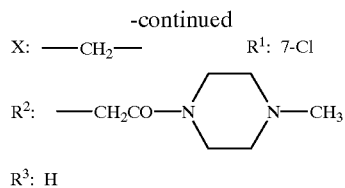

Crystalline form: White powder
Solvent for recrystallization: Acetone/n-hexane
M.p. 162–162.5° C.
Form: Free

EXAMPLE 15

Structure

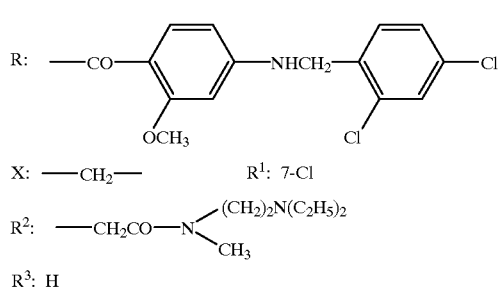

Crystalline form: Colorless amorphous
NMR analysis: 5)
Form: Free

EXAMPLE 16

Structure

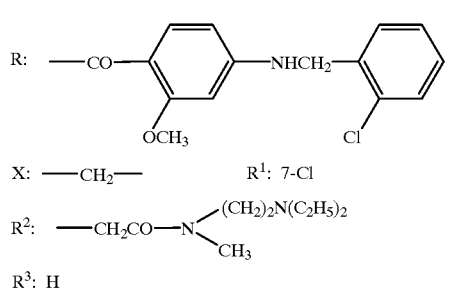

Crystalline form: Colorless amorphous
NMR analysis: 6)
Form: Free

EXAMPLE 17

Structure

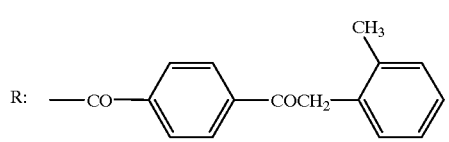

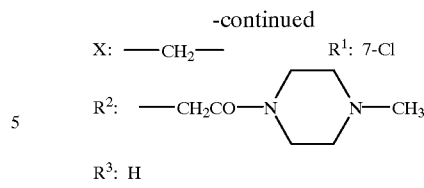

Crystalline form: Colorless needles
Solvent for recrystallization: Ethanol
M.p. 181–182.5° C.
Form: Free

EXAMPLE 18

Structure

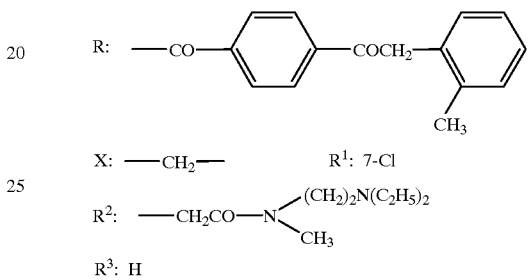

Crystalline form: Colorless needles
Solvent for recrystallization: Ethanol/diethyl ether
M.p. 123–126° C.
Form: Free

EXAMPLE 19

Structure

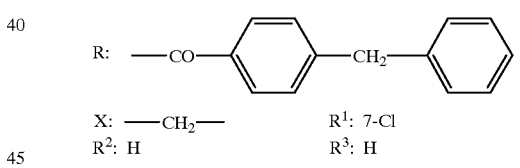

Crystalline form: Colorless plates
Solvent for recrystallization: Dichloromethane/n-hexane
M.p. 87.5–88° C.
Form: Free

EXAMPLE 20

Structure

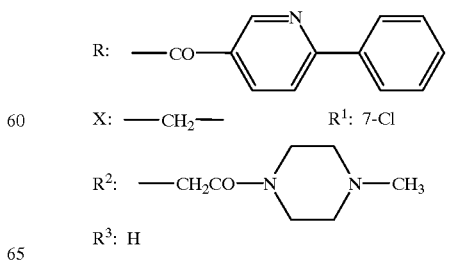

Crystalline form: White powder

Solvent for recrystallization: Acetone/n-hexane
M.p. 152–153° C.
Form: Free

EXAMPLE 21

Structure

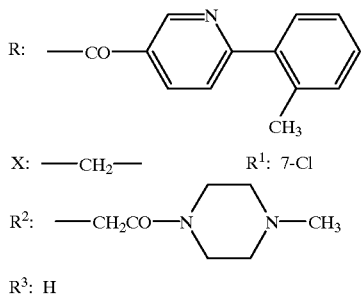

X: —CH$_2$—  R$^1$: 7-Cl
R$^2$: —CH$_2$CO—N(piperazine)—CH$_3$
R$^3$: H

Crystalline form: Colorless amorphous
NMR analysis: 7)
Form: Free

EXAMPLE 22

Structure

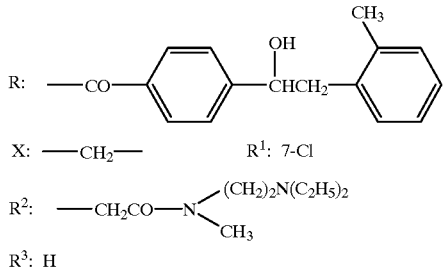

X: —CH$_2$—  R$^1$: 7-Cl
R$^2$: —CH$_2$CO—N((CH$_2$)$_2$N(C$_2$H$_5$)$_2$)(CH$_3$)
R$^3$: H

Crystalline form: Colorless amorphous
NMR analysis: 8)
Form: Free

EXAMPLE 23

Structure

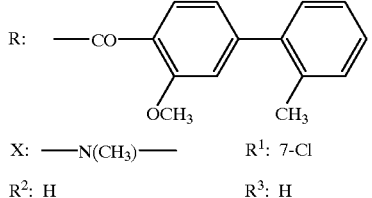

X: —N(CH$_3$)—  R$^1$: 7-Cl
R$^2$: H  R$^3$: H

Crystalline form: Colorless amorphous
NMR analysis: 9)
Form: Free

EXAMPLE 24

Structure

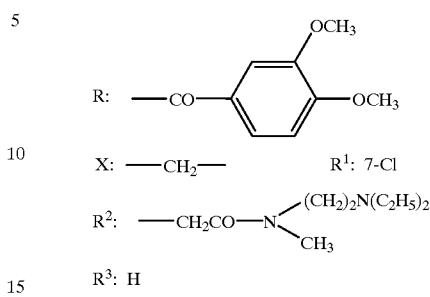

X: —CH$_2$—  R$^1$: 7-Cl
R$^2$: —CH$_2$CO—N((CH$_2$)$_2$N(C$_2$H$_5$)$_2$)(CH$_3$)
R$^3$: H

Crystalline form: Colorless amorphous
NMR analysis: 79)
Form: Free

EXAMPLE 25

Structure

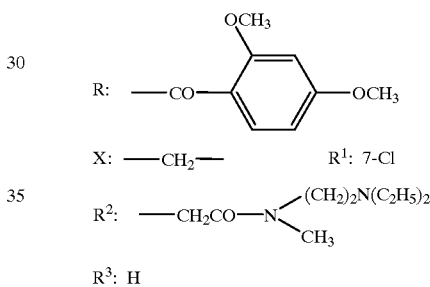

X: —CH$_2$—  R$^1$: 7-Cl
R$^2$: —CH$_2$CO—N((CH$_2$)$_2$N(C$_2$H$_5$)$_2$)(CH$_3$)
R$^3$: H

Crystalline form: Pale yellow amorphous
NMR analysis: 10)
Form: Hydrochloride

EXAMPLE 26

Structure

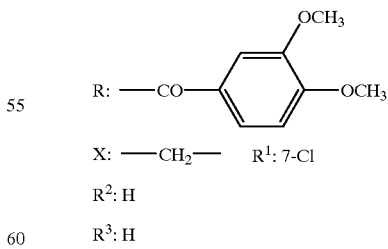

X: —CH$_2$—  R$^1$: 7-Cl
R$^2$: H
R$^3$: H

Crystalline form: Colorless amorphous
NMR analysis: 11)
Form: Free

EXAMPLE 27

Structure

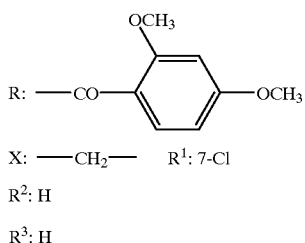

R²: H
R³: H

Crystalline form: Colorless oil

NMR analysis: 12)

Form: Free

EXAMPLE 28

Structure

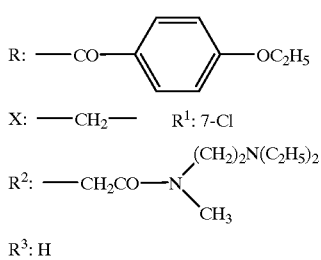

R³: H

Crystalline form: Colorless amorphous

NMR analysis: 13)

Form: Hydrochloride

EXAMPLE 29

Structure

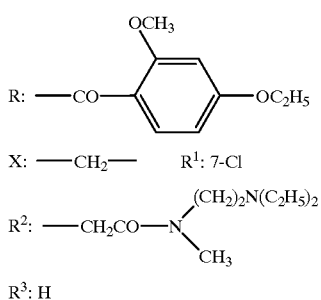

R³: H

Crystalline form: Colorless amorphous

NMR analysis: 14)

Form: Hydrochloride

EXAMPLE 30

Structure

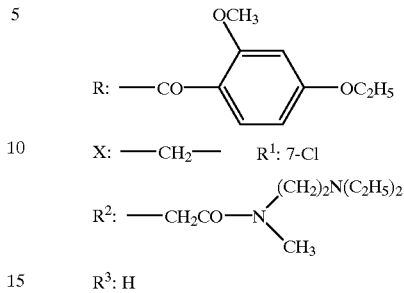

R³: H

Crystalline form: Colorless amorphous

NMR analysis: 15)

Form: Hydrochloride

EXAMPLE 31

Structure

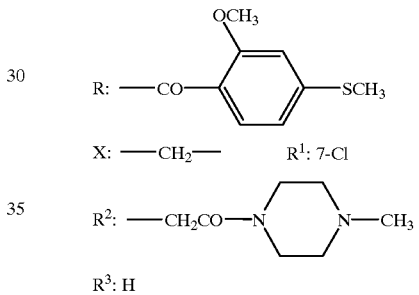

R³: H

Crystalline form: Colorless amorphous

NMR analysis: 16)

Form: Hydrochloride

EXAMPLE 32

Structure

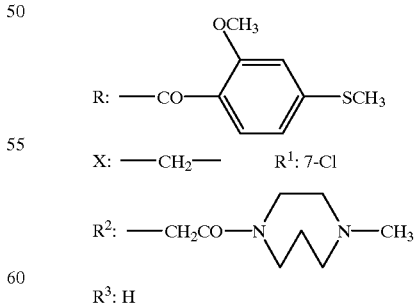

R³: H

Crystalline form: Colorless amorphous

NMR analysis: 17)

Form: Hydrochloride

EXAMPLE 33

Structure

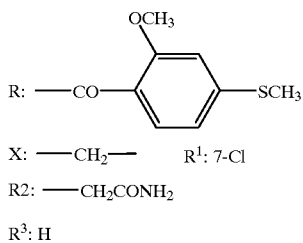

X: —CH₂—  R¹: 7-Cl
R²: —CH₂CONH₂
R³: H

Crystalline form: White powder
Solvent for recrystallization: Diethyl ether
M.p. 104–108° C.
Form: Free

EXAMPLE 34

Structure

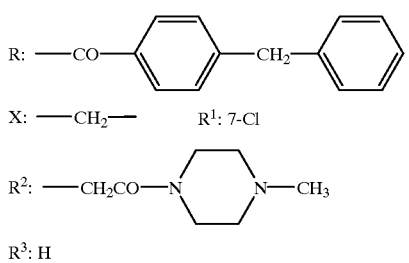

X: —CH₂—  R¹: 7-Cl

R²: —CH₂CO—N⟨piperazine⟩N—CH₃

R³: H

Crystalline form: Colorless amorphous
NMR analysis: 18)
Form: Free

EXAMPLE 35

Structure

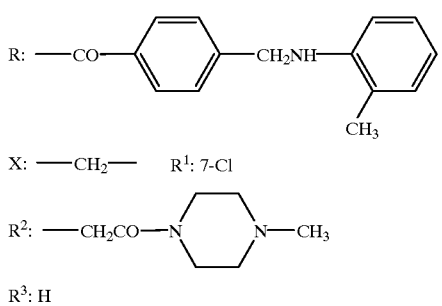

X: —CH₂—  R¹: 7-Cl

R²: —CH₂CO—N⟨piperazine⟩N—CH₃

R³: H

Crystalline form: Colorless amorphous
NMR analysis: 19)
Form: Free

EXAMPLE 36

Structure

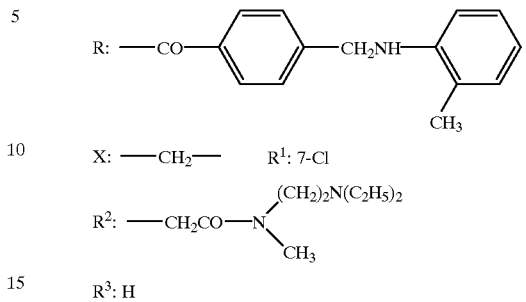

X: —CH₂—  R¹: 7-Cl

R²: —CH₂CO—N(CH₃)(CH₂)₂N(C₂H₅)₂

R³: H

Crystalline form: Colorless amorphous
NMR analysis: 20)
Form: Free

EXAMPLE 37

Structure

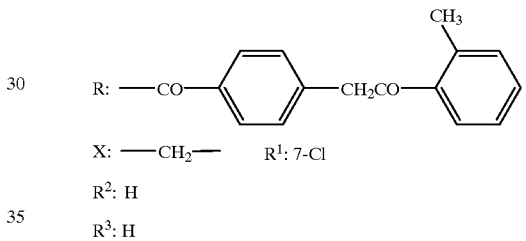

X: —CH₂—  R¹: 7-Cl
R²: H
R³: H

Crystalline form: Colorless prisms
Solvent for recrystallization: Ethyl acetate/diethyl ether/n-hexane
M.p. 145–147° C.
Form: Free

EXAMPLE 38

Structure

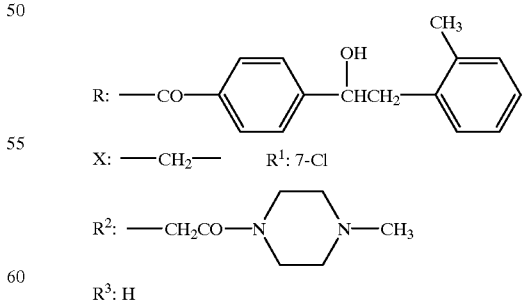

X: —CH₂—  R¹: 7-Cl

R²: —CH₂CO—N⟨piperazine⟩N—CH₃

R³: H

Crystalline form: Colorless amorphous
NMR analysis: 21)
Form: Free

EXAMPLE 39

Structure

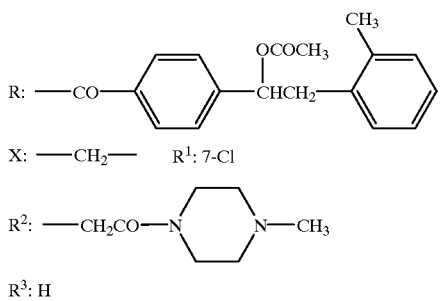

X: —CH₂—  R¹: 7-Cl

R²: —CH₂CO—N(piperazine)—CH₃

R³: H

Crystalline form: Colorless amorphous
NMR analysis: 22)
Form: Free

EXAMPLE 40

Structure

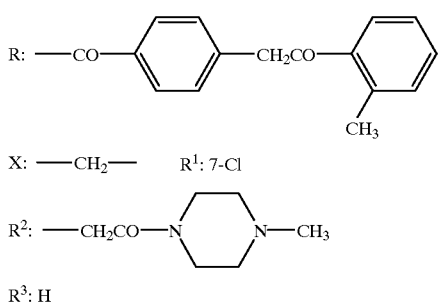

X: —CH₂—  R¹: 7-Cl

R²: —CH₂CO—N(piperazine)—CH₃

R³: H

Crystalline form: Pale yellow viscous oil
NMR analysis: 23)
Form: Free

EXAMPLE 41

Structure

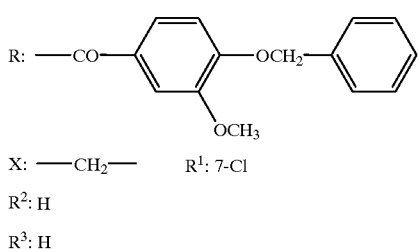

X: —CH₂—  R¹: 7-Cl

R²: H

R³: H

Crystalline form: White powder
Solvent for recrystallization: Acetone/n-hexane
M.p. 133–133.5° C.
Form: Free

EXAMPLE 42

Structure

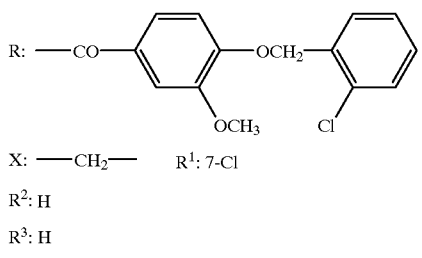

X: —CH₂—  R¹: 7-Cl

R²: H

R³: H

Crystalline form: White powder
Solvent for recrystallization: Acetone/diethyl ether
M.p. 135° C.
Form: Free

EXAMPLE 43

Structure

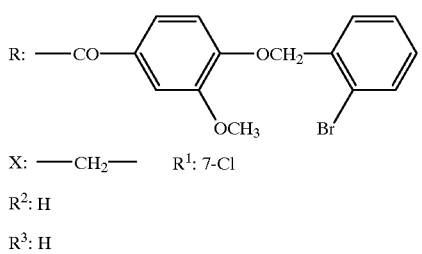

X: —CH₂—  R¹: 7-Cl

R²: H

R³: H

Crystalline form: White powder
Solvent for recrystallization: Acetone/diethyl ether
M.p. 133° C.
Form: Free

EXAMPLE 44

Structure

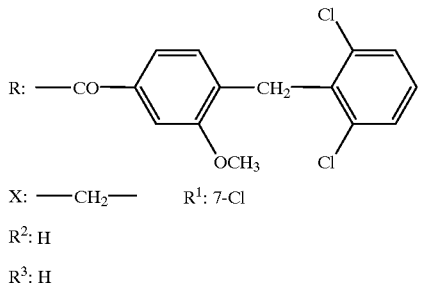

X: —CH₂—  R¹: 7-Cl

R²: H

R³: H

Crystalline form: White powder
Solvent for recrystallization: Acetone/diethyl ether
M.p. 154° C.
Form: Free

EXAMPLE 45

Structure

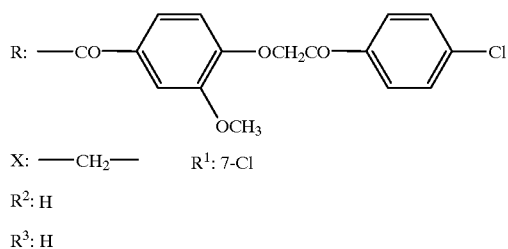

R²: H

R³: H

Crystalline form: White powder

Solvent for recrystallization: Acetone/diethyl ether

M.p. 166° C.

Form: Free

EXAMPLE 46

Structure

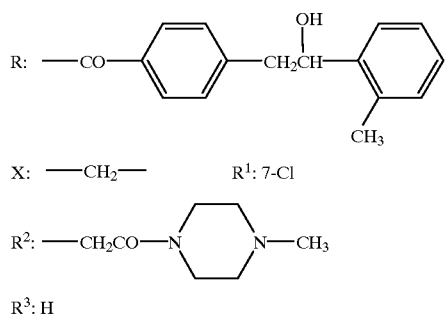

R³: H

Crystalline form: Colorless amorphous

NMR analysis: 24)

Form: Free

EXAMPLE 47

Structure

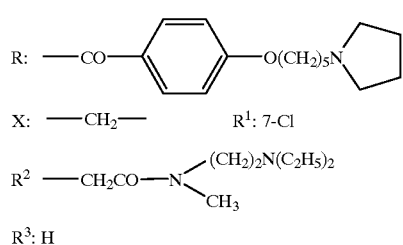

R³: H

Crystalline form: Colorless amorphous

NMR analysis: 25)

Form: Dihydrochloride

EXAMPLE 48

Structure

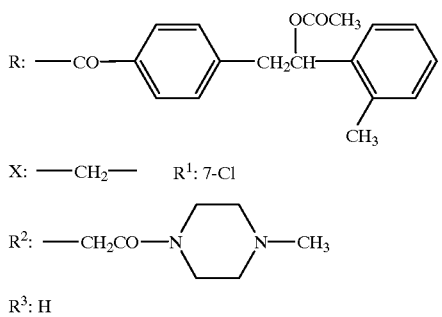

R³: H

Crystalline form: Colorless amorphous

NMR analysis: 26)

Form: Free

EXAMPLE 49

Structure

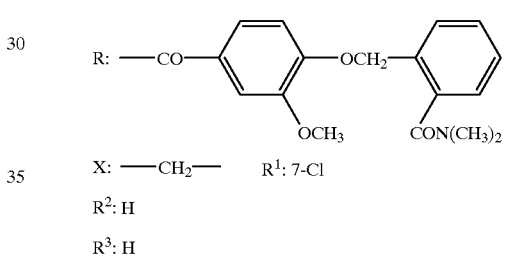

R²: H

R³: H

Crystalline form: Colorless amorphous

NMR analysis: 27)

Form: Free

EXAMPLE 50

Structure

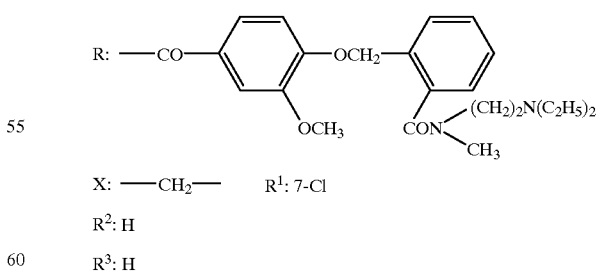

R²: H

R³: H

Crystalline form: Colorless amorphous

NMR analysis: 28)

Form: Hydrochloride

EXAMPLE 51

Structure

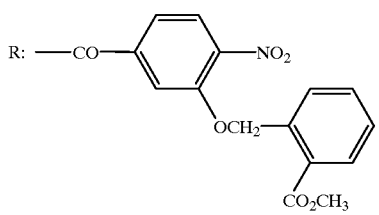

X: —CH$_2$—  R$^1$: 7-Cl
R$^2$: H
R$^3$: H

Crystalline form: Yellow plates
Solvent for recrystallization: Acetone/diethyl ether
M.p. 125° C.
Form: Free

EXAMPLE 52

Structure

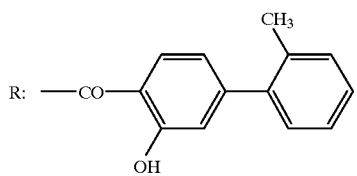

X: —CH$_2$—  R$^1$: 7-Cl
R$^2$: —CH$_2$COOH  R$^3$: H

Crystalline form: Colorless amorphous
NMR analysis: 80)
Form: Free

EXAMPLE 53

Structure

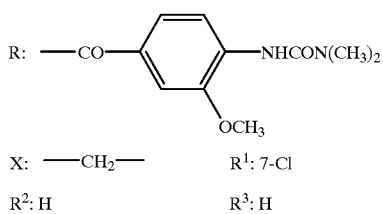

X: —CH$_2$—  R$^1$: 7-Cl
R$^2$: H  R$^3$: H

Crystalline form: White plates
Solvent for recrystallization: Ethanol/diethyl ether
M.p. 230–232° C.
Form: Free

EXAMPLE 54

Structure

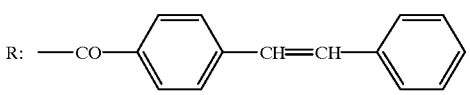

X: —CH$_2$—  R$^1$: 7-Cl
R$^2$: —CH$_2$COOH  R$^3$: H

Crystalline form: Colorless oil
NMR analysis: 81)
Form: Free

EXAMPLE 55

Structure

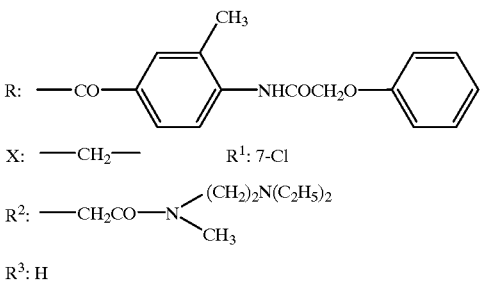

X: —CH$_2$—  R$^1$: 7-Cl

R$^2$: —CH$_2$CO—N(CH$_3$)(CH$_2$)$_2$N(C$_2$H$_5$)$_2$

R$^3$: H

Crystalline form: Colorless amorphous
NMR analysis: 82)
Form: Hydrochloride

EXAMPLE 56

Structure

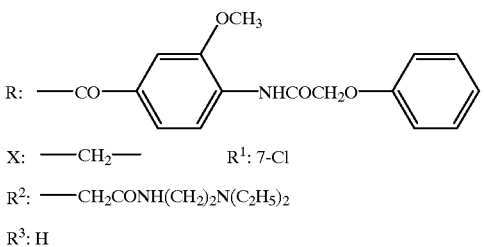

X: —CH$_2$—  R$^1$: 7-Cl
R$^2$: —CH$_2$CONH(CH$_2$)$_2$N(C$_2$H$_5$)$_2$
R$^3$: H

Crystalline form: Colorless amorphous
NMR analysis: 83)
Form: Hydrochloride

EXAMPLE 57

Structure

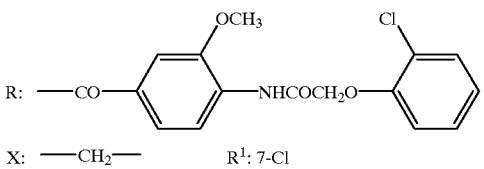

X: —CH$_2$—  R$^1$: 7-Cl

-continued

R²: —CH₂CO—N(CH₃)(CH₂)₂N(C₂H₅)₂

R³: H

Crystalline form: Colorless amorphous
NMR analysis: 84)
Form: Hydrochloride

EXAMPLE 58

Structure

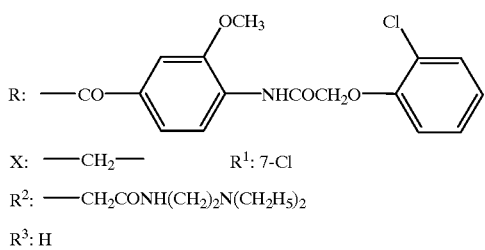

X: —CH₂—    R¹: 7-Cl
R²: —CH₂CONH(CH₂)₂N(CH₂H₅)₂
R³: H

Crystalline form: Colorless amorphous
NMR analysis: 85)
Form: Hydrochloride

EXAMPLE 59

Structure

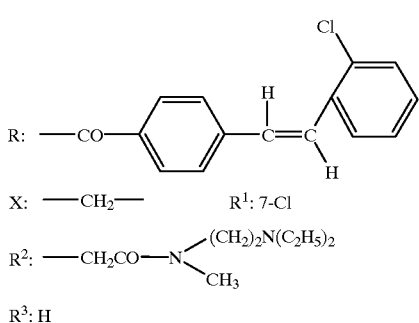

X: —CH₂—    R¹: 7-Cl
R²: —CH₂CO—N(CH₃)(CH₂)₂N(C₂H₅)₂
R³: H

Crystalline form: Colorless viscous oil
NMR analysis: 29)
Form: Free

EXAMPLE 60

Structure

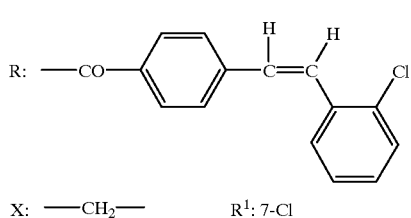

X: —CH₂—    R¹: 7-Cl

-continued

R²: —CH₂CO—N(CH₃)(CH₂)₂N(C₂H₅)₂

R³: H

Crystalline form: Colorless viscous oil
NMR analysis: 30)
Form: Free

EXAMPLE 61

Structure

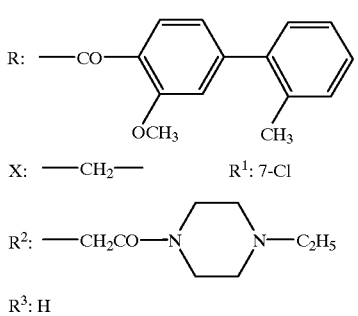

X: —CH₂—    R¹: 7-Cl

R²: —CH₂CO—N\_/N—C₂H₅

R³: H

Crystalline form: Colorless amorphous
NMR analysis: 31)
Form: Hydrochloride

EXAMPLE 62

Structure

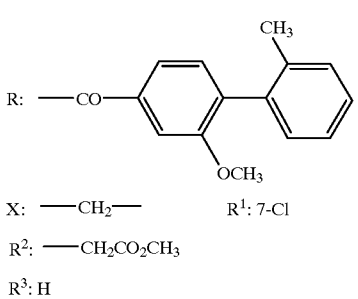

X: —CH₂—    R¹: 7-Cl
R²: —CH₂CO₂CH₃
R³: H

Crystalline form: Colorless amorphous
NMR analysis: 32)
Form: Free

EXAMPLE 63

Structure

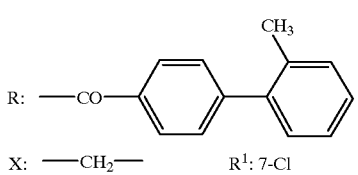

X: —CH₂—    R¹: 7-Cl

-continued

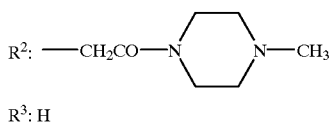

R³: H

Crystalline form: Colorless amorphous

NMR analysis: 33)

Form: Free

EXAMPLE 64

Structure

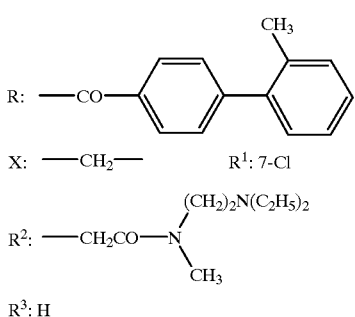

Crystalline form: Colorless amorphous

NMR analysis: 34)

Form: Free

EXAMPLE 65

Structure

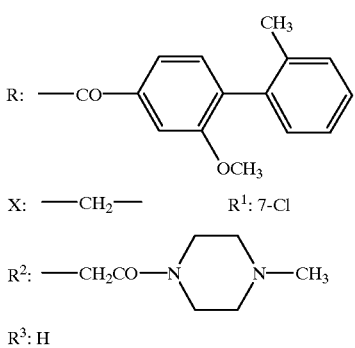

Crystalline form: Colorless amorphous

NMR analysis: 35)

Form: Hydrochloride

EXAMPLE 66

Structure

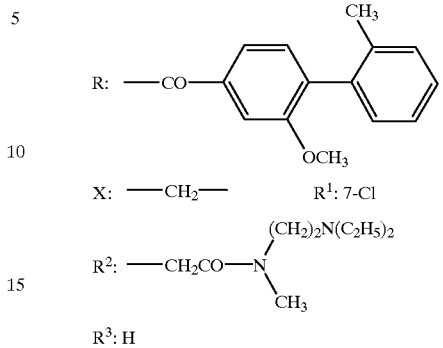

R³: H

Crystalline form: Colorless amorphous
NMR analysis: 36)
Form: Hydrochloride

EXAMPLE 67

Structure

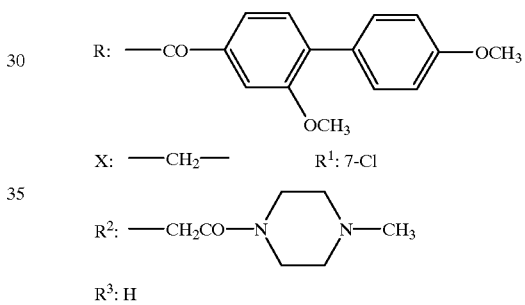

R³: H

Crystalline form: White powder
Solvent for recrystallization: Acetone/n-hexane
M.p. 174–176° C.
Form: Free

EXAMPLE 68

Structure

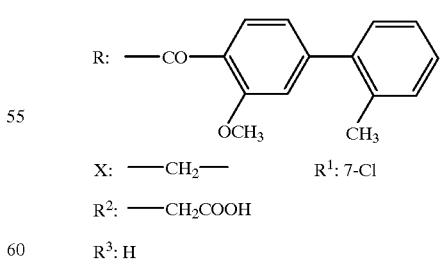

X: —CH₂—   R¹: 7-Cl

R²: —CH₂COOH

R³: H

Crystalline form: White powder
Solvent for recrystallization: Ethanol/diethyl ether
M.p. 203–204° C.
Form: Free

EXAMPLE 69

Structure

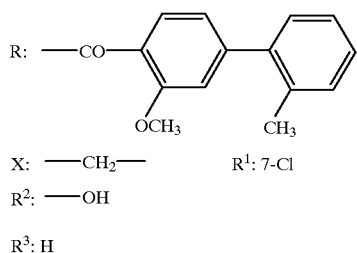

X: —CH₂—  R¹: 7-Cl

R²: —OH

R³: H

Crystalline form: Colorless amorphous
NMR analysis: 37)
Form: Free

EXAMPLE 70

Structure

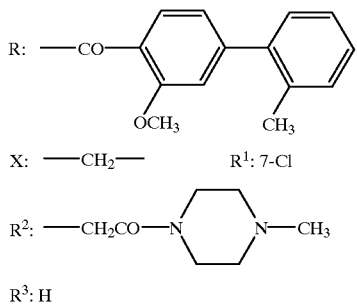

X: —CH₂—  R¹: 7-Cl

R²: —CH₂CO—N(piperazine)N—CH₃

R³: H

Crystalline form: White powder
Solvent for recrystallization: Ethyl acetate/n-hexane
M.p. 181–182° C.
Form: Free

EXAMPLE 71

Structure

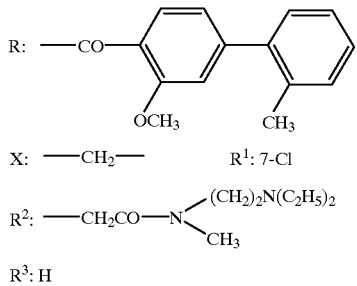

X: —CH₂—  R¹: 7-Cl

R²: —CH₂CO—N((CH₂)₂N(C₂H₅)₂, CH₃)

R³: H

Crystalline form: Colorless amorphous
NMR analysis: 38)
Form: Hydrochloride

EXAMPLE 72

Structure

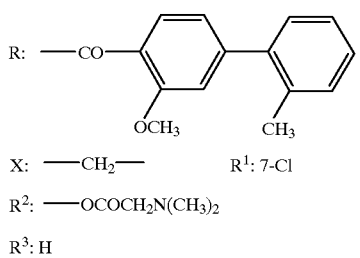

X: —CH₂—  R¹: 7-Cl

R²: —OCOCH₂N(CH₃)₂

R³: H

Crystalline form: White powder
Solvent for recrystallization: Acetone/n-hexane
M.p. 153–155° C.
Form: Hydrochloride

EXAMPLE 73

Structure

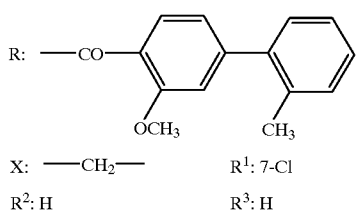

X: —CH₂—  R¹: 7-Cl

R²: H  R³: H

Crystalline form: Colorless amorphous
NMR analysis: 39)
Form: Free

EXAMPLE 74

Structure

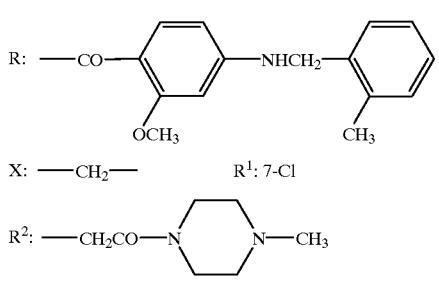

X: —CH₂—  R¹: 7-Cl

R²: —CH₂CO—N(piperazine)N—CH₃

R³: H

Crystalline form: White powder
Solvent for recrystallization: Acetone/diethyl ether
M.p. 153–154.5° C.
Form: Free

EXAMPLE 75

Structure

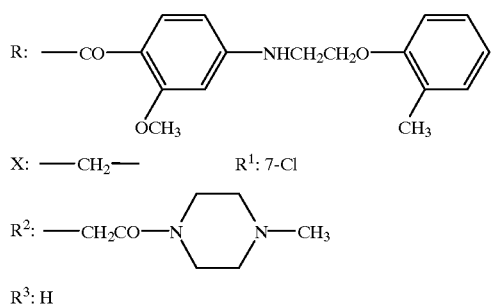

X: —CH$_2$—  R$^1$: 7-Cl

R$^2$: —CH$_2$CO—N(piperazine)—CH$_3$

R$^3$: H

Crystalline form: White powder
Solvent for recrystallization: Acetone/n-hexane
M.p. 160–161° C.
Form: Free

EXAMPLE 76

Structure

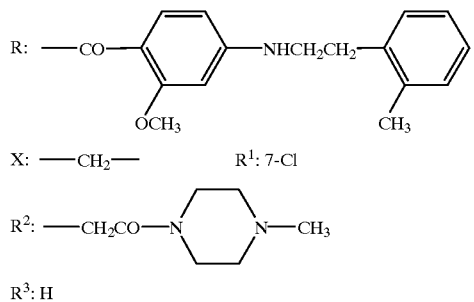

X: —CH$_2$—  R$^1$: 7-Cl

R$^2$: —CH$_2$CO—N(piperazine)—CH$_3$

R$^3$: H

Crystalline form: White powder
Solvent for recrystallization: Acetone/diethyl ether
NMR analysis: 135–136° C.
Form: Free

EXAMPLE 77

Structure

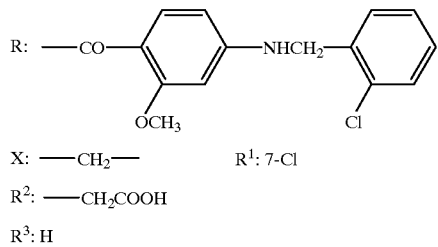

X: —CH$_2$—  R$^1$: 7-Cl

R$^2$: —CH$_2$COOH

R$^3$: H

Crystalline form: White powder
Solvent for recrystallization: Ethanol/diethyl ether
NMR analysis: 134–136.5° C.
Form: Free

EXAMPLE 78

Structure

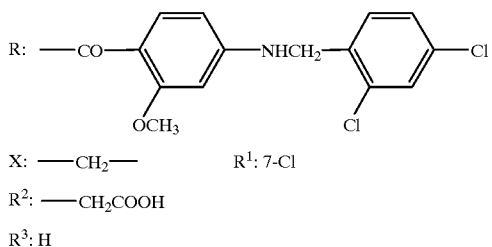

X: —CH$_2$—  R$^1$: 7-Cl

R$^2$: —CH$_2$COOH

R$^3$: H

Crystalline form: White powder
Solvent for recrystallization: Ethanol/diethyl ether
NMR analysis: 140.5–142° C.
Form: Free

EXAMPLE 79

Structure

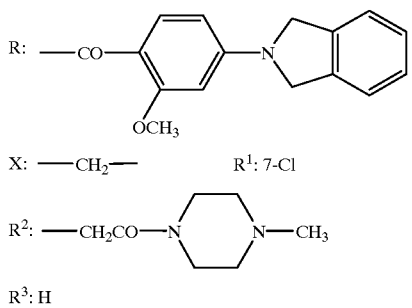

X: —CH$_2$—  R$^1$: 7-Cl

R$^2$: —CH$_2$CO—N(piperazine)—CH$_3$

R$^3$: H

Crystalline form: White powder
Solvent for recrystallization: Acetone/n-hexane
NMR analysis: 199.5–202° C.
Form: Free

EXAMPLE 80

Structure

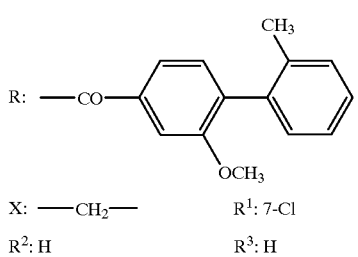

X: —CH$_2$—  R$^1$: 7-Cl

R$^2$: H  R$^3$: H

Crystalline form: Colorless amorphous
NMR analysis: 40)
Form: Free

EXAMPLE 81

Structure

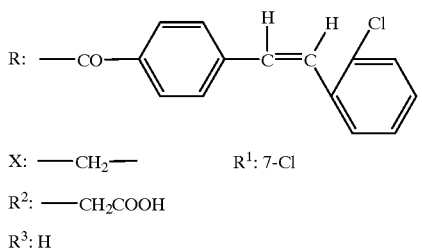

X: —CH$_2$— R$^1$: 7-Cl

R$^2$: —CH$_2$COOH

R$^3$: H

Crystalline form: White powder

Solvent for recrystallization: Dichloromethane/methanol/diethyl ether

M.p. 187–190° C.

Form: Free

EXAMPLE 82

Structure

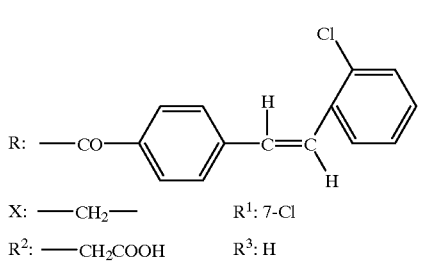

X: —CH$_2$— R$^1$: 7-Cl

R$^2$: —CH$_2$COOH R$^3$: H

Crystalline form: White powder

Solvent for recrystallization: Dichloromethane/methanol/diethyl ether

M.p. 189–192° C.

Form: Free

EXAMPLE 83

Structure

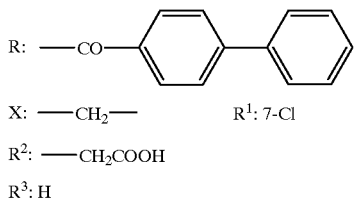

X: —CH$_2$— R$^1$: 7-Cl

R$^2$: —CH$_2$COOH

R$^3$: H

Crystalline form: White powder

M.p. 205–207° C.

Form: Free

EXAMPLE 84

Structure

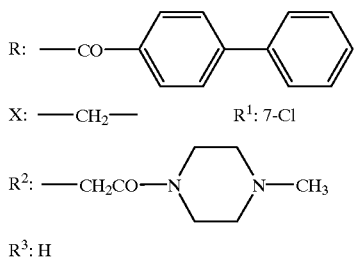

X: —CH$_2$— R$^1$: 7-Cl

R$^2$: —CH$_2$CO—N\_\_\_N—CH$_3$

R$^3$: H

Crystalline form: Colorless amorphous

NMR analysis: 41)

Form: Free

EXAMPLE 45

Structure

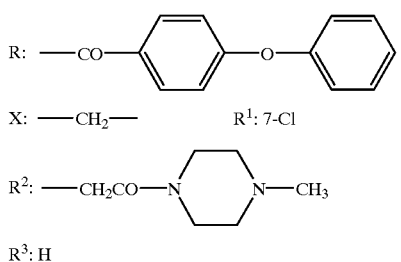

X: —CH$_2$— R$^1$: 7-Cl

R$^2$: —CH$_2$CO—N\_\_\_N—CH$_3$

R$^3$: H

Crystalline form: Colorless amorphous

NMR analysis: 42)

Form: Free

EXAMPLE 86

Structure

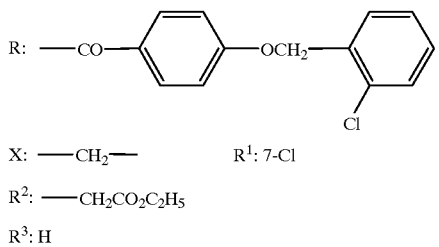

X: —CH$_2$— R$^1$: 7-Cl

R$^2$: —CH$_2$CO$_2$C$_2$H$_5$

R$^3$: H

Crystalline form: Colorless oil

NMR analysis: 43)

Form: Free

EXAMPLE 87

Structure

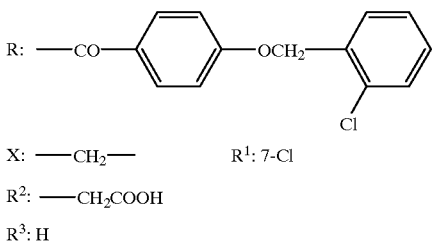

X: —CH$_2$—   R$^1$: 7-Cl

R$^2$: —CH$_2$COOH

R$^3$: H

Crystalline form: Colorless oil

NMR analysis: 44)

Form: Free

EXAMPLE 88

Structure

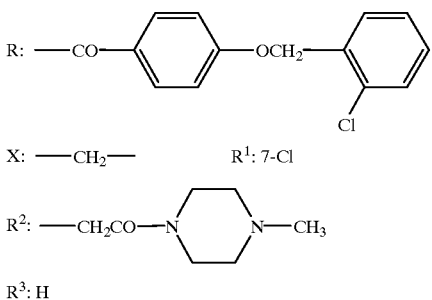

X: —CH$_2$—   R$^1$: 7-Cl

R$^2$: —CH$_2$CO—N‾‾N—CH$_3$

R$^3$: H

Crystalline form: Colorless oil

NMR analysis: 45)

Form: Free

EXAMPLE 89

Structure

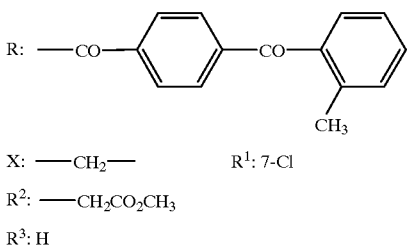

X: —CH$_2$—   R$^1$: 7-Cl

R$^2$: —CH$_2$CO$_2$CH$_3$

R$^3$: H

Crystalline form: Colorless oil

NMR analysis: 46)

Form: Free

EXAMPLE 90

Structure

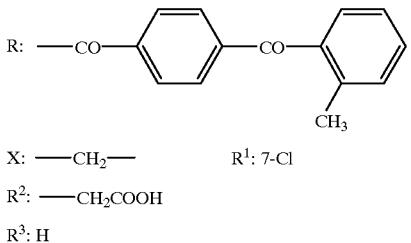

X: —CH$_2$—   R$^1$: 7-Cl

R$^2$: —CH$_2$COOH

R$^3$: H

Crystalline form: Colorless amorphous

NMR analysis: 47)

Form: Free

EXAMPLE 91

Structure

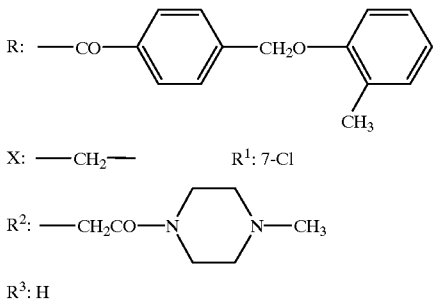

X: —CH$_2$—   R$^1$: 7-Cl

R$^2$: —CH$_2$CO—N‾‾N—CH$_3$

R$^3$: H

Crystalline form: White powder

Solvent for recrystallization: Dichloromethane/diethyl ether

M.p. 84–88° C.

Form: Free

EXAMPLE 92

Structure

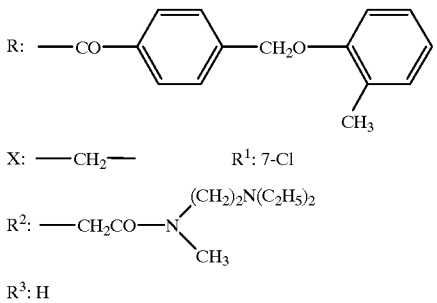

X: —CH$_2$—   R$^1$: 7-Cl

R$^2$: —CH$_2$CO—N(CH$_2$)$_2$N(C$_2$H$_5$)$_2$ / CH$_3$

R$^3$: H

Crystalline form: Colorless amorphous

NMR analysis: 48)

Form: Free

EXAMPLE 93

Structure

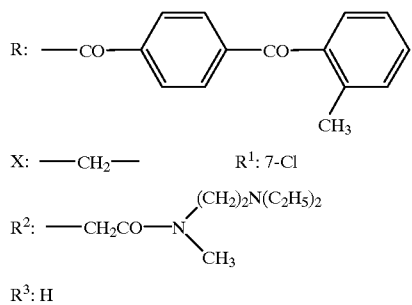

X: —CH$_2$—  R$^1$: 7-Cl

R$^2$: —CH$_2$CO—N(CH$_2$)$_2$N(C$_2$H$_5$)$_2$ / CH$_3$

R$^3$: H

Crystalline form: Colorless amorphous
NMR analysis: 49)
Form: Free

EXAMPLE 94

Structure

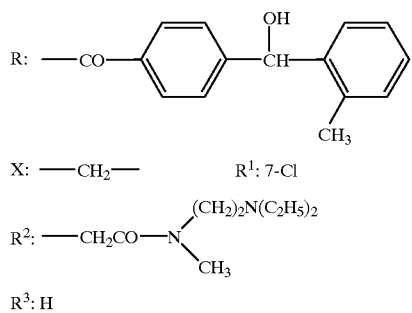

X: —CH$_2$—  R$^1$: 7-Cl

R$^2$: —CH$_2$CO—N(CH$_2$)$_2$N(C$_2$H$_5$)$_2$ / CH$_3$

R$^3$: H

Crystalline form: Colorless amorphous
NMR analysis: 50)
Form: Free

EXAMPLE 95

Structure

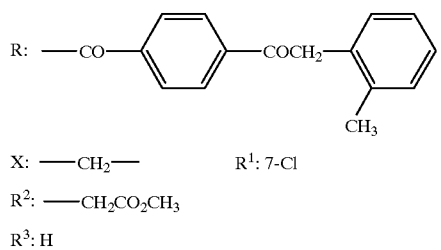

X: —CH$_2$—  R$^1$: 7-Cl

R$^2$: —CH$_2$CO$_2$CH$_3$

R$^3$: H

Crystalline form: White powder
Solvent for recrystallization: Ethyl acetate/diethyl ether/n-hexane
M.p. 120–122° C.
Form: Free

EXAMPLE 96

Structure

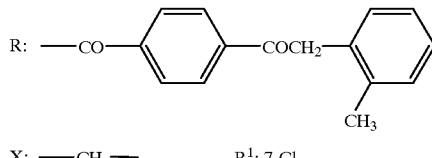

X: —CH$_2$—  R$^1$: 7-Cl

R$^2$: —CH$_2$COOH

R$^3$: H

Crystalline form: Colorless amorphous
NMR analysis: 51)
Form: Free

EXAMPLE 97

Structure

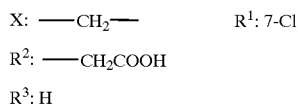

X: —CH$_2$—  R$^1$: 7-Cl

R$^2$: —CH$_2$CO$_2$CH$_3$

R$^3$: H

Crystalline form: Colorless oil
NMR analysis: 52)
Form: Free

EXAMPLE 98

Structure

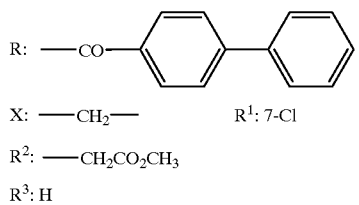

X: —CH$_2$—  R$^1$: 7-Cl

R$^2$: —CH$_2$CO—N(CH$_2$)$_2$N(C$_2$H$_5$)$_2$ / CH$_3$

R$^3$: H

Crystalline form: Colorless oil
NMR analysis: 53)
Form: Free

EXAMPLE 99

Structure

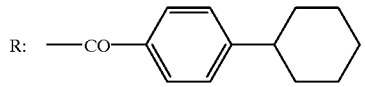

-continued

X: —CH$_2$—
R$^2$: —CH$_2$CO$_2$C$_2$H$_5$
R$^3$: H
R$^1$: 7-Cl

Crystalline form: Colorless oil
NMR analysis: 54)
Form: Free

EXAMPLE 100

Structure

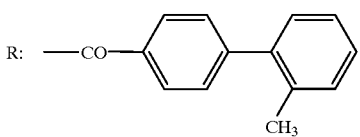

X: —CH$_2$—
R$^2$: —CH$_2$CO$_2$C$_2$H$_5$
R$^3$: H
R$^1$: 7-Cl

Crystalline form: Colorless amorphous
NMR analysis: 55)
Form: Free

EXAMPLE 101

Structure

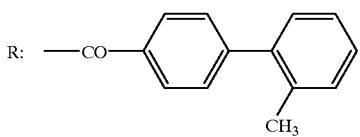

X: —CH$_2$—
R$^2$: —CH$_2$COOH
R$^3$: H
R$^1$: 7-Cl

Crystalline form: Colorless amorphous
NMR analysis: 56)
Form: Free

EXAMPLE 102

Structure

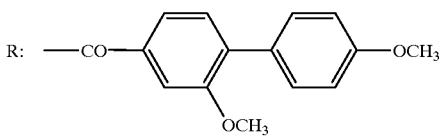

X: —CH$_2$—
R$^2$: —CH$_2$CO$_2$CH$_3$
R$^3$: H
R$^1$: 7-Cl

Crystalline form: Colorless amorphous
NMR analysis: 57)
Form: Free

EXAMPLE 103

Structure

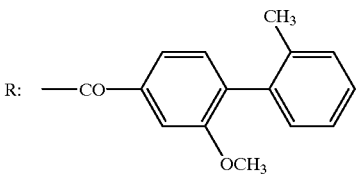

X: —CH$_2$—
R$^2$: —CH$_2$COOH
R$^3$: H
R$^1$: 7-Cl

Crystalline form: Colorless amorphous
NMR analysis: 58)
Form: Free

EXAMPLE 104

Structure

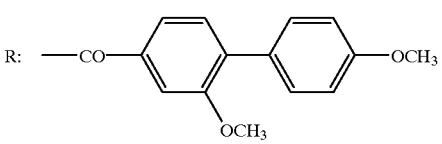

X: —CH$_2$—
R$^2$: —CH$_2$COOH
R$^3$: H
R$^1$: 7-Cl

Crystalline form: Colorless amorphous
NMR analysis: 59)
Form: Free

EXAMPLE 105

Structure

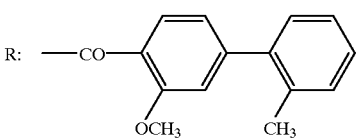

X: —CH$_2$—
R$^2$: —CH$_2$CO$_2$CH$_3$
R$^3$: H
R$^1$: 7-Cl

Crystalline form: Colorless amorphous
NMR analysis: 60)
Form: Free

EXAMPLE 106

Structure

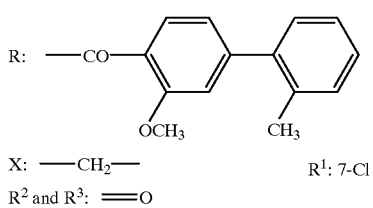

X: —CH$_2$—  R$^1$: 7-Cl
R$^2$ and R$^3$: =O

Crystalline form: White powder
Recrystallization solvent: Acetone/n-hexane
NMR analysis: 61)
Form: Free

EXAMPLE 107

Structure

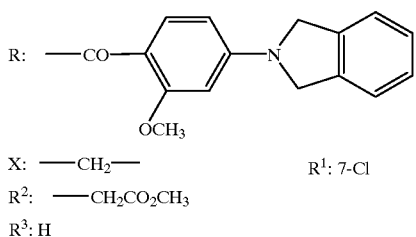

X: —CH$_2$—  R$^1$: 7-Cl
R$^2$: —CH$_2$CO$_2$CH$_3$
R$^3$: H

Crystalline form: Colorless amorphous
NMR analysis: 62)
Form: Free

EXAMPLE 108

Structure

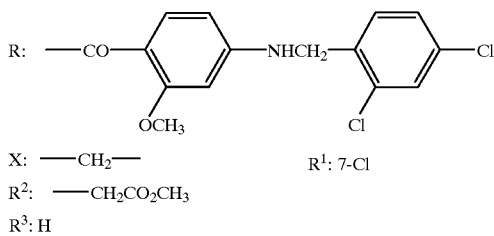

X: —CH$_2$—  R$^1$: 7-Cl
R$^2$: —CH$_2$CO$_2$CH$_3$
R$^3$: H

Crystalline form: Colorless amorphous
NMR analysis: 63)
Form: Free

EXAMPLE 109

Structure

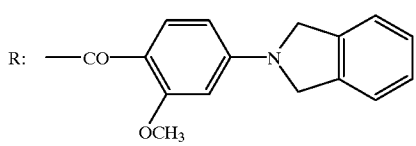

-continued

X: —CH$_2$—  R$^1$: 7-Cl
R$^2$: —CH$_2$COOH
R$^3$: H

Crystalline form: White powder
Solvent for recrystallization: Acetone/n-hexane
M.p. 169–171° C.
Form: Free

EXAMPLE 110

Structure

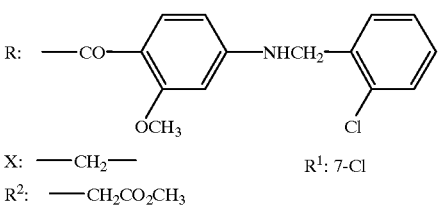

X: —CH$_2$—  R$^1$: 7-Cl
R$^2$: —CH$_2$CO$_2$CH$_3$
R$^3$: H

Crystalline form: Colorless amorphous
NMR analysis: 64)
Form: Free

EXAMPLE 111

Structure

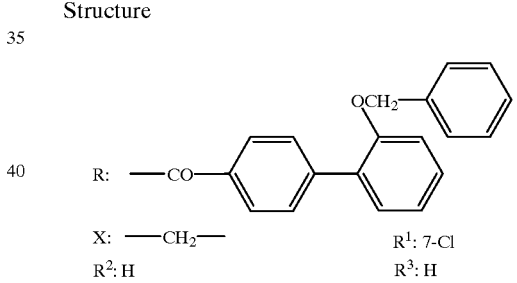

X: —CH$_2$—  R$^1$: 7-Cl
R$^2$: H  R$^3$: H

Crystalline form: Colorless amorphous
NMR analysis: 65)
Form: Free

EXAMPLE 112

Structure

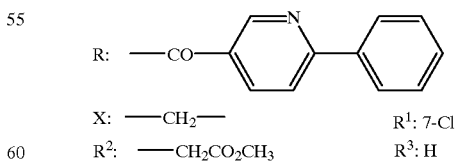

X: —CH$_2$—  R$^1$: 7-Cl
R$^2$: —CH$_2$CO$_2$CH$_3$  R$^3$: H

Crystalline form: White powder
Solvent for recrystallization: Acetone/n-hexane
M.p. 139.5–142° C.
Form: Free

EXAMPLE 113

Structure

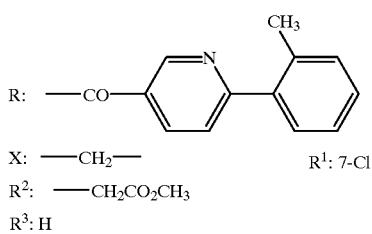

R:  —CO—

X:  —CH$_2$—  R$^1$: 7-Cl
R$^2$:  —CH$_2$CO$_2$CH$_3$
R$^3$: H

Crystalline form: Colorless amorphous
NMR analysis: 66)
Form: Free

EXAMPLE 114

Structure

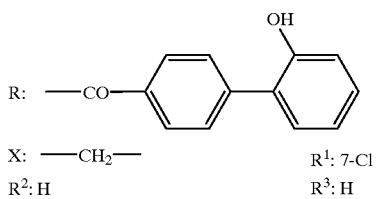

R:  —CO—

X:  —CH$_2$—  R$^1$: 7-Cl
R$^2$: H  R$^3$: H

Crystalline form: White powder
Solvent for recrystallization: Acetone/n-hexane
M.p. 226° C.
Form: Free

EXAMPLE 115

Structure

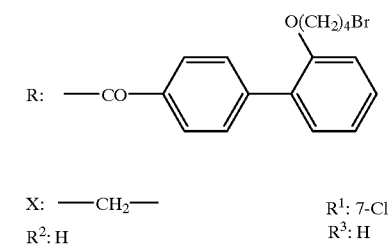

R:  —CO—

X:  —CH$_2$—  R$^1$: 7-Cl
R$^2$: H  R$^3$: H

Crystalline form: White powder
Solvent for recrystallization: Acetone/diethyl ether
M.p. 142–142.5° C.
Form: Free

EXAMPLE 116

Structure

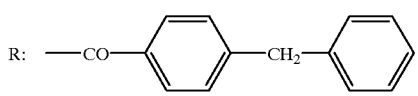

R:  —CO—

-continued

X:  —CH$_2$—  R$^1$: 7-Cl
R$^2$:  —CH$_2$CO$_2$CH$_3$  R$^3$: H

Crystalline form: Colorless amorphous
NMR analysis: 67)
Form: Free

EXAMPLE 117

Structure

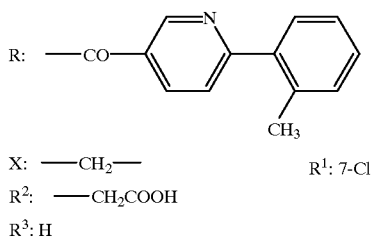

R:  —CO—

X:  —CH$_2$—  R$^1$: 7-Cl
R$^2$:  —CH$_2$COOH
R$^3$: H

Crystalline form: White powder
Solvent for recrystallization: Ethanol/diethyl ether
NMR analysis: 235–237° C. (decomposed)
Form: Free

EXAMPLE 118

Structure

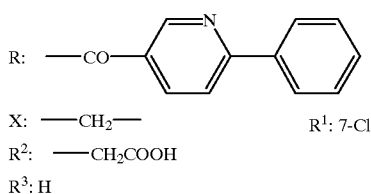

R:  —CO—

X:  —CH$_2$—  R$^1$: 7-Cl
R$^2$:  —CH$_2$COOH
R$^3$: H

Crystalline form: White powder
Solvent for recrystallization: Ethanol/diethyl ether
NMR analysis: 183° C.
Form: Free

EXAMPLE 119

Structure

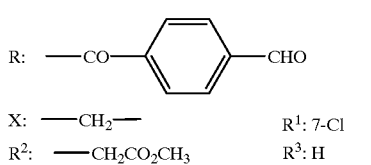

R:  —CO—

X:  —CH$_2$—  R$^1$: 7-Cl
R$^2$:  —CH$_2$CO$_2$CH$_3$  R$^3$: H

Crystalline form: White powder
Solvent for recrystallization: Acetone/n-hexane
NMR analysis: 68)
Form: Free

EXAMPLE 120

Structure

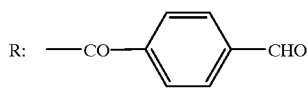

X: —CH$_2$—  R$^1$: 7-Cl
R$^2$: —CH$_2$COOH  R$^3$: H

Crystalline form: White powder
Solvent for recrystallization: Acetone/n-hexane
M.p. 192° C.
Form: Free

EXAMPLE 121

Structure

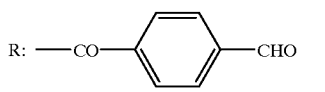

X: —CH$_2$—  R$^1$: 7-Cl

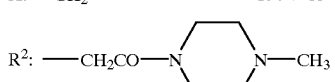

R$^3$: H

Crystalline form: Colorless amorphous
NMR analysis: 69)
Form: Free

EXAMPLE 122

Structure

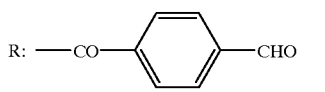

X: —CH$_2$—  R$^1$: 7-Cl

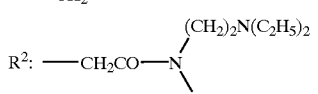

R$^3$: H

Crystalline form: Colorless amorphous
NMR analysis: 70)
Form: Free

EXAMPLE 123

Structure

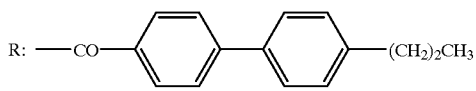

X: —CH$_2$—  R$^1$: 7-Cl

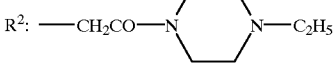

R$^3$: H

Crystalline form: Colorless amorphous
NMR analysis: 71)
Form: Hydrochloride

EXAMPLE 124

Structure

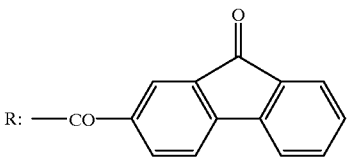

X: —CH$_2$—  R$^1$: 7-Cl

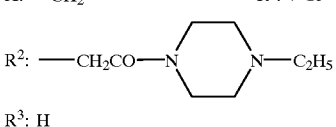

R$^3$: H

Crystalline form: Yellow powder
Solvent for recrystallization: Ethanol
M.p. 182–184° C.
Form: Hydrochloride

EXAMPLE 125

Structure

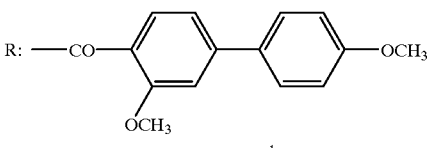

X: —CH$_2$—  R$^1$: 7-Cl

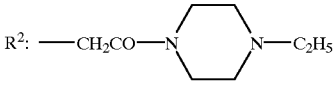

R$^3$: H

Crystalline form: Colorless amorphous
NMR analysis: 72
Form: Hydrochloride

EXAMPLE 126

Structure

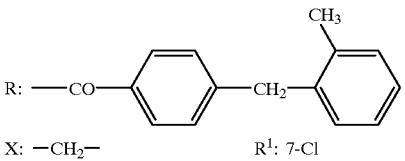

X: —CH$_2$—  R$^1$: 7-Cl

-continued

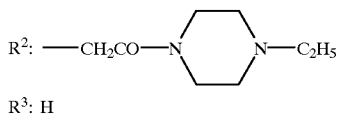

R³: H

Crystalline form: Colorless amorphous
NMR analysis: 73)
Form: Hydrochloride

EXAMPLE 127

Structure

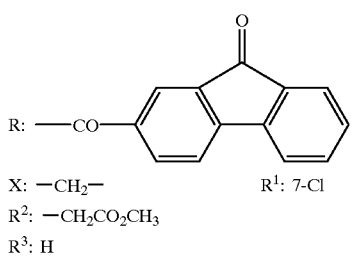

X: —CH$_2$—  R¹: 7-Cl
R²: —CH$_2$CO$_2$CH$_3$
R³: H

Crystalline form: Yellow powder
Solvent for recrystallization: Ethanol/diethyl ether
M.p. 168° C.
Form: Free

EXAMPLE 128

Structure

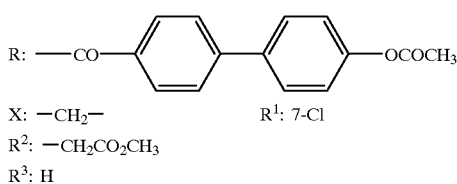

X: —CH$_2$—  R¹: 7-Cl
R²: —CH$_2$CO$_2$CH$_3$
R³: H

Crystalline form: White powder
Solvent for recrystallization: Dichloromethane/diethyl ether
M.p. 186–188° C.
Form: Free

EXAMPLE 129

Structure

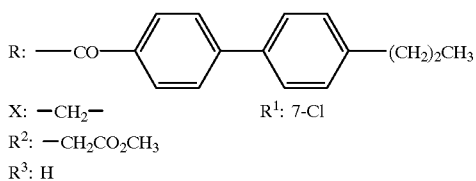

X: —CH$_2$—  R¹: 7-Cl
R²: —CH$_2$CO$_2$CH$_3$
R³: H

Crystalline form: White powder
Solvent for recrystallization: Ethanol/diethyl ether
M.p. 120° C.
Form: Free

EXAMPLE 130

Structure

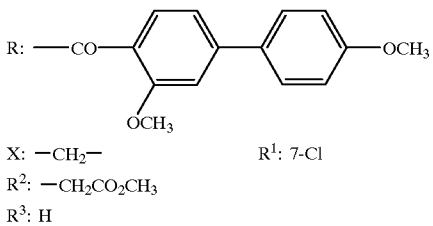

X: —CH$_2$—  R¹: 7-Cl
R²: —CH$_2$CO$_2$CH$_3$
R³: H

Crystalline form: Colorless amorphous
NMR analysis: 74)
Form: Free

EXAMPLE 131

Structure

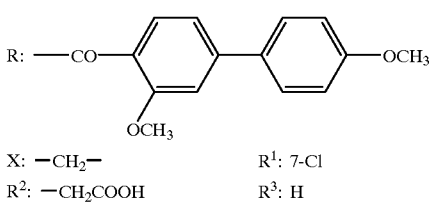

X: —CH$_2$—  R¹: 7-Cl
R²: —CH$_2$COOH  R³: H

Crystalline form: White needles
Solvent for recrystallization: Ethanol/diethyl ether
M.p. 109–111° C.
Form: Free

EXAMPLE 132

Structure

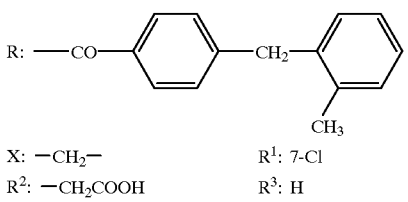

X: —CH$_2$—  R¹: 7-Cl
R²: —CH$_2$COOH  R³: H

Crystalline form: Colorless amorphous
NMR analysis: 75)
Form: Free

EXAMPLE 133

Structure

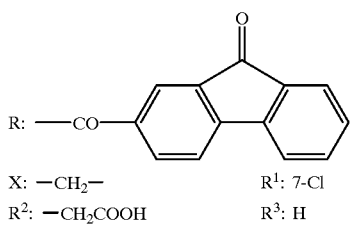

X: —CH$_2$—  R$^1$: 7-Cl
R$^2$: —CH$_2$COOH  R$^3$: H

Crystalline form: Yellow needles
Solvent for recrystallization: Methanol/diethyl ether
M.p. 202–203° C.
Form: Free

EXAMPLE 134

Structure

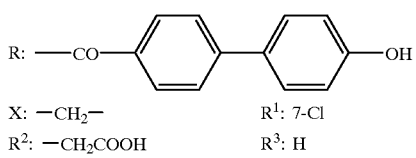

X: —CH$_2$—  R$^1$: 7-Cl
R$^2$: —CH$_2$COOH  R$^3$: H

Crystalline form: White needles
Solvent for recrystallization: Acetone/n-hexane
M.p. 235° C.
Form: Free

EXAMPLE 135

Structure

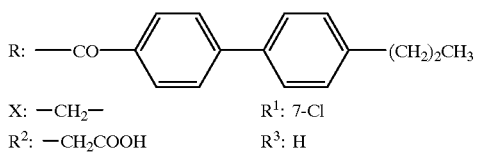

X: —CH$_2$—  R$^1$: 7-Cl
R$^2$: —CH$_2$COOH  R$^3$: H

Crystalline form: White powder
Solvent for recrystallization: Ethanol/diethyl ether
M.p. 176° C.
Form: Free

EXAMPLE 136

Structure

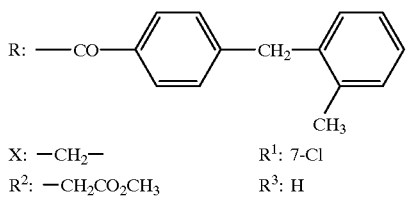

X: —CH$_2$—  R$^1$: 7-Cl
R$^2$: —CH$_2$CO$_2$CH$_3$  R$^3$: H

Crystalline form: Colorless amorphous
NMR analysis:76)
Form: Free

EXAMPLE 137

Structure

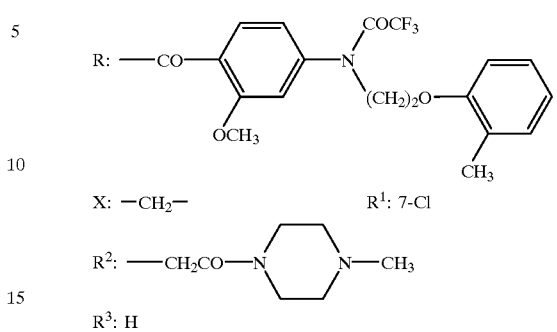

X: —CH$_2$—  R$^1$: 7-Cl
R$^2$: —CH$_2$CO—N(piperazine)N—CH$_3$
R$^3$: H

Crystalline form: Colorless amorphous
NMR analysis: 77)
Form: Free

EXAMPLE 138

Structure

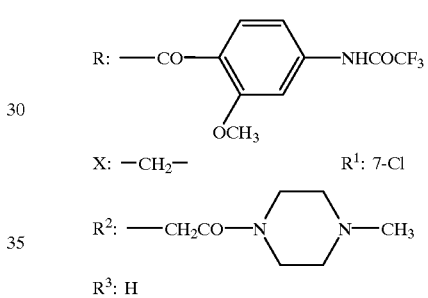

X: —CH$_2$—  R$^1$: 7-Cl
R$^2$: —CH$_2$CO—N(piperazine)N—CH$_3$
R$^3$: H

Crystalline form: White powder
NMR analysis: 78)
Form: Free

NMR analysis:

1) (Example 9)
$^1$H-NMR (200 MHz, CDCl$_3$) δ ppm: 0.78–5.25 (23H, m), 2.96 and 3.20 (all 3H, s), 3.71 (3H, s), 3.83 (3H, s), 6.51–7.18 (6H, m)

2) (Example 10)
$^1$H-NMR (200 MHz, CDCl$_3$) δ ppm: 1.20–2.25 (14H, m), 2.30–2.55 (1H, m), 2.60–3.30 (3H, m), 3.50–3.90 (1H, m), 4.45–4.60 and 5.10–5.30 (1H, m), 6.15 (1H, brs), 6.59 (1H, d, J=8.3 Hz), 6.85–7.00 (3H, m), 7.10–7.35 (3H, m)

3) (Example 11)
$^1$H-NMR (200 MHz, CDCl$_3$) δ ppm: 1.20–3.40 (22H, m), 2.21 and 2.34 (3H, s), 3.50–3.90 (5H, m), 4.40–4.60 and 5.05–5.20 (1H, m), 6.50–6.60 (1H, m), 6.85–6.95 (1H, m), 7.00–7.15 (3H, m), 7.25–7.50 (2H, m)

4) (Example 12)
$^1$H-NMR (200 MHz, CDCl$_3$) δ ppm: 0.82, 1.02 and 1.08 (all 6H, each t, J=7 Hz), 1.2–4.0, 4.35–4.65 and 4.95–5.24 (all 27H, m), 6.35–6.70 (1H, m), 6.75–7.65 (10H, m)

5) (Example 15)
$^1$H-NMR (200 MHz, CDCl$_3$) δ ppm: 0.71–2.24 (11H, m), 2.25–5.17 (21H, m), 5.71–7.54 (9H, m)

6) (Example 16)

$^1$H-NMR (200 MHz, CDCl$_3$) δ ppm: 0.78–5.16 (32H, m), 5.79–7.51 (10H, m)

7) (Example 21)

$^1$H-NMR (200 MHz, CDCl$_3$) δ ppm: 1.00–5.26 (17H, m), 2.28 and 2.34 (each 3H, each s), 6.54–6.75 (1H, m), 6.89–7.93 (8H, m), 8.48–8.74 (1H, m)

8) (Example 22)

$^1$H-NMR (200 MHz, CDCl$_3$) δ ppm: 0.85, 1.00 and 1.07 (all 6H, each t, J=7 Hz), 1.1–4.0, 4.35–4.65, 4.65–4.95 and 4.95–5.25 (all 27H, m), 6.4–6.65 (1H, m), 6.75–7.65 (10H, m)

9) (Example 23)

$^1$H-NMR (200 MHz, CDCl$_3$) δ ppm: 2.15 (3H, s), 2.40 (3H, s), 2.71–4.00 (7H, m), 4.01–4.39 (1H, m), 4.69–5.01 (1H, m), 6.42–7.55 (10H, m)

10) (Example 25)

$^1$H-NMR (200 MHz, DMSO-d$_6$) δ ppm: 1.03–2.08 (4H, m), 1.22 (6H, t, J=7.1 Hz), 2.62–4.95 (22H, m), 6.23–7.42 (6H, m), 10.45–11.47 (1H, m)

11) (Example 26)

$^1$H-NMR (200 MHz, CDCl$_3$) δ ppm: 1.34–1.72 (1H, m), 1.81–2.25 (3H, m), 2.57–3.18 (3H, m), 3.70 (3H, s), 3.82 (3H, s), 4.35–5.22 (1H, m), 6.53–6.69 (2H, m), 6.73 (1H, dd, J=8.4 Hz, 1.8 Hz), 6.82 (1H, d, J=1.8 Hz), 6.91 (1H, dd, J=8.4 Hz, 2.4 Hz), 7.24. (1H, d, J=2.4 Hz)

12) (Example 27)

$^1$H-NMR (200 MHz, CDCl$_3$) δ ppm: 1.32–2.14 (4H, m), 2.57–3.20 (3H, m), 3.52 (3H, s), 3.73 (3H, s), 4.82–5.05 (1H, m), 6.16 (1H, d, J=2.2 Hz), 6.35 (1H, dd, J=8.4 Hz, 2.2 Hz), 6.64 (1H, d, J=8.2 Hz), 6.81 (1H, dd, J=8.4 Hz, 2.4 Hz), 7.06–7.24 (2H, m)

13) (Example 28)

$^1$H-NMR (200 MHz, DMSO-d$_6$) δ ppm: 0.78–2.13 (13H, m), 2.65–5.12 (13H, m), 3.17 and 3.33 (all 3H, s), 3.95 (2H, q, J=6.8 Hz), 6.55–7.58 (7H, m), 10.53–11.48 (1H, m)

14) (Example 29)

$^1$H-NMR (200 MHz, DMSO-d$_6$) δ ppm: 0.98–2.06 (13H, m), 2.61–4.88 (21H, m), 6.18–7.45 (6H, m), 10.42–11.52 (1H, m)

15) (Example 30)

$^1$H-NMR (200 MHz, DMSO-d$_6$) δ ppm: 0.92–1.95 (7H, m), 2.34–4.43 (14H, m), 2.41 and 2.53 (all 3H, s), 2.77 (6H, s), 6.52–7.38 (6H, m), 10.58–11.57 (2H, m)

16) (Example 31)

$^1$H-NMR (200 MHz, DMSO-d$_6$) δ ppm: 0.96–2.03 (4H, m), 2.33–4.62 (13H, m), 2.41 and 2.53 (all 3H, s), 2.76 (3H, s), 3.34 (3H, s), 6.52–7.48 (6H, m), 11.48 (1H, brs)

17) (Example 32)

$^1$H-NMR (200 MHz, DMSO-d$_6$) δ ppm: 0.96–4.87 (22H, m), 2.40 and 2.53 (all 3H, s), 2.73 and 2.77 (all 3H, s), 6.51–7.45 (6H, m), 11.36 (1H, brs)

18) (Example 34)

$^1$H-NMR (200 MHz, CDCl$_3$) δ ppm: 1.17–5.24 (22H, m), 6.41–7.58 (12H, m)

19) (Example 35)

$^1$H-NMR (200 MHz, CDCl$_3$) δ ppm: 1.10–5.24 (26H, m), 6.32–7.69 (11H, m)

20) (Example 36)

$^1$H-NMR (200 MHz, CDCl$_3$) δ ppm: 0.74–5.24 (32H, m), 6.28–7.70 (11H, m)

21) (Example 38)

$^1$H-NMR (200 MHz, CDCl$_3$) δ ppm: 1.1–4.0, 4.35–4.65, 4.65–5.0 and 5.0–5.25 (all 27H, m), 6.4–6.65 (1H, m), 6.75–7.6 (10H, m)

22) (Example 39)

$^1$H-NMR (200 MHz, CDCl$_3$) δ ppm: 1.1–4.0, 4.35–4.7 and 4.95–5.25 (all 28H, m), 5.7–6.0 (1H, m), 6.4–6.65 (1H, m), 6.75–7.6 (10H, m)

23) (Example 40)

$^1$H-NMR (200 MHz, CDCl$_3$) δ ppm: 1.2–4.65 and 4.95–5.25 (all 25H, m), 6.35–6.65 and 6.65–8.2 (all 11H, m)

24) (Example 46)

$^1$H-NMR (200 MHz, CDCl$_3$) δ ppm: 1.2–3.95, 4.45–4.65, 4.7–4.9 and 5.0–5.25 (all 27H, m), 6.4–6.65 and 6.75–7.6 (all 11H, m)

25) (Example 47)

$^1$H-NMR (200 MHz, DMSO-d$_6$) δ ppm: 1.12–2.06 (20H, m), 2.66–4.40 (21H, m), 3.18 and 3.33 (all 3H, s), 6.53–7.41 (7H, m), 10.67–11.53 (2H, m)

26) (Example 48)

$^1$H-NMR (200 MHz, CDCl$_3$) δ ppm: 1.1–3.95, 4.45–4.65 and 4.95–5.25 (all 29H, m), 5.7–6.05 (1H, m), 6.35–6.65 (1H, m), 6.75–7.65 (9H, m)

27) (Example 49)

$^1$H-NMR (200 MHz, CDCl$_3$) δ ppm: 1.22–2.34 (4H, m), 2.42–3.42 (3H, m), 2.82 (3H, s), 3.01 (3H, s), 3.68 (3H, s), 4.81–5.41 (1H, m), 5.08 (2H, s), 6.42–7.12 (5H, m), 7.13–7.72 (5H, m)

28) (Example 50)

$^1$H-NMR (200 MHz, DMSO-d$_6$) δ ppm: 0.90–2.25 (4H, m), 1.17 (6H, t, J=7.10 Hz), 2.40–3.90 (17H, m), 4.63–5.17 (1H, m), 4.98 (2H, s), 6.52–7.21 (5H, m), 7.24–7.65 (5H, m), 10.16–10.70 (1H, m)

29) (Example 59)

$^1$H-NMR (200 MHz, CDCl$_3$) δ ppm: 0.8–1.2 (6H, m), 1.2–4.0, 4.4–4.65 and 5.0–5.25 (20H, m), 6.45–6.65 (1H, m), 6.6–7.75 (12H, m)

30) (Example 60)

$^1$H-NMR (200 MHz, CDCl$_3$) δ ppm: 0.8–1.15 (6H, m), 1.15–3.95, 4.35–4.65 and 4.95–5.25 (all 20H, m, 2.96, 3.17 (each s)), 6.4–7.6 (13H, m)

31) (Example 61)

$^1$H-NMR (200 MHz, CDCl$_3$) δ ppm: 1.06–2.41 (7H, m), 2.31 (3H, s), 2.51–4.38 (16H, m), 4.51–4.92 (2H, m), 6.53–7.52 (10H, m), 12.52–12.94 (1H, m)

32) (Example 62)

$^1$H-NMR (200 MHz, CDCl$_3$) δ ppm: 1.13–2.26 (5H, m), 2.02 (3H, s), 2.58–5.29 (7H, m), 3.69 (3H, s), 6.49–7.45 (10H, m)

33) (Example 63)

$^1$H-NMR (200 MHz, CDCl$_3$) δ ppm: 1.15–5.29 (17H, m), 2.16 (3H, s), 2.34 (3H, s), 6.47–7.62 (11H, m)

34) (Example 64)

$^1$H-NMR (200 MHz, CDCl$_3$) δ ppm: 0.70–1.19 (6H, m), 1.20–5.25 (20H, m), 2.16 (3H, m), 6.48–7.62 (11H, m)

35) (Example 65)

$^1$H-NMR (200 MHz, CDCl$_3$) δ ppm: 1.02–5.28 (23H, m), 2.02 (3H, s), 6.52–7.50 (10H, m), 11.68–12.41 (1H, m)

36) (Example 66)

$^1$H-NMR (200 MHz, CDCl$_3$) δ ppm: 1.04–5.32 (29H, m), 2.02 (3H, s), 6.48–7.51 (10H, m), 11.87–12.28 (1H, m)

37) (Example 69)

¹H-NMR (200 MHz, CDCl₃) δ ppm: 1.46–2.41 (4H, m), 2.14 (3H, s), 2.68–2.98 (1H, m), 3.27–3.83 (4H, m), 4.68–5.27 (2H, m), 6.47–7.54 (9H, m), 7.60 (1H, d, J=2.16 Hz)

38) (Example 71)

¹H-NMR (200 MHz, CDCl₃) δ ppm: 0.86–5.20 (32H, m), 6.51–7.52 (10H, m), 11.62–12.24 (1H, m)

39) (Example 73)

¹H-NMR (200 MHz, CDCl₃) δ ppm: 1.28–2.28 (4H, m), 2.14 (3H, s), 2.58–2.92 (2H, m), 2.93–3.28 (1H, m), 3.58 (3H, s), 4.82–5.12 (1H, m), 6.56 (1H, s), 6.65–6.96 (3H, m), 6.97–7.48 (6H, m)

40) (Example 80)

¹H-NMR (200 MHz, CDCl₃) δ ppm: 1.21–2.25 (4H, m), 2.01 (3H, s), 2.26–3.20 (3H, m), 3.59 (3H, s), 4.86–5.22 (1H, m), 6.42–7.45 (10H, m)

41) (Example 84)

¹H-NMR (200 MHz, CDCl₃) δ ppm: 1.1–4.0, 4.35–4.65 and 5.0–5.25 (all 20H, m, 2.34 (s)), 6.45–6.7 (1H, m), 6.91 (1H, dd, J=2 Hz, 8 Hz), 7.05 (1H, d, J=2 Hz), 7.15–7.7 (9H, m)

42) (Example 85)

¹H-NMR (200 MHz, CDCl₃) δ ppm: 1.2–3.95, 4.35–4.65, 5.0–5.25 (all 20H, m, 2.33 (s)), 6.4–7.55 [12H, m, 6.59 (d, J=8 Hz), 6.79 (d, J=8.5 Hz)]

43) (Example 86)

¹H-NMR (200 MHz, CDCl₃) δ ppm: 1.1–2.2 (7H, m), 2.45–3.3, 3.35–3.9, 4.0–4.35, 4.35–4.65 and 4.95–5.35 (all 9H, m, 5.09 (s)), 6.45–6.65 (1H, m), 6.77 (2H, d, J=8.5 Hz), 6.92 (1H, dd, J=2 Hz, 8.5 Hz), 7.05–7.6 (7H, m)

44) (Example 87)

¹H-NMR (200 MHz, CDCl₃) δ ppm: 1.15–2.2 (4H, m), 2.5–3.3, 3.35–3.9, 4.3–4.6 and 4.9–5.3 (all 7H, m, 5.06 (s)), 4.45–6.65 (1H, m), 6.74 (2H, d, J=8.5 Hz), 6.93 (1H, dd, J=2 Hz, 8.5 Hz), 7.12 (1H, d, J=2 Hz), 7.12–7.55 (6H, m)

45) (Example 88)

¹H-NMR (200 MHz, CDCl₃) δ ppm: 1.15–2.85, 2.85–4.0, 4.35–4.65 and 4.9–5.35 (all 22H, 2.33, 5.10 (each s)), 6.4–6.65 (1H, m), 6.80 (2H, d, J=8.5 Hz), 6.92 (1H, dd, J=2 Hz, 8.5 Hz), 7.04 (1H, d, J=2 Hz), 7.04–7.6 (6H, m)

46) (Example 89)

¹H-NMR (200 MHz, CDCl₃) δ ppm: 1.20–2.45 (7H, m, 2.27 (s)), 2.5–3.1, 3.1–3.4, 3.4–3.9, 4.35–4.65 and 5.02–5.30 (all 8H, m, 3.72 (s)),6.56 (1H, d, J=8.3 Hz), 6.92 (1H, dd, J=2.3 Hz, 8.4 Hz), 7.10 (1H, d, J=2.2 Hz), 7.10–7.71 (8H, m)

47) (Example 90)

¹H-NMR (200 MHz, CDCl₃) δ ppm: 1.23–2.47 (4H, m), 2.26 (3H, s), 2.6–3.05 (2H, m), 3.10–3.43, 3.48–3.90, 4.35–4.62 and 5.05–5.29 (all 3H, m), 6.56 (1H, d, J=8.3 Hz), 6.90 (1H, dd, J=2.2 Hz, 8.3 Hz), 7.08 (1H, d, J=2.2 Hz), 7.12–7.55 (6H, m), 7.61 (2H, d, J=8.5 Hz)

48) (Example 92)

¹H-NMR (200 MHz, CDCl₃) δ ppm: 0.84, 1.05 and 1.08 (all 6H, each t, J=7 Hz), 1.2–4.0, 4.1–4.7 and 4.8–5.3 (all 25H, m, 2.24 (s)), 2.61 (q, J=7 Hz), 2.99, 3.19 (each s)), 6.4–7.7 (11H, m, 6.55 (d, J=8 Hz))

49) (Example 93)

¹H-NMR (200 MHz, CDCl₃) δ ppm: 0.90, 0.97 and 1.07 (all 6H, each t, J=7 Hz), 1.15–4.02, 4.38–4.65 and 4.95–5.25 (all 23H, m, 2.26, 3.18 (each s)), 6.54 (1H, d, J=8.3 Hz), 6.77–7.70 (10H, m)

50) (Example 94)

¹H-NMR (200 MHz, CDCl₃) δ ppm: 0.82, 1.00 and 1.07 (all 6H, each t, J=7 Hz), 1.15–3.98, 4.47–4.68, 4.95–5.22 and 5.75–6.10 (all 25H, m), 6.40–6.68 and 6.73–7.68 (all 11H, m)

51) (Example 96)

¹H-NMR (200 MHz, CDCl₃) δ ppm: 1.2–2.4 (4H, m), 2.20 (3H, s), 2.5–3.35, 3.4–3.9, 4.25–4.6 and 4.9–6.2 (all 8H, m, 4.22 (s)), 6.4–6.65 (1H, m), 6.75–6.95 (1H, m), 6.95–7.35 (5H, m), 7.42 (2H, d, J=8.5 Hz), 7.81 (2H, d, J=8.5 Hz)

52) (Example 97)

¹H-NMR (200 MHz, CDCl₃) δ ppm: 1.2–2.3, 2.5–3.4, 3.5–4.3, 4.35–4.7 and 5.05–5.35 (all 12H, 3.75 (s)), 6.4–6.7 (1H, m), 6.93 (1H, dd, J=2 Hz, 8.5 Hz), 7.13 (1H, d, J=2 Hz), 7.2–7.8 (9H, m)

53) (Example 98)

¹H-NMR (200 MHz, CDCl₃) δ ppm: 0.85, 1.03 and 1.08 (all 6H, each t, J=7 Hz), 1.2–4.0, 4.3–4.65 and 4.9–5.3 (all 22H, 2.99, 3.19, 5.10 (each s)), 6.45–7.6 (11H, m)

54) (Example 99)

¹H-NMR (200 MHz, CDCl₃) δ ppm: 1.27 (3H, t, J=7.1 Hz), 1.20–2.20 (14H, m), 2.30–2.50 (1H, m), 2.60–3.05 (3H, m), 3.10–3.35 (1H, m), 4.10–4.40 (2H, m), 4.45–4.65 (1H, m), 6.57 (1H, d, J=8.4 Hz), 6.96 (1H, d, J=8.1 Hz), 7.00 (2H, d, J=8.0 Hz), 7.10–7.35 (3H, m)

55) (Example 100)

¹H-NMR (200 MHz, CDCl₃) δ ppm: 1.08–2.41 (5H, m), 1.25 (3H, t, J=7.10 Hz), 2.16 (3H, s), 2.54–5.32 (6H, m), 6.48–7.54 (11H, m)

56) (Example 101)

¹H-NMR (200 MHz, CDCl₃) δ ppm: 1.14–2.36 (5H, m), 2.26 (3H, s), 2.51–5.35 (4H, m), 6.45–7.50 (11H, m), 8.65–13.90 (1H, m)

57) (Example 102)

¹H-NMR (200 MHz, CDCl₃) δ ppm: 1.18–2.39 (5H, m), 2.57–3.05 (2H, m), 3.09–5.28 (2H, m), 3.67, 3.72 and 3.82 (each 3H, each s), 6.48–7.81 (10H, m)

58) (Example 103)

¹H-NMR (200 MHz, CDCl₃) δ ppm: 1.14–2.26 (4H, m), 2.01 (3H, s), 2.52–3.10 (2H, m), 3.01–5.28 (3H, m), 3.61 (3H, s), 6.48–7.88 (10H, m), 8.50–13.9 (1H, m)

59) (Example 104)

¹H-NMR (200 MHz, CDCl₃) δ ppm: 1.18–2.32 (4H, m), 2.57–3.09 (2H, m), 3.10–5.29 (3H, m), 3.66 and 3.81 (each 3H, each s), 6.45–7.80 (10H, m), 8.03–13.80 (1H, m)

60) (Example 105)

¹H-NMR (200 MHz, CDCl₃) δ ppm: 1.13–2.37 (4H, m), 2.14 (3H, s), 2.54–2.97 (2H, m), 2.98–5.20 (3H, m), 3.68 and 3.74 (each 3H, each s), 6.50–7.52 (10H, m)

61) (Example 106)

¹H-NMR (200 MHz, CDCl₃) δ ppm: 1.41–4.06 (5H, m), 2.13 (3H, s), 3.39 (3H, s), 4.36–5.41 (1H, m), 6.49 (1H, s), 6.79 (1H, d, J=8.44 Hz), 6.88 (1H, d, J=7.42 Hz), 7.01–7.62 (6H, m), 7.79 (1H, d, J=2.24 Hz)

62) (Example 107)

¹H-NMR (200 MHz, CDCl₃) δ ppm: 1.10–2.21 (5H, m), 2.51–3.26 (3H, m), 3.27–4.11 (4H, m), 3.77 (3H, s), 4.36–4.88 (4H, m), 5.71–7.58 (10H, m)

63) (Example 108)

¹H-NMR (200 MHz, CDCl₃) δ ppm: 1.06–2.21 (4H, m), 2.49–5.23 (11H, m), 3.73 (3H, s),5.78–7.50 (9H, m)

64) (Example 110)

¹H-NMR (200 MHz, CDCl₃) δ ppm: 1.04–2.26 (4H, m), 2.47–5.20 (14H, m), 5.58–7.72 (10H, m)

65) (Example 111)

¹H-NMR (200 MHz, CDCl₃) δ ppm: 1.31–1.69 (1H, m), 1.70–2.24 (3H, m), 2.55–3.20 (3H, m), 4.88–5.20 (1H, m), 5.03 (2H, s), 6.51–7.51 (16H, m)

66) (Example 113)

¹H-NMR (200 MHz, CDCl₃) δ ppm: 1.15–2.40 (4H, m), 2.28 (3H, s), 2.60–5.29 (5H, m), 3.74 (3H, s), 6.54–6.78 (1H, m), 6.88–7.06 (1H, m), 7.09–7.46 (6H, m), 7.58–7.79 (1H, m), 8.46–8.66 (1H, m)

67) (Example 116)

¹H-NMR (200 MHz, CDCl₃) δ ppm: 1.10–2.30 (4H, m), 2.49–5.29 (5H, m), 3.70 (3H, s), 3.87 (2H, s), 6.41–7.75 (12H, m)

68) (Example 119)

¹H-NMR (200 MHz, CDCl₃) δ ppm: 1.21–2.31 (4H, m), 2.60–5.27 (5H, m), 3.75 (3H, s), 6.41–6.63 (1H, m), 6.80–7.53 (2H, m), 7.48 (2H, d, J=8.24 Hz), 7.74 (2H, d, J=8.42 Hz), 9.99–10.02 (1H, m)

69) (Example 121)

¹H-NMR (200 MHz, CDCl₃) δ ppm: 1.16–5.23 (17H, m), 2.35 (3H, s), 6.41–6.62 (1H, m), 6.78–7.53 (2H, m), 7.61 (2H, d, J=8.3 Hz), 7.73 (2H, d, J=8.3 Hz), 9.94 (1H, s)

70) (Example 122)

¹H-NMR (200 MHz, CDCl₃) δ ppm: 0.90–5.24 (26H, m), 6.40–6.61 (1H, m), 6.74–7.82 (6H, m), 9.88–10.01 (1H, m)

71) (Example 123)

¹H-NMR (200 MHz, CDCl₃) δ ppm: 0.94 (3H, t, J=7.3 Hz), 0.78–5.25 (26H, m), 6.48–7.82 (11H, m), 12.35–13.74 (1H, m)

72) (Example 125)

¹H-NMR (200 MHz, CDCl₃) δ ppm: 0.85–5.23 (28H, m), 6.37–7.80 (10H, m), 12.29–13.40 (1H, m)

73) (Example 126)

¹H-NMR (200 MHz, CDCl₃) δ ppm: 1.02–5.22 (27H, m), 6.37–7.76 (11H, m), 12.54–13.50 (1H, m)

74) (Example 130)

1H-NMR (200 MHz, CDCl₃) δ ppm: 1.08–2.37 (4H, m), 2.51–5.45 (11H, m), 3.83 (3H, s), 6.34–7.62 (10H, m)

75) (Example 132)

¹H-NMR (200 MHz, CDCl₃) δ ppm: 1.11–2.32 (4H, m), 2.12 (3H, s), 2.41–5.30 (7H, m), 6.38–8.08 (11H, m), 8.91–13.00 (1H, m)

76) (Example 136)

¹H-NMR (200 MHz, CDCl₃) δ ppm: 1.03–2.36 (4H, m), 2.13 (3H, s), 2.38–5.28 (7H, m), 3.71 (3H, s), 6.41–8.09 (11H, m)

77) (Example 137)

¹H-NMR (200 MHz, CDCl₃) δ ppm: 1.05–5.10 (25H, m), 6.05–7.50 (15H, m)

78) (Example 138)

¹H-NMR (200 MHz, CDCl₃) δ ppm: 1.03–5.08 (20H, m), 2.34 (3H, s), 6.58–7.53 (6H, m), 8.39–9.04 (1H, m)

79) (Example 24)

¹H-NMR (200 MHz, CDCl₃) δ ppm: 0.78–5.25 (23H, m), 2.96 and 3.20 (all 3H, s), 3.71 (3H, s), 3.83 (3H, s), 6.51–7.18 (6H, m)

80) (Example 52)

¹H-NMR (200 MHz, CDCl₃) δ ppm: 1.12–2.36 (4H, m), 2.20 (3H, s), 2.56–4.00 (4H, m), 4.25–5.41 (1H, m), 6.27–7.76 (11H, m), 10.73–11.74 (1H, m)

81) (Example 54)

¹H-NMR (200 MHz, CDCl₃) δ ppm: 1.3–1.7 (1H, m), 1.7–2.2 (3H, m), 2.55–3.2 (3H, m), 4.85–5.2 (1H, m), 6.3–7.7 (14H, m)

82) (Example 55)

¹H-NMR (200 MHz, DMSO-d₆) δ ppm: 1.07–2.04 (10H, m), 2.58–3.98 (18H, m), 4.13–4.36 (1H, m), 4.73 (2H, s), 6.61–7.43 (10H, m), 7.87–8.01 (1H, m), 9.21 (1H, s), 10.32(1H, brs)

83) (Example 56)

¹H-NMR (200 MHz, DMSO-₆) δ ppm: 1.05–2.06 (10H, m), 2.43–3.80 (15H, m), 4.17–4.40 (1H, m), 4.73 (2H, m), 6.63–7.48 (10H, m), 7.84–7.98 (1H, m), 8.56–8.71 (1H, m), 9.22 (1H, s), 10.34 (1H, brs)

84) (Example 57)

¹H-NMR (200 MHz, DMSO-d₆) δ ppm: 1.08–2.02 (10H, m), 2.62–3.99 (18H, m), 4.12–4.39 (1H, m), 4.82 (2H, s), 6.61–7.57 (9H, m), 7.96–8.11 (1H, m), 9.33 (1H, s), 10.21 (1H, brs)

85) (Example 58)

¹H-NMR (200 MHz, DMSO-d₆) δ ppm: 1.04–2.01 (10H, m), 2.43–3.80 (18H, m), 4.13–4.40 (1H, m), 4.82 (2H, s), 6.60–7.53 (9H, m), 7.92–8.08 (1H, m), 8.56–8.71 (1H, m), 9.33 (1H, s), 10.35 (1H, brs)

EXAMPLE 139

To a solution of 7-chloro-5-[(4-methyl-1-piperazinyl)carbonyl-methyl]-1-[2-methoxy-4-{N-[2-(2-methylphenoxy)ethyl]-N-trifluoroacetylamino}-benzoyl]-2,3,4,5-tetrahydro-1H-benzazepine (0.45 g) in methanol (20 ml) is added a solution of potassium carbonate (0.11 g) in water (5 ml), and the mixture is stirred at room temperature for 12 hours. The mixture is evaporated to remove the solvent, and thereto is added water. The mixture is extracted with ethyl acetate, and the extract is dried, evaporated to remove the solvent. The resulting residue is purified by silica gel column chromatography (solvent; dichloromethane:methanol=80:1→50:1→30:1), and recrystallized from acetone/n-hexane to give 7-chloro-5-[(4-methyl-1-piperazinyl)carbonylmethyl]-1-{2-methoxy-4-[2-(2-methylphenoxy)ethylamino]benzoyl}-2,3,4,5-tetrahydro-1H-benzazepine (0.12 g) as white powder.

M.p. 160–161° C.

EXAMPLE 140

To a solution of 7-chloro-5-[(4-methyl-1-piperazinyl)carbonyl-methyl]-1-(2-methoxy-4-trifluoroacetylaminobenzoyl)-2,3,4,5-tetrahydro-1H-benzazepine (0.4 g) in dry tetrahydrofuran (20 ml) are added triphenyl-phosphine (0.54 g) and o-(2-hydroxyethoxy)toluene (0.29 g) at room temperature. To the mixture is added dropwise a solution of diethyl azodicarboxylate (0.32 ml) in dry tetrahydrofuran (5 ml), and the mixture is stirred at room temperature for 16 hours. To the mixture is added water, and the mixture is extracted with diethyl ether. The ether layer is dried, evaporated to remove the solvent, and the residue is purified by silica gel column chromatography (solvent; dichloromethane:methanol=50:1→30:1) to give 7-chloro-5-[(4-methyl-1-piperazinyl)carbonylmethyl]-1-[2-methoxy-4-{N-[2-(2-methylphenoxy)ethyl]-N-trifluoroacetylamino}benzoyl]-2,3,4,5-tetrahydro-1H-benzazepine (0.46 g) as colorless amorphous.

¹H-NMR (200 MHz, CDCl₃) δ ppm: 1.05–5.10 (25H, m), 6.05–7.50 (15H, m)

The suitable starting compounds are treated in the same manner as in Example 140 to give the compounds of Examples 13–16, 74–78, 108 and 110.

EXAMPLE 141

To a solution of 7-chloro-5-[(4-methyl-1-piperazinyl)carbonyl-methyl]-1-(2-methoxy-2-aminobenzoyl)-2,3,4,5-tetrahydro-1H-benzazepine (2.0 g) in pyridine (30 ml) is added dropwise trifluoroacetic anhydride (1.14 ml) under ice-cooling. To the reaction solution is added a saturated aqueous sodim hydrogen carbonate solution, and the mixture is extracted with ethyl acetate. The extract is washed with water, dried, and evaporated to remove the solvent. The residue is purified by silica gel column chromatography (solvent; dichloromethane:methanol=50:1→30:1), and crystallized from acetone/n-hexane to give 7-chloro-5-[(4-methyl-1-piperazinyl)carbonylmethyl]-1-(2-methoxy-4-trifluoroacetylaminobenzoyl)-2,3,4,5-tetrahydro-1H-benzazepine (1.86 g) as white powder.

$^1$H-NMR (200 MHz, CDCl$_3$) δ ppm: 1.03–5.08 (20H, m), 2.34 (3H, s), 6.58–7.53 (6H, m), 8.39–9.04 (1H, m)

The suitable starting compounds are treated in the same manner as in Example 141 to give the compounds of Examples 7, 8 and 55–58.

EXAMPLE 142

To a solution of 7-chloro-5-[(4-methyl-1-piperazinyl)carbonyl-methyl]-1-(2-methoxy-2-aminobenzoyl)-2,3,4,5-tetrahydro-1H-benzazepine (0.8 g) in methanol (30 ml) are added o-tolualdehyde (0.35 ml) and acetic acid (1 ml), and the mixture is stirred at 50–60° C. for 2–3 hours. To the mixture is added sodium cyanoborohydride (0.11 g) at room temperature, and the mixture is stirred for two hours. The mixture is evaporated to remove the solvent, and to the residue is added water. The mixture is extracted with ethyl acetate, and the extract is dried, and evaporated. The residue is purified by silica gel column chromatography (solvent; dichloromethane:methanol =50:1→25:1), and recrystallized from acetone/diethyl ether to give 7-chloro-5-[(4-methyl-1-piperazinyl)carbonylmethyl]-1-[2-methoxy-4-(2-methylbenzylamino)benzoyl]-2,3,4,5-tetrahydro-1H-benzazepine (0.71 g) as white powder.

M.p. 153–154.5° C.

The suitable starting compounds are treated in the same manner as in Example 142 to give the compounds of Examples 13–16, 75–78, 108, 110 and 137.

EXAMPLE 143

To a suspension of 7-chloro-5-methoxycarbonylmethyl-1-(2-methoxy-4-aminobenzoyl)-2,3,4,5-tetrahydro-1H-benzazepine (2.6 g) in ethanol (100 ml) are added sodium carbonate (1.5 g), o-xylene dibromide (1.87 g) and sodium iodide (2.42 g), and the mixture is stirred at 60–70° C. for three hours. The mixture is evaporate to remove the solvent, and to the residue is added water, and the mixture is extracted with ethyl acetate. The extract is dried, and evaporate to remove the solvent. The residue is purified by silica gel column chromatography (solvent; ethyl acetate:n-hexane =1:10→1:5) to give 7-chloro-5-methoxycarbonylmethyl-1-[2-methoxy-4-(2-isoindolinyl)benzoyl]-2,3,4,5-tetrahydro-1H-benzazepine (0.32 g) as colorless amorphous.

$^1$H-NMR (200 MHz, CDCl$_3$) δ ppm: 1.10–2.21 (5H, m), 2.51–3.26 (3H, m), 3.27–4.11 (4H, m), 3.77 (3H, s), 4.36–4.88 (4H, m), 5.71–7.58 (10H, m)

The suitable starting compounds are treated in the same manner as in Example 143 to give the compounds of Examples 79 and 101.

EXAMPLE 144

To a solution of 7-chloro-1-(3-methoxy-4-hydroxybenzoyl)-2,3,4,5-tetrahydro-1H-benzazepine (0.7 g) in dry dimethylformamide (20 ml) are added potassium carbonate (0.35 g) and 2-chlorobenzyl chloride (0.32 ml), and the mixture is stirred at room temperature overnight. To the reaction solution is added water, and the mixture is extracted with ethyl acetate. The extract is washed with water, dried, and evaporated to remove the solvent. The residue is recrystallized from acetone/diethyl ether to give 7-chloro-1-[3-methoxy-4-(2-chlorobenzyloxy)benzoyl]-2,3,4,5-tetrahydro-1H-benzazepine (0.76 g) as white powder.

M.p. 135° C.

The suitable starting compounds are treated in the same manner as in Example 144 to give the compounds of Examples 24–33, 41, 43–45, 47, 49–51, 86–88 and 98.

EXAMPLE 145

To a solution of 7-chloro-5-[(4-methyl-1-piperazinyl)carbonyl-methyl]-1-(4-formylbenzoyl)-2,3,4,5-tetrahydro-1H-benzazepine (0.29 g) in methanol (30 ml) are added o-toluizine (0.2 ml) and acetic acid until the mixture becomes pH 4. The mixture is heated with stirring at 50° C. for 8 hours, and thereto is added sodium cyanoborohydride (0.085 g) with ice-cooling, and the mixture is stirred for one hour. The mixture is evaporated to remove the methanol, and thereto is added water. The mixture is extracted with ethyl acetate, and the extract is washed with water, dried, and evaporated to remove the solvent. The residue is purified by silica gel column chromatography (solvent; dichloromethane:methanol =100:1→50:1) to give 7-chloro-5-[(4-methyl-1-piperazinyl)carbonylmethyl]-1-[4-(2-methylanilinomethyl)benzoyl]-2,3,4,5-tetrahydro-1H-benzazepine (0.1 g) as colorless amorphous.

$^1$H-NMR (200 MHz, CDCl$_3$) δ ppm: 1.10–5.24 (26H, m), 6.32–7.69 (11H, m)

The suitable starting compounds are treated in the same manner as in Example 145 to give the compound of Example 36.

EXAMPLE 146

To a solution of 7-chloro-1-(3-methoxy-4-aminobenzoyl)-2,3,4,5-tetrahydro- 1H-benzazepine (0.7 g) in pyridine (5 ml) is added N,N-dimethyl-carbamic chloride (0.42 ml), and the mixture is stirred at 60–70° C. for two hours. The mixture is made acidic with hydrochloric acid, and then extracted with ethyl acetate. The mixture is washed with a saturated aqueous sodium hydrogen carbonate solution, and evaporated to remove the solvent. The residue is purified by silica gel column chromatography (solvent; ethyl acetate:n-hexane=1:10→1:1→3:1), and recrystallized from ethanol/diethyl ether to give 7-chloro-1-(3-methoxy-4-dimethylaminocarbonylaminobenzoyl)-2,3,4,5-tetrahydro-1H-benzazepine (0.33 g) as white plates.

M.p. 230–232° C.

The suitable starting compounds are treated in the same manner as in Examples 1 and 2 to give the following compounds.

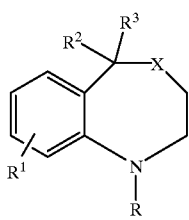

EXAMPLE 147

Structure

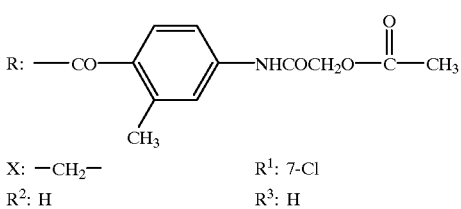

X: —CH₂—  R¹: 7-Cl
R²: H  R³: H

Crystalline form: Colorless amorphous
Form: Free

EXAMPLE 148

Structure

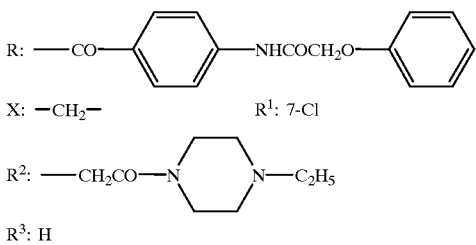

R³: H

Crystalline form Colorless amorphous
Form: Free

EXAMPLE 149

Structure

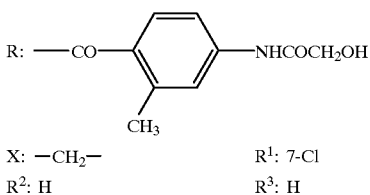

X: —CH₂—  R¹: 7-Cl
R²: H  R³: H

Crystalline form: White powder
M.p. 194–195° C.
Form: Free

EXAMPLE 150

Structure

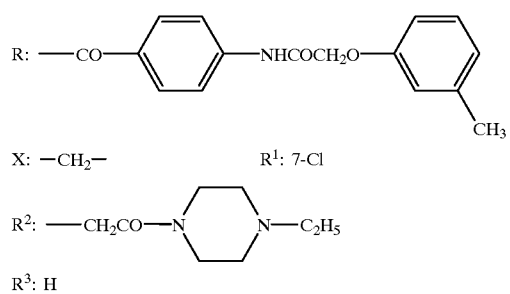

X: —CH₂—  R¹: 7-Cl

R²: —CH₂CO—N⟨piperazine⟩N—C₂H₅

R³: H

Crystalline form: Colorless amorphous
Form: Free

EXAMPLE 151

Structure

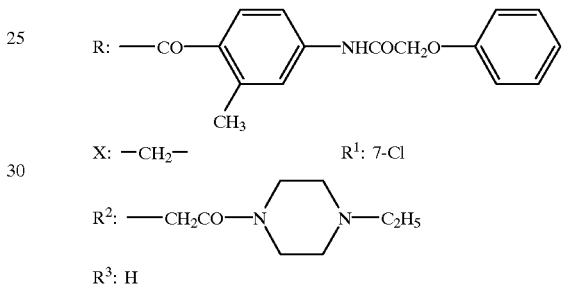

X: —CH₂—  R¹: 7-Cl

R²: —CH₂CO—N⟨piperazine⟩N—C₂H₅

R³: H

Crystalline form: Colorless amorphous
Form: Free

EXAMPLE 152

Structure

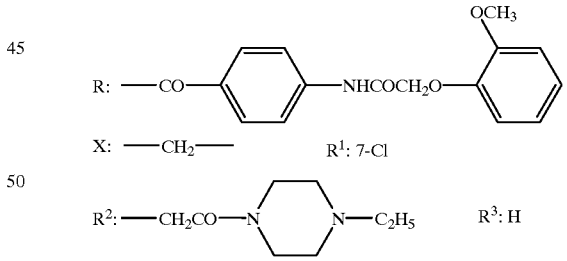

X: —CH₂—  R¹: 7-Cl

R²: —CH₂CO—N⟨piperazine⟩N—C₂H₅  R³: H

Crystalline form: Colorless amorphous
Form: Free

EXAMPLE 153

Structure

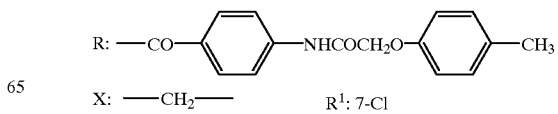

X: —CH₂—  R¹: 7-Cl

-continued

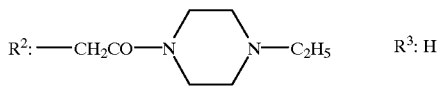

Crystalline form: Colorless amorphous
Form: Free

EXAMPLE 154

Structure

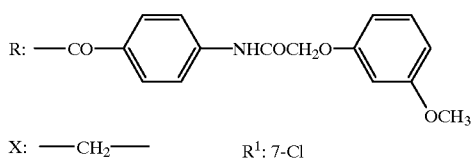
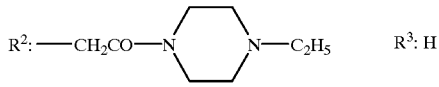

Crystalline form: Colorless amorphous
Form: Free

EXAMPLE 155

Structure

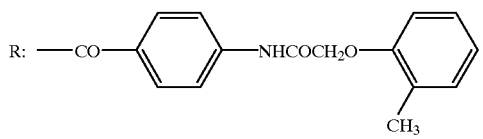
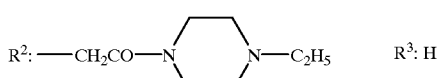

Crystalline form: Colorless amorphous
Form: Free

EXAMPLE 156

Structure

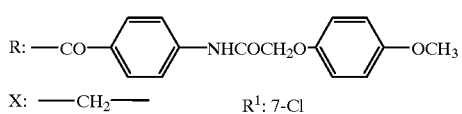
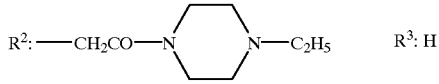

Crystalline form: Colorless amorphous
Form: Free

EXAMPLE 157

Structure

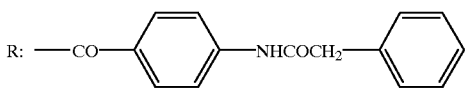
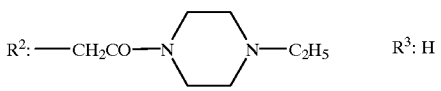

Crystalline form: Colorless amorphous
Form: Free

EXAMPLE 158

Structure

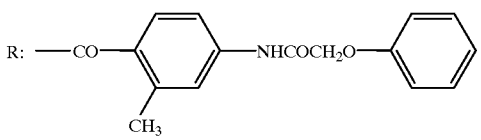
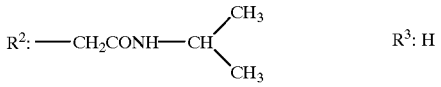

Crystalline form: Colorless amorphous
Form: Free

EXAMPLE 159

Structure

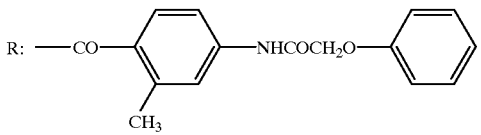
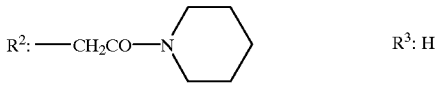

Crystalline form: Colorless amorphous
Form: Free

EXAMPLE 160

Structure

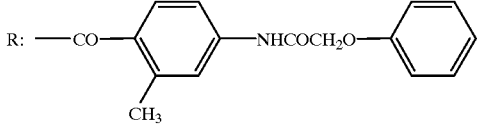

-continued

R²: —CH₂CONH(CH₂)₂N(C₂H₅)₂    R³: H

Crystalline form: Colorless amorphous

Form: Free

EXAMPLE 161

Structure

R: —CO—[phenyl with CH₃]—NHCOCH₂O—[phenyl]

X: —CH₂—    R¹: 7-Cl

R²: —CH₂CON(CH₂)₂OH / (CH₂)₂OH    R³: H

Crystalline form: Colorless amorphous

Form: Free

EXAMPLE 162

Structure

R: —CO—[phenyl with CH₃]—NHCOCH₂O—[phenyl]

X: —CH₂—    R¹: 7-Cl

R²: —CH₂CONH₂    R³: H

Crystalline form: Brown amorphous

Form: Free

EXAMPLE 163

Structure

R: —CO—[phenyl with CH₃]—NHSO₂C₂H₅

X: —CH₂—    R¹: H

R²: H    R³: H

Crystalline form: Brown amorphous

Form: Free

EXAMPLE 164

Structure

R: —CO—[phenyl with CH₃]—NHCOCH₂O—[tetrahydronaphthyl]

X: —CH₂—    R¹: H

R²: H    R³: H

Crystalline form: White powder
M.p. 230–232° C. (decomposed)
Form: Free

EXAMPLE 165

Structure

R: —CO—[phenyl with OCH₃]—N(CH₃)COCH₂O—[phenyl]

X: —CH₂—    R¹: 7-Cl

R²: —CH₂CO—N(piperazine)N—C₂H₅    R³: H

Crystalline form: Yellow amorphous
Form: Free

EXAMPLE 166

Structure

R: —CO—[phenyl with CH₃]—NHCOCH₂O—[3,4-dihydroquinolin-2(1H)-one]

X: —CH₂—    R¹: H

R²: H    R³: H

Crystalline form: White powder
M.p. 243–245° C. (decomposed)
Form: Free

EXAMPLE 167

Structure

R: —CO—[phenyl with CH₃]—NHCOOCH₂CH(CH₃)₂

X: —CH₂—    R¹: H

-continued

R²: H   R³: H

Crystalline form: Colorless amorphous
Form: Free

EXAMPLE 168
Structure

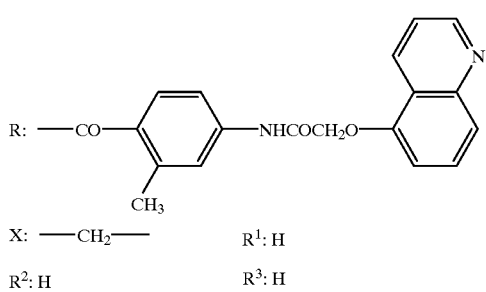

X: —CH₂—   R¹: H
R²: H   R³: H

Crystalline form: Pale yellow powder
M.p. 203–205° C. (decomposed)
Form: Free

EXAMPLE 169
Structure

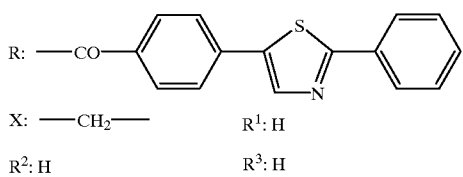

X: —CH₂—   R¹: H
R²: H   R³: H

Crystalline form: Brown powder
M.p. 178–180° C.
Form: Free

EXAMPLE 170
Structure

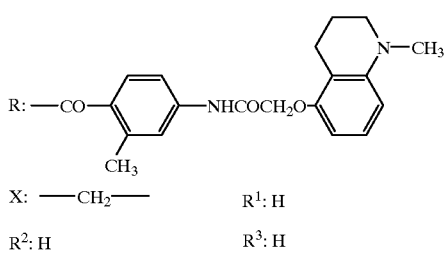

X: —CH₂—   R¹: H
R²: H   R³: H

Crystalline form: White powder
M.p. 202–204° C. (decomposed)
Form: Free

EXAMPLE 171
Structure

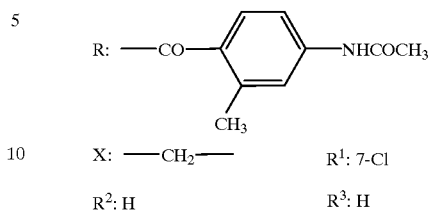

X: —CH₂—   R¹: 7-Cl
R²: H   R³: H

Crystalline form: White powder
M.p. 118–120° C.
Form: Free

EXAMPLE 172
Structure

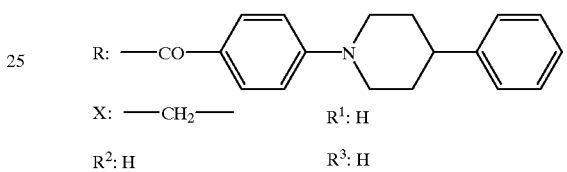

X: —CH₂—   R¹: H
R²: H   R³: H

Crystalline form: White powder
M.p. 179–181° C. (decomposed)
Form: Free

EXAMPLE 173
Structure

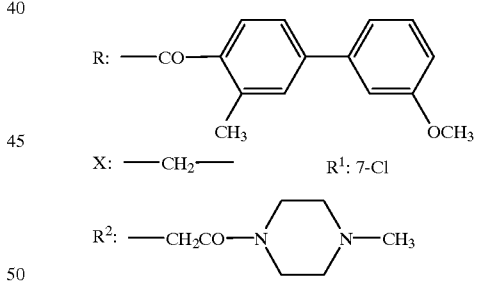

X: —CH₂—   R¹: 7-Cl
R²: —CH₂CO—N(piperazine)N—CH₃   R³: H

Crystalline form: Colorless amorphous
Form: Free

EXAMPLE 174
Structure

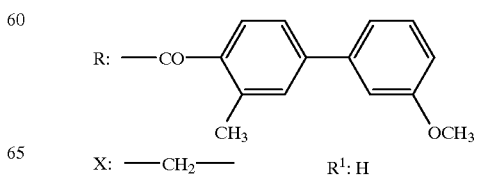

X: —CH₂—   R¹: H

-continued

Crystalline form: Colorless amorphous

Form: Free

EXAMPLE 175

Structure

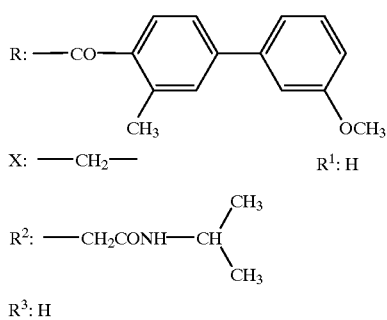

Crystalline form: Colorless amorphous

Form: Free

EXAMPLE 176

Structure

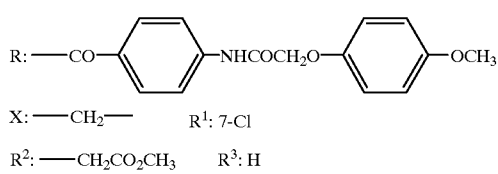

Crystalline form: Colorless amorphous

Form: Free

EXAMPLE 177

Structure

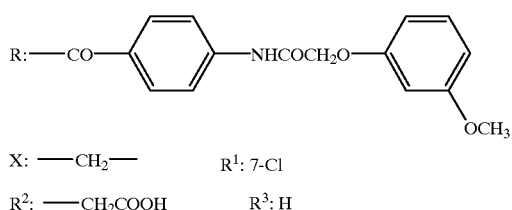

Crystalline form: Colorless amorphous

Form: Free

EXAMPLE 178

Structure

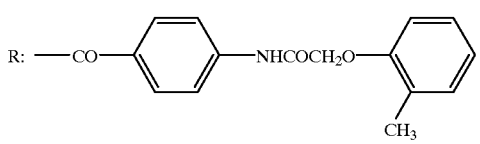

X: —$CH_2$—   $R^1$: 7-Cl $R^2$: —$CH_2COOH$   $R^3$: H

Crystalline form: Colorless amorphous

Form: Free

EXAMPLE 179

Structure

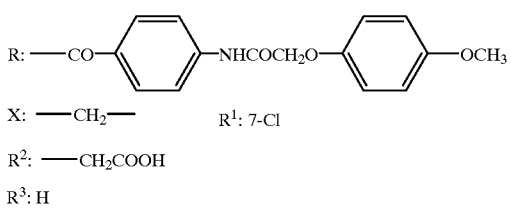

X: —$CH_2$—   $R^1$: 7-Cl $R^2$: —$CH_2COOH$ $R^3$: H

Crystalline form: Colorless amorphous

Form: Free

EXAMPLE 180

Structure

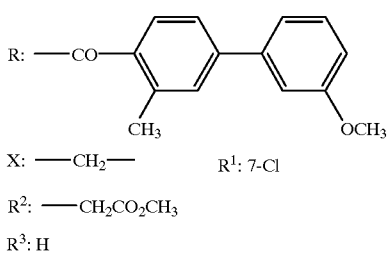

X: —$CH_2$—   $R^1$: 7-Cl $R^2$: —$CH_2CO_2CH_3$ $R^3$: H

Crystalline form: Colorless amorphous

Form: Free

EXAMPLE 181

Structure

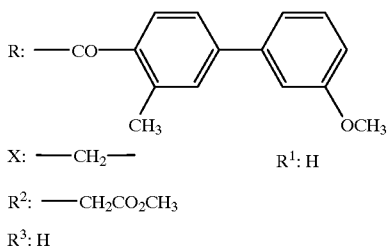

X: —$CH_2$—   $R^1$: H $R^2$: —$CH_2CO_2CH_3$ $R^3$: H

Crystalline form: Colorless amorphous

Form: Free

EXAMPLE 182

Structure

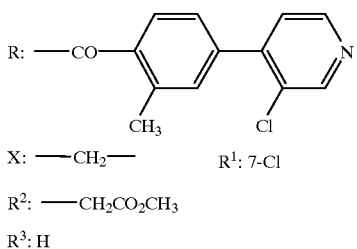

X: —CH₂— R¹: 7-Cl

R²: —CH₂CO₂CH₃

R³: H

Crystalline form: Pale yellow oil
Form: Free

EXAMPLE 183

Structure

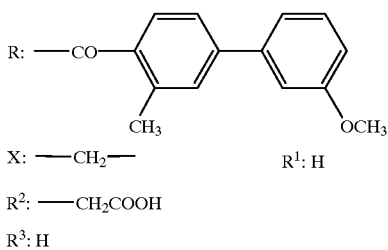

X: —CH₂— R¹: H

R²: —CH₂COOH

R³: H

Crystalline form: Colorless amorphous
Form: Free

EXAMPLE 184

Structure

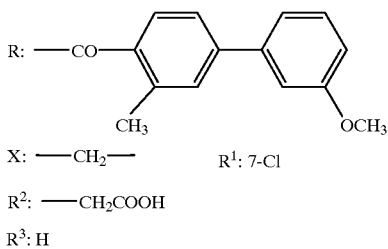

X: —CH₂— R¹: 7-Cl

R²: —CH₂COOH

R³: H

Crystalline form: Colorless amorphous
Form: Free

EXAMPLE 185

Structure

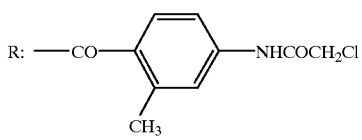

-continued

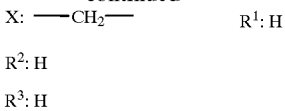

X: —CH₂— R¹: H

R²: H

R³: H

Crystalline form: Colorless amorphous
Form: Free

EXAMPLE 186

Structure

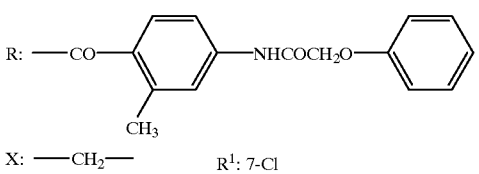

X: —CH₂— R¹: 7-Cl

R²: —CH₂COOH

R³: H

Crystalline form: Colorless amorphous
Form: Free

EXAMPLE 187

Structure

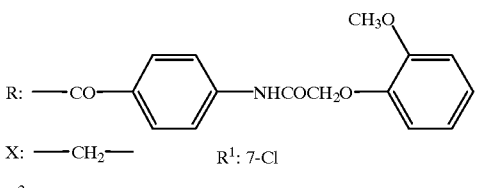

X: —CH₂— R¹: 7-Cl

R²: —CH₂CO₂CH₃

R³: H

Crystalline form: Colorless amorphous
Form: Free

EXAMPLE 188

Structure

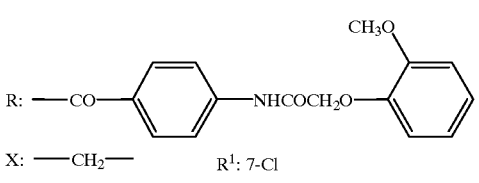

X: —CH₂— R¹: 7-Cl

R²: —CH₂COOH

R³: H

Crystalline form: Colorless amorphous
Form: Free

EXAMPLE 189

Structure

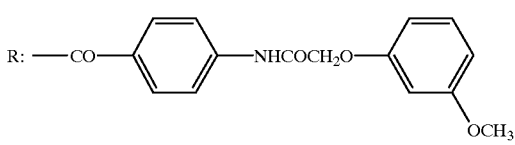

X: —CH$_2$—  R$^1$: 7-Cl

R$^2$: —CH$_2$CO$_2$CH$_3$

R$^3$: H

Crystalline form: Colorless amorphous
Form: Free

EXAMPLE 190

Structure

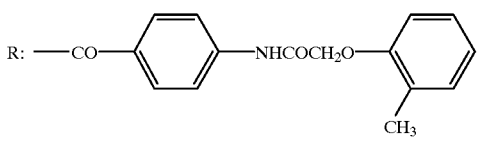

X: —CH$_2$—  R$^1$: 7-Cl

R$^2$: —CH$_2$CO$_2$CH$_3$

R$^3$: H

Crystalline form: Colorless amorphous
Form: Free

EXAMPLE 191

Structure

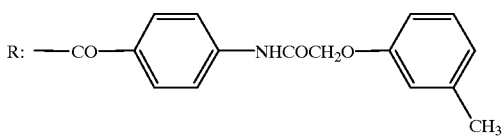

X: —CH$_2$—  R$^1$: 7-Cl

R$^2$: —CH$_2$CO$_2$CH$_3$

R$^3$: H

Crystalline form: White powder
M.p. 130–132° C.
Form: Free

EXAMPLE 192

Structure

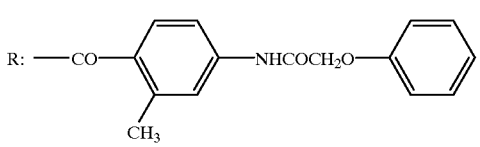

X: —CH$_2$—  R$^1$: 7-Cl

R$^2$: —CH$_2$CO$_2$CH$_3$

R$^3$: H

Crystalline form: Colorless amorphous
Form: Free

EXAMPLE 193

Structure

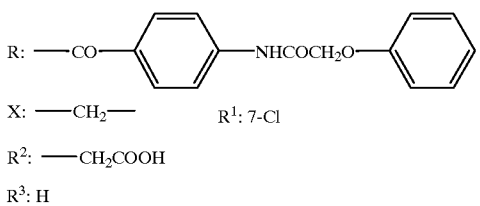

X: —CH$_2$—  R$^1$: 7-Cl

R$^2$: —CH$_2$COOH

R$^3$: H

Crystalline form: Colorless amorphous
Form: Free

EXAMPLE 194

Structure

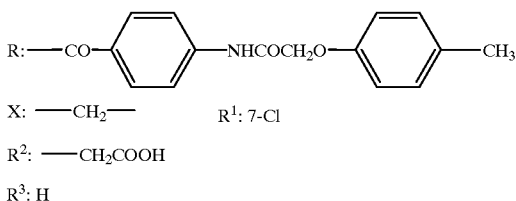

X: —CH$_2$—  R$^1$: 7-Cl

R$^2$: —CH$_2$COOH

R$^3$: H

Crystalline form: Colorless amorphous
Form: Free

EXAMPLE 195

Structure

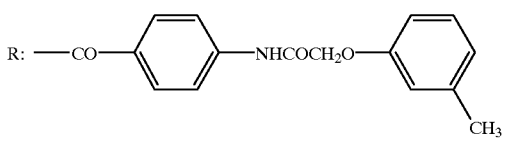

X: —CH$_2$—  R$^1$: 7-Cl

R$^2$: —CH$_2$COOH

R$^3$: H

Crystalline form: Colorless amorphous
Form: Free

EXAMPLE 196

Structure

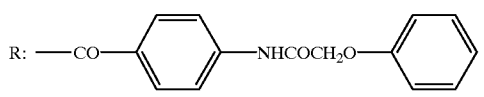

R: —CO—⟨C6H4⟩—NHCOCH2O—⟨C6H5⟩

X: —CH2—   R¹: 7-Cl

R²: —CH2CO2CH3

R³: H

Crystalline form: Colorless amorphous
Form: Free

EXAMPLE 197

Structure


R: —CO—⟨C6H4⟩—NHCOCH2O—⟨C6H5⟩

X: —CH2—   R¹: 7-Cl

R²: —CH2COOH

R³: H

Crystalline form: White powder
Form: Free

EXAMPLE 198

Structure

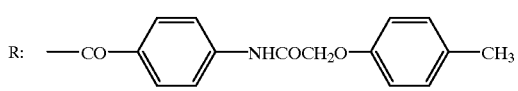

R: —CO—⟨C6H4⟩—NHCOCH2O—⟨C6H4⟩—CH3

X: —CH2—

R¹: 7-Cl

R²: —CH2CO2CH3

R³: H

Crystalline form: Colorless amorphous
Form: Free

EXAMPLE 199

Structure

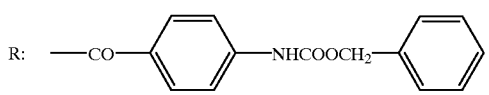

R: —CO—⟨C6H4⟩—NHCOOCH2—⟨C6H5⟩

X: —CH2—

R¹: 7-Cl

R²: —CH2CO2CH3

R³: H

Crystalline form: White powder
Form: Free

EXAMPLE 200

Structure

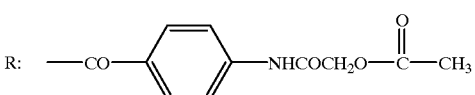

R: —CO—⟨C6H3(Cl)⟩—NHCOCH2O—C(=O)—CH3

X: —CH2—

R¹: H

R²: H

R³: H

Crystalline form: White powder
Solvent for recrystallization: Ethanol
M.p. 188–190° C.
Form: Free

EXAMPLE 201

Structure

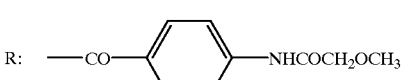

R: —CO—⟨C6H3(Cl)⟩—NHCOCH2OCH3

X: —CH2—

R¹: H

R²: H

R³: H

Crystalline form: Colorless amorphous
Form: Free

EXAMPLE 202

Structure

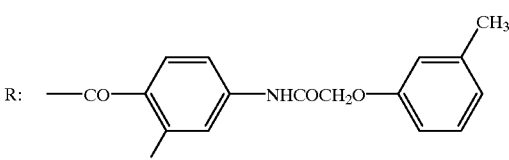

R: —CO—⟨C6H3(CH3)⟩—NHCOCH2O—⟨C6H4⟩—CH3

X: —CH2—

R¹: H

R²: —CH2CO—N(piperazine)N—CH3 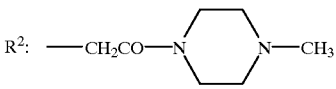

R³: H

Crystalline form: Colorless amorphous
Form: Hydrochloride

EXAMPLE 203

Structure

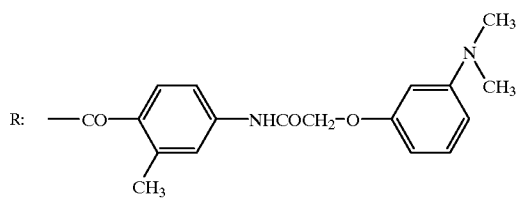

X: —CH$_2$—
R$^1$: H
R$^2$: H
R$^3$: H

Crystalline form: Colorless amorphous
Form: Free

EXAMPLE 204

Structure

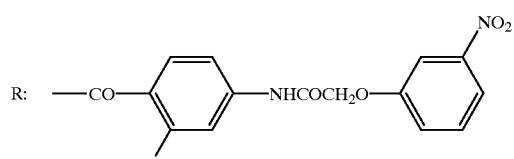

X: —CH$_2$—
R$^1$: H
R$^2$: H
R$^3$: H

Crystalline form: White powder
Solvent for recrystallization: Ethanol
M.p. 186.5–188° C.
Form: Free

EXAMPLE 205

Structure

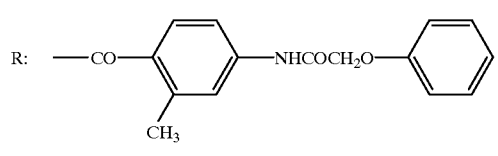

X: —CH$_2$—
R$^1$: H
R$^2$: 
R$^3$: H

Crystalline form: Colorless amorphous
Form: Hydrochloride

EXAMPLE 206

Structure

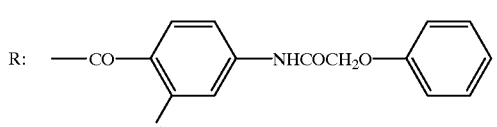

X: —CH$_2$—
R$^1$: H
R$^2$: 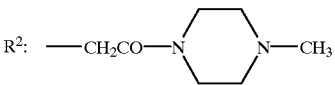
R$^3$: H

Crystalline form: Yellow amorphous
Form: Hydrochloride

EXAMPLE 207

Structure

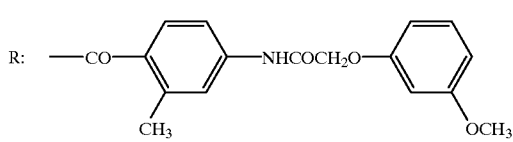

X: —CH$_2$—
R$^1$: H
R$^2$: —CH$_2$CO—N⟨piperazine⟩N—CH$_3$
R$^3$: H

Crystalline form: Colorless amorphous
Form: Hydrochloride

EXAMPLE 208

Structure

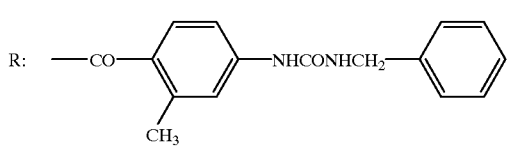

X: —CH$_2$—
R$^1$: 7-Cl
R$^2$: 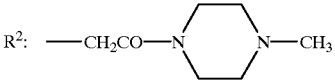
R$^3$: H

Crystalline form: Colorless amorphous
Form: Free

EXAMPLE 209

Structure

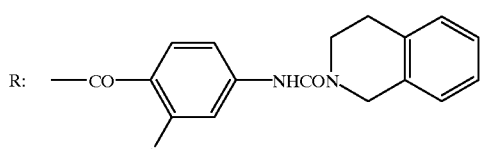

X: —CH₂—

R¹: H

R²: H

R³: H

Crystalline form: Colorless amorphous

Form: Free

EXAMPLE 210

Structure

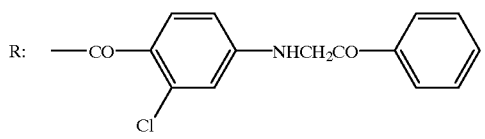

X: —CH₂—

R¹: H

R²: H

R³: H

Crystalline form: Colorless amorphous

Form: Free

EXAMPLE 211

Structure

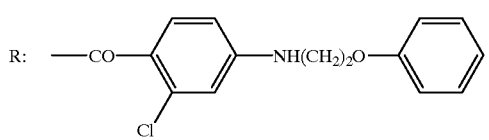

X: —CH₂—

R¹: H

R²: H

R³: H

Crystalline form: White powder

Form: Free

EXAMPLE 212

Structure

X: —CH₂—

R¹: H

R²: H

R³: H

Crystalline form: Colorless needles

Solvent for recrystallization: Ethyl acetate

M.p. 204–205° C.

Form: Free

EXAMPLE 213

Structure

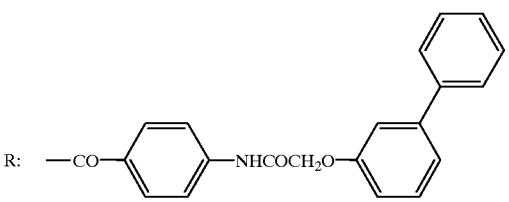

X: 

R¹: H

R²: H

R³: H

Crystalline form: Colorless prisms

Solvent for recrystallization: Ethyl acetate

M.p. 157.5–159° C.

Form: Free

EXAMPLE 214

Structure

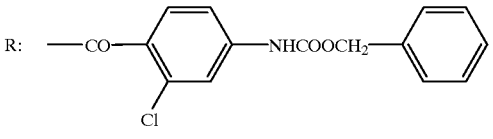

X: —CH₂—

R¹: 7-Cl

R²: 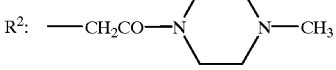

R³: 

Crystalline form: Colorless amorphous

Form: Free

EXAMPLE 215

Structure

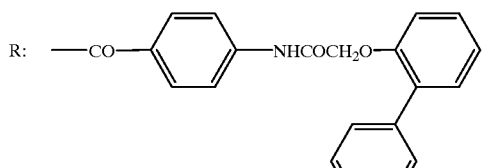

X: —CH$_2$—
R$^1$: H
R$^2$: H
R$^3$: H

Crystalline form: White powder
Solvent for recrystallization: Ethyl acetate
M.p. 168.5–169.5° C.
Form: Free

EXAMPLE 216

Structure

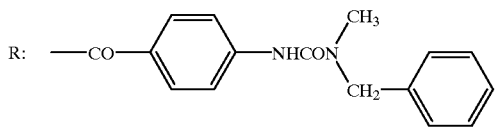

X: —CH$_2$—
R$^1$: H
R$^2$: H
R$^3$: H

Crystalline form: White powder
Solvent for recrystallization: Ethyl acetate
M.p. 177–178° C.
Form: Free

EXAMPLE 217

Structure

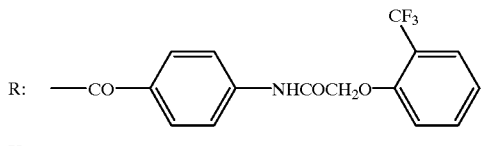

X: —CH$_2$—
R$^1$: H
R$^2$: H
R$^3$: H

Crystalline form: Yellow powder
M.p. 195.5–197° C.
Form: Free

EXAMPLE 218

Structure

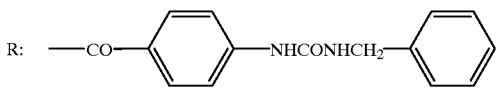

X: —CH$_2$—
R$^1$: H
R$^2$: H
R$^3$: H

Crystalline form: White powder
Solvent for recrystallization: Ethanol
M.p. 177–178° C.
Form: Free

EXAMPLE 219

Structure

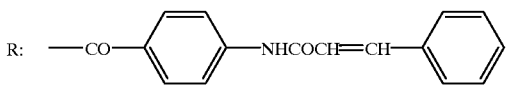

X: —CH$_2$—
R$^1$: H
R$^2$: H
R$^3$: H

Crystalline form: White powder
M.p. 234–234.5° C.
Form: Free

EXAMPLE 220

Structure

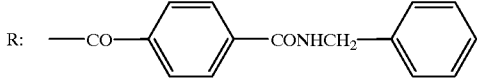

X: —CH$_2$—
R$^1$: H
R$^2$: H
R$^3$: H

Crystalline form: Colorless amorphous
Form: Free

EXAMPLE 221

Structure

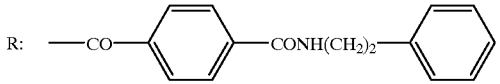

X: —CH$_2$—

-continued

R¹: H
R²: H
R³: H

Crystalline form: White powder
M.p. 143–144.5° C.
Form: Free

EXAMPLE 222

Structure

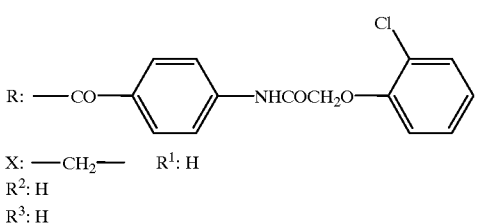

X: —CH₂—  R¹: H
R²: H
R³: H

Crystalline form: Slightly orange powder
Solvent for recrystallization: Acetone/diethyl ether
M.p. 231.5–233° C.
Form: Free

EXAMPLE 223

Structure

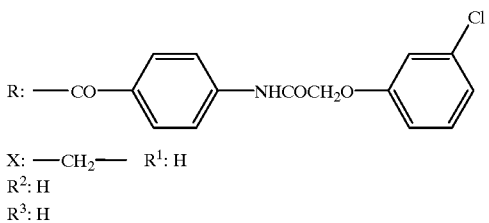

X: —CH₂—  R¹: H
R²: H
R³: H

Crystalline form: White powder
Solvent for recrystallization: Ethanol
M.p. 164–165° C.
Form: Free

EXAMPLE 224

Structure

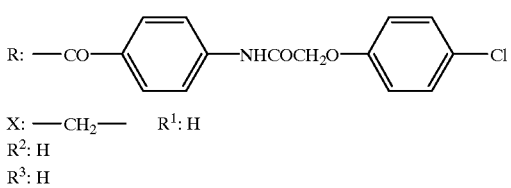

X: —CH₂—  R¹: H
R²: H
R³: H

Crystalline form: Slightly orange powder
Solvent for recrystallization: Ethanol
M.p. 175–176.5° C.
Form: Free

EXAMPLE 225

Structure

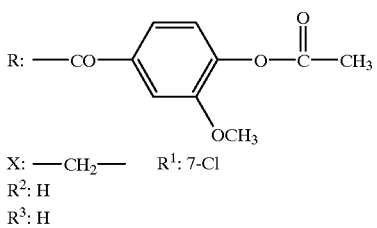

X: —CH₂—  R¹: 7-Cl
R²: H
R³: H

Crystalline form: White powder
Solvent for recrystallization: Ethanol
M.p. 127.5–128.5° C.
Form: Free

EXAMPLE 226

Structure

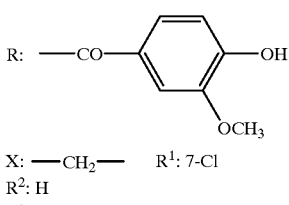

X: —CH₂—  R¹: 7-Cl
R²: H
R³: H

Crystalline form: White powder
Solvent for recrystallization: Ethanol
M.p. 176–177° C.
Form: Free

EXAMPLE 227

Structure

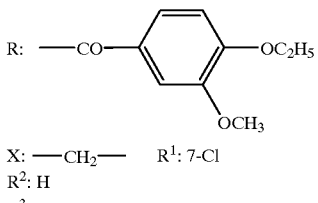

X: —CH₂—  R¹: 7-Cl
R²: H
R³: H

Crystalline form: White powder
Solvent for recrystallization: Ethanol
M.p. 104.5–105.5° C.
Form: Free

EXAMPLE 228

Structure

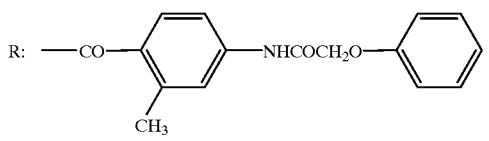

X: —CH₂—  R¹: H
R²: —CH₂COOH
R³: H

Crystalline form: Colorless amorphous

Form: Free

EXAMPLE 229

Structure

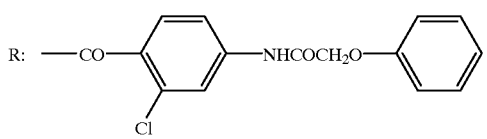

X: —CH₂—  R¹: H
R²: —CH₂COOH
R³: H

Crystalline form: Yellow amorphous

Form: Free

EXAMPLE 230

Structure

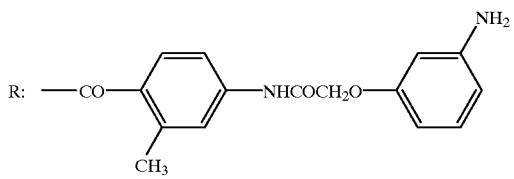

X: —CH₂—  R¹: H
R²: H
R³: H

Crystalline form: White powder

Form: Free

EXAMPLE 231

Structure

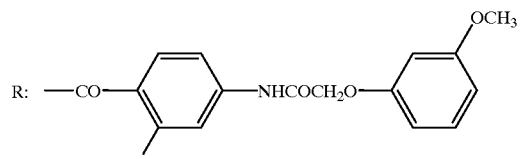

X: —CH₂—  R¹: H
R²: —CH₂CO₂H
R³: H

Crystalline form: Yellow amorphous

Form: Free

EXAMPLE 232

Structure

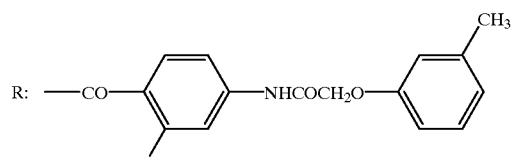

X: —CH₂—  R¹: H
R²: —CH₂COOH
R³: H

Crystalline form: Yellow amorphous

Form: Free

EXAMPLE 233

Structure

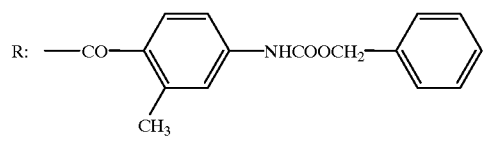

X: —CH₂—  R¹: 7-Cl
R²: —CH₂CO₂H
R³: H

Crystalline form: White powder

Form: Free

EXAMPLE 234

Structure

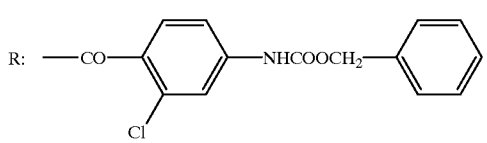

X: —CH₂—  R¹: 7-Cl
R²: —CH₂CO₂H
R³: H

Crystalline form: Colorless amorphous

Form: Free

EXAMPLE 235

Structure

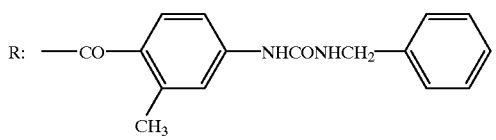

X: —CH₂—  R¹: 7-Cl
R²: —CH₂CO₂H
R³: H

Crystalline form: Colorless amorphous

Form: Free

EXAMPLE 236

Structure

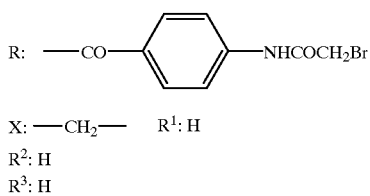

X: —CH₂—  R¹: H
R²: H
R³: H

Crystalline form: Brown powder

M.p. 156–159° C.

Form: Free

EXAMPLE 237

Structure

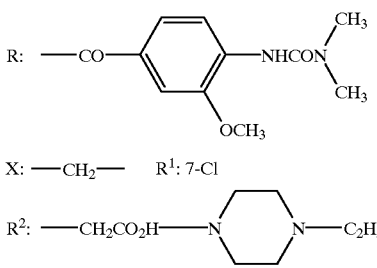

X: —CH₂—  R¹: 7-Cl

R²: —CH₂CO₂H—N(piperazine)N—C₂H₅

R³: H

Crystalline form: Colorless amorphous

Form: Free

EXAMPLE 238

Structure

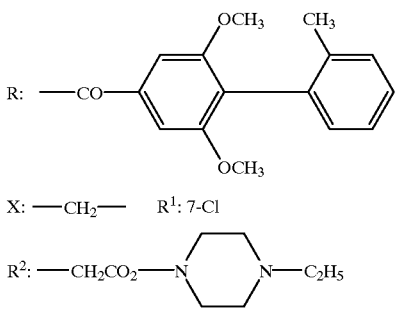

X: —CH₂—  R¹: 7-Cl

R²: —CH₂CO₂—N(piperazine)N—C₂H₅

R³: H

Crystalline form: Colorless amorphous

Form: Hydrochloride

EXAMPLE 239

Structure

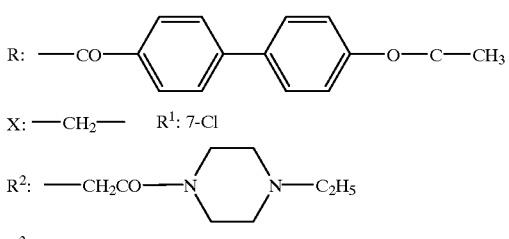

X: —CH₂—  R¹: 7-Cl

R²: —CH₂CO—N(piperazine)N—C₂H₅

R³: H

Crystalline form: Colorless amorphous

Form: Free

EXAMPLE 240

Structure

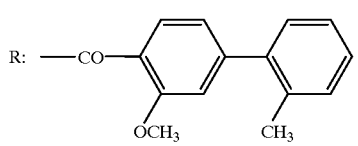

X: —CH$_2$—  R$^1$: 7-Cl

R$^2$: 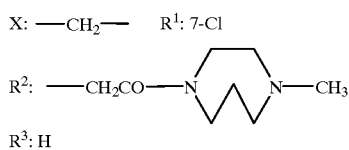

R$^3$: H

Crystalline form: Colorless amorphous

Form: Hydrochoride

EXAMPLE 241

Structure

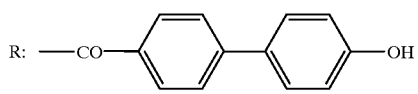

X: —CH$_2$—  R$^1$: 7-Cl

R$^2$: 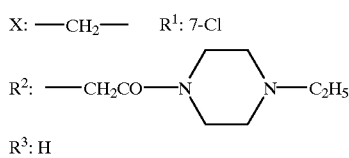

R$^3$: H

Crystalline form: Colorless amorphous

Form: Free

EXAMPLE 242

Structure

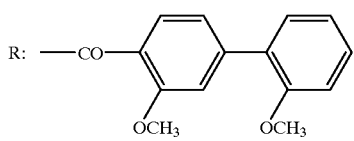

X: —CH$_2$—  R$^1$: 7-Cl

R$^2$: 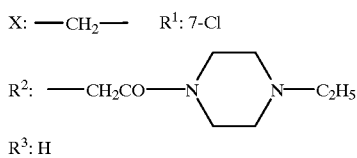

R$^3$: H

Crystalline form: Colorless amorphous

Form: Hydrochloride

EXAMPLE 243

Structure

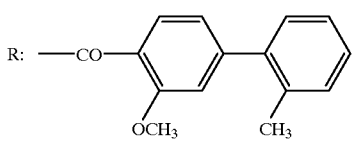

X: —CH$_2$—  R$^1$: 7-Cl

R$^2$: —OCH$_2$CO$_2$CH$_3$

R$^3$: H

Crystalline form: Colorless amorphous

Form: Free

EXAMPLE 244

Structure

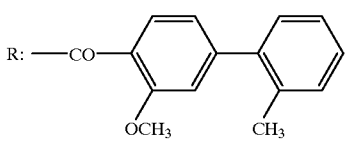

X: —CH$_2$—  R$^1$: 7-Cl

R$^2$: —OCH$_2$COOH

R$^3$: H

Crystalline form: Colorless amorphous

Form: Free

EXAMPLE 245

Structure

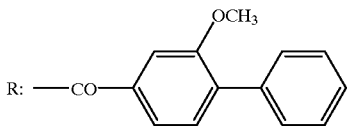

X: —CH$_2$—  R$^1$: 7-Cl

R$^2$: 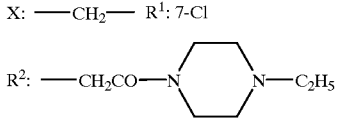

R$^3$: H

Crystalline form: Colorless amorphous

Form: Hydrochloride

EXAMPLE 246

Structure

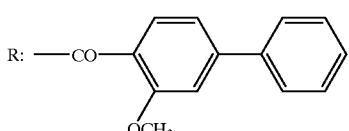

X: 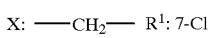 R$^1$: 7-Cl

R²: 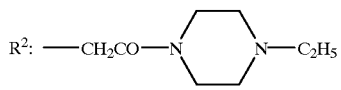

R³: H

Crystalline form: Colorless amorphous
Form: Hydrochloride

EXAMPLE 247

Structure

R: 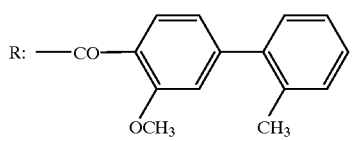

X: —CH₂— R¹: 7-Cl

R²: 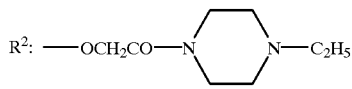

R³: H

Crystalline form: Colorless amorphous
Form: Hydrochloride

EXAMPLE 248

Structure

R: 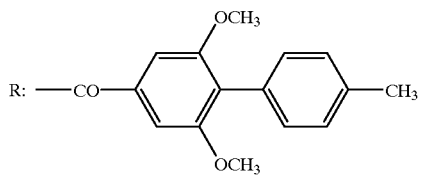

X: —CH₂— R¹: 7-Cl

R²: 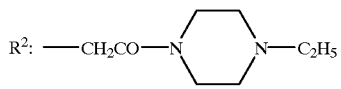

R³: H

Crystalline form: Colorless amorphous
Form: Hydrochloride

EXAMPLE 249

Structure

R: 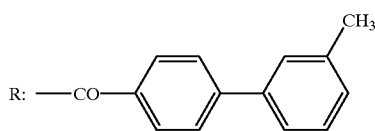

X: —CH₂— R¹: 7-Cl

R²: H

R³: H

Crystalline form: White powder
Solvent for recrystallization: Acetone/n-hexane
M.p. 84–85.5° C.
Form: Free

EXAMPLE 250

Structure

R: 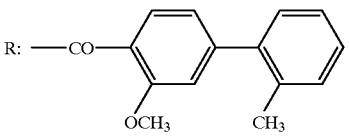

X: —CH₂— R¹: 7-Cl

R²: —CH₂CONH(CH₂)₂N(C₂H₅)₂

R³: H

Crystalline form: Colorless amorphous
Form: Hydrochloride

EXAMPLE 251

Structure

R: 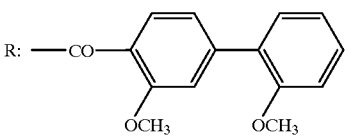

X: —CH₂— R¹: 7-Cl

R²: 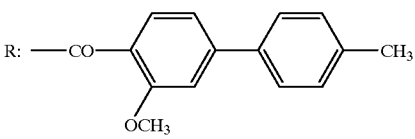

R³: H

Crystalline form: Colorless amorphous
Form: Hydrochloride

EXAMPLE 252

Structure

R: 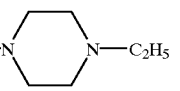

X: —CH₂— R¹: 7-Cl

R²: —CH₂CO—N⟨piperazine⟩—C₂H₅

R³: H

Crystalline form: Colorless amorphous
Form: Hydrochloride

EXAMPLE 253

Structure

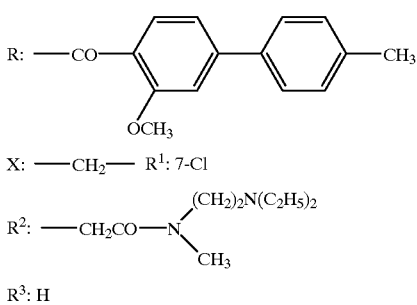

X: —CH$_2$— R$^1$: 7-Cl

R$^2$: —CH$_2$CO—N$\begin{matrix}(CH_2)_2N(C_2H_5)_2 \\ CH_3\end{matrix}$

R$^3$: H

Crystalline form: Colorless amorphous
Form: Hydrochloride

EXAMPLE 254

Structure

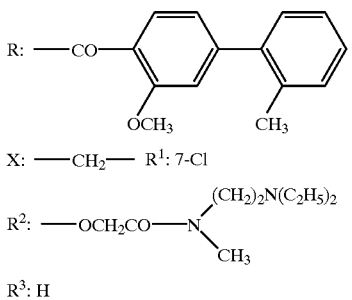

X: —CH$_2$— R$^1$: 7-Cl

R$^2$: —OCH$_2$CO—N$\begin{matrix}(CH_2)_2N(C_2H_5)_2 \\ CH_3\end{matrix}$

R$^3$: H

Crystalline form: Colorless amorphous
Form: Hydrochloride

EXAMPLE 255

Structure

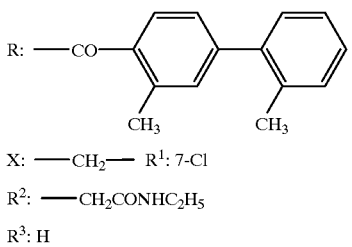

X: —CH$_2$— R$^1$: 7-Cl

R$^2$: —CH$_2$CONHC$_2$H$_5$

R$^3$: H

Crystalline form: Colorless amorphous
Form: Free

EXAMPLE 256

Structure

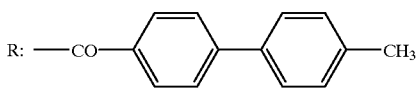

X: —CH$_2$— R$^1$: 7-Cl

R$^2$: H

R$^3$: H

Crystalline form: White powder
Solvent for recrystallization: Acetone/n-hexane
M.p. 181.5–182° C.
Form: Free

EXAMPLE 257

Structure

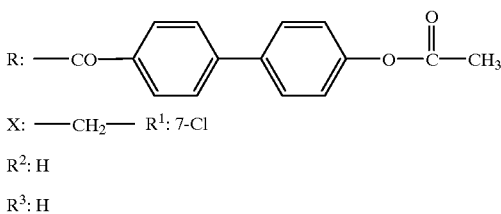

X: —CH$_2$— R$^1$: 7-Cl

R$^2$: H

R$^3$: H

Crystalline form: White powder
Solvent for recrystallization: Acetone/n-hexane
M.p. 181–182° C.
Form: Free

EXAMPLE 258

Structure

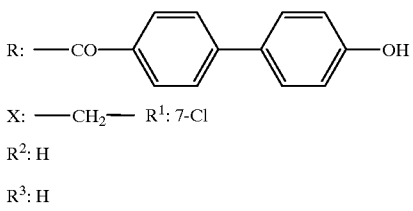

X: —CH$_2$— R$^1$: 7-Cl

R$^2$: H

R$^3$: H

Crystalline form: White powder
Solvent for recrystallization: Ethanol/diethyl ether
M.p. 262–265° C.
Form: Free

EXAMPLE 259

Structure

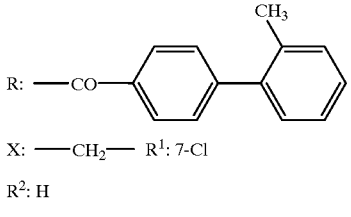

X: —CH$_2$— R$^1$: 7-Cl

R$^2$: H

R$^3$: H

Crystalline form: White powder
Solvent for recrystallization: Acetone/n-hexane
M.p. 159–160° C.
Form: Free

EXAMPLE 260

Structure

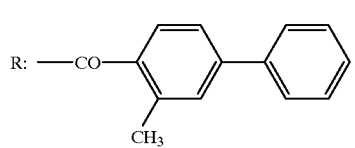

X: —CH$_2$— R$^1$: 7-Cl

R$^2$: —CH$_2$CONHC$_2$H$_5$

R$^3$: H

Crystalline form: Coloreless amorphous

Form: Free

EXAMPLE 261

Structure

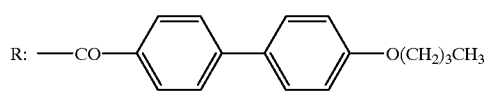

X: —CH$_2$— R$^1$: 7-Cl

R$^2$: H

R$^3$: H

Crystalline form: White powder

Solvent for recrystallization: Acetone/n-hexane

M.p. 153° C.

Form: Free

EXAMPLE 262

Structure

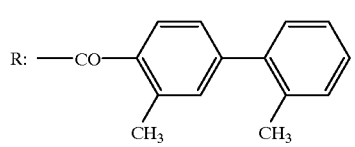

X: —CH$_2$— R$^1$: 7-Cl

R$^2$: H

R$^3$: H

Crystalline form: Colorless amorphous

Form: Free

EXAMPLE 263

Structure

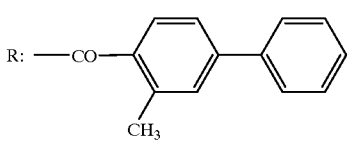

X: —CH$_2$— R$^1$: 7-Cl

R$^2$: H

R$^3$: H

Crystalline form: Colorless amorphous

Form: Free

EXAMPLE 264

Structure

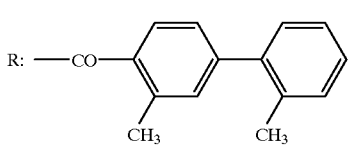

X: —CH$_2$— R$^1$: 7-Cl

R$^2$: —CH$_2$CO—N(CH$_3$)(CH$_2$)$_2$N(C$_2$H$_5$)$_2$

R$^3$: H

Crystalline form: Colorless amorphous

Form: Hydrochloride

EXAMPLE 265

Structure

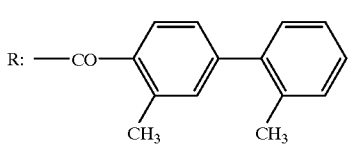

X: —CH$_2$— R$^1$: 7-Cl

R$^2$: —CH$_2$CONHCH$_3$

R$^3$: H

Crystalline form: Colorless amorphous

Form: Free

EXAMPLE 266

Structure

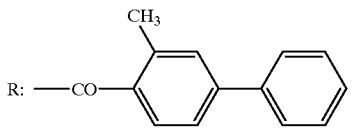

-continued

X: —CH₂— R¹: 7-Cl

R²: —CH₂CONH₂

R³: H

Crystalline form: Colorless amorphous
Form: Free

EXAMPLE 267

Structure

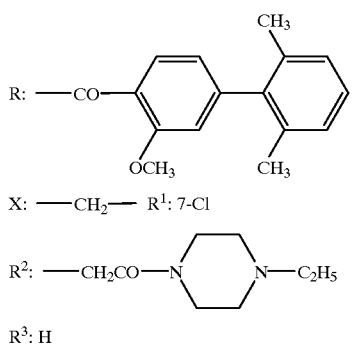

X: —CH₂— R¹: 7-Cl

R²: —CH₂CO—N⌒N—C₂H₅

R³: H

Crystalline form: Colorless amorphous
Form: Hydrochloride

EXAMPLE 268

Structure

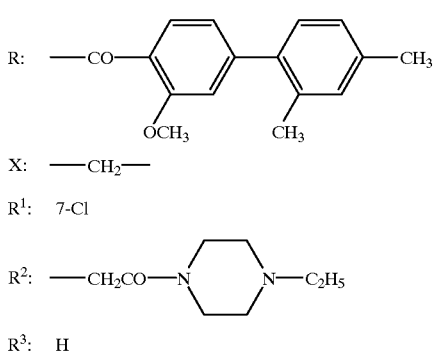

X: —CH₂—

R¹: 7-Cl

R²: —CH₂CO—N⌒N—C₂H₅

R³: H

Crystalline form: Colorless amorphous
Form: Hydrochloride

EXAMPLE 269

Structure

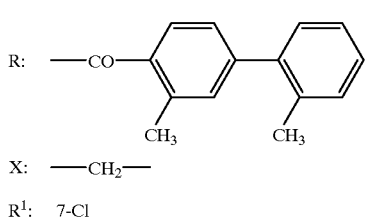

X: —CH₂—

R¹: 7-Cl

-continued

R²: —CH₂CONH₂

R³: H

Crystalline form: Colorless amorphous
Form: Free

EXAMPLE 270

Structure

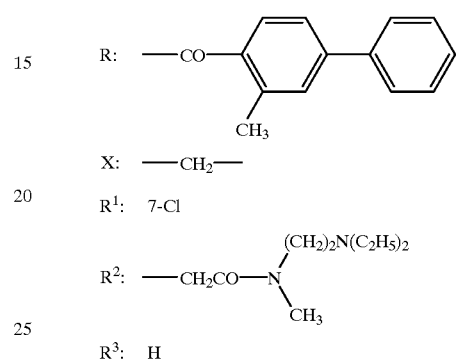

X: —CH₂—

R¹: 7-Cl

R²: —CH₂CO—N(CH₃)((CH₂)₂N(C₂H₅)₂)

R³: H

Crystalline form: Colorless amorphous
Form: Hydrochloride

EXAMPLE 271

Structure

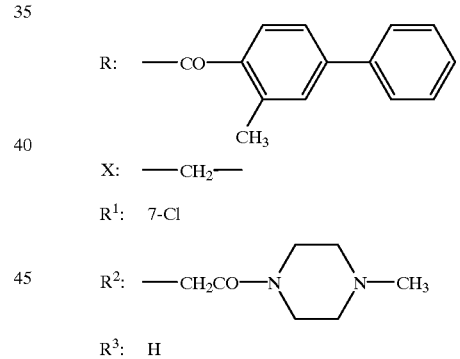

X: —CH₂—

R¹: 7-Cl

R²: —CH₂CO—N⌒N—CH₃

R³: H

Crystalline form: Colorless amorphous
Form: Hydrochloride

EXAMPLE 272

Structure

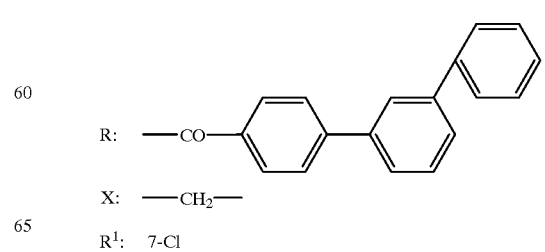

X: —CH₂—

R¹: 7-Cl

-continued

R²: —CH₂CONHC₂H₅

R³: H

Crystalline form: Colorless amorphous

Form: Free

EXAMPLE 273

Structure

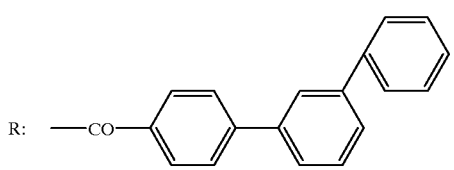

R: —CO—

X: —CH₂—

R¹: 7-Cl

R²: —CH₂CO—N⟨piperazine⟩N—CH₃

R³: H

Crystalline form: Colorless amorphous

Form: Hydrochloride

EXAMPLE 274

Structure

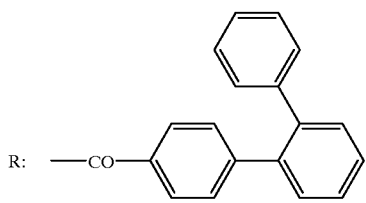

R: —CO—

X: —CH₂—

R¹: 7-Cl

R²: —CH₂—N⟨piperazine⟩N—C₂H₅

R³: H

Crystalline form: Colorless amorphous

Form: Hydrochloride

EXAMPLE 275

Structure

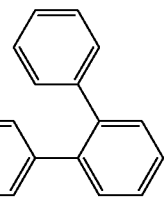

R: —CO—

X: —CH₂—

R¹: 7-Cl

R²: —CH₂—N⟨piperazine⟩N—CH₃

R³: H

Crystalline form: Colorless amorphous
Form: Hydrochloride

EXAMPLE 276

Structure

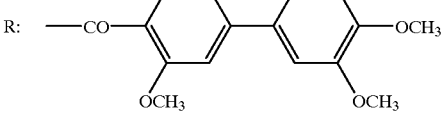

X: —CH₂—

R¹: 7-Cl

R²: —CH₂CO—N(CH₃)((CH₂)₂N(C₂H₅)₂)

R³: H

Crystalline form: Colorless amorphous
Form: Hydrochloride

EXAMPLE 277

Structure

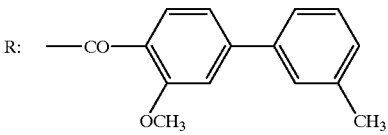

X: —CH₂—

R¹: 7-Cl

R²: —CH₂CO—N(CH₃)((CH₂)₂N(C₂H₅)₂)

R³: H

Crystalline form: Colorless amorphous
Form: Hydrochloride

EXAMPLE 278

Structure

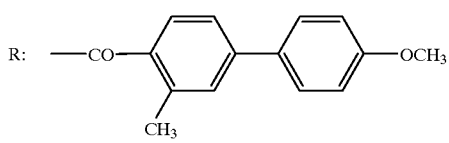

X: —CH₂—

R¹: H

R²: 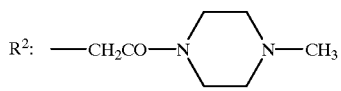

R³: H

Crystalline form: Colorless amorphous
Form: Hydrochloride

EXAMPLE 279

Structure

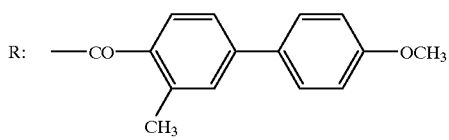

X: —CH₂—

R¹: H

R²: 

R³: H

Crystalline form: Colorless amorphous
Form: Free

EXAMPLE 280

Structure

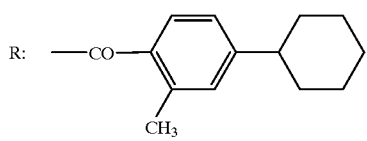

X: —CH₂—

R¹: H

R²: 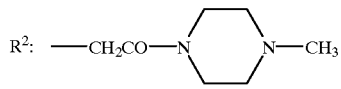

R³: H

Crystalline form: White powder
Solvent for recrystallization: Ethanol/n-hexane
M.p. 218–221° C.
Form: Hydrochloride

EXAMPLE 281

Structure

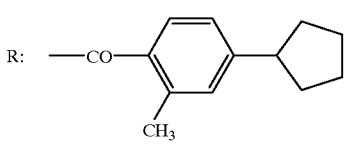

X: —CH₂—

R¹: H

R²: 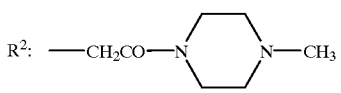

R³: H

Crystalline form: White powder
Solvent for recrystallization: Ethanol/diethyl ether
M.p. 214–217° C.
Form: Hydrochloride

EXAMPLE 282

Structure

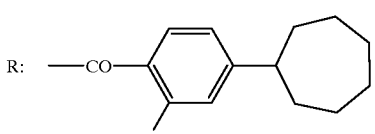

X: —CH₂—

R¹: H

R²: 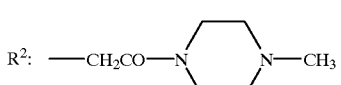

R³: H

Crystalline form: White powder
Solvent for recrystallization: Ethanol/diethyl ether
M.p. 204–206° C.
Form: Hydrochloride

EXAMPLE 283

Structure

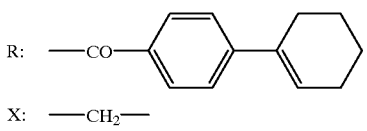

X: —CH₂—

R¹: 7-Cl

R²: —CH₂CONHCH₃

R³: H

Crystalline form: Colorless amorphous
Form: Free

EXAMPLE 284

Structure

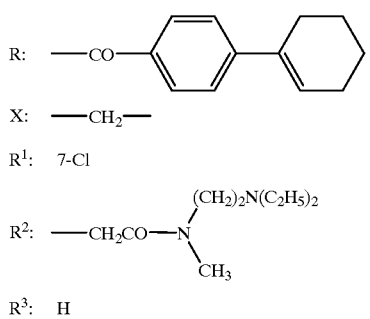

R: —CO—⟨aryl-cyclohexenyl⟩

X: —CH$_2$—

R$^1$: 7-Cl

R$^2$: —CH$_2$CO—N(CH$_2$)$_2$N(C$_2$H$_5$)$_2$ / CH$_3$

R$^3$: H

Crystalline form: Colorless amorphous
Form: Hydrochloride

EXAMPLE 285

Structure

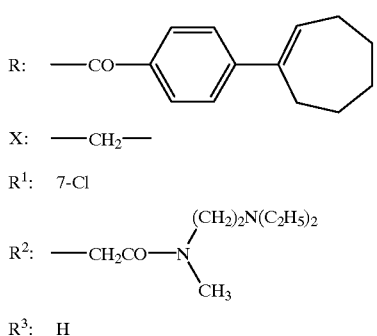

R: —CO—⟨aryl-cycloheptenyl⟩

X: —CH$_2$—

R$^1$: 7-Cl

R$^2$: —CH$_2$CO—N(CH$_2$)$_2$N(C$_2$H$_5$)$_2$ / CH$_3$

R$^3$: H

Crystalline form: Colorless amorphous
Form: Hydrochloride

EXAMPLE 286

Structure

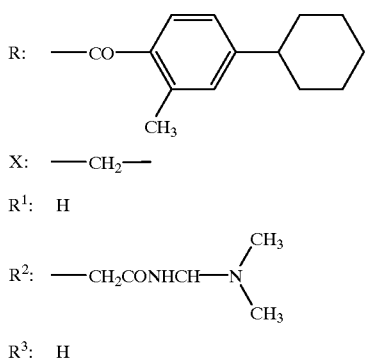

R: —CO—⟨aryl-cyclohexyl⟩ with CH$_3$

X: —CH$_2$—

R$^1$: H

R$^2$: —CH$_2$CONHCH—N(CH$_3$)$_2$ / CH$_3$

R$^3$: H

Crystalline form: Colorless amorphous
Form: Free

EXAMPLE 287

Structure

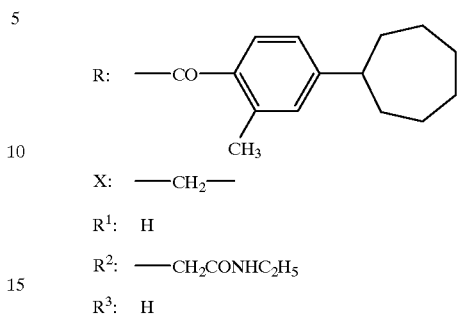

R: —CO—⟨aryl-cycloheptyl⟩ with CH$_3$

X: —CH$_2$—

R$^1$: H

R$^2$: —CH$_2$CONHC$_2$H$_5$

R$^3$: H

Crystalline form: Colorless amorphous
Form: Free

EXAMPLE 288

Structure

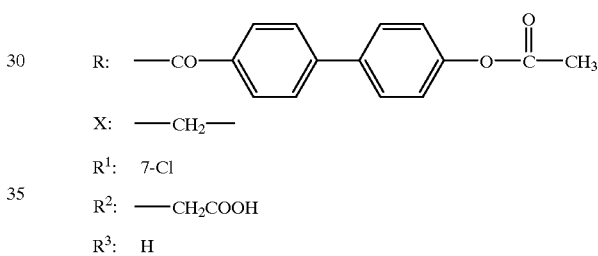

R: —CO—⟨biphenyl⟩—O—C(O)CH$_3$

X: —CH$_2$—

R$^1$: 7-Cl

R$^2$: —CH$_2$COOH

R$^3$: H

Crystalline form: Colorless amorphous
Form: Free

EXAMPLE 289

Structure

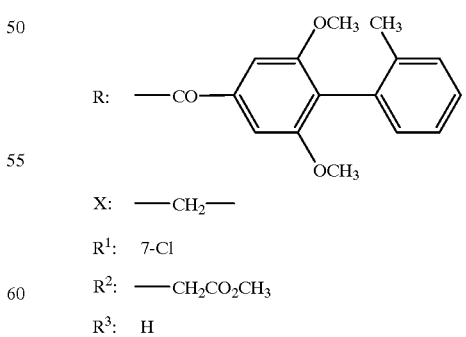

R: —CO—⟨aryl with OCH$_3$, CH$_3$, OCH$_3$, and phenyl⟩

X: —CH$_2$—

R$^1$: 7-Cl

R$^2$: —CH$_2$CO$_2$CH$_3$

R$^3$: H

Crystalline form: Colorless amorphous
Form: Free

EXAMPLE 290

Structure

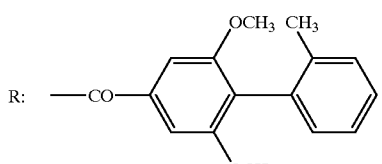

X: —CH₂—

R¹: 7-Cl

R²: —CH₂COOH

R³: H

Crystalline form: White powder
Solvent for recrystallization: Methanol/diethyl ether
M.p. 240–242° C.
Form: Free

EXAMPLE 291

Structure

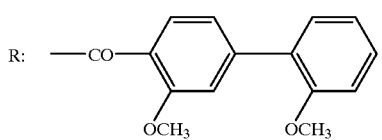

X: —CH₂—

R¹: 7-Cl

R²: —CH₂CO₂CH₃

R³: H

Crystalline form: Colorless amorphous
Form: Free

EXAMPLE 292

Structure

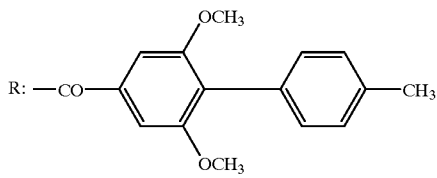

X: —CH₂—    R¹: 7-Cl

R²: —CH₂CO₂CH₃

R³: H

Crystalline form: Colorless amorphous
Form: Free

EXAMPLE 293

Structure

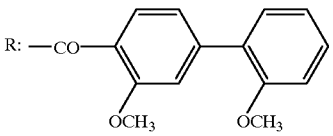

X: —CH₂—    R¹: 7-Cl

R²: —CH₂COOH

R³: H

Crystalline form: Colorless amorphous
Form: Free

EXAMPLE 294

Structure

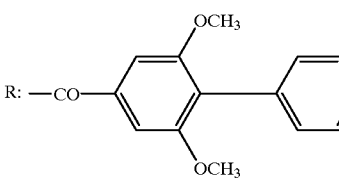

X: —CH₂—    R¹: 7-Cl

R²: —CH₂COOH

R³: H

Crystalline form: Colorless amorphous
Form: Free

EXAMPLE 295

Structure

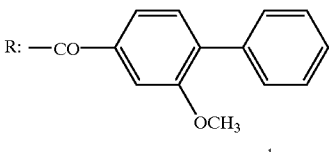

X: —CH₂—    R¹: 7-Cl

R²: —CH₂CO₂CH₃

R³: H

Crystalline form: Colorless amorphous
Form: Free

EXAMPLE 296

Structure

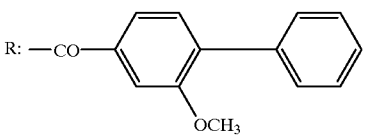

-continued
X: —CH₂—   R¹: 7-Cl
R²: —CH₂COOH
R³: H

Crystalline form: Colorless amorphous
Form: Free

EXAMPLE 297

Structure

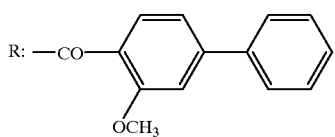

X: —CH₂—   R¹: 7-Cl
R²: —CH₂CO₂CH₃
R³: H

Crystalline form: Colorless amorphous
Form: Free

EXAMPLE 298

Structure

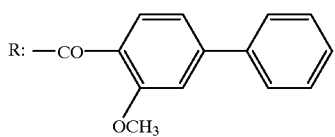

X: —CH₂—   R¹: 7-Cl
R²: —CH₂COOH
R³: H

Crystalline form: Colorless amorphous
Form: Free

EXAMPLE 299

Structure

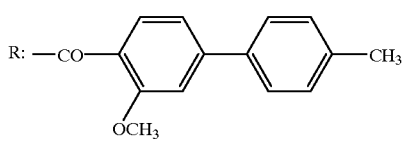

X: —CH₂—   R¹: 7-Cl
R²: —CH₂CO₂CH₃
R³: H

Crystalline form: Colorless amorphous
Form: Free

EXAMPLE 300

Structure

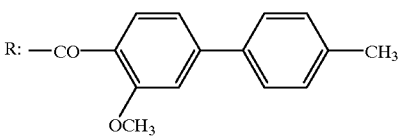

X: —CH₂—   R¹: 7-Cl
R²: —CH₂COOH
R³: H

Crystalline form: Colorless amorphous
Form: Free

EXAMPLE 301

Structure

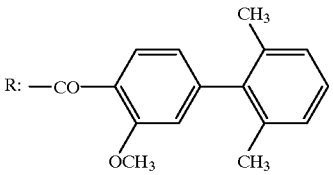

X: —CH₂—   R¹: 7-Cl
R²: —CH₂CO₂CH₃
R³: H

Crystalline form: Colorless amorphous
Form: Free

EXAMPLE 302

Structure

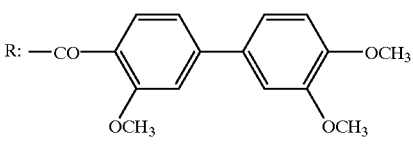

X: —CH₂—   R¹: 7-Cl
R²: —CH₂CO₂CH₃
R³: H

Crystalline form: Coloreless amorphous
Form: Free

EXAMPLE 303

Structure

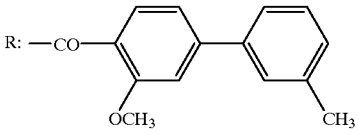

-continued
X: —CH₂—   R¹: 7-Cl
R²: —CH₂CO₂CH₃
R³: H

Crystalline form: Colorless amorphous
Form: Free

EXAMPLE 304
Structure

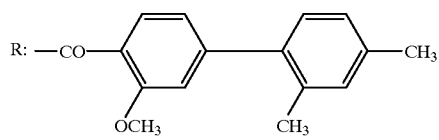

X: —CH₂—   R¹: 7-Cl
R²: —CH₂CO₂CH₃
R³: H

Crystalline form: Colorless amorphous
Form: Free

EXAMPLE 305
Structure

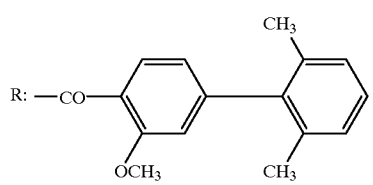

X: —CH₂—   R¹: 7-Cl
R²: —CH₂COOH
R³: H

Crystalline form: Colorless prisms
Solvent for recrystallization: Acetone/n-hexane
M.p. 251–253° C.
Form: Free

EXAMPLE 306
Structure

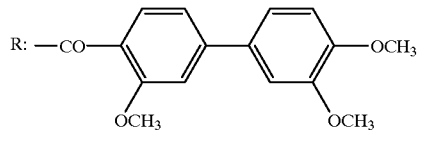

X: —CH₂—   R¹: 7-Cl
R²: —CH₂COOH
R³: H

Crystalline form: White powder
Solvent for recrystallization: Acetone/n-hexane
M.p. 128–131° C.
Form: Free

EXAMPLE 307
Structure

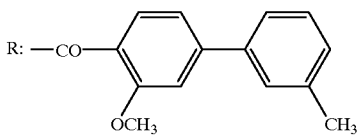

X: —CH₂—   R¹: 7-Cl
R²: —CH₂COOH
R³: H

Crystalline form: Colorless amorphous
Form: Free

EXAMPLE 308
Structure

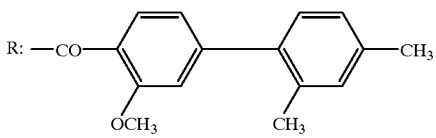

X: —CH₂—   R¹: 7-Cl
R²: —CH₂COOH
R³: H

Crystalline form: Colorless prisms
Solvent for recrsytallization: Ethanol
M.p. 224–225° C.
Form: Free

EXAMPLE 309
Structure

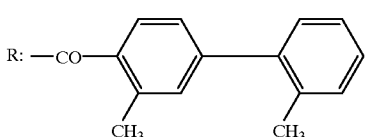

X: —CH₂—   R¹: 7-Cl
R²: —CH₂CO₂CH₃
R³: H

Crystalline form: Colorless amorphous
Form: Free

EXAMPLE 310

Structure

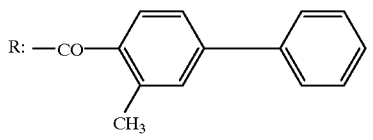

X: —CH$_2$—    R$^1$: 7-Cl
R$^2$: —CH$_2$CO$_2$CH$_3$
R$^3$: H

Crystalline form: Colorless amorphous
Form: Free

EXAMPLE 311

Structure

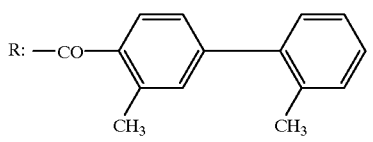

X: —CH$_2$—    R$^1$: 7-Cl
R$^2$: —CH$_2$COOH
R$^3$: H

Crystalline form: Colorless amorphous
Form: Free

EXAMPLE 312

Structure

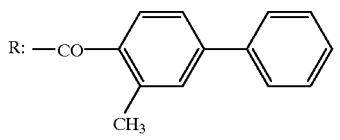

X: —CH$_2$—    R$^1$: 7-Cl
R$^2$: —CH$_2$COOH
R$^3$: H

Crystalline form: Colorless amorphous
Form: Free

EXAMPLE 313

Structure


X: —CH$_2$—    R$^1$: 7-Cl
R$^2$: —CH$_2$CO$_2$CH$_3$

-continued

R$^3$: H

Crystalline form: Colorless amorphous
Form: Free

EXAMPLE 314

Structure

X: —CH$_2$—
R$^2$: —CH$_2$CO$_2$CH$_3$
R$^3$: H
R$^1$: 7-Cl

Crystalline form: Colorless amorphous
Form: Free

EXAMPLE 315

Structure


X: —CH$_2$—
R$^2$: —CH$_2$CO$_2$CH$_3$
R$^3$: H
R$^1$: 7-Cl

Crystalline form: White powder
Form: Free

EXAMPLE 316

Structure


X: —CH$_2$—
R$^2$: —CH$_2$COOH
R$^3$: H
R$^1$: 7-Cl

Crystalline form: Colorless prisms
Solvent for recrystallization: Acetone/n-hexane
M.p. 124–128° C.
Form: Free

EXAMPLE 317

Structure

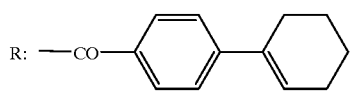

X: —CH$_2$—
R$^2$: —CH$_2$COOH
R$^3$: H
R$^1$: 7-Cl

Crystalline form: White powder

Form: Free

EXAMPLE 318

Structure

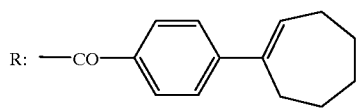

X: —CH$_2$—
R$^2$: —CH$_2$COOH
R$^3$: H
R$^1$: 7-Cl

Crystalline form: Colorless amorphous

Form: Free

EXAMPLE 319

Structure

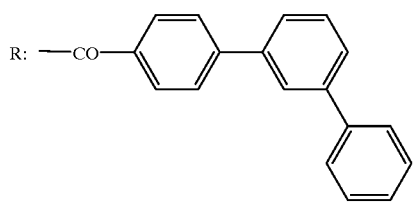

X: —CH$_2$—
R$^2$: —CH$_2$CO$_2$CH$_3$
R$^3$: H
R$^1$: 7-Cl

Crystalline form: Colorless amorphous

Form: Free

EXAMPLE 320

Structure

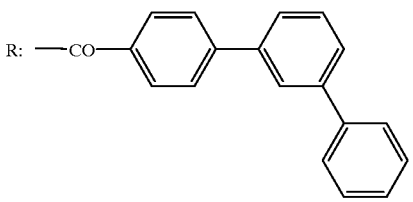

X: —CH$_2$—
R$^2$: —CH$_2$COOH
R$^3$: H
R$^1$: 7-Cl

Crystalline form: Colorless amorphous

Form: Free

EXAMPLE 321

Structure

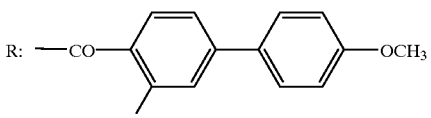

X: —CH$_2$—
R$^2$: —CH$_2$CO$_2$CH$_3$
R$^3$: H
R$^1$: H

Crystalline form: Colorless amorphous

Form: Free

EXAMPLE 322

Structure

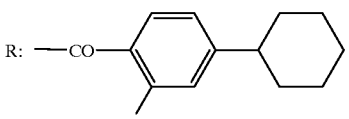

X: —CH$_2$—
R$^2$: —CH$_2$CO$_2$CH$_3$
R$^3$: H
R$^1$: H

Crystalline form: Colorless amorphous

Form: Free

EXAMPLE 323

Structure

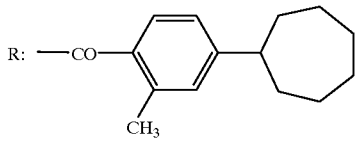

X: —CH$_2$—
R$^2$: —CH$_2$CO$_2$CH$_3$
R$^3$: H
R$^1$: H

Crystalline form: Colorless amorphous

Form: Free

EXAMPLE 324

Structure

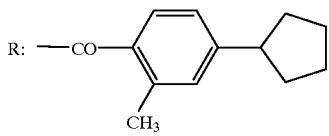

X: —CH$_2$—
R$^2$: —CH$_2$CO$_2$CH$_3$
R$^3$: H
R$^1$: H

Crystalline form: Colorless amorphous

Form: Free

EXAMPLE 325

Structure

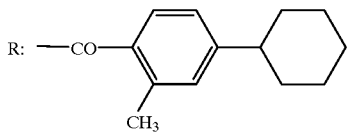

X: —CH$_2$—
R$^2$: —CH$_2$COOH
R$^3$: H
R$^1$: H

Crystalline form: Colorless amorphous

Form: Free

EXAMPLE 326

Structure

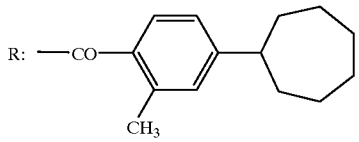

X: —CH$_2$—
R$^2$: —CH$_2$COOH
R$^3$: H
R$^1$: 7-Cl

Crystalline form: Colorless amorphous

Form: Free

EXAMPLE 327

Structure

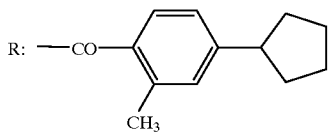

X: —CH$_2$—
R$^2$: —CH$_2$COOH
R$^3$: H
R$^1$: 7-Cl

Crystalline form: Colorless amorphous

Form: Free

EXAMPLE 328

Structure

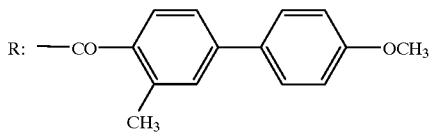

X: —CH$_2$—
R$^2$: —CH$_2$COOH
R$^3$: H
R$^1$: H

Crystalline form: Colorless amorphous

Form: Free

EXAMPLE 329

Structure

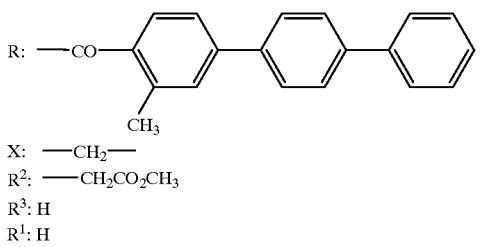

X: —CH$_2$—
R$^2$: —CH$_2$CO$_2$CH$_3$
R$^3$: H
R$^1$: H

Crystalline form: Colorless amorphous

Form: Free

EXAMPLE 330

Structure

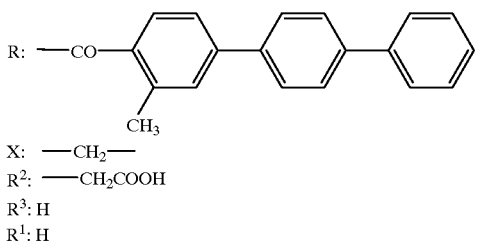

X: —CH$_2$—
R$^2$: —CH$_2$COOH
R$^3$: H
R$^1$: H

Crystalline form: White powder

Solvent for recrystallization: Acetone/n-hexane

M.p. 203–204° C.

Form: Free

EXAMPLE 331

Structure

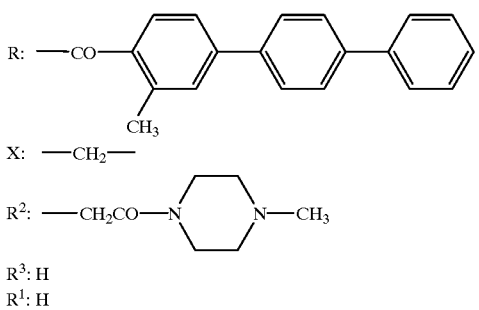

X: —CH$_2$—

R$^2$: —CH$_2$CO—N⌒N—CH$_3$

R$^3$: H
R$^1$: H

Crystalline form: White powder

Solvent for recrystallization: Acetone/n-hexane

M.p. 255–258° C.

Form: Hydrochloride

EXAMPLE 332

Structure

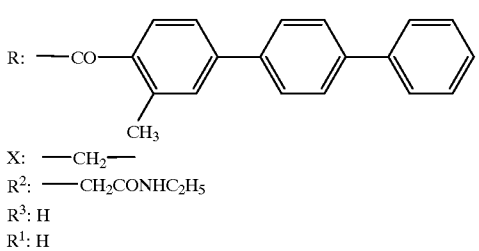

X: —CH$_2$—
R$^2$: —CH$_2$CONHC$_2$H$_5$
R$^3$: H
R$^1$: H

Crystalline form: Colorless amorphous

Form: Free

EXAMPLE 333

Structure

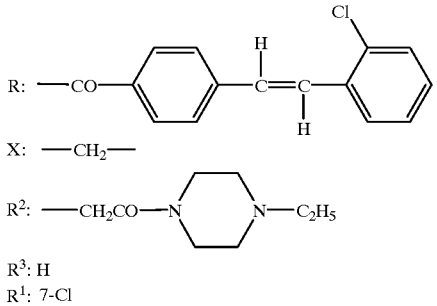

X: —CH$_2$—

R$^2$: —CH$_2$CO—N⌒N—C$_2$H$_5$

R$^3$: H
R$^1$: 7-Cl

Crystalline form: Colorless oil

Form: Free

EXAMPLE 334

Structure

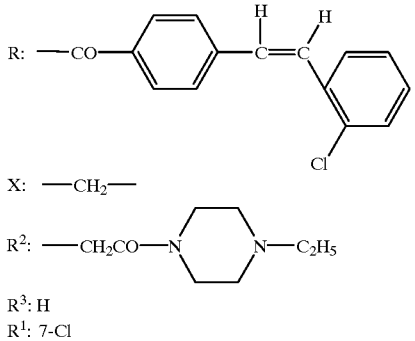

X: —CH$_2$—

R$^2$: —CH$_2$CO—N⌒N—C$_2$H$_5$

R$^3$: H
R$^1$: 7-Cl

Crystalline form: Colorless amorphous

Form: Hydrochloride

EXAMPLE 335
Structure

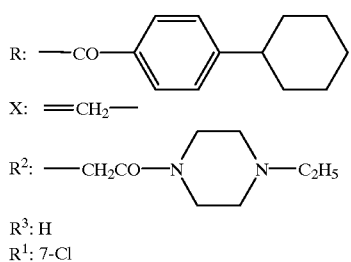

R³: H
R¹: 7-Cl

Crystalline form: Colorless amorphous
Form: Hydrochloride

EXAMPLE 336
Structure

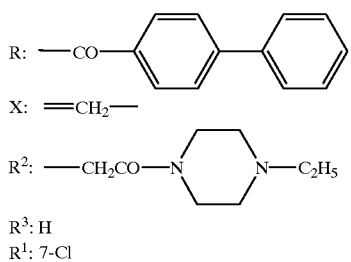

R³: H
R¹: 7-Cl

Crystalline form: Colorless amorphous
Form: Hydrochloride

EXAMPLE 337
Structure

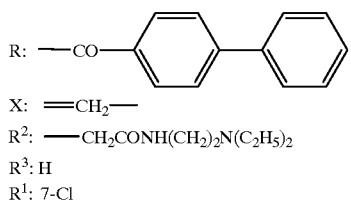

R³: H
R¹: 7-Cl

Crystalline form: Colorless amorphous
Form: Free

EXAMPLE 338
Structure

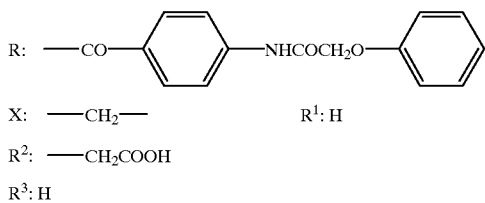

Crystalline form: White powder
M.p. 102–106° C.
Form: Free

EXAMPLE 339
Structure

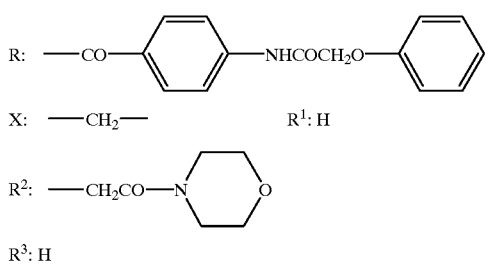

R³: H

Crystalline form: Colorless amorphous
Form: Free

EXAMPLE 340
Structure

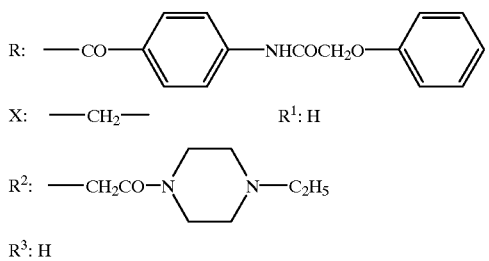

R³: H

Crystalline form: Colorless amorphous
Form: Hydrochloride

EXAMPLE 341
Structure

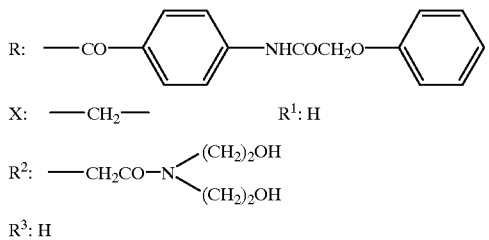

R³: H

Crystalline form: Colorless amorphous
Form: Free

EXAMPLE 342
Structure

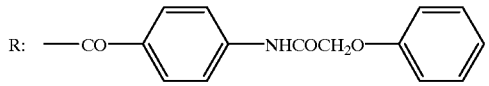

-continued

X: —CH$_2$—  R$^1$: H

R$^2$: 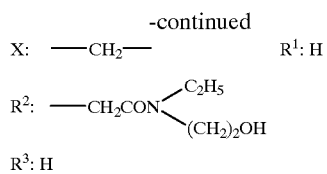

R$^3$: H

Crystalline form: Colorless amorphous
Form: Free

EXAMPLE 301

Structure

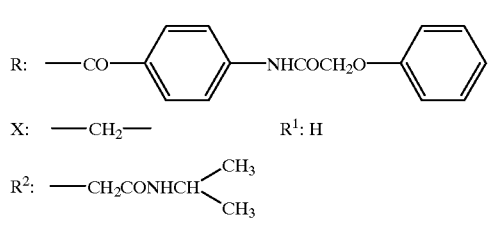

R$^3$: H

Crystalline form: Colorless needles
Solvent for recrystallization: Dichloromethane/ethanol/diethyl ether
M.p. 190–193° C.
Form: Free

EXAMPLE 344

Structure

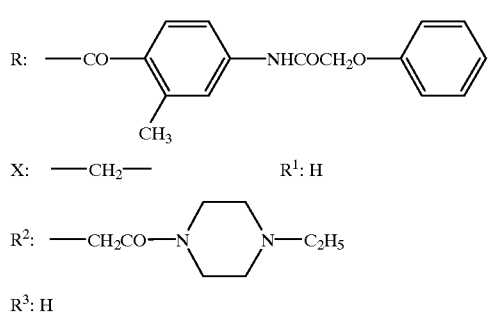

R$^3$: H

Crystalline form: Coloreless oil
Form: Free

EXAMPLE 345

Structure

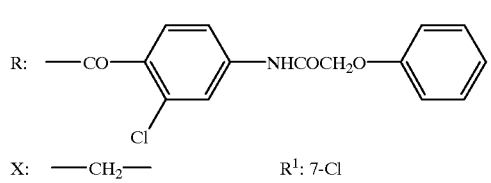

-continued

R$^2$: 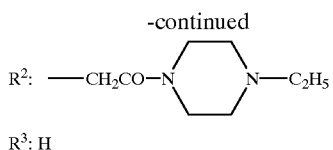

R$^3$: H

Crystalline form: Colorless viscous oil
Form: Free

EXAMPLE 346

Structure

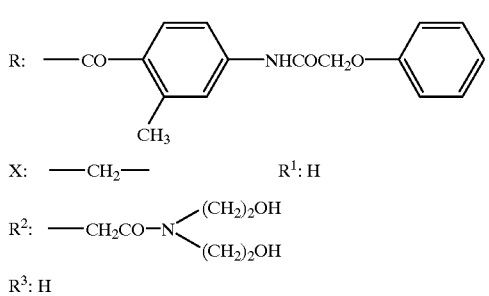

R$^3$: H

Crystalline form: Colorless amorphous
Form: Free

EXAMPLE 347

Structure

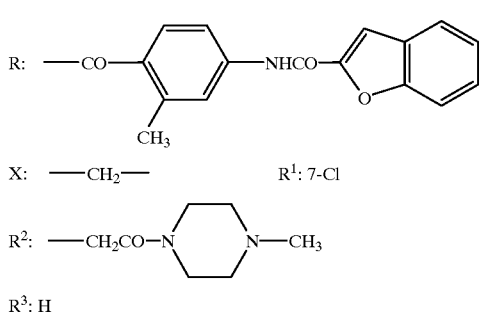

R$^3$: H

Crystalline form: White powder
Solvent for recrystallization: Dichloromethane/diethyl ether
M.p. 180–182° C.
Form: Free

EXAMPLE 348

Structure

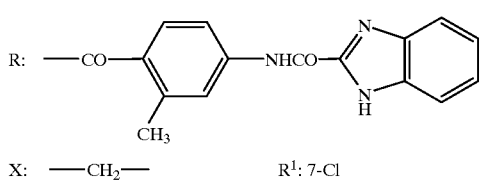

-continued

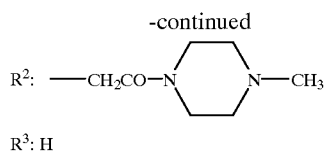

R³: H

Crystalline form: Yellow powder
Solvent for recrystallization: Ethanol/dichloromethane/diethyl ether
M.p. 239–241° C.
Form: Free

EXAMPLE 349

Structure

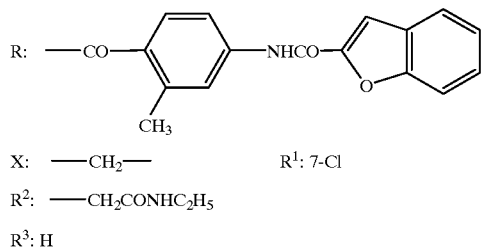

X: —CH₂—     R¹: 7-Cl
R²: —CH₂CONHC₂H₅
R³: H

Crystalline form: Colorless prisms
Solvent for recrystallization: Dichloromethane/ethanol/diethyl ether
M.p. 252–254° C.
Form: Free

EXAMPLE 350

Structure

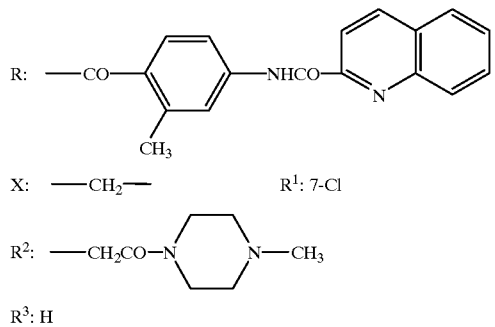

X: —CH₂—     R¹: 7-Cl

R²: —CH₂CO—N(piperazine)—CH₃

R³: H

Crystalline form: Colorless viscous oil
Form: Free

EXAMPLE 309

Structure

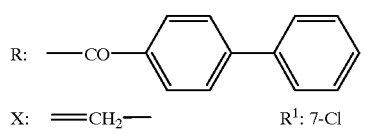

X: =CH₂—     R¹: 7-Cl

-continued

R²: —CH₂CO₂C₂H₅
R³: H

Crystalline form: Pale yellow powder
M.p. 71–75° C.
Form: Free

EXAMPLE 352

Structure

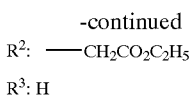

X: =CH—     R¹: 7-Cl
R²: —CH₂CO₂C₂H₅
R³: H

Crystalline form: Pale yellow oil
Form: Free

EXAMPLE 353

Structure

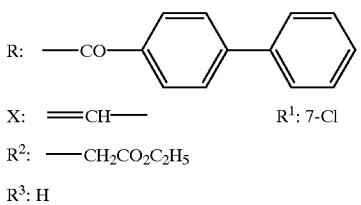

X: =CH—     R¹: 7-Cl
R²: —CH₂COOH
R³: H

Crystalline form: White powder
Form: Free

EXAMPLE 354

Structure

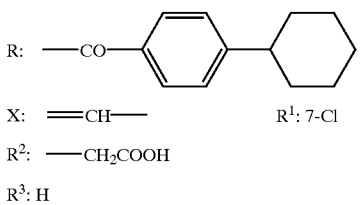

X: =CH—     R¹: 7-Cl
R²: —CH₂COOH
R³: H

Crystalline form: White powder
Form: Free

EXAMPLE 355

Structure

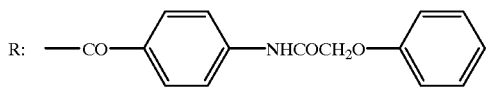

R³: H

Crystalline form: White powder
M.p. 63–69° C.
Form: Free

EXAMPLE 356

Structure

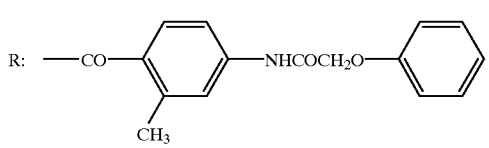

R³: H

Crystalline form: White powder
Form: Free

EXAMPLE 357

Structure

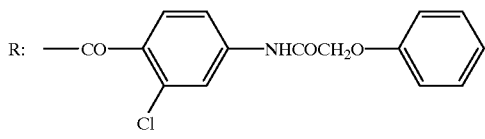

R³: H

Crystalline form: Pale yellow powder
Form: Free

EXAMPLE 358

Structure

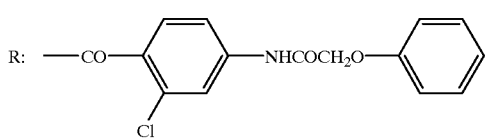

R³: H

Crystalline form: Colorless viscous oil
Form: Free

EXAMPLE 359

Structure

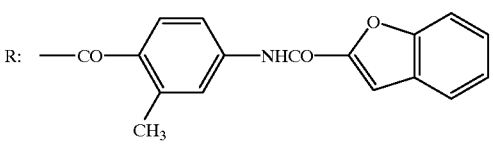

R³: H

Crystalline form: Colorless viscous oil

Form: Free

EXAMPLE 360

Structure

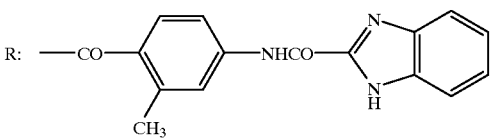

R³: H

Crystalline form: Colorless viscous oil

Form: Free

EXAMPLE 361

Structure

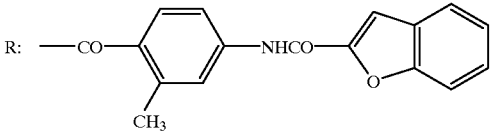

R³: H

Crystalline form: Colorless amorphous

Form: Free

EXAMPLE 362

Structure

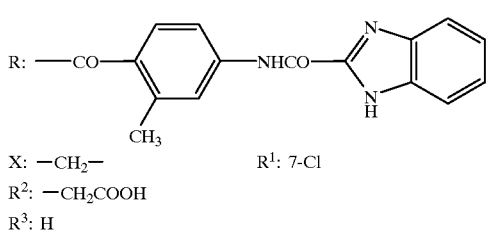

X: —CH$_2$—  R$^1$: 7-Cl
R$^2$: —CH$_2$COOH
R$^3$: H

Crystalline form: Colorless amorphous
Form: Free

EXAMPLE 363

Structure

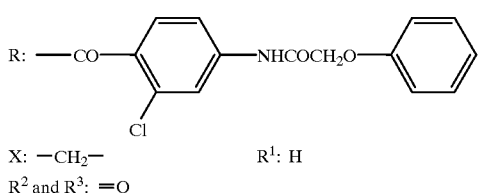

X: —CH$_2$—  R$^1$: H
R$^2$ and R$^3$: =O

Crystalline form: Pale yellow amorphous
Form: Free

EXAMPLE 364

Structure

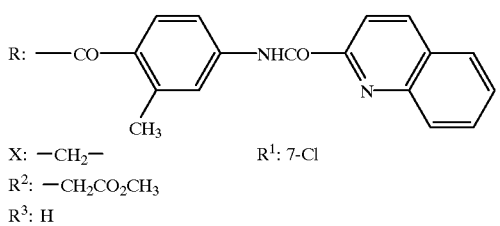

X: —CH$_2$—  R$^1$: 7-Cl
R$^2$: —CH$_2$CO$_2$CH$_3$
R$^3$: H

Crystalline form: Pale yellow powder
Solvent for recrystallization: Dichloromethane/methanol/diethyl ether
M.p. 194–197° C.
Form: Free

EXAMPLE 365

Structure

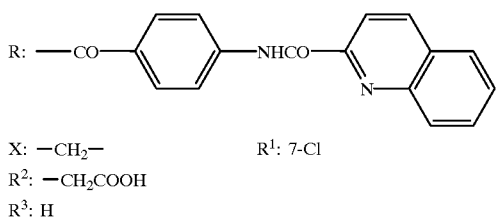

X: —CH$_2$—  R$^1$: 7-Cl
R$^2$: —CH$_2$COOH
R$^3$: H

Crystalline form: White powder
Form: Free

EXAMPLE 366

Structure

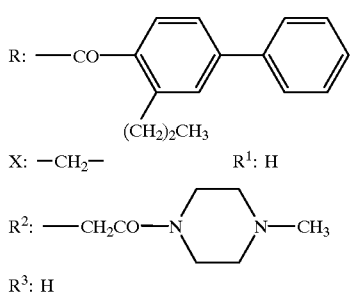

X: —CH$_2$—  R$^1$: H
R$^2$: —CH$_2$CO—N(piperazine)N—CH$_3$
R$^3$: H

Crystalline form: Colorless amorphous
Form: Free

EXAMPLE 367

Structure

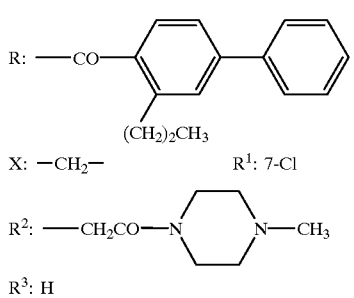

X: —CH$_2$—  R$^1$: 7-Cl
R$^2$: —CH$_2$CO—N(piperazine)N—CH$_3$
R$^3$: H

Crystalline form: Colorless amorphous
Form: Free

EXAMPLE 368

Structure

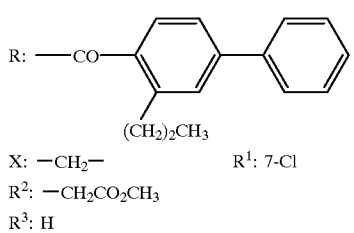

X: —CH$_2$—  R$^1$: 7-Cl
R$^2$: —CH$_2$CO$_2$CH$_3$
R$^3$: H

Crystalline form: White powder
Solvent for recrystallization: n-Hexane/ethyl acetate
M.p. 134–136° C.
Form: Free

EXAMPLE 369
Structure

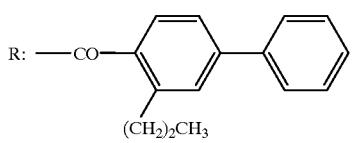

X: —CH$_2$—   R$^1$: H
R$^2$: —CH$_2$CO$_2$CH$_3$
R$^3$: H

Crystalline form: White powder
Solvent for recrystallization: n-Hexane/ethyl acetate
M.p. 97–100° C.
Form: Free

EXAMPLE 370
Structure

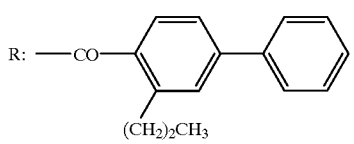

X: —CH$_2$—   R$^1$: H
R$^2$: —CH$_2$COOH
R$^3$: H

Crystalline form: Colorless amorphous
Form: Free

EXAMPLE 371
Structure

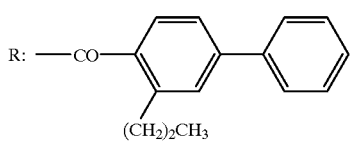

X: —CH$_2$—   R$^1$: 7-Cl
R$^2$: —CH$_2$COOH
R$^3$: H

Crystalline form: Colorless amorphous
Form: Free

EXAMPLE 372
Structure

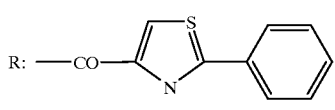

X: —CH$_2$—   R$^1$: 7-Cl
R$^2$: —CH$_2$CO$_2$CH$_3$
R$^3$: H

Crystalline form: Colorless needles
Solvent for recrystallization: Diethyl ether/n-hexane
M.p. 135–138° C.
Form: Free

EXAMPLE 373
Structure

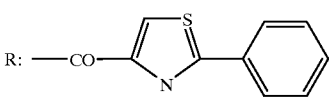

X: —CH$_2$—   R$^1$: 7-Cl
R$^2$: —CH$_2$COOH
R$^3$: H

Crystalline form: White powder

Solvent for recrystallization: Ethyl acetate

M.p. 136–139° C.

Form: Free

EXAMPLE 374

Structure

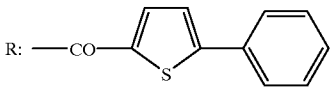

X: —CH$_2$—   R$^1$: 7-Cl
R$^2$: —CH$_2$CO$_2$CH$_3$
R$^3$: H

Crystalline form: White powder

Solvent for recrystallization: Diethyl ether/ethyl acetate

M.p. 143–145° C.

Form: Free

EXAMPLE 375

Structure

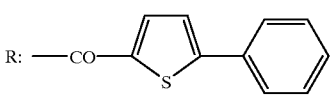

X: —CH$_2$—   R$^1$: 7-Cl
R$^2$: —CH$_2$COOH
R$^3$: H

Crystalline form: Colorless amorphous

Form: Free

EXAMPLE 376

Structure

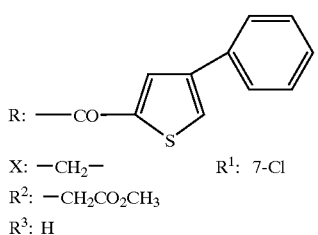

X: —CH$_2$—  R$^1$: 7-Cl
R$^2$: —CH$_2$CO$_2$CH$_3$
R$^3$: H

Crystalline form: White powder

Solvent for recrystallization: Diethyl ether/ethyl acetate

M.p. 123–125° C.

Form: Free

EXAMPLE 377

Structure

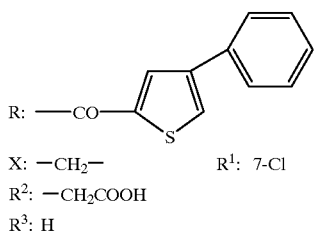

X: —CH$_2$—  R$^1$: 7-Cl
R$^2$: —CH$_2$COOH
R$^3$: H

Crystalline form: Colorless amorphous

Form: Free

EXAMPLE 378

Structure

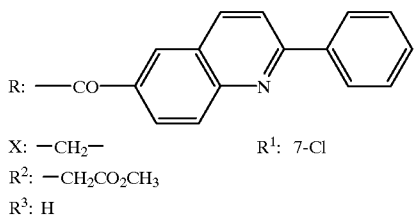

X: —CH$_2$—  R$^1$: 7-Cl
R$^2$: —CH$_2$CO$_2$CH$_3$
R$^3$: H

Crystalline form: White powder

Solvent for recrystallization: n-Hexane/ethyl acetate

M.p. 164–166° C.

Form: Free

EXAMPLE 379

Structure

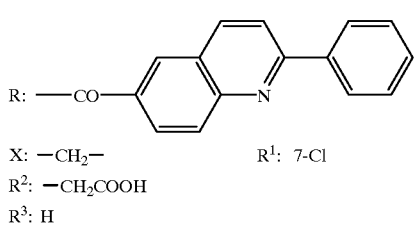

X: —CH$_2$—  R$^1$: 7-Cl
R$^2$: —CH$_2$COOH
R$^3$: H

Crystalline form: Colorless amorphous

Form: Free

EXAMPLE 380

Structure

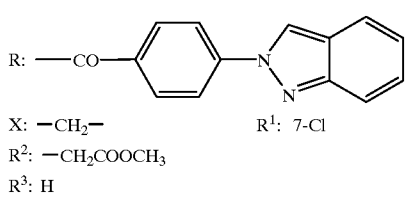

X: —CH$_2$—  R$^1$: 7-Cl
R$^2$: —CH$_2$COOCH$_3$
R$^3$: H

Crystalline form: White powder

Solvent for recrystallization: n-Hexane/ethyl acetate

M.p. 168–170° C.

Form: Free

EXAMPLE 381

Structure

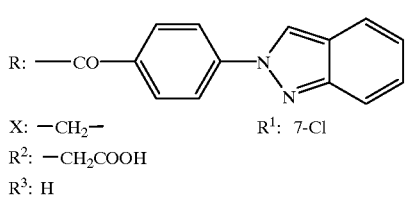

X: —CH$_2$—  R$^1$: 7-Cl
R$^2$: —CH$_2$COOH
R$^3$: H

Crystalline form: White powder

Solvent for recrystallization: Dichloromethane/n-hexane

M.p. 226–229° C.

Form: Free

EXAMPLE 382

Structure

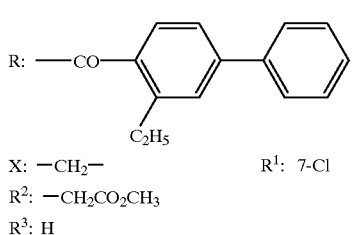

X: —CH$_2$—   R$^1$: 7-Cl
R$^2$: —CH$_2$CO$_2$CH$_3$
R$^3$: H

Crystalline form: White powder

Solvent for recrystallization: n-Hexane/ethyl acetate

M.p. 131–134° C.

Form: Free

EXAMPLE 383

Structure

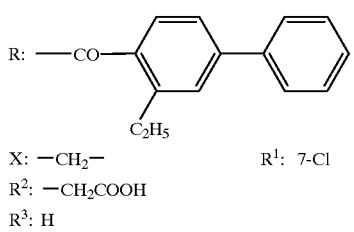

X: —CH$_2$—   R$^1$: 7-Cl
R$^2$: —CH$_2$COOH
R$^3$: H

Crystalline form: Colorless amorphous

Form: Free

EXAMPLE 384

Structure

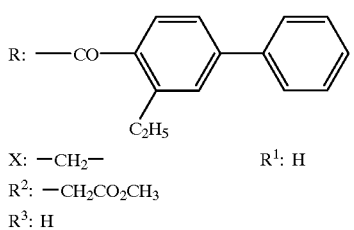

X: —CH$_2$—   R$^1$: H
R$^2$: —CH$_2$CO$_2$CH$_3$
R$^3$: H

Crystalline form: Pale yellow powder

Solvent for recrystallization: n-Hexane/ethyl acetate

M.p. 133–134.5° C.

Form: Free

EXAMPLE 385

Structure

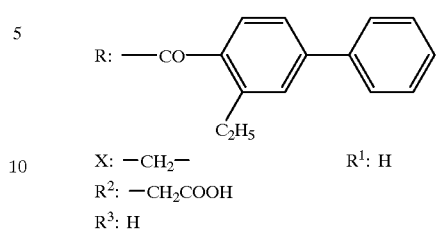

X: —CH$_2$—   R$^1$: H
R$^2$: —CH$_2$COOH
R$^3$: H

Crystalline form: Colorless amorphous
Form: Free

EXAMPLE 386

Structure

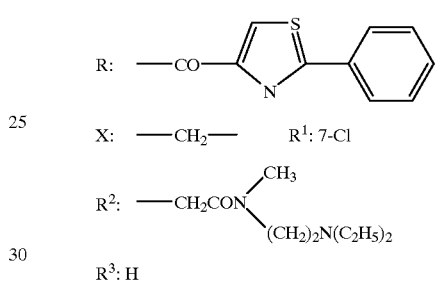

X: —CH$_2$—   R$^1$: 7-Cl

R$^2$: —CH$_2$CON(CH$_3$)(CH$_2$)$_2$N(C$_2$H$_5$)$_2$

R$^3$: H

Crystalline form: Colorless viscous oil
Form: Free

EXAMPLE 387

Structure

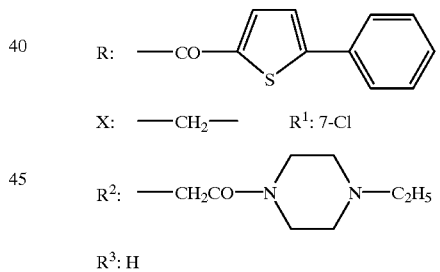

X: —CH$_2$—   R$^1$: 7-Cl

R$^2$: —CH$_2$CO—N(piperazine)N—C$_2$H$_5$

R$^3$: H

Crystalline form: Colorless amorphous
Form: Free

EXAMPLE 388

Structure

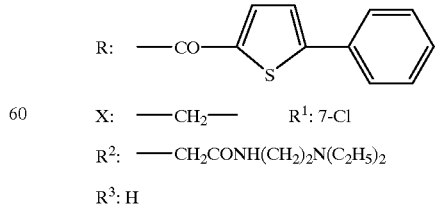

X: —CH$_2$—   R$^1$: 7-Cl
R$^2$: —CH$_2$CONH(CH$_2$)$_2$N(C$_2$H$_5$)$_2$
R$^3$: H

Crystalline form: Colorless amorphous
Form: Free

EXAMPLE 389

Structure

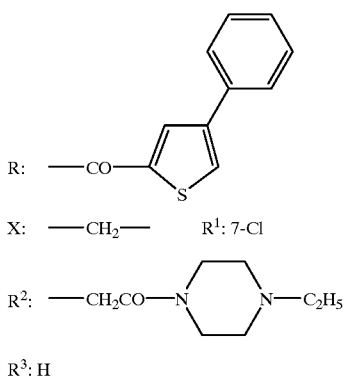

R: —CO—
X: —CH₂—  R¹: 7-Cl
R²: —CH₂CO—N(piperazine)—C₂H₅
R³: H

Crystalline form: Colorless amorphous
Form: Free

EXAMPLE 390

Structure

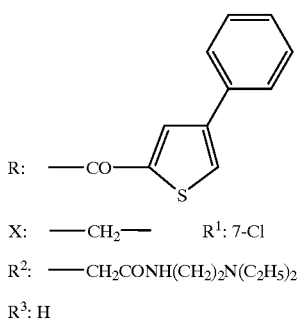

R: —CO—
X: —CH₂—  R¹: 7-Cl
R²: —CH₂CONH(CH₂)₂N(C₂H₅)₂
R³: H

Crystalline form: Colorless amorphous
Form: Free

EXAMPLE 391

Structure

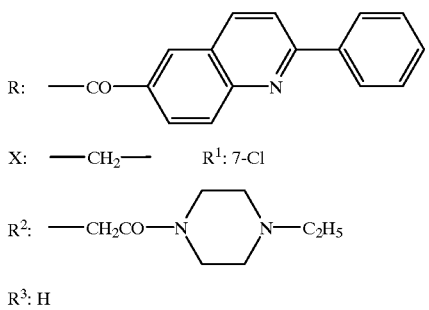

R: —CO—
X: —CH₂—  R¹: 7-Cl
R²: —CH₂CO—N(piperazine)—C₂H₅
R³: H

Crystalline form: Colorless amorphous
Form: Free

EXAMPLE 392

Structure

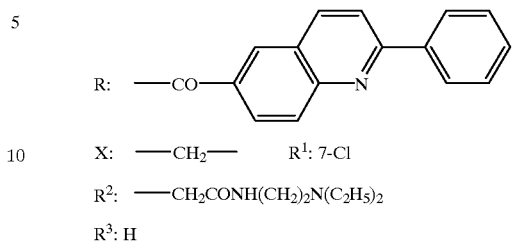

R: —CO—
X: —CH₂—  R¹: 7-Cl
R²: —CH₂CONH(CH₂)₂N(C₂H₅)₂
R³: H

Crystalline form: Colorless amorphous
Form: Free

EXAMPLE 393

Structure

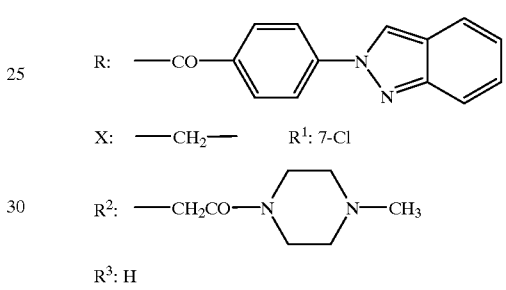

R: —CO—
X: —CH₂—  R¹: 7-Cl
R²: —CH₂CO—N(piperazine)—CH₃
R³: H

Crystalline form: Colorless amorphous
Form: Free

EXAMPLE 394

Structure

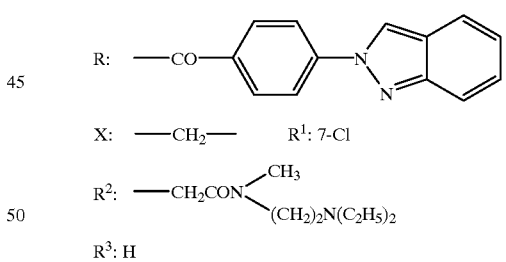

R: —CO—
X: —CH₂—  R¹: 7-Cl
R²: —CH₂CON(CH₃)(CH₂)₂N(C₂H₅)₂
R³: H

Crystalline form: Pale yellow amorphous
Form: Free

EXAMPLE 395

Structure

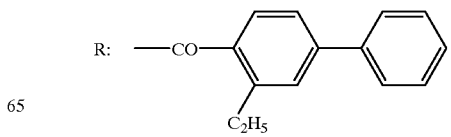

R: —CO—

X: —CH₂—  R¹: H

R²: H

R³: H

Crystalline form: Colorless needles
Solvent for recrystallization: Ethyl acetate/n-hexane
M.p. 134–135.5° C.
Form: Free

EXAMPLE 396

Structure

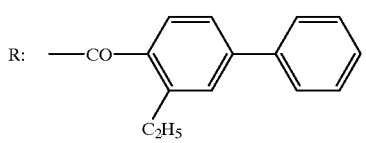

X: —CH₂—  R¹: 7-Cl

R²: H

R³: H

Crystalline form: Colorless needles
Solvent for recrystallization: n-Hexane
M.p. 108–110.5° C.
Form: Free

EXAMPLE 397

Structure

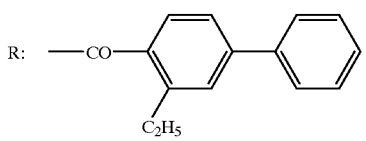

X: —CH₂—  R¹: 7-Cl

R²: 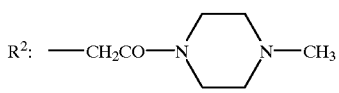

R³: H

Crystalline form: Colorless amorphous
Form: Free

EXAMPLE 398

Structure

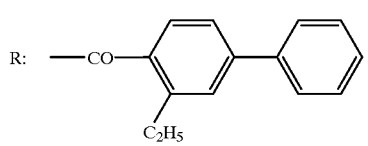

X: —CH₂—  R¹: H

R²: —CH₂CO—N⟨piperazine⟩N—CH₃

R³: H

Crystalline form: Colorless amorphous
Form: Free

EXAMPLE 399

Structure

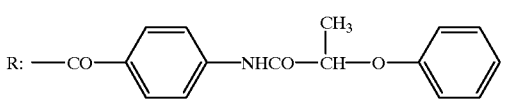

X: —CH₂—  R¹: H

R²: H

R³: H

Crystalline form: White powder
Solvent for recrystallization: Ethanol
M.p. 131–133° C.
Form: Free

EXAMPLE 400

Structure

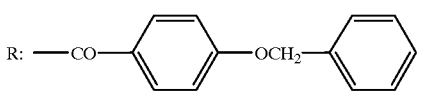

X: —CH₂—  R¹: H

R²: H

R³: H

Crystalline form: Colorless flakes
Solvent for recrystallization: Ethanol
M.p. 125–126° C.
Form: Free

EXAMPLE 401

Structure

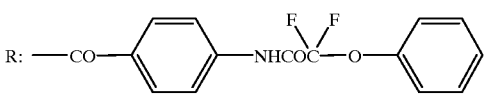

X: —CH₂—  R¹: H

R²: H

R³: H

Crystalline form: White powder
Solvent for recrystallization: Ethanol
M.p. 134–135° C.
Form: Free

EXAMPLE 402

Structure

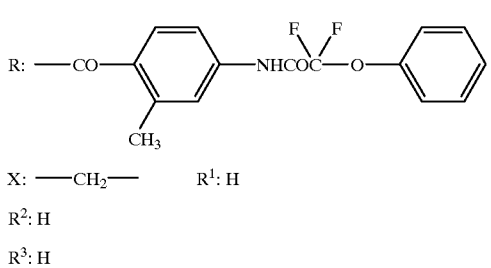

X: —CH₂—    R¹: H

R²: H

R³: H

Crystalline form: White powder

Solvent for recrystallization: Ethanol

M.p. 190–192° C.

Form: Free

EXAMPLE 403

Structure

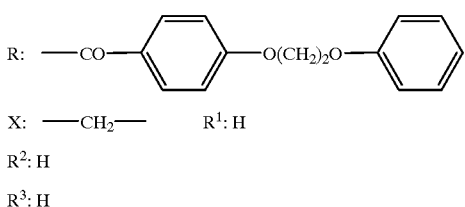

X: —CH₂—    R¹: H

R²: H

R³: H

Crystalline form: White powder

Solvent for recrystallization: Ethanol

M.p. 139–142° C.

Form: Free

EXAMPLE 404

Structure

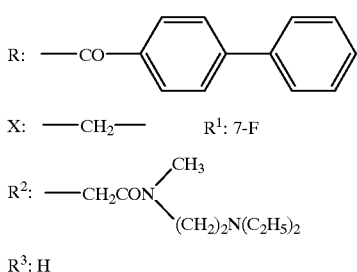

X: —CH₂—    R¹: 7-F

R²: —CH₂CON(CH₃)(CH₂)₂N(C₂H₅)₂

R³: H

Crystalline form: Colorless amorphous

Form: Hydrochloride

EXAMPLE 405

Structure

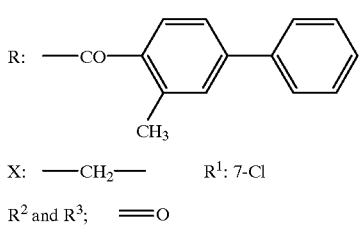

X: —CH₂—    R¹: 7-Cl

R² and R³;  =O

Crystalline form: Pale brown powder

M.p. 157–159° C.

Form: Free

EXAMPLE 406

Structure

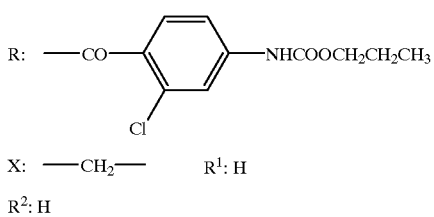

X: —CH₂—    R¹: H

R²: H

R³: H

Crystalline form: White powder

Solvent for recrystallization: Methanol

M.p. 166–167° C.

Form: Free

EXAMPLE 407

Structure

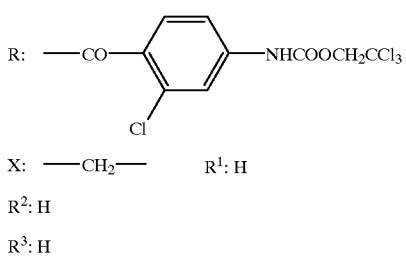

X: —CH₂—    R¹: H

R²: H

R³: H

Crystalline form: White powder

M.p. 181–182° C.

Form: Free

EXAMPLE 408

Structure

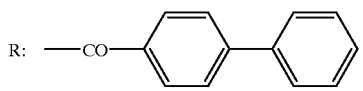

-continued

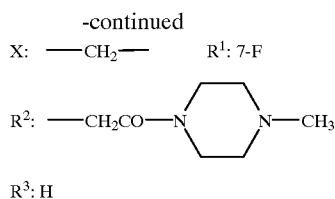

X: —CH₂—  R¹: 7-F
R²: —CH₂CO—N(piperazine)N—CH₃
R³: H

Crystalline form: Colorless amorphous
Form: Hydrochloride

EXAMPLE 409

Structure

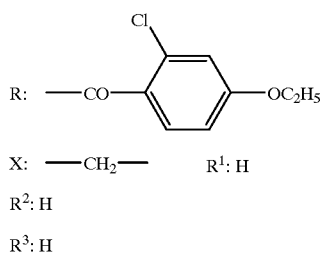

R: —CO—
X: —CH₂—  R¹: H
R²: H
R³: H

Crystalline form: White powder
Solvent for recrystallization: Diethyl ether
M.p. 108–109° C.
Form: Free

EXAMPLE 410

Structure

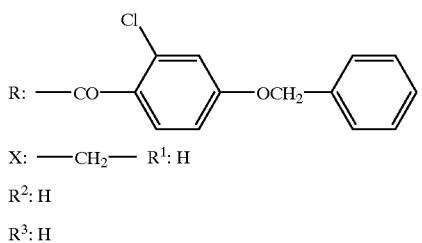

R: —CO—
X: —CH₂—  R¹: H
R²: H
R³: H

Crystalline form: White powder
Solvent for recrystallization: Diethyl ether
M.p. 104–106° C.
Form: Free

EXAMPLE 411

Structure

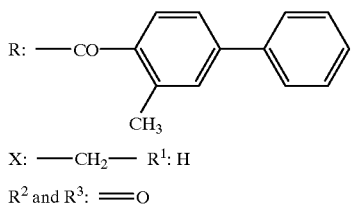

R: —CO—
X: —CH₂—  R¹: H
R² and R³: ═O

Crystalline form: White powder
Solvent for recrystallization: Chloroform/diethy ether
M.p. 130–132° C.
Form: Free

EXAMPLE 412

Structure

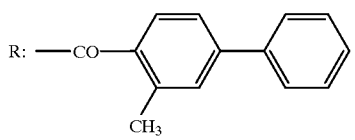

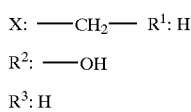

X: —CH₂—  R¹: H
R²: —OH
R³: H

Crystalline form: Pale brown powder
Solvent for recrystallization: Chloroform/diethyl ether
M.p. 191–193° C.
Form: Free

EXAMPLE 413

Structure

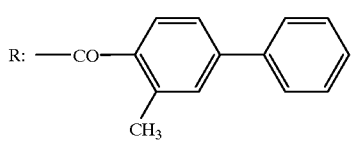

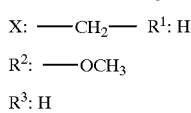

X: —CH₂—  R¹: H
R²: —OCH₃
R³: H

Crystalline form: Colorless viscous oil
Form: Free

EXAMPLE 414

Structure

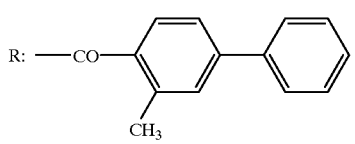

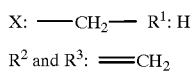

X: —CH₂—  R¹: H
R² and R³: ═CH₂

Crystalline form: White powder
Solvent for recrystallization: Diethyl ether/n-hexane
M.p. 123–124° C.
Form: Free

EXAMPLE 415

Structure

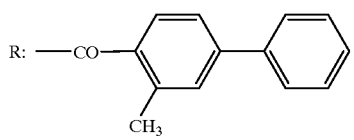

X: —CH$_2$— R$^1$: H

R$^2$: —OH

R$^3$: —CH$_2$OH

Crystalline form: White powder

Solvent for recrystallization: Chloroform/diethyl ether

Form: Free

EXAMPLE 416

Structure

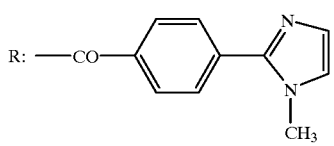

X: —CH$_2$— R$^1$: 7-Cl

R$^2$: H

R$^3$: H

Crystalline form: White powder

Solvent for recrystallization: Chloroform/diethyl ether

M.p. 194–197° C.

Form: Free

EXAMPLE 417

Structure

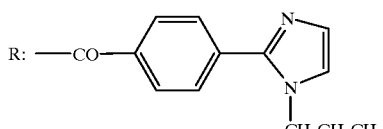

X: —CH$_2$— R$^1$: 7-Cl

R$^2$: H

R$^3$: H

Crystalline form: Pale yellow amorphous

Form: Hydrochloride

EXAMPLE 418

Structure

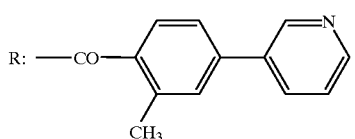

X: —CH$_2$— R$^1$: 7-Cl

R$^2$: —CH$_2$CO—N(piperazine)N—C$_2$H$_5$

R$^3$: H

Crystalline form: Colorless amorphous

Form: Free

EXAMPLE 419

Structure

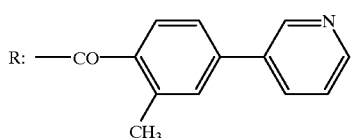

X: —CH$_2$— R$^1$: 7-Cl

R$^2$: —CH$_2$CONHC$_2$H$_5$

R$^3$: H

Crystalline form: Colorless amorphous

Form: Free

EXAMPLE 420

Structure

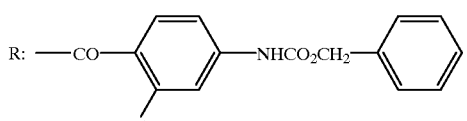

X: —CH$_2$— R$^1$: 7-Cl

R$^2$: —CH$_2$CO—N(piperazine)N—CH$_3$

R$^3$: H

Crystalline form: Colorless amorphous

Form: Free

EXAMPLE 421

Structure

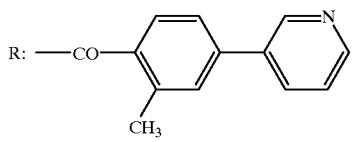

X: —CH₂— R¹: 7-Cl

R²: H

R³: H

Crystalline form: Pale brown amorphous

Form: Hydrochloride

EXAMPLE 422

Structure

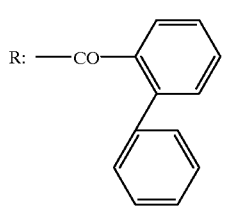

X: —CH₂— R¹: 7-Cl

R²: H

R³: H

Crystalline form: White powder

Solvent for recrystallization: Chloroform/diethyl ether

Form: Free

EXAMPLE 423

Structure

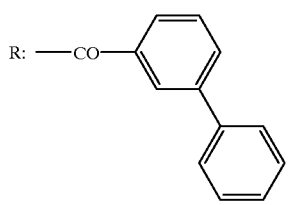

X: —CH₂— R¹: 7-Cl

R²: H

R³: H

Crystalline form: Colorless viscous oil

Form: Free

EXAMPLE 424

Structure

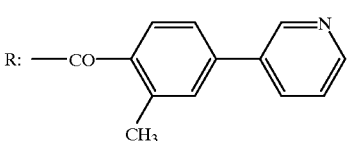

X: —CH₂— R¹: 7-Cl

R²: —CH₂CO—N⟩N—CH₃

R³: H

Crystalline form: Colorless amorphous

Form: Free

EXAMPLE 425

Structure

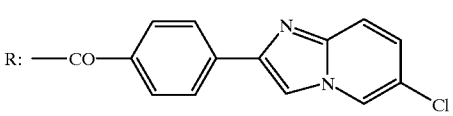

X: —CH₂— R¹: 7-Cl

R²: H

R³: H

Crystalline form: White powder

Form: Free

EXAMPLE 426

Structure

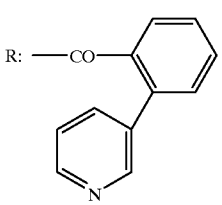

X: —CH₂— R¹: 7-Cl

R²: H

R³: H

Crystalline form: Pale brown amorphous

Form: Free

EXAMPLE 427

Structure

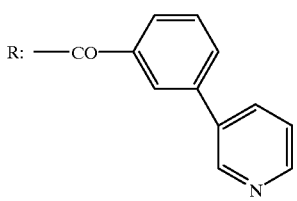

X: —CH$_2$— R$^1$: 7-Cl

R$^2$: H

R$^3$: H

Crystalline form: White powder
Solvent for recrystallization: Ethanol/diethyl ether
M.p. 223–227° C.
Form: Hydrochloride

EXAMPLE 428

Structure

X: —CH$_2$— R$^1$: 7-Cl

R$^2$: H

R$^3$: H

Crystalline form: White powder
Solvent for recrystallization: Chloroform/diethyl ether/n-hexane
M.p. 152–154° C.
Form: Free

EXAMPLE 429

Structure

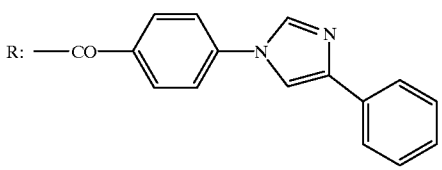

X: —CH$_2$— R$^1$: 7-Cl

R$^2$: H

R$^3$: H

Crystalline form: White powder
Solvent for recrystallization: Chloroform/diethyl ether
M.p. 166–168° C.
Form: Free

EXAMPLE 430

Structure

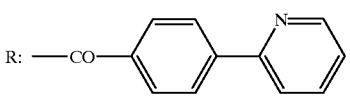

X: —CH$_2$— R$^1$: 7-Cl

R$^2$: H

R$^3$: H

Crystalline form: White powder
Solvent for recrystallization: Chloroform/diethyl ether
M.p. 190–192° C.
Form: Free

EXAMPLE 431

Structure

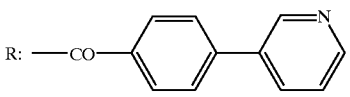

X: —CH$_2$— R$^1$: 7-Cl

R$^2$: H

R$^3$: H

Crystalline form: Pale yellow powder
Solvent for recrystallization: Chloroform/diethyl ether
M.p. 185–187° C.
Form: Free

EXAMPLE 432

Structure

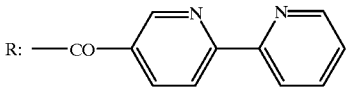

X: —CH$_2$— R$^1$: 7-Cl

R$^2$: H

R$^3$: H

Crystalline form: Pale brown powder
Solvent for recrystallization: Ethanol/diethyl ether
M.p. 154–158° C.
Form: Free

EXAMPLE 433

Structure

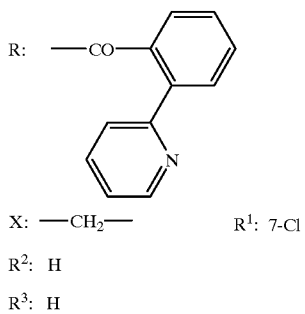

X: —CH$_2$—    R$^1$: 7-Cl

R$^2$: H

R$^3$: H

Crystalline form: Pale brown amorphous
Form: Free

EXAMPLE 434

Structure

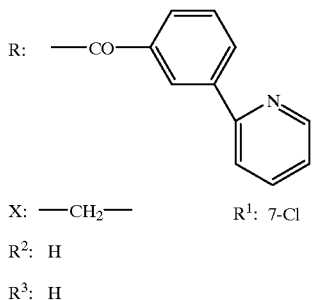

X: —CH$_2$—    R$^1$: 7-Cl

R$^2$: H

R$^3$: H

Crystalline form: White powder
Solvent for recrystallization: Ethanol/diethyl ether
M.p. 222–225° C.
Form: Hydrochloride

EXAMPLE 435

Structure

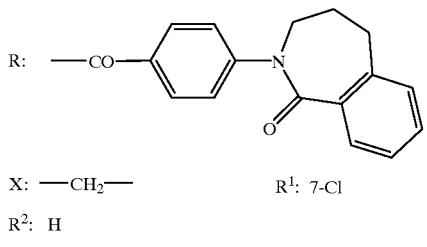

X: —CH$_2$—    R$^1$: 7-Cl

R$^2$: H

R$^3$: H

Crystalline form: Colorless prisms
Solvent for recrystallization: Ethanol/dichloromethane/diethyl ether
M.p. 199–201° C.
Form: Free

EXAMPLE 436

Structure

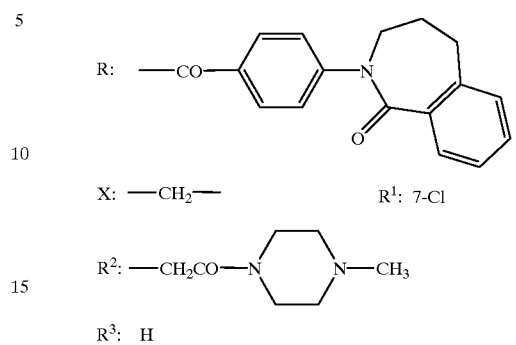

X: —CH$_2$—    R$^1$: 7-Cl

R$^2$: —CH$_2$CO—N⟨piperazine⟩N—CH$_3$

R$^3$: H

Crystalline form: Colorless viscous oil
Form: Free

EXAMPLE 437

Structure

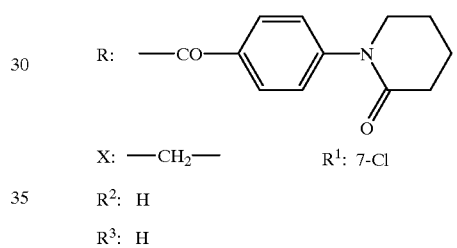

X: —CH$_2$—    R$^1$: 7-Cl

R$^2$: H

R$^3$: H

Crystalline form: White powder
Solvent for recrystallization: Chloroform/diethyl ether
M.p. 173–175° C.
Form: Free

EXAMPLE 438

Structure

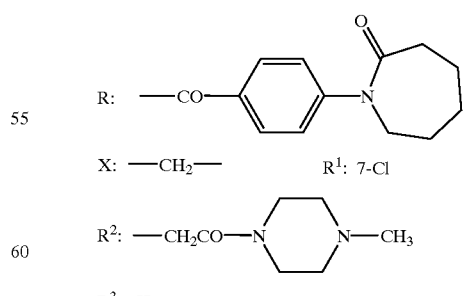

X: —CH$_2$—    R$^1$: 7-Cl

R$^2$: —CH$_2$CO—N⟨piperazine⟩N—CH$_3$

R$^3$: H

Crystalline form: Colorless amorphous
Form: Free

EXAMPLE 439

Structure

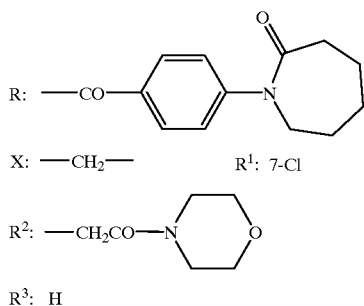

R³: H

Crystalline form: White powder
Solvent for recrystallization: Chloroform/diethyl ether
M.p. 218–219° C.
Form: Free

EXAMPLE 440

Structure:

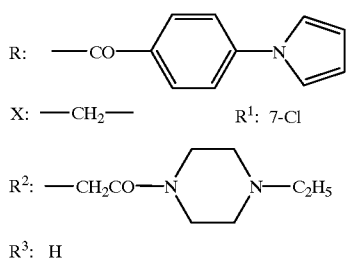

R³: H

Crystalline form: Yellow viscous oil
Form: Free

EXAMPLE 441

Structure

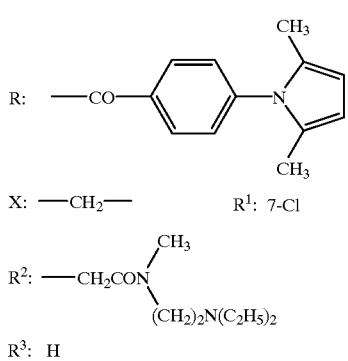

R³: H

Crystalline form: Yellow oil
Form: Free

EXAMPLE 442

Structure

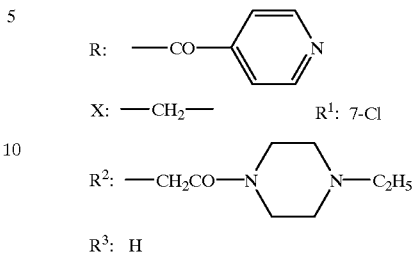

R³: H

Crystalline form: White powder
Solvent for recrystallization: Diethyl ether
M.p. 143–145° C.

EXAMPLE 443

Structure

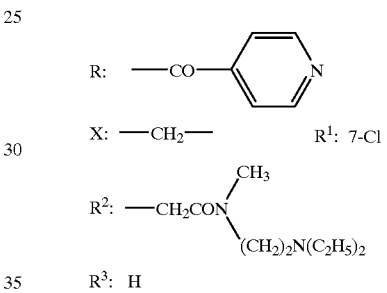

R³: H

EXAMPLE 444

Structure

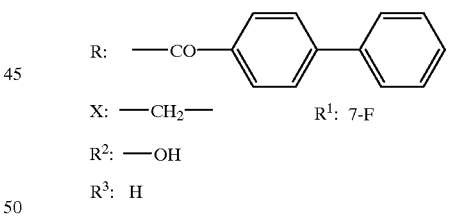

R²: —OH
R³: H

Crystalline form: Colorless amorphous
Form: Free

EXAMPLE 445

Structure

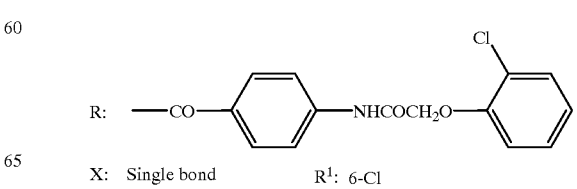

X: Single bond    R¹: 6-Cl

-continued

R²: —CH₂CO—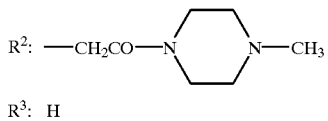

R³: H

Crystalline form: Colorless amorphous
Form: Free

EXAMPLE 446
Structure

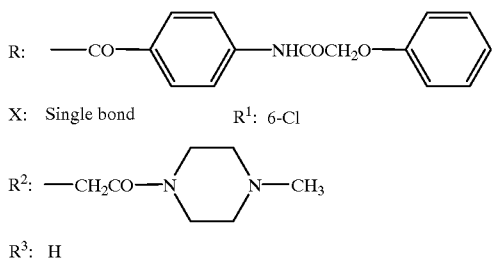

R: —CO—⟨⟩—NHCOCH₂O—⟨⟩

X: Single bond    R¹: 6-Cl

R²: —CH₂CO—N⌒N—CH₃

R³: H

Crystalline form: Colorless amorphous
Form: Free

EXAMPLE 447
Structure

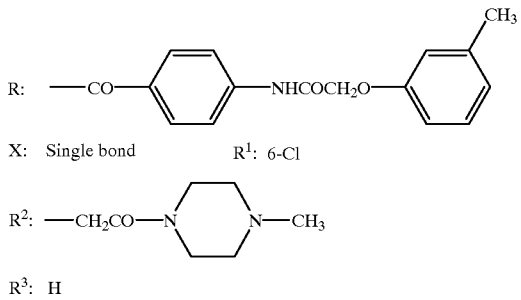

R: —CO—⟨⟩—NHCOCH₂O—⟨⟩—CH₃

X: Single bond    R¹: 6-Cl

R²: —CH₂CO—N⌒N—CH₃

R³: H

Crystalline form: Colorless amorphous
Form: Free

EXAMPLE 448
Structure

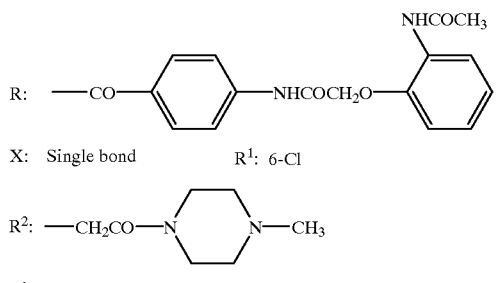

R: —CO—⟨⟩—NHCOCH₂O—⟨⟩—NHCOCH₃

X: Single bond    R¹: 6-Cl

R²: —CH₂CO—N⌒N—CH₃

R³: H

Crystalline form: Colorless amorphous
Form: Free

EXAMPLE 449
Structure

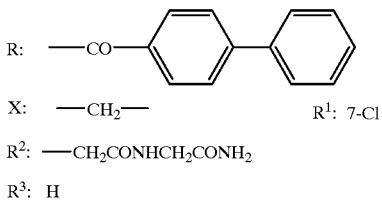

R: —CO—⟨⟩—⟨⟩

X: —CH₂—    R¹: 7-Cl

R²: —CH₂CONHCH₂CONH₂

R³: H

Crystalline form: White powder
Solvent for recrystallization: Diethyl ether
M.p. 208–209° C.
Form: Free

EXAMPLE 450
Structure

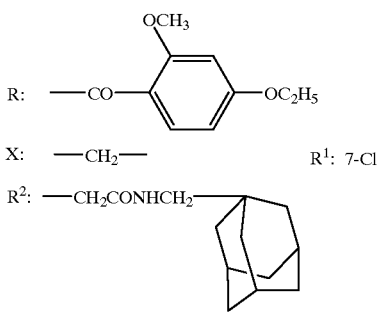

R: —CO—⟨OCH₃ / OC₂H₅⟩

X: —CH₂—    R¹: 7-Cl

R²: —CH₂CONHCH₂—(adamantyl)

R³: H

Crystalline form: Colorless amorphous
Form: Free

EXAMPLE 451
Structure

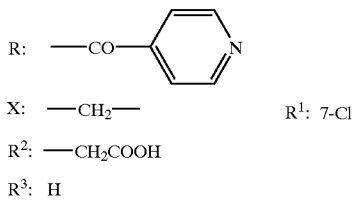

R: —CO—⟨pyridyl⟩

X: —CH₂—    R¹: 7-Cl

R²: —CH₂COOH

R³: H

Crystalline form: White powder
Solvent for recrystallization: Diethy ether
M.p. 222–224° C.
Form: Free

EXAMPLE 452

Structure

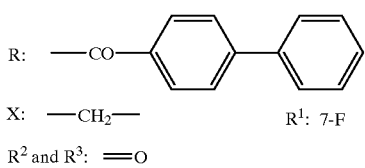

R: —CO—⟨phenyl⟩—⟨phenyl⟩

X: —CH$_2$—    R$^1$: 7-F

R$^2$ and R$^3$: =O

Crystalline form: Colorless flakes
Solvent for recrystallization: Diethyl ether
M.p. 97–100° C.
Form: Free

EXAMPLE 453

Structure

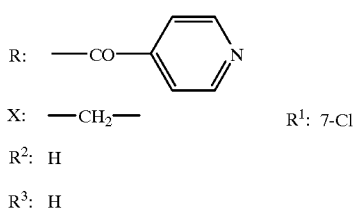

R: —CO—⟨pyridyl⟩

X: —CH$_2$—    R$^1$: 7-Cl

R$^2$: H

R$^3$: H

Crystalline form: Colorless prisms
Solvent for recrystallization: Diethyl ether
M.p. 116–118° C.
Form: Free

EXAMPLE 454

Structure

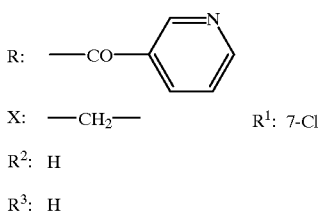

R: —CO—⟨pyridyl⟩

X: —CH$_2$—    R$^1$: 7-Cl

R$^2$: H

R$^3$: H

Crystalline form: White powder
Solvent for recrystallization: Diethyl ether
M.p. 115–116° C.
Form: Free

EXAMPLE 455

Structure

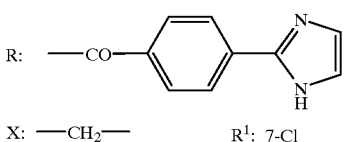

R: —CO—⟨phenyl⟩—⟨imidazolyl⟩

X: —CH$_2$—    R$^1$: 7-Cl

-continued

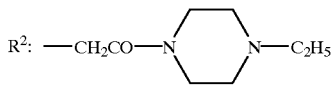

R$^2$: —CH$_2$CO—N⟨piperazine⟩N—C$_2$H$_5$

R$^3$: H

Crystalline form: Pale yellow amorphous
Form: Free

EXAMPLE 456

Structure

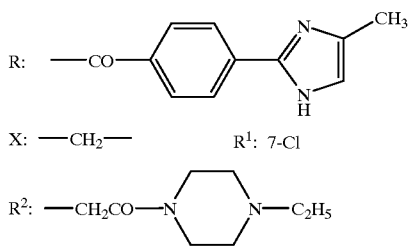

R: —CO—⟨phenyl⟩—⟨methylimidazolyl⟩

X: —CH$_2$—    R$^1$: 7-Cl

R$^2$: —CH$_2$CO—N⟨piperazine⟩N—C$_2$H$_5$

R$^3$: H

Crystalline form: Pale yellow amorphous
Form: Free

EXAMPLE 457

Structure

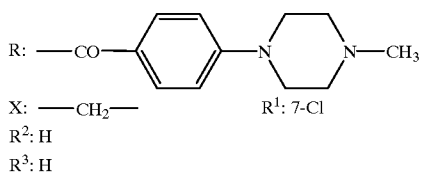

R: —CO—⟨phenyl⟩—N⟨piperazine⟩N—CH$_3$

X: —CH$_2$—    R$^1$: 7-Cl

R$^2$: H

R$^3$: H

Crystalline form: White powder
Solvent for recrystallization: Chloroform/diethyl ether/n-hexane
M.p. 194–197° C.
Form: Free

EXAMPLE 458

Structure

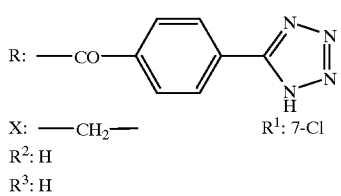

R: —CO—⟨phenyl⟩—⟨tetrazolyl⟩

X: —CH$_2$—    R$^1$: 7-Cl

R$^2$: H

R$^3$: H

Crystalline form: Pale brown powder
Solvent for recrystallization: Chloroform/diethyl ether
M.p. 150–154° C.
Form: Free

EXAMPLE 459

Structure

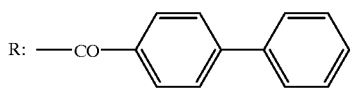

X: Single bond R¹: H
R²: —CH$_2$CONH(CH$_2$)$_2$N(C$_2$H$_5$)$_2$
R³: H

Crystalline form: Colorless amorphous
Form: Hydrochloride

EXAMPLE 460

Structure

X: Single bond R¹: H
R²: —CH$_2$CO—N⟨ ⟩N—C$_2$H$_5$
R³: H

Crystalline form: Slightly orange amorphous
Form: Dihydrochloride

EXAMPLE 461

Structure

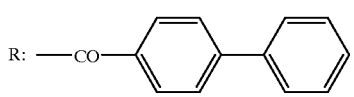

X: Single bond R¹: 6-Cl
R²: —CH$_2$CONH(CH$_2$)$_2$N(C$_2$H$_5$)$_2$
R³: H

Crystalline form: Slightly yellow amorphous
Form: Free

EXAMPLE 462

Structure

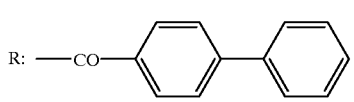

X: Single bond R¹: 6-Cl
R²: —CH$_2$CO—N⟨ ⟩N—C$_2$H$_5$
R³: H

Crystalline form: Colorless amorphous
Form: Free

EXAMPLE 463

Structure

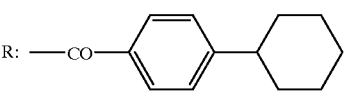

X: Single bond R¹: 6-Cl
R²: —CH$_2$CONH(CH$_2$)$_2$N(C$_2$H$_5$)$_2$
R³: H

Crystalline form: Colorless amorphous
Form: Hydrochloride

EXAMPLE 464

Structure

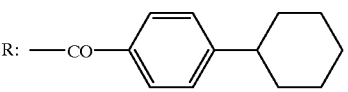

X: Single bond R¹: 6-Cl
R²: —CH$_2$CO—N⟨ ⟩N—C$_2$H$_5$
R³: H

Crystalline form: Colorless amorphous
Form: Free

EXAMPLE 465

Structure

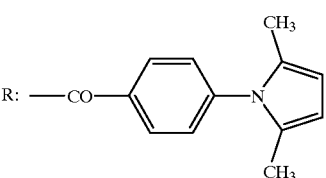

X: —CH$_2$— R¹: 7-Cl
R²: —CH$_2$CO—N⟨ ⟩N—C$_2$H$_5$
R³: H

Crystalline form: White powder
M.p. 154–156° C.
Form: Free

EXAMPLE 466

Structure

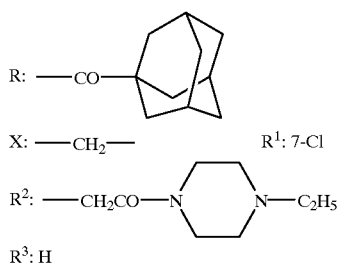

R: —CO—[adamantyl]

X: —CH$_2$—   R$^1$: 7-Cl

R$^2$: —CH$_2$CO—N(piperazine)N—C$_2$H$_5$

R$^3$: H

Crystalline form: White powder

Solvent for recrystallization: Chloroform/diethyl ether

M.p. 195–196° C.

Form: Free

EXAMPLE 467

Structure

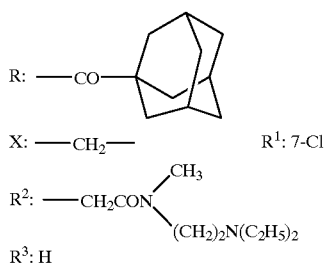

R: —CO—[adamantyl]

X: —CH$_2$—   R$^1$: 7-Cl

R$^2$: —CH$_2$CON(CH$_3$)(CH$_2$)$_2$N(C$_2$H$_5$)$_2$

R$^3$: H

Crystalline form: Colorless amorphous

Form: Hydrochloride

EXAMPLE 468

Structure

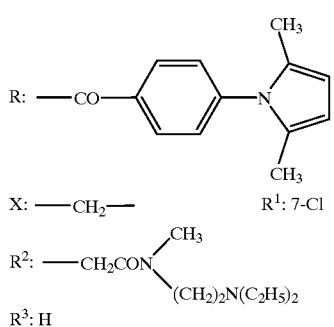

R: —CO—[4-(2,5-dimethylpyrrol-1-yl)phenyl]

X: —CH$_2$—   R$^1$: 7-Cl

R$^2$: —CH$_2$CON(CH$_3$)(CH$_2$)$_2$N(C$_2$H$_5$)$_2$

R$^3$: H

EXAMPLE 469

Structure

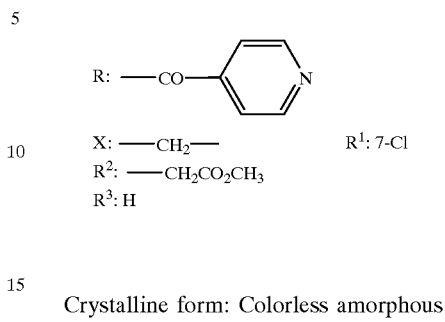

R: —CO—[pyridyl]

X: —CH$_2$—   R$^1$: 7-Cl

R$^2$: —CH$_2$CO$_2$CH$_3$

R$^3$: H

Crystalline form: Colorless amorphous

Form: Free

EXAMPLE 470

Structure

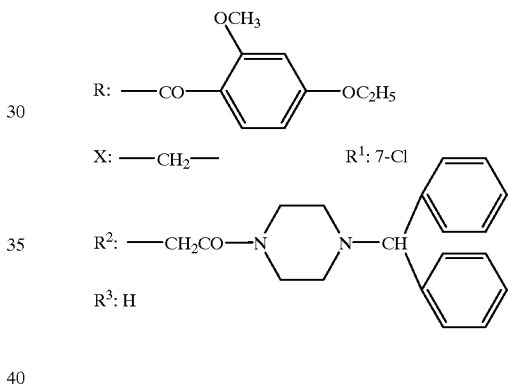

R: —CO—[3-OCH$_3$, 4-OC$_2$H$_5$-phenyl]

X: —CH$_2$—   R$^1$: 7-Cl

R$^2$: —CH$_2$CO—N(piperazine)N—CH(phenyl)$_2$

R$^3$: H

Crystalline form: Colorless amorhpus

Form: Free

EXAMPLE 471

Structure

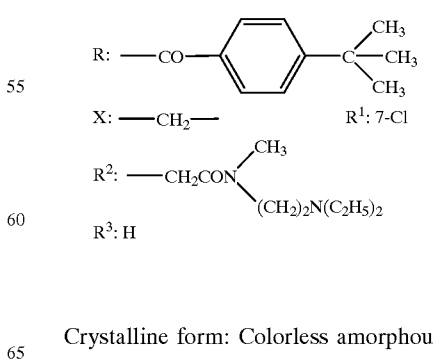

R: —CO—[4-C(CH$_3$)$_3$-phenyl]

X: —CH$_2$—   R$^1$: 7-Cl

R$^2$: —CH$_2$CON(CH$_3$)(CH$_2$)$_2$N(C$_2$H$_5$)$_2$

R$^3$: H

Crystalline form: Colorless amorphous

Form: Hydrochloride

EXAMPLE 472

Structure

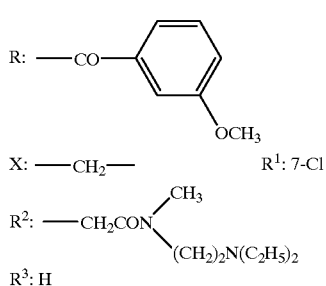

R: —CO—(3-OCH₃-phenyl)
X: —CH₂—  R¹: 7-Cl
R²: —CH₂CON(CH₃)(CH₂)₂N(C₂H₅)₂
R³: H

Crystalline form: Colorless amorphous

Form: Hydrochloride

EXAMPLE 473

Structure

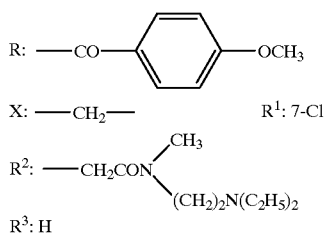

R: —CO—(4-OCH₃-phenyl)
X: —CH₂—  R¹: 7-Cl
R²: —CH₂CON(CH₃)(CH₂)₂N(C₂H₅)₂
R³: H

Crystalline form: Colorless amorphous

Form: Hydrochloride

EXAMPLE 474

Structure

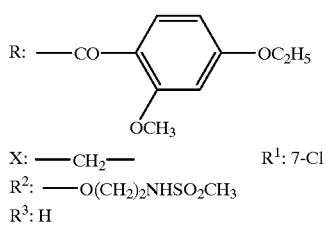

R: —CO—(4-OC₂H₅, 3-OCH₃-phenyl)
X: —CH₂—  R¹: 7-Cl
R²: —O(CH₂)₂NHSO₂CH₃
R³: H

Crystalline form: Pale yellow powder

Solvent for recrystallization: Chloroform/diethyl ether

M.p. 158–159° C.

Form: Free

EXAMPLE 475

Structure

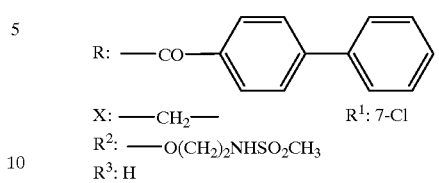

R: —CO—(biphenyl)
X: —CH₂—  R¹: 7-Cl
R²: —O(CH₂)₂NHSO₂CH₃
R³: H

Crystalline form: Pale yellow powder
Solvent for recrystallization: Chloroform/diethyl ether
M.p. 193–194° C.
Form: Free

EXAMPLE 476

Structure

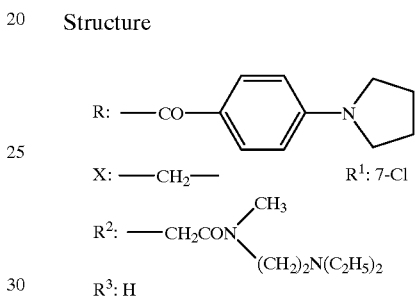

R: —CO—(4-pyrrolidinyl-phenyl)
X: —CH₂—  R¹: 7-Cl
R²: —CH₂CON(CH₃)(CH₂)₂N(C₂H₅)₂
R³: H Crystalline form: Colorless amorphous
Form: Hydrochloride

EXAMPLE 477

Structure

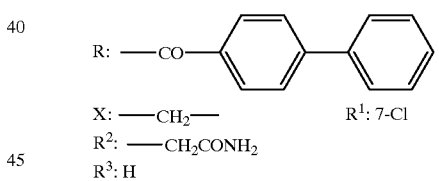

R: —CO—(biphenyl)
X: —CH₂—  R¹: 7-Cl
R²: —CH₂CONH₂
R³: H

Crystalline form: Colorless amorphous
Form: Free

EXAMPLE 478

Structure

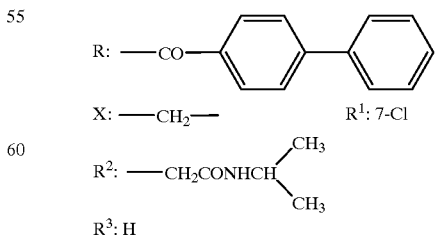

R: —CO—(biphenyl)
X: —CH₂—  R¹: 7-Cl
R²: —CH₂CONHCH(CH₃)₂
R³: H

Crystalline form: Colorless amorphous
Form: Free

EXAMPLE 479
Structure

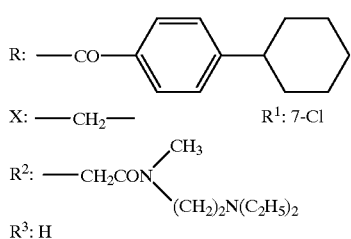

R³: H

Crystalline form: Pale yellow amorphous
Form: Free

EXAMPLE 480
Structure

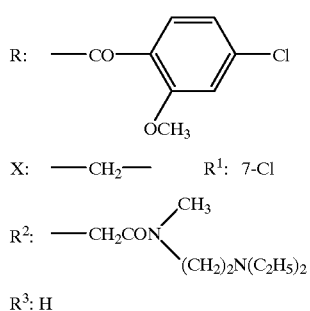

R³: H

Crystalline form: Pale yellow amorphous
Form: Free

EXAMPLE 481
Structure

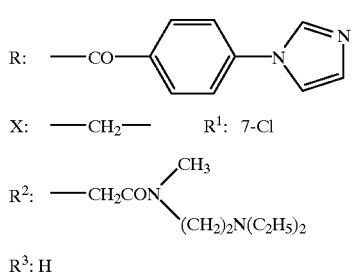

R³: H

Crystalline form: Pale yellow amorphous
Form: Hydrochloride

EXAMPLE 482
Structure

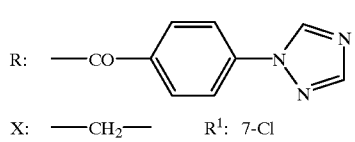

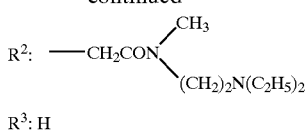

R³: H

Crystalline form: Pale yellow amorphous
Form: Hydrochloride

EXAMPLE 483
Structure

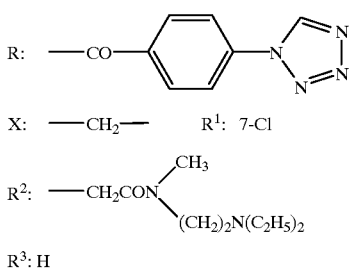

R³: H

Crystalline form: White powder
Solvent for recrystallization: Chloroform/diethyl ether
M.p. 155–158° C.
Form: Free

EXAMPLE 484
Structure

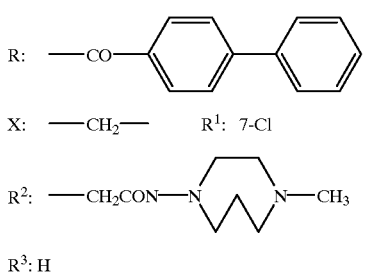

R³: H

Crystalline form: Colorless amorphous
Form: Hydrochloride

EXAMPLE 485
Structure

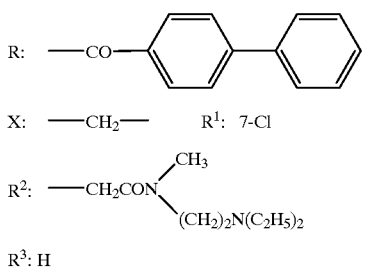

R³: H

Crystalline form: Colorless amorphous
Form: Hydrochloride

EXAMPLE 486

Structure

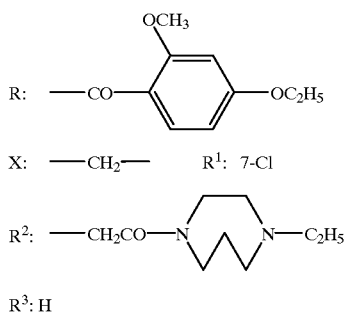

R: —CO-[2-OCH₃, 4-OC₂H₅-phenyl]

X: —CH₂—   R¹: 7-Cl

R²: —CH₂CO—N(piperazine)—C₂H₅

R³: H

Crystalline form: Colorless amorphous

Form: Hydrochloride

EXAMPLE 487

Structure

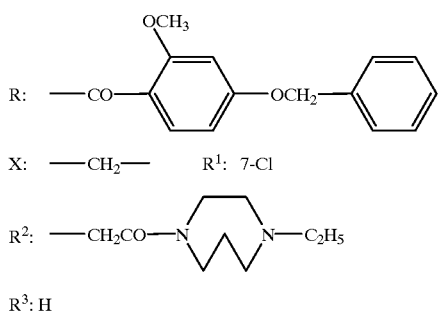

R: —CO-[2-OCH₃, 4-OCH₂Ph-phenyl]

X: —CH₂—   R¹: 7-Cl

R²: —CH₂CO—N(piperazine)—C₂H₅

R³: H

Crystalline form: Colorless amorphous

Form: Free

EXAMPLE 488

Structure

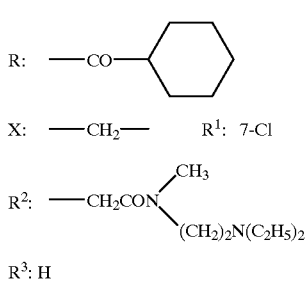

R: —CO-cyclohexyl

X: —CH₂—   R¹: 7-Cl

R²: —CH₂CON(CH₃)(CH₂)₂N(C₂H₅)₂

R³: H

Crystalline form: Pale yellow amorphous

Form: Free

EXAMPLE 489

Structure

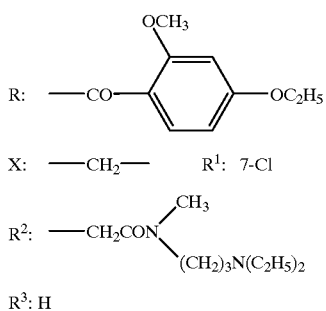

R: —CO-[2-OCH₃, 4-OC₂H₅-phenyl]

X: —CH₂—   R¹: 7-Cl

R²: —CH₂CON(CH₃)(CH₂)₃N(C₂H₅)₂

R³: H

Crystalline form: Colorless amorphous

Form: Hydrochloride

EXAMPLE 490

Structure

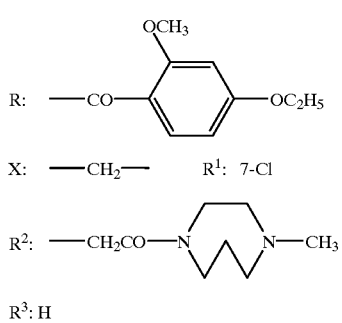

R: —CO-[2-OCH₃, 4-OC₂H₅-phenyl]

X: —CH₂—   R¹: 7-Cl

R²: —CH₂CO—N(piperazine)—CH₃

R³: H

Crystalline form: Colorless amorphous

Form: Hydrochloride

EXAMPLE 491

Structure

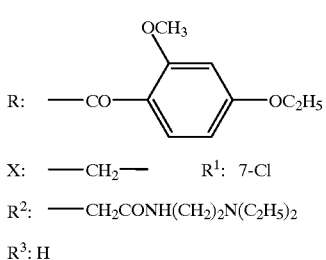

R: —CO-[2-OCH₃, 4-OC₂H₅-phenyl]

X: —CH₂—   R¹: 7-Cl

R²: —CH₂CONH(CH₂)₂N(C₂H₅)₂

R³: H

Crystalline form: Colorless amorphous

Form: Hydrochloride

EXAMPLE 492

Structure

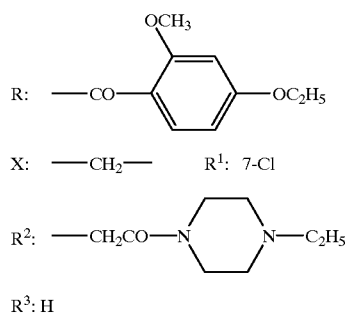

R³: H

Crystalline form: Colorless amorphous

Form: Hydrochloride

EXAMPLE 493

Structure

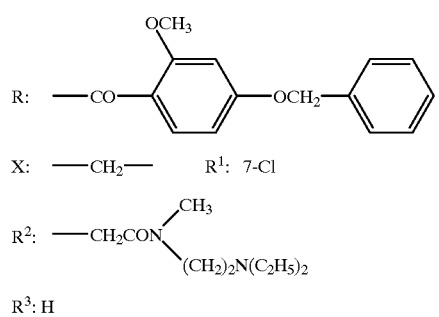

R³: H

Crystalline form: Colorless amorphous

Form: Hydrochloride

EXAMPLE 494

Structure

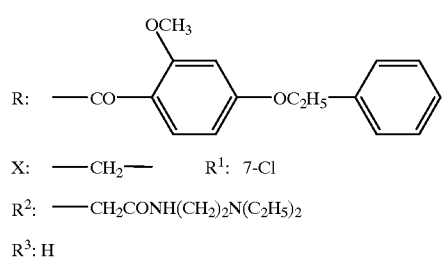

R³: H

Crystalline form: Colorless amorphous

Form: Hydrochloride

EXAMPLE 495

Structure

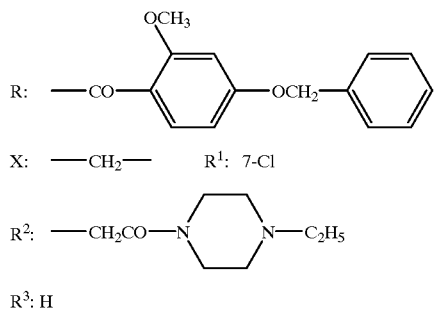

R³: H

Crystalline form: Colorless amorphous

Form: Hydrochloride

EXAMPLE 496

Structure

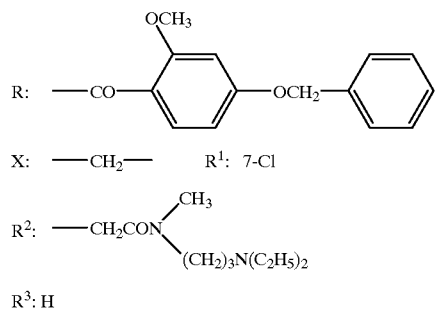

R³: H

Crystalline form: Colorless amorphous

Form: Free

EXAMPLE 497

Structure

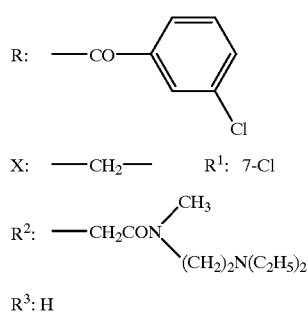

R³: H

Crystalline form: Colorles amorphous

Form: Hydrochloride

EXAMPLE 498

Structure

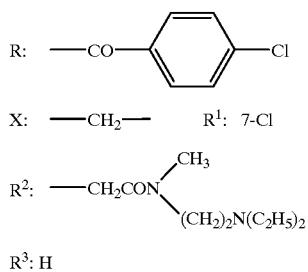

R³: H

Crystalline form: Colorless amorphous

Form: Hydrochloride

EXAMPLE 499

Structure

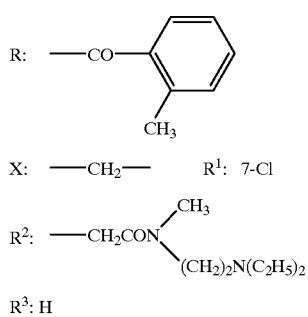

R³: H

Crystalline form: Pale yellow amorphous

Form: Hydrochloride

EXAMPLE 500

Structure

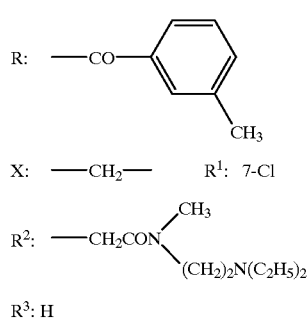

R³: H

Crystalline form: Colorless amorphous

Form: Hydrochloride

EXAMPLE 501

Structure

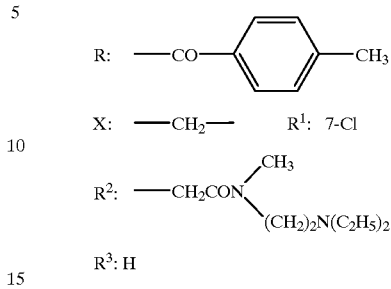

R³: H

Crystalline form: Colorless amorphous

Form: Hydrochloride

EXAMPLE 502

Structure

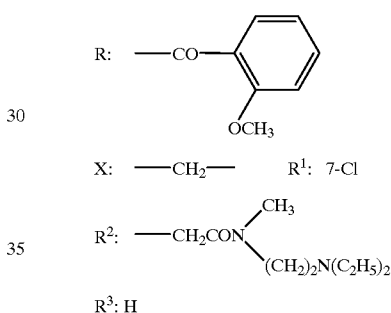

R³: H

Crystalline form: Pale yellow amorphous

Form: Hydrochloride

EXAMPLE 503

Structure

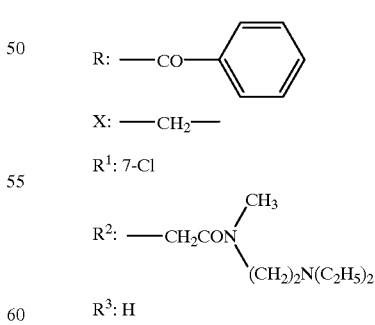

R³: H

Crystalline form: White powder

Solvent for recrystallization: Chloroform/diethyl ether

Form: Free

EXAMPLE 504

Structure

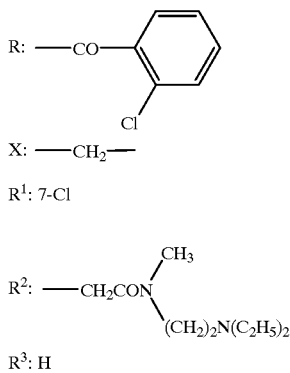

X: —CH₂—

R¹: 7-Cl

R²: —CH₂CON(CH₃)(CH₂)₂N(C₂H₅)₂

R³: H

Crystalline form: Pale yellow amorphous
Form: Hydrochloride

EXAMPLE 505

Structure

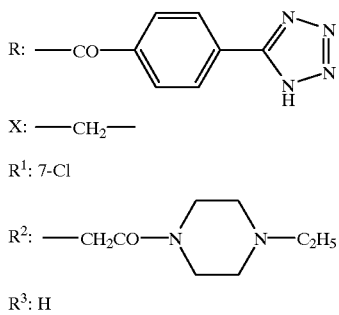

X: —CH₂—

R¹: 7-Cl

R²: —CH₂CO—N(piperazine)N—C₂H₅

R³: H

Crystalline form: Pale brown powder
Form: Free

EXAMPLE 506

Structure

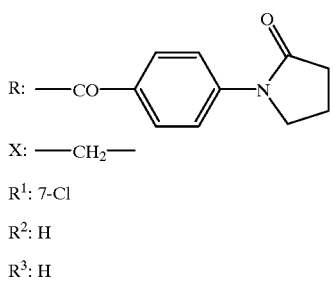

X: —CH₂—

R¹: 7-Cl

R²: H

R³: H

Crystalline form: White powder
Solvent for recrystallization: Chloroform/diethyl ether
M.p. 209–211° C.
Form: Free

EXAMPLE 507

Structure

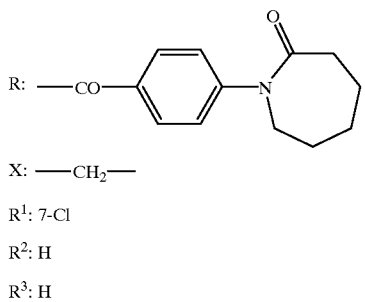

X: —CH₂—

R¹: 7-Cl

R²: H

R³: H

Crystalline form: White powder
Solvent for recrystallization: chloroform/diethyl ether
M.p. 169–170° C.
Form: Free

EXAMPLE 508

Structure

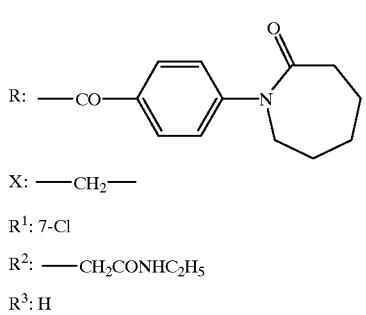

X: —CH₂—

R¹: 7-Cl

R²: —CH₂CONHC₂H₅

R³: H

Crystalline form: Colorless amorphous
Form: Free

EXAMPLE 509

Structure

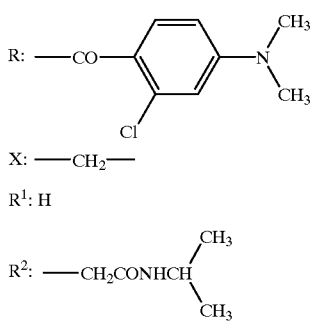

X: —CH₂—

R¹: H

R²: —CH₂CONHCH(CH₃)₂

R³: H

Crystalline form: Colorless amorphous
Form: Free

EXAMPLE 510

Structure

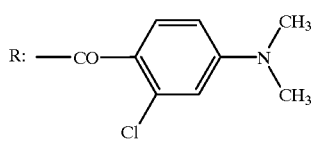

X: —CH$_2$—

R$^1$: H

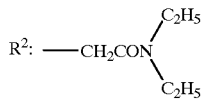

R$^3$: H

Crystalline form: Colorless amorphous
Form: Free

EXAMPLE 511

Structure

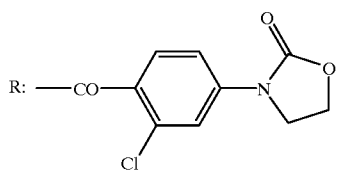

X: —CH$_2$—

R$^1$: H

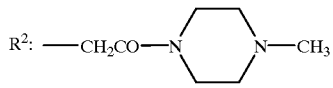

R$^3$: H

Crystalline form: Colorless amorphous
Form: Free

EXAMPLE 512

Structure

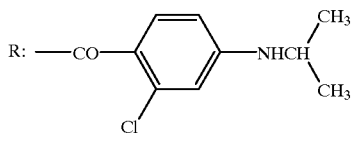

X: —CH$_2$—

R$^1$: H

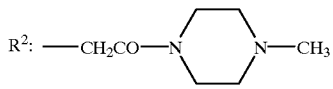

R$^3$: H

Crystalline form: Colorless amorphous
Form: Free

EXAMPLE 513

Structure

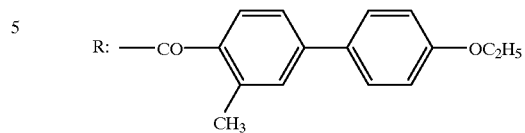

X: —CH$_2$—

R$^1$: H

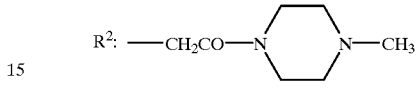

R$^3$: H

Crystalline form: White powder
Solvent for recrystallization: Acetone/n-hexane
M.p. 204–207° C.
Form: Hydrochloride

EXAMPLE 514

Structure

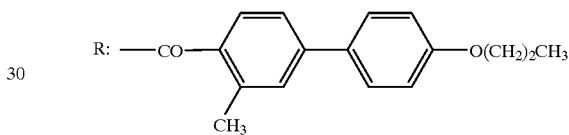

X: —CH$_2$—

R$^1$: H

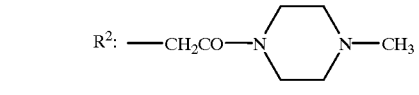

R$^3$: H

Crystalline form: White powder
Solvent for recrystallization: Acetone/n-hexane
M.p. 217–220° C.
Form: Hydrochloride

EXAMPLE 515

Structure

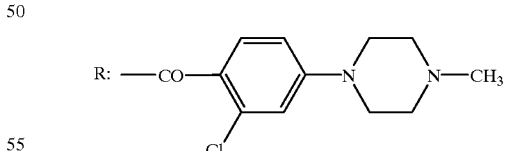

X: —CH$_2$—

R$^1$: H

R$^2$: H

R$^3$: H

Crystalline form: Yellow needles
Solvent for recrystallization: Water
M.p. 198–202° C. (decomposed)
Form: Hydroiodide

EXAMPLE 516

Structure

R: —CO—(3-CH₃, 4-(pyridin-4-yl)phenyl)

X: —CH₂—

R¹: 7-Cl

R²: H

R³: H

Crystalline form: White powder
Solvent for recrystallization: Chloroform/diethyl ether
Form: Free

EXAMPLE 517

Structure

R: —CO—(3-CH₃, 4-(3-chloropyridin-4-yl)phenyl)

X: —CH₂—

R¹: 7-Cl

R²: H

R³: H

Crystalline form: White powder
Solvent for recrystallization: Chloroform/diethyl ether
Form: Free

EXAMPLE 518

Structure

R: —CO—(3-CH₃, 4-NHCO—CF₂—O-phenyl)phenyl

X: —CH₂—

R¹: 7-Cl

R²: —CH₂CONHCH(CH₃)₂

R³: H

Crystalline form: White powder
Solvent for recrystallization: Diethyl ether
M.p. 154–155° C.
Form: Free

EXAMPLE 519

Structure

R: —CO—(3-CH₃, 4-NHCO—CH(CH₃)—O-phenyl)phenyl

X: —CH₂—

R¹: 7-Cl

R²: —CH₂CONHCH(CH₃)₂

R³: H

Crystalline form: White powder
Solvent for recrystallization: Diethyl ether
M.p. 188–190° C.

EXAMPLE 520

Structure

R: —CO—(4-(3-chloropyridin-4-yl), 3-CH₃ phenyl)

X: —CH₂—

R¹: 7-Cl

R²: —CH₂CONHCH(CH₃)₂

R³: H

Crystalline form: Colorless amorphous
Form: Hydrochloride

EXAMPLE 521

Structure

R: —CO—(3-Cl, 4-N(CH₃)₂ phenyl)

X: —CH₂—

R¹: H

R²: —CH₂CO—N(piperazinyl)N—CH₃

R³: H

Crystalline form: Colorless amorphous
Form: Hydrochloride

EXAMPLE 522

Structure

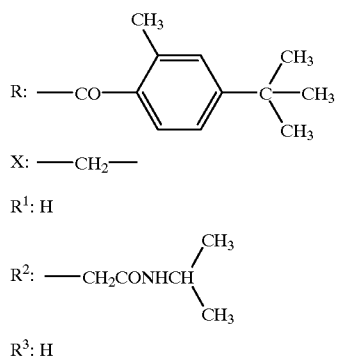

Crystalline form: White powder
Solvent for recrystallization: Diethyl ether
M.p. 149–151° C.

EXAMPLE 523

Structure

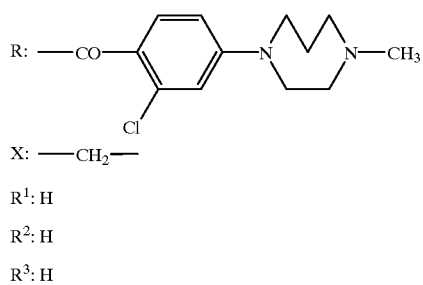

Crystalline form: Yellow amorphous
Form: Free

EXAMPLE 524

Structure

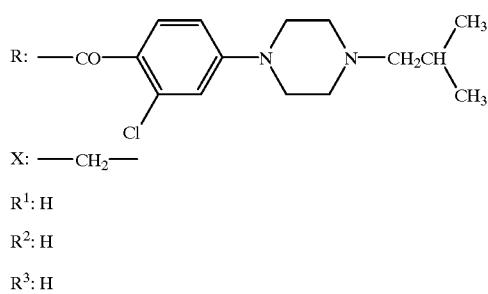

Crystalline form: Colorless amorphous
Form: Free

EXAMPLE 525

Structure

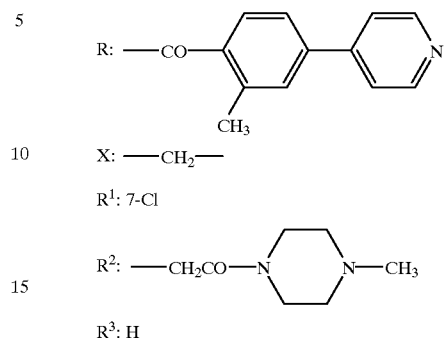

Crystalline form: Colorless amorphous
Form: Hydrochloride

EXAMPLE 526

Structure

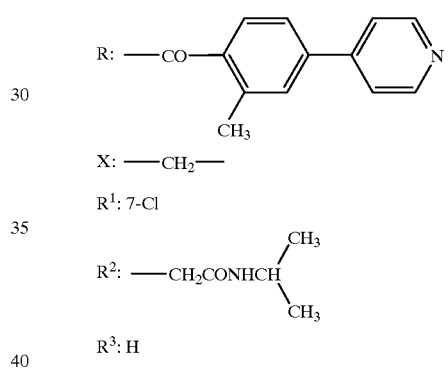

Crystalline form: Colorless amorphous
Form: Hydrochloride

EXAMPLE 527

Structure

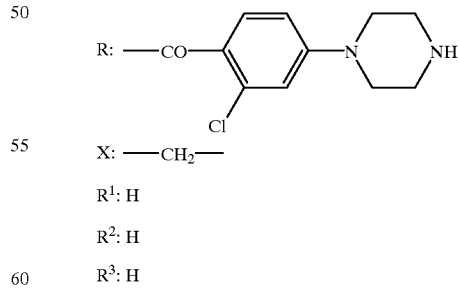

Crystalline form: Brown powder Sovelnt for recrystallization: Diethyl ether
M.p. 155–159° C. (decomposed)
Form: Hydrochloride

EXAMPLE 528

Structure

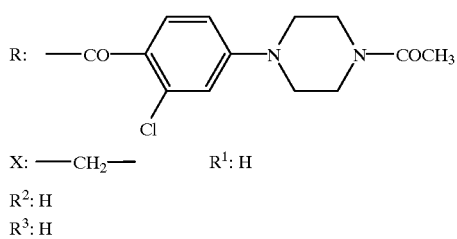

R²: H
R³: H

Crystalline form: White powder Sovelnt for recrystallization: Diethyl ether

M.p. 142–145° C.

Form: Free

EXAMPLE 529

Structure

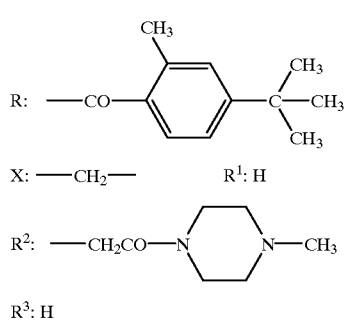

Crystalline form: Colorless amorphous

Form: Hydrochloride

EXAMPLE 530

Structure

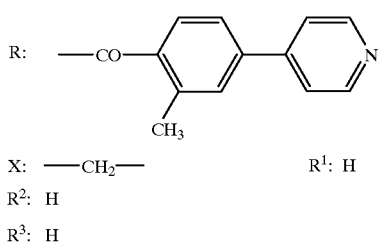

R²: H
R³: H

Crystalline form: Pale yellow powder

Solvent for recrystallization: Chloroform/diethyl ether/n-hexane

Form: Free

EXAMPLE 531

Structure

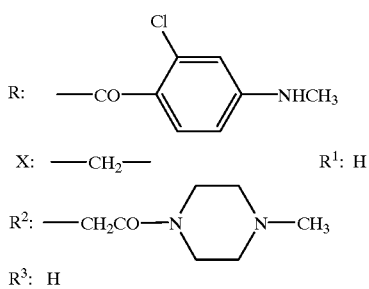

R³: H

Crystalline form: Colorless amorphous

Form: Dihydrochloride

EXAMPLE 532

Structure

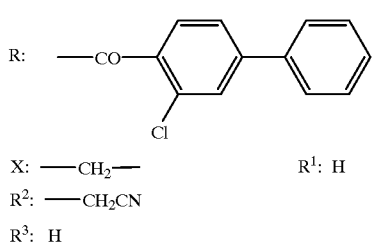

R²: —CH₂CN
R³: H

Crystalline form: Colorless amorphous

Form: Free

EXAMPLE 533

Structure

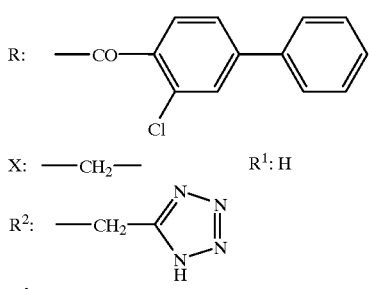

R³: H

Crystalline form: White powder

Solvent for recrystallization: Dichloromethane/diethyl ether

M.p. 191–194° C.

Form: Free

EXAMPLE 534

Structure

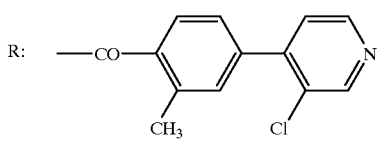

X: —CH₂—   R¹: H
R²: H
R³: H

Crystalline form: Pale brown amorphous
Form: Free

EXAMPLE 535

Structure

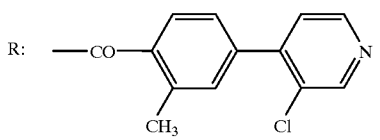

X: —CH₂—   R¹: 7-Cl

R²: 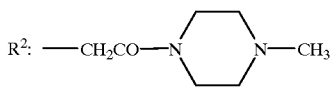

R³: H

Crystalline form: Colorless amorphous
Form: Hydrochloride

EXAMPLE 536

Structure

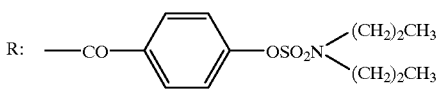

X: —CH₂—   R¹: H

R²: 

R³: H

Crystalline form: White powder
Solvent for recrystallization: Diethyl ether
M.p. 146–147° C.

EXAMPLE 537

Structure

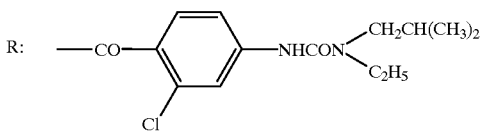

X: —CH₂—   R¹: H
R²: H
R³: H

Crystalline form: White powder
Solvent for recrystallization: Ethanol
M.p. 201–202° C.
Form: Free

EXAMPLE 538

Structure

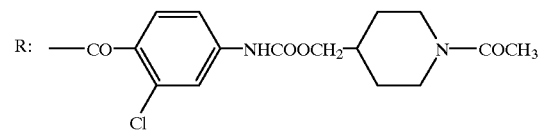

X: —CH₂—   R¹: H
R²: H
R³: H

Crystalline form: White powder
M.p. 118–120° C.
Form: Free

EXAMPLE 539

Structure

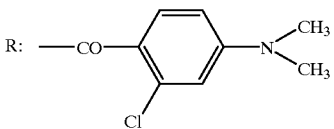

X: —CH₂—   R¹: H
R²: H
R³: H

Crystalline form: White powder
Solvent for recrystallization: Ethanol/diisopropyl ether
M.p. 173–174.5° C.
Form: Free

EXAMPLE 540

Structure

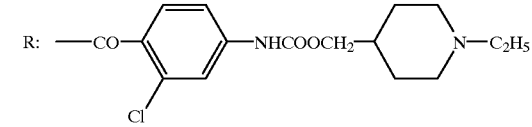

X: —CH₂—   R¹: H
R²: H
R³: H

Crystalline form: White powder
M.p. 159–161° C.
Form: Free

EXAMPLE 541

Structure

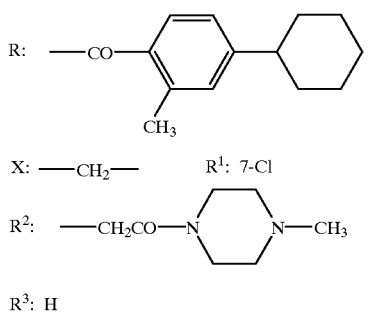

X: —CH₂—  R¹: 7-Cl

R²: —CH₂CO—N⌒N—CH₃

R³: H

Crystalline form: Colorless amorphous

Form: Hydrochloride

EXAMPLE 542

Structure

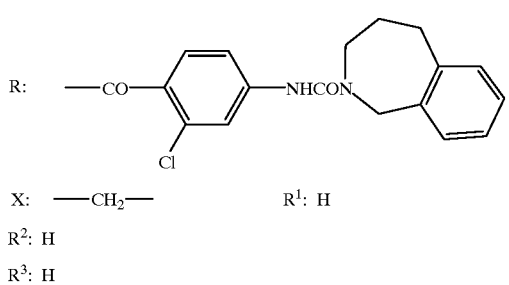

X: —CH₂—  R¹: H

R²: H

R³: H

Crystalline form: Colorless amorphous

Form: Free

EXAMPLE 543

Structure

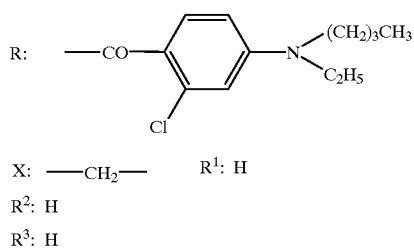

X: —CH₂—  R¹: H

R²: H

R³: H

Crystalline form: White powder

Solvent for recrystallization: n-Hexane

M.p. 94–95° C.

Form: Free

EXAMPLE 544

Structure

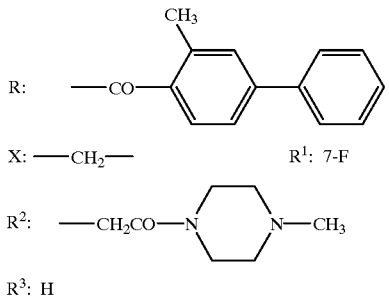

X: —CH₂—  R¹: 7-F

R²: —CH₂CO—N⌒N—CH₃

R³: H

Crystalline form: Colorless amorphous

Form: Hydrochloride

EXAMPLE 545

Structure

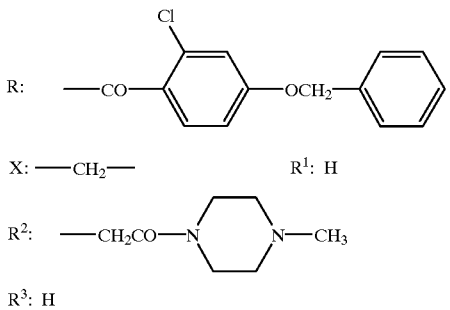

X: —CH₂—  R¹: H

R²: —CH₂CO—N⌒N—CH₃

R³: H

Crystalline form: Colorless amorphous

Form: Hydrochloride

EXAMPLE 546

Structure

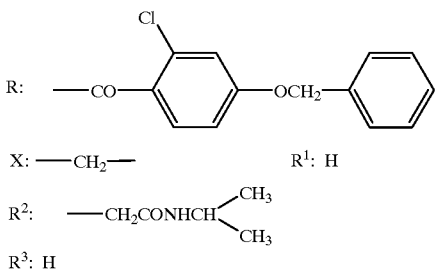

X: —CH₂—  R¹: H

R²: —CH₂CONHCH(CH₃)₂

R³: H

Crystalline form: White powder

Solvent for recrystallization: Diethyl ether

M.p. 174–176° C.

Form: Free

EXAMPLE 547

Structure

R: 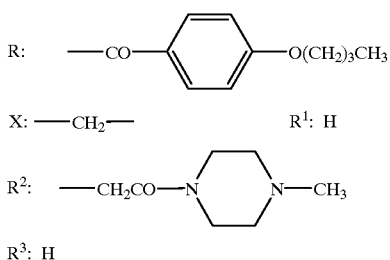

X: —CH₂—   R¹: H

R²: —CH₂CO—[piperazine]—CH₃

R³: H

Crystalline form: Colorless amorphous
Form: Hydrochloride

EXAMPLE 548

Structure

R: 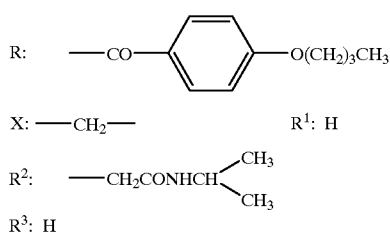

X: —CH₂—   R¹: H

R²: —CH₂CONHCH(CH₃)₂

R³: H

Crystalline form: White powder
Solvent for recrystallization: Diethyl ether
M.p. 133–135° C.
Form: Free

EXAMPLE 549

Structure

R: 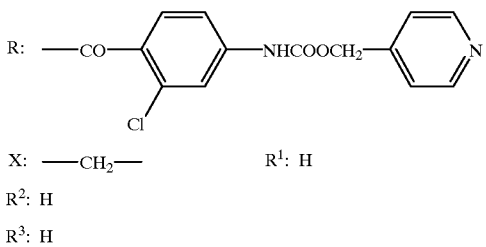

X: —CH₂—   R¹: H

R²: H

R³: H

Crystalline form: White powder
M.p. 181–184° C.
Form: Free

EXAMPLE 550

Structure

R: 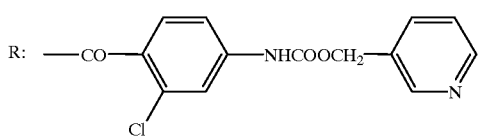

-continued

X: —CH₂—   R¹: H

R²: H

R³: H

Crystalline form: White powder
Solvent for recrystallization: Methanol/diethyl ether
M.p. 197–200° C.
Form: Free

EXAMPLE 551

Structure

R: 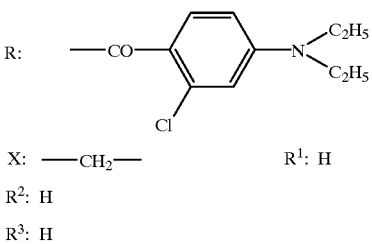

X: —CH₂—   R¹: H

R²: H

R³: H

Crystalline form: White powder
Solvent for recrystallization: Ethyl acetate
M.p. 162–163.5° C.
Form: Free

EXAMPLE 552

Structure

R: 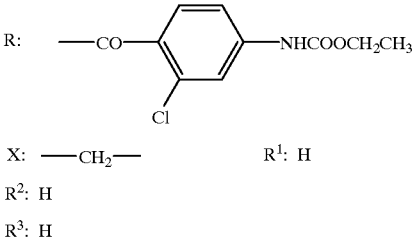

X: —CH₂—   R¹: H

R²: H

R³: H

Crystalline form: White powder
M.p. 168–171° C.
Form: Free

EXAMPLE 553

Structure

R: 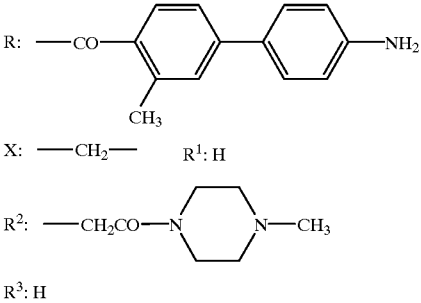

X: —CH₂—   R¹: H

R²: —CH₂CO—[piperazine]—CH₃

R³: H

Crystalline form: Colorless amorphous
Form: Free

EXAMPLE 554

Structure

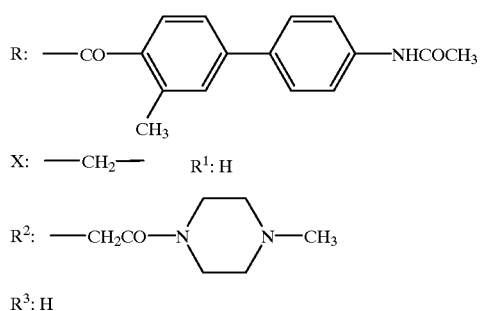

X: —CH₂—   R¹: H

R²: —CH₂CO—N(piperazine)N—CH₃

R³: H

Crystalline form: Colorless amorphous
Form: Free

EXAMPLE 555

Structure

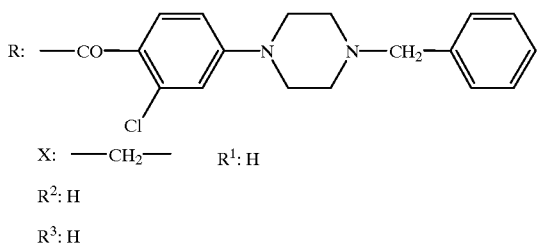

X: —CH₂—   R¹: H

R²: H

R³: H

Crystalline form: Colorless amorphous
Form: Free

EXAMPLE 556

Structure

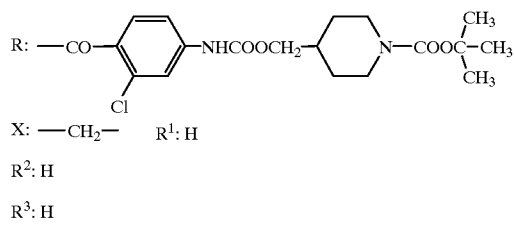

X: —CH₂—   R¹: H

R²: H

R³: H

Crystalline form: Colorless amorphous
Form: Free

EXAMPLE 557

Structure

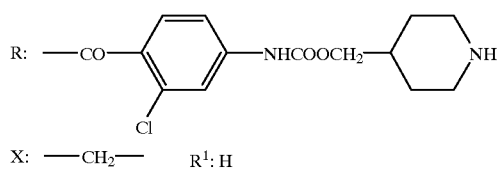

X: —CH₂—   R¹: H

R²: H

R³: H

Crystalline form: White powder
Solvent for recrystallization: Diethyl ether
M.p. 150–152° C.
Form: Trifluoroacetate

EXAMPLE 558

Structure

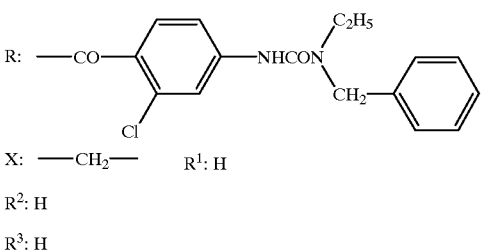

X: —CH₂—   R¹: H

R²: H

R³: H

Crystalline form: White powder
Form: Free

EXAMPLE 559

Structure

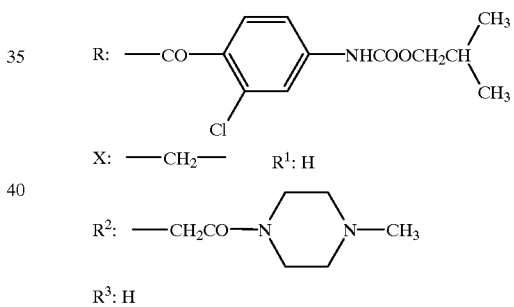

X: —CH₂—   R¹: H

R²: —CH₂CO—N(piperazine)N—CH₃

R³: H

Crystalline form: White powder
Solvent for recrystallization: Diisopropyl ether
Form: Free

EXAMPLE 560

Structure

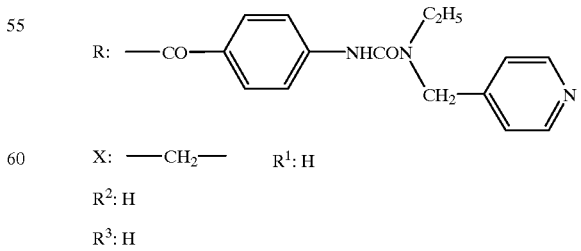

X: —CH₂—   R¹: H

R²: H

R³: H

Crystalline form: Slightly orange amorphous
Form: Hydrochloride

EXAMPLE 561

Structure

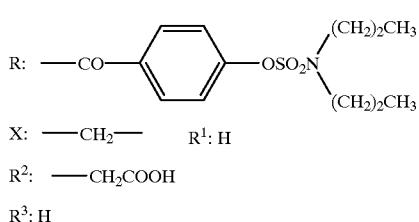

X: —CH$_2$—  R$^1$: H

R$^2$: —CH$_2$COOH

R$^3$: H

Crystalline form: White powder

Solvent for recrystallization: Diethyl ether

M.p. 186–188° C.

Form: Free

EXAMPLE 562

Structure

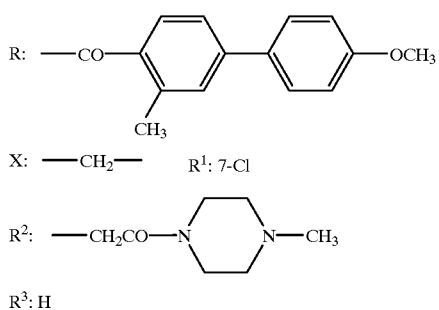

X: —CH$_2$—  R$^1$: 7-Cl

R$^3$: H

Crystalline form: Yellow amorphous

Form: Free

EXAMPLE 563

Structure

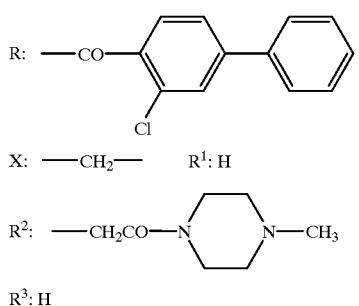

X: —CH$_2$—  R$^1$: H

R$^3$: H

Crystalline form: Colorless amorphous

Form: Hydrochloride

EXAMPLE 564

Structure

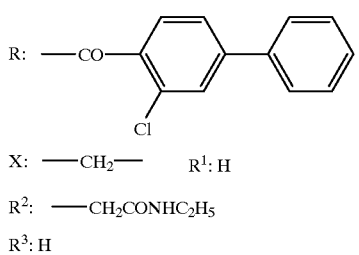

X: —CH$_2$—  R$^1$: H

R$^2$: —CH$_2$CONHC$_2$H$_5$

R$^3$: H

Crystalline form: Colorless amorphous

Form: Free

EXAMPLE 565

Structure

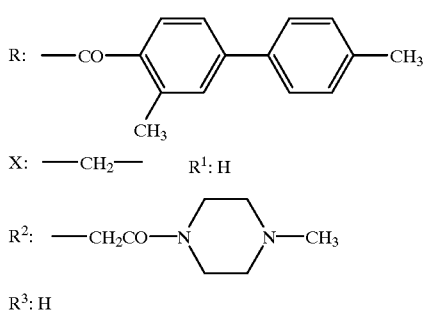

X: —CH$_2$—  R$^1$: H

R$^3$: H

Crystalline form: Colorless amorphous

Form: Hydrochloride

EXAMPLE 566

Structure

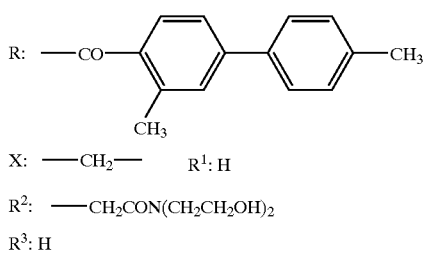

X: —CH$_2$—  R$^1$: H

R$^2$: —CH$_2$CON(CH$_2$CH$_2$OH)$_2$

R$^3$: H

Crystalline form: Colorless amorphous

Form: Free

EXAMPLE 567

Structure

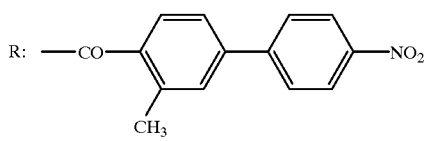

-continued

X: —CH$_2$—   R$^1$: H

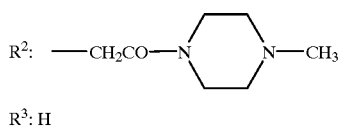

R$^3$: H

Crystalline form: Colorless amorphous
Form: Hydrochloride

EXAMPLE 568

Structure

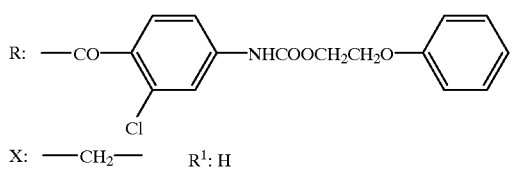

X: —CH$_2$—   R$^1$: H
R$^2$: H
R$^3$: H

Crystalline form: White powder
Solvent for recrystallization: Diethyl ether
M.p. 144–146° C.
Form: Free

EXAMPLE 569

Structure

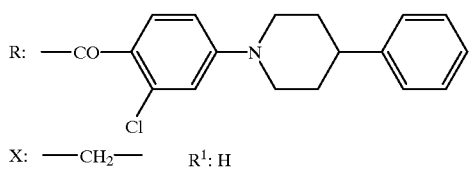

X: —CH$_2$—   R$^1$: H
R$^2$: H
R$^3$: H

Crystalline form: White powder
Sovelnt for recrystallization: Diethyl ether
M.p. 128–130° C.
Form: Free

EXAMPLE 570

Structure

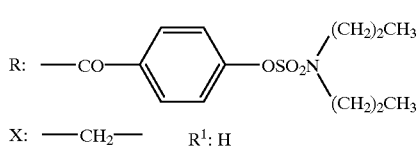

X: —CH$_2$—   R$^1$: H
R$^2$: —CH$_2$COOCH$_3$
R$^3$: H

Crystalline form: White powder
Sovelnt for recrystallization: Diethyl ether
M.p. 110–111° C.
Form: Free

EXAMPLE 571

Structure

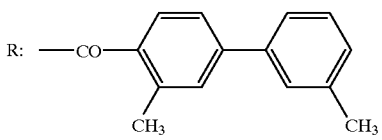

X: —CH$_2$—   R$^1$: H

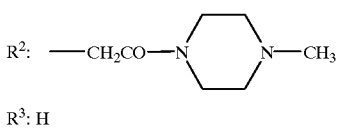

R$^3$: H

Crystalline form: White powder
Solvent for recrystallization: Acetone/diethyl ether
M.p. 161.5–163° C.
Form: Hydrochloride

EXAMPLE 572

Structure

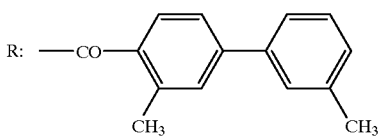

X: —CH$_2$—   R$^1$: H
R$^2$: —CH$_2$CONHC$_2$H$_5$
R$^3$: H

Crystalline form: Colorless amorphous
Form: Free

EXAMPLE 573

Structure

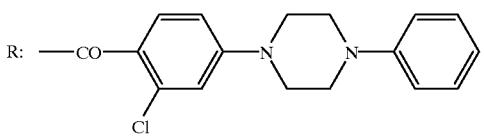

X: —CH$_2$—   R$^1$: H
R$^2$: H
R$^3$: H

Crystalline form: White powder
Solvent for recrystallization: Diisopropyl ether
M.p. 160–162° C.
Form: Free

EXAMPLE 574

Structure

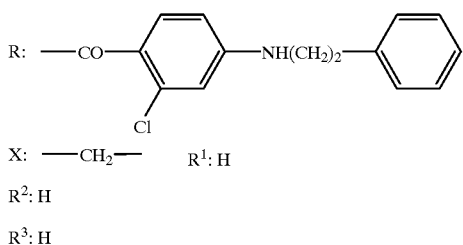

X: —CH₂—  R¹: H
R²: H
R³: H

Crystalline form: White powder
Solvent for recrystallization: Ethanol/ethyl acetate/n-hexane
M.p. 108–109° C.
Form: Free

EXAMPLE 575

Structure

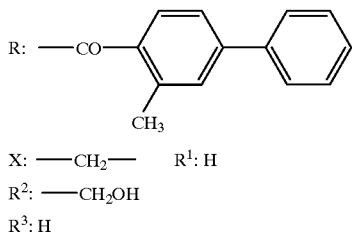

X: —CH₂—  R¹: H
R²: —CH₂OH
R³: H

Crystalline form: White powder
Solvent for recrystallization: Chloroform/diethyl ether
M.p. 104–106° C.
Form: Free

EXAMPLE 576

Structure

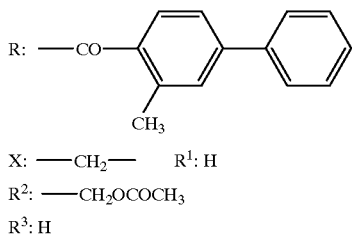

X: —CH₂—  R¹: H
R²: —CH₂OCOCH₃
R³: H

Crystalline form: White powder
Solvent for recrystallization: Chloroform/diethyl ether
M.p. 115–116° C.
Form: Free

EXAMPLE 577

Structure

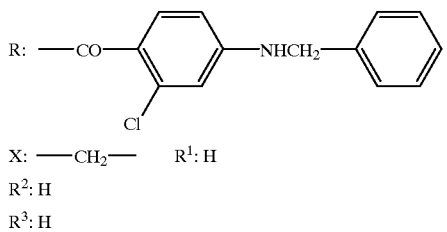

X: —CH₂—  R¹: H
R²: H
R³: H

Crystalline form: Colorless amorphous
Form: Free

EXAMPLE 578

Structure

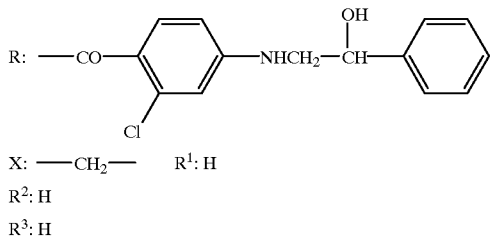

X: —CH₂—  R¹: H
R²: H
R³: H

Crystalline form: Colorless amorphous
Form: Free

EXAMPLE 579

Structure

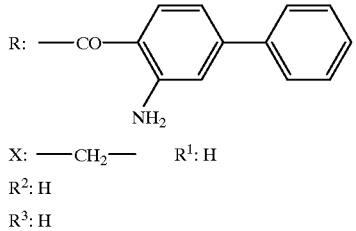

X: —CH₂—  R¹: H
R²: H
R³: H

Crystalline form: Pale yellow powder
Solvent for recrystallization: n-Hexane/ethyl acetate
M.p. 201.5–203° C.
Form: Free

EXAMPLE 580

Structure

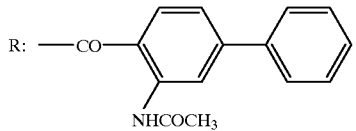

-continued

X: —CH₂—  R¹: H
R²: H
R³: H

Crystalline form: White powder
Solvent for recrystallization: n-Hexane/ethyl acetate
M.p. 196–198° C.
Form: Free

EXAMPLE 581

Structure

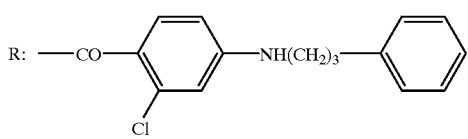

X: —CH₂—  R¹: H
R²: H
R³: H

Crystalline form: White powder
Solvent for recrystallization: Diethyl ether/n-hexane
M.p. 130–133° C.
Form: Free EXAMPLEs 582

Structure

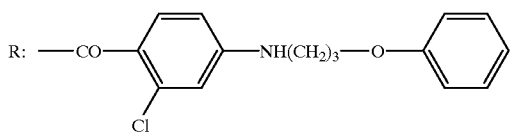

X: —CH₂—  R¹: H
R²: H
R³: H

Crystalline form: White powder
Solvent for recrystallization: Ethyl acetate/n-hexane
M.p. 125–127° C.
Form: Free

EXAMPLE 583

Structure

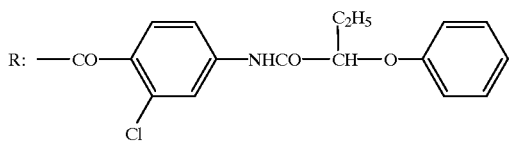

-continued

X: —CH₂—  R¹: H

R²: —CH₂CO—N(piperazine)N—CH₃

R³: H

Crystalline form: Coloreless amorphous
Form: Hydrochloride

EXAMPLE 584

Structure

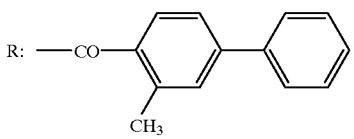

X: —CH₂—  R¹: H
R²: —CH₂CONHC₂H₅
R³: H

Crystalline form: Coloreless amorphous
Form: Free

EXAMPLE 585

Structure

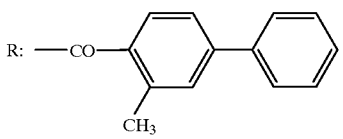

X: —CH₂—  R¹: H

R²: —CH₂CO—N(piperazine)N—CH₃

R³: H

Crystalline form: Coloreless amorphous
Form: Free

EXAMPLE 586

Structure

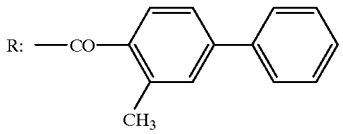

X: —CH₂—  R¹: 7-Cl
R²: —OCH₃
R³: H

Crystalline form: Coloreless amorphous
Form: Free

EXAMPLE 587

Structure

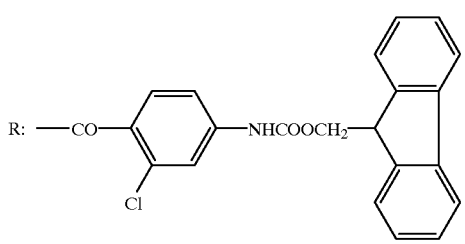

X: —CH$_2$—  R$^1$: H
R$^2$: H
R$^3$: H

Crystalline form: White powder

M.p. 196–198° C.

Form: Free

EXAMPLE 588

Structure

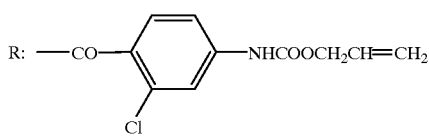

X: —CH$_2$—  R$^1$: H
R$^2$: H
R$^3$: H

Crystalline form: White powder

Solvent for recrystallization: Methanol

M.p. 169–170° C.

Form: Free

EXAMPLE 589

Structure

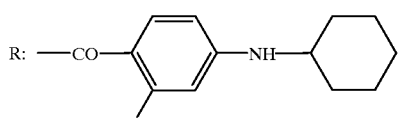

X: —CH$_2$—  R$^1$: H
R$^2$: H
R$^3$: H

Crystalline form: Slightly yellow amorphous

Form: Free

EXAMPLE 590

Structure

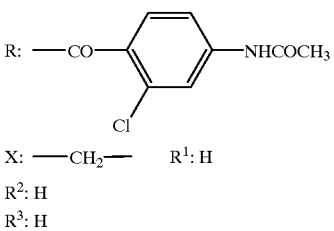

X: —CH$_2$—  R$^1$: H
R$^2$: H
R$^3$: H

Crystalline form: White powder

Solvent for recrystallization: Ethanol

M.p. 218–220° C.

Form: Free

EXAMPLE 591

Structure

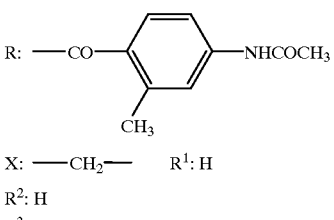

X: —CH$_2$—  R$^1$: H
R$^2$: H
R$^3$: H

Crystalline form: White powder

Solvent for recrystallization: Ethanol

M.p. 194–195° C.

Form: Free

EXAMPLE 592

Structure

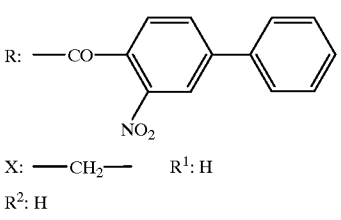

X: —CH$_2$—  R$^1$: H
R$^2$: H
R$^3$: H

Crystalline form: Pale yellow powder

Solvent for recrystallization: n-Hexane/ethyl acetate

M.p. 158–159° C.

Form: Free

EXAMPLE 593

Structure

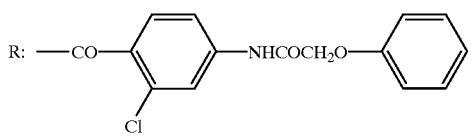

X: —CH$_2$—    R$^1$: H
R$^2$: —OCH$_3$
R$^3$: H

Crystalline form: Colorless amorphous
Form: Free

EXAMPLE 594

Structure

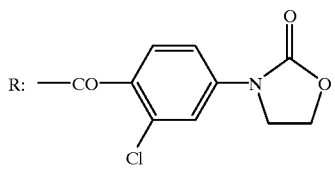

X: —CH$_2$—    R$^1$: H
R$^2$: H
R$^3$: H

Crystalline form: White powder
Form: Free

EXAMPLE 595

Structure

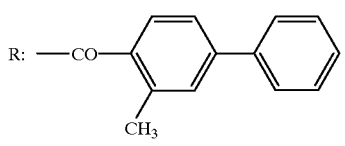

X: —CH$_2$—    R$^1$: H
R$^2$: —N(C$_2$H$_5$)$_2$
R$^3$: H

Crystalline form: Yellow amorphous
Form: Free

EXAMPLE 596

Structure

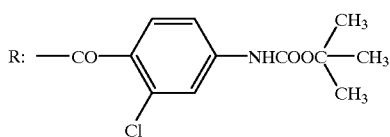

-continued
X: —CH$_2$—    R$^1$: H
R$^2$: H
R$^3$: H

Crystalline form: White powder
Solvent for recrystallizatin: Diisopropyl ether
M.p. 205–206° C.
Form: Free

EXAMPLE 597

Structure

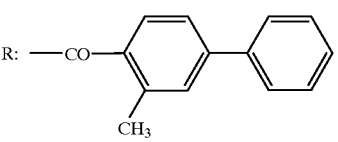

X: —CH$_2$—    R$^1$: 7-Cl
R$^2$: —OH
R$^3$: —CH$_2$OH

Crystalline form: White powder
Solvent for recrystallization: Chloroform/diethyl ether
M.p. 142–144° C.
Form: Free

EXAMPLE 598

Structure

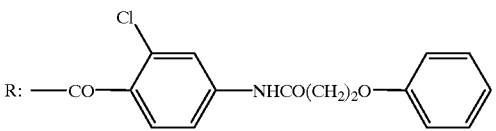

X: —CH$_2$—    R$^1$: H
R$^2$: H
R$^3$: H

Crystalline form: White powder
Solvent for recrystallization: Diethyl ether
M.p. 132–135° C.
Form: Free

EXAMPLE 599

Structure

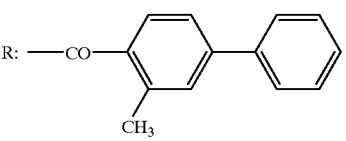

-continued

X: —CH$_2$—  R$^1$: H

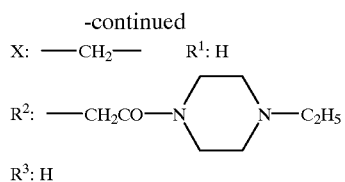

R$^2$: —CH$_2$CO—N-piperazine-N—C$_2$H$_5$

R$^3$: H

Crystalline form: Pale yellow amorphous
Form: Hydrochloride

EXAMPLE 600

Structure

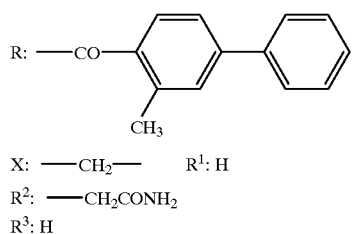

X: —CH$_2$—  R$^1$: H
R$^2$: —CH$_2$CONH$_2$
R$^3$: H

Crystalline form: Pale brown powder
Solvent for recrystallization: Chloroform/diethyl ether
M.p. 119–121° C.
Form: Hydrochloride

EXAMPLE 601

Structure

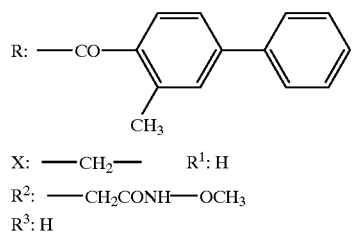

X: —CH$_2$—  R$^1$: H
R$^2$: —CH$_2$CONH—OCH$_3$
R$^3$: H

Crystalline form: Colorless amorphous
Form: Free

EXAMPLE 602

Structure

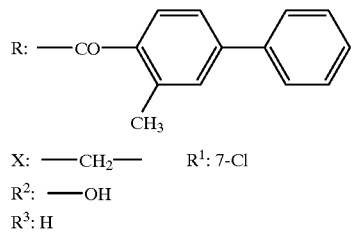

X: —CH$_2$—  R$^1$: 7-Cl
R$^2$: —OH
R$^3$: H

Crystalline form: White powder
Solvent for recrystallization: Chloroform/diethyl ether
M.p. 175–178° C.
Form: Free

EXAMPLE 603

Structure

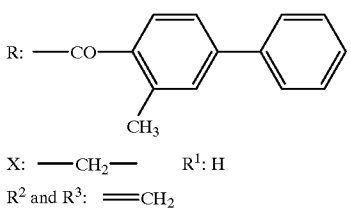

X: —CH$_2$—  R$^1$: H
R$^2$ and R$^3$: =CH$_2$

Crystalline form: Pale yellow powder

Solvent for recrystallization: Diisopropyl ether/n-hexane

M.p. 113–115° C.

Form: Free

EXAMPLE 604

Structure

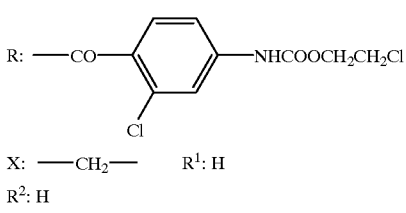

X: —CH$_2$—  R$^1$: H
R$^2$: H
R$^3$: H

Crystalline form: White powder

M.p. 128–130° C.

Form: Free

EXAMPLE 605

Structure

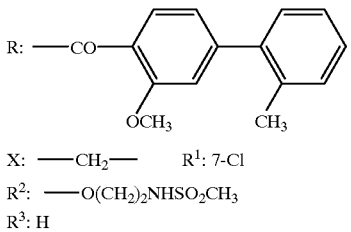

X: —CH$_2$—  R$^1$: 7-Cl
R$^2$: —O(CH$_2$)$_2$NHSO$_2$CH$_3$
R$^3$: H

Crystalline form: Pale yellow powder

Solvent for recrystallization: Chloroform/diethyl ether

M.p. 182–183° C.

Form: Free

EXAMPLE 606

Structure

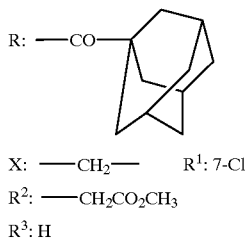

X: —CH$_2$—　R$^1$: 7-Cl
R$^2$: —CH$_2$CO$_2$CH$_3$
R$^3$: H

Crystalline form: Colorless oil
Form: Free

EXAMPLE 607

Structure

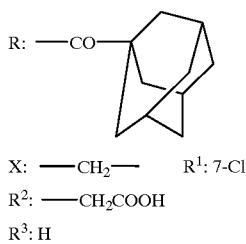

X: —CH$_2$—　R$^1$: 7-Cl
R$^2$: —CH$_2$COOH
R$^3$: H

Crystalline form: Colorless amorphous
Form: Free

EXAMPLE 608

Structure

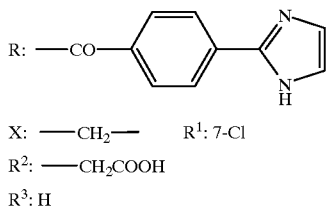

X: —CH$_2$—　R$^1$: 7-Cl
R$^2$: —CH$_2$COOH
R$^3$: H

Crystalline form: Yellow amorphous
Form: Free

EXAMPLE 609

Structure

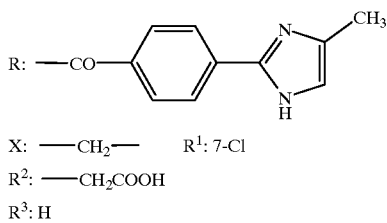

X: —CH$_2$—　R$^1$: 7-Cl
R$^2$: —CH$_2$COOH
R$^3$: H

Crystalline form: Yellow amorphous
Form: Free

EXAMPLE 610

Structure

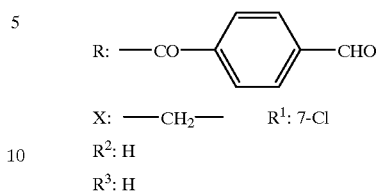

X: —CH$_2$—　R$^1$: 7-Cl
R$^2$: H
R$^3$: H

Crystalline form: Yellow amorphous
Form: Free

EXAMPLE 611

Structure

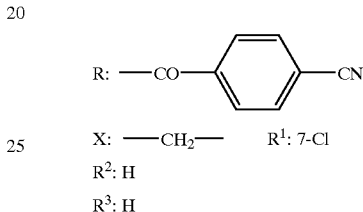

X: —CH$_2$—　R$^1$: 7-Cl
R$^2$: H
R$^3$: H

Crystalline form: Brown amorphous
Form: Free

EXAMPLE 612

Structure

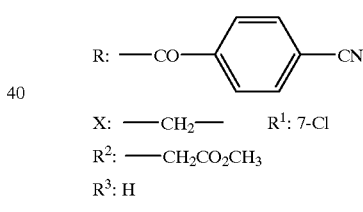

X: —CH$_2$—　R$^1$: 7-Cl
R$^2$: —CH$_2$CO$_2$CH$_3$
R$^3$: H

Crystalline form: Pale brown powder
Solvent for recrystallization: Chloroform/diethyl ether
M.p. 149–151° C.
Form: Free

EXAMPLE 613

Structure

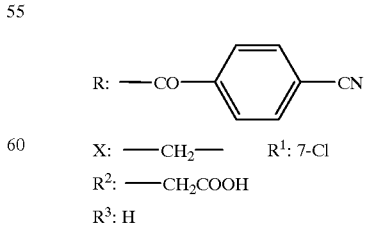

X: —CH$_2$—　R$^1$: 7-Cl
R$^2$: —CH$_2$COOH
R$^3$: H

Crystalline form: Pale brown amorphous
Form: Free

EXAMPLE 614

Structure

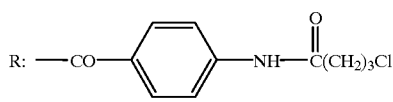

X: —CH$_2$—   R$^1$: 7-Cl

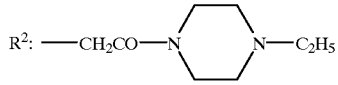

R$^3$: H

Crystalline form: Pale yellow amorphous
Form: Free

EXAMPLE 615

Structure

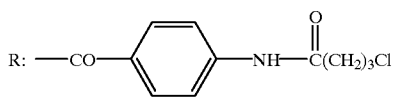

X: —CH$_2$—   R$^1$: 7-Cl

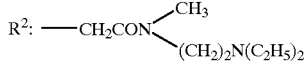

R$^3$: H

Crystalline form: Colorless oil
Form: Free

EXAMPLE 616

Structure

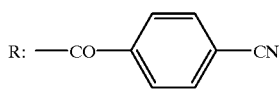

X: —CH$_2$—   R$^1$: 7-Cl

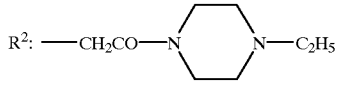

R$^3$: H

Crystalline form: Colorless amorphous
Form: Free

EXAMPLE 617

Structure

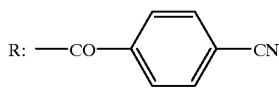

-continued

X: —CH$_2$—   R$^1$: 7-Cl

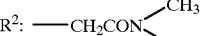
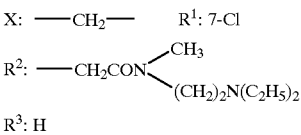

R$^3$: H

Crystalline form: Pale brown oil
Form: Free

EXAMPLE 618

Structure

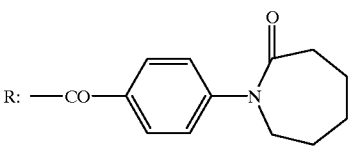

X: —CH$_2$—   R$^1$: 7-Cl
R$^2$: —CH$_2$CO$_2$CH$_3$
R$^3$: H

Crystalline form: Pale yellow oil
Form: Free

EXAMPLE 619

Structure

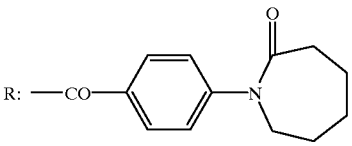

X: —CH$_2$—   R$^1$: 7-Cl
R$^2$: —CH$_2$COOH
R$^3$: H

Crystalline form: Colorless amorphous
Form: Free

EXAMPLE 620

Structure

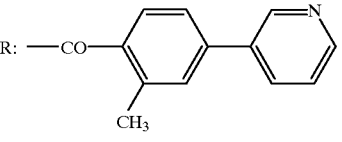

X: —CH$_2$—   R$^1$: 7-Cl
R$^2$: —CH$_2$CO$_2$CH$_3$
R$^3$: H

Crystalline form: Pale yellow powder
Solvent for recrystallization: Chloroform/diethyl ether
M.p. 151–161° C.

EXAMPLE 621

Structure

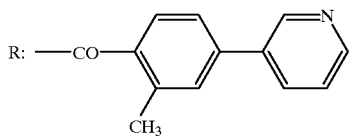

X: —CH₂— R¹: 7-Cl
R²: —CH₂COOH
R³: H

Crystalline form: White powder
Solvent for recrystallization: Methanol/diethyl ether
M.p. 258–260° C.
Form: Hydrochloride

EXAMPLE 622

Structure

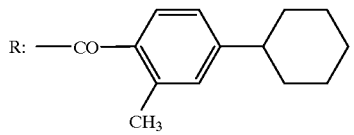

X: —CH₂— R¹: 7-Cl
R²: —CH₂COOH
R³: H

Crystalline form: Colorless amorphous
Form: Free

EXAMPLE 623

Structure

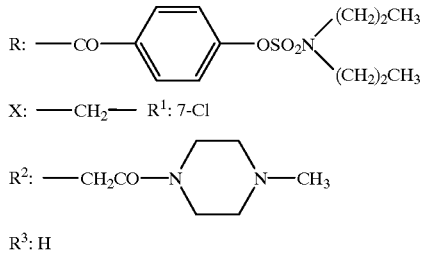

X: —CH₂— R¹: 7-Cl
R²: —CH₂CO—N(piperazine)N—CH₃
R³: H

Crystalline form: Colorless amorphous
Form: Hydrochloride

EXAMPLE 624

Structure

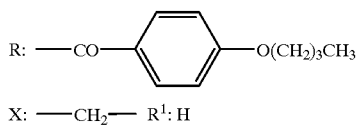

X: —CH₂— R¹: H
R²: —CH₂CO₂CH₃
R³: H

Crystalline form: Colorless amorphous
Form: Free

EXAMPLE 625

Structure

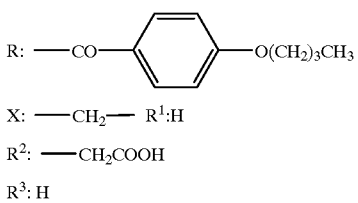

X: —CH₂— R¹: H
R²: —CH₂COOH
R³: H

Crystalline form: White powder
Solvent for recrystallization: Diethyl ether
M.p. 188–189° C.
Form: Free

EXAMPLE 626

Structure

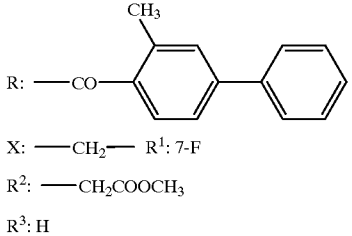

X: —CH₂— R¹: 7-F
R²: —CH₂COOCH₃
R³: H

Crystalline form: Colorless amorphous
Form: Free

EXAMPLE 627

Structure

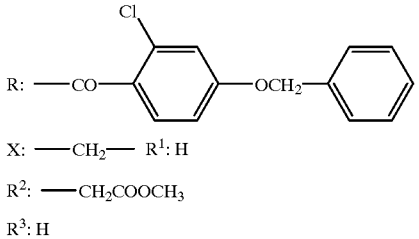

X: —CH₂— R¹: H
R²: —CH₂COOCH₃
R³: H

Crystalline form: Colorless amorphous
Form: Free

EXAMPLE 628

Structure

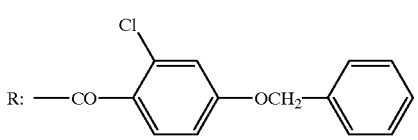

X: —CH$_2$— R$^1$: H
R$^2$: —CH$_2$COOH
R$^3$: H

Crystalline form: White powder
Solvent for recrystallization: Diethyl ether
M.p. 178–179° C.
Form: Free

EXAMPLE 629

Structure

X: —CH$_2$— R$^1$: 7-F
R$^2$: —CH$_2$COOCH$_3$
R$^3$: H

Crystalline form: Colorless oil
Form: Free

EXAMPLE 630

Structure

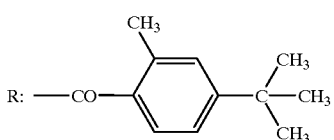

X: —CH$_2$— R$^1$: H
R$^2$: —CH$_2$COOCH$_3$
R$^3$: H

Crystalline form: Colorless oil
Form: Free

EXAMPLE 631

Structure

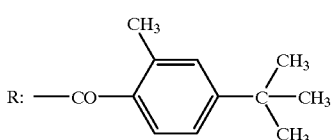

X: —CH$_2$— R$^1$: H

-continued

R$^2$: —CH$_2$COOH
R$^3$: H

Crystalline form: White powder
Form: Free

EXAMPLE 632

Structure

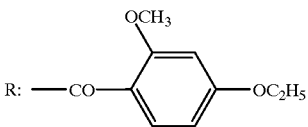

X: —CH$_2$— R$^1$: 7-Cl
R$^2$: —CH$_2$CO$_2$CH$_3$
R$^3$: H

Crystalline form: Colorless amorphous
Form: Free

EXAMPLE 633

Structure

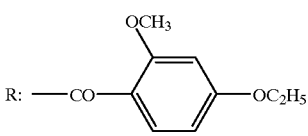

X: —CH$_2$— R$^1$: 7-Cl
R$^2$: —CH$_2$COOH
R$^3$: H

Crystalline form: Colorless amorphous
Form: Free

EXAMPLE 634

Structure

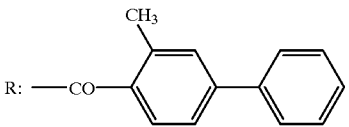

X: —CH$_2$— R$^1$: 7-F
R$^2$: —CH$_2$COOH
R$^3$: H

Crystalline form: Colorless amorphous
Form: Free

EXAMPLE 635

Structure

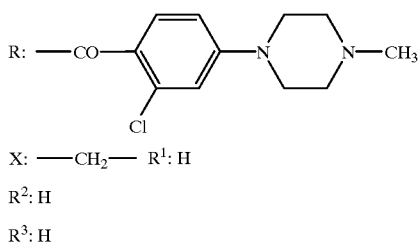

X: —CH₂— R¹: H

R²: H

R³: H

Crystalline form: White powder

M.p. 138–140° C.

Form: Free

EXAMPLE 636

Structure

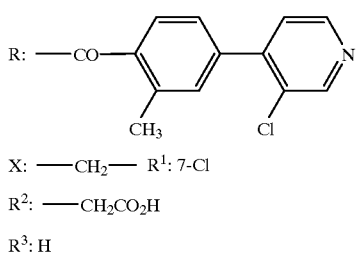

X: —CH₂— R¹: 7-Cl

R²: —CH₂CO₂H

R³: H

Crystalline form: White powder

Solvent for recrystallizatin: Ethanol/diethyl ether

M.p. 208–211° C.

Form: Free

EXAMPLE 637

Structure

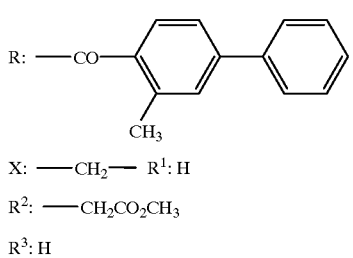

X: —CH₂— R¹: H

R²: —CH₂CO₂CH₃

R³: H

Crystalline form: Pale brown oil

Form: Free

EXAMPLE 638

Structure

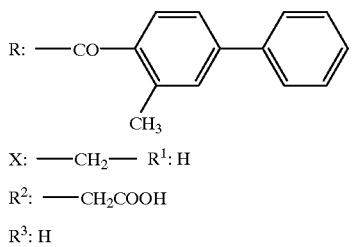

X: —CH₂— R¹: H

R²: —CH₂COOH

R³: H

Crystalline form: Pale brown powder

Solvent for recrystallization: Chloroform/diethyl ether

M.p. 192–194° C.

Form: Free

EXAMPLE 639

Structure

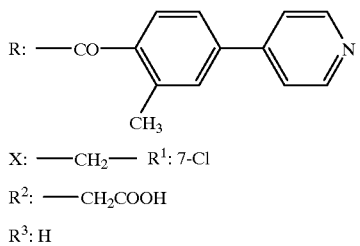

X: —CH₂— R¹: 7-Cl

R²: —CH₂COOH

R³: H

Crystalline form: White powder

Solvent for recrystallization: Ethanol/diethyl ether

M.p. 238–239° C.

Form: Hydrochloride

EXAMPLE 640

Structure

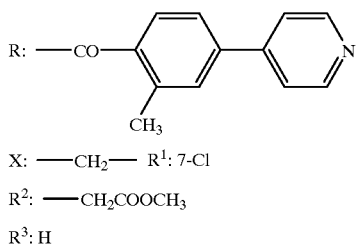

X: —CH₂— R¹: 7-Cl

R²: —CH₂COOCH₃

R³: H

Crystalline form: Pale yellow solid

Form: Free

EXAMPLE 641

Structure

R: —CO—[4-phenyl]—N(benzazepinone)

X: —CH₂—  R¹: 7-Cl
R²: —CH₂COOCH₃
R³: H

Crystalline form: White powder
M.p. 82–87° C.
Form: Free

EXAMPLE 642

Structure

R: —CO—[4-phenyl]—N(benzazepinone)

X: —CH₂—  R¹: 7-Cl
R²: —CH₂COOH
R³: H

Crystalline form: White powder
M.p. 121–127° C.
Form: Free

EXAMPLE 643

Structure

R: —CO—[4-(3-Cl)phenyl]—NHCOOCH₂CH(CH₃)₂

X: —CH₂—  R¹: H
R²: —CH₂COOCH₃
R³: H

Crystalline form: Colorless amorphous
Form: Free

EXAMPLE 644

Structure

R: —CO—[4-(3-Cl)phenyl]—NHCOOCH₂CH(CH₃)₂

X: —CH₂—  R¹: H
R²: —CH₂COOH
R³: H

Crystalline form: Colorless amorphous
Form: Free

EXAMPLE 645

Structure

R: —CO—[4-(3-Cl)phenyl]—NHCOOCH₂CH₂Cl

X: —CH₂—  R¹: H
R²: —CH₂COOCH₃
R³: H

Crystalline form: White powder
Form: Free

EXAMPLE 646

Structure

R: —CO—[4-(3-Cl)phenyl]—N(oxazolidinone)

X: —CH₂—  R¹: H
R²: —CH₂COOCH₃
R³: H

Crystalline form: Colorless amorphous
Form: Free

EXAMPLE 647

Structure

R: —CO—[4-(3-Cl)phenyl]—NHCOO(CH₂)₃Cl

-continued

X: —CH$_2$— R$^1$: H
R$^2$: —CH$_2$COOCH$_3$
R$^3$: H

Crystalline form: Colorless amorphous

Form: Free

EXAMPLE 648

Structure

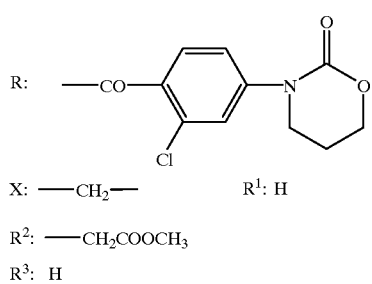

X: —CH$_2$— R$^1$: H
R$^2$: —CH$_2$COOCH$_3$
R$^3$: H

Crystalline form: Brown amorphous

Form: Free

EXAMPLE 649

Structure

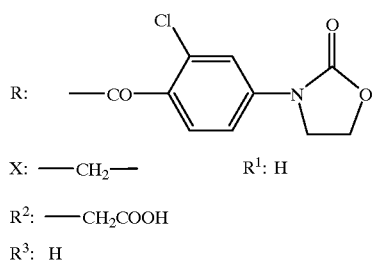

X: —CH$_2$— R$^1$: H
R$^2$: —CH$_2$COOH
R$^3$: H

Crystalline form: White powder

Form: Free

EXAMPLE 650

Structure

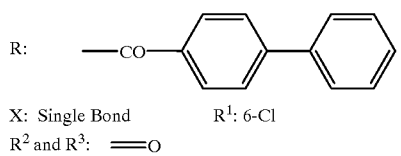

X: Single Bond R$^1$: 6-Cl
R$^2$ and R$^3$: =O

Crystalline form: Slightly yellow powder

Form: Free

EXAMPLE 651

Structure

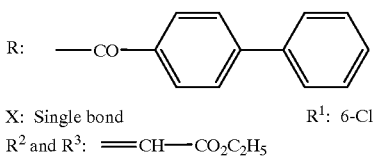

X: Single bond R$^1$: 6-Cl
R$^2$ and R$^3$: =CH—CO$_2$C$_2$H$_5$

Crystalline form: Slightly yellow amorphous

Form: Free

EXAMPLE 652

Structure

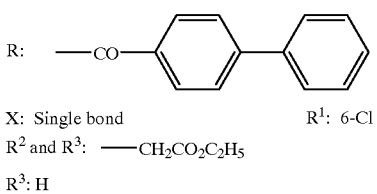

X: Single bond R$^1$: 6-Cl
R$^2$ and R$^3$: —CH$_2$CO$_2$C$_2$H$_5$
R$^3$: H

Crystalline form: Slightly yellow amorphous

Form: Free

EXAMPLE 653

Structure

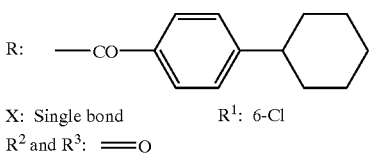

X: Single bond R$^1$: 6-Cl
R$^2$ and R$^3$: =O

Crystalline form: Yellow solid

Form: Free

EXAMPLE 654

Structure

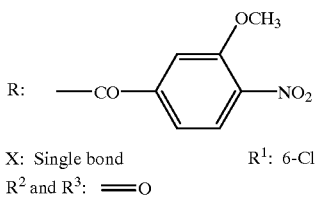

X: Single bond R$^1$: 6-Cl
R$^2$ and R$^3$: =O

Crystalline form: Yellow powder

Form: Free

EXAMPLE 655

Structure

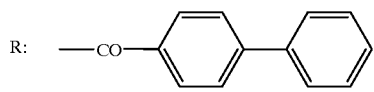

X: Single bond R¹: 6-Cl
R²: —CH₂CO₂H
R³: H

Crystalline form: Colorless amorphous
Form: Free

EXAMPLE 656

Structure

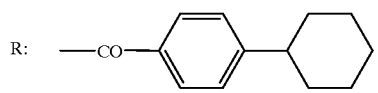

X: Single bond R¹: 6-Cl
R² and R³: =CH—COOC₂H₅

Crystalline form: White powder
Form: Free

EXAMPLE 657

Structure

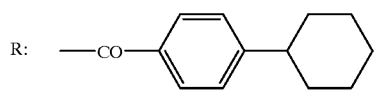

X: Single bond R¹: 6-Cl
R²: —CH₂COOH
R³: H

Crystalline form: Colorless amorphous
Form: Free

EXAMPLE 658

Structure

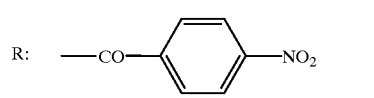

X: Single bond R¹: 6-Cl
R²: —CH₂CO₂CH₃
R³: H

Crystalline form: Yellow powder
Form: Free

EXAMPLE 659

Structure

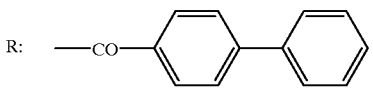

X: Single bond R¹: 6-Cl
R²: —CH₂COOH
R³: H

Crystalline form: Colorless amorphous
Form: Free

EXAMPLE 660

Structure

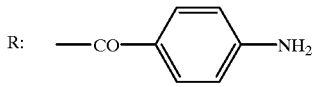

X: Single bond R¹: 6-Cl
R²: —CH₂CO₂CH₃
R³: H

Crystalline form: White powder
Form: Free

EXAMPLE 661

Structure

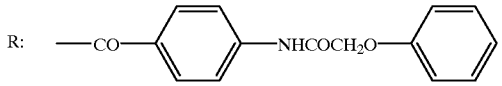

X: Single bond R¹: 6-Cl
R²: —CH₂CO₂CH₃
R³: H

Crystalline form: Coloreless amorphous
Form: Free

EXAMPLE 662

Structure

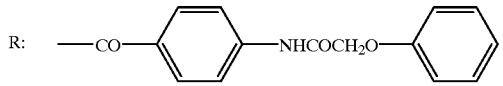

X: Single bond R¹: 6-Cl
R²: —CH₂COOH
R³: H

Crystalline form: Colorless amorphous
Form: Free

EXAMPLE 663

Structure

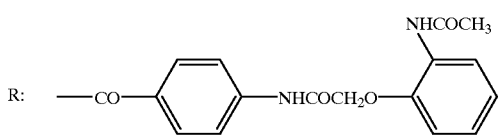

X: Single bond  R¹: 6-Cl
R²: —CH$_2$CO$_2$CH$_3$
R³: H

Crystalline form: Colorless amorphous
Form: Free

EXAMPLE 664

Structure

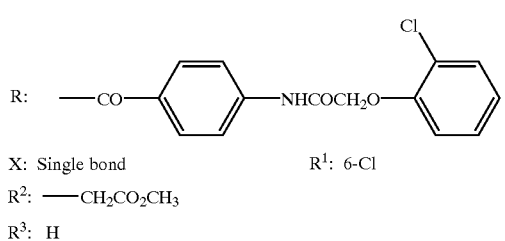

X: Single bond  R¹: 6-Cl
R²: —CH$_2$CO$_2$CH$_3$
R³: H

Crystalline form: Red amorphous
Form: Free

EXAMPLE 665

Structure

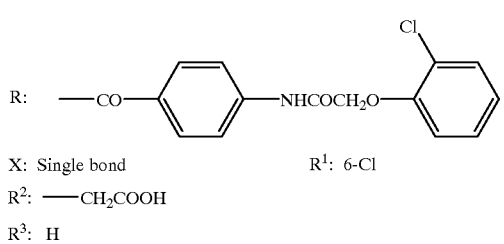

X: Single bond  R¹: 6-Cl
R²: —CH$_2$COOH
R³: H

Crystalline form: Yellow amorphous
Form: Free

EXAMPLE 666

Structure

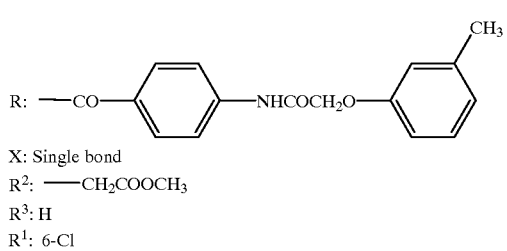

X: Single bond
R²: —CH$_2$COOCH$_3$
R³: H
R¹: 6-Cl

Crystalline form: Colorless amorphous
Form: Free

EXAMPLE 667

Structure

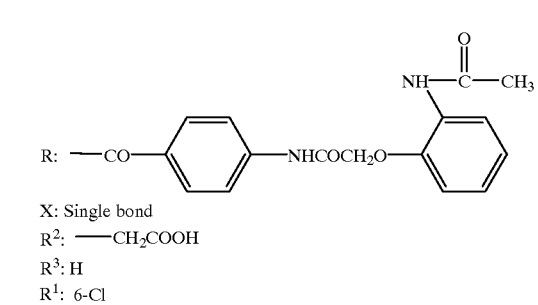

X: Single bond
R²: —CH$_2$COOH
R³: H
R¹: 6-Cl

Crystalline form: Colorless amorphous

Form: Free

EXAMPLE 668

Structure

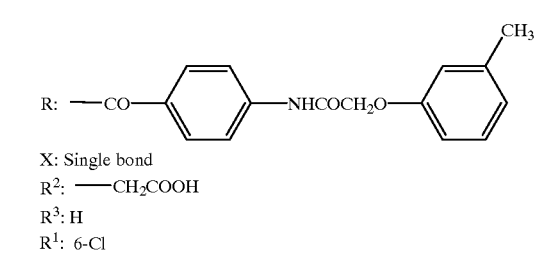

X: Single bond
R²: —CH$_2$COOH
R³: H
R¹: 6-Cl

Crystalline form: Colorless amorphous

Form: Free

EXAMPLE 669

Structure

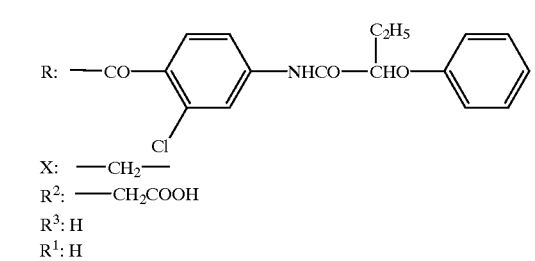

X: —CH$_2$—
R²: —CH$_2$COOH
R³: H
R¹: H

Crystalline form: Colorless amorphous

Form: Free

EXAMPLE 670

Structure

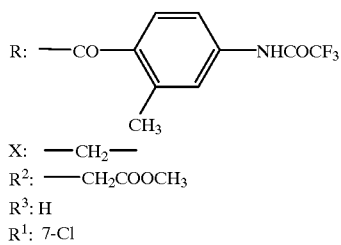

X: —CH₂—
R²: —CH₂COOCH₃
R³: H
R¹: 7-Cl

Crystalline form: Slightly red powder

Form: Free

EXAMPLE 671

Structure

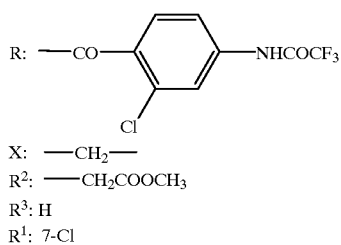

X: —CH₂—
R²: —CH₂COOCH₃
R³: H
R¹: 7-Cl

Crystalline form: White powder

Form: Free

EXAMPLE 672

Structure

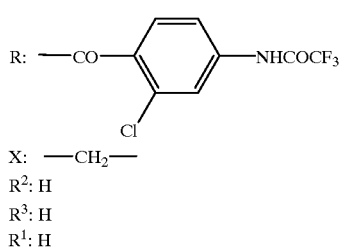

X: —CH₂—
R²: H
R³: H
R¹: H

Crystalline form: Slightly red powder

Form: Free

EXAMPLE 673

Structure

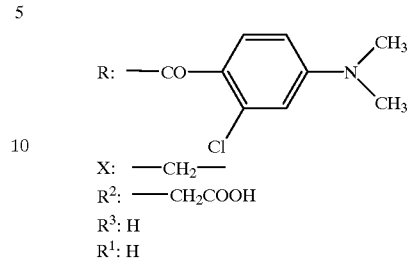

X: —CH₂—
R²: —CH₂COOH
R³: H
R¹: H

Crystalline form: Colorless amorphous

Form: Free

EXAMPLE 674

Structure

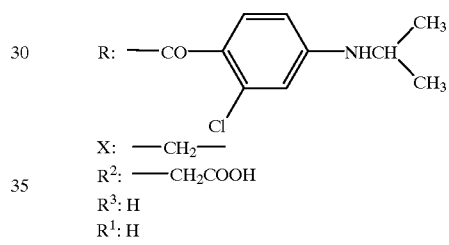

X: —CH₂—
R²: —CH₂COOH
R³: H
R¹: H

Crystalline form: Colorless amorphous

Form: Free

EXAMPLE 675

Structure

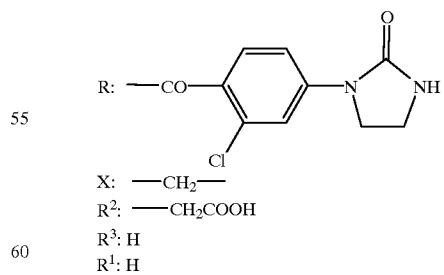

X: —CH₂—
R²: —CH₂COOH
R³: H
R¹: H

Crystalline form: Colorless amorphous

Form: Free

EXAMPLE 676

Structure

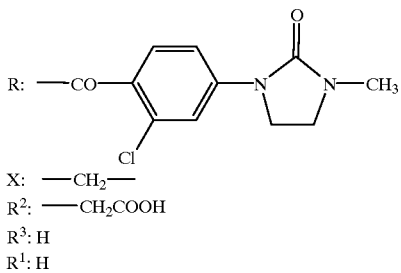

X: —CH$_2$—
R$^2$: —CH$_2$COOH
R$^3$: H
R$^1$: H

Crystalline form: Colorless amorphous

Form: Free

EXAMPLE 677

Structure

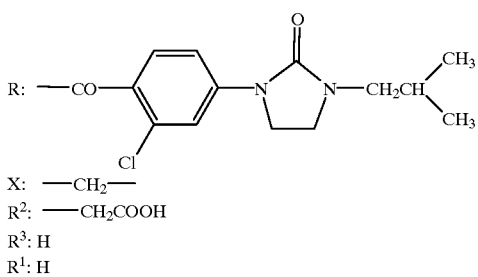

X: —CH$_2$—
R$^2$: —CH$_2$COOH
R$^3$: H
R$^1$: H

Crystalline form: Colorless amorphous

Form: Free

EXAMPLE 678

Structure

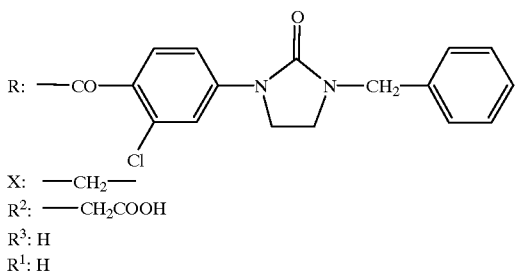

X: —CH$_2$—
R$^2$: —CH$_2$COOH
R$^3$: H
R$^1$: H

Crystalline form: Colorless amorphous

Form: Free

EXAMPLE 679

Structure

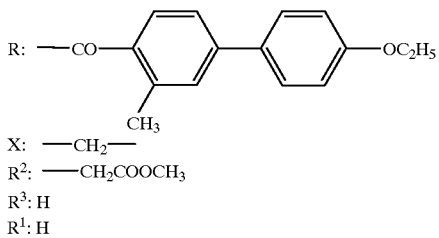

X: —CH$_2$—
R$^2$: —CH$_2$COOCH$_3$
R$^3$: H
R$^1$: H

Crystalline form: Colorless amorphous

Form: Free

EXAMPLE 680

Structure

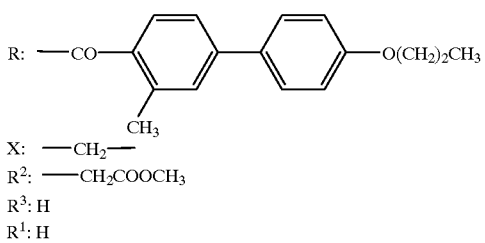

X: —CH$_2$—
R$^2$: —CH$_2$COOCH$_3$
R$^3$: H
R$^1$: H

Crystalline form: Colorless amorphous

Form: Free

EXAMPLE 681

Structure

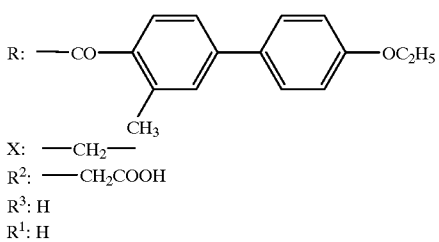

X: —CH$_2$—
R$^2$: —CH$_2$COOH
R$^3$: H
R$^1$: H

Crystalline form: White powder

Solvent for recrystallization: Ethanol/diethyl ether

M.p. 183–183.5° C.

Form: Free

EXAMPLE 682

Structure

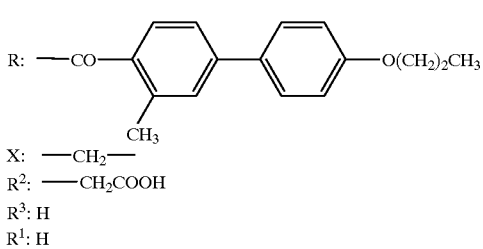

X: —CH$_2$—
R$^2$: —CH$_2$COOH
R$^3$: H
R$^1$: H

Crystalline form: White powder

Solvent for recrystallization: Ethanol/diethyl ether

M.p. 169.5–170° C.

Form: Free

EXAMPLE 683

Structure

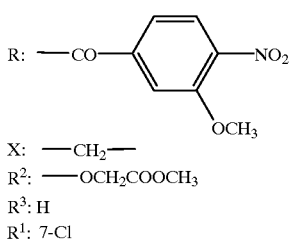

X: —CH$_2$—
R$^2$: —OCH$_2$COOCH$_3$
R$^3$: H
R$^1$: 7-Cl

Crystalline form: Slightly yellow powder

Form: Free

EXAMPLE 684

Structure

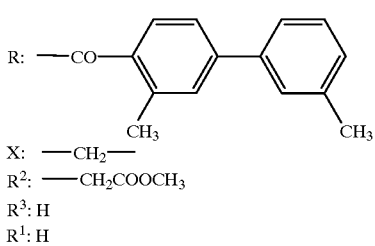

X: —CH$_2$—
R$^2$: —CH$_2$COOCH$_3$
R$^3$: H
R$^1$: H

Crystalline form: Colorless amorphous

Form: Free

EXAMPLE 685

Structure

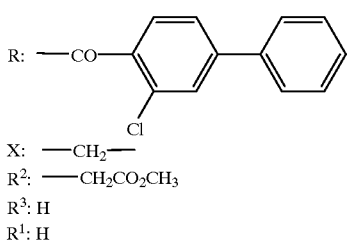

X: —CH$_2$—
R$^2$: —CH$_2$CO$_2$CH$_3$
R$^3$: H
R$^1$: H

Crystalline form: Colorless amorphous
Form: Free

EXAMPLE 686

Structure

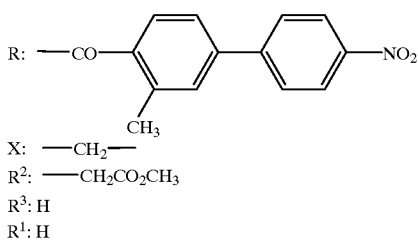

X: —CH$_2$—
R$^2$: —CH$_2$CO$_2$CH$_3$
R$^3$: H
R$^1$: H

Crystalline form: Slightly yellow powder
Form: Free

EXAMPLE 687

Structure

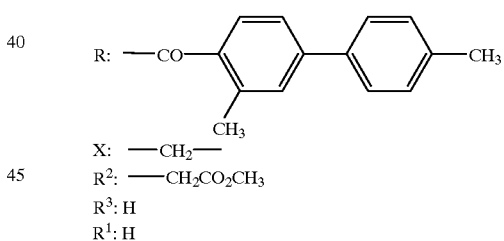

X: —CH$_2$—
R$^2$: —CH$_2$CO$_2$CH$_3$
R$^3$: H
R$^1$: H

Crystalline form: Colorless amorphous
Form: Free

EXAMPLE 688

Structure

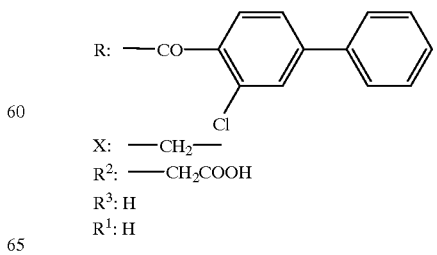

X: —CH$_2$—
R$^2$: —CH$_2$COOH
R$^3$: H
R$^1$: H

Crystalline form: White powder

Solvent for recrystallization: Ethanol/diethyl ether
M.p. 176–177° C.
Form: Free

EXAMPLE 689

Structure

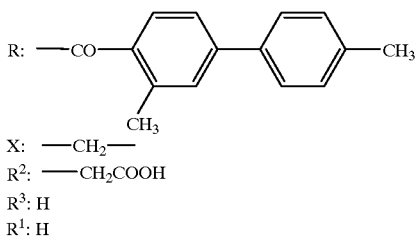

X: —CH$_2$—
R$^2$: —CH$_2$COOH
R$^3$: H
R$^1$: H

Crystalline form: Colorless amorphous
Form: Free

EXAMPLE 690

Structure

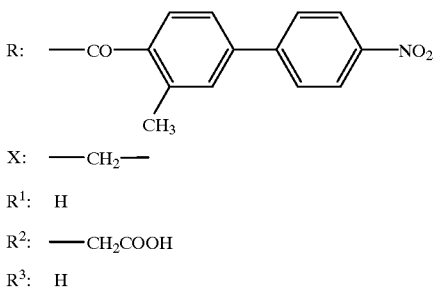

X: —CH$_2$—
R$^1$: H
R$^2$: —CH$_2$COOH
R$^3$: H

Crystalline form: Slightly yellow powder
Form: Free

EXAMPLE 691

Structure

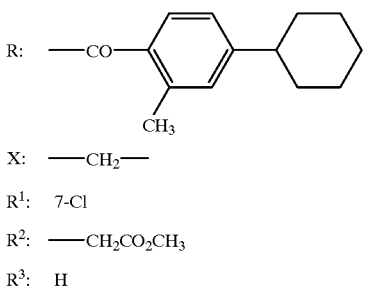

X: —CH$_2$—
R$^1$: 7-Cl
R$^2$: —CH$_2$CO$_2$CH$_3$
R$^3$: H

Crystalline form: Colorless amorphous
Form: Free

The sutiable starting compounds are treated in the same manner as in Examples 1 and 2 to give the following compounds.

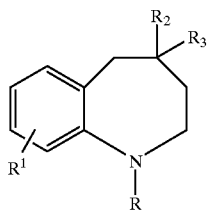

EXAMPLE 692

Structure

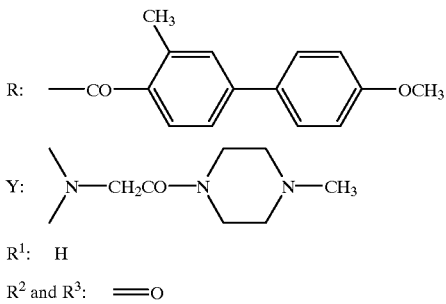

R$^1$: H
R$^2$ and R$^3$: =O

Crystalline form: Colorless amorphous
Form: Free

EXAMPLE 693

Structure

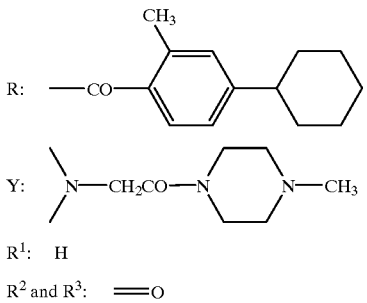

R$^1$: H
R$^2$ and R$^3$: =O

Crystalline form: Colorless amorphous
Form: Free

EXAMPLE 694

Structure

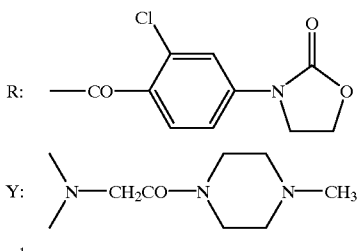

R$^1$: H

-continued

R² and R³: ═O

Crystalline form: White powder
M.p. 166–170° C.
Form: Free

EXAMPLE 695

Structure

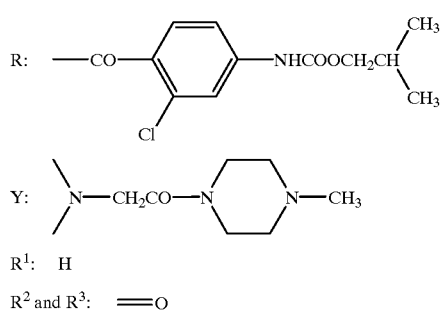

R¹: H
R² and R³: ═O

Crystalline form: White powder
Solvent for recrystallization: Diethyl ether
M.p. 215–218° C. (decomposed)
Form: Free

EXAMPLE 696

Structure

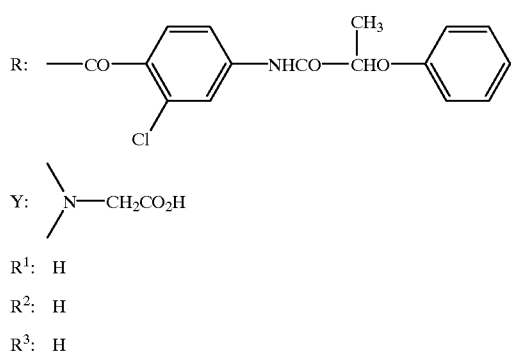

R¹: H
R²: H
R³: H

Crystalline form: White powder
Solvent for recrystallization: Diethyl ether
M.p. 182–188° C. (decomposed)
Form: Free

EXAMPLE 697

Structure

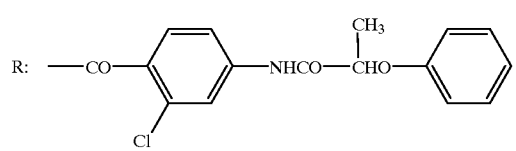

-continued

Y: \N—CH₂CO—N⟨piperazine⟩N—CH₃

R¹: H
R²: H
R³: H

Crystalline form: White powder
Solvent for recrystallization: Diethyl ether
M.p. 105–108° C.
Form: Free

EXAMPLE 698

Structure

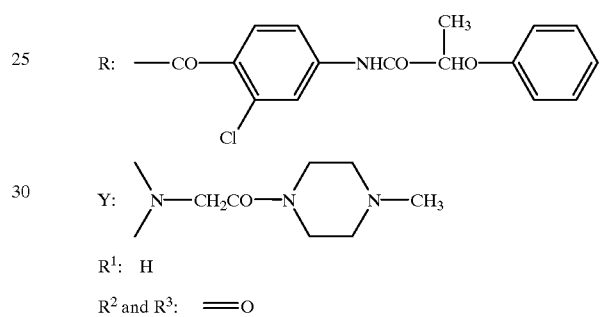

R¹: H
R² and R³: ═O

Crystalline form: White powder
M.p. 154–158° C.
Form: Free

EXAMPLE 699

Structure

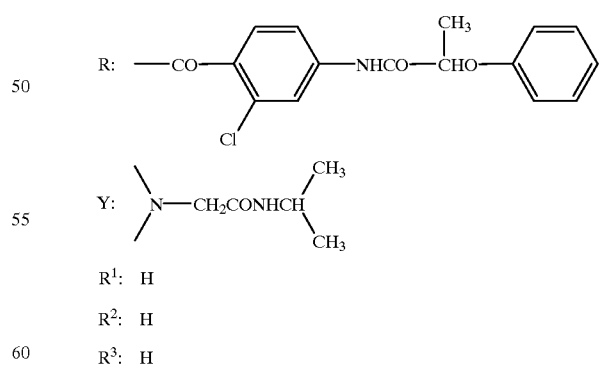

R¹: H
R²: H
R³: H

Crystalline form: White powder
Solvent for recrystallization: Diethyl ether
M.p. 144–145° C.

EXAMPLE 700

Structure

R: 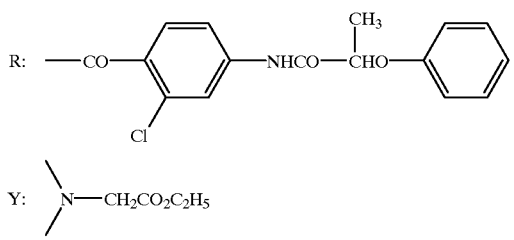

Y: N—CH₂CO₂C₂H₅ (dimethylamino ethyl ester)

R¹: H
R²: H
R³: H

Crystalline form: Pale yellow powder
Form: Free

EXAMPLE 701

Structure

R: 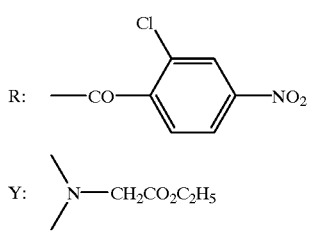

Y: N—CH₂CO₂C₂H₅

R¹: H
R² and R³: =O

Crystalline form: Brown powder
Form: Free

EXAMPLE 702

Structure

R: 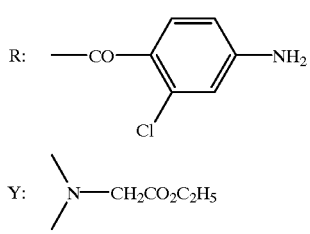

Y: N—CH₂CO₂C₂H₅

R¹: H
R² and R³: =O

Crystalline form: Colorless powder
Form: Free

EXAMPLE 703

Structure:

R: 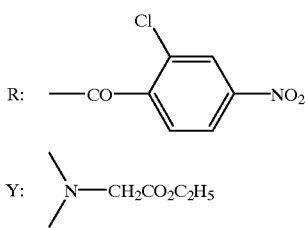

Y: N—CH₂CO₂C₂H₅

R¹: H
R²: H
R³: H

Crystalline form: Pale yellow oil
Form: Free

EXAMPLE 704

Structure

R: 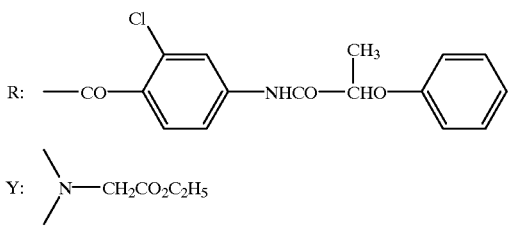

Y: N—CH₂CO₂C₂H₅

R¹: H
R² and R³: =O

Crystalline form: Colorless amorphous
Form: Free

EXAMPLE 705

Structure:

R: 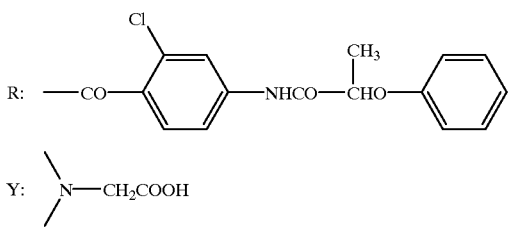

Y: N—CH₂COOH

R¹: H
R² and R³: =O

Crystalline form: Colorless amorphous
Form: Free

EXAMPLE 706

Structure:

R: —CO—(3-Cl,4-)C₆H₃—NHCOOCH₂CH(CH₃)₂

Y: >N—CH₂CO₂C₂H₅

R¹: H

R² and R³: =O

Crystalline form: Colorless amorphous

Form: Free

EXAMPLE 707

Structure:

R: —CO—(3-Cl,4-)C₆H₃—NHCOOCH₂CH₂Cl

Y: >N—CH₂CO₂C₂H₅

R¹: H

R² and R³: =O

Crystalline form: White powder

Form: Free

EXAMPLE 708

Structure:

R: —CO—(3-Cl,4-)C₆H₃—N(oxazolidin-2-one)

Y: >N—CH₂CO₂C₂H₅

R¹: H

R² and R³: =O

Crystalline form: Colorless amorphous

Form: Free

EXAMPLE 709

Structure:

R: —CO—(3-Cl,4-)C₆H₃—NHCOOCH₂CH(CH₃)₂

Y: >N—CH₂COOH

R¹: H

R² and R³: =O

Crystalline form: White powder

Form: Free

EXAMPLE 710

Structure:

R: —CO—(3-Cl,4-)C₆H₃—N(oxazolidin-2-one)

Y: >N—CH₂COOH

R¹: H

R² and R³: =O

Crystalline form: Yellow amorphous

Form: Free

EXAMPLE 711

Structure:

R: —CO—(2-CH₃,4-cyclohexyl)C₆H₃

Y: >NH

R¹: H

R² and R³: =O

Crystalline form: Colorless amorphous

Form: Free

EXAMPLE 712

Structure:

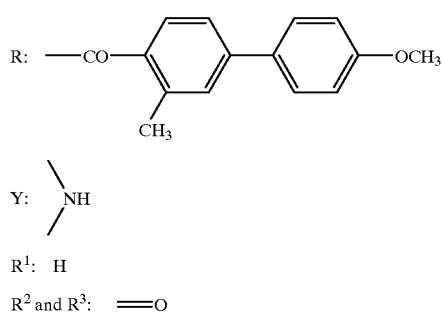

Y: >NH

R¹: H

R² and R³: ═O

Crystalline form: White powder

Form: Free

EXAMPLE 713

Structure:

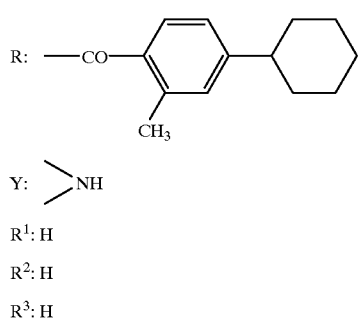

Y: >NH

R¹: H

R²: H

R³: H

Crystalline form: Colorless amorphous

Form: Free

EXAMPLE 714

Structure:

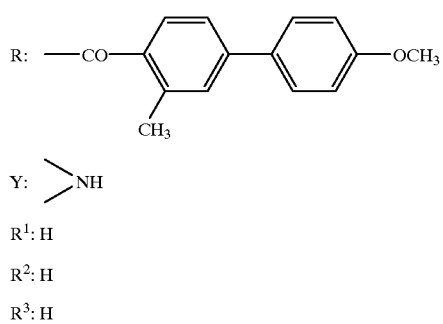

Y: >NH

R¹: H

R²: H

R³: H

Crystalline form: Colorless prisms

Form: Free

EXAMPLE 715

Structure:

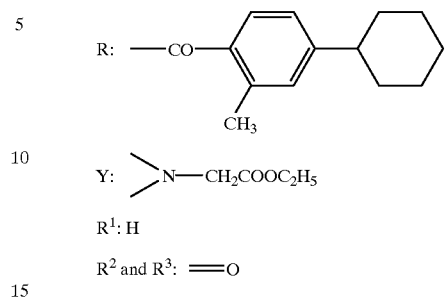

Y: >N—CH₂COOC₂H₅

R¹: H

R² and R³: ═O

Crystalline form: Yellow amorphous

Form: Free

EXAMPLE 716

Structure:

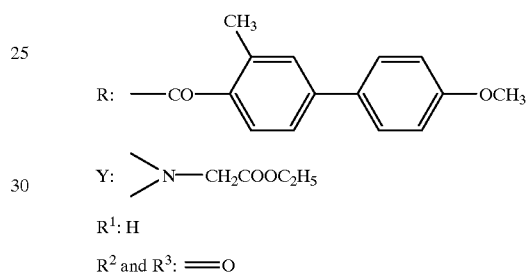

Y: >N—CH₂COOC₂H₅

R¹: H

R² and R³: ═O

Crystalline form: Colorless amorphous

Form: Free

EXAMPLE 717

Structure:

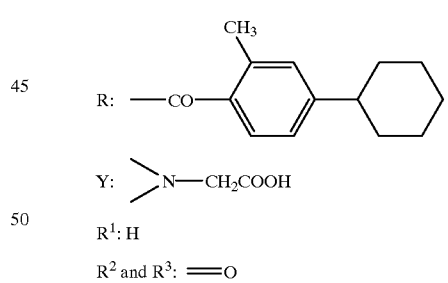

Y: >N—CH₂COOH

R¹: H

R² and R³: ═O

Crystalline form: Yellow amorphous

Form: Free

EXAMPLE 718

Structure:

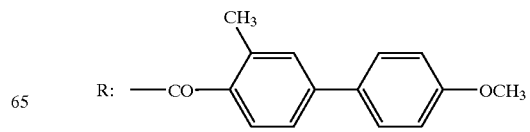

-continued

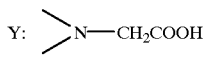

R¹: H

R² and R³: ═O

Crystalline form: White powder
Form: Free

EXAMPLE 719

Structure:

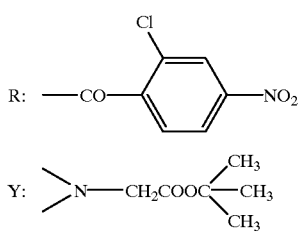

R¹: H

R² and R³: ═O

Crystalline form: Yellow amorphous
Form: Free

EXAMPLE 720

Structure:

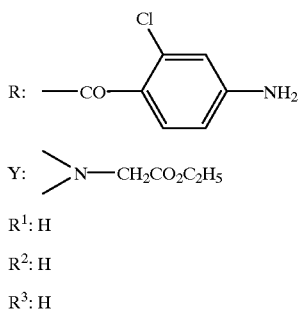

R¹: H

R²: H

R³: H

Crystalline form: White powder
Solvent for recrystallization: Diethyl ether
M.p. 120–123° C.
Form: Free The data of NMR analysis of the compounds of the above Examples are as follows.

NMR analysis:

The compound of Example 147

¹H-NMR (200 MHz, CDCl₃) δ ppm: 1.35–3.55, 4.50–5.10 [total 16H, m, 2.20 (s), 2.39 (s), 4.69 (s)], 6.54 (1H, d, J=8.27 Hz), 6.71 (1H, d, J=12.82 Hz), 6.78–6.95 (1H, m), 7.05–7.50, 7.75–8.20 (total 3H, m)

The compound of Example 148

¹H-NMR (200 MHz, CDCl₃) δ ppm: 0.98–3.94, 4.41–4.61 and 5.03–5.19 [all 24H, m, 1.12 (t, J=6.67 Hz), 4.57 (s)], 6.38–7.52 and 8.16–8.38 (all 13H, m)

The compound of Example 150

¹H-NMR (200 MHz, CDCl₃) δ ppm: 0.86–3.91, 4.36–4.61 and 5.00–5.20 [all 27H, m, 1.12 (t, J=7.08 Hz), 2.34 (s), 4.54 (s)], 7.39–7.53 and 8.14–8.42 (all 12H, m)

The compound of Example 151

¹H-NMR (200 MHz, CDCl₃) δ ppm: 0.90–4.24, 4.52–4.81 and 5.08–5.24 [all 27H, m, 1.25 (t, J=7.27 Hz), 2.60 (s), 4.67 (s), 4.76 (s)], 6.48–7.71 and 8.25–8.62 (all 12H, m)

The compound of Example 152

¹H-NMR (200 MHz, CDCl₃) δ ppm: 0.93–4.18, 4.35–4.69 and 5.00–5.21 [all 27H, m, 1.12 (t, J=6.62 Hz), 2.30 (s), 4.53 (s)], 6.48–7.62 and 8.18–8.40 (all 12H, m)

The compound of Example 153

¹H-NMR (200 MHz, CDCl₃) δ ppm: 0.90–4.18, 4.35–4.70 and 5.05–5.18 [all 27H, m, 3.89 (s), 4.59 (s)], 6.45–8.12 and 8.90–9.25 (all 12H, m)

The compound of Example 154

¹H-NMR (200 MHz, CDCl₃) δ ppm: 0.95–3.91, 4.31–4.68 and 4.98–5.20 [all 27H, m, 1.12 (t, J=7.20 Hz), 3.80 (s), 4.53 (s)], 6.48–7.61 and 8.29–8.42 (all 12H, m)

The compound of Example 155

¹H-NMR (200 MHz, CDCl₃) δ ppm: 0.96–3.94, 4.40–4.62 and 5.00–5.20 [all 27H, m, 1.12 (t, J=7.18 Hz), 2.33 (s), 4.56 (s)], 6.50–7.60 and 8.34–8.48 (all 12H, m)

The compound of Example 156

¹H-NMR (200 MHz, CDCl₃) δ ppm: 0.96–3.92, 4.31–4.62 and 5.0–5.21 [all 27H, m, 1.12 (t, J=7.24 Hz), 3.77 (s), 4.50 (s)l, 6.45–7.65 and 8.32–8.52 (all 12H, m)

The compound of Example 157

¹H-NMR (200 MHz, CDCl₃) δ ppm: 0.84–4.15, 4.39–4.62 and 5.05–5.40 [all 24H, m, 1.11 (t, J=5.70 Hz), 5.15 (s), 5.29 (s)], 6.54 (1H, d, J=6.48 Hz), 6.78 (1H, d, J=6.66 Hz), 6.98–7.75 and 7.95–8.12 [all 11H, m, 7.35 (s), 7.99 (s)]

The compound of Example 158

¹H-NMR (200 MHz, CDCl₃) δ ppm: 0.61 (3H, d, J=5.16 Hz), 0.97 (3H, d, J=5.28 Hz), 1.12–5.15 and 5.76–5.86 [all 15H, m, 2.51 (s), 4.63 (s)], 6.38–8.75 [all 12H, m, 8.47 (s)]

The compound of Example 159

¹H-NMR (200 MHz, CDCl₃) δ ppm: 1.11–4.20 and 4.31–4.62 [all 21H, m, 4.53 (s), 4.62 (s)], 2.46 (3H, s), 6.35–7.68 and 8.18–8.56 (all 12H, m)

The compound of Example 160

¹H-NMR (200 MHz, CDCl₃) δ ppm: 0.81–4.29, 4.31–4.71 and 4.95–5.13 (all 28H, m), 1.02 (t, J=5.66 Hz), 1.15 (J=5.78 Hz), 4.54 (s), 4.63 (s)], 6.35–7.76 and 8.23–8.69 (all 13H, m, 8.53 (s)]

The compound of Example 161

¹H-NMR (200 MHz, CDCl₃) δ ppm: 0.79–4.72 and 4.90–5.08 [all 22H, m, 2.45 (s), 4.51 (s), 4.61 (s)], 6.30–7.69 and 8.21–8.63 [all 12H, m, 6.38 (d, J=6.80 Hz), 6.50 (d, J=6.66 Hz), 8.53 (s)]

The compound of Example 162

¹H-NMR (200 MHz, CDCl₃) δ ppm: 0.72–4.01, 4.31–4.73 and 4.89–5.18 [all 14H, m, 2.50 (s), 4.52 (s), 4.64 (s), 5.04 (s)], 5.80–7.70 and 8.12–8.58 [all 12H, m, 6.54 (d, J=6.64 Hz), 8.42 (s)]

The compound of Example 163

¹H-NMR (200 MHz, CDCl₃) δ ppm: 0.81–3.59 [all 15H, m, 1.22 (t, J=5.96 Hz), 2.39 (s), 2.98 (q, J=5.94 Hz)], 4.75–5.05 (1H, m), 6.50–7.62 [all 8H, m, 6.60 (d, J=6.20 Hz), 6.85 (t, J=6.10 Hz), 7.01 (t, J=5.96 Hz), 7.56 (s)]

The compound of Example 165

$^1$H-NMR (200 MHz, DMSO-d$_6$) δ ppm: 0.36–1.15, 1.35–3.89 and 4.98–5.09 [all 30H, m, 2.27 (s), 2.29 (s)], 5.65–6.70 (all 11H, m)

The compound of Example 167

$^1$H-NMR (200 MHz, CDCl$_3$) δ ppm: 0.92 (6H, d, J=5.36 Hz), 1.35–3.13, 3.28–3.58, 3.69–4.01 and 4.82–5.09 [all 14H, m, 2.40 (s), 3.88 (d, J=5.24 Hz)], 6.42–7.40 [all 8H, m, 7.00 (t, J=5.84 Hz)]

The compound of Example 173

$^1$H-NMR (200 MHz, CDCl$_3$) δ ppm: 1.01–4.10, 4.41–4.68 and 4.92–5.15 [all 26H, m, 2.33 (s), 2.52 (s), 3.88 (s)], 6.35–7.60 [all 10H, m, 6.59 (d, J=8.35 Hz)]

The compound of Example 174

$^1$H-NMR (200 MHz, CDCl$_3$) δ ppm: 1.01–4.12, 4.45–4.70 and 4.92–5.16 [all 26H, m, 2.33 (s), 2.53 (s), 3.88 (s)], 6.41–7.63 (all 11H, m)

The compound of Example 175

$^1$H-NMR (200 MHz, CDCl$_3$) δ ppm: 0.52 (3H, d, J=6.52 Hz), 0.96 (3H, d, J=6.59 Hz), 1.05–2.15, 2.21–4.67 and 5.60–5.76 [all 16H, m, 2.59 (s), 3.88 (s)], 6.29–7.62 (all 11H, m)

The compound of Example 176

$^1$H-NMR (200 MHz, CDCl$_3$) δ ppm: 1.15–2.20, 2.49–4.61 and 5.01–5.28 [all 17H, m, 3.74 (s), 3.77 (s), 4.51 (s)], 6.38–7.60 and 8.21–8.49 [all 12H, m, 6.55 (d, J=8.32 Hz)]

The compound of Example 177

$^1$H-NMR (200 MHz, CDCl$_3$) δ ppm: 1.18–2.31, 2.51–3.96 and 4.26–5.51 [all 15H, m, 3.77 (s), 4.53 (s)], 6.40–6.69, 6.81–7.00, 7.08–7.51 and 8.25–8.41 (all 12H, m)

The compound of Example 179

$^1$H-NMR (200 MHz, CDCl$_3$) δ ppm: 1.21–2.30, 2.55–3.96 and 4.25–5.80 [all 15H, m, 3.76 (s), 4.49 (s)], 6.39–6.65, 6.78–7.51 and 8.25–8.45 [all 12H, m, 6.55 (s), J=8.32 Hz)]

The compound of Example 180

$^1$H-NMR (200 MHz, CDCl$_3$) δ ppm: 1.15–4.65 and 5.05–5.21 [all 18H, m, 2.51 (s), 3.84 (s), 3.88 (s)], 6.40–7.42 [all 10H, m, 6.60 (d, J=7.62 Hz)]

The compound of Example 181

$^1$H-NMR (200 MHz, CDCl$_3$) δ ppm: 1.14–4.36, 4.45–4.83 and 5.0–5.25 [all 18H, m, 2.56 (s), 3.71 (s), 3.81 (s)], 6.43–7.78 [all 11H, m, 6.68 (d, J=7.67 Hz)]

The compound of Example 182

$^1$H-NMR (200 MHz, CDCl$_3$) δ ppm: 1.20–2.30, 2.45–3.94 and 4.44–4.65 [all 12H, m, 2.52 (s), 3.72 (s)], 6.42–6.77 (1H, m), 6.80–7.55 (6H, m), 8.35–8.75 (2H, m)

The compound of Example 183

$^1$H-NMR (200 MHz, CDCl$_3$) δ ppm: 1.19–4.01, 4.42–4.69 and 5.0–5.21 [all 15H, m, 2.55 (s), 3.81 (s)], 7.49–7.60 (all 11H, m)

The compound of Example 184

$^1$H-NMR (200 MHz, CDCl$_3$) δ ppm: 1.06–4.05, 4.39–4.65 and 4.99–5.20 [all 15H, m, 2.50 (s), 3.80 (s)], 6.35–7.52 [all 10H, m, 6.72 (d, J=7.32 Hz)]

The compound of Example 185

$^1$H-NMR (200 MHz, CDCl$_3$) δ ppm: 1.18–3.65, 3.92–4.30 and 4.80–5.10 [all 13H, m, 2.43 (s), 4.10 (s)], 6.46–7.58 and 8.01–8.49 [all 7H, m, 6.62 (d, J=5.48 Hz), 6.74 (d, J=6.66 Hz)]

The compound of Example 186

$^1$H-NMR (200 MHz, CDCl$_3$) δ ppm: 1.11–4.78 and 5.02–5.20 [all 14H, m, 2.44 (s), 4.62 (s)], 6.44–7.15 and 8.19–8.51 [all 12H, m, 6.55 (d, J=8.36 Hz)]

The compound of Example 187

$^1$H-NMR (200 MHz, CDCl$_3$) δ ppm: 1.19–2.30, 2.52–3.31, 3.42–4.78 and 5.09–5.28 [all 17H, m, 3.74 (s), 3.91 (s), 4.61 (s)], 6.42–7.58 and 8.85–9.10 [all 12H, m, 5.80 (d, J=8.36 Hz)]

The compound of Example 188

$^1$H-NMR (200 MHz, CDCl$_3$) δ ppm: 1.19–4.80 and 5.09–5.18 [all 14H, m, 3.88 (s), 4.59 (s)], 5.72–7.60 and 8.87–9.12 [all 13H, m, 6.56 (d, J=8.4 Hz)]

The compound of Example 189

$^1$H-NMR (200 MHz, CDCl$_3$) δ ppm: 1.08–4.23, 4.38–4.68 and 5.03–5.19 [all 17H, m, 3.74 (s), 3.79 (s), 4.54 (s)], 6.31–7.80 and 8.10–8.71 (all 12H, m)

The compound of Example 190

$^1$H-NMR (200 MHz, CDCl$_3$) δ ppm: 1.18–3.29, 3.41–4.69 and 5.07–5.27 [all 17H, m, 2.34 (s), 3.74 (s), 4.57 (s)], 6.43–7.71 and 8.21–8.50 [all 12H, m, 6.58 (d, J=6.36Hz), 6.85 (d, J=8.21 Hz)]

The compound of Example 192

$^1$H-NMR (200 MHz, CDCl$_3$) δ ppm: 1.09–3.85, 4.01–4.71 and 5.01–5.20 [all 17H, m, 2.46 (s), 3.74 (s), 4.64 (s)], 6.31–7.65 and 8.05–8.41 [all 13H, m, 6.55 (d, J=8.34 Hz)]

The compound of Example 193

$^1$H-NMR (200 MHz, CDCl$_3$) δ ppm: 1.18–4.73 and 5.03–5.26 [all 11H, m, 4.57 (s)], 6.49–7.52 and 8.20–8.41 [all 13H, m, 6.55 (d, J=8.39 Hz)]

The compound of Example 194

$^1$H-NMR (200 MHz, CDCl$_3$) δ ppm: 1.19–3.90, 4.28–4.72 and 5.09–5.26 [all 14H, m, 2.28 (s), 4.51 (s)], 5.60–7.50 and 8.20–8.45 [all 13H, m, 6.55 (d, J=8.58 Hz)]

The compound of Example 195

$^1$H-NMR (200 MHz, CDCl$_3$) δ ppm: 1.12–4.65 and 5.03–5.26 [all 14H, m, 2.33 (s), 4.54 (s)], 6.40–7.51and 8.21–8.43 [all 12H, m, 6.55 (d, J=8.06 Hz)]

The compound of Example 196

$^1$H-NMR (200 MHz, CDCl$_3$) δ ppm: 1.19–2.31, 2.49–4.65 and 5.08–5.26 [all 14H, m, 3.74 (s), 4.57 (s)], 6.45–6.67, 6.80–7.68 and 7.92–8.43 [all 13H, m, 6.57 (d, J=8.22 Hz)]

The compound of Example 197

$^1$H-NMR (200 MHz, CDCl$_3$) δ ppm: 1.11–2.22 and 2.41–5.95 (all 9H, m), 5.14 (2H, s), 6.62–6.48 and 6.75–7.59 [all 13H, m, 6.52 (d, J=8.24 Hz), 7.34 (s)]

The compound of Example 198

$^1$H-NMR (200 MHz, CDCl$_3$) δ ppm: 1.13–4.70 and 5.03–5.25 [all 17H, m, 2.30 (s), 3.74 (s), 4.53 (s)], 6.41–7.65 and 7.91–8.43 [all 13H, m, 6.56 (d, J=8.41 Hz)]

The compound of Example 199

$^1$H-NMR (200 MHz, CDCl$_3$) δ ppm: 1.15–2.22, 2.48–3.29 and 3.41–4.80 [all 14H, m, 3.67 (s), 3.72 (s)], 5.16 (2H, s), 6.15–6.20, 6.40–6.68, 6.75–8.40 and 9.31–9.48 [all 13H, m, 6.55 (d, J=8.24 Hz), (7.36 (s)]

The compound of Example 201

$^1$H-NMR (200 MHz, CDCl$_3$) δ ppm: 1.35–2.25 and 2.70–3.25 (all 7.2H, m), 3.45 (2.5H, s), 3.52 (0.5H, s), 3.94 (1.7H, s), 4.03 (0.3H, s), 4.75–5.10 (0.8H, m), 6.75–7.95 (7.2H, m), 8.18 (0.7H, s), 8.40 (0.1H, s)

The compound of Example 202

¹H-NMR (200 MHz, DMSO-d₆) δ ppm: 1.10–5.0 (28H, m), 6.60–7.80 (11H, m), 10.0–10.5 (1H, m), 11.0–11.8 (1H, m)

The compound of Example 203

¹H-NMR (200 MHz, CDCl₃) δ ppm: 1.35–2.25, 2.60–3.15 and 4.85–5.05 (all 8H, m), 2.45 and 2.49 (all 3H, each s), 2.95 and 2.97 (all 6H, each s), 4.53 and 4.65 (all 2H, each s), 6.26–7.55 (11.3H, m), 8.17 (0.7H, s)

The compound of Example 205

¹H-NMR (200 MHz, DMSO-d₆) δ ppm: 1.20–3.80 and 4.30–4.60 [all 23H, m, 2.34 (s), 2.37 (s)], 4.63 and 4.73 (all 2H, each s), 6.40–7.80 (12H, m), 10.1 and 10.35 (all 1H, each s), 10.7–11.4 (1H, m)

The compound of Example 206

¹H-NMR (200 MHz, DMSO-d₆) δ ppm: 1.10–4.90 [all 28H, m, 4.64 (s), 4.66 (s), 4.77 (s), 4.86 (s)], 6.65–8.05 (12H, m), 10.4–11.5 (2H, m)

The compound of Example 207

¹H-NMR (200 MHz, DMSO-d₆) δ ppm: 1.20–2.10 and 2.70–4.90 [all 25H, m, 3.70 (s)], 1.87 (3H, s), 6.50–7.70 (11H, m), 10.1–11.4 (2H, m)

The compound of Example 208

¹H-NMR (250 MHz, CDCl₃) δ ppm: 1.20–2.20, 2.20–3.20, 3.20–4.0 and 4.30–4.50 [all 25H, m, 2.29 (s)], 5.70–6.10, 6.51–7.40 and 7.40–8.00 (all 13H, m)

The compound of Example 209

¹H-NMR (200 MHz, CDCl₃) δ ppm: 1.35–2.15, 2.70–3.10 and 4.80–5.00 (all 10H, m), 3.66 and 3.76 [all 2H, each t, J=5.8 Hz], 4.60 and 4.71 [all 2H, each s], 6.70–7.050 (12H, m)

The compound of Example 210

¹H-NMR (200 MHz, CDCl₃) δ ppm: 1.20–2.30, 2.70–3.20 and 4.40–5.20 (all 10H, m), 6.25–8.10 (13H, m)

The compound of Example 211

¹H-NMR (200 MHz, CDCl₃) δ ppm: 1.35–2.20, 2.70–3.15, 3.20–3.60, 3.90–4.25 and 4.85–5.05 (all 13H, m), 6.21 (0.6H, dd, J=8.4Hz, J=2.2 Hz), 6.50 (0.7H, d, J=1.8Hz), 6.70 (0.9H, d, J=8.4 Hz), 6.80–7.40 (9.8H, m)

The compound of Example 214

¹H-NMR (250 MHz, CDCl₃) δ ppm: 1.20–4.60 [all 20H, m, 2.33 (s)], 5.15 and 5.21 (all 2H, each s), 6.70–8.10 (12H, m)

The compound of Example 220

¹H-NMR (200 MHz, CDCl₃) δ ppm: 1.35–1.75 (1H, m), 1.85–2.25 (3H, m), 2.75–3.25 (3H, m), 4.58 (2H, d, J=5.6 Hz), 4.9–5.1 (1H, m), 6.3–6.5 (1H, m), 6.58 (1H, d, J=7.4 Hz), 6.87 (1H, t, J=7.6 Hz), 7.06 (1H, t, J=7.3 Hz), 7.19–7.32 (8H, m), 7.55 (2H, d, J=8.3 Hz)

The compound of Example 228

¹H-NMR (200 MHz, CDCl₃) δ ppm: 1.20–2.20, 2.30–3.35, 3.60–3.90 and 4.40–4.70 [all 14H, m, 2.45 (s), 4.48 (s)], 6.45–7.60 (12H, m), 8.28 and 8.49 (all 1H, each s)

The compound of Example 229

¹H-NMR (200 MHz, CDCl₃) δ ppm: 1.30–2.30, 2.70–3.90 and 4.40–4.60 (all 9H, m), 4.62 and 4.64 (all 2H, each s), 6.80–7.65 (12.5H, m), 8.48 and 8.75 (all 0.5H, each s)

The compound of Example 230

¹H-NMR (200 MHz, CDCl₃) δ ppm: 1.30–2.20, 2.70–3.10, 3.20–4.00 and 4.90–5.10 (all 10H, m), 2.44 and 2.48 (all 3H, each s), 4.48 and 4.57 (all 2H, each s), 6.20–7.35 (11H, m), 8.12 and 8.30 (all 1H, each s)

The compound of Example 231

¹H-NMR (200 MHz, CDCl₃) δ ppm: 1.20–2.20, 2.65–3.85 and 4.40–4.65 (all 9H, m), 2.42 (3H, s), 3.72 and 3.77 (all 3H, each s), 4.43 and 4.57 (all 2H, each s), 6.40–8.10 (12.2H, m), 8.36 and 8.64 (all 0.8H, each s)

The compound of Example 232

¹H-NMR (200 MHz, CDCl₃) δ ppm: 1.2–2.2, 2.2–3.35, 3.65–3.75 and 4.40–4.65 (all 9H, m), 2.29 and 2.33 (all 3H, each s), 2.42 (3H, s), 4.44 and 4.57 (all 2H, each s), 6.60–7.60 (13.5H, m), 8.36 and 8.62 (all 0.5H, each s)

The compound of Example 233

¹H-NMR (250 MHz, DMSO-d₆) δ ppm: 1.20–2.20, 2.60–3.65 and 4.20–4.40 (all 9H, m), 2.31 (3H, s), 5.10–5.16 (all 2H, each s), 6.46 (0.1H, d, J=8.3 Hz), 6.65 (0.9H, d, J=8.3 Hz), 6.82 (0.9H, d, J=8.4 Hz), 6.98–7.50 (9.4H, m), 9.72, 9.76 and 9.90 (all 0.7H, each s)

The compound of Example 234

¹H-NMR (250 MHz, DMSO-d₆) δ ppm: 1.20–1.65, 1.80–2.10, 2.65–3.80 and 4.20–4.40 (all 9H, m), 5.11 and 5.18 (all 2H, each s), 6.70–7.80 (11.3H, m), 10.0 and 10.2 (all 0.7H, each s)

The compound of Example 235

¹H-NMR (250 MHz, CDCl₃) δ ppm: 1.20–3.85 and 4.05–4.50 [all 14H, m, 2.18 (s)], 5.50–7.60 (13.2H, m), 7.97 and 18.32 (all 0.8H, each s)

The compound of Example 237

¹H-NMR (200 MHz, CDCl₃) δ ppm: 0.82–4.26, 4.29–4.62 and 4.97–5.22 (all 31H, m), 6.42–8.18 (7H, m)

The compound of Example 238

¹H-NMR (200 MHz, CDCl₃) δ ppm: 1.08–5.25 (31H, m), 6.16–7.80 (9H, m), 12.08–13.75 (1H, m)

The compound of Example 239

¹H-NMR (200 MHz, CDCl₃) δ ppm: 0.91–4.02, 4.43–4.68 and 5.04–5.23 (all 22H, m), 2.31 (3H, s), 6.50–7.74 (11H, m)

The compound of Example 240

¹H-NMR (200 MHz, CDCl₃) δ ppm: 1.51–4.75 [all 28H, m, 2.31 (s), 3.90 (s)], 6.46–7.63 (10H, m), 12.01–12.51 (1H, m)

The compound of Example 241

¹H-NMR (200 MHz, CDCl₃) δ ppm: 0.90–5.24 (22H, m), 6.51–7.72 (12H, m)

The compound of Example 242

¹H-NMR (200 MHz, CDCl₃) δ ppm: 1.17–2.55 (10H, m), 2.64–4.91 [all 18H, m, 3.86 (s), 3.90 (s)], 6.79–7.63 (10H, m), 12.42–12.83 (1H, m)

The compound of Example 243

¹H-NMR (200 MHz, CDCl₃) δ ppm: 1.49–2.68 (4H, m), 2.15 (3H, s), 2.69–3.04 and 4.44–5.21 (all 2H, m), 3.66, 3.76, 3.80 and 3.90 (all 6H, each s), 4.04–4.43 (2H, m), 6.54–7.62 (10H, m)

The compound of Example 244

¹H-NMR (200 MHz, CDCl₃) δ ppm: 1.45–2.62 [all 7H, m, 2.13 (s)], 2.71–3.06 and 3.07–5.19 [all 8H, m, 3.65 (s)], 6.00–7.65 (11H, m)

The compound of Example 245

¹H-NMR (200 MHz, CDCl₃) δ ppm: 1.00–5.22 (25H, m), 6.45–7.82 (11H, m), 12.52–13.54 (1H, m)

The compound of Example 246

¹H-NMR (200 MHz, CDCl₃) δ ppm: 1.14–2.55, 2.56–4.42 and 4.51–4.95 [all 25H, m, 3.95 (s)], 6.76–7.80 (11H, m), 12.40–12.98 (1H, m)

The compound of Example 247

$^1$H-NMR (200 MHz, CDCl$_3$) δ ppm: 1.21–5.12 [all 28H, m, 2.15 (s), 2.30 (s)], 6.52–7.72 (10H, m), 12.08–13.78 (1H, m)

The compound of Example 248

$^1$H-NMR (200 MHz, CDCl$_3$) δ ppm: 1.10–5.28 (22H, m), 2.36, 3.45 and 3.52 (each 3H, each s), 6.37–7.82 (9H, m), 12.34–13.35 (1H, m)

The compound of Example 250

$^1$H-NMR (200 MHz, CDCl$_3$) δ ppm: 1.14–4.29 and 4.42–4.68 [all 29H, m, 2.14 (s), 2.30 (s)], 6.47–7.62 (10H, m), 8.49–8.74 (1H, m), 11.17–12.00 (1H, m)

The compound of Example 251

$^1$H-NMR (200 MHz, CDCl$_3$) δ ppm: 1.10–4.22, 4.48–4.73 and 4.92–5.19 [all 32H, m, 3.74 (s), 3.85 (s), 3.93 (s)], 6.70–7.50 (10H, m), 11.62–12.22 (1H, m)

The compound of Example 252

$^1$H-NMR (200 MHz, CDCl$_3$) δ ppm: 1.09–2.51, 2.62–4.29 and 4.47–4.88 [all 28H, m, 2.43 (s), 3.94 (s)], 6.69–7.60 (10H, m), 12.06–13.01 (1H, m)

The compound of Example 253

$^1$H-NMR (200 MHz, CDCl$_3$) δ ppm: 1.08–4.22, 4.50–4.75 and 4.91–5.10 [all 32H, m, 2.37 (s), 2.42 (s), 3.77 (s)], 6.70–7.60 (10H, m), 11.60–12.50 (1H, m)

The compound of Example 254

$^1$H-NMR (200 MHz, CDCl$_3$) δ ppm: 1.05–2.62 and 2.63–5.19 [all 32H, m, 2.15 (s), 3.91 (s)], 6.51–7.68 (10H, m), 12.00–12.39 (1H, m)

The compound of Example 255

$^1$H-NMR (200 MHz, CDCl$_3$) δ ppm: 0.64–4.16 and 4.44–4.68 [all 20H, m, 0.73 (t, J=7.26 Hz), 2.29 (s), 2.55 (s)], 5.60–5.85 and 6.48–7.50 (all 11H, m)

The compound of Example 260

$^1$H-NMR (200 MHz, CDCl$_3$) δ ppm: 0.62–1.40, 1.41–2.19, 2.20–4.13 and 4.39–4.69 [all 17H, m, 0.73 (t, J=7.25 Hz), 2.57 (s)], 5.60–5.89 and 6.31–7.73 (all 12H, m)

The compound of Example 262

$^1$H-NMR (200 MHz, CDCl$_3$) δ ppm: 1.38–1.82, 1.83–2.35, 2.40–2.58, 2.65–3.78 and 4.82–5.15 [all 14H, m, 2.12 (s), 2.45 (s)], 6.60 (1H, d, J=8.36 Hz), 6.68–6.90 and 6.97–7.48 (all 9H, m)

The compound of Example 263

$^1$H-NMR (200 MHz, CDCl$_3$) δ ppm: 1.19–2.24, 2.37–2.60, 2.64–3.92 and 4.81–5.15 [all 11H, m, 2.48 (s)], 6.61 (1H, d, J=8.38 Hz), 6.71–6.92 and 7.02–7.68 (all 10H, m)

The compound of Example 264

$^1$H-NMR (200 MHz, CDCl$_3$) δ ppm: 1.16–4.38, 4.45–4.68 and 4.95–5.18 [all 32H, m, 1.32 (t), 2.12 (s), 2.29 (s), 2.50 (s), 3.30 (s)], 6.40–7.68 (10H, m), 11.48–12.38 (1H, m)

The compound of Example 265

$^1$H-NMR (200 MHz, CDCl$_3$) δ ppm: 0.74–4.08 and 4.42–4.69 [all 18H, m, 2.29 (s), 2.54 (s)], 5.59–5.80 and 6.29–7.51 (all 11H, m)

The compound of Example 266

$^1$H-NMR (200 MHz, CDCl3) δ ppm: 0.75–4.05, 4.40–4.66, 4.76–5.09, 5.36–5.81 and 6.30–7.68 [all 25H, m, 2.57 (s), 4.96 (brs)], 6.45 (brs)]

The compound of Example 267

$^1$H-NMR (200 MHz, CDCl$_3$) δ ppm: 0.76–2.60 and 2.61–4.92 [all 31H, m, 2.08 (s), 3.85 (s)], 6.30–7.50 (9H, m), 12.22–12.86 (1H, m)

The compound of Example 268

$^1$H-NMR (200 MHz, CDCl$_3$) δ ppm: 0.73–2.56 and 2.57–4.94 [all 31H, m, 2.28 (s), 2.39 (s), 3.87 (s)], 6.52–7.52 (9H, m), 12.17–13.00 (1H, m)

The compound of Example 269

$^1$H-NMR (200 MHz, CDCl$_3$) δ ppm: 1.14–4.08, 4.41–4.68, 4.82–5.09, 5.37–5.96 and 6.30–7.58 [all 27H, m, 2.29 (s), 2.54 (s), 5.00 (brs), 6.45 (brs)]

The compound of Example 270

$^1$H-NMR (200 MHz, CDCl$_3$) δ ppm: 1.10–4.29, 4.41–4.68 and 4.96–5.15 [all 29H, m, 2.53 (s), 3.31 (s)], 6.38–7.72 (11H, m), 11.64–12.47 (1H, m)

The compound of Example 271

$^1$H-NMR (200 MHz, CDCl$_3$) δ ppm: 0.80–4.98 [23H, m, 2.52 (s), 2.58 (d, J=4.4 Hz)], 6.47–7.72 (11H, m), 12.56–13.30 (1H, m)

The compound of Example 272

$^1$H-NMR (200 MHz, CDCl$_3$) δ ppm: 0.58–4.00, 4.12–4.68 and 5.06–5.24 [all 14H, m, 1.63 (s)], 5.45–5.82 and 6.49–8.09 (all 17H, m)

The compound of Example 273

$^1$H-NMR (200 MHz, CDCl$_3$) δ ppm: 1.08–5.20 [all 20H, m, 2.85 (s)], 6.48–6.72, 6.81–7.08 and 7.09–7.79 [all 16H, m, 6.74 (d, J=8.2 Hz)], 12.62–13.78 (1H, m)

The compound of Example 274

$^1$H-NMR (250 MHz, CDCl$_3$) δ ppm: 1.04–5.24 (22H, m), 6.38–6.71 and 6.72–7.60 (all 16H, m), 12.49–13.31 (1H, m)

The compound of Example 275

$^1$H-NMR (250 MHz, CDCl$_3$) δ ppm: 1.10–5.19 [20H, m, 1.74 (s)], 6.41–6.68 and 6.79–7.60 (all 16H, m)

The compound of Example 276

$^1$H-NMR (200 MHz, CDCl$_3$) δ ppm: 0.78–2.34, 2.35–4.48, 4.49–4.74 and 4.92–5.12 [all 35H, m, 1.39 (t, d, J=7.0 Hz), 1.83 (s), 3.90 (s), 3.93 (s), 3.95 (s), 3.98 (s)], 6.70–7.60 (9H, m), 11.61–12.24 (1H, m)

The compound of Example 277

$^1$H-NMR (200 MHz, CDCl$_3$) δ ppm: 0.75–2.28, 2.29–4.33, 4.50–4.76 and 4.91–5.13 [all 32H, m, 1.85 (s), 2.39 (s), 2.45 (s), 3.30 (s), 3.77 (s), 3.99 (s)], 6.70–7.58 (10H, m), 11.58–12.27 (1H, m)

The compound of Example 278

$^1$H-NMR (200 MHz, CDCl$_3$) δ ppm: 1.12–4.29 and 4.42–4.93 [all 26H, m, 1.41 (t, J=7.3 Hz), 2.53 (s), 3.87 (s)], 6.58–7.68 (11H, m), 12.52–13.50 (1H, m)

The compound of Example 279

$^1$H-NMR (200 MHz, CDCl$_3$) δ ppm: 0.48–1.41, 1.49–2.88, 2.94–3.28, 3.32–4.80 and 5.31–5.62 [all 22H, m, 0.52 (d, J=6.5 Hz), 0.96 (d, J=6.5 Hz), 2.58 (s), 3.87 (s)], 6.37–6.79 and 6.80–7.75 (all 12H, m)

The compound of Example 283

$^1$H-NMR (250 MHz, CDCl$_3$) δ ppm: 1.10–2.96, 2.97–3.91, 4.05–4.61 and 5.05–5.19 [all 20H, m, 1.63 (s), 2.87 (d, J=4.5 Hz)], 5.49–5.78, 6.07–6.32, 6.46–6.69 and 6.81–7.62 (all 9H, m)

The compound of Example 284

$^1$H-NMR (250 MHz, CDCl$_3$) δ ppm: 0.79–4.32, 4.33–4.66 and 4.99–5.26 [all 34H, m, 1.41 (t, J=5.8 Hz), 3.31 (s)], 6.02–6.37, 6.45–6.68 and 6.78–7.81 (all 8H, m), 11.83–12.39 (1H, m)

The compound of Example 285

$^1$H-NMR (250 MHz, CDCl$_3$) δ ppm: 1.17–3.40, 3.52–4.10, 4.11–4.62 and 5.04–5.23 [all 36H, m, 1.41 (t, J=7.18 Hz), 3.31 (s)], 6.05 (1H, t, J=6.68 Hz), 6.51–6.69 and 6.82–7.68 (7H, m), 11.99–12.39 (1H, m)

The compound of Example 286

$^1$H-NMR (200 MHz, CDCl$_3$) δ ppm: 0.35–0.65, 0.80–2.12, 2.13–2.88, 2.89–3.23, 3.32–4.24, 4.34–4.65, 5.26–5.47 and 6.31–7.44 [all 38H, m, 0.50 (d, J=6.5 Hz), 0.94 (d, J=6.5 Hz), 2.49 (s)]

The compound of Example 287

$^1$H-NMR (200 MHz, CDCl$_3$) δ ppm: 0.50–0.81, 1.00–2.13, 2.14–3.17, 3.21–4.00, 4.36–4.62, 5.48–5.71 and 6.39–7.43 [all 38H, m, 0.65 (t, J=7.3 Hz), 2.49 (s)]

The compound of Example 288

$^1$H-NMR (200 MHz, CDCl$_3$) δ ppm: 0.81–2.55 (5H, m), 2.31 (3H, s), 2.56–3.97, 4.31–4.70 and 5.08–5.50 (all 4H, m), 6.50–7.83 (12H, m)

The compound of Example 289

$^1$H-NMR (200 MHz, CDCl$_3$) δ ppm: 1.15–2.49 [all 8H, m, 1.95 (s)], 2.59–3.94, 4.00–4.25, 4.40–4.67 and 5.09–5.29 [all 13H, m, 3.47 (s), 3.55 (s), 3.68 (s)], 6.30–7.48 (9H, m)

The compound of Example 291

$^1$H-NMR (200 MHz, CDCl$_3$) δ ppm: 1.15–2.27 (5H, m), 2.52–4.33, 4.51–4.73 and 5.00–5.19 [all 13H, m, 3.70 (s), 3.74 (s), 3.75 (s)], 6.71–7.54 (10H, m)

The compound of Example 292

$^1$H-NMR (200 MHz, CDCl$_3$) δ ppm: 1.27–2.42 (5H, m), 2.36 (3H, s), 2.58–3.07 (2H, m), 3.10–4.31, 4.38–4.67 and 5.19–5.29 [all 11H, m, 3.53 (s), 3.68 (s)], 6.41–7.48 (9H, m)

The compound of Example 293

$^1$H-NMR (200 MHz, CDCl$_3$) δ ppm: 1.09–2.42 (5H, m), 2.58–4.24, 4.49–4.74 and 5.01–5.22 (all 10H, m), 5.24–7.56 (11H, m)

The compound of Example 294

$^1$H-NMR (200 MHz, CDCl$_3$) δ ppm: 1.18–2.58 (4H, m), 2.35 (3H, s), 2.60–4.09, 4.36–4.68 and 5.02–5.30 (all 5H, m), 3.49 (6H, s), 6.31–7.49 (10H, m)

The compound of Example 295

$^1$H-NMR (200 MHz, CDCl$_3$) δ ppm: 1.16–2.47 (4H, m), 2.58–3.40, 3.41–4.38, 4.39–4.68 and 5.09–5.30 (all 11H, m), 3.67 and 3.71 (each 3H, each s), 6.55–7.83 (11H, m)

The compound of Example 296

$^1$H-NMR (200 MHz, CDCl$_3$) δ ppm: 1.19–2.39 (4H, m), 2.51–3.95, 4.36–4.64 and 5.05–5.31 [all 8H, m, 3.65 (s)], 6.50–7.80 (11H, m), 8.99–10.36 (1H, m)

The compound of Example 297

$^1$H-NMR (200 MHz, CDCl$_3$) δ ppm: 1.18–2.34, 2.58–3.30, 3.31–4.37, 4.51–4.72 and 5.01–5.19 [all 15H, m, 3.76 (s)], 6.71–7.69 (11H, m)

The compound of Example 298

$^1$H-NMR (200 MHz, CDCl$_3$) δ ppm: 1.15–2.29 (4H, m), 2.57–3.21, 3.30–4.13, 4.49–4.72 and 4.99–5.21 [all 8H, m, 3.73 (s)], 5.41–7.69 (12H, m)

The compound of Example 299

$^1$H-NMR (200 MHz, CDCl$_3$) δ ppm: 1.12–2.22, 2.24–2.52, 2.57–3.19, 3.28–4.41, 4.51–4.73 and 4.99–5.20 [all 18H, m, 2.37 (s), 3.76 (s)], 6.71–7.58 (10H, m)

The compound of Example 300

$^1$H-NMR (200 MHz, CDCl$_3$) δ ppm: 1.07–4.14 and 4.15–5.58 [all 16H, m, 2.35 (s), 3.73 (s)], 6.62–7.64 (10H, m)

The compound of Example 301

$^1$H-NMR (200 MHz, CDCl$_3$) δ ppm 1.13–2.31. [all 10H, m, 1.90 (s)], 2.54–3.23, 3.33–3.97, 4.05–4.31, 4.51–4.71 and 5.01–5.18 [all 11H, m, 3.74 (s)], 6.31–7.50 (9H, m)

The compound of Example 302

$^1$H-NMR (200 MHz, CDCl$_3$) δ ppm: 1.14–2.22 (4H, m), 2.57–3.20, 3.36–4.35, 4.50–4.71 and 5.02–5.20 [all 17H, m, 3.76 (s), 3.91 (s), 3.93 (s)], 6.71–7.55 (9H, m)

The compound of Example 303

$^1$H-NMR (200 MHz, CDCl$_3$) δ ppm: 1.11–2.51 [all 7H, m, 2.39 (s)], 2.57–3.21, 3.22–4.35, 4.51–4.73 and 5.01–5.19 [all 11H, m, 3.76 (s)], 6.70–7.55 (10H, m)

The compound of Example 304

$^1$H-NMR (200 MHz, CDCl$_3$) δ ppm: 1.15–2.49 [all 10H, m, 2.11 (s), 2.34 (s)], 2.56–3.22, 3.30–4.32, 4.49–4.73 and 5.02–5.19 [all 11H, m, 3.67 (s), 3.74 (s)], 6.48–7.52 (9H, m)

The compound of Example 307

$^1$H-NMR (200 MHz, CDCl$_3$) δ ppm: 1.09–2.25 (4H, m), 2.37 and 2.44 (all 3H, each s), 2.55–3.30, 3.31–4.22 and 4.49–6.21 [all 9H, m, 3.73 (s)], 6.70–7.58 (10H, m)

The compound of Example 309

$^1$H-NMR (200 MHz, CDCl$_3$) δ ppm: 1.14–4.23, 4.42–4.69 and 5.03–5.25 [all 18H, m, 2.13 (s), 2.48 (s), 3.71 (s)], 6.30–7.54 (10H, m)

The compound of Example 310

$^1$H-NMR (200 MHz, CDCl$_3$) δ ppm: 1.17–2.29 (4H, m), 2.39–4.32, 4.43–4.65 and 5.02–5.22 [all 11H, m, 2.51 (s), 3.74 (s)], 6.41–7.69 (11H, m)

The compound of Example 311

$^1$H-NMR (200 MHz, CDCl$_3$) δ ppm: 1.05–3.99, 4.38–4.65 and 5.01–5.22 [all 15H, m, 2.12 (s), 2.47 (s)], 6.40–7.48 (10H, m)

The compound of Example 312

$^1$H-NMR (200 MHz, CDCl$_3$) δ ppm: 1.12–2.34 (4H, m), 2.35–4.09, 4.40–4.68 and 5.03–5.25 [all 8H, m, 2.50 (s)], 6.40–7.70 (11H, m)

The compound of Example 313

$^1$H-NMR (200 MHz, CDCl$_3$) δ ppm: 1.19–2.52, 2.53–3.94, 3.97–4.32, 4.37–4.62 and 5.07–5.28 [all 20H, m, 3.74 (s)], 6.00–6.32, 6.40–6.68, 6.70–7.01 and 7.02–7.40 (all 8H, m)

The compound of Example 314

$^1$H-NMR (250 MHz, CDCl$_3$) δ ppm: 1.08–2.37, 2.38–3.92, 4.01–4.64 and 5.08–5.28 [all 22H, m, 3.74 (s)], 6.07 (1H, t, J=6.7 Hz), 6.41–6.71 and 6.72–7.41 (all 7H, m)

The compound of Example 315

$^1$H-NMR (250 MHz, CDCl$_3$) δ ppm: 1.12–2.31, 2.48–3.32, 3.37–3.82, 3.83–4.36, 4.37–4.58 and 5.10–5.25 [all 12H, m, 1.58 (s), 3.59 (s)], 6.43–6.66 and 6.79–7.52 (all 16H, m)

The compound of Example 316

$^1$H-NMR (250 MHz, CDCl$_3$) δ ppm: 1.22–3.06, 3.07–3.25, 3.32–3.79, 4.38–4.60 and 5.08–5.24 [all 9H, m, 3.48 (s), 3.58 (s)], 6.42–6.63 and 6.78–8.51 (all 17H, m)

The compound of Example 317

$^1$H-NMR (250 MHz, CDCl$_3$) δ ppm: 1.12–2.52, 2.53–3.33, 3.34–3.88, 3.89–4.65, and 5.08–5.25 (all 17H, m), 5.99–6.36, 6.44–6.70 and 6.78–7.55 (all 9H, m)

The compound of Example 318

$^1$H-NMR (250 MHz, CDCl$_3$) δ ppm: 1.16–3.32, 3.33–4.62 and 5.08–5.26 (all 19H, m), 6.05 (1H, t, J=6.7 Hz), 6.48–6.74 and 6.75–7.81 (all 8H, m)

The compound of Example 319

$^1$H-NMR (250 MHz, CDCl$_3$) δ ppm: 1.19–2.30, 2.57–3.90, 3.91–4.67 and 5.12–5.31 [all 12H, m, 1.59 (s), 3.75 (s)], 6.49–6.74 and 6.81–7.87 (all 16H, m)

The compound of Example 320

¹H-NMR (250 MHz, CDCl₃) δ ppm: 1.18–2.26 (4H, m), 2.55–3.36, 3.37–3.90, 4.38–4.62 and 5.10–5.30 (all 5H, m), 6.50–6.71 and 6.82–7.81 (all 17H, m)

The compound of Example 321

¹H-NMR (200 MHz, CDCl₃) δ ppm: 1.18–2.39, 2.40–4.27, 4.46–4.68 and 5.06–5.22 [all 18H, m, 2.52 (s), 3.72 (s), 3.82 (s) and 3.87 (s)], 6.48–7.68 (11H, m)

The compound of Example 322

¹H-NMR (200 MHz, CDCl₃) δ ppm: 0.86–4.31, 4.43–4.67 and 5.03–5.20 [all 26H, m, 2.43 (s), 2.47 (s), 3.72 (s)], 6.41–7.46 (7H, m)

The compound of Example 323

¹H-NMR (200 MHz, CDCl₃) δ ppm: 1.07–4.31, 4.40–4.67 and 5.02–5.20 [all 28H, m, 2.43 (s), 2.47 (s), 3.72 (s)], 6.40–7.46 (7H, m)

The compound of Example 324

¹H-NMR (200 MHz, CDCl₃) δ ppm: 1.15–4.31, 4.43–4.65 and 5.02–5.20 [all 24H, m, 2.43 (s), 2.48 (s), 3.71 (s)], 6.44–7.48 (7H, m)

The compound of Example 325

¹H-NMR (200 MHz, CDCl₃) δ ppm: 0.98–5.26 [24H, m, 2.43 (s), 2.48 (s)], 6.42–7.53 [7H, m, 6.64 (d, J=7.3 Hz)]

The compound of Example 326

¹H-NMR (200 MHz, CDCl₃) δ ppm: 1.03–4.04, 4.42–4.64 and 5.01–5.21 [all 25H, m, 2.43 (s), 2.48 (s)], 6.41–7.45 (7H, m)

The compound of Example 327

¹H-NMR (200 MHz, CDCl₃) δ ppm: 1.04–4.01, 4.40–4.66 and 5.02–5.22 [all 21H, m, 2.43 (s), 2.48 (s)], 6.43–7.48 (7H, m)

The compound of Example 328

¹H-NMR (200 MHz, CDCl₃) δ ppm: 1.14–2.28, 2.38–4.02, 4.41–4.68 and 5.02–5.22 [all 15H, m, 2.51 (s), 2.56 (s), 3.78 (s)], 6.48–7.62 (11H, m)

The compound of Example 329

¹H-NMR (200 MHz, CDCl₃) δ ppm: 1.15–2.32 (4H, m), 2.43–4.32, 4.45–4.68 and 5.03–5.22 [all 11H, m, 2.55 (s), 2.58 (s), 3.73 (s)], 6.43–7.80 (16H, m)

The compound of Example 332

¹H-NMR (200 MHz, CDCl₃) δ ppm: 0.54–1.04, 1.05–2.25, 2.26–4.18, 4.36–4.74 and 5.52–5.84 [all 17H, m, 0.67 (t, J=7.3 Hz), 2.60 (s)], 6.38–7.82 (17H, m)

The compound of Example 333

¹H-NMR (200 MHz, CDCl₃) δ ppm: 0.9–4.2, 4.4–4.65 and 5.0–5.25 (all 22H, m), 6.45–6.67 and 6.78–7.88 [all 13H, m, 6.58 (d, J=8.3 Hz)]

The compound of Example 334

¹H-NMR (200 MHz, CDCl₃) δ ppm: 0.9–4.1, 4.45–4.65 and 5.0–5.2 [all 22H, m, 1.23 (t, J=7.1 Hz)], 6.35–7.55 (13H, m)

The compound of Example 335

¹H-NMR (200 MHz, CDCl₃) δ ppm: 1.06 (3H, t, J=7.2 Hz), 1.1–1.55 (5H, m), 1.6–2.0 (5H, m), 2.2–2.7 (9H, m), 3.4–3.9 (7H, m), 4.55–4.85 (1H, m), 6.19 (1H, t, J=5.5 Hz), 6.62 (1H, d, J=8.2 Hz), 6.8–7.1 (1H, m), 6.99 (2H, d, J=7.9 Hz), 7.16 (2H, d, J=7.9 Hz), 7.33 (1H, d, J=2.4 Hz)

The compound of Example 336

¹H-NMR (200 MHz, CDCl₃) δ ppm: 1.05 (3H, t, J=7.2 Hz), 2.2–2.7 (8H, m), 3.4–3.9 (7H, m), 4.6–4.9 (1H, m), 6.21 (1H, t, J=5.8 Hz), 6.65 (1H, d, J=8.3 Hz), 6.8–7.1 (1H, m), 7.2–7.6 (10H, m)

The compound of Example 337

¹H-NMR (200 MHz, CDCl₃) δ ppm: 0.99 and 1.21 (all 6H, each t, J=7 Hz), 2.0–2.8 (7H, m), 3.0–4.9 (7H, m), 6.34 (1H, t, J=5.5 Hz), 6.65 (1H, d, J=8.1 Hz), 6.75–7.8 (12H, m)

The compound of Example 339

¹H-NMR (200 MHz, CDCl₃) δ ppm: 1.2–4.2, 4.4–4.7 and 5.0–5.2 (all 19H, m), 6.5–6.7 [1H, m, 6.63 (d, J=7.1 Hz)], 6.8–7.8 (12H, m), 8.2–8.7 (1H, m)

The compound of Example 340

¹H-NMR (200 MHz, CDCl₃+DMSO-d₆) δ ppm: 1.0–4.8 and 5.0–5.2 [all 24H, m, 1.47 (t, J=7.1 Hz)], 6.5–8.0 (13H, m), 8.9–9.8 (1H, m), 11.6–12.5 (1H, m)

The compound of Example 341

¹H-NMR (200 MHz, CDCl₃) δ ppm: 1.1–2.3, 2.4–4.7 and 4.9–5.15 (all 21H, m), 6.58 (1H, d, J=7.7 Hz), 6.7–7.8 (12H, m), 8.35–8.8 (1H, m)

The compound of Example 342

¹H-NMR (200 MHz, CDCl₃) δ ppm: 0.9–4.0, 4.4–4.7 and 5.0–5.25 (all 21H, m), 6.5–6.7 (1H, m), 6.8–7.7 (12H, m), 8.2–8.5 (1H, m)

The compound of Example 344

¹H-NMR (200 MHz, CDCl₃) δ ppm: 0.9–4.1, 4.4–4.7 and 4.9–5.15 [all 27H, m, 1.12 (t, J=5.7 Hz), 2.49 (s), 4.52 (s)], 6.4–7.7 [12H, m, 6.62 (d, J=6.1 Hz)], 8.1–8.5 [1H, m, 8.15 (s), 8.41 (s)]

The compound of Example 345

¹H-NMR (250 MHz, CDCl₃) δ ppm: 0.9–4.1, 4.3–4.8 and 4.9–5.1 (all 24H, m), 6.7–8.0 (11H, m), 8.3–8.8 [1H, m, 8.38 (s), 8.67 (s)]

The compound of Example 346

¹H-NMR (200 MHz, CDCl₃) δ ppm: 1.0–5.1 [24H, m, 2.46 (s), 2.47 (s), 4.48 (s), 4.61 (s)], 6.35–6.7 [1H, m, 6.58 (d, J=5.5 Hz)], 6.75–8.0 (12H, m), 8.3–8.7 [1H, m, 8.42 (s), 8.59 (s)]

The compound of Example 350

¹H-NMR (200 MHz, CDCl₃) δ ppm: 1.2–4.2, 4.4–4.7 and 4.9–5.2 [all 23H, m, 2.35 (s), 2.53 (s)], 6.4–8.5 [12H, m, 6.58 (d, J=8.3 Hz), 6.87 (dd, J=8.3, J=2.3 Hz), 6.99 (d, J=2.2 Hz), 7.10 (d, J=8.3 Hz), 10.0–10.04 (1H, m)

The compound of Example 352

¹H-NMR (200 MHz, CDCl₃) δ ppm: 1.05–1.55 and 1.6–2.0 [all 13H, 1.25 (t, J=7 Hz)], 2.2–2.8 (3H, m), 3.2–3.55 (2H, m), 3.6–3.9 (1H, m), 4.0–4.4 (2H, m), 4.6–4.9 (1H, m), 6.29 (1H, t, J=5.6 Hz), 5.62 (1H, d, J=8 Hz), 6.89 (1H, dd, J=8 Hz, J=2 Hz), 6.99 (2H, d, J=8.2 Hz), 7.18 (2H, d, J=8.2 Hz), 7.35 (1H, d, J=2 Hz)

The compound of Example 353

¹H-NMR (200 MHz, CDCl₃) δ ppm: 1.1–2.0 (10H, m), 2.2–2.8 (3H, m), 3.2–3.6 (2H, m), 3.65–3.9 (1H, m), 4.6–4.95 (1H, m), 6.28 (1H, t, J=5.4 Hz), 6.61 (1H, d, J=8 Hz), 6.8–7.1 (1H, m), 6.98 (2H, d, J=8 Hz), 7.21 (2H, d, J=8 Hz), 7.35 (1H, d, J=2.3 Hz), 9.03 (1H, brs)

The compound of Example 354

¹H-NMR (200 MHz, CDCl₃) δ ppm: 2.15–2.8 (2H, m), 3.25–3.6 (2H, m), 3.65–3.95 (1H, m), 4.6–4.9 (1H, m), 6.25 (1H, t, J=5.6 Hz), 6.63 (1H, d, J=8.1 Hz), 6.8–7.0 (1H, m), 7.2–7.6 (10H, m), 9.1 (1H, br)

The compound of Example 355

¹H-NMR (200 MHz, CDCl₃) δ ppm: 1.1–2.2, 2.6–3.35, 3.4–3.95, 4.0–4.7 and 5.05–5.25 [all 14H, 3.72 (s)], 6.45–6.7 [1H, m, 6.63 (d, J=7.6 Hz)], 6.8–7.5 (12H, m), 8.15–8.4 (1H, m)

The compound of Example 356

¹H-NMR (250 MHz, CDCl$_3$) δ ppm: 1.2–4.9 and 5.0–5.25 [all 17H, m, 2.46 (s), 3.70 (s), 4.51 (s)], 6.4–7.6 [12H, m, 6.62 (d, J=8.1 Hz)], 8.1–8.6 (1H, m)

The compound of Example 357

¹H-NMR (250 MHz, CDCl$_3$) δ ppm: 1.1–2.2 (4H, m), 2.6–3.0 (2H, m), 3.1–3.3, 3.4–3.9, 4.4–4.7 and 4.9–5.2 [all 8H, m, 3.73 (s), 4.56 (s)], 6.8–8.0, 8.2–8.4 and 8.45–8.6 (all 12H, m)

The compound of Example 358

¹H-NMR (250 MHz, CDCl$_3$) δ ppm: 1.1–2.25 (4H, m), 2.5–5.2 (7H, m), 6.2–8.1 (11H, m), 8.3–8.8 [1H, m, 8.42 (s)]

The compound of Example 359

¹H-NMR (200 MHz, CDCl$_3$) δ ppm: 1.2–4.7 and 5.0–5.2 [all 15H, m, 2.48 (s), 3.74 (s)], 6.3–6.7 [1H, m, 6.57 (d, J=8.7 Hz)], 6.7–7.8 (10H, m), 8.3–8.8 [1H, m, 8.41 (s), 8.72 (s)]

The compound of Example 360

¹H-NMR (200 MHz, CDCl$_3$) δ ppm: 1.1–4.7 and 5.0–5.2 [all 15H, m, 2.49 (s), 3.68 (s)], 6.1–8.0 [10H, m, 6.60 (d, J=8.4 Hz)], 9.4–8.8 [1H, m, 9.54 (s), 9.75 (s)], 12.1–12.4 [1H, m, 12.27 (s)]

The compound of Example 361

¹H-NMR (200 MHz, CDCl$_3$) δ ppm: 1.1–3.9 and 4.3–5.3 [all 12H, m, 2.45 (s)], 6.3–6.7 [1H, m, 6.57 (d, J=8.4 Hz)], 6.7–7.8 (10H, m), 8.40 and 8.65 (all 1H, each s)

The compound of Example 362

¹H-NMR (200 MHz, CDCl$_3$) δ ppm: 1.1–3.9, 4.2–4.6 and 4.9–5.2 [all 12H, m, 2.43 (s)], 6.3–7.9 [11H, m, 6.57 (d, J=8.3 Hz)], 8.44 and 8.74 (all 1H, each s)

The compound of Example 363

¹H-NMR (200 MHz, CDCl$_3$) δ ppm: 1.7–2.4 (2H, m), 2.87 (2H, t, J=6 Hz), 3.4–5.2 [4H, m, 4.55 (s)], 6.8–8.1 (12H, m), 8.2–8.7 [1H, m, 8.35 (s)]

The compound of Example 365

¹H-NMR (200 MHz, DMSO-d$_6$) δ ppm: 1.1–5.1 [12H, m, 2.42 (s)], 6.4–8.8 [13H, m, 6.72 (d, J=8.4 Hz), 8.60 (d, J=8.3 Hz)], 10.5–10.9 (1H, m)

The compound of Example 366

¹H-NMR (200 MHz, CDCl$_3$) δ ppm: 0.95–4.05, 4.48–4.72 and 4.96–5.14 [all 27H, m, 1.06 (t, J=7.3 Hz), 2.38 (s)], 6.48–7.73 [12H, m, 6.68 (d, J=7.5 Hz)]

The compound of Example 367

¹H-NMR (200 MHz, CDCl$_3$) δ ppm: 1.05 (3H, t, J=7.3 Hz), 1.18–4.18, 4.42–4.72 and 4.97–5.15 [all 24H, m, 2.34 (s)], 6.40–6.68 and 6.73–7.74 [all 11H, m, 6.61 (d, J=8.3 Hz)]

The compound of Example 370

¹H-NMR (200 MHz, CDCl$_3$) δ ppm: 1.05 (3H, t, J=7.3 Hz), 1.20–2.32, 2.59–4.00, 4.43–4.72 and 5.03–5.21 (all 13H, m), 6.51–7.72 fall 12H, m, 6.69 (d, J=7.4 Hz)]

The compound of Example 371

¹H-NMR (200 MHz, CDCl$_3$) δ ppm: 1.05 (3H, t, J=7.3 Hz), 1.17–2.28, 2.55–3.90, 4.34–4.66 and 5.01–5.22 (all 13H, m), 6.43–7.69 [all 11H, m, 6.63 (d, J=8.3 Hz)]

The compound of Example 375

¹H-NMR (200 MHz, CDCl$_3$) δ ppm: 1.18–2.25 (4H, m), 2.60–3.15 (3H, m), 3.35–3.80 (1H, m), 4.50–5.20 (1H, m), 6.60–6.72 (1H, m), 6.90–7.00 (1H, m), 7.02 (1H, d, J=8.2 Hz), 7.16 (1H, dd, J=2.3 Hz, J=8.3 Hz), 7.21–7.54 (5H, m)

The compound of Example 377

¹H-NMR (200 MHz, CDCl$_3$) δ ppm: 1.13–2.28 (4H, m), 2.50–3.18 (3H, m), 3.31–3.60 (1H, m), 4.48–5.19 (1H, m), 7.02 (1H, dd, J=1.7 Hz, J=8.2 Hz), 7.06–7.52 (9H, m)

The compound of Example 379

¹H-NMR (200 MHz, CDCl$_3$) δ ppm: 1.17–2.30 (4H, m), 2.61–3.20 (2H, m), 3.20–3.45 (1H, m), 3.50–3.98 (1H, m), 4.42–5.33 (1H, m), 6.50–6.65 (1H, m), 6.72–7.56 (6H, m), 7.62 (1H, dd, J=2.0 Hz, J=8.8 Hz), 7.71 (1H, d, J=8.6 Hz), 7.78–8.08 (4H, m), 8.12 (1H, d, J=8.6 Hz)

The compound of Example 383

¹H-NMR (200 MHz, CDCl$_3$) δ ppm: 1.17–2.22 (7H, m), 2.69–3.93 (6H, m), 4.41–5.23 (1H, m), 6.45–7.73 (11H, m)

The compound of Example 385

¹H-NMR (200 MHz, CDCl$_3$) δ ppm: 1.15–2.28 (7H, m), 2.56–3.08 (4H, m), 3.08–3.96 (2H, m), 4.40–5.21 (1H, m), 6.40–7.16 (4H, m), 7.16–7.75 (8H, m)

The compound of Example 386

¹H-NMR (200 MHz, CDCl$_3$) δ ppm: 0.70–1.16 (6H, m), 1.20–3.66 (18H, m), 3.66–3.97 (1H, m), 4.48–5.19 (1H, m), 6.51–7.21 (2H, m), 7.21–8.10 (7H, m)

The compound of Example 387

¹H-NMR (200 MHz, CDCl$_3$) δ ppm: 0.80–1.18 (3H, m), 1.19–2.58 (10H, m), 2.58–3.21 (4H, m), 3.29–3.80 (4H, m), 4.52–5.11 (1H, m), 6.40–6.87 (1H, m), 6.90–7.11 (2H, m), 7.11–7.44 (4H, m), 7.44–7.68 (3H, m)

The compound of Example 388

¹H-NMR (200 MHz, CDCl$_3$) δ ppm: 0.85 (3H, t, J=7.1 Hz), 1.02 (3H, t, J=7.1 Hz), 1.15–2.28 (3H, m), 2.38 (4H, q, J=7.1 Hz), 2.56 (4H, q, J=7.1 Hz), 2.63–3.49 (4H, m), 3.50–3.79 (1H, m), 4.51–5.14 (1H, m), 5.65–6.79 (2H, m), 6.90–7.10 (2H, m), 7.10–7.21(1H, m), 7.10–7.62 (6H, m)

The compound of Example 389

¹H-NMR (200 MHz, CDCl$_3$) δ ppm: 0.82–1.19 (3H, m), 1.20–2.55 (10H, m), 2.55–3.19 (4H, m), 3.19–3.87 (4H, m), 4.55–5.13 (1H, m), 6.81–7.72 (10H, m)

The compound of Example 390

¹H-NMR (250 MHz, CDCl$_3$) δ ppm: 0.84 (3H, t, J=7.1 Hz), 1.00 (3H, t, J=7.2 Hz), 1.21–2.42 (8H, m), 2.42–2.68 (4H, m), 2.68–3.46 (3H, m), 3.52–3.81 (1H, m), 4.53–5.14 (1H, m), 5.65–6.51 (1H, m), 6.88–7.11 (2H, m), 7.11–7.22 (1H, m), 7.11–7.65 (8H, m)

The compound of Example 391

¹H-NMR (250 MHz, CDCl$_3$) δ ppm: 0.88–1.27 (3H, m), 1.30–2.89 (10H, m), 2.99–3.20 (1H, m), 3.20–4.12 (7H, m), 4.45–5.29 (1H, m), 6.48–6.67 (1H, m), 6.75–6.90 (1H, m), 7.02 (1H, d, J=2.1 Hz), 7.40–8.09 (7H, m), 8.09–8.20 (2H, m), 8.31 (1H, d, J=8.6 Hz)

The compound of Example 392

¹H-NMR (250 MHz, CDCl$_3$) δ ppm: 0.81–1.19 (6H, m), 1.25–2.30 (4H, m), 2.30–2.77 (7H, m), 2.77–5.30 (6H, m), 6.29–6.78 (2H, m), 6.81 (1H, dd, J=2.2 Hz, J=8.3 Hz), 7.11–7.38 (1H, m), 7.38–7.66 (3H, m), 7.66–7.89 (2H, m), 7.89–8.24 (4H, m), 8.31 (1H, d, J=8.6 Hz)

The compound of Example 393

¹H-NMR (250 MHz, CDCl$_3$) δ ppm: 0.78–2.30 (5H, m), 2.35 (3H, s), 2.41–2.60 (3H, m), 2.60–3.52 (3H, m), 3.52–4.01 (5H, m), 4.46–5.26 (1H, m), 6.50–6.69 (1H, m), 6.89 (1H, dd, J=2.2 Hz, J=8.3 Hz), 7.02 (1H, d, J=2.2 Hz), 7.09–7.20 (1H, m), 7.28–7.55 (1H, m), 7.60–7.90 (6H, m), 8.38 (1H, s)

The compound of Example 394

¹H-NMR (250 MHz, CDCl$_3$) δ ppm: 0.79–1.20 (6H, m), 1.29–2.82 (10H, m), 2.82–4.02 [9H, m, 3.00 (s), 3.22 (s)], 4.40–5.25 (1H, m), 6.50–6.68 (1H, m), 6.83–7.20 (3H, m), 7.25–7.52 (1H, m), 7.58–7.87 (6H, m), 8.37 (1H, d, J=5.2 Hz)

The compound of Example 397

¹H-NMR (200 MHz, CDCl₃) δ ppm: 1.20–4.18, 4.40–4.72 and 4.96–5.20 [all 25H, m, 2.34 (s), 2.88 (q, J=7.4 Hz)], 6.40–7.85 (11H, m)

The compound of Example 398

¹H-NMR (200 MHz, CDCl₃) δ ppm: 1.15–4.10, 4.49–4.75 and 4.98–5.18 [all 25H, m, 2.33 (s)], 6.45–7.72 (12H, m)

The compound of Example 404

¹H-NMR (200 MHz, CDCl₃) δ ppm: 1.18–2.28 (10H, m), 2.54–4.08 (15H, m), 4.18–5.22 (1H, m), 6.50–6.70 (2H, m), 6.72–6.90 (1H, m), 7.08–7.78 (9H, m), 12.02 (1H, brs)

The compound of Example 408

¹H-NMR (200 MHz, CDCl₃) δ ppm: 1.15–5.15 (17H, m), 2.86 (3H, s), 6.49–6.70 (2H, m), 6.72–6.90 (1H, m), 6.93–7.81 (9H, m), 12.27 (1H, brs)

The compound of Example 413

¹H-NMR (200 MHz, CDCl₃) δ ppm: 1.46–4.00, 4.27–4.80 and 5.03–5.17 (all 13H, m), 6.68 (1H, d, J=8.3 Hz), 6.80–7.69 (12H, m)

The compound of Example 415

¹H-NMR (200 MHz, CDCl₃) δ ppm: 1.35–4.15 and 4.80–5.10 (all 13H, m), 6.45–7.90 (12H, m)

The compound of Example 417

¹H-NMR (200 MHz, CDCl₃) δ ppm: 0.87 (3H, t, J=7.3 Hz), 1.35–2.22, 2.66–3.17 and 4.88–5.09 (all 10H, m), 4.08 (2H, t, J=7.3 Hz), 6.57 (1H, d, J=8.3 Hz), 6.89 (1H, dd, J=2 Hz, J=8.3 Hz), 7.15–7.49 (3H, m), 7.53–7.69 (2H, m), 11.39–11.64 (1H, brs)

The compound of Example 418

¹H-NMR (200 MHz, CDCl₃) δ ppm: 0.99–4.17 and 4.45–4.65 [all 25H, m, 1.84 (s)], 6.56–6.65, 6.82–7.02 and 7.11–7.58 (all 6H, m), 7.75–7.96 (1H, m), 8.50–8.66 (1H, m), 8.71–8.93 (1H, m)

The compound of Example 419

¹H-NMR (200 MHz, CDCl₃) δ ppm: 0.64–0.85, 1.10–4.00, 4.40–4.70 and 5.58–5.72 (all 17H, m), 6.36–7.62 (8H, m), 7.75–7.96 (1H, m), 8.49–8.70 (1H, m), 8.70-7.95 (1H, m)

The compound of Example 420

¹H-NMR (200 MHz, CDCl₃) δ ppm: 1.2–4.2, 4.45–4.6 [all 20H, m, 2.04 (s), 2.34 (s)], 5.15 and 5.22 (all 2H, each s), 6.8–7.8 (all 12H, m)

The compound of Example 421

¹H-NMR (250 MHz, CDCl₃) δ ppm: 1.40–1.85, 1.85–2.14, 2.68–3.10 and 4.85–5.06 (all 8H, m), 2.53 and 2.59 (all 3H, each s), 6.60 (1H, d, J=8.3 Hz), 6.85 (1H, dd, J=2.9 Hz, J=8.3 Hz), 6.96 (1H, d, J=7.9 Hz), 7.12–7.22 (2H, m), 7.29, 7.40 and 7.58 (all 2H, each s), 7.89–8.09 (1H, m), 8.43–8.66 (1H, m), 8.69–8.86 (1H, m), 8.90–9.11 (1H, m)

The compound of Example 422

¹H-NMR (200 MHz, CDCl₃) δ ppm: 0.75–2.10, 2.32–2.90, 3.20–3.45 and 4.70–4.90 (all 8H, m), 6.42 (1H, d, J=6.8 Hz), 6.71 (1H, dd, J=2.0 Hz, J=6.8 Hz), 6.85 (1H, d, J=2.0 Hz), 7.00–7.65 (10H, m)

The compound of Example 423

¹H-NMR (200 MHz, CDCl₃) δ ppm: 1.36–1.73, 1.84–2.25, 2.65–3.16 and 4.93–5.16 (all 8H, m), 6.61 (1H, d, J=8.3 Hz), 6.90 (1H, dd, J=2 Hz, J=8.3 Hz), 7.08–7.70 (10H, m)

The compound of Example 424

¹H-NMR (200 MHz, CDCl₃) δ ppm: 1.15–4.00 and 4.45–4.65 [all 23H, m, 1.62 (s), 2.34 (s), 2.54 (s)], 6.55–6.65, 6.82–7.01 and 7.10–7.56 (all 6H, m), 7.74–7.93 (1H, m), 8.50–8.67 (1H, m), 8.74–8.90 (1H, m)

The compound of Example 425

¹H-NMR (200 MHz, CDCl₃) δ ppm: 1.38–2.22, 2.65–3.15 and 4.95–5.12 (all 8H, m), 6.61 (1H, d, J=8.4 Hz), 6.80–7.00 (2H, m), 7.20–7.38 (4H, m), 7.62 (1H, d, J=9.1 Hz), 7.98 (2H, d, J=8.3 Hz), 8.09 (1H, d, J=6.9 Hz)

The compound of Example 426

¹H-NMR (250 MHz, CDCl₃) δ ppm: 0.90–1.90, 1.90–2.23, 2.46–2.70 and 4.67–4.90 (all 8H, m), 8.44 (1H, d, J=8.4 Hz), 6.75 (1H, dd, J=2.4 Hz, J=8.4 Hz), 6.92 (1H, d, J=2.4 Hz), 7.05–7.75 and 7.96–8.04 (all 6H, m), 8.30–8.45, 8.53–8.74 and 8.80–8.87 (all 2H, m)

The compound of Example 433

¹H-NMR (250 MHz, CDCl₃) δ ppm: 1.22–3.13, 3.44–3.73 and 4.71–4.93 (all 8H, m), 6.80 (1H, dd, J=2.5 Hz, J=8.5 Hz), 6.96–7.85 (9H, m), 8.63–8.76 (1H, m)

The compound of Example 436

¹H-NMR (200 MHz, CDCl₃) δ ppm: 1.15–4.2, 4.4–4.7 and 5.0–5.2 [all 16H, m, 2.34 (s)], 6.5–6.75 (1H, m), 6.8–7.8 [all 11H, m, 7.50 (d, J=6.7 Hz), 7.70 (d, J=5.7 Hz)]

The compound of Example 438

¹H-NMR (250 MHz, CDCl₃) δ ppm: 1.22–3.95, 4.43–4.62 and 5.03–5.24 [all 30H, m), 2.34 (s)], 6.56 and 6.63 (all 1H, each d, J=8.3 Hz), 6.89–7.32 (4H, m), 7.37–7.55 (2H, m)

The compound of Example 440

¹H-NMR (200 MHz, CDCl₃) δ ppm: 0.84–4.00 and 4.39–4.60 (all 22H, m), 6.23–6.39 (2H, m), 6.50–6.66 (1H, m), 6.82–6.99 (1H, m), 6.99–7.15 (3H, m), 7.15–7.36 (2H, m), 7.42–7.62 (2H, m)

The compound of Example 441

¹H-NMR (200 MHz, CDCl₃) δ ppm: 0.80–4.00 and 4.38–4.65 [all 32H, m, 1.92 (s), 3.23 (s)], 5.85 and 5.87 (all 2H, each s), 6.57 (1H, d, J=8.5 Hz), 6.80–7.20 (4H, m), 7.45–7.65 (2H, m)

The compound of Example 444

¹H-NMR (200 MHz, CDCl₃) δ ppm: 1.57–2.34 (4H, m), 2.51–2.90 (2H, m), 4.74–5.23 (2H, m), 6.53–6.76 (2H, m), 6.91–7.62 (9H, m)

The compound of Example 445

¹H-NMR (200 MHz, CDCl₃) δ ppm: 1.75–2.0, 2.2–3.10 and 3.45–4.10 (all 18H, m), 4.65 (2H, s), 6.66–7.70 [all 11H, m, 6.67 (d, J=8.6 Hz)], 7.59 (d, J=8.5 Hz), 8.80 (1H, s)

The compound of Example 446

¹H-NMR (200 MHz, CDCl₃) δ ppm: 1.8–2.0 and 2.25–2.50 (all 6H, m), 2.31 (3H, s), 2.60 (1H, dd, J=15.7 Hz, J=8.3 Hz), 2.80 (1H, dd, J=15.7 Hz, J=5.7 Hz), 3.45–3.60 (3H, m), 3.60–3.80 (2H, m), 3.89 (2H, t, J=6.6 Hz), 4.60 (2H, s), 6.67 (1H, d, J=8.7 Hz), 6.88 (1H, dd, J=8.7 Hz, J=2.2 Hz), 7.00–7.50 (8H, m), 7.56 (2H, d, J=8.6 Hz), 8.41 (1H, s)

The compound of Example 447

¹H-NMR (200 MHz, CDCl₃) δ ppm: 1.65–2.0 and 2.1–2.55 [all 12H, m, 2.32 (s), 2.35 (s)], 2.60 (1H, dd, J=15.7 Hz, J=8.2 Hz), 2.80 (1H, dd, J=15.7 Hz, J=5.8 Hz), 3.48–3.52 and 3.67–3.72 (all 5H, m), 3.89 (2H, t, J=6.6 Hz), 4.59 (2H, s), 6.67 (1H, d, J=8.6 Hz), 6.78 (2H, d, J=8 Hz), 6.87 (2H, d, J=8.6 Hz), 7.20 (2H, d, J=8 Hz), 7.37 (2H, d, J=8.6 Hz), 7.55 (2H, d, J=8.6 Hz), 8.37 (1H, s)

The compound of Example 448

¹H-NMR (200 MHz, CDCl₃) δ ppm: 1.70–2.10, 2.20–2.90 and 3.50–4.0 [all 21H, m, 2.23 (s), 2.31 (s)], 4.71

(2H, s), 6.68 (1H, d, J=8.6 Hz), 6.85–7.03, 7.15–7.43 and 7.60–7.67 (all 11H, m), 9.57 (1H, s)

The compound of Example 450

¹H-NMR (200 MHz, CDCl₃) δ ppm: 0.96–4.70 (29H, m), 1.45 (3H, t, J=7.0 Hz), 4.07 (2H, q, J=7.0 Hz), 5.58–7.36 (7H, m)

The compound of Example 455

¹H-NMR (200 MHz, CDCl₃) δ ppm: 0.95–4.00, 4.42–4.63 and 5.04–5.18 (all 22H, m), 6.46–6.67 (1H, m), 6.79–6.95 (1H, m), 6.95–7.25 (4H, m), 7.32–7.51 (2H, m), 7.52–7.75 (2H, m)

The compound of Example 456

¹H-NMR (200 MHz, CDCl₃) δ ppm: 0.95–3.93, 4.41–4.62 and 5.01–5.20 [all 25H, m, 2.24 (s)], 6.45–6.62 (1H, m), 6.72–6.95 (2H, m), 6.95–7.08 (1H, m), 7.10–7.45 (3H, m), 7.45–7.69 (2H, m)

The compound of Example 459

¹H-NMR (200 MHz, CDCl₃) δ ppm: 1.42 (6H, t, J=7.2 Hz), 1.75–2.05 (1H, m), 2.15–2.40 (1H, m), 2.40–3.90 (11H, m), 3.94 (2H, t, J=6.5 Hz), 6.73–7.15 (3H, m), 7.25–7.60 (10H, m), 8.35–8.75 (1H, m), 11.3–11.7 (1H, m)

The compound of Example 460

¹H-NMR (200 MHz, CDCl₃) δ ppm: 1.24 (3H, t, J=7 Hz), 1.4–1.5, 1.85–3.30, 3.40–4.20 and 4.65–4.85 (all 15H, m), 3.72 (2H, q, J=7 Hz), 6.8–7.7 (13H, m), 12.6–12.9 (1H, m)

The compound of Example 461

¹H-NMR (200 MHz, CDCl₃) δ ppm: 1.03 (6H, t, J=7 Hz), 1.75–2.0 (1H, m), 2.10–2.30 (1H, m), 2.35–2.90 (8H, m), 3.35–3.80 (3H, m), 3.90 (2H, t, J=6.6 Hz), 6.72 (1H, d, J=8.6 Hz), 6.8–7.0 (2H, m), 7.23 (1H, d, J=2.2 Hz), 7.35–7.66 (9H, m)

The compound of Example 462

¹H-NMR (200 MHz, CDCl₃) δ ppm: 1.03 (3H, t, J=7.2 Hz), 1.75–2.0 (1H, m), 2.15–2.40 (1H, m), 2.40–2.90 (8H, m), 3.50–3.60 (3H, m), 3.65–3.85 (2H, m), 3.93 (2H, m), 6.75–7.0 and 7.2–7.65 (all 12H, m)

The compound of Example 463

¹H-NMR (200 MHz, CDCl₃) δ ppm: 1.20–1.70, 1.70–3.0, 3.0–3.6, 3.6–3.8 and 3.8–4.0 (all 32H, m), 6.73 (1H, d, J=8.6 Hz), 6.87 (1H, dd, J=8.6 Hz, J=2.4 Hz), 7.13 (2H, d, J=8 Hz), 7.23 (1H, d, J=2.4 Hz), 7.33 (2H, d, J=8 Hz), 8.4–8.7 (1H, m), 11.2–11.6 (1H, m)

The compound of Example 464

¹H-NMR (200 MHz, CDCl₃) δ ppm: 1.10 (3H, t, J=7.2 Hz), 1.2–1.65, 1.7–2.0, 2.1–2.9, 3.4–3.6, 3.6–3.8 and 3.8–4.0 (all 28H, m), 6.77 (1H, d, J=8.7 Hz), 6.90 (1H, dd, J=8.7 Hz, J=2.3 Hz), 7.13 (2H, d, J=8.2 Hz), 7.19 (1H, d, J=2.3 Hz), 7.31 (2H, d, J=8.2 Hz)

The compound of Example 467

¹H-NMR (250 MHz, CDCl₃) δ ppm: 1.10–2.10, 2.55–4.05, 4.45–4.61 and 4.68–4.71 (all 41H, m), 6.94–7.38 (3H, m), 12.00–12.27 (1H, brs)

The compound of Example 469

¹H-NMR (200 MHz, CDCl₃) δ ppm: 1.20–2.24 (5H, m), 2.63–3.31 (3H, m), 3.70 and 3.75 (all 3H, s), 4.08–5.20 (1H, m), 6.46–6.62 (1H, m), 6.36–7.00 (1H, m), 7.10–7.48 (3H, m), 8.43–8.56 (2H, m)

The compound of Example 470

¹H-NMR (200 MHz, CDCl₃) δ ppm: 1.05–5.08 (26H, m), 6.15–7.53 (16H, m)

The compound of Example 471

¹H-NMR (200 MHz, CDCl₃) δ ppm: 0.97–2.20, 2.20–4.06 and 4.40–4.63 [all 36H, m], 1.41 (t, J=7.2 Hz), 1.71 (s), 3.31 (s)], 6.59 (1H, d, J=8.5 Hz), 6.84–7.60 (6H, m), 12.7–13.4 (1H, brs)

The compound of Example 472

¹H-NMR (200 MHz, CDCl₃) δ ppm: 1.20–226, 2.50–4.10, 4.40–4.60 and 5.00–5.15 (all 29H, m), 6.58 (1H, d, J=8.2 Hz), 6.65–7.48 (6H, m), 12.12 (1H, brs)

The compound of Example 473

¹H-NMR (200 MHz, CDCl₃) δ ppm: 1.30–2.20, 2.50–4.10, 4.38–4.60 and 4.98–5.16 (all 29H, m), 6.50–7.20 (5H, m), 7.36 (2H, d, J=8.6 Hz), 12.15 (1H, brs)

The compound of Example 476

¹H-NMR (200 MHz, CDCl₃) δ ppm: 1.16–4.10 and 4.30–4.53 (all 35H, m), 6.47–6.80, 6.80–7.65 and 7.86–8.10 (all 7H, m), 15.51–15.98 (1H, br)

The compound of Example 477

¹H-NMR (200 MHz, CDCl₃) δ ppm: 1.12–2.11 (4H, m), 2.45–3.78 (5H, m), 4.23–5.10 (1H, m), 6.61–7.75 (14H, m)

The compound of Example 478

¹H-NMR (200 MHz, CDCl₃) δ ppm: 0.62 (1.5H, d, J=6.5 Hz), 0.99 (1.5H, d, J=6.5 Hz), 1.03–5.74 (14H, m), 6.43–7.80 (11H, m)

The compound of Example 479

¹H-NMR (200 MHz, CDCl₃) δ ppm: 0.80–3.90, 4.41–4.64 an 5.05–5.70 (all 35H, m), 6.49–6.63 (1H, m), 6.71–7.20 (4H, m), 7.20–7.50 (2H, m)

The compound of Example 480

¹H-NMR (200 MHz, CDCl₃) δ ppm: 0.92–2.25, 2.38–3.27, 3.27–4.00, 4.50–4.60 and 4.85–5.02 (all 29H, m), 6.62–7.45 (6H, m)

The compound of Example 481

¹H-NMR (200 MHz, CDCl₃) δ ppm: 0.82–4.17, 4.36–4.60 and 5.07–5.13 [all 26H, m, 2.99 (s), 3.23 (s)], 6.40–6.66 (1H, m), 6.75–7.78 (8H, m), 7.84 (1H, d, J=3.7 Hz)

The compound of Example 482

¹H-NMR (200 MHz, CDCl₃) δ ppm: 0.77–1.14, 1.14–2.24, 2.24–4.04, 4.33–4.53 and 4.97–5.13 [all 27H, m, 2.89 (s), 3.14 (s)], 6.42–6.61 (1H, m), 6.77–7.10 (2H, m), 7.28–7.80, 7.80–8.12 [all 6H, m, 7.88 (s)]

The compound of Example 484

¹H-NMR (200 MHz, CDCl₃) δ ppm: 1.19–5.33 (22H, m), 6.49–7.32 (12H, m), 11.92–12.70 (1H, m)

The compound of Example 485

¹H-NMR (200 MHz, CDCl₃) δ ppm: 1.20–5.28 (20H, m), 1.38 (3H, t, J=7.2 Hz), 3.32 (3H, s), 6.61 (1H, d, J=8.3 Hz), 6.91 (1H, dd, J=8.3 Hz, J=2.2 Hz), 7.03 (1H, d, J=2.2 Hz), 7.18–7.76 (9H, m), 11.94 (1H, brs)

The compound of Example 486

¹H-NMR (200 MHz, CDCl₃) δ ppm: 1.19–5.13 (24H, m), 1.35 (3H, t, J=7.3 Hz), 1.45 (3H, t, J=7.0 Hz), 4.08 (2H, q, J=7.0 Hz), 6.18–7.46 (6H, m), 11.59–12.58 (1H, m)

The compound of Example 487

¹H-NMR (200 MHz, CDCl₃) δ ppm: 0.93–3.98 (26H, m), 4.51–5.15 (1H, m), 4.97 and 5.10 (all 2H, s), 6.23–7.51 (11H, m)

The compound of Example 488

¹H-NMR (200 MHz, CDCl₃) δ ppm: 0.90–2.12, 2.12–2.40, 2.40–3.63 and 4.45–4.84 (all 38H, m), 6.98–7.35 (2H, m), 7.38–7.44 (1H, m)

The compound of Example 489

¹H-NMR (200 MHz, CDCl₃) δ ppm: 1.06–5.19 (36H, m), 6.16–7.49 (6H, m), 11.28–11.99 (1H, m)

The compound of Example 490

¹H-NMR (200 MHz, CDCl₃) δ ppm: 1.32–4.57 (22H, m), 1.45 (3H, t, J=7.0 Hz), 2.58 and 2.60 (all 3H, s), 4.08 (2H, q, J=7.0 Hz), 6.43–6.63 (2H, m), 7.05–7.44 (4H, m), 12.15 (1H, brs)

The compound of Example 491

¹H-NMR (200 MHz, CDCl₃) δ ppm: 1.20–5.21 (31H, m), 6.11–7.61 (6H, m), 8.54–8.72 (1H, m), 11.27–12.03 (1H, m)

The compound of Example 492

¹H-NMR (200 MHz, CDCl₃) δ ppm: 1.23–5.03 (25H, m), 1.46 (3H, t, J=7.0 Hz), 4.08 (2H, q, J=7.0 Hz), 6.16–7.44 (6H, m), 12.47 (1H, brs)

The compound of Example 493

¹H-NMR (200 MHz, CDCl₃) δ ppm: 1.11–4.67 (29H, m), 4.97, 5.10 (all 2H, s), 6.22–7.51 (11H, m), 11.43–12.04 (1H, m)

The compound of Example 494

¹H-NMR (200 MHz, CDCl₃) δ ppm: 1.21–4.62 (26H, m), 4.98 and 5.11 (all 2H, s), 6.22–7.51 (11H, m), 8.55–8.71 (1H, m), 11.39–11.81 (1H, m)

The compound of Example 495

¹H-NMR (200 MHz, CDCl₃) δ ppm: 1.21–4.90 (22H, m), 1.34 (3H, t, J=7.3 Hz), 4.98 and 5.11 (all 2H, s), 6.27–7.53 (11H, m), 12.48 (1H, brs)

The compound of Example 496

¹H-NMR (200 MHz, CDCl₃) δ ppm: 0.83–3.98 (24H, m), 2.99 and 3.15 (all 3H, s), 3.62 and 3.86 (all 3H, s), 4.49–5.19 (1H, m), 4.97 and 5.10 (all 2H, s), 6.23–7.53 (11H, m)

The compound of Example 497

¹H-NMR (200 MHz, CDCl₃) δ ppm: 1.18–2.20, 2.60–4.55 (all 26H, m), 6.45–6.55 (1H, m), 6.80–6.95 (1H, m), 6.95–7.60 (4H, m), 7.90–8.08 (1H, m), 11.86 (1H, brs)

The compound of Example 498

¹H-NMR (200 MHz, CDCl₃) δ ppm: 1.20–2.20, 2.55–3.40, 3.40–4.10, 4.35–4.53 and 4.96–5.20 (all 26H, m), 6.53 (1H, d, J=8 Hz), 6.91 (1H, dd, J=0.2 Hz, J=8 Hz), 7.04 (1H, d, J=0.2 Hz), 7.13 (2H, d, J=8.6 Hz), 7.40 (2H, d, J=8.6 Hz). 12.15 (1H, s)

The compound of Example 499

¹H-NMR (200 MHz, CDCl₃) δ ppm: 1.20–2.20, 2.20–3.45, 3.45–4.10 and 4.45–4.65 (all 29H, m), 6.50–6.62, 6.75–7.55 and 7.95–8.07 (all 7H, m), 11.8–12.2 (1H, m)

The compound of Example 500

¹H-NMR (200 MHz, CDCl₃) δ ppm: 1.25–3.40, 3.40–4.15 and 4.40–4.60 (all 29H, m), 6.50–6.62, 6.80–7.45 and 7.85–7.95 (all 7H, m), 12.06 (1H, brs)

The compound of Example 501

¹H-NMR (200 MHz, CDCl₃) δ ppm: 1.20–4.10, 4.45–4.60 and 5.00–5.20 (all 29H, m), 6.56 (1H, d, J=6.4 Hz), 6.80–7.50 (5H, m), 7.96 (1H, d, J=8.2 Hz), 12.01 (1H, brs)

The compound of Example 502

¹H-NMR (200 MHz, CDCl₃) δ ppm: 1.20–4.18 and 4.50–4.70 (all 29H, m), 6.60–6.90, 6.90–7.51, 7.51–7.66 and 8.15–8.22 (all 7H, m), 11.8–12.25 (1H, br)

The compound of Example 503

¹H-NMR (200 MHz, CDCl₃) δ ppm: 0.78–3.95, 4.42–4.60 and 5.05–5.21 (all 26H, m), 6.49–6.62 (1H, m), 6.82–6.98 (1H, m), 6.98–7.52 (6H, m)

The compound of Example 504

¹H-NMR (200 MHz, CDCl₃) δ ppm: 1.16–4.06, 4.43–4.64 and 4.92–5.10 (all 26H, m), 6.72–7.65 (7H, m), 11.87–12.18 (1H, br)

The compound of Example 505

¹H-NMR (200 MHz, CDCl₃) δ ppm: 1.00–3.95, 4.20–4.44 and 4.90–5.05 (all 22H, m), 5.10–6.50 (1H, br), 6.65–6.76 (1H, m), 6.90–7.05 (1H, m), 7.20–7.35 (1H, m), 7.35–7.50 (2H, m), 7.70–7.85 (2H, m)

The compound of Example 508

¹H-NMR (250 MHz, CDCl₃) δ ppm: 0.65–0.82, 1.00–2.17, 2.17–2.95, 2.95–3.51, 3.55–3.90, 4.18–4.35, 4.42–4.63, 5.03–5.18 and 5.50–5.75 (all 25H, m), 6.51–6.68 (1H, m), 6.85–7.45 (5H, m), 7.51–7.65 (1H, m)

The compound of Example 509

¹H-NMR (200 MHz, CDCl₃) δ ppm: 0.49 (3H, d, J=6.3 Hz), 0.95 (3H, d, J=6.3 Hz), 1.1–4.2 [all 16H, m, 3.02 (s)], 6.55–6.80 (3H, m), 7.15–7.45 (5H, m)

The compound of Example 510

¹H-NMR (200 MHz, CDCl₃) δ ppm: 1.0–2.2, 2.4–4.0 and 4.5–4.6 [all 25H, m, 2.87 (s), 3.0 (s)], 6.1–7.5 [all 7H, m, 6.26 (dd, J=8.8 Hz, J=2.5 Hz)]

The compound of Example 511

¹H-NMR (200 MHz, CDCl₃) δ ppm: 1.10–5.35 [24H, m, 2.33 (s)], 6.75–8.26 (7H, m)

The compound of Example 512

¹H-NMR (200 MHz, CDCl₃) δ ppm: 1.1–1.5, 1.5–4.0, 4.4–4.7 and 4.9–5.1 (all 28H, m, 2.02 (s), 2.18 (s)), 6.13–7.70 (7H, m)

The compound of Example 516

¹H-NMR (200 MHz, CDCl₃) δ ppm: 1.30–1.85, 1.85–2.22, 2.61–3.16 and 4.82–5.06 (8H, m), 2.50 and 2.56 (all 3H, each s), 6.55–6.65, 6.78–6.95 and 7.10–7.60 (all 8H, m), 8.52–8.70 (2H, m)

The compound of Example 517

¹H-NMR (200 MHz, CDCl₃) δ ppm: 1.30–2.30, 2.30–3.15, 3.36–3.60 and 4.98–5.08 [all 11H, m, 2.49 (s), 2.54 (s)], 6.60 (1H, d, J=8.4 Hz), 6.75–6.95 (2H, m), 6.95–7.10 (1H, m), 7.10–7.51 (5H, m), 8.38–8.87 (2H, m)

The compound of Example 520

¹H-NMR (200 MHz, CDCl₃) δ ppm: [all 6H, m, 0.651 (d, J=6.5 Hz), 1.02 (d, J=6.5 Hz), 1.15 (d, J=6.5 Hz, 1.22 (d, J=6.5 Hz), 1.25–2.22, 2.45–2.90, 3.00–3.21, 3.50–4.00 and 4.44–4.67 [all 13H, m, 2.57 (s), 2.63 (s)], 6.50–7.96 and 8.65–8.95 (11H, m)

The compound of Example 521

¹H-NMR (200 MHz, CDCl₃) δ ppm: 1.1–4.9 [all 26H, m, 3.06 (s)], 6.65–7.75 (all 7H, m), 12.4–13.2 (1H, m)

The compound of Example 523

¹H-NMR (200 MHz, CDCl₃) δ ppm: 1.18–2.20, 2.29–3.12, 3.29–3.61 and 4.81–5.10 [all 21H, m, 2.34 (s)], 6.23 (1H, dd, J=8.72 Hz, J=8.73 Hz), 6.50 (1H, d, J=2.48 Hz), 6.56–7.49 (5H, m)

The compound of Example 524

¹H-NMR (200 MHz, CDCl₃) δ ppm: 0.89 (6H, d, J=6.54 Hz), 1.32–2.20, 2.30–3.31, 3.42–3.95 and 4.82–5.12 (all 19H, m), 6.39–7.49 (7H, m)

The compound of Example 525

¹H-NMR (200 MHz, CDCl₃) δ ppm: 1.10–2.20 and 2.20–4.90 (all 23H, m), 6.35–6.69, 6.69–7.00, 7.00–8.34 and 8.65–9.16 (all 10H, m), 1.65–12.8 (1H, br)

The compound of Example 526

¹H-NMR (200 MHz, CDCl₃) δ ppm: 0.64, 0.98, 1.16 and 1.19 (all 6H, each d, J=6.5 Hz), 1.20–1.49, 1.49–2.23, 2.23–4.60 and 4.95–5.12 [all 13H, m, 2.58 (s), 2.65 (s)], 6.05–6.50, 6.50–6.65, 6.70–6.95, 7.05–7.45, 7.45–7.90, 7.90–8.33 and 8.75–9.15 (all 12H, m)

The compound of Example 529
¹H-NMR (200 MHz, CDCl₃) δ ppm: 1.13–4.88 (20H, m), 1.19 and 1.35 (all 9H, s), 2.46, 2.49 and 2.51 (all 6H, s), 6.58–7.47 (7H, m), 12.76 (1H, brs)

The compound of Example 530
¹H-NMR (200 MHz, CDCl₃) δ ppm: 1.35–2.25, 2.36–3.60 and 4.47–5.09 [all 11H, m, 2.52 (s), 2.58 (s)], 6.60–6.75 (1H, m), 6.75–7.09 (8H, m), 8.52–8.75 (2H, m)

The compound of Example 531
¹H-NMR (200 MHz, DMSO-d₆) δ ppm: 1.05–2.0, 2.5–4.0 and 4.2–4.6 (all 24H, m), 6.14–7.5 [all 7H, m, 6.16 (d, J=8.8 Hz)], 11.1–11.5 (2H, m)

The compound of Example 532
¹H-NMR (200 MHz, CDCl₃) δ ppm: 1.3–2.4, 2.7–4.1, 4.5–4.7 and 5.0–5.2 (all 9H, m), 6.7–7.8 (12H, m)

The compound of Example 534
¹H-NMR (200 MHz, CDCl₃) δ ppm: 1.30–2.25, 2.40–3.50 and 4.86–5.08 [all 11H, m, 2.53 (s), 2.58 (s)], 6.00–7.60 and 8.55–8.85 (all 10H, m)

The compound of Example 535
¹H-NMR (200 MHz, CDCl₃) δ ppm: 1.10–4.90 (23H, m), 6.50–6.66, 6.80–7.68 and 8.60–8.91 (all 9H, m), 12.77–13.45 (1H, br)

The compound of Example 541
¹H-NMR (200 MHz, DMSO-d₆) δ ppm: 1.00–2.11, 2.12–3.90 and 4.18–4.71 [all 34H, m, 2.32 (s), 2.36 (s)], 6.40–7.55 (6H, m), 9.82–10.16 and 10.80–11.24 (all 1H, m)

The compound of Example 542
¹H-NMR (200 MHz, CDCl₃) δ ppm: 1.35–2.15, 2.6–3.15, 3.65–4.0, 4.47, 4.57 and 4.85–5.0 [all 16H, m, 4.47 (s), 4.57 (s)], 6.48 and 6.7–7.45 [all 12H, m, 6.48 (s)]

The compound of Example 544
¹H-NMR (200 MHz, CDCl₃) δ ppm: 1.16–4.92 (20H, m), 2.53 and 2.59 (all 3H, s), 6.54–6.75 (1H, m), 6.91–7.18 (2H, m), 7.23–7.68 (8H, m), 12.83 (1H, brs)

The compound of Example 545
¹H-NMR (200 MHz, CDCl₃) δ ppm: 1.17–5.20 (20H, m), 4.93 and 5.11 (all 2H, s), 6.53–7.56 (12H, m), 12.34–13.15 (1H, m)

The compound of Example 547
¹H-NMR (200 MHz, CDCl₃) δ ppm: 0.82–5.25 (27H, m), 3.87 (2H, t, J=6.4 Hz), 6.53–6.80 (2H, m), 6.83–7.68 (6H, m), 12.32–13.22 (1H, m)

The compound of Example 553
¹H-NMR (200 MHz, CDCl₃) δ ppm: 1.11–4.21, 4.49–4.71 and 4.98–5.20 (all 25H, m), 6.28–7.61 (1H, m)

The compound of Example 554
¹H-NMR (200 MHz, CDCl₃) δ ppm: 1.19–4.04, 4.48–4.71 and 4.97–5.19 [all 26H, m, 2.17 (s), 2.21 (s)], 6.42–7.74 (12H, m)

The compound of Example 555
¹H-NMR (200 MHz, CDCl₃) δ ppm: 2.57 (4H, t, J=5.10 Hz), 3.32 (4H, t, J=5.10 Hz), 3.56 (2H, s), 3.86 (3H, s), 6.74 (1H, dd, J=8.94 Hz, J=8.96 Hz), 6.85 (1H, d, J=2.55 Hz), 7.25–7.45 (5H, m), 7.83 (1H, d, J=8.91 Hz)

The compound of Example 556
¹H-NMR (200 MHz, CDCl₃) δ ppm: 1.03–2.22, 2.60–3.15, 3.90–4.28 and 4.80–5.00 [all 28H, m, 1.45 (s), 3.98 (d, J=6.31 Hz)], 6.68–7.42 and 7.58–7.71 (all 7H, m)

The compound of Example 558
¹H-NMR (200 MHz, DMSO-d₆) δ ppm: 0.9–2.2, 2.6–3.2 and 4.5–4.9 [all 15H, m, 4.51 (s), 4.58 (s)], 6.8–7.15, 7.15–7.40 and 7.40–7.90 (all 12.2H, m), 8.47 and 8.7 (all 0.8H, each s)

The compound of Example 559
¹H-NMR (200 MHz, CDCl₃) δ ppm: 0.80–4.08 and 4.42–4.69 [all 29H, m, 2.40 (s)], 6.58–7.78 [all 8H, m, 7.51 (d, J=2.01 Hz)]

The compound of Example 560
¹H-NMR (200 MHz, CDCl₃) δ ppm: 1.0–1.25, 1.25–2.25, 2.5–3.7 and 4.4–5.0 (all 15H, m), 6.73–7.75 (all 10H, m), 8.53 (2H, d, J=5 Hz)

The compound of Example 562
¹H-NMR (200 MHz, CDCl₃) δ ppm: 1.17–4.86 (26H, m), 6.50–7.65 (10H, m), 12.67 (1H, brs)

The compound of Example 563
¹H-NMR (200 MHz, DMSO-d₆) δ ppm: 0.96–2.35 and 2.36–4.97 (all 20H, m), 6.79–8.06 (12H, m), 10.02–10.46 and 11.00–11.60 (all 1H, m)

The compound of Example 564
¹H-NMR (200 MHz, CDCl₃) δ ppm: 0.52–2.22, 2.23–4.24, 4.34–4.71 and 4.91–5.17 [all 14H, m, 0.66 (t, J=7.3 Hz)], 5.53–5.74 and 6.29–6.58 (all 1H, m), 6.89–7.88 (12H, m)

The compound of Example 565
¹H-NMR (200 MHz, DMSO-d₆) δ ppm: 1.08–2.21, 2.23–4.08 and 4.21–5.11 [all 26H, m, 2.31 (s), 2.44 (s)], 6.46–7.78 (11H, m), 10.00–10.28 and 10.96–11.45 (all 1H, m)

The compound of Example 566
¹H-NMR (200 MHz, CDCl₃) δ ppm: 1.16–2.20, 2.28–4.10, 4.42–4.71 and 4.89–5.11 [all 25H, m, 2.42 (s), 2.56 (s)], 6.59–7.68 (11H, m)

The compound of Example 567
¹H-NMR (200 MHz, DMSO-d₆) δ ppm: 0.79–2.19, 2.29–3.80 and 3.96–4.67 (all 23H, m), 6.52–7.48 and 7.49–8.45 (11H, m), 9.83–10.21 and 10.86–11.51 (all 1H, each br)

The compound of Example 572
¹H-NMR (200 MHz, CDCl₃) δ ppm: 0.57–0.90, 1.03–2.22, 2.27–4.69 and 5.49–5.71 [all 20H, m, 0.67 (t, J=7.3 Hz), 2.44 (s), 2.59 (s)], 5.49–5.71 and 6.36–7.65 (all 12H, m)

The compound of Example 577
¹H-NMR (200 MHz, CDCl₃) δ ppm: 1.3–2.2, 2.65–3.2, 4.0–4.4 and 4.8–5.0 (all 11H, m), 6.18 (1H, dd, J=8.4 Hz, J=2.4 Hz), 6.48 (1H, d, J=2.2 Hz), 6.69 (1H, d, J=8.4 Hz), 6.85–7.45 (9H, m)

The compound of Example 578
¹H-NMR (200 MHz, CDCl₃) δ ppm: 1.2–2.2, 2.5–3.4, 4.15–4.4 and 4.7–5.1 (all 14H, m), 6.15 (0.88H, d, J=8 Hz), 6.43 (0.94H, s), 6.67 (1.07H, d, J=8 Hz), 6.8–7.5 (9.1H, m)

The compound of Example 583
¹H-NMR (200 MHz, CDCl₃) δ ppm: 0.95–4.9 [all 26H, m, 1.10 (t, J=7.2 Hz), 2.47 (d, J=4 Hz)], 6.8–7.2, 7.2–7.55, 7.55–8.25 and 8.25–8.60 fall 14H, m, 8.44 (s)]

The compound of Example 584
¹H-NMR (200 MHz, CDCl₃) δ ppm: 0.666 (3H, t, J=7.3 Hz), 1.50–4.00 (17H, m), 6.40–7.20 (13H, m)

The compound of Example 585
¹H-NMR (200 MHz, CDCl₃) δ ppm: 1.00–4.20 and 4.40-4.35 [all 23H, m, 2.50 (s), 2.54 (s)], 6.80–7.65 (12H, m)

The compound of Example 586
¹H-NMR (200 MHz, CDCl₃) δ ppm: 1.45–3.13, 3.20–4.00 and 4.20–5.18 (all 13H, m), 6.62–7.66 (12H, m)

The compound of Example 589

¹H-NMR (200 MHz, CDCl₃) δ ppm: 0.8–3.7 and 4.85–5.15 [all 24H, m, 2.37 (s)], 5.9–7.2 [all 7H, m, 6.27 (s)]

The compound of Example 593

¹H-NMR (200 MHz, CDCl₃) δ ppm: 1.3–3.8, 4.2–4.8 and 4.9–5.15 [all 12H, m, 3.36 (s), 3.48 (s), 4.55 (s)], 6.6–7.95 (12H, m), 8.15–8.7 (1H, m)

The compound of Example 594

¹H-NMR (200 MHz, CDCl₃) δ ppm: 1.19–2.35, 2.60–3.15, 3.75–4.20, 4.30–4.61 and 4.79–5.11 (all 12H, m), 6.71–7.75 (7H, m)

The compound of Example 595

¹H-NMR (200 MHz, CDCl₃) δ ppm: 0.75–3.30, 3.30–4.18 and 4.40–4.62 (all 20H, m), 6.55–6.72 (1H, m), 6.72–6.97 (2H, m), 6.97–7.18 (2H, m), 7.18–7.67 (7H, m)

The compound of Example 599

¹H-NMR (200 MHz, CDCl₃) δ ppm: 1.18–1.58, 1.58–4.29 and 4.50–4.85 [all 25H, m, 1.71 (s), 2.54 (s)], 7.05–7.72 (12H, m), 14.5–17.8 (1H, brs)

The compound of Example 601

¹H-NMR (200 MHz, CDCl₃) δ ppm: 1.50–2.20, 2.20–2.73 and 2.90–4.00 [all 16H, m, 1.62 (s), 2.59 (s), 3.24 (s)], 7.16–7.69 (12H, m), 9.42 (1H, s)

The compound of Example 606

¹H-NMR (200 MHz, CDCl₃) δ ppm: 1.15–2.00, 2.55–2.90, 3.35–3.70 and 4.40–4.60 [all 27H, m, 1.57 (s)], 7.00–7.34 (3H, m)

The compound of Example 607

¹H-NMR (200 MHz, CDCl₃) δ ppm: 1.15–2.09, 2.56–2.97, 3.30–3.65, 4.40–4.60 and 4.71–4.82 (all 24H, m), 6.95–7.28 (3H, m)

The compound of Example 608

¹H-NMR (250 MHz, DMSO-d₆) δ ppm: 1.15–1.55, 1.70–2.35, 2.55–3.16, 3.44–3.65, 4.20–4.40 and 4.70–5.07 (all 9H, m), 6.49–6.57, 6.57–6.85, 6.9–7.05 and 7.05–7.5 (all 8H, m), 7.62–7.75 (2H, m)

The compound of Example 609

¹H-NMR (250 MHz, DMSO-d₆) δ ppm: 1.15–2.14, 2.14–4.40 and 4.90–5.54 (all 12H, m), 6.65 and 6.72 (all 1H, each d, J=8.3 Hz), 6.92–7.46 and 7.60–7.81 (all 8H, m)

The compound of Example 610

¹H-NMR (200 MHz, CDCl₃) δ ppm: 2.15–2.63, 2.27–3.18, 3.55–4.06 and 5.82–6.03 (all 8H, m), 7.46 (1H, d, J=8.3 Hz), 7.78 (1H, dd, J=2.4 Hz, J=8.3 Hz), 8.16 (1H, d, J=2.4 Hz), 8.21–8.33 (2H, m), 8.54–8.70 (2H, m), 10.87 (1H, s)

The compound of Example 611

¹H-NMR (200 MHz, CDCl₃) δ ppm: 1.49–1.76, 1.86–2.22, 2.67–3.09 and 4.90–5.08 (all 8H, m), 6.51 (1H, d, J=8.3 Hz), 6.89 (1H, dd, J=2 Hz, J=8.3 Hz), 7.13–7.35 (3H, m), 7.42–7.56 (2H, m)

The compound of Example 613

¹H-NMR (200 MHz, CDCl₃) δ ppm: 1.27–1.70, 1.80–2.30, 2.68–3.37, 3.40–3.85, 4.35–4.58 and 5.08–5.20 (all 9H, m), 6.47 and 6.54 (all 1H, each d, J=8.3 Hz), 6.86–7.01 (1H, m), 7.15 and 7.32 (all 1H, each d, J=2 Hz), 7.35–7.56 (4H, m)

The compound of Example 614

¹H-NMR (200 MHz, CDCl₃) δ ppm: 0.75–3.90, 4.40–4.55 and 5.03–5.20 (all 28H, m), 6.45–6.65 (1H, m), 6.70–7.35 (6H, m), 7.65–7.95 (1H, m)

The compound of Example 615

¹H-NMR (200 MHz, CDCl₃) δ ppm: 0.80–3.90, 4.35–4.56, 5.08–5.20 and 6.45–6.67 (1H, m), 6.90–7.55 (6H, m), 7.80–8.25 and 8.75–8.85 (all 1H, m)

The compound of Example 616

¹H-NMR (200 MHz, CDCl₃) δ ppm: 1.00–3.95, 4.37–4.57 and 5.00–5.17 (all 22H, m), 6.45 and 6.50 (all 1H, each d, J=8.3 Hz), 6.90 (1H, dd, J=2.3 Hz, J=8.3 Hz), 6.96–7.06 and 7.29–7.36 (all 2H, m), 7.44–7.68 (4H, m)

The compound of Example 617

¹H-NMR (200 MHz, CDCl₃) δ ppm: 0.85–3.92, 4.35–4.52 and 4.95–5.15 (all 26H, m), 6.40–6.55 (1H, m), 6.85–6.95 (1H, m), 6.95–7.15 (1H, m), 7.30–7.70 (4H, m)

The compound of Example 618

¹H-NMR (200 MHz, CDCl₃) δ ppm: 1.15–2.20, 2.52–3.90, 4.40–4.59 and 5.08–5.26 (all 22H, m), 6.54–6.68 (1H, m), 6.87–7.44 (6H, m)

The compound of Example 619

¹H-NMR (200 MHz, CDCl₃) δ ppm: 1.15–2.21, 2.47–3.01, 3.07–3.32, 3.41–3.78, 4.35–4.57 and 5.08–5.23 (all 19H, m), 6.00–6.51 (1H, brs), 6.59 (1H, d, J=8.3 Hz), 6.89–7.41 (6H, m)

The compound of Example 622

¹H-NMR (200 MHz, CDCl₃) δ ppm: 0.76–2.21, 2.22–4.31, 4.38–4.64 and 5.01–5.24 [all 23H, m, 2.41 (s), 2.46 (s)], 6.38–7.43 (6H, m)

The compound of Example 623

¹H-NMR (200 MHz, CDCl₃) δ ppm: 0.73–5.18 (24H, m), 6.52–8.03 (8H, m), 12.50–13.30 (1H, m)

The compound of Example 624

¹H-NMR (200 MHz, CDCl₃) δ ppm: 0.93 (3H, t, J=7.2 Hz), 1.10–2.30 (8H, m), 2.56–4.30 (5H, m), 3.65 and 3.70 (all 3H, s), 3.88 (2H, t, J=6.5 Hz), 4.38–5.33 (1H, m), 6.51–7.40 (8H, m)

The compound of Example 626

¹H-NMR (200 MHz, CDCl₃) δ ppm: 1.20–2.22 (4H, m), 2.40–5.23 (5H, m), 2.52 and 2.56 (all 3H, s), 3.72 and 3.73 (all 3H, s), 6.45–7.70 (10H, m)

The compound of Example 627

¹H-NMR (200 MHz, CDCl₃) δ ppm: 1.17–2.21 (4H, m), 2.61–3.02 (2H, m), 3.09–3.85 (1H, m), 3.69 (3H, s), 4.01–4.27 (1H, m), 4.43–5.18 (1H, m), 4.94 and 5.10 (all 2H, s), 6.46–6.67 (1H, m), 6.83–7.50 (11H, m)

The compound of Example 629

¹H-NMR (200 MHz, CDCl₃) δ ppm: 1.09–2.32 (4H, m), 2.56–5.33 (5H, m), 3.69 and 3.74 (all 3H, s), 6.53–7.78 (12H, m)

The compound of Example 630

¹H-NMR (200 MHz, CDCl₃) δ ppm: 1.12–2.18 (4H, m), 1.18 and 1.34 (all 9H, s), 2.33–5.24 (5H, m), 2.45 and 2.49 (all 3H, s), 7.32 (3H, s), 6.43–7.51 (7H, m)

The compound of Example 631

¹H-NMR (200 MHz, CDCl₃) δ ppm: 1.08–2.25 (4H, m), 1.18 and 1.33 (all 9H, s), 2.34–3.96 (5H, m), 2.45 and 2.50 (all 3H, s), 6.47–7.50 (7H, m), 9.00 (1H, brs)

The compound of Example 632

¹H-NMR (200 MHz, CDCl₃) δ ppm: 1.15–2.35 (7H, m), 2.58–3.28 (3H, m), 3.35–5.20 (10H, m), 6.15–7.56 (6H, m)

The compound of Example 633

¹H-NMR (200 MHz, CDCl₃) δ ppm: 1.16–2.22 (7H, m), 2.58–3.29 (3H, m), 3.35–4.18 (6H, m), 4.45–5.21 (1H, m), 6.12–7.48 (6H, m), 10.82 (1H, brs)

The compound of Example 634

$^1$H-NMR (200 MHz, DMSO-d$_6$) δ ppm: 1.13–2.21 (4H, m), 2.36–4.31 (4H, m), 2.49 (3H, s), 4.33–5.13 (1H, m), 6.76–7.88 (11H, m), 12.43 (1H, brs)

The compound of Example 637

$^1$H-NMR (200 MHz, CDCl$_3$) δ ppm: 1.15–2.33, 2.33–3.99, 3.99–4.31, 4.50–4.65 and 5.05–5.18 (all 15H, m), 6.50–7.70 and 8.10–8.20 (all 12H, m)

The compound of Example 640

$^1$H-NMR (200 MHz, CDCl$_3$) δ ppm: 1.13–2.26, 2.35–3.90, 4.43–4.66 and 5.03–5.22 (all 15H, m), 6.40–6.70 (1H, m), 6.73–6.95 (1H, m), 6.95–7.65 (6H, m), 8.50–8.75 (2H, m)

The compound of Example 641

$^1$H-NMR (200 MHz, CDCl$_3$) δ ppm: 1.22–2.35, 2.5–3.3, 3.4–3.9, 4.35–4.7 and 5.0–5.3 (all 18H, m), 6.65 (1H, d, J=8.3 Hz), 6.85–7.5 (9H, m), 7.6–7.8 (1H, m)

The compound of Example 642

$^1$H-NMR (200 MHz, CDCl$_3$) δ ppm: 1.2–1.65, 1.9–2.25, 2.6–3.1, 3.1–3.35, 3.4–3.75, 4.3–4.6 and 4.9–5.6 (all 14H, m), 6.62 (1H, d, J=8.3 Hz), 6.85–7.5 (9H, m), 7.6–7.8 (1H, m)

The compound of Example 643

$^1$H-NMR (200 MHz, CDCl$_3$) δ ppm: 0.78–1.06, 1.14–2.19, 2.59–3.30, 3.40–4.65 and 4.94–5.16 [all 21H, m, 3.69 (s)], 6.78–7.75 and 8.56–8.70 [all 8H, m, 7.45 (s)]

The compound of Example 644

$^1$H-NMR (200 MHz, CDCl$_3$) δ ppm: 0.92 (6H, d, J=6.71 Hz), 1.19–2.32, 2.55–4.62 and 4.95–5.16 (all 12H, m), 6.32–7.95 [all 9H, m, 7.55 (s)]

The compound of Example 645

$^1$H-NMR (200 MHz, CDCl$_3$) δ ppm: 1.15–2.31, 2.52–4.70 and 4.90–5.15 [all 14H, m, 3.69 (s)], 6.79–7.81 and 8.55–8.72 (all 8H, m)

The compound of Example 646

$^1$H-NMR (200 MHz, CDCl$_3$) δ ppm: 1.13–2.35, 2.62–4.71 and 4.98–5.19 [all 16H, 3.70 (s)], 6.81–7.92 [all 7H, m, 7.52 (d, J=2.06 Hz)l The compound of Example 649

$^1$H-NMR (200 MHz, DMSO-d$_6$) δ ppm: 0.98–4.60 and 4.78–4.90 (all 13H, m), 6.05–6.21 and 6.40–8.08 (all 7H, m)

The compound of Example 647

$^1$H-NMR (200 MHz, CDCl$_3$) δ ppm: 1.25–2.32, 2.60–3.31, 3.40–4.68 and 5.05–5.20 [all 18H, m, 3.69 (s)], 6.58–7.81 (8H, m)

The compound of Example 648

$^1$H-NMR (200 MHz, CDCl$_3$) δ ppm: 1.05–2.32, 2.58–3.90, 4.00–4.68 and 5.00–5.18 [all 18H, m, 3.70 (s)], 6.80–7.64 (7H, m)

The compound of Example 650

$^1$H-NMR (200 MHz, CDCl$_3$) δ ppm: 2.89 (2H, t, J=6 Hz), 4.35 (2H, t, J=6 Hz), 7.0 (1H, d, J=7 Hz), 7.2–7.7 (10H, m), 7.99 (1H, d, J=2.5 Hz)

The compound of Example 651

$^1$H-NMR (200 MHz, CDCl$_3$) δ ppm: 1.33 (3H, t, J=7 Hz), 3.44 (2H, dt, J=6.4 Hz, J=2.4 Hz), 3.98 (2H, t, J=6.4 Hz), 4.23 (2H, q, J=7 Hz), 6.41 (1H, t, J=2.4 Hz), 6.86 (1H, d, J=8.6 Hz), 7.0 (1H, dd, J=8.4 Hz, J=2.4 Hz), 7.35–7.70 (10H, m)

The compound of Example 652

$^1$H-NMR (200 MHz, CDCl$_3$) δ ppm: 1.29 (3H, t, J=7 Hz), 1.8–2.3 (2H, m), 2.6–2.8 (1H, m), 2.8–3.0 (1H, m), 3.3–3.56 (1H, m), 3.85–4.1 (2H, m), 4.22 (2H, q, J=7 Hz), 6.69 (1H, d, J=8.6 Hz), 6.89 (1H, dd, J=8.6 Hz, J=2.4 Hz), 7.2–7.7 (10H, m)

The compound of Example 653

$^1$H-NMR (200 MHz, CDCl$_3$) δ ppm: 1.1–1.7 (5H, m), 1.7–2.1 (5H, m), 2.4–2.75 (1H, m), 2.85 (2H, t, J=6 Hz), 4.3 (2H, t, J=6 Hz), 7.0 (1H, d, J=8.8 Hz), 7.19–7.27 (3H, m), 7.40–7.45 (2H, m), 7.96 (1H, d, J=2.5 Hz)

The compound of Example 654

$^1$H-NMR (200 MHz, CDCl$_3$) δ ppm: 2.9 (2H, t, J=6.4 Hz), 3.96 (3H, s), 4.31 (2H, t, J=6.4 Hz), 6.94–7.1 (2H, m), 7.35–7.40 (2H, m), 7.77 (1H, d, J=8.3 Hz), 8.0 (1H, d, J=2.5 Hz)

The compound of Example 655

$^1$H-NMR (200 MHz, CDCl$_3$) δ ppm: 1.85–2.05 (1H, m), 2.15–2.35 (1H, m), 2.65 (1H, m), 2.85 (1H, m), 3.35–3.55 (1H, m), 3.85–4.10 (2H, m), 6.70 (1H, d, J=8.6 Hz), 6.90 (1H, dd, J=8.6 Hz, J=2.4 Hz), 7.25–7.65 (10H, m)

The compound of Example 656

$^1$H-NMR (200 MHz, CDCl$_3$) δ ppm: 1.1–1.55 (5H, m), 1.33 (3H, t, J=7.2 Hz), 1.65–2.0 (5H, m), 2.45–2.65 (1H, m), 3.35–3.5 (2H, m), 3.94 (2H, t, J=6.4 Hz), 4.22 (2H, q, J=7.2 Hz), 6.40 (1H, t, J=2.3 Hz), 6.85 (1H, d, J=8.7 Hz), 7.05 (1H, dd, J=8.7 Hz, J=2.3 Hz), 7.15 (2H, d, J=8.2 Hz), 7.34 (2H, d, J=8.2 Hz), 7.65 (1H, d, J=2.3 Hz)

The compound of Example 657

$^1$H-NMR (200 MHz, CDCl$_3$) δ ppm: 1.35–1.60 (5H, m), 1.70–2.0 (6H, m), 2.10–2.35 (1H, m), 2.35–2.65 (1H, m), 2.67 (1H, dd, J=16 Hz, J=6 Hz), 2.90 (1H, dd, J=16 Hz, J=6 Hz), 3.35–3.55 (1H, m), 3.85–4.05 (2H, m), 6.70 (1H, d, J=8.7 Hz), 6.89 (1H, dd, J=8.7 Hz, J=2.3 Hz), 7.12 (2H, d, J=8.2 Hz), 7.19 (1H, d, J=2.3 Hz), 7.28 (2H, d, J=8.2 Hz)

The compound of Example 658

$^1$H-NMR (200 MHz, CDCl$_3$) δ ppm: 1.85–2.10 (1H, m), 2.15–2.35 (1H, m), 2.68 (1H, dd, J=16 Hz, J=8 Hz), 2.87 (1H, dd, J=16 Hz, J=6.2 Hz), 3.3–3.5 (1H, m), 3.75 (3H, s), 3.8–4.15 (2H, m), 6.4–6.55 (1H, m), 6.88 (1 Hz dd, J=8.6 Hz, J=2.3 Hz), 7.20 (1H, d, J=2.3 Hz), 7.54 (2H, d, J=8.9 Hz), 8.16 (2H, d, J=8.9 Hz)

The compound of Example 659

$^1$H-NMR (200 MHz, CDCl$_3$) δ ppm: 1.85–2.10 (1H, m), 2.20–2.40 (1H, m), 2.71 (1H, dd, J=16 Hz, J=8.4 Hz), 2.94 (1H, dd, J=16 Hz, J=6 Hz), 3.35–3.55 (1H, m), 3.85–4.10 (2H, m), 6.70 (1H, d, J=8.6 Hz), 6.90 (1H, dd, J=8.6 Hz, J=2.3 Hz), 7.21 (1H, d, J=2.3 Hz), 7.35–7.70 (9H, m)

The compound of Example 660

$^1$H-NMR (200 MHz, CDCl$_3$) δ ppm: 1.80–2.0 (1H, m), 2.10–2.30 (1H, m), 2.62 (1H, dd, J=15.6 Hz, J=8.6 Hz). 2.84 (1H, dd, J=15.6 Hz, J=6 Hz), 3.3–3.5 (1H, m), 3.73 (3H, s), 3.80–4.10 (4H, m), 6.50 (2H, d, J=8.5 Hz), 6.67 (1H, d, J=8.5 Hz), 6.89 (1H, dd, J=8.7 Hz, J=2.2 Hz), 7.15–7.35 (3H, m)

The compound of Example 661

$^1$H-NMR (200 MHz, CDCl$_3$) δ ppm: 1.75–1.95 (1H, m), 2.10–2.30 (1H, m), 2.63 (1H, dd, J=15.6 Hz, J=8.4 Hz), 2.85 (1H, dd, J=15.6 Hz, J=6.2 Hz), 3.3–3.5 (1H, m), 3.74 (3H, s), 3.80–4.05 (2H, m), 4.61 (2H, s), 6.6 (1H, d, J=8.6 Hz), 6.88 (1H, dd, J=8.6 Hz, J=2.2 Hz), 6.95–7.65, 8.36 [all 11H, m, 8.36 (s)]

The compound of Example 662

$^1$H-NMR (200 MHz, CDCl$_3$) δ ppm: 1.80–2.10 (1H, m), 2.15–2.30 (1H, m), 2.71 (1H, dd, J=16 Hz, J=8 Hz), 2.90 (1H, dd, J=16 Hz, J=6 Hz), 3.3–3.5 (1H, m), 3.75–4.10 (2H, m), 4.60 (2H, s), 6.59 (1H, d, J=8.6 Hz), 6.88 (1H, dd, J=8.6 Hz, J=2.2 Hz), 6.97 (2H, d, J=7.8 Hz), 6.99–7.10 (1H, m), 7.20 (1H, d, J=2.2 Hz), 7.31–7.39 (4H, m), 7.54 (2H, d, J=8.6 Hz), 8.38 (1H, s)

The compound of Example 663

$^1$H-NMR (200 MHz, CDCl$_3$) δ ppm: 1.75–1.95 (1H, m), 2.10–2.20 (1H, m), 2.2 (3H, s), 2.60 (1H, dd, J=15.7 Hz, J=8.6 Hz), 2.83 (1H, dd, J=15.7 Hz, J=6 Hz), 3.3–3.4 (1H, m), 3.78 (3H, s), 3.8–4.0 (2H, m), 4.69 (2H, s), 6.60 (1H, d, J=8.7 Hz), 6.87 (2H, dt, J=8.6 Hz, J=2.2 Hz), 6.94–7.01 (1H, m), 7.10–7.50 (5H, m), 7.64 (2H, d, J=8.7 Hz), 7.74 (1H, s), 9.60 (1H, s)

The compound of Example 664

$^1$H-NMR (200 MHz, CDCl$_3$) δ ppm: 1.75–2.00 (1H, m), 2.15–2.35 (1H, m), 2.64 (1H, dd, J=15.7 Hz, J=8.6 Hz), 2.86 (1H, dd, J=15.7 Hz, J=6 Hz), 3.3–3.5 (1H, m), 3.75 (3H; s), 3.80–4.00 (2H, m), 4.72 (2H, s), 6.61 (1H, d, J=8.6 Hz), 6.87 (1H, dd, J=8.8 Hz, J=2.2 Hz), 6.93–7.07 (2H, m), 7.17 (1H, d, J=2.2 Hz), 7.25–7.50 (4H, m), 7.58 (2H, d, J=8.6 Hz), 8.78 (1H, s)

The compound of Example 665

$^1$H-NMR (200 MHz, CDCl$_3$) δ ppm: 1.80–2.05 (1H, m), 2.10–2.30 (1H, m), 2.71 (1H, dd, J=16 Hz, J=8.2 Hz), 2.92 (1H, dd, J=16 Hz, J=6 Hz), 3.30–3.50 (1H, m), 3.75–4.10 (2H, m), 4.65 (2H, s), 6.55–7.65 [all 11H, m, 6.60 (d, J=8.6 Hz), 7.57 (d, J=8.6 Hz)], 8.79 (1H, s)

The compound of Example 666

$^1$H-NMR (200 MHz, CDCl$_3$) δ ppm: 1.80–2.0 (1H, m), 2.1–2.3 (1H, m), 2.36 (3H, s), 2.63 (1H, dd, J=15.6 Hz, J=8.5 Hz), 2.86 (1H, dd, J=15.6 Hz, J=6 Hz), 3.3–3.5 (1H, m), 3.74 (3H, s), 3.83–3.99 (2H, m), 4.59 (2H, s), 6.60 (1H, d, J=8.6 Hz), 6.78 (2H, d, J=8 Hz), 6.88 (2H, dd, J=8.6 Hz, J=2 Hz), 7.16–7.26 (2H, m), 7.38 (2H, d, J=8.7 Hz), 7.55 (2H, d, J=8.7 Hz), 8.36 (1H, s)

The compound of Example 667

$^1$H-NMR (200 MHz, CDCl$_3$) δ ppm: 1.8–2.25, 2.65–4.10 (all 10H, m), 4.68 (2H, s), 6.4–7.85 (all 13H, m), 9.48 (1H, s)

The compound of Example 668

$^1$H-NMR (200 MHz, CDCl$_3$) δ ppm: 1.8–3.0 (all 7H, m), 3.25–3.50 (1H, m), 3.70–4.05 (2H, m), 4.56 (2H, s), 6.60 (1H, d, J=8.5 Hz), 6.75–6.90 (4H, m), 7.18–7.26 (2H, m), 7.35 (2H, d, J=8.6 Hz), 7.52 (2H, d, J=8.7 Hz), 8.4 (1H, s)

The compound of Example 669

$^1$H-NMR (200 MHz, CDCl$_3$) δ ppm: 0.9–2.25, 2.6–4.1, 4.3–4.75 [all 15H, m, 0.99 (t, J=7.2 Hz)], 6.8–7.5, 7.55–7.65, 8.2–8.5 [all 13H, m, 7.60 (d, J=4 Hz), 8.25 (d, J=4 Hz)]

The compound of Example 670

$^1$H-NMR (200 MHz, CDCl$_3$) δ ppm: 1.3–2.2, 2.35–2.5, 2.7–3.9 and 4.4–4.65 [all 15H, m, 2.40 (s), 3.73 (s)], 6.55 (0.6H, d, J=8.3 Hz), 6.89 (1.3H, d, J=8.3 Hz), 7.0–7.5 (all 4H, m), 8.35–8.50 (0.8H, m), 8.9–9.05 (0.25H, m)

The compound of Example 671

$^1$H-NMR (200 MHz, CDCl$_3$) δ ppm: 1.1–2.2, 2.7–3.4, 3.5–3.8 and 4.45–4.65 [all 12H, m, 3.69 (s)], 6.85–7.5 and 8.9–9.1 (all 8H, m)

The compound of Example 672

$^1$H-NMR (200 MHz, CDCl$_3$) δ ppm: 1.4–2.3, 2.75–3.25 and 4.75–5.05 (all 8H, m), 6.75–7.45 (all 7H, m), 9.55 and 10.03 (all 1H, each s)

The compound of Example 673

$^1$H-NMR (200 MHz, CDCl$_3$) δ ppm: 1.15–2.2, 2.6–3.85 and 4.4–4.65 [all 15H, m, 2.83 (s)], 6.21 (0.7H, dd, J=8.7 Hz, J=2.5 Hz), 6.51 (0.6H, d, J=2.5 Hz), 6.6–7.4 (all 5.7H, m)

The compound of Example 674

$^1$H-NMR (200 MHz, CDCl$_3$) δ ppm: 1.0–2.1, 2.7–3.9, 4.4–5.3 [all 17H, m, 1.1 (d, J=6 Hz)], 6.0–6.1 and 6.4–7.6 (all 8H, m)

The compound of Example 675

$^1$H-NMR (200 MHz, CDCl$_3$) δ ppm: 1.2–2.2, 2.7–4.0 and 4.45–4.7 (all 13H, m), 5.9 and 6.9–7.7 [all 8H, m, 5.9 (s)]

The compound of Example 676

$^1$H-NMR (200 MHz, CDCl$_3$) δ ppm: 1.2–2.35, 2.75–3.10, 3.10–3.95 and 4.4–4.6 [all 16H, m, 2.79 (s)], 6.3–7.6 (all 7H, m)

The compound of Example 677

$^1$H-NMR (200 MHz, CDCl$_3$) δ ppm: 1.1–1.25, 1.25–2.2, 2.7–3.95 and 4.45–4.65 (all 22H, m), 6.85–7.8 (all 7H, m), 7.8–8.5 (1H, m)

The compound of Example 678

$^1$H-NMR (200 MHz, CDCl$_3$) δ ppm: 1.35–2.05, 2.65–4.0 and 4.3–4.65 [all 15H, m, 4.39 (s)], 5.8–6.85 (1H, m), 6.85–8.15 (all 12H, m)

The compound of Example 679

$^1$H-NMR (200 MHz, CDCl$_3$) δ ppm: 1.04–2.20 [all 7H, m, 1.41 (t, J=7.0 Hz)], 2.32–3.32, 3.33–4.30, 4.43–4.70 and 5.00–5.22 (all 13H, m, 2.51 (s), 3.72 (s)], 6.43–7.67 (11H, m)

The compound of Example 680

$^1$H-NMR (200 MHz, CDCl$_3$) δ ppm: 1.03 (3H, t, J=7.0 Hz), 0.90–2.30 (6H, m), 2.38–3.30, 3.38–4.36, 4.43–4.70 and 5.04–5.23 [all 13H, m, 2.52 (s), 3.72 (s), 3.93 (t)], 6.43–7.64 (11H, m)

The compound of Example 683

$^1$H-NMR (200 MHz, CDCl$_3$) δ ppm: 1.24–3.02 (5H, m), 3.04–3.89, 3.90–4.88 and 4.93–5.14 (all 10H, m, 3.71 (s), 3.74 (s), 3.76 (s), 3.82 (s)], 6.49–6.65, 6.71–6.86, 6.94–7.10, 7.11–7.42 and 7.58–7.78 (all 6H, m)

The compound of Example 684

$^1$H-NMR (200 MHz, CDCl$_3$) δ ppm: 1.12–2.23, 2.24–3.93, 4.01–4.31, 4.43–4.70 and 5.01–5.22 [all 18H, m, 2.37 (s), 2.44 (s), 2.53 (s), 2.57 (s), 3.72 (s)], 6.47–7.59 (11H, m)

The compound of Example 685

$^1$H-NMR (200 MHz, CDCl$_3$) δ ppm: 1.11–2.26 (4H, m), 2.56–4.32, 4.45–4.73 and 5.00–5.20 [all 8H, m, 3.71 (s)], 6.68–7.81 (12H, m)

The compound of Example 686

$^1$H-NMR (200 MHz, CDCl$_3$) δ ppm: 1.13–2.37, 2.42–4.39, 4.47–4.75 and 5.04–5.26 [all 15H, m, 2.56 (s), 3.73 (s)], 6.49–7.95 and 8.13–8.49 (all 11H, m)

The compound of Example 687

$^1$H-NMR (200 MHz, CDCl$_3$) δ ppm: 1.18–2.27 (4H, m), 2.28–4.39, 4.45–4.72 and 5.03–5.27 [all 14H, m, 2.35 (s), 2.41 (s), 2.52 (s), 2.56 (s)], 6.49–7.64 (11H, m)

The compound of Example 689

$^1$H-NMR (200 MHz, DMSO-d$_6$) δ ppm: 1.00–3.76, 4.28–4.55 and 4.81–5.05 [all 15H, m, 2.31 (s), 2.44 (s)], 6.49–7.79 (11H, m), 12.31 (1H, s)

The compound of Example 690

$^1$H-NMR (200 MHz, DMSO-d$_6$) δ ppm: 1.04–2.22 (4H, m), 2.32–3.76, 4.27–4.58 and 4.81–5.08 (all 8H, m), 6.49–8.48 (11H, m), 11.97–12.54 (1H, m)

The compound of Example 691

$^1$H-NMR (200 MHz, CDCl$_3$) δ ppm: 1.02–3.86, 4.36–4.62 and 5.01–5.30 [all 26H, m, 2.41 (s), 3.74 (s)], 6.36–7.40 (6H, m)

The compound of Example 692

$^1$H-NMR (200 MHz, CDCl$_3$) δ ppm: 2.20–3.01, 3.32–4.28 and 4.78–5.49 [all 23H, m, 2.35 (s), 2.44 (s), 3.82 (s)], 6.55–7.75 (11H, m)

The compound of Example 693

$^1$H-NMR (200 MHz, CDCl$_3$) δ ppm: 1.12–2.05 (10H, m), 2.19–2.95, 3.42–4.25 and 4.75–5.39 [all 21H, m, 2.35 (s)], 6.59–7.55 (7H, m)

The compound of Example 696

$^1$H-NMR (200 MHz, DMSO-d$_6$) δ ppm: 1.48 (3H, d, J=6.6 Hz),1.57–2.13 (2H, m), 2.86–3.13 (2H, m), 3.36–3.65 (1H, m), 4.43–4.63 (1H, m), 4.70–4.93 (1H, m), 6.48–8.00 (12H, m), 10.19 and 10.46 (all 1H, s), 12.68 (1H, brs)

The compound of Example 700

$^1$H-NMR (200 MHz, CDCl$_3$) δ ppm: 1.31 (3H, t, J=7.1 Hz), 1.58 (3H, d, J=6.7 Hz), 1.51–2.33 (2H, m), 2.97–3.23 (2H, m), 3.40–3.70 (1H, m), 3.81–4.18 (2H, m), 4.25 (2H, q, J=7.1 Hz), 4.40–4.91 (1H, m), 4.73 (1H, q, J=6.7 Hz), 6.51–7.65 (12H, m), 8.22 (1H, brs)

The compound of Example 701

$^1$H-NMR (200 MHz, CDCl$_3$) δ ppm: 1.34 (3H, t, J=7.11 Hz), 2.28–3.00 (2H, m), 3.71–5.12 (all 6H, m), 6.85–7.65 and 7.75–8.45 (all 7H, m)

The compound of Example 702

$^1$H-NMR (200 MHz, CDCl$_3$) δ ppm: 1.32 (3H, t, J=7.12 Hz), 2.32–2.90 (2H, m), 3.61–4.49 (all 6H, m), 4.65–5.05 (2H, m), 6.10–7.68 (all 7H, m)

The compound of Example 703

$^1$H-NMR (200 MHz, CDCl$_3$) δ ppm: 1.22–1.43 (3H, m), 1.78–2.38 (2H, m), 2.99–3.24 (2H, m), 3.43–3.66 (1H, m), 3.78–4.39 (4H, m), 4.65–4.89 (1H, m), 6.67 (1H, dt, J=7.6 Hz, J=1.3 Hz), 6.70 (1H, dd, J=8.2 Hz, J=1.3 Hz), 6.89–6.99 (1H, m), 7.05 (1H, dd, J=7.3 Hz, J=1.7 Hz), 7.37 (1H, d, J=8.4 Hz), 7.81 (1H, dd, J=8.4 Hz, J=2.1 Hz), 8.10 (1H, d, J=2.1 Hz)

The compound of Example 704

$^1$H-NMR (200 MHz, CDCl$_3$) δ ppm: 1.32 (3H, t, J=7.16 Hz), 1.50–1.81 [all 3H, m, 1.59 (d, J=6.71 Hz)], 2.50–2.95 and 3.69–5.15 (all 9H, m), 6.81–8.55 [13H, m, 7.55 (s), 8.26 (s)]

The compound of Example 705

$^1$H-NMR (200 MHz, CDCl$_3$) δ ppm: 1.41–1.75 [all 3H, m, 1.59 (d, J=6.76 Hz)], 1.75–2.89, 3.60–4.48 and 4.60–5.10 (all 7H, m), 6.79–8.20 and 8.36–8.88 (all 12H, m)

The compound of Example 706

$^1$H-NMR (200 MHz, CDCl$_3$) δ ppm: 0.72–1.10 (6H, m), 1.33 (3H, t, J=7.13 Hz), 1.80–2.10, 2.55–2.90, 3.69–4.59 and 4.75–5.05 [all 11H, m, 7.29 (q, J=7.13 Hz)], 6.71–7.85, 8.59–8.70 [all 8H, m, 6.63 (s)]

The compound of Example 707

$^1$H-NMR (200 MHz, CDCl$_3$) δ ppm: 1.33 (3H, t, J=6.17 Hz), 2.31–2.95 and 3.39–5.10 (all 12H, m), 6.72–7.89 (8H, m)

The compound of Example 708

$^1$H-NMR (200 MHz, CDCl$_3$) δ ppm: 1.34 (3H, t, J=7.15 Hz), 2.55–3.05, 3.70–4.61 and 4.79–5.08 [all 12H, m, 4.29 (q, J=7.15 Hz), 4.46 (t, J=7.88 Hz)], 6.81–7.72 (7H, m)

The compound of Example 709

$^1$H-NMR (200 MHz, DMSO-d$_6$) δ ppm: 0.89 (6H, d, J=6.69 Hz), 1.70–2.05, 2.30–4.20 and 4.45–4.82 (all 9H, m), 6.85–7.79, 8.10–8.20 and 9.65–9.95 [all 8H, m, 8.14 (s), 9.70 (s)]

The compound of Example 710

$^1$H-NMR (200 MHz, DMSO-d$_6$) δ ppm: 2.05–5.05 (11H, m), 6.70–8.00 (7H, m)

The compound of Example 711

$^1$H-NMR (200 MHz, CDCl$_3$) δ ppm: 0.99–1.98, 2.18–3.00 and 3.64–4.01 [all 18H, m, 2.34 (s)], 6.50–7.61 and 8.40–8.73 (all 8H, m)

The compound of Example 712

$^1$H-NMR (200 MHz, CDCl$_3$) δ ppm: 2.43 (3H, s), 2.62–3.00, 3.71–4.20 and 4.55–5.29 [all 7H, m, 3.82 (s)], 6.62–7.65 and 8.45–8.75 [all 12H, m, 7.42 (d, J=8.45 Hz)]

The compound of Example 713

$^1$H-NMR (200 MHz, CDCl$_3$) δ ppm: 1.10–3.81 and 4.81–5.35 [all 21H, m, 2.37 (s)], 6.35–7.50 (7H, m)

The compound of Example 714

$^1$H-NMR (200 MHz, CDCl$_3$) δ ppm: 1.55–4.05 and 4.85–5.25 [all 13H, m, 2.46 (s), 3.81 (s)], 6.40–7.61 (11H, m)

The compound of Example 715

$^1$H-NMR (200 MHz, CDCl$_3$) δ ppm: 1.04–2.01, 2.18–3.10, 3.56–4.49 and 4.61–5.65 [all 20H, m, 2.35 (s)], 6.51–7.65 (7H, m)

The compound of Example 716

$^1$H-NMR (200 MHz, CDCl$_3$) δ ppm: 1.34 (3H, t, J=7.08 Hz), 2.15–3.10, 3.61–4.51 and 4.78–5.11 [all 14H, m, 2.44 (s), 3.83 (s)], 6.61–7.58 (11H, m)

The compound of Example 717

$^1$H-NMR (200 MHz, CDCl$_3$) δ ppm: 1.01–2.97, 3.51–4.28 and 4.75–5.19 [all 20H, m, 2.34 (s)], 6.40–7.70 (8H, m)

The compound of Example 718

$^1$H-NMR (200 MHz, CDCl$_3$) δ ppm: 2.29–2.94, 3.56–4.29.and 4.75–5.08 [all 12H, m, 2.43 (s), 3.82 (s)], 6.59–7.65 (7H, m), 8.55–9.07 (1H, m)

The compound of Example 719

$^1$H-NMR (200 MHz, CDCl$_3$) δ ppm: 1.53 (9H, s), 2.51–2.96, 3.72–4.31 and 4.51–5.18 (all 6H, m), 6.85–7.62 and 7.78–8.41 (all 7H, m)

EXAMPLE 721

To dimethylsulfide (170 ml) is added dropwise with stirring aluminum chloride (23.6 g) under ice-cooling, and further thereto is added dropwise a solution of 5-methoxycarbonylmethyl-1-[4-(2-phenoxyacetylamino)-benzoyl]-2,3,4,5-tetrahydro-1H-benzazepine (16.76 g) in dichloromethane (150 ml), and the mixture is stirred at room temperature for two hours. The reaction mixture is poured into a mixture of conc. hydrochloric acid and crashed ice, and the mixture is extracted with dichloromethane. The organic layer is washed with water, dried over magnesium sulfate, and evaporated to remove the solvent. The residue is purified by silica gel column chromatography (solvent; dichloromethane:methanol=30:1) to give 5-carboxymethyl-1-[4-(2-phenoxyacetylamino)benzoyl]-2,3,4,5-tetrahydro-1H-benzazepine (13.67 g) as white powder.

M.p. 102–106° C.

EXAMPLE 722

7-Chloro-1-[2-methyl-4-(2-acetylacetylamino)benzoyl]-2,3,4,5-tetrahydro-1H-benzazepine (0.48 g) is dissolved in tetrahydrofuran (7 ml), and thereto is added a 5 N aqueous sodium hydroxide solution (0.5 ml), and the mixture is stirred at room temperature for two hours. The reaction solution is neutralized with a 2 N hydrochloric acid, and extracted with ethyl acetate. The extract is dried over magnesium sulfate, filtered, and concentrated. To the resulting residue is added n-hexane/ethyl acetate (1:1), and the mixture is washed, filtered, and the obtained powder is dried to give 7-chloro-1-[2-methyl-4-(2-hydroxyacetylamino) benzoyl]-2,3,4,5-tetrahydro-1H-benzazepine (0.38 g) as white powder.

M.p. 194–195° C.

EXAMPLE 723

1-[2-Methyl-4-(2-chloroacetylamino)benzoyl]-2,3,4,5-tetrahydro-1H-benzazepine (0.8 g) is dissolved in dimethylformamide (5 ml), and thereto are added potassium carbonate (0.47 g), sodium iodide (0.51 g) and 5,6,7,8-tetrahydro-1-naphthol (0.40 g), and the mixture is stirred at 60° C. for three hours. To the reaction solution is added ethyl acetate, and the mixture is washed with a saturated aqueous potassium hydrogen sulfate solution and a saturated aqueous sodium chloride solution, dried over magnesium sulfate, filtered, and concentrated. The resulting residue is allowed to stand for one day, washed with dichloromethane, filtered, and dried to give 1-{2-methyl-4-[2-(5-tetrahydronaphthyloxy)acetylamino]benzoyl}-2,3,4,5-tetrahydro-1H-benzazepine (0.72 g) as white powder.

M.p. 230–232° C. (decomposed)

The suitable starting compounds are treated in the same manner as in Example 723 to give the compounds of Examples 55–58, 147, 148, 150–156, 158–162, 165–166, 160, 170, 176–179, 186–196, 198, 200–207, 212, 213, 215, 217, 222–224, 228–232, 338–346, 355–358, 363, 399–402, 445–448, 583, 593, 598, 661–669, 696–700 and 704–705.

EXAMPLE 724

A mixture of 1-(4-amino-2-chlorobenzoyl)-2,3,4,5-tetrahydro-1H-benzazepine (1 g), triphosgen (0.3 g) and o-dichlorobenzene (10 ml) is heated with stirring at 130–140° C. for four hours. To the mixture is added triethylamine (0.8 ml), and the mixture is stirred for 0.5 hour, and thereto is further added triethylamine (0.8 ml), and the mixture is stirred for 0.5 hour. To the mixture is added 1,2,3,4-tetrahydroisoquinoline (0.38 ml), and the mixture is heated with stirring at 80° C. for one hour. The mixture is diluted with dichloromethane, and washed with water and a saturated aqueous sodium chloride solution, dried over magnesium sulfate, filtered, and evaporated to remove the solvent to give an oily residue (2.9 g). The residue is purified by silica gel column chromatography (solvent; ethyl acetate:n-hexane=1:1) to give 1-[4-(2-tetrahydroisoquinolylcarbonylamino)-2-chlorobenzoyl]-2,3,4,5-tetrahydro-1H-benzazepine (0.47 g) as colorless amorphous.

$^1$H-NMR (200 MHz, CDCl$_3$) δ ppm: 1.35–2.15, 2.70–3.10 and 4.80–5.00 (all 10H, m), 3.66 and 3.76 (all 2H, each t, J=5.8 Hz), 4.60 and 4.71 (all 2H, each s), 6.70–7.50 (12H, m)

EXAMPLE 725

To a solution of 1-(4-amino-2-chlorobenzoyl)-2,3,4,5-tetrahydro-1H-benzazepine (0.8 g) in o-dichlorobenzene (5 ml) is added triphosgen (0.26 g), and the mixture is stirred at 120° C. for three hours. To the mixture is added triethylamine (0.27 g), and the mixture is stirred at 120° C. for two hours. To the mixture is added (4-pyridyl)methanol (0.29 g), and the mixture is stirred at 120° C. for two hours. To the reaction solution is added ethyl acetate, and the mixture is washed with water, and the organic layer is dried over magnesium sulfate, filtered, and evaporated to remove the solvent. The resulting residue is purified by silica gel column chromatography (solvent; ethyl acetate:n-hexane= 1:5→dichloromethane:methanol=25:1), and the residue is washed with methanol/diethyl ether to give 1-{4-[(4-pyridyl)methoxycarbonylamino]-2-chlorobenzoyl}-2,3,4,5-tetrahydro-1H-benzazepine (0.45 g) as white powder.

M.p. 181–184° C.

EXAMPLE 726

To chloroform (5 ml) is added triphosgen (0.72 g), and thereto is added with stirring 2-phenoxyethanol (1.0 g) under ice-cooling, during which the temperature of the reaction solution is kept at below 10° C., and the mixture is stirred at 0° C. for one hour. To the reaction solution are added with stirring dropwise 1-(4-amino-2-chlorobenzoyl)-2,3,4,5-tetrahydro-1H-benzazepine (1.9 g) and a solution of piperidine (2.5 g) in chloroform (30 ml) under ice-cooling. The mixture is stirred at room temperature for three hours, washed with a saturated aqueous potassium hydrogen sulfate solution, distilled water and a saturated aqueous sodium hydrogen carbonate solution, and dried over magnesium sulfate, filtered, and evaporated to remove the solvent. The residue is recrystallized from diethyl ether to give 1-[4-(2-phenoxyethoxy-carbonylamino)-2-chlorobenzoyl]-2,3,4,5-tetrahydro-1H-benzazepine (1.3 g) as white powder.

M.p. 144–146° C.

The suitable starting compounds are treated in the same manner as in Examples 725 and 726 to give the compounds of Examples 157, 167, 197, 199, 214, 233, 234, 406, 407, 420, 538, 540, 549, 550, 552, 556, 557, 559, 568, 587, 588, 596, 604, 643, 645, 647, 695, 706, 707 and 709.

EXAMPLE 727

A mixture of 5-ethoxycarbonylmethyl-1-[4-(2-chloroethoxycarbonylamino)-2-chlorobenzoyl]-2,3,4,5-tetrahydro-1H-1,5-benzodiazepine (0.9 g), potassium carbonate (0.40 g) and sodium iodide (0.43 g) in dimethylformamide (15 ml) is stirred at 80° C. for 8 hours. To the reaction solution is added ethyl acetate, and the mixture is washed with water, and the organic layer is dried over magnesium sulfate, filtered, and evaporated to remove the solvent. The residue is purified by silica gel column chromatography (solvent; dichloromethane:methanol=30:1) to give 5-ethoxycarbonylmethyl-1-[4-(2-oxotetrahydrooxazol-3-yl)-2 -chlorobenzoyl]-2,3,4,5-tetrahydro-1H-1,5-benzodiazepine (0.65 g) as colorless amorphous.

$^1$H-NMR (200 MHz, CDCl$_3$) δ ppm: 1.34 (3H, t, J=7.15 Hz), 2.55–3.05, 3.70–4.61 and 4.79–5.08 [all 12H, m, 4.29 (q, J=7.15Hz, 4.46 (t, J=7.88 Hz)], 6.81–7.72 (7H, m)

The suitable starting compounds are treated in the same manner as in Example 727 to give the compounds of Examples 511, 594, 646, 649, 694 and 710.

EXAMPLE 728

To a mixture of 1-[4-(1-piperazinyl)-2-chlorobenzoyl]-2,3,4,5-tetrahydro-1H-benzazepine (0.25 g), 37% formaldehyde (0.45 g) and sodium cyanoborohydride (0.12 g) in methanol (5 ml) is added with stirring acetic acid (0.12 g) under ice-cooling, and the mixture is stirred at room temperature for one hour. To the reaction solution is added ethyl acetate, and the mixture is washed with a 2 N aqueous sodium hydroxide solution and distilled water. The organic layer is dried over magnesium sulfate, filtered, and concentrated, and the resulting residue is purified by silica gel column chromatography (solvent; dichloromethane:methanol=10:1) to give 1-[4-(4-methyl-1-piperazinyl)-2-chlorobenzoyl]-2,3,4,5-tetrahydro-1H-benzazepine (0.10 g) as white powder.

M.p. 138–140° C.

The suitable starting compounds are treated in the same manner in Example 728 to give the compounds of Examples 416, 417, 457, 515, 523, 524, 677 and 678.

EXAMPLE 729

1-[4-Nitro-2-chlorobenzoyl]-1,5-benzodiazepine (5 g) and ethyl bromoacetate (16.7 ml) are dissolved in acetonitrile (100 ml), and thereto is added dropwise 1,8-diazabicyclo[5.4.0]-7-undecene (11.3 ml). The mixture is refluxed for two days, concentrated, and thereto are added water and chloroform, and extracted. The extract is dried over sodium carbonate, and purified by silica gel column chromatography (solvent; n-hexane:ethyl acetate=4:1→1:1) to give 1-(4-nitro-2-chlorobenzoyl)-5-ethoxycarbonylmethyl-2,3,4,5-tetrahydro-1H-1,5-benzodiazepine (4.4 g) as pale yellow oil.

$^1$H-NMR (200 MHz, CDCl$_3$) δ ppm: 1.22–1.43 (3H, m), 1.78–2.38 (2H, m), 2.99–3.24 (2H, m), 3.43–3.66 (1H, m), 3.78–4.39 (4H, m), 4.65–4.89 (1H, m), 6.67 (1H, dt, J=7.6 Hz, J=1.3 Hz), 6.70 (1H, dd, J=8.2 Hz, J=1.3 Hz), 6.89–6.99 (1H, m), 7.05 (1H, dd, J=7.3 Hz, J=1.7 Hz), 7.37 (1H, d, J=8.4 Hz), 7.81 (1H, dd, J=8.4 Hz, J=2.1 Hz), 8.10 (1H, d, J=2.1 Hz)

The suitable starting compounds are treated in the same manner as in Example 729 to give the compounds of Examples 692–702, 704–710 and 715–720.

EXAMPLE 730

5-Cyanomethyl-1-(4-phenyl-2-chlorobenzoyl)-2,3,4,5-tetrahydro-1H-benzazepine (1 g), ammonium chloride (0.4 g) and sodium azide (0.48 g) are suspended in dimethylformamide (10 ml), and the mixture is heated at 110–120° C. for 16 hours. To the mixture are added ammonium chloride (0.4 g) and sodium azide (0.48 g), and the mixture is heated for 16 hours. The mixture is evaporated to remove dimethylformamide, and the resultant is acidified with a 1 N hydrochloric acid. The mixture is extracted with chloroform, and the organic layer is washed with water, dried over magnesium sulfate, and concentrated. The residue is purified by silica gel column chromatography (solvent; dichloromethane→dichloromethane:methanol=20:1), and the resulting oily product is crystallized from diethyl ether to give 5-(5-tetrazolyl)methyl-1-(4-phenyl-2-chlorobenzoyl)-2,3,4,5-tetrahydro-1H-benzazepine (0.9 g) as white powder.

M.p. 191–194° C.

The suitable starting compounds are treated in the same manner as in Examples 1 and 2 to give the following compounds.

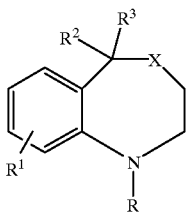

EXAMPLE 731

Structure:

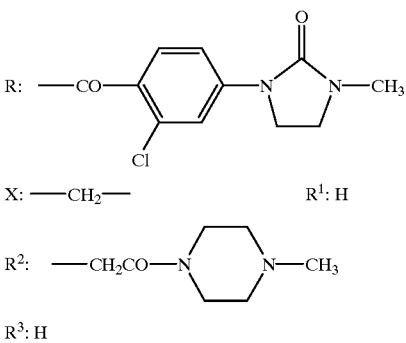

X: —CH$_2$—     R$^1$: H

R$^3$: H

Crystalline form: Colorless amorphous

Form: Hydrochloride

EXAMPLE 732

Structure:

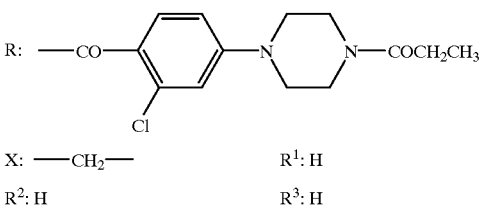

X: —CH$_2$—     R$^1$: H
R$^2$: H     R$^3$: H

Crystalline form: White powder

Solvent for recrystallization: Methanol/diethyl ether

M.p. 136–138° C.

Form: Free

EXAMPLE 733

Structure:

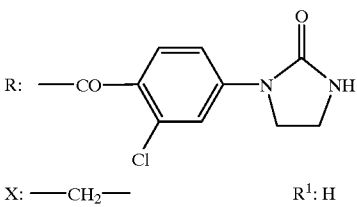

X: —CH$_2$—     R$^1$: H

-continued

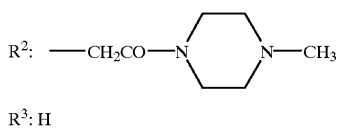

R³: H

Crystalline form: Colorless amorphous
Form: Hydrochloride

EXAMPLE 734

Structure:

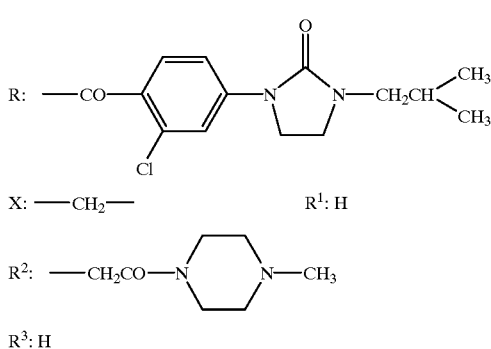

Crystalline form: Colorless amorphous
Form: Hydrochloride

EXAMPLE 735

Structure:

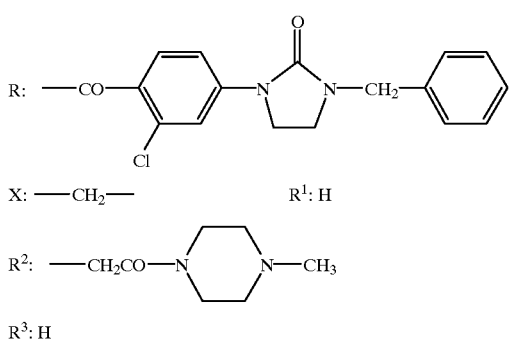

Crystalline form: Colorless amorphous
Form: Hydrochloride

EXAMPLE 736

Structure:

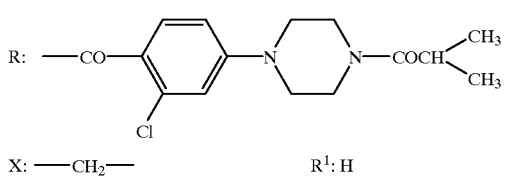

X: —CH₂—            R¹: H

-continued

R²: H                R³: H

Crystalline form: Colorless amorphous
Form: Free

EXAMPLE 737

Structure:

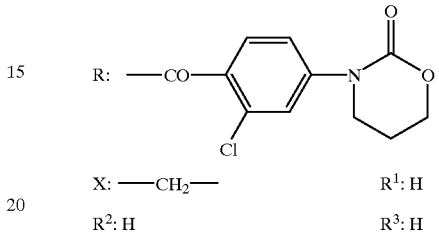

X: —CH₂—            R¹: H
R²: H                R³: H

Crystalline form: White powder
M.p. 196–198° C.
Form: Free

EXAMPLE 738

Structure:

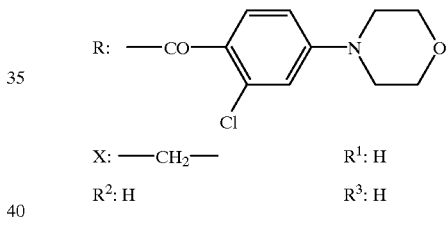

X: —CH₂—            R¹: H
R²: H                R³: H

Crystalline form: White powder
Solvent for recrystallization: Diethyl ether/n-hexane
M.p. 124–126° C.
Form: Free

EXAMPLE 739

Structure:

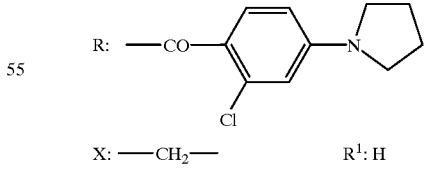

X: —CH₂—            R¹: H
R²: H                R³: H

Crystalline form: White powder
Solvent for recrystallization: Methanol
M.p. 160–162° C.
Form: Free

EXAMPLE 740

Structure:

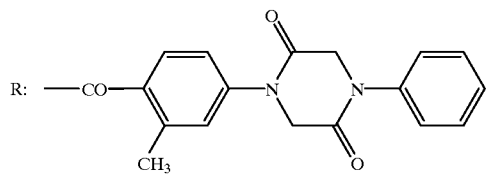

X: —CH₂—  R¹: 7-Cl
R²: H  R³: H

Crystalline form: Colorless amorphous

Form: Free

EXAMPLE 741

Structure:

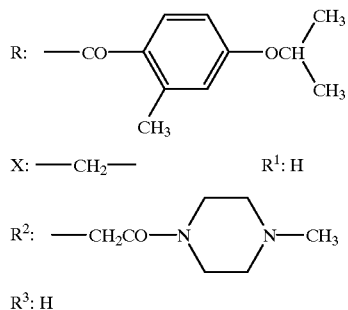

X: —CH₂—  R¹: H

R²: —CH₂CO—N⟨piperazine⟩N—CH₃

R³: H

Crystalline form: Colorless amorphous

Form: Free

EXAMPLE 742

Structure:

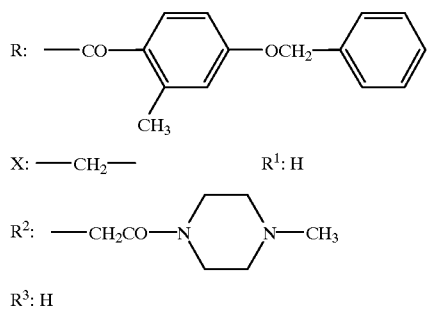

X: —CH₂—  R¹: H

R²: —CH₂CO—N⟨piperazine⟩N—CH₃

R³: H

Crystalline form: Colorless amorphous

Form: Free

EXAMPLE 743

Structure:

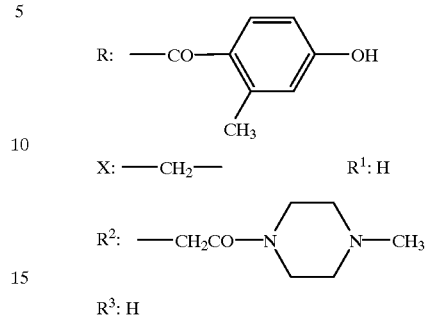

X: —CH₂—  R¹: H

R²: —CH₂CO—N⟨piperazine⟩N—CH₃

R³: H

Crystalline form: Colorless amorphous

Form: Free

EXAMPLE 744

Structure:

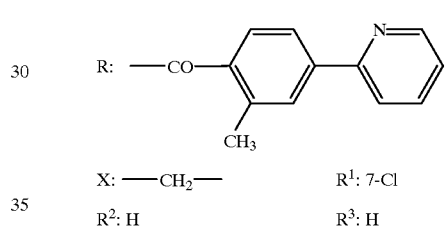

X: —CH₂—  R¹: 7-Cl
R²: H  R³: H

Crystalline form: White powder

Solvent for recrystallization: Diethyl ether/n-hexane

Form: Free

EXAMPLE 745

Structure:

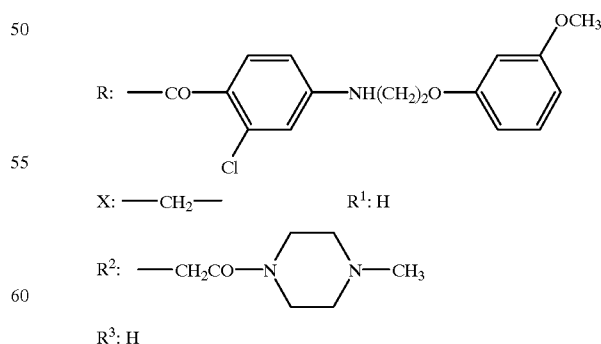

X: —CH₂—  R¹: H

R²: —CH₂CO—N⟨piperazine⟩N—CH₃

R³: H

Crystalline form: Colorless amorphous

Form: Hydrochloride

EXAMPLE 746

Structure:

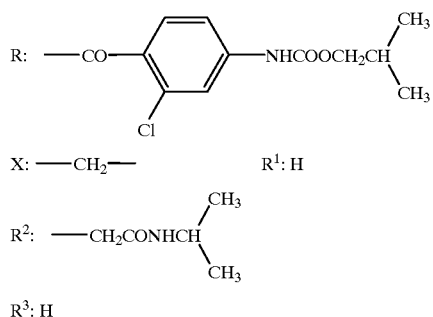

R: —CO—<aryl>
X: —CH₂—    R¹: H
R²: —CH₂CONHCH(CH₃)₂
R³: H

Crystalline form: White powder
Solvent for recrystallization: n-Hexane/ethyl acetate
M.p. 162–164° C.
Form: Free

EXAMPLE 747

Structure:

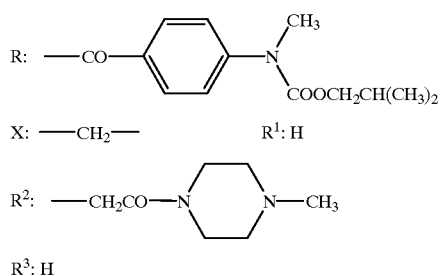

X: —CH₂—    R¹: H
R²: —CH₂CO—N(piperazine)N—CH₃
R³: H

Crystalline form: Colorless amorphous
Form: Hydrochloride

EXAMPLE 748

Structure:

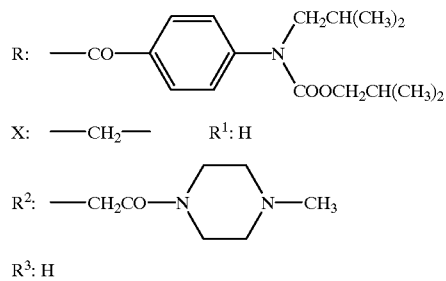

X: —CH₂—    R¹: H
R²: —CH₂CO—N(piperazine)N—CH₃
R³: H

Crystalline form: Colorless amorphous
Form: Hydrochloride

EXAMPLE 749

Structure:

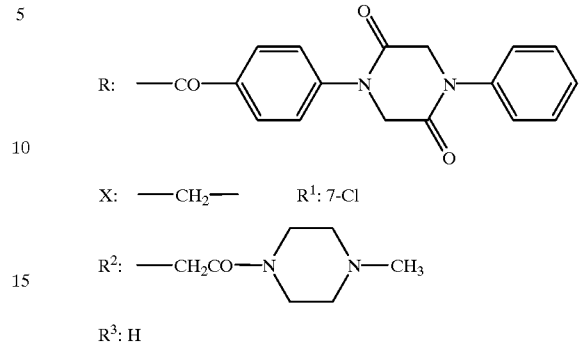

X: —CH₂—    R¹: 7-Cl
R²: —CH₂CO—N(piperazine)N—CH₃
R³: H

Crystalline form: Colorless amorphous
Form: Hydrochloride

EXAMPLE 750

Structure:

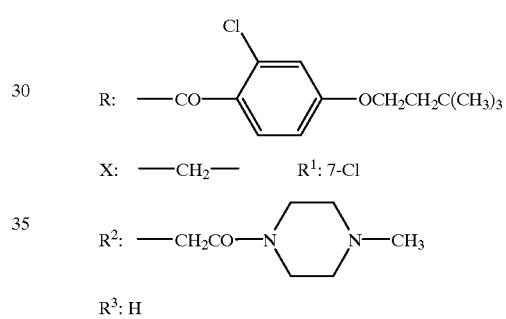

R: —CO—<aryl>—OCH₂CH₂C(CH₃)₃
X: —CH₂—    R¹: 7-Cl
R²: —CH₂CO—N(piperazine)N—CH₃
R³: H Crystalline form: White powder
Solvent for recrystallization: Diethyl ether
M.p. 118–119° C.
Form: Free

EXAMPLE 751

Structure:

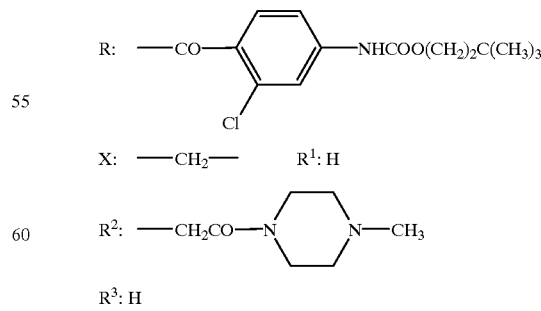

R: —CO—<aryl>—NHCOO(CH₂)₂C(CH₃)₃
X: —CH₂—    R¹: H
R²: —CH₂CO—N(piperazine)N—CH₃
R³: H Crystalline form: Colorless amorphous
Form: Free

EXAMPLE 752

Structure:

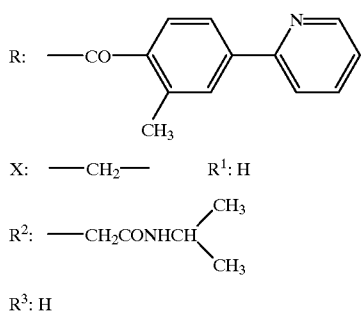

X: —CH₂— R¹: H

R²: —CH₂CONHCH(CH₃)₂

R³: H

Crystalline form: Colorless amorphous
Form: Free

EXAMPLE 753

Structure:

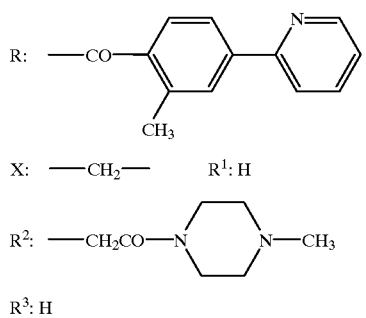

X: —CH₂— R¹: H

R²: —CH₂CO—N(piperazine)N—CH₃

R³: H

Crystalline form: Colorless amorphous
Form: Hydrochloride

EXAMPLE 754

Structure:

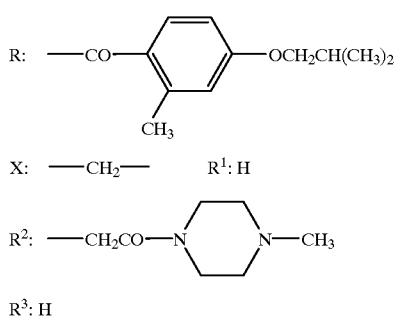

X: —CH₂— R¹: H

R²: —CH₂CO—N(piperazine)N—CH₃

R³: H

Crystalline form: Colorless amorphous
Form: Free

EXAMPLE 755

Structure:

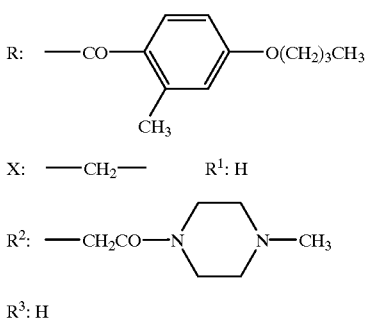

X: —CH₂— R¹: H

R²: —CH₂CO—N(piperazine)N—CH₃

R³: H

Crystalline form: Colorless amorphous
Form: Free

EXAMPLE 756

Structure:

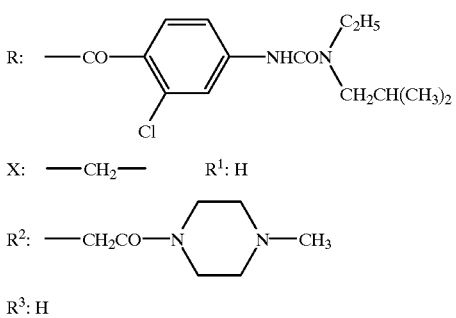

X: —CH₂— R¹: H

R²: —CH₂CO—N(piperazine)N—CH₃

R³: H

Crystalline form: Colorless amorphous
Form: Dihydrochloride

EXAMPLE 757

Structure:

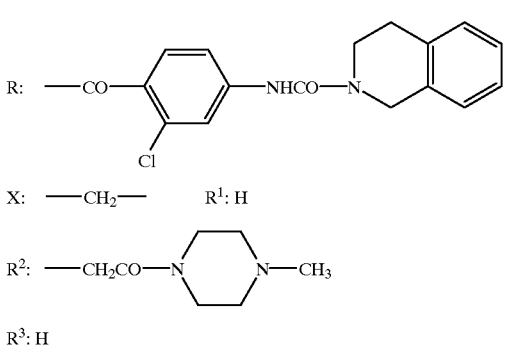

X: —CH₂— R¹: H

R²: —CH₂CO—N(piperazine)N—CH₃

R³: H

Crystalline form: White powder
Solvent for recrystallization: Ethanol
M.p. 201.5–204° C.
Form: Hydrochloride

EXAMPLE 758

Structure:

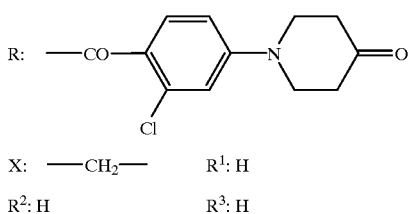

X: —CH$_2$—  R$^1$: H
R$^2$: H  R$^3$: H

Crystalline form: White powder
M.p. 120–122° C.
Form: Free

EXAMPLE 759

Structure:

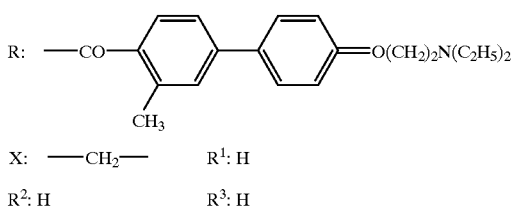

X: —CH$_2$—  R$^1$: H
R$^2$: H  R$^3$: H

Crystalline form: Colorless amorphous
Form: Hydrochloride

EXAMPLE 760

Structure:

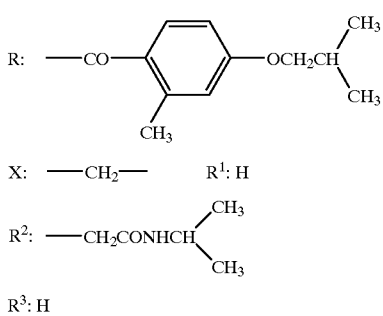

X: —CH$_2$—  R$^1$: H

R$^2$: —CH$_2$CONHCH(CH$_3$)$_2$

R$^3$: H

Crystalline form: Colorless amorphous
Form: Free

EXAMPLE 761

Structure:

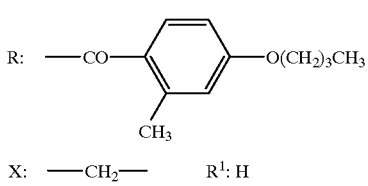

X: —CH$_2$—  R$^1$: H

-continued

R$^2$: —CH$_2$CONHCH(CH$_3$)$_2$

R$^3$: H

Crystalline form: Colorless amorphous
Form: Free

EXAMPLE 762

Structure:

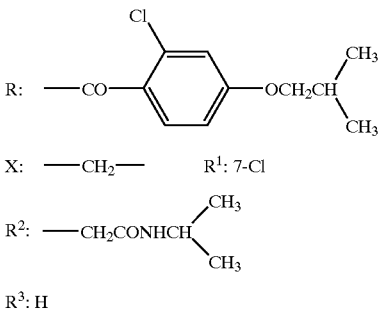

X: —CH$_2$—  R$^1$: 7-Cl

R$^2$: —CH$_2$CONHCH(CH$_3$)$_2$

R$^3$: H

Crystalline form: White powder
Solvent for recrystallization: Diethyl ether
M.p. 147–148° C.
Form: Free

EXAMPLE 763

Structure:

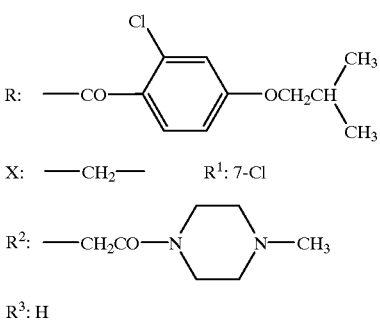

X: —CH$_2$—  R$^1$: 7-Cl

R$^2$: —CH$_2$CO—N(piperazine)N—CH$_3$

R$^3$: H

Crystalline form: White powder
Solvent for recrystallization: Diethyl ether
M.p. 178–179° C.
Form: Free

EXAMPLE 764

Structure:

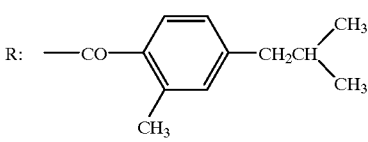

-continued

X: —CH₂—  R¹: H

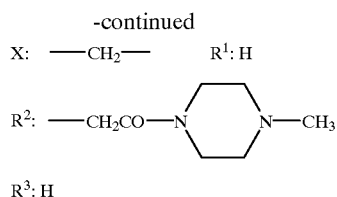

R³: H

Crystalline form: Colorless amorphous
Form: Hydrochloride

EXAMPLE 765
Structure:

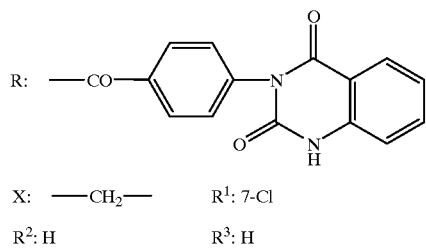

X: —CH₂—  R¹: 7-Cl
R²: H  R³: H

Crystalline form: Colorless flakes
Solvent for recrystallization: Methanol/chloroform/diethyl ether
M.p. >300° C.
Form: Free

EXAMPLE 766
Structure:

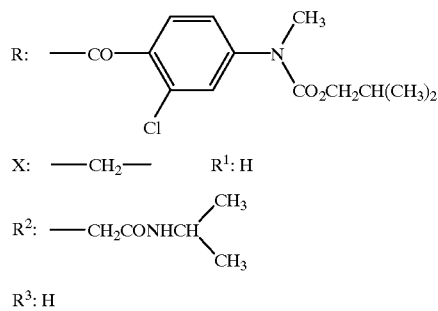

X: —CH₂—  R¹: H

R²: —CH₂CONHCH(CH₃)₂

R³: H

Crystalline form: White powder
Solvent for recrystallization: Diethyl ether
Form: Free

EXAMPLE 767
Structure:

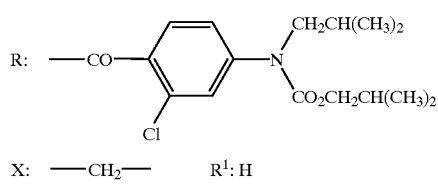

X: —CH₂—  R¹: H

-continued

R²: —CH₂CONHCH(CH₃)₂

R³: H

Crystalline form: White powder
Solvent for recrystallization: Diethyl ether
Form: Free

EXAMPLE 768
Structure:

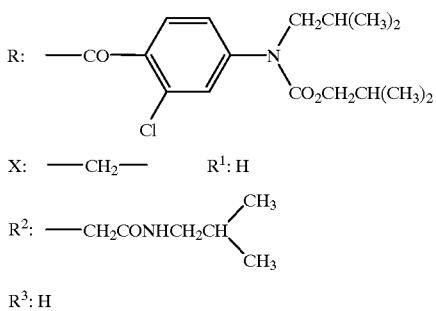

X: —CH₂—  R¹: H

R²: —CH₂CONHCH₂CH(CH₃)₂

R³: H

Crystalline form: White powder
Solvent for recrystallization: Diethyl ether
Form: Free

EXAMPLE 769
Structure:

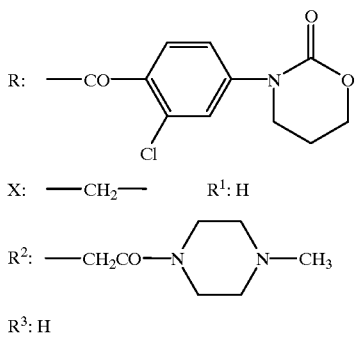

X: —CH₂—  R¹: H

R²: —CH₂CO—N(piperazine)N—CH₃

R³: H

Crystalline form: Colorless amorphous
Form: Free

EXAMPLE 770
Structure:

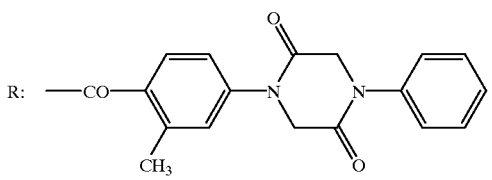

-continued

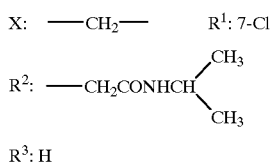

R³: H

Crystalline form: Colorless amorphous
Form: Free

EXAMPLE 771

Structure:

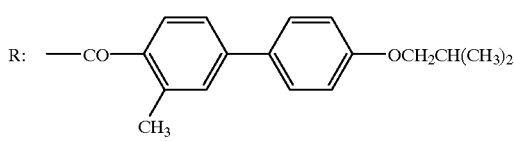

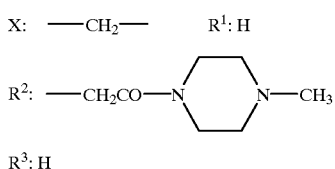

R³: H

Crystalline form: Colorless amorphous
Form: Hydrochloride

EXAMPLE 772

Structure:

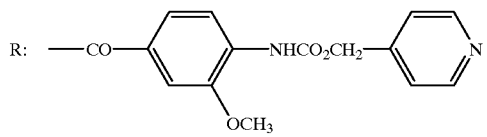

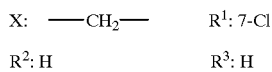

Crystalline form: Yellow powder
M.p. 130–133° C.
Form: Free

EXAMPLE 773

Structure:

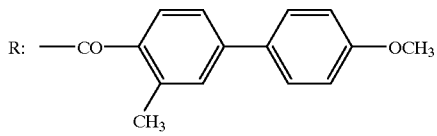

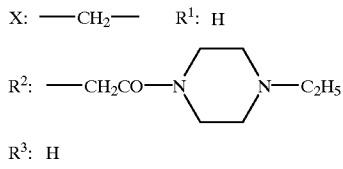

R³: H

Crystalline form: Colorless amorphous
Form: Hydrochloride

EXAMPLE 774

Structure:

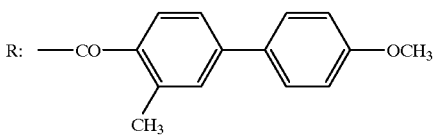

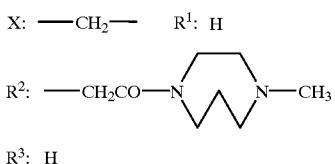

R³: H

Crystalline form: Colorless amorphous

Form: Hydrochloride

EXAMPLE 775

Structure:

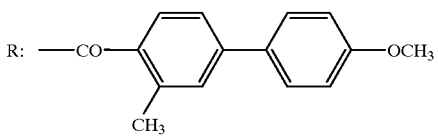

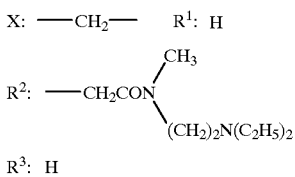

R³: H

Crystalline form: Colorless amorphous

Form: Hydrochloride

EXAMPLE 776

Structure:

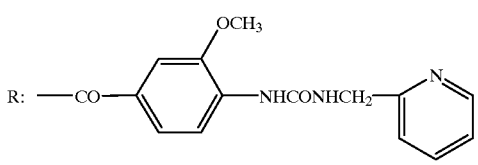

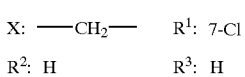

Crystalline form: White powder

Solvent for recrystallization: Ethyl acetate

M.p. 174.5–175.5° C.

Form: Free

EXAMPLE 777

Structure:

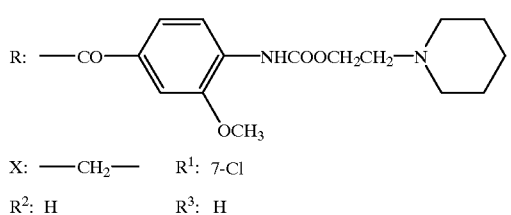

X: —CH₂—  R¹: 7-Cl
R²: H  R³: H

Crystalline form: Brown amorphous
Form: Free

EXAMPLE 778

Structure:

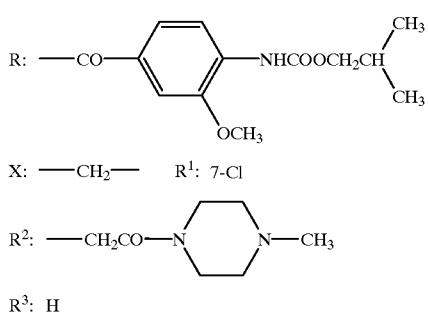

X: —CH₂—  R¹: 7-Cl

R²: —CH₂CO—N(piperazine)N—CH₃

R³: H

Crystalline form: Colorless amorphous
Form: Free

EXAMPLE 779

Structure:

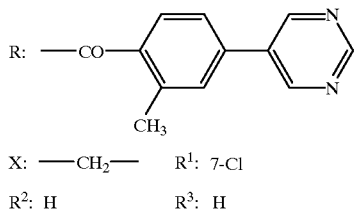

X: —CH₂—  R¹: 7-Cl
R²: H  R³: H

Crystalline form: Pale yellow powder
Solvent for recrystallization: Chloroform/diethyl ether
Form: Free

EXAMPLE 780

Structure:

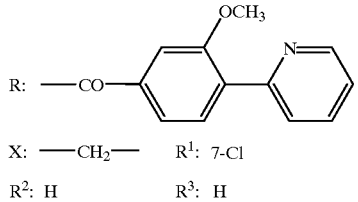

X: —CH₂—  R¹: 7-Cl
R²: H  R³: H

Crystalline form: Yellow powder
Solvent for recrystallization: Chloroform/diethyl ether
Form: Free

EXAMPLE 781

Structure:

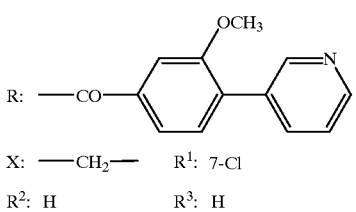

X: —CH₂—  R¹: 7-Cl
R²: H  R³: H

Crystalline form: Pale yellow powder

Solvent for recrystallization: Chloroform/diethyl ether

Form: Free

EXAMPLE 782

Structure:

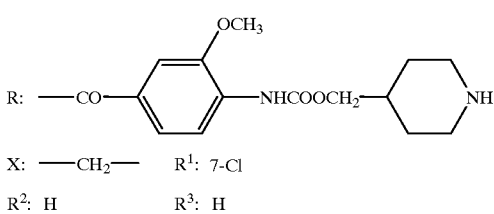

X: —CH₂—  R¹: 7-Cl
R²: H  R³: H

Crystalline form: White powder

M.p. 123–125° C.

Form: Free

EXAMPLE 783

Structure:

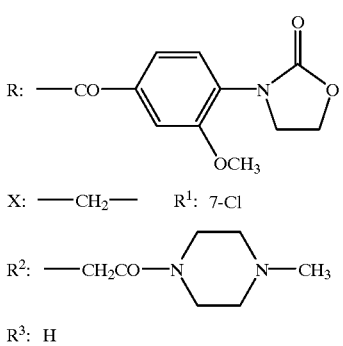

X: —CH₂—  R¹: 7-Cl

R²: —CH₂CO—N(piperazine)N—CH₃

R³: H

Crystalline form: Colorless amorphous

Form: Free

EXAMPLE 784

Structure:

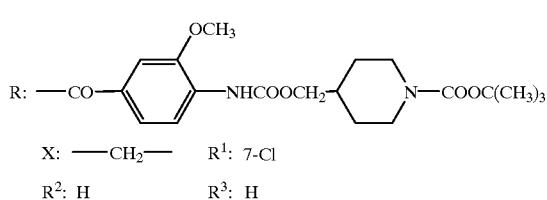

X: —CH$_2$—    R$^1$: 7-Cl
R$^2$: H        R$^3$: H

Crystalline form: Colorless amorphous
Form: Free

EXAMPLE 785

Structure:

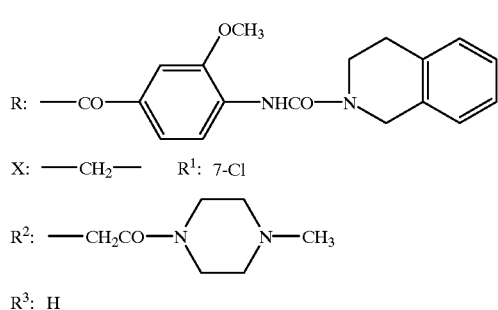

Crystalline form: Colorless amorphous
Form: Hydrochloride

EXAMPLE 786

Structure:

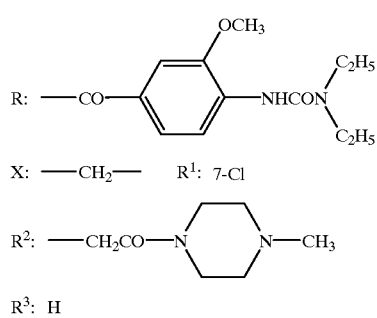

Crystalline form: Colorless amorphous
Form: Hydrochloride

EXAMPLE 787

Structure:

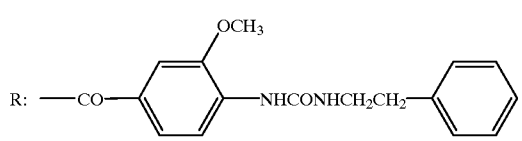

-continued

X: —CH$_2$—    R$^1$: 7-Cl

R$^2$: 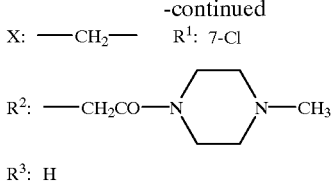

R$^3$: H

Crystalline form: Colorless amorphous
Form: Hydrochloride

EXAMPLE 788

Structure:

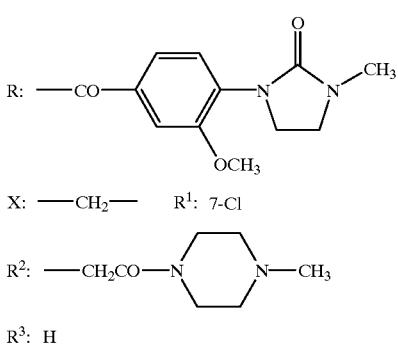

X: —CH$_2$—    R$^1$: 7-Cl

R$^2$: —CH$_2$CO—N⌒N—CH$_3$

R$^3$: H

Crystalline form: Colorless amorphous
Form: Free

EXAMPLE 789

Structure:

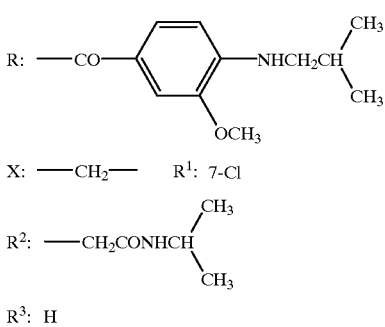

X: —CH$_2$—    R$^1$: 7-Cl

R$^2$: —CH$_2$CONHCH(CH$_3$)$_2$

R$^3$: H

Crystalline form: Colorless amorphous
Form: Free

EXAMPLE 790

Structure:

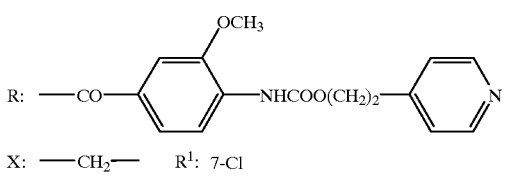

X: —CH$_2$—    R$^1$: 7-Cl

R²: H  R³: H

Crystalline form: Yellow amorphous

Form: Free

EXAMPLE 791

Structure:

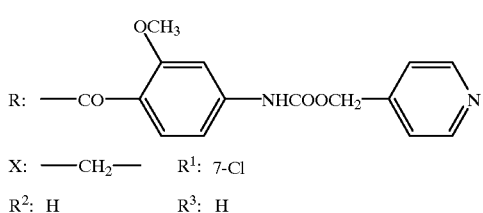

X: —CH₂—  R¹: 7-Cl
R²: H  R³: H

Crystalline form: Yellow powder

M.p. 135–139° C.

Form: Free

EXAMPLE 792

Structure:

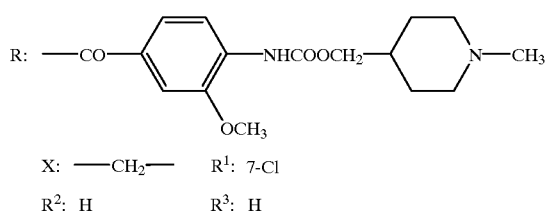

X: —CH₂—  R¹: 7-Cl
R²: H  R³: H

Crystalline form: Colorless amorphous

Form: Free

EXAMPLE 793

Structure:

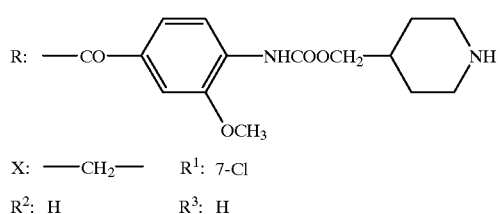

X: —CH₂—  R¹: 7-Cl
R²: H  R³: H

Crystalline form: White powder

M.p. 123–125° C.

Form: Free

EXAMPLE 794

Structure:

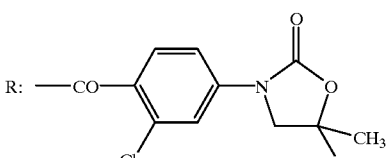

X: —CH₂—  R¹: H

R²: —CH₂CO—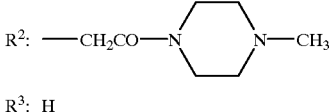

R³: H

Crystalline form: Colorless amorphous

Form: Free

EXAMPLE 795

Structure:

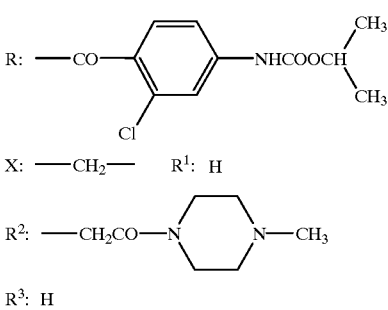

X: —CH₂—  R¹: H

R²: —CH₂CO—N⟨piperazine⟩N—CH₃

R³: H

Crystalline form: Colorless amorphous

Form: Free

EXAMPLE 796

Structure:

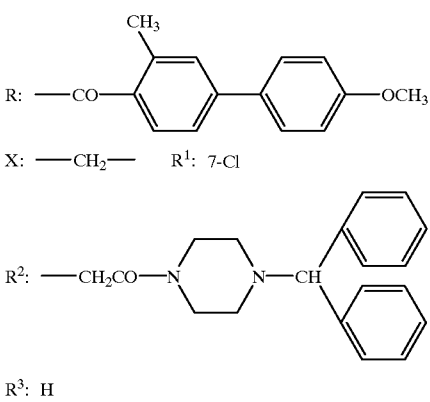

X: —CH₂—  R¹: 7-Cl

R²: —CH₂CO—N⟨piperazine⟩N—CH(C₆H₅)₂

R³: H

Crystalline form: Pale yellow amorphous

Form: Free

EXAMPLE 797

Structure:

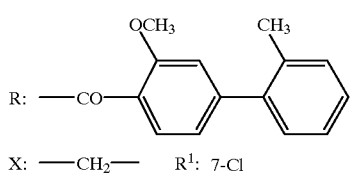

R: —CO—
X: —CH₂—  R¹: 7-Cl

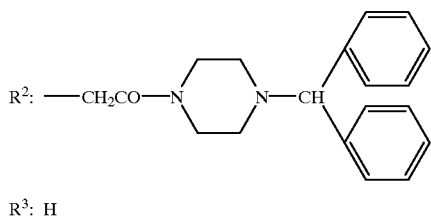

R²: —CH₂CO—N(piperazine)N—CH(phenyl)₂

R³: H

Crystalline form: Colorless amorphous
Form: Free

EXAMPLE 798

Structure:

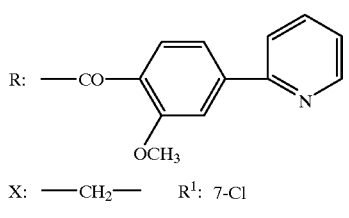

X: —CH₂—  R¹: 7-Cl
R²: H  R³: H

Crystalline form: Pale yellow powder
Solvent for recrystallization: Chloroform/diethyl ether
Form: Free

EXAMPLE 799

Structure:

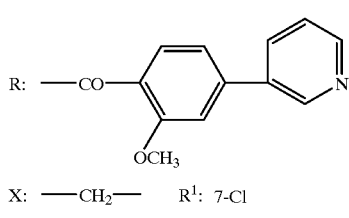

X: —CH₂—  R¹: 7-Cl
R²: H  R³: H

Crystalline form: Pale yellow powder
Solvent for recrystallization: Chloroform/diethyl ether
Form: Free

EXAMPLE 800

Structure:

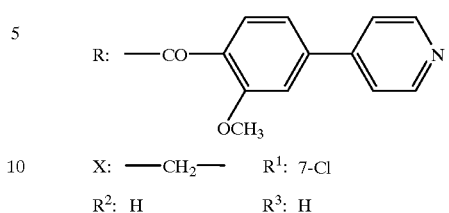

X: —CH₂—  R¹: 7-Cl
R²: H  R³: H

EXAMPLE 801

Structure:

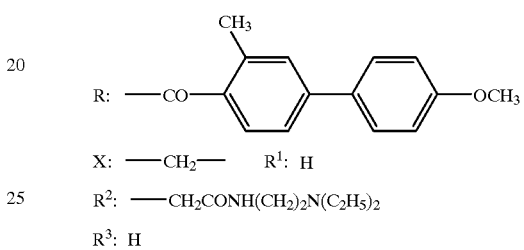

X: —CH₂—  R¹: H
R²: —CH₂CONH(CH₂)₂N(C₂H₅)₂
R³: H

Crystalline form: Colorless amorphous
Form: Hydrochloride

EXAMPLE 802

Structure:

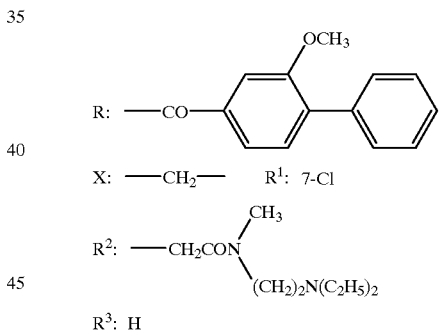

X: —CH₂—  R¹: 7-Cl
R²: —CH₂CON(CH₃)(CH₂)₂N(C₂H₅)₂
R³: H

Crystalline form: Colorless amorphous
Form: Hydrochloride

EXAMPLE 803

Structure:

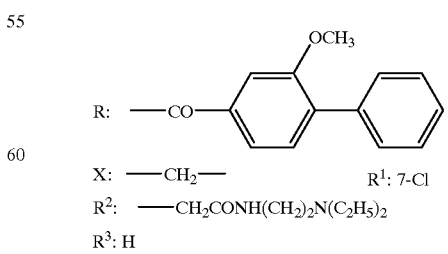

X: —CH₂—  R¹: 7-Cl
R²: —CH₂CONH(CH₂)₂N(C₂H₅)₂
R³: H

Crystalline form: Colorless amorphous
Form: Hydrochloride

EXAMPLE 804

Structure:

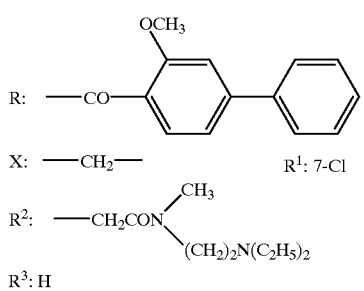

R: —CO—
X: —CH$_2$—  R$^1$: 7-Cl
R$^2$: —CH$_2$CON(CH$_3$)(CH$_2$)$_2$N(C$_2$H$_5$)$_2$
R$^3$: H

Crystalline form: Colorless amorphous

Form: Hydrochloride

EXAMPLE 805

Structure:

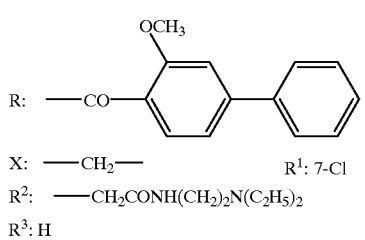

R: —CO—
X: —CH$_2$—  R$^1$: 7-Cl
R$^2$: —CH$_2$CONH(CH$_2$)$_2$N(C$_2$H$_5$)$_2$
R$^3$: H

Crystalline form: Colorless amorphous

Form: Hydrochloride

EXAMPLE 806

Structure:

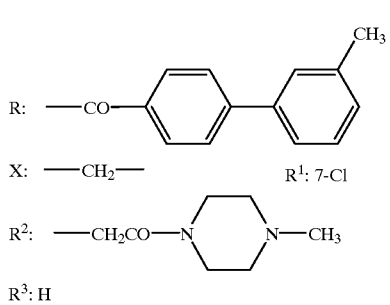

R: —CO—
X: —CH$_2$—  R$^1$: 7-Cl
R$^2$: —CH$_2$CO—N(piperazine)N—CH$_3$
R$^3$: H Crystalline form: Colorless amorphous Form: Hydrochloride

EXAMPLE 807

Structure:

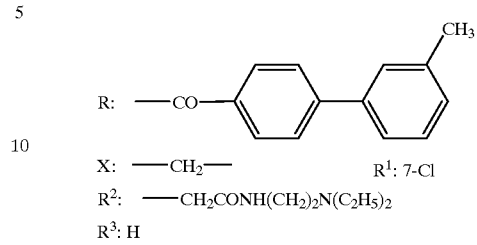

R: —CO—
X: —CH$_2$—  R$^1$: 7-Cl
R$^2$: —CH$_2$CONH(CH$_2$)$_2$N(C$_2$H$_5$)$_2$
R$^3$: H

Crystalline form: Colorless amorphous

Form: Hydrochloride

EXAMPLE 808

Structure:

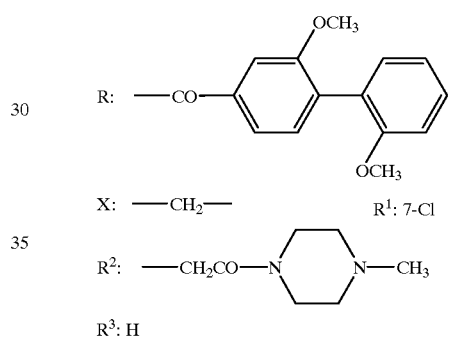

R: —CO—
X: —CH$_2$—  R$^1$: 7-Cl
R$^2$: —CH$_2$CO—N(piperazine)N—CH$_3$
R$^3$: H Crystalline form: Colorless amorphous Form: Hydrochloride

EXAMPLE 809

Structure:

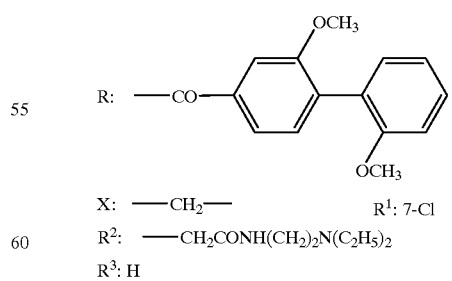

R: —CO—
X: —CH$_2$—  R$^1$: 7-Cl
R$^2$: —CH$_2$CONH(CH$_2$)$_2$N(C$_2$H$_5$)$_2$
R$^3$: H

Crystalline form: Colorless amorphous

Form: Hydrochloride

EXAMPLE 810

Structure:

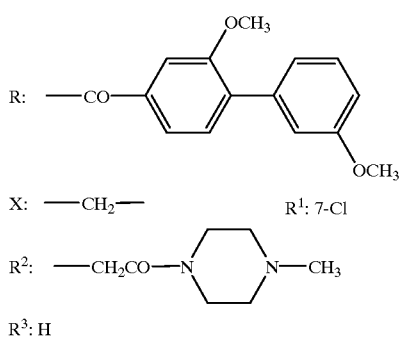

R: —CO—⟨2-OCH3, 3'-OCH3 biphenyl⟩
X: —CH2—
R¹: 7-Cl
R²: —CH2CO—N(piperazine)N—CH3
R³: H Crystalline form: Colorless amorphous
Form: Hydrochloride

EXAMPLE 811

Structure:

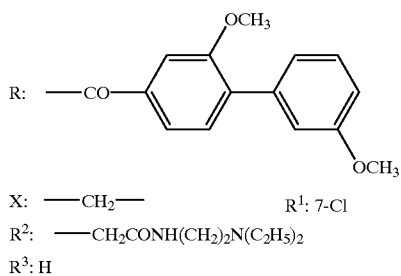

R: —CO—⟨2-OCH3, 3'-OCH3 biphenyl⟩
X: —CH2—
R¹: 7-Cl
R²: —CH2CONH(CH2)2N(C2H5)2
R³: H Crystalline form: Colorless amorphous
Form: Hydrochloride

EXAMPLE 812

Structure:

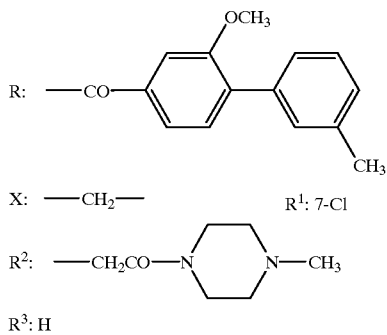

R: —CO—⟨2-OCH3, 3'-CH3 biphenyl⟩
X: —CH2—
R¹: 7-Cl
R²: —CH2CO—N(piperazine)N—CH3
R³: H Crystalline form: Colorless amorphous
Form: Hydrochloride

EXAMPLE 813

Structure:

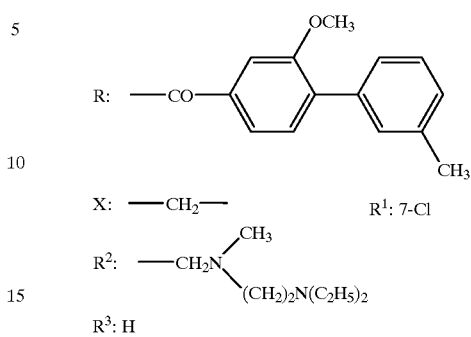

R: —CO—⟨2-OCH3, 3'-CH3 biphenyl⟩
X: —CH2—
R¹: 7-Cl
R²: —CH2N(CH3)(CH2)2N(C2H5)2
R³: H Crystalline form: Colorless amorphous
Form: Hydrochloride

EXAMPLE 814

Structure:

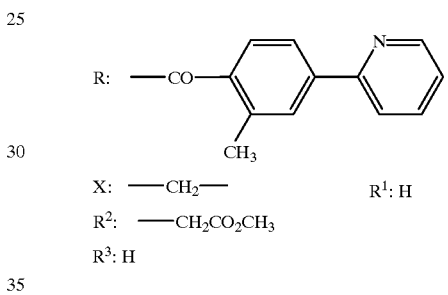

R: —CO—⟨3-CH3, 4-(2-pyridyl)phenyl⟩
X: —CH2—
R¹: H
R²: —CH2CO2CH3
R³: H

Crystalline form: White powder
Solvent for recrystallization: Chloroform/diethyl ether
Form: Hydrochloride

EXAMPLE 815

Structure:

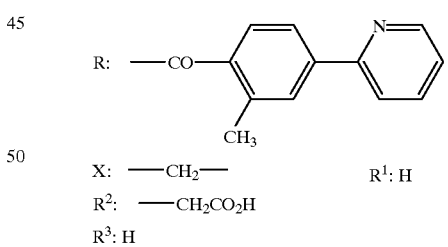

R: —CO—⟨3-CH3, 4-(2-pyridyl)phenyl⟩
X: —CH2—
R¹: H
R²: —CH2CO2H
R³: H

Form: Hydrochloride

EXAMPLE 816

Structure:

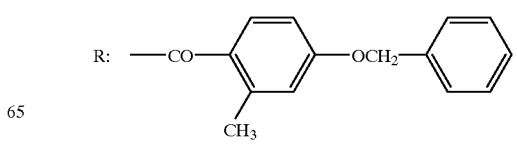

R: —CO—⟨3-CH3, 4-OCH2Ph phenyl⟩

-continued

X: —CH$_2$—  R$^1$: H
R$^2$: —CH$_2$CO$_2$CH$_3$
R$^3$: H

Crystalline form: White powder
Solvent for recrystallization: Ethyl acetate/n-hexane
Form: Free

EXAMPLE 817

Structure:

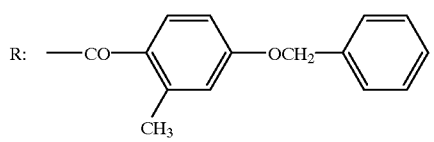

X: —CH$_2$—  R$^1$: H
R$^2$: —CH$_2$CO$_2$H
R$^3$: H

Crystalline form: Colorless amorphous
Form: Free

EXAMPLE 818

Structure:

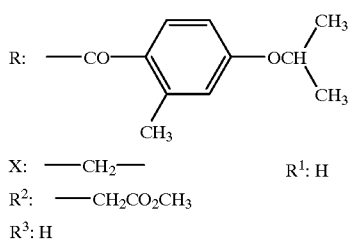

X: —CH$_2$—  R$^1$: H
R$^2$: —CH$_2$CO$_2$CH$_3$
R$^3$: H

Crystalline form: Yellow viscous oil
Form: Free

EXAMPLE 819

Structure:

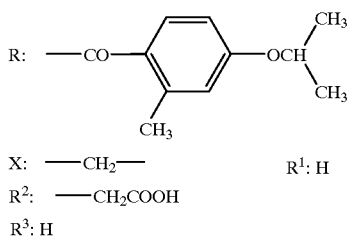

X: —CH$_2$—  R$^1$: H
R$^2$: —CH$_2$COOH
R$^3$: H

Crystalline form: Colorless amorphous
Form: Free

EXAMPLE 820

Structure:

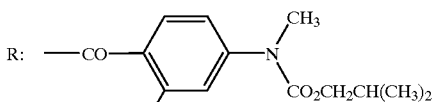

X: —CH$_2$—  R$^1$: H
R$^2$: —CH$_2$CO$_2$CH$_3$
R$^3$: H

Crystalline form: Pale yellow oil
Form: Free

EXAMPLE 821

Structure:

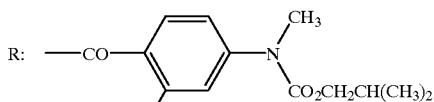

X: —CH$_2$—  R$^1$: H
R$^2$: —CH$_2$COOH
R$^3$: H

Crystalline form: Colorless amorphous
Form: Free

EXAMPLE 822

Structure:

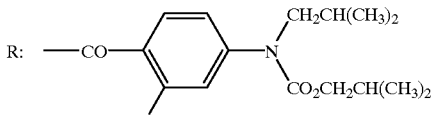

X: —CH$_2$—  R$^1$: H
R$^2$: —CH$_2$CO$_2$CH$_3$
R$^3$: H

Crystalline form: Pale yellow oil
Form: Free

EXAMPLE 823

Structure:

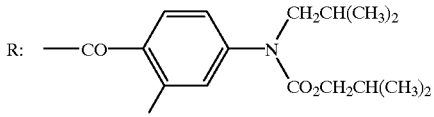

X: —CH$_2$—  R$^1$: H
R$^2$: —CH$_2$CO$_2$H
R$^3$: H

Crystalline form: Pale yellow amorphous
Form: Free

EXAMPLE 824

Structure:

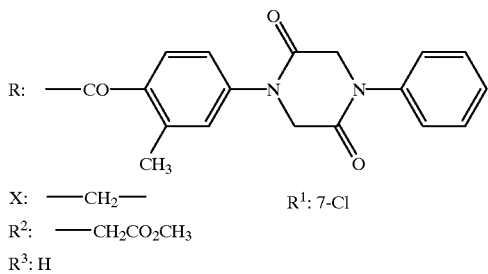

R: —CO—
X: —CH$_2$—
R$^1$: 7-Cl
R$^2$: —CH$_2$CO$_2$CH$_3$
R$^3$: H

Crystalline form: Colorless amorphous

Form: Free

EXAMPLE 825

Structure:

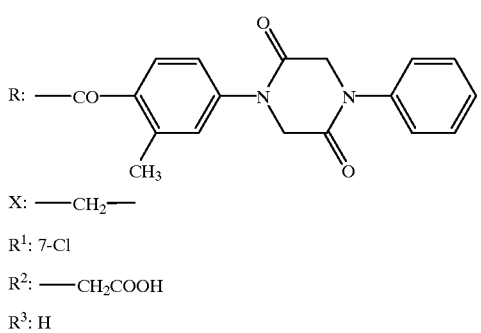

R: —CO—
X: —CH$_2$—
R$^1$: 7-Cl
R$^2$: —CH$_2$COOH
R$^3$: H

Crystalline form: Colorless amorphous

Form: Free

EXAMPLE 826

Structure:

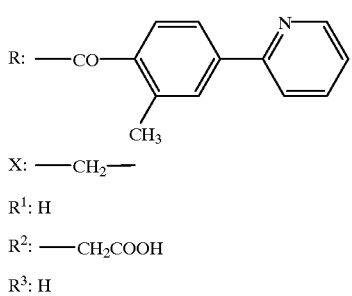

R: —CO—
X: —CH$_2$—
R$^1$: H
R$^2$: —CH$_2$COOH
R$^3$: H

Crystalline form: Colorless amorphous

Form: Hydrochloride

EXAMPLE 827

Structure:

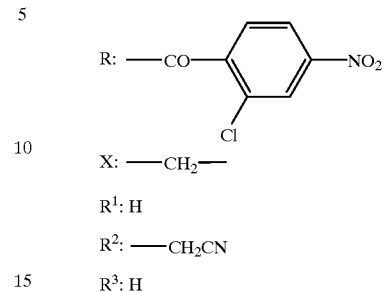

R: —CO—
X: —CH$_2$—
R$^1$: H
R$^2$: —CH$_2$CN
R$^3$: H

Crystalline form: White powder

Form: Free

EXAMPLE 828

Structure:

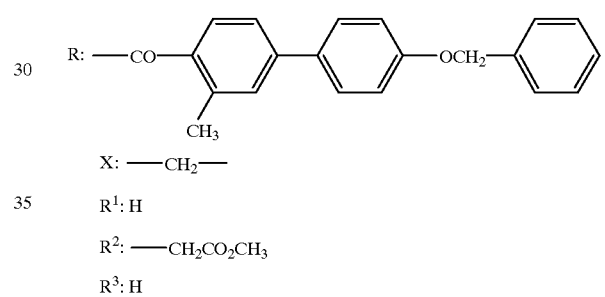

R: —CO—
X: —CH$_2$—
R$^1$: H
R$^2$: —CH$_2$CO$_2$CH$_3$
R$^3$: H

Crystalline form: White powder

Form: Free

EXAMPLE 829

Structure:

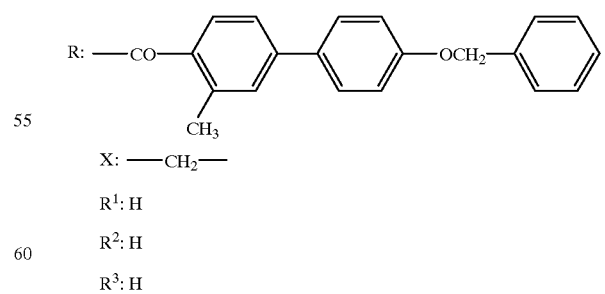

R: —CO—
X: —CH$_2$—
R$^1$: H
R$^2$: H
R$^3$: H

Crystalline form: Pale yellow powder

Form: Free

EXAMPLE 830

Structure:

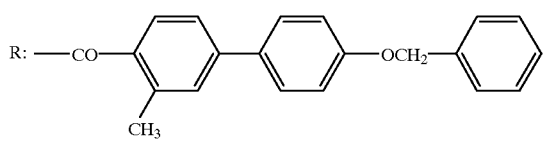

X: —CH$_2$—

R$^1$: H

R$^2$: —CH$_2$COOH

R$^3$: H

Crystalline form: White powder
M.p. 170° C.
Form: Free

EXAMPLE 831

Structure:

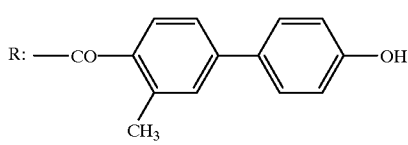

X: —CH$_2$—

R$^1$: H

R$^2$: H

R$^3$: H

Crystalline form: White powder
M.p. 177–178° C.
Form: Free

EXAMPLE 832

Structure:

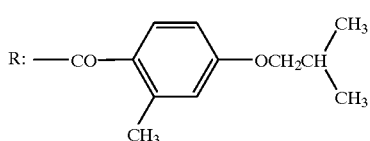

X: —CH$_2$—

R$^1$: H

R$^2$: —CH$_2$COOH

R$^3$: H

Crystalline form: White powder
Solvent for recrystallization: Ethyl acetate/n-hexane
M.p. 87–89° C.
Form: Free

EXAMPLE 833

Structure:

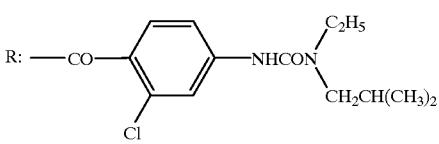

X: —CH$_2$—

R$^1$: H

R$^2$: —CH$_2$COOH

R$^3$: H

Crystalline form: Slightly yellow amorphous
Form: Free

EXAMPLE 834

Structure:

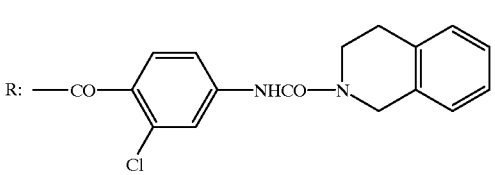

X: —CH$_2$—

R$^1$: H

R$^2$: —CH$_2$COOH

R$^3$: H

Crystalline form: Colorless amorphous
Form: Free

EXAMPLE 835

Structure:

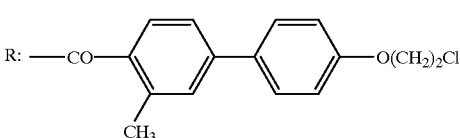

X: —CH$_2$—

R$^1$: H

R$^2$: H

R$^3$: H

Crystalline form: White powder
Form: Free

EXAMPLE 836

Structure:

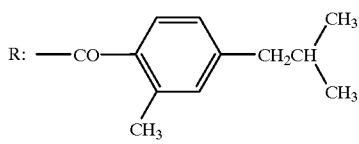

X: —CH$_2$—

R$^1$: H

R$^2$: —CH$_2$CO$_2$CH$_3$

R$^3$: H

Crystalline form: Yellow oil

Form: Free

EXAMPLE 837

Structure:

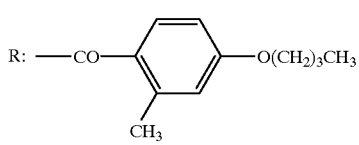

X: —CH$_2$—

R$^1$: H

R$^2$: —CH$_2$CO$_2$CH$_3$

R$^3$: H

Crystalline form: White powder

Solvent for recrystallization: Ethyl acetate/n-hexane

M.p. 99–101° C.

Form: Free

EXAMPLE 838

Structure:

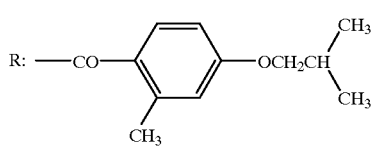

X: —CH$_2$—

R$^1$: H

R$^2$: —CH$_2$CO$_2$H

R$^3$: H

Crystalline form: Colorless amorphous

Form: Free

EXAMPLE 839

Structure:

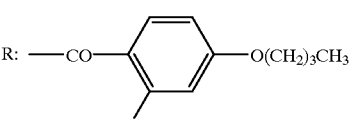

X: —CH$_2$—

R$^1$: H

R$^2$: —CH$_2$CO$_2$CH$_3$

R$^3$: H

Crystalline form: Colorless amorphous

Form: Free

EXAMPLE 840

Structure:

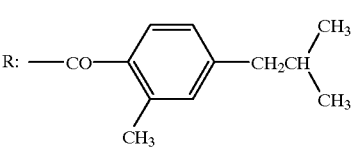

X: —CH$_2$—

R$^1$: H

R$^2$: —CH$_2$CO$_2$H

R$^3$: H

Crystalline form: Colorless amorphous

Form: Free

EXAMPLE 841

Structure:

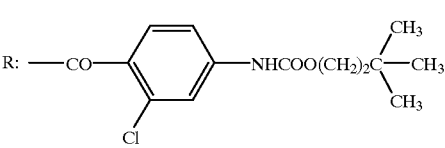

X: —CH$_2$—

R$^1$: H

R$^2$: —CH$_2$COOCH$_3$

R$^3$: H

Crystalline form: Colorless amorphous

Form: Free

EXAMPLE 842

Structure:

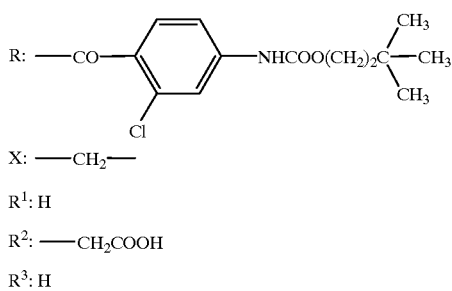

X: —CH$_2$—

R$^1$: H

R$^2$: —CH$_2$COOH

R$^3$: H

Crystalline form: Pale yellow powder

Form: Free

EXAMPLE 843

Structure:

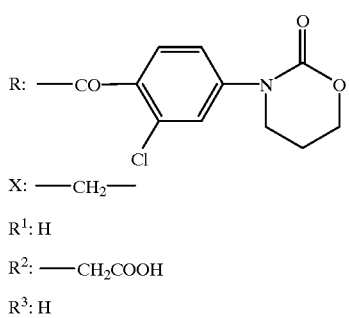

X: —CH$_2$—

R$^1$: H

R$^2$: —CH$_2$COOH

R$^3$: H

Crystalline form: White powder

Form: Free

EXAMPLE 844

Structure:

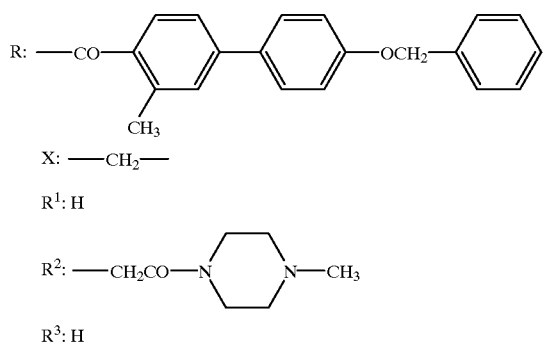

X: —CH$_2$—

R$^1$: H

R$^2$: —CH$_2$CO—N(piperazine)N—CH$_3$

R$^3$: H

Crystalline form: Colorless amorphous

Form: Free

EXAMPLE 845

Structure:

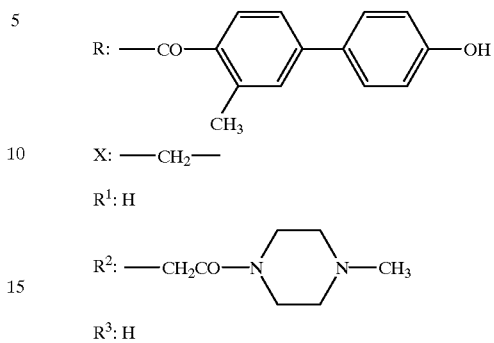

X: —CH$_2$—

R$^1$: H

R$^2$: —CH$_2$CO—N(piperazine)N—CH$_3$

R$^3$: H

Crystalline form: Colorless amorphous

Form: Free

EXAMPLE 846

Structure:

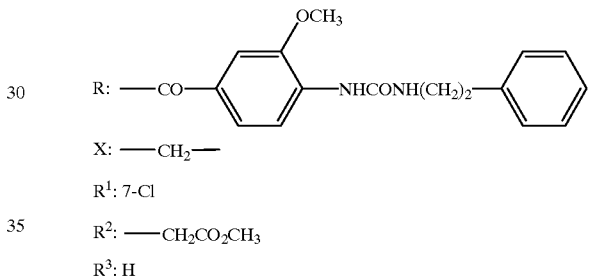

X: —CH$_2$—

R$^1$: 7-Cl

R$^2$: —CH$_2$CO$_2$CH$_3$

R$^3$: H

Crystalline form: White powder

Solvent for recrystallization: Acetone

M.p. 185–187° C.

Form: Free

EXAMPLE 847

Structure:

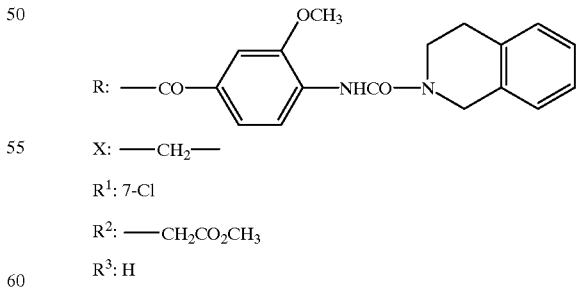

X: —CH$_2$—

R$^1$: 7-Cl

R$^2$: —CH$_2$CO$_2$CH$_3$

R$^3$: H

Crystalline form: White powder

Solvent for recrystallization: Ethyl acetate/n-hexane

M.p. 148.5–150.5° C.

Form: Free

EXAMPLE 848

Structure:

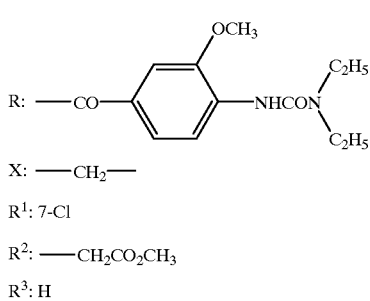

X: —CH₂—

R¹: 7-Cl

R²: —CH₂CO₂CH₃

R³: H

Crystalline form: White powder

Solvent for recrystallization: Ethyl acetate/n-hexane

M.p. 160–162° C.

Form: Free

EXAMPLE 849

Structure:

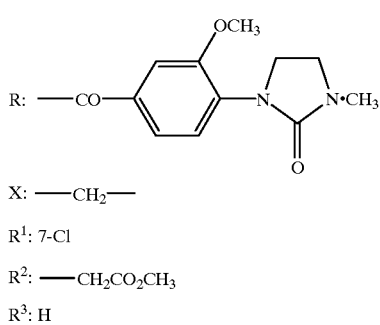

X: —CH₂—

R¹: 7-Cl

R²: —CH₂CO₂CH₃

R³: H

Crystalline form: Colorless amorphous

Form: Free

EXAMPLE 850

Structure:

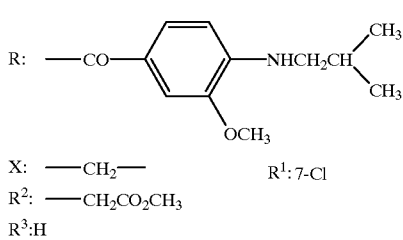

X: —CH₂—   R¹: 7-Cl

R²: —CH₂CO₂CH₃

R³: H

Crystalline form: Yellow oil

Form: Free

EXAMPLE 851

Structure:

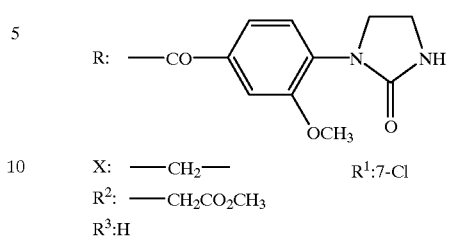

X: —CH₂—   R¹: 7-Cl

R²: —CH₂CO₂CH₃

R³: H

Crystalline form: Slightly yellow amorphous

Form: Free

EXAMPLE 852

Structure:

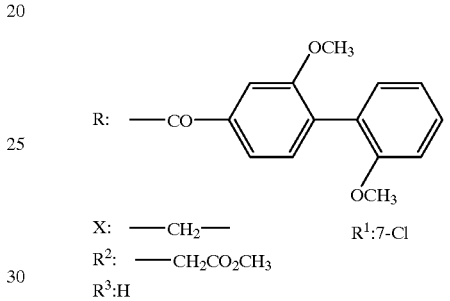

X: —CH₂—   R¹: 7-Cl

R²: —CH₂CO₂CH₃

R³: H

Crystalline form: Colorless amorphous

Form: Free

EXAMPLE 853

Structure:

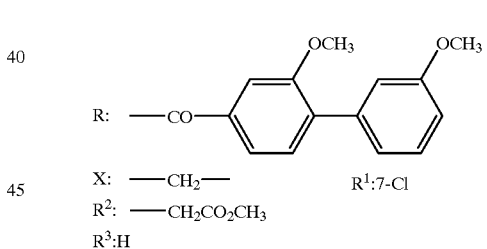

X: —CH₂—   R¹: 7-Cl

R²: —CH₂CO₂CH₃

R³: H

Crystalline form: Colorless amorphous

Form: Free

EXAMPLE 854

Structure:

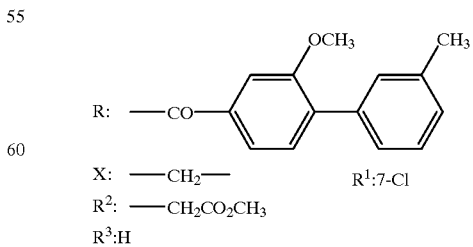

X: —CH₂—   R¹: 7-Cl

R²: —CH₂CO₂CH₃

R³: H

Crystalline form: Colorless amorphous

Form: Free

EXAMPLE 855

Structure:

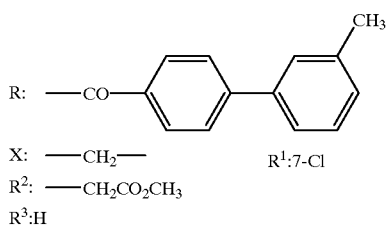

R: —CO—
X: —CH$_2$—
R$^2$: —CH$_2$CO$_2$CH$_3$
R$^3$: H
R$^1$: 7-Cl

Crystalline form: Colorless amorphous
Form: Free

EXAMPLE 856

Structure:

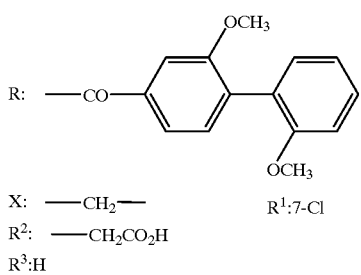

R: —CO—
X: —CH$_2$—
R$^2$: —CH$_2$CO$_2$H
R$^3$: H
R$^1$: 7-Cl

Crystalline form: Colorless amorphous
Form: Free

EXAMPLE 857

Structure:

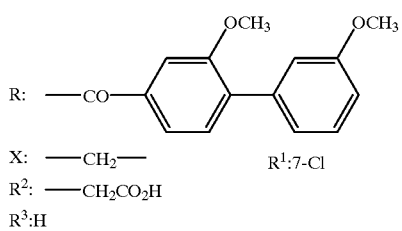

R: —CO—
X: —CH$_2$—
R$^2$: —CH$_2$CO$_2$H
R$^3$: H
R$^1$: 7-Cl

Crystalline form: Colorless amorphous
Form: Free

EXAMPLE 858

Structure:

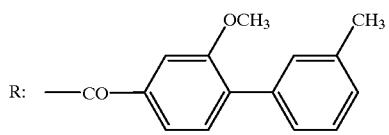

-continued
X: —CH$_2$—
R$^2$: —CH$_2$COOH
R$^3$:
R$^1$: 7-Cl

Crystalline form: Colorless amorphous
Form: Free

EXAMPLE 859

Structure:

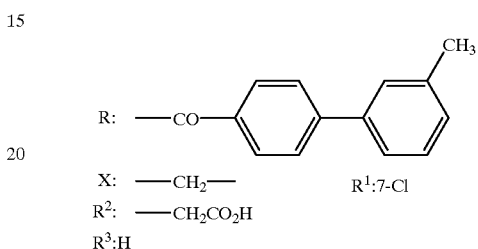

R: —CO—
X: —CH$_2$—
R$^2$: —CH$_2$CO$_2$H
R$^3$: H
R$^1$: 7-Cl

Crystalline form: Colorless amorphous
Form: Free

EXAMPLE 860

Structure:

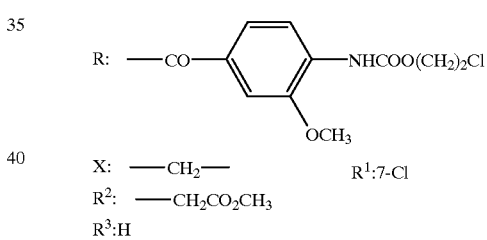

R: —CO—
X: —CH$_2$—
R$^2$: —CH$_2$CO$_2$CH$_3$
R$^3$: H
R$^1$: 7-Cl

Crystalline form: Colorless amorphous
Form: Free

EXAMPLE 861

Structure:

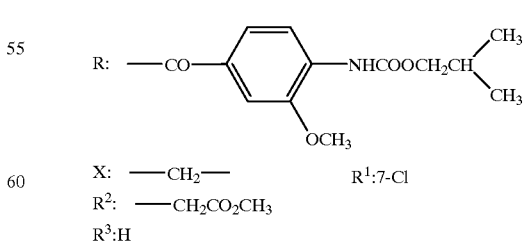

R: —CO—
X: —CH$_2$—
R$^2$: —CH$_2$CO$_2$CH$_3$
R$^3$: H
R$^1$: 7-Cl

Crystalline form: Colorless amorphous
Form: Free

EXAMPLE 862

Structure:

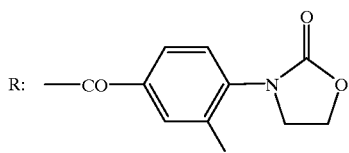

X: —CH$_2$—   R$^1$:7-Cl
R$^2$: —CH$_2$CO$_2$CH$_3$
R$^3$:H

Crystalline form: Colorless amorphous
Form: Free

EXAMPLE 863

Structure:

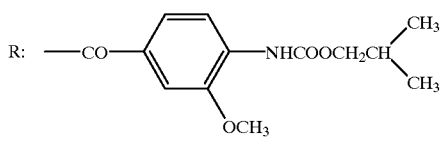

X: —CH$_2$—   R$^1$:7-Cl
R$^2$: —CH$_2$CO$_2$H
R$^3$:H

Crystalline form: White powder
Form: Free

EXAMPLE 864

Structure:

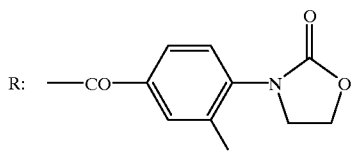

X: —CH$_2$—   R$^1$:7-Cl
R$^2$: —CH$_2$COOH
R$^3$:H

Crystalline form: White powder
Form: Free

EXAMPLE 865

Structure:

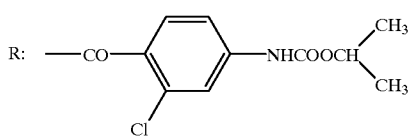

-continued

X: —CH$_2$—   R$^1$:H
R$^2$: —CH$_2$COOH$_3$
R$^3$:H

Crystalline form: Colorless amorphous
Form: Free

EXAMPLE 866

Structure:

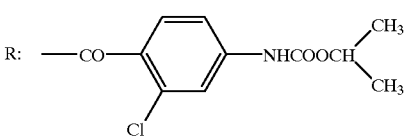

X: —CH$_2$—   R$^1$:H
R$^2$: —CH$_2$COOH
R$^3$:H

Crystalline form: Colorless amorphous
Form: Free

EXAMPLE 867

Structure:

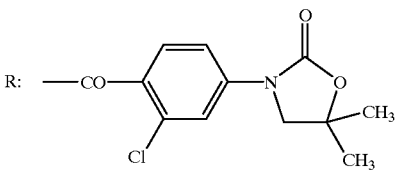

X: —CH$_2$—   R$^1$:H
R$^2$: —CH$_2$CO$_2$CH$_3$
R$^3$:H

Crystalline form: White powder
Solvent for recrystallization: Diethyl ether
Form: Free The suitable starting compounds are treated in the same manner as in Examples 1 and 2 to give the following compounds.

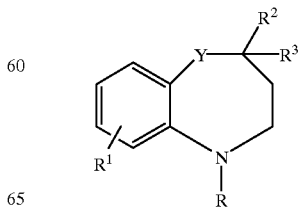

EXAMPLE 868

Structure:

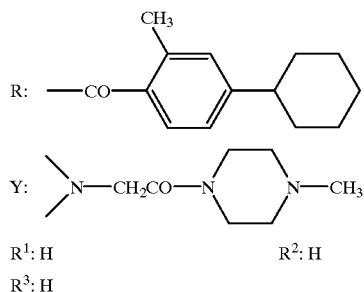

R¹: H  R²: H
R³: H

Crystalline form: Colorless amorphous

Form: Free

EXAMPLE 869

Structure:

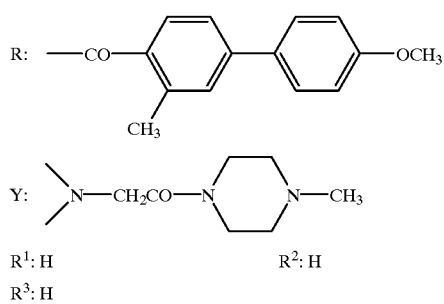

R¹: H  R²: H
R³: H

Crystalline form: Colorless amorphous

Form: Free

EXAMPLE 870

Structure:

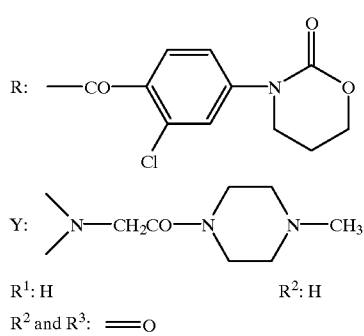

R¹: H  R²: H
R² and R³: =O

Crystalline form: Colorless amorphous

Form: Free

EXAMPLE 871

Structure:

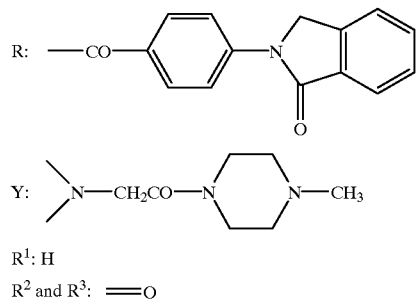

R¹: H
R² and R³: =O

Crystalline form: Colorless amorphous

Form: Free

EXAMPLE 872

Structure:

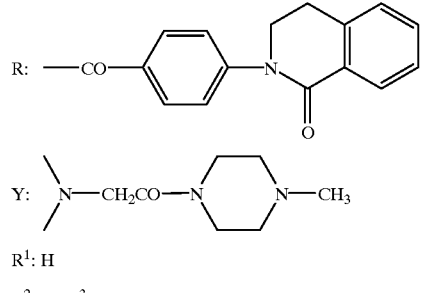

R¹: H
R² and R³: =O

Crystalline form: White powder

M.p. 168–171° C.

Form: Free

EXAMPLE 873

Structure:

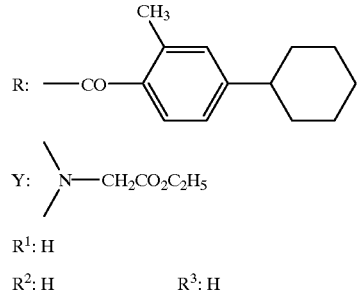

R¹: H
R²: H  R³: H

Crystalline form: Brown amorphous

Form: Free

EXAMPLE 874

Structure:

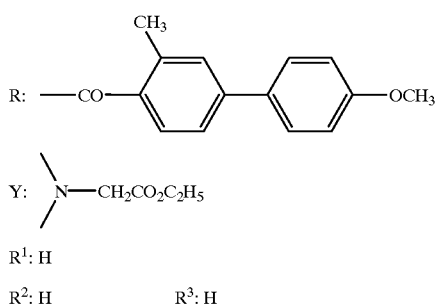

R¹: H
R²: H    R³: H

Crystalline form: Brown amorphous

Form: Free

EXAMPLE 875

Structure:

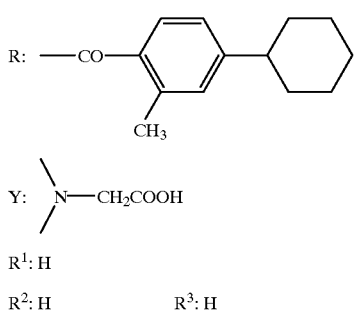

R¹: H
R²: H    R³: H

Crystalline form: White powder

Form: Free

EXAMPLE 876

Structure:

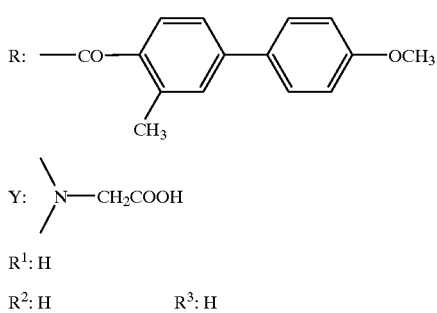

R¹: H
R²: H    R³: H

Crystalline form: Colorless amorphous

Form: Free

EXAMPLE 877

Structure:

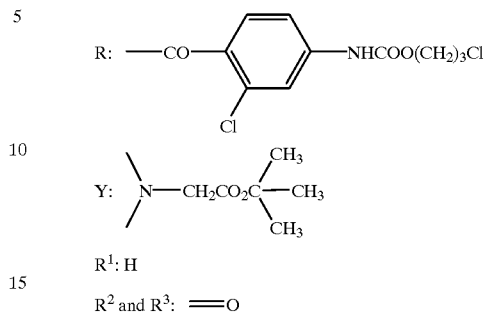

R¹: H
R² and R³: =O

Crystalline form: Yellow amorphous

Form: Free

EXAMPLE 878

Structure:

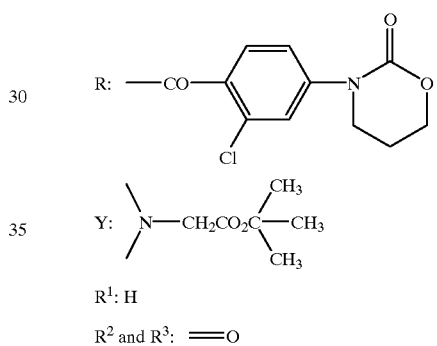

R¹: H
R² and R³: =O

Crystalline form: Yellow amorphous

Form: Free

EXAMPLE 879

Structure:

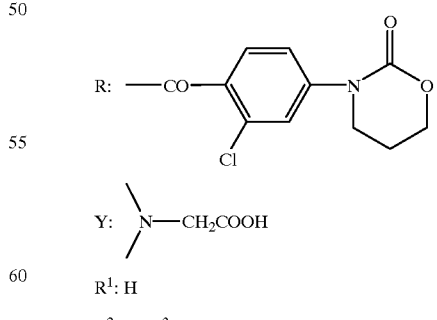

R¹: H
R² and R³: =O

Crystalline form: Brown amorphous

Form: Free

EXAMPLE 880

Structure:

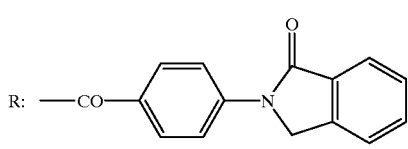

R: —CO—⟨C6H4⟩—N(isoindolin-1-one)

Y: ══NH

R¹: H

R² and R³: ══O

Crystalline form: White powder

Form: Free

EXAMPLE 881

Structure:

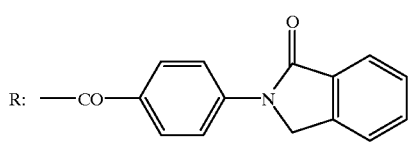

R: —CO—⟨C6H4⟩—N(isoindolin-1-one)

Y: \N—CH$_2$COOCH$_2$CH$_3$ /

R¹: H

R² and R³: ══O

Crystalline form: Brown oil

Form: Free

EXAMPLE 882

Structure:

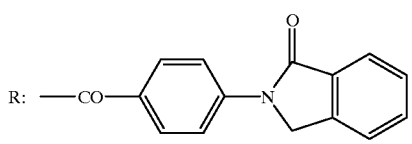

R: —CO—⟨C6H4⟩—N(isoindolin-1-one)

Y: \N—CH$_2$COOH /

R¹: H

R² and R³: ══O

Crystalline form: White powder

Form: Free

EXAMPLE 883

Structure:

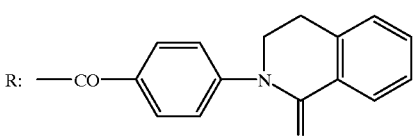

R: —CO—⟨C6H4⟩—N(3,4-dihydroisoquinolin-1(2H)-one)

Y: ══NH

R¹: H

R² and R³: ══O

Crystalline form: Brown amorphous

Form: Free

EXAMPLE 884

Structure:

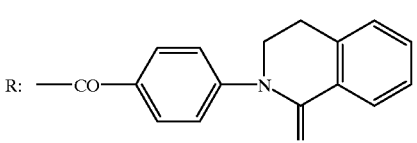

R: —CO—⟨C6H4⟩—N(3,4-dihydroisoquinolin-1(2H)-one)

Y: \N—CH$_2$COOC$_2$H$_5$ /

R¹: H

R² and R³: ══O

Crystalline form: Brown amorphous

Form: Free

EXAMPLE 885

Structure:

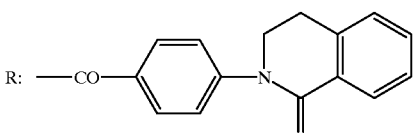

R: —CO—⟨C6H4⟩—N(3,4-dihydroisoquinolin-1(2H)-one)

Y: \N—CH$_2$COOH /

R¹: H

R² and R³: ══O

Crystalline form: Brown powder

Form: Free

The data of NMR analysis of the compounds of the above Examples are as follows.

NMR analysis:

The compound of Example 741

$^1$H-NMR (200 MHz, CDCl$_3$) δ ppm: 1.08–1.88 [9H, m, (1.22, 1.35, each 3H, each d, J=6.0 Hz)], 1.88–2.61 [11H, m, (2.33, 2.43 each s)], 2.61–4.04, 4.31–4.70, 4.98–5.19 (total 10H, m), 6.12–7.43 (7H, m)

The compound of Example 742

¹H-NMR (200 MHz, CDCl₃) δ ppm: 1.10–2.59 [15H, m, (2.33, 2.45, each s)], 2.59–3.09 (2H, m), 3.09–4.01, 4.43–4.64 (total 6H, m), 4.93, 5.09 (total 2H, each s), 6.24–7.51 (12H, m)

The compound of Example 743

¹H-NMR (200 MHz, CDCl₃) δ ppm: 1.08–2.61 [15H, m, 2.34 (s)], 2.61–3.02 (2H, m), 3.02–4.11, 4.43–4.64, 4.90–5.12 (total 6H, m), 5.30 (1H, s), 6.00–7.45 (7H, m)

The compound of Example 754

¹H-NMR (200 MHz, CDCl₃) δ ppm: 0.82–1.14 [6H, m, 0.95, 1.04, (each d, J=6.7 Hz)], 1.15–1.93 (1H, m), 1.95–2.59 [14H, m, 2.33, 4.45, (each s)], 2.59–4.02, 4.45–4.67, 4.98–5.17 (total 11H, m), 6.12–7.46 (7H, m)

The compound of Example 755

¹H-NMR (200 MHz, CDCl₃) δ ppm: 0.92, 0.99 (total 6H, each t, J=7.3 Hz), 1.19–2.59 [18H, m, 2.33, 2.44, (each s)], 2.59–4.09, 4.41–4.65, 4.95–5.18 [11H, m, 3.83, 3.98, (each t, J=6.5 Hz)], 6.11–7.45 (7H, m)

The compound of Example 760

¹H-NMR (200 MHz, CDCl₃) δ ppm: 0.50, 0.95 (total 6H, each d, J=6.5 Hz), 1.01–1.32 [7H, m, 1.04 (3H, d, J=6.7 Hz)], 1.48–3.18 [10H, m, 2.49 (s)], 3.30–4.65, 5.46–5.72 [total 5H, m, (3.75, d, J=6.5 Hz)], 6.40–7.39 (8H, m)

The compound of Example 761

¹H-NMR (200 MHz, CDCl₃) δ ppm: 0.50 (3H, d, J=6.5 Hz), 0.85–1.29 [7H, m, 0.95 (3H, d, J=6.5 Hz), 0.99, 1.16 (total 3H, each t, J=5.5 Hz)], 1.35–2.18 (10H, m), 2.19–2.58 [5H, m, 2.49 (s)], 2.58–2.78, 2.89–3.18 (total 2H, m), 3.30–4.65, 5.41–5.67 (total 6H, m), 6.81–7.40 (8H, m)

The compound of Example 816

¹H-NMR (200 MHz, CDCl₃) δ ppm: 1.15–2.21 (4H, m), 2.33–2.55, 3.09–3.87, 4.39–4.62 [total 11H, m, (2.45, 3.69 each s)], 2.60–3.05 (2H, m), 4.81–5.19 [2H, m, 4.93, 5.09 (each s)], 6.25–7.53 (12H, m)

The compound of Example 817

¹H-NMR (200 MHz, CDCl₃) δ ppm: 1.15–2.19 (4H, m), 2.44, 2.47 (total 3H, each s), 2.11–3.08 (2H, m), 3.08–3.90, 4.39–4.62, 4.79–5.31 [total 7H, 4.89, 5.06 (total 2H, eash s)], 6.25–7.52 (12H, m)

The compound of Example 818

¹H-NMR (200 MHz, CDCl₃) δ ppm: 1.12–2.17 [10H, m, 1.24, 1.35, (each d, J=6.0 Hz)], 2.32–2.59 [3H, m, 2.43 (s)], 2.61–3.32 (3H, m), 3.41–3.92 [6H, m, 3.70 (s)], 4.29–4.63, 5.01–5.22 (total 2H, m), 6.18–7.42 (7H, m)

The compound of Example 819

¹H-NMR (200 MHz, CDCl₃) δ ppm: 1.09–2.22 [10H, m, 1.22, 1.35 (each d, J=6.0 Hz)], 2.30–2.58 [3H, m, 2.43, 2.47 (each s)], 2.11–4.01 (4H, m), 4.28–4.70, 4.99–5.22 (total 2H, m), 6.13–7.48 (8H, m)

The compound of Example 838

¹H-NMR (200 MHz, CDCl₃) δ ppm: 0.96, 1.04 (total 6H, each d, J=6.7 Hz), 1.18–2.20 (4H, m), 2.44, 2.48 (total 3H, each s), 2.61–3.31, 3.39–4.16, 5.02–5.27 (total 8H, m), 6.19–7.42 (8H, m)

The compound of Example 839

¹H-NMR (200 MHz, CDCl₃) δ ppm: 0.92, 0.99 (total 3H, each t, J=7.2 Hz), 1.15–2.22 (8H, m), 2.43, 2.47 (total 3H, each s), 2.62–3.31, 3.36–4.09, 4.38–4.65, 5.01–5.23 (total 7H, m, (3.82, 3.97, each t, J=6.5 Hz)), 6.17–7.41 (8H, m)

The compound of Example 765

¹H-NMR (200 MHz, CDCl₃+DMSO-d₆) δ ppm: 1.2–2.3 (4H, m), 2.5–3.4, 4.7–5.1, 5.3–5.6 (total 4H, each m), 6.5–7.5 (9H, m), 7.60 (1H, dd, J=7.5 Hz, 7.5 Hz), 7.95 (1H, d, J=7.5 Hz), 11.43 (1H, s)

The compound of Example 731

¹H-NMR (200 MHz, CDCl₃) δ ppm: 1.25–4.30, 4.6–4.85 [total 27H, m, 2.49 (s), 2.84 (s), 2.94 (s)], 6.85–8.0 (total 7H, m)

The compound of Example 733

¹H-NMR (200 MHz, DMSO-d₆) δ ppm: 1.1–2.1, 2.4–4.1, 4.1–4.7 (total 24H, m), 6.7–7.8, 7.8–8.0, 8.35–8.7 (total 7H, m), 11.1–11.7 (1H, m)

The compound of Example 734

¹H-NMR (200 MHz, DMSO-d₆) δ ppm: 0.81–2.20, 2.6–4.0, 4.2–4.6 (total 33H, m), 6.8–8.0 (total 7H, m), 10.8–11.3 (1H, m)

The compound of Example 735

¹H-NMR (200 MHz, DMSO-d₆) δ ppm: 1.1–2.2, 2.6–4.1, 4.3–4.6 (total 26H, m), 6.8–7.9 [total 12H, m, 7.63 (s), 7.93 (s)], 10.8–11.4 (1H, m)

The compound of Example 736

¹H-NMR (200 MHz, CDCl₃) δ ppm: 0.99–2.20, 2.63–3.91, 4.81–5.08 [total 23H, m, 1.12 (d, J=6.77 Hz)], 6.48 (1H, dd, J=8.6 Hz, J=8.5 Hz), 6.71–7.48 (6H, m)

The compound of Example 740

¹H-NMR (200 MHz, CDCl₃) δ ppm: 1.35–1.80, 1.80–2.25, 2.35–2.60, 2.60–3.15, 3.25–3.55, 4.35–4.65, 4.85–5.05 [total 15H, m, 2.46 (s), 4.43 (s), 4.48 (s)], 6.52–6.65, 6.78–6.95, 7.12–7.55 (total 11H, m)

The compound of Example 744

¹H-NMR (200 MHz, CDCl₃) δ ppm: 1.32–2.26, 2.45–2.65, 2.65–3.30, 4.85–5.12 [total 11H, m, 2.53 (s)], 6.65–6.75, 6.75–7.06, 7.06–7.54, 7.54–7.96, 8.58–8.76 (total 11H, m)

The compound of Example 745

¹H-NMR (200 MHz, DMSO-d₆) δ ppm: 1.0–2.2, 2.7–4.8 (total 28H, m), 6.15–7.35 (11H, m), 10.3–10.95 (1H, m)

The compound of Example 747

¹H-NMR (200 MHz, CDCl₃) δ ppm: 0.75–1.00, 1.15–2.35, 2.35–4.27, 4.45–480 [total 32H, m, 3.38 (s)], 6.75–7.55 (7H, m), 12.6–13.4 (1H, br)

The compound of Example 748

¹H-NMR (200 MHz, CDCl₃) δ ppm: 0.66–1.10, 1.10–1.49, 1.49–2.34, 2.34–4.23, 4.35–4.80 (total 38H, m), 6.73–7.55 (7H, m), 12.6–13.5 (1H, br)

The compound of Example 749

¹H-NMR (200 MHz, CDCl₃) δ ppm: 0.75–0.96, 0.96–2.22, 2.22–4.30, 4.30–4.83 [total 27H, m, 4.58 (s), 2.49 (s)], 6.48–7.53 (11H, m), 12.75–13.45 (1H, br)

The compound of Example 751

¹H-NMR (200 MHz, CDCl₃) δ ppm: 0.78–1.05, 1.15–4.30, 4.42–4.75 [total 33H, m, 0.93, 0.99 and 2.33 (each s)], 6.68–7.89 (8H, m)

The compound of Example 752

¹H-NMR (200 MHz, CDCl₃) δ ppm: 0.52 (3H, d, J=6.6 Hz), 0.97 (3H, d, J=6.6 Hz), 1.10–2.20, 2.20–3.20, 3.35–4.15 [total 13H, m, 2.62 (s)], 6.35–6.55, 7.00–7.60, 7.60–8.05 (total 10H, m), 8.65–8.80 (1H, m)

The compound of Example 753

¹H-NMR (200 MHz, CDCl₃) δ ppm: 1.25–2.45, 2.45–4.30, 4.30–4.90 (total 23H, m), 6.45–8.55 (total 11H, m), 8.75–9.00 (1H, m)

The compound of Example 756

¹H-NMR (200 MHz, DMSO-d₆) δ ppm: 0.7–0.95, 0.95–2.25, 2.60–4.20, 4.20–4.55 [total 34H, m, 0.8 (d, J=6.6

Hz), 2.66 (s)], 6.75–7.95, 8.29, 8.57 [total 8H, m, 7.62, 7.83, 8.29, 8.57 each (s)]

The compound of Example 759

$^1$H-NMR (200 MHz, DMSO-d$_6$) δ ppm: 1.09–2.19 [12H, m, 1.25 (t, J=7.2 Hz)], 2.28–3.67, 4.24–4.57, 4.68–4.98 [total 10H, m, 2.41 (s)], 6.68–7.81 (11H, m), 10.26–10.64 (1H, m)

The compound of Example 764

$^1$H-NMR (200 MHz, DMSO-d$_6$) δ ppm: 0.64–2.12 [11H, m, 0.75, 0.89 (each d, each J=6.5 Hz)], 2.12–5.05 [21H, m, 2.33 (s)], 6.37–7.52 (7H, m), 10.92–11.43 (1H, m)

The compound of Example 765

$^1$H-NMR (200 MHz, CDCl$_3$+DMSO-d$_6$) δ ppm: 1.2–2.3 (4H, m), 2.5–3.4, 4.7–5.1, 5.3–5.6 (total 4H, each m), 6.5–7.5 (9H, m), 7.60 (1H, dd, J=7.5 Hz, J=7.5 Hz,), 7.95 (1H, d, J=7.5 Hz),1 11.43 (1H, s)

The compound of Example 766

$^1$H-NMR (200 MHz, CDCl$_3$) δ ppm: 0.50 (3H, d, J=6.6 Hz), 0.76–1.40, 1.50–2.18, 2.18–2.70, 2.70–4.18 [total 24H, m, 3.36 (s)], 6.28–6.42, 6.82–7.54 (total 8H, m)

The compound of Example 767

$^1$H-NMR (200 MHz, CDCl$_3$) δ ppm: 0.50 (3H, d, J=6.6 Hz), 0.69–1.05, 1.05–1.41, 1.41–2.19, 2.19–2.70, 2.95–4.15 (total 31H, m), 6.27–6.38, 6.75–7.52 (8H, m)

The compound of Example 768

$^1$H-NMR (200 MHz, CDCl$_3$) δ ppm: 0.55–0.65, 0.72–0.99, 1.20–1.44, 1.55–2.10, 2.10–2.90, 2.90–3.25, 3.25–4.10 (total 36H, m), 6.30–6.45, 6.75–6.94, 7.00–7.50 (total 8H, m)

The compound of Example 769

$^1$H-NMR (200 MHz, CDCl$_3$) δ ppm: 1.05–4.70, 4.89–5.12 [total 26H, m, 2.34 (s), 4.33 (t, J=5.4 Hz), 4.40 (t, J=5.3 Hz)], 6.72–7.70 (7H, m)

The compound of Example 770 hu 1H-NMR (200 MHz, CDCl$_3$) δ ppm: 0.61 (3H, d, J=6.6 Hz), 0.97 (3H, d, J=6.6 Hz), 1.15, 1.30, 1.55–2.15, 2.25–2.70, 2.90–3.20, 3.32–3.52, 3.60–3.95 (total 19H, m), 4.40–4.60 (4H, m), 6.20–6.40, 6.51–6.52, 6.82–7.55 (total 13H, m)

The compound of Example 771

$^1$H-NMR (200 MHz, DMSO-d$_6$) δ ppm: 0.82–2.25 [1 1H, m, 0.97 (d, J=6.6 Hz)], 2.29–4.98 [21H, m, 2.43 (s)], 6.49–7.79 (11H, m), 10.85–11.30 (1H, m)

The compound of Example 773

$^1$H-NMR (200 MHz, DMSO-d$_6$) δ ppm: 1.00–2.30 [7H, m, 1.28 (t, J=7.2 Hz)], 2.31–5.08 [21H, m, 2.43 (s), 3.76 (s)], 6.48–7.81 (11H, m), 10.81–11.31 (1H, m)

The compound of Example 774

$^1$H-NMR (200 MHz, DMSO-d$_6$) δ ppm: 1.01–2.38 (4H, m), 2.39–5.02 [24H, m, 2.43 (s), 3.76 (s), 3.81 (s)], 6.49–7.78 (11H, m), 10.47–11.08 (1H, m)

The compound of Example 775

$^1$H-NMR (200 MHz, DMSO-d$_6$) δ ppm: 1.01–2.28 [10H, m, 1.19 (t, J=7.1 Hz)], 2.29–5.02 [22H, m, 2.44 (s), 3.77 (s), 3.81 (s)], 6.49–7.81 (11H, m), 9.92–10.32 (1H, m)

The compound of Example 777

$^1$H-NMR (200 MHz, CDCl$_3$) δ ppm: 1.21–3.18, 3.58–3.85, 4.15–4.40, 4.82–5.15 [total 25H, m, 2.63 (t, J=5.73 Hz), 4.27 (t, J=5.8 Hz)], 6.41–7.01, 7.18–7.49, 7.75–7.92 [total 7H, m, 7.85 (d, J=8.5 Hz)]

The compound of Example 778

$^1$H-NMR (200 MHz, CDCl$_3$) δ ppm: 0.96 (6H, d, J=1 0.7 Hz), 1.21–4.11, 4.31–4.59, 5.01–5.22 [total 21H, m, 2.41 (s), 3.70 (s), 3.92 (d, J=6.6 Hz)], 6.49–7.67, 7.80–8.05 [total 8H, m, 7.92 (d, J=8.4 Hz)]

The compound of Example 779

$^1$H-NMR (200 MHz, CDCl$_3$) δ ppm: 1.35–1.86, 1.86–2.29, 2.40–2.63, 2.63–3.16, 3.32–3.52, 4.85–5.08 [total 11H, m, 2.52 (s), 2.57 (s)], 6.56–6.68, 6.82–7.56 (6H, m), 8.86, 8.97 (total 2H, each s), 9.17, 9.23 (total 1H, each s)

The compound of Example 780

$^1$H-NMR (200 MHz, CDCl$_3$) δ ppm: 1.38–1.66, 1.85–2.22, 2.62–3.16, 4.90–5.15 (8H, m), 3.71 (3H, s), 6.58–6.70 (1H, m), 6.70–6.82 (1H, m), 6.82–7.00 (2H, m), 7.12–7.31 (2H, m), 7.50–7.80 (3H, m), 7.60–7.70 (1H, m)

The compound of Example 781

$^1$H-NMR (200 MHz, CDCl$_3$) δ ppm: 1.35–2.20, 2.65–3.15, 4.92–5.13 (total 8H, m), 3.67 (3H, s), 6.55–6.84 (2H, m), 6.84–7.00 (2H, m), 7.00–7.19 (1H, m), 7.19–7.34 (2H, m), 7.73–7.85 (1H, m), 8.48–8.60 (1H, m), 8.60–8.72 (1H, m)

The compound of Example 783

$^1$H-NMR (200 MHz, CDCl$_3$) δ ppm: 1.19–4.68, 5.00–5.19 [total 27H, m, 2.36 (s), 3.75 (s)l, 6.48–7.59 (7H, m)

The compound of Example 784

$^1$H-NMR (200 MHz, CDCl$_3$) δ ppm: 1.05–2.21, 2.55–3.19, 3.41–3.55, 3.65–3.80, 3.95–4.23, 4.89–5.12 [total 31H, m, 1.45 (s), 3.73 (s)], 6.51–6.74, 6.82–6.95, 7.19–7.35, 7.80–7.90 [total 7H, m, 7.84 (d, J=8.4 Hz)]

The compound of Example 785

$^1$H-NMR (200 MHz, CDCl$_3$) δ ppm: 1.0–4.0, 4.0–5.2 (total 29H, m), 6.1–8.2 (total 11H, m)

The compound of Example 786

$^1$H-NMR (200 MHz, CDCl$_3$) δ ppm: 1.0–1.4, 1.4–4.0, 4.0–5.2 (total 33H, m), 6.15–6.35, 6.6–8.25 (total 7H, m), 12.4–13.4 (1H, m)

The compound of Example 787

$^1$H-NMR (200 MHz, CDCl$_3$) δ ppm: 1.2–1.6, 1.6–2.2, 2.6–3.75, 3.9–4.6 (total 28H, m), 6.5–7.6, 7.8–8.2 (total 12H, m), 10.8–11.2 (1H, m)

The compound of Example 788

$^1$H-NMR (200 MHz, CDCl$_3$) δ ppm: 1.25–4.0, 4.35–4.55, 5.0–5.20 [total 30H, m, 2.33 (s), 2.82 (s), 3.63 (s)], 6.55–7.55 [total 6H, m, 6.6 (d, J=6.6 Hz), 6.96 (d, J=6.6 Hz), 7.20 (d, J=6.6 Hz), 7.49 (s)]

The compound of Example 790

$^1$H-NMR (200 MHz, CDCl$_3$) δ ppm: 1.35–1.69, 1.78–2.26, 2.53–3.14, 3.30–3.81, 4.29–4.51, 4.90–5.18 [total 15H, m, 2.98 (t, J=5.3 Hz), 4.39 (t, J=5.3 Hz), 3.72 (s)J, 6.45–7.35, 7.65–7.92, 8.40–8.65 (total 11H, m)

The compound of Example 794

$^1$H-NMR (200 MHz, CDCl$_3$) δ ppm: 1.11–3.95, 4.41–4.63, 4.95–5.15 [total 28H, m, 1.49 (s), 1.58 (s), 2.38 (s)], 6.75–7.92 (7H, m)

The compound of Example 795

$^1$H-NMR (200 MHz, CDCl$_3$) δ ppm: 1.11–4.05, 4.45–4.70, 4.81–5.13 [total 27H, m, 2.40 (s), 1.25 (d, J=6.2 Hz), 1.31 (d, J=6.3 Hz)], 6.60–7.82 (8H, m)

The compound of Example 796

$^1$H-NMR (200 MHz, CDCl$_3$) δ ppm: 1.35–2.18, 2.18–4.20, 4.25–470, 4.90–5.15 [total 24H, m, 3.85 (s)], 6.55–7.15, 7.15–7.60, 7.70–8.10 (total 21H, m)

The compound of Example 801

¹H-NMR (200 MHz, DMSO-d₆) δ ppm: 1.03–2.04 (10H, m), 2.31–3.88, 4.29–4.54, 4.84–5.07 [total 19H, m, 2.43 (s), 3.77 (s)], 6.50–7.78 (11H, m), 8.44–8.69 (1H, m), 9.91–10.27 (1H, m)

The compound of Example 802

¹H-NMR (200 MHz, DMSO-d₆) δ ppm: 1.05–2.36 [total 10H, m, 1.18 (t, J=7.0 Hz)], 2.48–4.54, 4.79–5.21 [total 19H, m, 3.60 (s)], 6.67–7.62 (11H, m), 10.04–10.39 (1H, m)

The compound of Example 803

¹H-NMR (200 MHz, DMSO-d₆) δ ppm: 1.05–2.10 (10H, m), 2.39–3.94, 4.18–4.49, 4.88–5.12 [total 16H, m, 3.58 (s)], 6.69–7.70 (11H, m), 8.34–8.71 (1H, m), 10.00–10.34 (1H, m)

The compound of Example 804

¹H-NMR (200 MHz, DMSO-d₆) δ ppm: 1.00–2.28 [10H, m, 1.23 (t, J=7.2 Hz)], 2.42–4.13, 4.26–4.52, 4.69–4.91 (total 19H, m), 6.76–7.85 (11H, m), 10.09–10.48, 11.10–11.26 (total 1H, m)

The compound of Example 805

¹H-NMR (200 MHz, DMSO-d₆) δ ppm: 0.99–2.06 [10H, m, 1.20 (t, J=7.0 Hz)], 2.38–4.08, 4.25–4.52, 4.72–4.92 (total 1 6H, m), 6.78–7.84 (11H, m), 8.43–8.68 (1H, m), 10.09–10.45 (1H, m)

The compound of Example 806

¹H-NMR (200 MHz, DMSO-d₆) δ ppm: 1.03–2.11 (4H, m), 2.34 (3H, s), 2.44–4.79, 4.88–5.10 (total 16H, m), 6.12–8.03 (11H, m), 11.08–11.55 (1H, m)

The compound of Example 807

¹H-NMR (200 MHz, DMSO-d₆) δ ppm: 1.03–2.13 (10H, m), 2.22–3.83, 4.17–4.48, 4.88–5.10 (total 16H, m, 2.35 (s)], 6.58–7.90 (11H, m), 8.39–8.81 (1H, m), 10.20–10.65 (1H, m)

The compound of Example 808

¹H-NMR (200 MHz, DMSO-d₆) δ ppm: 1.10–2.28 (4H, m), 2.52–4.68, 4.87–5.10 [total 22H, m, 3.51 (s), 3.65 (s)], 6.11–6.29, 6.42–7.65 (total 10H, m), 11.07–11.48 (1H, brs)

The compound of Example 809

¹H-NMR (200 MHz, DMSO-d₆) δ ppm: 0.95–2.26 (10H, m), 2.38–4.08, 4.20–4.52, 4.78–5.08 [total 19H, m, 3.58 (s), 3.75 (s)], 6.62–7.62 (10H, m), 8.36–8.68 (1H, m), 9.82–10.20 (1H, m)

The compound of Example 810

¹H-NMR (200 MHz, DMSO-d₆) δ ppm: 1.07–2.29 (4H, m), 2.30–4.78, 4.87–5.10 [total 22H, m, 3.51 (s), 3.65 (s)], 6.11–6.29, 6.42–7.63 (total 10H, m), 11.13–11.58 (1H, brs)

The compound of Example 811

¹H-NMR (200 MHz, DMSO-d₆) δ ppm: 1.03–2.30 (10H, m), 2.40–4.00, 4.18–4.76, 4.83–5.08 [total 19H, m, 3.58 (s), 3.75 (s)], 6.63–7.64 (10H, m), 8.34–8.71 (1H, m), 9.92–10.39 (1H, m)

The compound of Example 812

¹H-NMR (200 MHz, DMSO-d₆) δ ppm: 1.05–2.09 (4H, m), 2.30 (3H, s), 2.58–4.71, 4.88–5.08 [total 19H, m, 3.57 (s)], 6.12–7.68 (10H, m), 11.00–11.50 (1H, brs)

The compound of Example 813

¹H-NMR (200 MHz, DMSO-d₆) δ ppm: 0.96–2.19 [10H, m, 1.19 (t, J=7.0 Hz)], 2.31 (3H, s), 2.55–4.69, 4.82–5.08 [total 19H, m, 3.59 (s)], 6.14–7.63 (10H, m), 10.19–10.52, 11.00–11.30 (1H, m)

The compound of Example 814

¹H-NMR (200 MHz, CDCl₃) δ ppm: 1.15–2.30, 2.50–3.85, 4.48–4.67, 5.06–5.24 [total 15H, m, 2.56 (a), 3.72 (s)], 6.50–6.72 (1H, m), 6.72–7.95 (9H, m), 8.57–8.75 (1H, m)

The compound of Example 820

¹H-NMR (200 MHz, CDCl₃) δ ppm: 0.75–1.00, 1.00–2.20, 2.60–3.05, 3.05–3.43, 3.43–3.96, 4.45–4.62 [total 24H, m, 1.59 (s), 3.19 (s), 3.69(s)], 6.80–7.50 (7H, m)

The compound of Example 821

¹H-NMR (200 MHz, CDCl₃) δ ppm: 0.70–1.00, 1.10–2.20, 2.60–3.95, 4.45–4.65, 5.02–5.15 (total 21H, m), 6.80–7.55 (7H, m)

The compound of Example 822

¹H-NMR (200 MHz, CDCl₃) δ ppm: 0.60–1.05, 1.15–2.20, 2.60–3.05, 3.15–3.95, 4.45–4.60, 5.02–5.15 (total 30H, m), 6.72–7.60 (7H, m)

The compound of Example 823

¹H-NMR (200 MHz, CDCl₃) δ ppm: 0.63–1.00, 1.10–2.20, 2.60–3.95, 4.45–4.60, 5.00–5.20 (total 27H, m), 6.68–7.58 (7H, m)

The compound of Example 825

¹H-NMR (200 MHz, CDCl₃) δ ppm: 1.20–2.20, 2.35–2.60, 2.60–3.85, 4.25–4.65 (total 16H, m), 6.40–6.66 (1H, m), 6.70–7.55 (11H, m)

The compound of Example 826

¹H-NMR (200 MHz, CDCl₃) δ ppm: 1.20–2.25, 2.25–3.26, 3.26–3.90, 4.50–4.70 [total 2H, m, 2.61 (s)], 6.72–6.85 (1H, m), 6.85–6.97 (1H, m), 7.00–7.35 (3H, m), 7.35–7.45 (1H, d, J=8.2 Hz), 7.56–7.78 (2H, m), 7.85–8.12 (2H, m), 8.20–8.38 (1H, m), 8.70–8.80 (1H, m)

The compound of Example 827

¹H-NMR (200 MHz, CDCl₃) δ ppm: 1.2–2.4 (4H, m), 2.7–3.8, 4.4–4.7, 4.9–5.2 (total 5H, each m), 6.8–8.4(7H, m)

The compound of Example 828

¹H-NMR (200 MHz, CDCl₃) δ ppm: 1.13–2.30 (4H, m), 2.35–4.08, 4.40–4.64, 4.92–5.20 [total 13H, m, 2.52 (s), 3.72 (s), 5.08 (s)], 6.48–7.62 (16H, m)

The compound of Example 829

¹H-NMR (200 MHz, CDCl₃) δ ppm: 1.13–2.26, 2.32–3.69, 4.81–5.20 [total 13H, m, 2.49 (s), 5.07 (s)], 6.57–7.63 (16H, m)

The compound of Example 833

¹H-NMR (200 MHz, CDCl₃) δ ppm: 0.86, 0.93, 1.07, 1.15–2.15, 2.60–3.80, 4.35–4.60 [total 23H, m, 0.86 (d, J=6.6 Hz), 0.93 (d, J=6.6 Hz), 1.07 (t, J=7 Hz)], 6.75–7.60 (total 7H, m), 8.25–8.80 (1H, m)

The compound of Example 834

¹H-NMR (200 MHz, CDCl₃) δ ppm: 1.20–2.15, 2.55–3.85, 4.35–4.55, 4.67 [total 15H, m, 4.67 (s)], 6.70–7.40, 7.44, 7.50–7.90 [total 12H, m, 7.44 (s)]

The compound of Example 835

¹H-NMR (200 MHz, CDCl₃) δ ppm: 1.35–2.24, 2.39–2.62, 2.63–3.18, 3.29–3.99, 4.06–4.63, 4.83–5.11 [total 15H, m, 2.49 (s), 3.81 (t, J=6.0 Hz)], 6.58–7.62 (11H, m)

The compound of Example 836

¹H-NMR (200 MHz, CDCl₃) δ ppm: 0.67–1.03, 1.05–2.54, 2.55–4.28, 4.41–4.63, 5.00–5.21 [total 24H, m, 0.78 (d, J=6.6 Hz), 0.92 (d, J=6.6 Hz), 2.28 (d, J=7.2 Hz), 2.43 (s), 3.71 (s)], 6.40–7.41 (7H, m)

The compound of Example 840

¹H-NMR (200 MHz, DMSO-d₆) δ ppm: 0.65–0.98, 1.04–2.12, 2.13–3.70, 4.26–4.51, 4.81–5.02 [total 21H, m, 0.75 (d, J=6.5 Hz), 0.89 (d, J=6.5 Hz), 2.27 (d, J=7.1 Hz), 2.33 (s)], 6.38–7.42 (7H, m), 12.14–12.42 (1H, m)

The compound of Example 844

¹H-NMR (200 MHz, CDCl₃) δ ppm: 1.13–4.01, 4.48–4.72 [total 23H, m, 2.33 (s)], 5.10 (2H, d, J=10.3 Hz), 6.43–7.64 (16H, m)

The compound of Example 845

¹H-NMR (200 MHz, CDCl₃) δ ppm: 1.09–4.20, 4.50–4.70, 4.96–5.16 [total 23H, m, 2.36 (s)], 6.41–7.48 (12H, m)

The compound of Example 849

¹H-NMR (200 MHz, CDCl₃) δ ppm: 1.2–2.2 (4.5H, m), 2.7–3.0 [total 5H, m, 2.83 (s)], 3.1–3.3, 3.3–3.5, 3.6–3.85, 4.35–4.5, 5.05–5.35 [total 12.5H, m, 3.40 (t, J=7.4 Hz), 3.67 (s), 3.77 (s)], 6.62 (1H, d, J=8.1 Hz), 6.82 (1H, d, J=8.1 Hz), 6.9–7.4 (4H, m)

The compound of Example 850

¹H-NMR (200 MHz, CDCl₃) δ ppm: 0.95 (6H, d, J=6.2 Hz), 1.25–2.15, 2.7–3.3, 3.67, 3.72, 4.35–4.65, 5.10–5.4 [total 19H, m, 3.67 (s), 3.72 (s)], 6.26, 6.64, 6.73–6.78, 6.96, 7.12–7.4 [total 6H, m, 6.26 (d, J=8.1 Hz)], 6.64 (d, J=8.1 Hz), 6.96 (dd, J=8.1 Hz, J=2.2 Hz)]

The compound of Example 851

¹H-NMR (200 MHz, CDCl₃) δ ppm: 1.2–2.2, 2.7–3.05, 3.15–3.3, 3.4–4.0, 4.4–4.55, 4.6–4.8, 5.05–5.26 [total 20H, m, 3.69 (s), 3.71 (s)], 6.60–7.45 [total 6H, m, 6.63 (d, J=8.1 Hz), 6.85 (d, J=8.1 Hz)]

The compound of Example 852

¹H-NMR (200 MHz, CDCl₃) δ ppm: 1.17–2.30 (4H, m), 2.57–3.03, 3.09–3.33, 3.43–3.92, 4.38–4.63, 5.08–5.28 [total 10H, m, 3.62 (s), 3.70 (s)], 6.53–7.43 (10H, m)

The compound of Example 853

¹H-NMR (200 MHz, CDCl₃) δ ppm: 1.18–2.30 (4H, m), 2.60–3.05, 3.10–3.37, 3.46–4.33, 4.38–4.62, 5.08–5.29 [total 10H, m, 3.67 (s), 3.71 (s), 3.81 (s)], 6.52–7.46 (10H, m)

The compound of Example 854

¹H-NMR (200 MHz, CDCl₃) δ ppm: 1.19–2.46 [7H, m, 2.37 (s)], 2.58–3.04, 3.05–4.26, 4.38–4.63, 5.06–5.28 [total 11H, m, 3.67 (s), 3.71 (s)], 6.54–7.48 (10H, m)

The compound of Example 855

¹H-NMR (200 MHz, CDCl₃) δ ppm: 1.20–2.28 (4H, m), 2.39 (3H, s), 2.57–3.10, 3.11–4.35, 4.40–4.63, 5.08–5.30 [total 8H, m, 3.75 (s)], 6.47–6.71, 6.81–7.78 (total 11H, m)

The compound of Example 856

¹H-NMR (200 MHz, DMSO-d₆) δ ppm: 1.12–2.19 (4H, m), 2.57–4.08, 4.20–4.66, 4.81–5.08 [total 11H, m, 3.52 (s), 3.65 (s)], 6.62–7.62 (10H, m), 12.36 (1H, s)

The compound of Example 857

¹H-NMR (200 MHz, DMSO-d₆) δ ppm: 1.10–2.19 (4H, m), 2.43–4.14, 4.20–4.71, 4.83–5.10 [total 11H, m, 3.59 (s), 3.75 (s)], 6.67–7.65 (10H, m), 12.20–12.57(1H, brs)

The compound of Example 858

¹H-NMR (200 MHz, DMSO-d₆) δ ppm: 1.13–2.38 [7H, m, 2.31 (s)], 2.51–4.02, 4.19–4.75, 4.82–5.08 [total 8H, m, 3.59 (s)], 6.62–7.80 (10H, m), 12.20–12.58 (1H, brs)

The compound of Example 859

¹H-NMR (200 MHz, DMSO-d₆) δ ppm: 1.18–2.18 (4H, m), 2.34 (3H, s), 2.48–4.12, 4.20–4.80, 4.89–5.12 (total 5H, m), 6.61–7.88 (11H, m), 12.12–12.60 (1H, m)

The compound of Example 868

¹H-NMR (200 MHz, CDCl₃) δ ppm: 1.06–2.69, 2.98–4.26, 4.60–4.81 [total 33H, m, 2.32 (s), 2.39 (s)], 6.42–7.45 (7H, m)

The compound of Example 869

¹H-NMR (200 MHz, CDCl₃) δ ppm: 1.68–2.72, 3.01–4.25, 4.65–4.92 [total 25H, m, 2.32 (s), 2.47 (s), 3.82 (s)], 6.46–7.12 (11H, m)

The compound of Example 871

¹H-NMR (200 MHz, CDCl₃) δ ppm: 2.16–2.98, 3.42–3.91, 4.02–4.25, 4.60–4.88, 5.02–5.40 [total 19H, m, 2.35 (s), 4.79 (s)], 6.61–7.05, 7.13–7.94 (total 12H, m)

The compound of Example 870

¹H-NMR (200 MHz, CDCl₃) δ ppm: 1.93–2.98, 3.29–4.59, 4.69–5.31 [total 23H, m, 2.35 (s), 3.60 (t, J=5.50 Hz), 4.35 (t, J=5.3 Hz)], 6.69–7.70 (7H, m)

The compound of Example 841

¹H-NMR (200 MHz, CDCl₃) δ ppm: 0.85–2.22, 2.55–3.31, 3.41–3.80, 4.05–4.31, 4.41–4.62 [total 25H, m, 3.69 (s)], 6.71–7.70 (7H, m)

The compound of Example 842

¹H-NMR (200 MHz, CDCl₃) δ ppm: 0.82–1.03, 1.15–2.20, 2.45–4.62 [total 22H, m, 0.93 (s)], 6.48–8.21 (8H, m)

The compound of Example 843

¹H-NMR (200 MHz, CDCl₃) δ ppm: 1.10–2.41, 2.56–4.65, 4.90–5.16 (total 15H, m), 6.52–7.61 (7H, m), 9.39–10.05 (1H, m)

The compound of Example 860

¹H-NMR (200 MHz, CDCl₃) δ ppm: 1.15–2.25, 2.50–3.03, 3.10–3.30, 3.48–3.91, 4.25–4.55, 5.05–5.28 [total 19H, m, 3.71 (s), 3.74 (s), 4.40 (t, J=5.9 Hz)], 6.42–7.42, 7.71–7.99 [total 7H, m, 6.58 (d, J=8.3 Hz), 7.86 (d, J=8.3 Hz)]

The compound of Example 861

¹H-NMR (200 MHz, CDCl₃) δ ppm: 0.75–2.21, 2.51–3.31, 3.45–4.10, 4.30–4.60, 5.03–5.31 [total 24H, m, 0.95 (d, J=6.7 Hz), 3.92 (d, J=7.2 Hz), 3.72 (s), 3.74 (s)], 6.42–7.41, 7.65–8.00 [total 7H, m, 6.58 (d, J=8.3 Hz), 7.88 (d, J=8.3 Hz)]

The compound of Example 862

¹H-NMR (200 MHz, CDCl₃) δ ppm: 1.11–2.31, 2.51–3.32, 3.42–4.09, 4.30–4.58, 5.05–5.21 [total 19H, m, 3.79 (s), 4.44 (t, J=7.8 Hz)], 6.49–7.42 [6H, m, 6.62 (d, J=8.3 Hz)]

The compound of Example 863

¹H-NMR (200 MHz, DMSO-d₆) δ ppm: 0.88 (6H, d, J=6.7 Hz), 1.10–2.07, 2.52–4.45, 4.85–5.02 [total 15H, m, 3.63 (s), 3.98 (d, J=7.2 Hz)], 6.50–6.88, 6.98–7.29, 7.38–7.79, 8.28–8.49 [total 7H, m, 6.70 (d, J=8.3 Hz), 7.52 (d, J=8.3 Hz)]

The compound of Example 864

¹H-NMR (200 MHz, DMSO-d₆) δ ppm: 1.01–2.10, 2.39–4.51, 4.86–5.05 [total 13H, m, 3.67 (s)], 6.0–7.75 (6H, m), 9.99 (1H, s)

The compound of Example 865

¹H-NMR (200 MHz, CDCl₃) δ ppm: 1.1 1–2.21, 2.60–3.29, 3.41–3.90, 4.41–4.65, 4.82–5.20 [total 19H, m, 1.26 (d, J=6.4 Hz), 3.69 (s)], 6.53–7.80 [8H, m, 6.71 (s), 7.46 (s)]

The compound of Example 867

¹H-NMR (200 MHz, CDCl₃) δ ppm: 1.11–2.29, 2.68–3.92, 4.38–4.70, 5.01–5.19 [total 20H, m, 1.50 (s), 1.58 (s), 2.16 (s), 3.70 (s)], 6.78–7.90 [7H, m, 7.59 (d, J=2.1 Hz)]

The compound of Example 873

¹H-NMR (200 MHz, CDCl₃) δ ppm: 0.80–2.61, 2.88–3.72, 3.85–4.40, 4.62–5.01 [total 27H, m, 1.31 (t, J=7.0 Hz), 2.35 (s), 4.22 (q, J=7.1 Hz)], 6.41–7.49 (7H, m)

The compound of Example 874

$^1$H-NMR (200 MHz, CDCl$_3$) δ ppm: 1.18–1.48, 1.68–2.62, 2.95–4.41, 4.71–5.05 [total 19H, m, 1.31 (t, J=7.1 Hz), 2.50 (s), 3.80 (s), 4.22 (q, J=6.8 Hz)], 6.45–7.65 (total 11H, m)

The compound of Example 875

$^1$H-NMR (200 MHz, CDCl$_3$) δ ppm: 1.10–2.62, 2.90–3.70, 3.85–4.21, 4.65–4.95 [total 22H, m, 2.35 (s)], 6.35–7.45 (7H, m)

The compound of Example 876

$^1$H-NMR (200 MHz, CDCl$_3$) δ ppm: 1.69–2.62, 2.81–4.28, 4.65–4.98 [total 14H, m, 2.43 (s), 3.80 (s)], 6.41–7.62 [11H, m, 7.38 (d, J=9.2 Hz)]

The compound of Example 877

$^1$H-NMR (200 MHz, CDCl$_3$) δ ppm: 1.53 (9H, s), 1.71–2.24, 2.50–2.91, 3.40–4.45, 4.61–5.10 [total 12H, m, 3.59 (t, J=6.3 Hz), 4.28 (t, J=6.0 Hz)], 6.65–7.80, 8.55–8.68 (total 8H, m)

The compound of Example 878

$^1$H-NMR (200 MHz, CDCl$_3$) δ ppm: 1.53 (9H, s), 2.09–2.31, 2.52–2.82, 3.55–4.51, 4.62–5.09 [total 12H, m, 2.17 (t, J=5.1 Hz), 4.37 (t, J=5.5 Hz)], 6.89–7.71 (7H, m)

The compound of Example 879

$^1$H-NMR (200 MHz, CDCl$_3$) δ ppm: 2.05–2.90, 3.46–5.10 [total 12H, m, 3.60 (t, J=5.8 Hz), 4.38 (t, J=5.3 Hz)], 6.81–7.71 (7H, m), 10.1–10.6 (1H, m)

The compound of Example 880

$^1$H-NMR (200 MHz, DMSO-d$_6$) δ ppm: 2.51–2.88, 3.10–5.15 [total 6H, m, 4.94 (s)], 6.70–7.35, 7.45–7.85, 7.92–8.28, 8.55–8.65 (total 13H, m)

The compound of Example 881

$^1$H-NMR (200 MHz, CDCl$_3$) δ ppm: 1.12–1.41, 2.51–2.86, 3.69–4.01, 4.10–4.48, 4.62–4.98 [total 13H, m, 1.29 (t, J=4.0 Hz), 4.69 (s)], 6.65–7.10, 7.19–7.92 [total 12H, m, 7.73 (d, J=8.8 Hz), 7.84 (d, J=7.0 Hz)]

The compound of Example 882

$^1$H-NMR (200 MHz, DMSO-d$_6$) δ ppm: 2.30–2.76, 3.56–3.96, 4.27–4.80 (total 4H, m), 4.94 (2H, s), 6.71–7.90 (8H, m)

The compound of Example 883

$^1$H-NMR (200 MHz, CDCl$_3$) δ ppm: 1.60–2.09, 2.28–4.32, 4.60–5.10 (total 10H, m), 6.41–8.25, 8.41–8.90 [total 13H, m, 8.12 (d, J=7.4 Hz)]

The compound of Example 884

$^1$H-NMR (200 MHz, CDCl$_3$) δ ppm: 1.05–1.49, 2.25–4.99 [total 15H, m, 1.31 (t, J=7.1 Hz)], 6.60–7.90, 8.00–8.28 [total 12H, m, 8.12 (d, J=7.7 Hz)]

The compound of Example 885

$^1$H-NMR (200 MHz, DMSO-d$_6$) δ ppm: 0.85–4.70, 4.88–6.20 (total 11H, m), 6.51–8.62 [total 12H, m, 7.94 (d, J=7.2 Hz)]

The compound of Example 866

$^1$H-NMR (200 MHz, CDCl$_3$) δ ppm: 0.85–2.18, 2.45–3.90, 4.29–4.60, 4.78–5.18 [total 16H, m, 1.28 (d, J=7.2 Hz)], 6.40–7.81 (8H, m), 7.90–9.60 (1H, m)

The compound of Example 789

$^1$H-NMR (200 MHz, CDCl$_3$) δ ppm: 0.4–1.4, 1.4–2.4, 2.4–2.85, 2.85–3.3, 3.3–5.0, 5.0–5.8 (total 29H, m), 6.29, 6.5–7.5 [total 6H, m, 6.29 (d, J=8.4 Hz)]

The compound of Example 792

$^1$H-NMR (200 MHz, CDCl$_3$) δ ppm: 0.75–0.98, 1.21–2.20, 2.42–4.19, 4.85–5.19 [total 25H, m, 2.60 (s), 3.73 (s)], 6.45–6.75, 6.80–7.00 (total 5H, m), 7.23 (1H, d, J=2.4 Hz), 7.81 (1H, d, J=6.6 Hz)

The compound of Example 797

$^1$H-NMR (200 MHz, CDCl$_3$) δ ppm: 1.03–1.40, 1.50–2.23, 2.23–2.58, 2.58–4.05, 4.05–4.30, 4.52–4.73 [total 24H, m, 1.60 (s), 2.13 (s)], 6.55–7.05, 7.05–7.50 (total 20H, m)

The compound of Example 798

$^1$H-NMR (200 MHz, CDCl$_3$) δ ppm: 1.30–2.20, 2.62–3.18, 4.85–5.05 (total 8H, m), 3.68 (3H, brs), 6.67–6.90, 7.00–7.50 (total 7H, m), 7.75–7.85 (1H, m), 8.50–8.65 (1H, m), 8.65–8.85 (1H, m)

The compound of Example 799

$^1$H-NMR (200 MHz, CDCl$_3$) δ ppm: 1.30–1.80, 1.80–2.20, 2.62–2.93, 2.93–3.20, 4.82–5.03 (total 8H, m), 3.71 (3H, s), 6.69–6.85 (2H, m), 7.10–7.48 (5H, m), 7.60–7.80 (2H, m), 8.60–8.70 (1H, m)

PHARMACOLOGICAL TEST

EXPERIMENT 1

V$_1$ receptor binding assay

Using rat liver plasma membrane preparations prepared according to Ichihara's method [cf: Akira Ichihara, J. Bio. Chem., 258, 9283 (1983)], the plasma membrane (50000 dpm, 2×10$^{-10}$ M) of [$^3$H]-Arg-vasopressin and a test compound (60 µg, 10$^{-8}$ to 10$^{-4}$ M) are incubated at 37° C. for 10 minutes in 100 mM Tris-HCl buffer (pH 8.0) (250 µl) containing 5 mM MgCl$_2$, 1 mM EDTA and 0.1 % BSA. After incubation, the mixture is filtered three times using the glass filter (GF/F) so as to separate the membrane preparation binding with vasopressin and then washed with the buffer (5 ml). This glass filter is taken out and mixed with liquid scintillation cocktail. The amount of [$^3$H]-vasopressin binding with the membrane is measured by liquid scintillation counter and the rate of the inhibitory effect of the test compound is estimated according to the following equation.

Rate of the inhibitory effect (%)=100−[(C$_1$−B$_1$)/(C$_0$−B$_1$)]×100

C$_1$: The amount of [$^3$H]-vasopressin binding with the membrane in the presence of the test compound (known amount)

C$_0$: The amount of [$^3$H]-vasopressin binding with the membrane in the absence of the test compound B$_1$: The amount of [$^3$H]-vasopressin binding with the membrane in the presence of the excess amount of vasopressin (10$^{-6}$ M)

The results are expressed as IC$_{50}$ value, which is the concentration of the test compound required to achieve the inhibitory effect in the rate of 50%.

The results are shown in the following Table.

EXPERIMENT 2

V$_2$ receptor binding assay

Using rat kidney plasma membrane preparations prepared according to O. Hechter's method [cf: J. Bio. Chem., 253, 3211 (1978)], the plasma membrane (100000 dpm, 4×10$^{-10}$ M) of [$^3$H]-Arg-vasopressin and a test compound (0.6 mg, 10$^{-10}$ to 10$^{-5}$ M) are incubated at 4° C. for 3 hours in 100 mM Tris-HCl buffer (pH 8.0) (250 µl) containing 5 mM MgCl$_2$, 1 mM EDTA and 0.1% BSA. After incubation, the mixture is filtered using the glass filter (GF/F) so as to separate the membrane preparation binding with vasopressin and then washed twice with the buffer (each 5 ml). This glass filter is taken out and mixed with liquid scintillation cocktail. The amount of [$^3$H]-vasopressin binding with the membrane is measured by liquid scintillation counter and the rate of the inhibitory effect of the test compound is estimated according to the following equation.

Rate of the inhibitory effect (%)=100−[($C_1$−$B_1$)/($C_0$−$B_1$)]×100

$C_1$: The amount of [$^3$H]-vasopressin binding with the membrane in the presence of the test compound (known amount)

$C_0$: The amount of [$^3$H]-vasopressin binding with the membrane in the absence of the test compound $B_1$: The amount of [$^3$H]-vasopressin binding with the membrane in the presence of the excess amount of vasopressin ($10^{-6}$ M)

The results are expressed as $IC_{50}$ value, which is the concentration of the test compound required to achieve the inhibitory effect in the rate of 50%.

The results are shown in the following Table.

| Test compound | $IC_{50}$ (μM) in $V_1$ receptor binding assay | $IC_{50}$ (μM) in $V_2$ receptor binding assay |
| --- | --- | --- |
| Compound of Ex. 29 | 0.021 | 0.15 |

EXPERIMENT 3

Anti-vasopressor activity in vivo

The spinal cord of mal SD rat (weighing 300–400 g) is broken to give a pith rat. The blood pressure of the pith rat is measured through the cannula inserted into the femoral artery thereof by using a pressure transducer. The test compound and Arg-vasopressin are administered to the pith rat through the cannula inserted into the femoral vein. Anti-vasopressor activity of the test compound in vivo is determined according to the following equation. Anti-vasopressor activity (%)=P/$P_0$×100

$P_0$: The increase of diastolic pressure when Arg-vasopressin (30 mU/kg) is administered intravenously.

P: The increase of diastolic pressure when Arg-vasopressin (30 mU/kg) is administered intravenously 3 minutes after the intravenous administration of the test compound.

The results are expressed as $ED_{50}$ value, which is the dose of the test compound required to reduce the increase of diastolic pressure caused by the intravenous administration of Arg-vasopressin (30 mU/kg) to 50 % of its control value: $P_0$.

The results are shown in the following Table.

| Test compound | $ED_{50}$ (mg/kg) |
| --- | --- |
| Compound of Ex. 29 | 1.0 |
| Compound of Ex. 70 | 2.8 |

EXPERIMENT 4

Anti-antidiuretic activity (effect on endogenous ADH)

A test compound or a solvent (dimethylformamide) is administered into a caudal vein of untreated, unrestrained SD rats (male, weight: 300–350 g) and the amount of urine, which is spontaneously excreted for a period of two hours thereafter, is collected and measured by using a metabolic gauge. During this measurement, the rats are allowed to take water and feed freely.

In the group treated by administration of the compound of Example 493 at a dose of 10 mg/kg, the amount of urine, which is excreted for two hours from the administration of the test compound, is four times larger than that in the control group.

EXPERIMENT 5

Antidiuretic activity

A test compound is dissolved in polyethylene glycol 400 or water, or suspended in 5 % gum arabic solution to give a test compound solution. The test compound solution is orally and forcibly administered to untreated, unrestrained Brattleburo rats, which hereditarily lack vasopressin. In the control group, a solvent is administered instead of a test compound solution. After the administration, the rats are put into a metabolic gauge, and the spontaneously excreted urine is collected for two hours, and the amount thereof is measured. During this measurement, the rats are allowed to take water and feed freely.

In the group treated by oral administration of Example 562 at a dose of 1 mg/kg, the amount of the urine, which is excreted for two hours after the administration of the test compound, is one fifth of that in the control group.

We claim:

1. A benzoheterocyclic compound of the following formula (1):

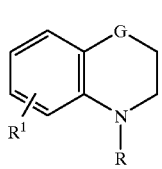

(1)

wherein G is a group of the formula:

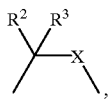

$R^1$ is a hydrogen atom or a halogen atom, $R^2$ is a hydrogen atom, or a group of the formula: -(O)$_m$-A-(CO)$_u$-NR$^6$R$^7$ (in which m is 0 and u is 1, A is a lower alkylene group, $R^6$ and $R^7$ are the same or different and each is a hydrogen atom, a lower alkyl group, or an amino-substituted lower alkyl group having optionally a lower alkyl substituent, or $R^6$ and $R^7$ may bind together with the nitrogen atom to which they bond to form a 5- to 7-membered saturated heterocyclic group selected from the group consisting of a pyrrolidinyl group, piperidinyl group, a piperazinyl group, a morpholino group and a homopiperazinyl group, said heterocyclic group being optionally substituted by a lower alkyl group or a phenyl-lower alkyl group), $R^3$ is a hydrogen atom, R is a pyridylcarbonyl group which may optionally have a substituent selected from a phenyl group having optionally a lower alkyl substituent and a pyridyl group on the pyridine ring, a quinolylcarbonyl group having optionally a phenyl substituent on the quinoline ring, an adamantylcarbonyl group, a thienylcarbonyl group having optionally a phenyl substituent on the thiophene ring, or a group of the formula:

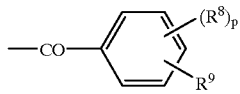

(in which p is 1 or 2), $R^8$ is a hydrogen atom, a lower alkyl group, a halogen atom or a lower alkoxy group, and $R^9$ is a hydrogen atom, a lower alkoxy group, a cycloalkyl group, a lower alkyl group, a phenyl group having optionally a substituent selected from a lower alkyl group, a lower alkoxy group, a phenyl-lower alkoxy group, a hydroxy group, a lower alkanoyloxy group, a halogen-substituted lower alkoxy group, a nitro group, an amino group having optionally a lower alkanoyl substituent, a phenyl group, and an amino-substituted lower alkoxy group having optionally a lower alkyl substituent, or a cycloalkenyl group), X is a methylene group, provided that when $R^2$ is a hydrogen atom, and when R is a group of the formula:

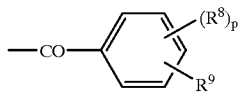

and $R^8$ in said group is a hydrogen atom, a lower alkyl group, a halogen atom, or a lower alkoxy group, then $R^9$ should not be a hydrogen atom, or when $R^1$ is a hydrogen atom, $R^2$ is a hydrogen atom, then $R^9$ should not be a phenyl group having optionally a substituent selected from a hydroxy group, a lower alkyl group, a lower alkoxy group and a lower alkanoyloxy group on the phenyl ring, or when $R^1$ and $R^2$ are simultaneously a hydrogen atom, then R should not be an unsubstituted pyridylcarbonyl group, nor an unsubstituted thienylcarbonyl group, or when $R^3$ is a hydrogen atom, $R^2$ is a hydrogen atom, then $R^9$ should not be a hydrogen atom, a lower alkoxy group nor a lower alkyl group; or a pharmaceutically acceptable salt thereof.

2. The compound according to claim 1, wherein R is a pyridylcarbonyl group having optionally a substituent selected from a phenyl group having optionally a lower alkyl substituent and a pyridyl group on the pyridine ring; a quinolylcarbonyl group having optionally a phenyl substituent on the quinoline ring; an adamantylcarbonyl group; and a thienyl-carbonyl group having optionally a phenyl substituent on the thiophene ring; or a pharmaceutically acceptable salt thereof.

3. The compound according to claim 1, wherein R is a group of the formula:

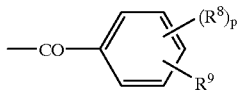

or a pharmaceutically acceptable salt thereof.

4. The compound according to claim 3, wherein $R^9$ is a cycloalkyl group or a phenyl group having optionally a substituent selected from a lower alkyl group, a lower alkoxy group, a phenyl-lower alkoxy group, a hydroxy group, a lower alkanoyloxy group, a halogen-substituted lower alkoxy group, a nitro group, an amino group having optionally a lower alkanoyl substituent, a phenyl group and an amino-lower alkoxy group having optionally a lower alkyl substituent on the phenyl ring, or a pharmaceutically acceptable salt thereof.

5. The compound according to claim 3, wherein $R^9$ is a hydrogen atom; a lower alkyl group; a cycloalkenyl group; or a pharmaceutically acceptable salt thereof.

6. The compound according to claim 4, wherein $R^2$ is a group of the formula: $-(O)_m-A-(CO)_u NR^6R^7$, $R^3$ is a hydrogen atom, or a pharmaceutically acceptable salt thereof.

7. The compound according to claim 4, wherein $R^2$ is a hydrogen atom and $R^3$ is a hydrogen atom, or a pharmaceutically acceptable salt thereof.

8. The compound according to claim 6, wherein m is 0, u is 1, $R^6$ and $R^7$ are the same or different and each is a hydrogen atom, a lower alkyl group, or an amino-substituted lower alkyl group having optionally a lower alkyl substituent, or a pharmaceutically acceptable salt thereof.

9. The compound according to claim 6, wherein m is 0, u is 1, and $R^6$ and $R^7$ bind together with the nitrogen atom to which they bond to form the 5- to 7-membered saturated heterocyclic group, said heterocyclic group being optionally substituted by a lower alkyl group or a phenyl-lower alkyl group, or a pharmaceutically acceptable salt thereof.

10. The compound according to claim 1, wherein m is 0, n is 1, $R^6$ and $R^7$ are the same or different and each a hydrogen atom, a lower alkoxy group, a lower alkyl group, an amino-substituted lower alkyl group having optionally a lower alkyl substituent, a carbamoyl-substituted lower alkyl group, an adamantyl-substituted lower alkyl group, a lower alkylsulfonyl group, or a phenyl group having optionally a halogen substituent, or a pharmaceutically acceptable salt thereof.

11. The compound according to claim 1, wherein m is 0, u is 1, and $R^6$ and $R^7$ bind together with the nitrogen atom to which they bond to form the 5- to 7-membered saturated heterocyclic group, said heterocyclic group being optionally substituted by a lower alkyl group or a phenyl-lower alkyl group, or a pharmaceutically acceptable salt thereof.

12. The compound according to any one of claims 2 or 3, wherein $R^1$ is a hydrogen atom or a halogen atom, or a pharmaceutically acceptable salt thereof.

13. The compound according to claim 1, wherein $R^2$ is a group of the formula: $-(O)_m-A-(CO)_u NR^6R^7$, and $R^3$ is a hydrogen atom, or a pharmaceutically acceptable salt thereof.

14. 5-[(4-Methyl-1-piperazinyl)carbonylmethyl]-1-[4-(4-methoxyphenyl)-2-methylbenzoyl]-2,3,4,5-tetrahydro-1H-benzazepine.

15. 5-[(4-Methyl-1-piperazinyl)carbonylmethyl]-1-[4-cyclohexyl-2-methylbenzoyl]-2,3,4,5-tetrahydro-1H-benzazepine.

16. A vasopressin agonist, which comprises, as an active vasopressin agonist ingredient, a benzoheterocyclic compound as set forth in claim 1, or a pharmaceutically acceptable salt thereof, in admixture with a pharmaceutically acceptable carrier or diluent.

17. A compound selected from the group consisting of

5-[di(2-hydroxyethyl)aminocarbonylmethyl]-1-[2-methyl-4-(4-methylphenyl) benzoyl]-2,3,4,5-tetrahydro-1H-benzazepine.

\* \* \* \* \*